(12) United States Patent
Bharathan et al.

(10) Patent No.: US 10,538,533 B2
(45) Date of Patent: *Jan. 21, 2020

(54) HETEROARYLS AND USES THEREOF

(71) Applicant: Millennium Pharmaceuticals, Inc., Cambridge, MA (US)

(72) Inventors: Indu T. Bharathan, Cambridge, MA (US); Chris Blackburn, Natick, MA (US); Jeffrey P. Ciavarri, Reading, MA (US); Jouhara Chouitar, Stoughton, MA (US); Courtney A. Cullis, Bedford, MA (US); Natalie D'Amore, Lynnfield, MA (US); Paul E. Fleming, Wellesley, MA (US); Kenneth M. Gigstad, Westford, MA (US); Krista E. Gipson, Medford, MA (US); Mario Girard, Quincy, MA (US); Yongbo Hu, Winchester, MA (US); Janice Lee, Cambridge, MA (US); Gang Li, Westborough, MA (US); Mansoureh Rezaei, Quincy, MA (US); Michael D. Sintchak, Winchester, MA (US); Francois Soucy, Stoneham, MA (US); Stephen G. Stroud, Medford, MA (US); Tricia J. Vos, Boston, MA (US); Tzu-Tshin Wong, Acton, MA (US); He Xu, Needham, MA (US); Tianlin Xu, Shrewsbury, MA (US); Yingchun Ye, Belmont, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/665,506

(22) Filed: Aug. 1, 2017

(65) Prior Publication Data

US 2018/0118762 A1    May 3, 2018

Related U.S. Application Data

(63) Continuation of application No. 15/347,334, filed on Nov. 9, 2016, now Pat. No. 9,751,854, which is a (Continued)

(51) Int. Cl.
    *C07D 513/04* (2006.01)
    *C07D 401/04* (2006.01)
    (Continued)

(52) U.S. Cl.
    CPC .......... *C07D 513/04* (2013.01); *A61K 31/437* (2013.01); *A61K 31/444* (2013.01); *A61K 31/497* (2013.01); *A61K 31/506* (2013.01); *A61K 31/549* (2013.01); *A61K 45/06* (2013.01); *C07D 401/04* (2013.01); (Continued)

(58) Field of Classification Search
    CPC .. C07D 513/04; C07D 213/22; C07D 401/04; C07D 401/14; C07D 417/14; C07D 471/04; A61K 31/437; A61K 31/44; A61K 31/444; A61K 31/506; A61K 31/549; A61K 45/06
    See application file for complete search history.

(56) References Cited

U.S. PATENT DOCUMENTS 7,601,716 B2    10/2009  Dorsey et al.
8,859,768 B2 *  10/2014  Cullis .................. A61K 31/422
                                                        544/298
(Continued)

FOREIGN PATENT DOCUMENTS

WO    WO 2004/041789 A1    5/2004
WO    WO 2004/070050 A2    8/2004
(Continued)

OTHER PUBLICATIONS

CAS Abstract 2011/026911 A1 (2011) (Year: 2011).*
(Continued)

*Primary Examiner* — Alexander R Pagano
(74) *Attorney, Agent, or Firm* — Sterne, Kessler, Goldstein & Fox P.L.L.C.

(57) ABSTRACT

The present invention provides a compound of formula I:

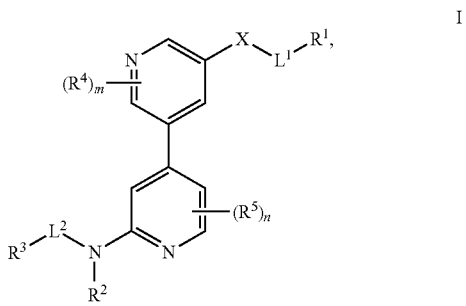

and pharmaceutically acceptable salts thereof, wherein X, $R^1$, $R^2$, $R^3$, $R^4$, $R^5$, $L^1$, $L^2$, m, and n, are as described in the specification. Such compounds are inhibitors of VPS34 and thus useful for treating proliferative, inflammatory, or cardiovascular disorders.

23 Claims, 8 Drawing Sheets

Related U.S. Application Data continuation of application No. 14/596,052, filed on Jan. 13, 2015, now Pat. No. 9,802,960.

(60) Provisional application No. 61/927,055, filed on Jan. 14, 2014, provisional application No. 62/054,742, filed on Sep. 24, 2014.

(51) Int. Cl.
| | |
|---|---|
| A61K 31/444 | (2006.01) |
| A61K 45/06 | (2006.01) |
| C07D 417/14 | (2006.01) |
| C07D 401/14 | (2006.01) |
| A61K 31/506 | (2006.01) |
| C07D 471/04 | (2006.01) |
| A61K 31/437 | (2006.01) |
| A61K 31/549 | (2006.01) |
| A61K 31/497 | (2006.01) |

(52) U.S. Cl.
CPC ......... C07D 401/14 (2013.01); C07D 417/14 (2013.01); C07D 471/04 (2013.01)

(56) References Cited

U.S. PATENT DOCUMENTS

| | | | | |
|---|---|---|---|---|
| 9,120,783 | B2* | 9/2015 | Ruf | C07D 213/81 |
| 9,242,969 | B2* | 1/2016 | Barsanti | C07D 403/12 |
| 9,586,948 | B2* | 3/2017 | Seganish | C07D 401/14 |
| 9,751,854 | B2* | 9/2017 | Bharathan | C07D 513/04 |
| 9,802,960 | B2* | 10/2017 | Bharathan | C07D 513/04 |
| 9,809,610 | B2* | 11/2017 | Burger | A61K 31/675 |
| 10,167,279 | B2* | 1/2019 | Aversa | C07D 405/14 |
| 10,202,373 | B2* | 2/2019 | Bharathan | A61K 31/506 |
| 2008/0194584 | A1* | 8/2008 | Birault | C07D 213/38 514/255.05 |
| 2008/0280891 | A1 | 11/2008 | Kelly et al. | |
| 2009/0163489 | A1 | 6/2009 | Booker et al. | |
| 2010/0099684 | A1 | 4/2010 | Cook, II et al. | |
| 2011/0015173 | A1 | 1/2011 | Florjancic et al. | |
| 2011/0130380 | A1 | 6/2011 | Barsanti et al. | |
| 2012/0028979 | A1 | 2/2012 | Basarab et al. | |
| 2012/0142732 | A1 | 6/2012 | Cullis et al. | |
| 2013/0004859 | A1 | 1/2013 | Yu et al. | |
| 2013/0102608 | A1 | 4/2013 | Hoelzemann et al. | |
| 2013/0165483 | A1 | 6/2013 | Chau et al. | |
| 2013/0324530 | A1* | 12/2013 | Antonios-McCrea | C07D 213/74 514/235.5 |
| 2015/0225422 | A1 | 8/2015 | Bharathan et al. | |
| 2015/0274708 | A1 | 10/2015 | Seganish et al. | |
| 2015/0322063 | A1 | 11/2015 | Furuyama et al. | |
| 2016/0333007 | A1 | 11/2016 | Bharathan et al. | |
| 2017/0073326 | A1 | 3/2017 | Bharathan et al. | |

FOREIGN PATENT DOCUMENTS

| | | |
|---|---|---|
| WO | WO 2006/051270 A1 | 5/2006 |
| WO | WO 2006/051311 A1 | 5/2006 |
| WO | WO 2006/065946 A1 | 6/2006 |
| WO | WO 2007/130468 A2 | 11/2007 |
| WO | WO 2007/135398 A1 | 11/2007 |
| WO | WO 2008/008059 A1 | 1/2008 |
| WO | WO 2008/025821 A1 | 3/2008 |
| WO | WO 2008/068470 A1 | 6/2008 |
| WO | WO 2008/079933 A2 | 7/2008 |
| WO | WO 2008/157191 A2 | 12/2008 |
| WO | WO 2009/013348 A2 | 1/2009 |
| WO | WO 2009/017822 A2 | 2/2009 |
| WO | WO 2009/039140 A1 | 3/2009 |
| WO | WO 2009/055418 A1 | 4/2009 |
| WO | WO 2009/087212 A2 | 7/2009 |
| WO | WO 2009/115517 A2 | 9/2009 |
| WO | WO 2009/147187 A1 | 12/2009 |
| WO | WO 2009/155121 A2 | 12/2009 |
| WO | WO 2010/007100 A1 | 1/2010 |
| WO | WO 2010/008847 A2 | 1/2010 |
| WO | WO 2010/017179 A1 | 2/2010 |
| WO | WO 2010/056574 A1 | 5/2010 |
| WO | WO 2010/057877 A1 | 5/2010 |
| WO | WO 2010/135524 A1 | 11/2010 |
| WO | WO 2011/026911 A1 | 3/2011 |
| WO | WO 2011/095196 A1 | 8/2011 |
| WO | WO 2012/009227 A1 | 1/2012 |
| WO | WO 2012/015723 A1 | 2/2012 |
| WO | WO 2012/021655 A2 | 2/2012 |
| WO | WO 2012/021696 A1 | 2/2012 |
| WO | WO 2012/037108 A1 | 3/2012 |
| WO | WO 2012/066065 A1 | 5/2012 |
| WO | WO 2012/066070 A1 | 5/2012 |
| WO | WO 2012/085244 A1 | 6/2012 |
| WO | WO 2012/085815 A1 | 6/2012 |
| WO | WO 2012/101062 A1 | 8/2012 |
| WO | WO 2012/101064 A1 | 8/2012 |
| WO | WO 2012/101066 A1 | 8/2012 |
| WO | WO 2012/168084 A1 | 12/2012 |
| WO | WO 2013/053983 A1 | 4/2013 |
| WO | WO 2013/126608 A1 | 8/2013 |
| WO | WO 2013/152063 A1 | 10/2013 |
| WO | WO 2013/190510 A2 | 12/2013 |
| WO | WO 2014/058691 A1 | 4/2014 |
| WO | WO-2014053533 A1 * | 4/2014 ............ A61K 38/06 |
| WO | WO 2014/083327 A1 | 6/2014 |
| WO | WO 2014/096388 A2 | 6/2014 |
| WO | WO 2014/151616 A1 | 9/2014 |
| WO | WO 2014/160017 A1 | 10/2014 |
| WO | WO 2015/108861 A1 | 7/2015 |
| WO | WO 2015/108881 A1 | 7/2015 |
| WO | WO-2016038581 A1 * | 3/2016 ............ A61K 31/675 |

OTHER PUBLICATIONS

Backer, J. M., "The redulation and function of Class III PI3Ks: novel roles for Vps34," *Journal of Biochemistry*, vol. 410(1): 1-17 (2008).

Bago, R., et al., "Characterization of VPS34-IN1, a selective inhibitor of Vps34, reveals that the phosphatidylinositol 3-phosphate-binding SGK3 protein kinase is a downstream target of class III phosphoinositide 3-kinase," *Biochem. J.*, vol. 463: 413-427 (2014).

Berenbaum, M. C., "The Expected Effect of a Combination of Agents: the General Solution," *Journal of Theoretical Biology*, vol. 114(3): 413-431 (1985).

Berge, S. M., et al., "Pharmaceutical Salts," *Journal of Pharmaceutical Sciences*, vol. 66(1): 1-19 (1977).

Bilanges, B., et al., "Cinderella finds her shoe: the first Vps34 inhibitor uncovers a new PI3K-AGC protein kinase connection," *Biochem. J.*, vol. 464: e7-e10 (2014).

Bliss, C.I., "The Toxicity of Poisons Applied Jointly," *Annals of Applied Biology*, vol. 26: 585-615 (1939).

Bruno, N. C., et al., "Design and Preparation of New Palladium Precatalysts for C—C and C—N Cross-Coupling Reactions," *Chem Sci.*, vol. 4: 916-920 (2013).

Bunz, F., "The Genetic Basis of Cancer," *Principles of Cancer Genetics*, pp. 1-47 (2008).

Cashman, J. D., et al., "Fucoidan Film Safely Inhibits Surgical Adhesions in a Rat Model," *Journal of Surgical Research*, vol. 171: 495-503 (2011).

Charrier, J. D., et al., "Discovery and Structure—Activity Relationship of 3-Aminopyrid-2-ones as Potent and Selective Interleukin-2 Inducible T-Cell Kinase (Itk) Inhibitors," *Journal of Medicinal Chemistry*, vol. 54: 2341-2350 (2011).

Chen, N., et al., "Autophagy and tumorigenesis," *FEBS Letters*, vol. 584:1427-1435, 1433 (2010).

Chou, T., et al., "Quantitative Analysis of Dose-Effect Relationships: The Combined Effects of Multiple Drugs or Enzyme Inhibitors," *Advances in Enzyme Regulation*, vol. 22: 27-55 (1984).

Delgado, M., et al., "Autophagy and Pattern Recognition Receptors in Innate Immunity," *Immunological Reviews*, vol. 227(1): 189-202 (2009).

(56) References Cited

OTHER PUBLICATIONS

Dowdle, W., et al., "Selective VPS34 inhibitor blocks autophagy and uncovers a role for NCOA4 in ferritin degradation and iron homeostasis in vivo," *Nature Cell Biology*, vol. 16(11): 1069-1079, and Methods and Supplementary Information (12 pages, 23 pages total) (2014).

Driver, M., et al., A Second-Generation Catalyst for Aryl Halide Amination: Mixed Secondary Amines from Aryl Halides and Primary Amines Catalyzed by (DPPF)PdCl$_2$ , *J. Am. Chem. Soc.*, vol. 118: 7217-7218 (1996).

Dzierba, C., et al., "Synthesis and structure-activity relationships of pyrido [3,2-b]pyrazin-3(4H)-ones and pteridin-7(8H)-ones as corticotropin-releasing factor-1 receptor antagonists," *Bioorganic & Medicinal Chemistry Letters*, vol. 22: 4986-4989 (2012).

Engelman, J., et al., "The evolution of phosphatidylinositol 3-kinases as regulators of growth and metabolism," *Nature Reviews Genetics*, vol. 7(8): 606-619 (2006).

Fabbro, D., et al., "Targeting Cancer with Small-Molecular Weight Kinase Inhibitors," *Kinase Inhibitors: Methods and Protocols, Methods in Molecular Biology*, vol. 795, Chapter 1, pp. 1-34, *Springer Science+Business. Media, LLC*, United States (2012).

Funderburk, S.F., et al., "The Beclin 1-VPS34 complex—at the crossroads of autophagy and beyond," *Trends in Cell Biology*, vol. 20(6): 355-362 (2010).

Furuya, T., et al., "Negative Regulation of Vps34 by Cdk Mediated Phosphorylation," *Molecular Cell*, vol. 38: 500-511 (2010).

Gaestel, M. and Kotlyarov, A., "Small-Molecule Protein and Lipid Kinase Inhibitors in Inflammation and Specific Models for Their Evaluation," Kinase Inhibitors: Methods and Protocols, Methods in Molecular Biology, vol. 795, Chapter 1, pp. 35-44 , *Springer Science+Business Media, LLC*, United States (2012).

Ghiassi-Nejad, Z., et al., "Advances in Anti-fibrotic Therapy," *Expert Rev of Gastroenterol & Hepatol*, vol. 2(6): 803-816 (2008).

Goh, L. K., et al., "Endocytosis of Receptor Tyrosine Kinases," *Cold Spring Harb Perspect Biol*, vol. 5: a017459, 18 pages (2013).

Honda, A., et al., "Potent, Selective, and Orally Bioavailable Inhibitors of VPS34 Provide Chemical Tools to Modulate Autophagy in Vivo," *ACS Med Chem Lett*, vol. 7(1): 72-76, American Chemical Society, United States (2015).

International Search Report for PCT/US2015/011191, 3 pages (dated Apr. 9, 2015).

International Search Report for PCT/US2015/011250, 3 pages (dated Apr. 6, 2015).

International Preliminary Report on Patentability for International Application No. PCT/US2015/011191, The International Bureau of WIPO, Geneva, Switzerland, dated Jul. 19, 2016, 8 pages.

International Preliminary Report on Patentability for International Application No. PCT/US2015/011250, The International Bureau of WIPO, Geneva, Switzerland, dated Jul. 19, 2016, 7 pages.

Jaber, N., et al., "Class III PI3K Vps34 plays an essential role in autophagy and in heart and liver function," *PNAS*, vol. 109(6): 2003-2008 (2012).

Jovic, M., et al., "The early endosome: a busy sorting station for proteins at the crossroads," *Histol. Histopathol*, vol. 25(1): 99-112 (2010).

Kim, J., et al., "A Signaling Network in Phenylephrine-Induced Benign Prostatic Hyperplasia," *Endocrinology*, vol. 150(8): 3576-3583 (2009).

Knegtel, R., et al., "A Role for Hydration in Interleukin-2 Inducible T Cell Kinase (Itk) Selectivity," *Molecular Informatics*, vol. 30: 950-959 (2011).

Knight, S. D., et al., "Discovery of GSK2126458, a Highly Potent Inhibitor of PI3K and the Mammalian Target of Rapamycin," *ACS Med. Chem. Lett.*, vol. 1: 39-43 (2010).

Kok, R. J., "Targets in Fibrotic Disorders," *Pharmaceutical Research*, vol. 25(10): 2413-2415 (2008).

Kondo, Y., et al., "The Role of Autophagy in Cancer Development and Response to Therapy," *Nature Reviews Cancer*, vol. 5(9): 726-34 (2005).

Kong, D., et al., "Phosphatidylinositol 3-kinase inhibitors: promising drug candidates for cancer therapy," *Cancer Science*, vol. 99(9): 1734-1740 (2008).

Kuppen, P. J. K., et al., "Tumor structure and extracellular matrix as a possible barrier for therapeutic approaches to using immune cells or adenoviruses in colorectal cancer," *Histochemistry and Cell Biology*, vol. 115: 67-72 (2001).

Lebegue, N., et al., "Novel Benzopyridothiadiazepines as Potential Active Antitumor Agents," *J. Med. Chem.*, vol. 48(23): 7363-7373 (2005).

Lim, A. K. H., "Diabetic nephropathy—complications and treatment," *International Journal of Nephrology and Renovascular Disease*, vol. 7: 361-381, Dove Medical Press Limited, England (2014).

Lissoni, P., et al., "Biotherapy with the pineal hormone melatonin plus aloe and myrrh tincture in untreatable metastatic cancer patients as an essence therapy of cancer," *Cancer Research*, vol. 7: 397-401 (2009).

Liu, J. et al., "Discovery of AMG 853, a CRTH2 and DP Dual Antagonist," *ACS Med. Chem. Lett.*, vol. 2: 326-330 (2011).

Luo, J., et al., "Principles of Cancer Therapy: Oncogene and Non-oncogene Addiction," *Cell*, vol. 136: 823-837 (2009).

Mellman, I., et al., "Endocytosis and Cancer," *Cold Spring Harb Perspect Biol*, vol. 5: a016949, 25 pages (2013).

Miller, S., et al., "Shaping development of autophagy inhibitors with the structure of the lipid kinase Vps34," *Science*, vol. 327(5973): 1638-1642 (2010).

Nandeesha, H., et al., "Hyperinsulinemia and dyslipidemia in non-diabetic benign prostatic hyperplasia," *Clinica Chimica Acta*, vol. 370: 89-93 (2006).

National Cancer Institute, "A to Z List of Cancers," cancer.gov, accessed at http://www.cancer.gov/cancertopics/types/alphalist, accessed on May 29, 2014, 22 pages.

O'Brien, C. J., "Current Management of Benign Parotid Tumors—The Role of Limited Superficial Parotidectomy," *Head and Neck*, 946-952 (2003).

Pandarus, V., et al., "Efficient Screening and Library Generation in Parallel C—C Coupling Reactions Mediated by Organosilica SiliaCat Palladium Catalysts," *Organic Process Research & Development*, vol. 16: 117-122 (2012).

Pasquier, B., et al., "Discovery of (2S)-8-[(3R)-3-Methylmorpholin-4-yl]-1-(3-methyl-2-oxobutyl)-2-(trifluoro-methyl)-3.,4-dihydro-2H-pyrimido [1,2-a]pyrimidin-6-one: A Novel Potent and Selective Inhibitor of Vps34 for the Treatment of Solid Tumors," *J. Med. Chem.*, vol. 58(1): 376-400 (2015).

Peterson, J. J., et al., "Nonlinear Blending: A Useful General Concept for the Assessment of Combination Drug Synergy," *Journal of Receptors and Signal Transduction Research*, vol. 27: 125-146 (2007).

PubChem Substance summary for CID 10468190, (2-methylpyrrolidin-1-yl)-(5-pyridin-4-ylpyridin-3-yl)methanone CAS Registry No. 613661-01-1; Record created Oct. 25, 2006.

PubChem Substance summary for CID 11566395, 4-chloro-N-(5-pyridin-4-ylpyridin-3-yl)benzesulfonamide, CAS Registry No. 837374-50-7; Record created Oct. 26, 2006.

PubChem Substance summary for CID 13066345, N-(1-methyl-5-pyridin-4-ylpyrazolo[3,4-b]pyridin-3-yl)formamide; Record created Feb. 8, 2007.

PubChem Substance summary for CID 46315357, 2-chloro-4-methyl-5-pyridin-4-ylpyridine; Record created Jul. 21, 2010.

PubChem Substance summary for CID 4636058, 2-[benzenesulfonyl-[(4-methylphenyl)methyl]amino]-N-phenylacetamide; Record created Jul. 21, 2010.

Ronan, B., et al., "A highly potent and selective Vps34 inhibitor alters vesicle trafficking and autophagy," *Nature Chemical Biology*, vol. 10: 1013-1019 (2014).

Rostislavleva, K., et al., "Structure and flexibility of the endosomal Vps34 complex reveals the basis of its function on membranes," *Science* , vol. 350(6257): aac7365, American Association for the Advancement of Science, United States, 13 pages (2015).

Shintani, T., et al., "Autophagy in Health and Disease: A Double-Edged Sword," *Science*, vol. 306(5698): 990-995 (2004).

(56) References Cited

OTHER PUBLICATIONS

Soussi, T., "p53 Antibodies in the Sera of Patients with Various Types of Cancer: A Review," *Cancer Research*, vol. 60: 1777-1788 (2000).

Stec, M. M., et al., "Structure-Activity Relationships of Phosphoinositide 3-Kinase (PI3K)/Mammalian Target of Rapamycin (mTOR) Dual Inhibitors: Investigations of Various 6,5-Heterocycles to Improve Metabolic Stability," *J. Med. Chem.*, vol. 54(14): 5174-84 (2011).

Sun, Y-M, et al., "Recent advances in understanding the biochemical and molecular mechanism of diabetic nephropathy," *Biochemical and Biophysical Research Communications*, vol. 433: 359-361 (2013).

Sunose, M. et al., "Discovery of 5-(2-amino-[1,2,4]triazolo [1,5-a]pyridin-7-yl)-N-(tert-butyl) pyridine-3-sulfonamide (CZC24758), as a potent, orally bioavailable and selective inhibitor of PI3K for the treatment of inflammatory disease," *Bioorganic & Medicinal Chemistry Letters*, vol. 22: 4613-4618 (2012).

Suzuki, A., "Recent advances in cross-coupling reactions of organoboron derivatives with organic electrophiles, 1995-1998," *Journal of Organometallic Chemistry*, vol. 576:147-168 (1999).

Tallarida, R. J., "An Overview of Drug Combination Analysis with Isobolograms," *Journal of Pharmacology and Experimental Therapeutics*, vol. 319(1): 1-7 (2006).

Thoresen, S. B., et al., "A phosphatidylinositol 3-kinase class III sub-complex containing VPS15, VPS34, Beclin 1, UVRAG and BIF-1 regulates cytokinesis and degradative endocytic traffic," *Experimental Cell Research*, vol. 316: 3368-3378 (2010).

Triola, G., "Chemical tools for modulating autophagy," *Tetrahedron*, vol. 71(3): 387-406 (2015).

Uchida, Y., et al., "Endosomal phosphatidylinositol 3-kinase is essential for canonical GPCR signaling," *Molecular Pharmacology*, vol. 91(5): 65-73, *The American Society for Pharmacology and Experimental Therapeutics*, United States (2017).

Written Opinion for PCT/US2015/011191, 7 pages (dated Apr. 9, 2015).

Written Opinion for PCT/US2015/011250, 15 pages, (dated Apr. 6, 2015).

Wurz, R. P., et al., "Synthesis and structure-activity relationships of dual PI3K/mTOR inhibitors based on a 4-amino-6-methyl-1,3,5-triazine sulfonamide scaffold," *Bioorganic & Medicinal Chemistry Letters*, vol. 22: 5714-5720 (2012).

Yamada, S., et al., "Alpha-1 Adrencoceptors in Human Prostate: Characteriationand Alteration in Benign Prostatic Hypertrophy," *The Journal of Pharmacology and Experimental Therapeutics*, vol. 242(1): 326-330 (1987).

Yamamoto, T., et al., "Expression of transforming growth factor β and experimental diabetic nephropathy," *Proc. Natl. Acad. Sci. USA*, vol. 90: 1814-1818 (1993).

Yan, Y., et al., "Regulation of class III (Vps34) PI3Ks," *Biochemical Society Transactions*, vol. 35(2): 239-241 (2007).

Yin, J., et al., "Pd-Catalyed N-Acylation of Heteroarylamines," *Organic Letters*, vol. 4(20): 3481-3484 (2002).

\* cited by examiner

HETEROARYLS AND USES THEREOF

CROSS-REFERENCE TO RELATED APPLICATIONS

This application is a continuation of U.S. application Ser. No. 15/347,334, filed Nov. 9, 2016, which is a continuation of U.S. application Ser. No. 14/596,052, filed Jan. 13, 2015, which claims benefit of U.S. Provisional Application No. 62/054,742, filed Sep. 24, 2014, and U.S. Provisional Application No. 61/927,055, filed Jan. 14, 2014, each of which is incorporated by reference in its entirety.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

Vacuolar Protein Sorting 34 (VPS34) is the sole Class III PI3K family member. VPS34 functions in the formation and trafficking of multiple intracellular vesicles, including vacuoles, endosomes, multivessicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionsky Science 2004; Kondo et al Nat Rev Cancer 2005: Delgato et al Immunol Rev 2009). Therefore, it would be beneficial to provide novel VPS34 inhibitors that possess good therapeutic properties, especially for the treatment of proliferative, inflammatory, or cardiovascular disorders.

DETAILED DESCRIPTION OF THE INVENTION

1. GENERAL DESCRIPTION OF CERTAIN EMBODIMENTS OF THE INVENTION

This invention provides compounds that are inhibitors of VPS34, and accordingly can be useful for the treatment of proliferative, inflammatory, or cardiovascular disorders.

In some embodiments, the present invention provides a compound of formula I:

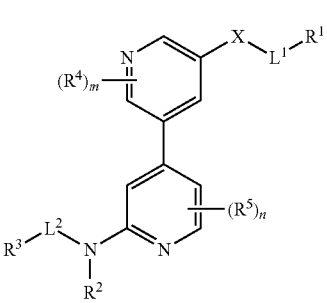

or a pharmaceutically acceptable salt thereof, wherein:

each of $R^1$ and $R^3$, independently, is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which being optionally substituted with 1-5 $R^6$ wherein:

each $R^6$ independently is —CN, halo or -$L^3$-$R^7$ wherein:
$L^3$ is a bond, $C_{1-4}$ alkylene, —O—, —N($R^x$)—, —S—, —S(O)—, —S(O)$_2$—, —C(O)—, —CO$_2$—, —C(O)NR$^x$—, —N($R^x$)C(O)—, —N($R^x$)CO$_2$—, —S(O)$_2$NR$^x$—, —N($R^x$)S(O)$_2$—, —OC(O)N($R^x$)—, —N($R^x$)C(O)N($R^x$), —N($R^x$)S(O)$_2$N($R^x$)— or —OC(O)—; where each $R^x$, independently, is hydrogen or $C_{1-4}$ alkyl, and $R^7$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;

X is a bond or $C_{1-4}$ aliphatic;

$L^1$ is —N($R^8$)C(O)—, —C(O)—N($R^9$)—, —N($R^{10}$)S(O)$_2$—, —S(O)$_2$NR$^{11}$—, —C(O)—, —C(S)—, —S(O)$_2$—, —N($R^{12}$)—, —O—C(O)—, —C(O)—O—, —O—S(O)$_2$—, —S(O)$_2$—O—, —N($R^{13}$)C(O)N($R^{14}$)—, or —N($R^{15}$)S(O)$_2$N($R^{16}$)—; and wherein each of $R^8$, $R^9$, $R^{10}$, $R^{11}$, $R^{12}$, $R^{13}$, $R^{14}$, $R^{15}$, and $R^{16}$, independently, is hydrogen or $C_{1-4}$ alkyl, and X or $L^1$ can optionally join with $R^1$ to form an optionally substituted 5-6-membered heterocyclyl or optionally substituted 5-6-membered heteroaryl;

$R^2$ is hydrogen or $C_{1-4}$ alkyl;

$L^2$ is a bond, —C(O)—, —S(O)$_2$—, —C(O)—O—, —C(O)N($R^y$)—, or —S(O)$_2$N($R^y$)—; wherein each $R^y$, independently, is hydrogen or $C_{1-4}$ alkyl;

each occurrence of $R^4$ and $R^5$, independently, is —CN, halo or -$L^4$-$R^{17}$ wherein $L^4$ is $C_{1-4}$ alkylene, —O—, —N($R^z$)—, —S—, —S(O)—, —S(O)$_2$—, —C(O)—, —CO$_2$—, —C(O)N($R^z$)—, —N($R^x$)C(O)—, —N($R^z$)C(O)O—, —S(O)$_2$N($R^z$)—, —N($R^z$)S(O)$_2$—, —OC(O)N($R^z$)—, —N($R^z$)C(O)N($R^z$)—, —N($R^z$)S(O)$_2$N($R^z$)— or —OC(O)—; where each $R^z$, independently, is hydrogen or $C_{1-4}$ alkyl, and
$R^{17}$ is hydrogen or $C_{1-6}$ aliphatic; and
each of m and n, independently, is 0-3;
provided that (1) if one $R^4$ is substituted at the ring carbon between the ring nitrogen and the ring carbon to which —X-$L^1$-$R^1$ is substituted, X or $L^1$ can join with said $R^4$ to form an optionally substituted 5-7-membered heterocyclyl or an optionally substituted 5-6-membered heteroaryl; or (2) if one $R^4$ is substituted at either ring carbon adjacent to the ring nitrogen, said $R^4$ can join with the ring nitrogen to form an optionally substituted 5-7-membered heterocyclyl or an optionally substituted 5-6-membered heteroaryl; or (3) if $L^2$ is a bond and $R^3$ is phenyl, naphthyl, or heteroaryl, $R^2$ can join with a substituent of $R^3$ to form an optionally substituted 5-7-membered heterocyclyl or an optionally substituted 5-6-membered heteroaryl. Note that provisos (1), (2), and (3) are not exclusive of each other.

For clarity, it is understood that the connectivity of the -$L^1$-moiety should be read from left to right. That is, the first listed atom in the exemplary $L^1$ groups (from left) described herein is covalently bonded to —X— moiety. Accordingly, exemplary —X-$L^1$-$R^1$ moieties described herein include —X—N($R^8$)C(O)—$R^1$, —X—C(O)—N($R^9$)—$R^1$, —X—N($R^{10}$)S(O)$_2$—$R^1$, —X—S(O)$_2$N$R^{11}$—$R^1$, —X—C(O)—$R^1$, —X—S(O)$_2$—$R^1$, —X—N($R^{12}$)—$R^1$, —X—O—C(O)—$R^1$, —X—O—S(O)$_2$—$R^1$, —X—S(O)$_2$—O—$R^1$, —X—N($R^{13}$)C(O)N($R^{14}$)—$R^1$, and —X—N($R^{15}$)S(O)$_2$N($R^{16}$)—$R^1$. Similarly, the connectivity of the -$L^2$-moiety should be read from right to left. That is, the first listed atom in the exemplary $L^2$ groups (from left) described herein is covalently bonded to the —NR$^2$— moiety. Accordingly, exemplary —NR$^2$-$L^2$-$R^3$ moieties described herein include —NR$^2$R$^3$, —NR$^2$—C(O)—$R^3$, —NR$^2$—S(O)$_2$-$R^3$, —NR$^2$—C(O)—O—$R^3$, —NR$^2$—C(O)N($R^y$)—$R^3$, and —NR$^2$—S(O)$_2$N($R^y$)—$R^3$. Other bivalent L groups should be read in similar manner.

2. COMPOUNDS AND DEFINITIONS

Compounds of this invention include those described generally for formula I, above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-2}$ hydrocarbon which is completely saturated or which contains one or more units of unsaturation. For example, suitable aliphatic groups include optionally substituted linear or branched alkyl, alkenyl, and alkynyl groups. Unless otherwise specified, in various embodiments, aliphatic groups have 1-12, 1-10, 1-8, 1-6, 1-4, 1-3, or 1-2 carbon atoms. It is apparent to a skilled person in the art that in some embodiments, the "aliphatic" group described herein can be bivalent.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The term "halogen" or "halo" means F, Cl, Br, or I.

The term "heteroatom" refers to one or more of oxygen, sulfur, nitrogen, phosphorus, and silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. For example, the aryl group is a $C_{6-10}$ aryl group (i.e., phenyl and naphthyl). Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. For example, the aralkyl group is $C_{6-10}$ aryl$C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, for example, mono-, bi-, or tricyclic (e.g., mono- or bicyclic). The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., $—(CH_2)_n—$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted or replaced by the functional group. Examples of suitable "interrupting functional groups" are described in the specification and claims herein.

For purposes of clarity, and unless otherwise stated, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaryl-alkoxy and the like) group may contain one or more substituents and thus may be "optionally substituted". In addition to the substituents defined above and herein, suitable substituents on the unsaturated carbon atom of an aryl group (e.g., phenyl or naphthyl) or heteroaryl group (e.g., pyridyl) also include and are generally selected from -halo, —NO$_2$, —CN, —R$^+$, —C(R$^+$)═C(R$^+$)$_2$, —C≡C—R$^+$, —OR$^1$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(═NR$^+$)—N(R$^+$)$_2$, —N(R$^+$)C(═NR)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^1$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(═NR$^+$)—N(R$^+$)$_2$, —N(R$^+$)C(═NR$^+$)—N(R$^+$)—C(O)R$^+$, —C(═NR$^+$)—N(R$^+$)$_2$, —C(═NR$^+$)—OR$^+$, —N(R$^+$)—N(R$^+$)$_2$, —C(═NR$^+$)—N(R$^+$)—OR$^+$, —C(R$^o$)═N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: ═O, ═S, ═C(R*)$_2$, ═N—N(R*)$_2$, ═N—OR*, ═N—NHC(O)R*, ═N—NHCO$_2$R$^o$═N—NHSO$_2$R$^o$ or ═N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(═NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

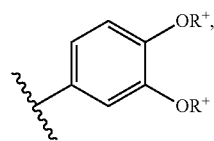

these two occurrences of R$^+$ are taken together with the oxygen atoms to which they are bound to form a fused 6-membered oxygen containing ring:

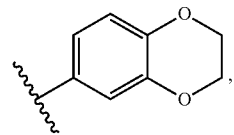 [SMILES: *c1ccc2c(c1)OCCO2]

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diastereomeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. BRIEF DESCRIPTION OF THE DRAWINGS

4. DESCRIPTION OF EXEMPLARY COMPOUNDS

Figure 1:
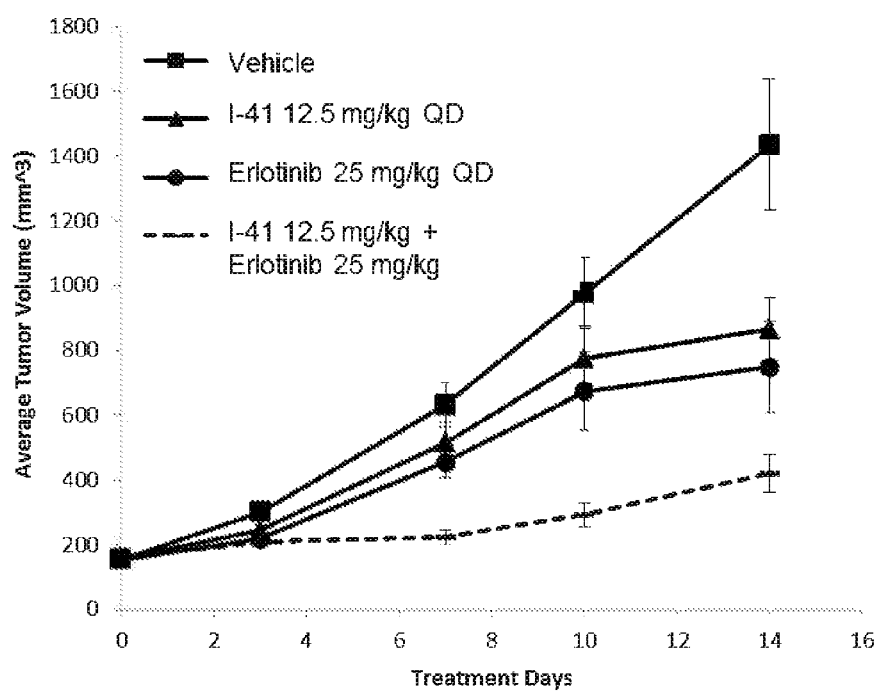
FIG. 1 is a graph showing the effect of treatment with a compound of formula I (I-41) and erlotinib when administered orally (po) daily (qd) as single agents and in combination to nude female mice bearing human colorectal adenocarcinoma SW48 tumor xenografts.

As described generally above, in some embodiments the present invention provides a compound of formula I:

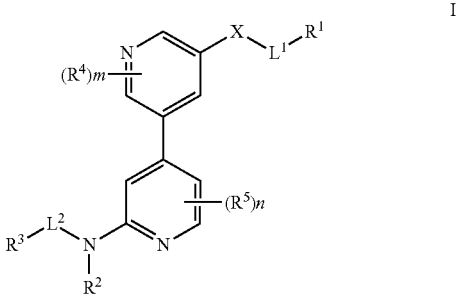

or a pharmaceutically acceptable salt thereof, wherein:

each of $R^1$ and $R^3$, independently, is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which being optionally substituted with 1-5 $R^6$ wherein:

each $R^6$ independently is —CN, halo or -$L^3$-$R^7$ wherein:
  $L^3$ is a bond, $C_{1-4}$ alkylene, —O—, —N($R^x$)—, —S—, —S(O)—, —S(O)$_2$—, —C(O)—, —CO$_2$—, —C(O)N$R^x$—, —N($R^x$)C(O)—, —N($R^x$)CO$_2$—, —S(O)$_2$N$R^x$—, —N($R^x$)S(O)$_2$—, —OC(O)N($R^x$)—, —N($R^x$)C(O)N($R^x$), —N($R^x$)S(O)$_2$N($R^x$)— or —OC(O)—; where each $R^x$, independently, is hydrogen or $C_{1-4}$ alkyl, and
  $R^7$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;

X is a bond or $C_{1-4}$ aliphatic;

$L^1$ is —N($R^8$)C(O)—, —C(O)—N($R^9$)—, —N($R^{10}$)S(O)$_2$—, —S(O)$_2$N$R^{11}$—, —C(O)—, —C(S)—, —S(O)$_2$—, —N($R^{12}$)—, —O—C(O)—, —C(O)—O—, —O—S(O)$_2$—, —S(O)$_2$—O—, —N($R^{13}$)C(O)N($R^{14}$)—, or —N($R^{15}$)S(O)$_2$N($R^{16}$)—; and wherein each of $R^8$, $R^9$, $R^{10}$, $R^{11}$, $R^{12}$, $R^{13}$, $R^{14}$, $R^{15}$, and $R^{16}$, independently, is hydrogen or $C_{1-4}$ alkyl; and X or $L^1$ can optionally join with $R^1$ to form an optionally substituted 5-6-membered heterocyclyl or optionally substituted 5-6-membered heteroaryl;

$R^2$ is hydrogen or $C_{1-4}$ alkyl;

$L^2$ is a bond, —C(O)—, —S(O)$_2$—, —C(O)—O—, —C(O)N($R^y$)—, or —S(O)$_2$N($R^y$)—; wherein each $R^y$, independently, is hydrogen or $C_{1-4}$ alkyl;

each occurrence of $R^4$ and $R^5$, independently, is —CN, halo or -$L^4$-$R^{17}$ wherein $L^4$ is $C_{1-4}$ alkylene, —O—, —N($R^z$)—, —S—, —S(O)—, —S(O)$_2$—, —C(O)—, —CO$_2$—, —C(O)N($R^z$)—, —N($R^z$)C(O)—, —N($R^z$)C(O)O—, —S(O)$_2$N($R^z$)—, —N($R^z$)S(O)$_2$—, —OC(O)N($R^z$)—, —N($R^z$)C(O)N($R^z$)—, —N($R^z$)S(O)$_2$N($R^z$)— or —OC(O)—; where each $R^z$, independently, is hydrogen or $C_{1-4}$ alkyl, and $R^{17}$ is hydrogen or $C_{1-6}$ aliphatic: and each of m and n, independently, is 0-3;

provided that (1) if one $R^4$ is substituted at the ring carbon between the ring nitrogen and the ring carbon to which —X-$L^1$-$R^1$ is substituted, X or $L^1$ can join with said $R^4$ to form an optionally substituted 5-7-membered heterocyclyl or an optionally substituted 5-6-membered heteroaryl; or (2) if one $R^4$ is substituted at either ring carbon adjacent to the ring nitrogen, said $R^4$ can join with the ring nitrogen to form an optionally substituted 5-7-membered heterocyclyl or an optionally substituted 5-6-membered heteroaryl: or (3) if $L^2$ is a bond and $R^3$ is phenyl, naphthyl, or heteroaryl, $R^2$ can join with a substituent of $R^3$ to form an optionally substituted 5-7-membered heterocyclyl or an optionally substituted 5-6-membered heteroaryl. Note that provisos (1), (2), and (3) are not exclusive of each other.

In some embodiments, the invention provides a compound of formula I:

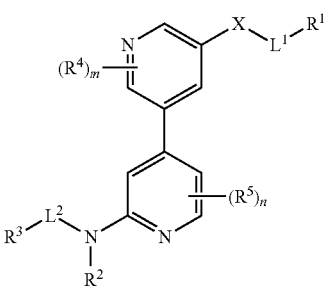

I or a pharmaceutically acceptable salt thereof, wherein:

each of $R^1$ and $R^3$, independently, is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which being optionally substituted with 1-5 $R^6$ wherein:

each $R^6$ independently is —CN, halo or -$L^3$-$R^7$ wherein:
$L^3$ is a bond, $C_{1-4}$ alkylene, —O—, —N($R^x$)—, —S—, —S(O)—, —S(O)$_2$—, —C(O)—, —CO$_2$—, —C(O)N$R^x$—, —N($R^x$)C(O)—, —N($R^x$)CO$_2$—, —S(O)$_2$N$R^x$—, —N($R^x$)S(O)$_2$—, —OC(O)N($R^x$)—, —N($R^x$)C(O)N($R^x$), —N($R^x$)S(O)$_2$N($R^x$)— or —OC(O)—; where each $R^x$, independently, is hydrogen or $C_{1-4}$ alkyl, and $R^7$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;

X is a bond or $C_{1-4}$ aliphatic;

L is —N($R^8$)C(O)—, —C(O)—N($R^9$)—, —N($R^{10}$)S(O)$_2$—, —S(O)$_2$N$R^{11}$—, —C(O)—, —S(O)$_2$—, —N($R^{12}$)—, —O—C(O)—, —C(O)—O—, —O—S(O)$_2$—, —S(O)$_2$—O—, —N($R^{13}$)C(O)N($R^{14}$)—, or —N($R^{15}$)S(O)$_2$N($R^{16}$)—; and wherein each of $R^8$, $R^9$, $R^{10}$, $R^{11}$, $R^{12}$, $R^{13}$, $R^{14}$, $R^{15}$, and $R^{16}$, independently, is hydrogen or $C_{1-4}$ alkyl; and X or $L^1$ can optionally join with $R^1$ to form an optionally substituted 5-6-membered heterocyclyl or optionally substituted 5-6-membered heteroaryl;

$R^2$ is hydrogen or $C_{1-4}$ alkyl;

$L^2$ is a bond, —C(O)—, —S(O)$_2$—, —C(O)—O—, —C(O)N($R^y$)—, or —S(O)$_2$N($R^y$)—; wherein each $R^y$, independently, is hydrogen or $C_{1-4}$ alkyl;

each occurrence of $R^4$ and $R^5$, independently, is —CN, halo or -$L^4$-$R^{17}$ wherein $L^4$ is $C_{1-4}$ alkylene, —O—, —N($R^z$)—, —S—, —S(O)—, —S(O)$_2$—, —C(O)—, —CO$_2$—, —C(O)N($R^z$)—, —N($R^z$)C(O)—, —N($R^z$)C(O)O—, —S(O)$_2$N($R^z$)—, —N($R^z$)S(O)$_2$—, —OC(O)N($R^z$)—, —N($R^z$)C(O)N($R^z$)—, —N($R^z$)S(O)$_2$N($R^z$)— or —OC(O)—; where each $R^z$, independently, is hydrogen or $C_{1-4}$ alkyl, and $R^{17}$ is hydrogen or $C_{1-6}$ aliphatic; and each of m and n, independently, is 0-3; and
provided that if one $R^4$ is substituted at the ring carbon between the ring nitrogen and the ring carbon to which —X-$L^1$-$R^1$ is substituted, X or $L^1$ can join with said $R^4$ to form an optionally substituted 5-7-membered heterocyclyl or an optionally substituted 5-6-membered heteroaryl.

In some embodiments, $R^1$ is H. In other embodiments, $R^1$ is $C_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which is optionally substituted with 1-5 $R^6$.

In other embodiments, $R^1$ is $C_{1-3}$ alkyl. In still other embodiments, $R^3$ is $C_{1-6}$ aliphatic, 3-6-membered cycloaliphatic, phenyl, naphthyl, 3-6-membered heterocyclyl having 1-4 heteroatoms independently selected from nitrogen, oxygen or sulfur, or 5-6-membered heteroaryl having 1-4 heteroatoms independently selected from nitrogen, oxygen or sulfur.

In some embodiments, X or $L^1$ optionally joins with $R^1$ to form an optionally substituted 5-6-membered heterocyclyl or an optionally substituted 5-6-membered heteroaryl. In other embodiments, X joins with $R^1$ to form an optionally substituted 5-6-membered heterocyclyl. In other embodiments, $L^1$ joins with $R^1$ to form an optionally substituted 5-6-membered heterocyclyl. In some embodiments, $R^1$ and $R^{10}$ join together to form an optionally substituted 5-6-membered heterocyclyl. In other embodiments, X joins with $R^1$ to form an optionally substituted 5-6-membered heteroaryl. In other embodiments, $L^1$ joins with $R^1$ to form an optionally substituted 5-6-membered heteroaryl. In some embodiments, $R^1$ and $R^{11}$ join together to form an optionally substituted 5-6-membered heteroaryl. In each case mentioned above, said heterocyclyl and heteroaryl are as defined above (e.g., each can be optionally substituted as described above and e.g., each heteroaryl can contain heteroatom nitrogen, oxygen, or sulfur, including oxidized form of nitrogen or sulfur). In other embodiments, said 5-6-membered heterocyclyl or 5-6-membered heteroaryl is unsubstituted. In still other embodiments, said 5-6-membered heterocyclyl or 5-6-membered heteroaryl is substituted (e.g., comprises 1, 2, 3, 4, or 5 substituent groups such as those described for R⁶ herein); in some embodiments, said substituents are independently -halo, —CN, —C$_{1-6}$ aliphatic, —OH, and —O—(C$_{1-6}$ aliphatic). In certain embodiments, two substituent groups of said 5-6-membered heterocyclyl or 5-6-membered heteroaryl combine to form an optionally substituted phenyl group or an optionally substituted 5-6-membered heteroaryl group.

In some embodiments, R¹ is C$_{1-4}$ alkyl, 3-6-membered cycloaliphatic, phenyl, naphthyl, 3-6-membered heterocyclyl having 1-3 heteroatoms independently selected from nitrogen, oxygen or sulfur, or 5-6-membered heteroaryl having 1-3 heteroatoms independently selected from nitrogen, oxygen or sulfur.

In some embodiments, R¹ is a C$_{1-6}$ aliphatic. In other embodiments, R¹ is a C$_{1-6}$ alkyl. In certain embodiments, R¹ is methyl, ethyl, n-propyl, isopropyl, n-butyl, iso-butyl, tert-butyl, n-pentyl, isopentyl, or n-hexyl.

In other embodiments, R¹ is methyl, cyclohexyl, pyridyl, phenyl, or naphthyl.

In some embodiments, R¹ is a C$_{1-6}$ aliphatic comprising a substituent that is =NH and/or a substituent that is —NH$_2$. In some embodiments, R¹ is methyl substituted with =NH and —NH$_2$.

In other embodiments, R¹ is

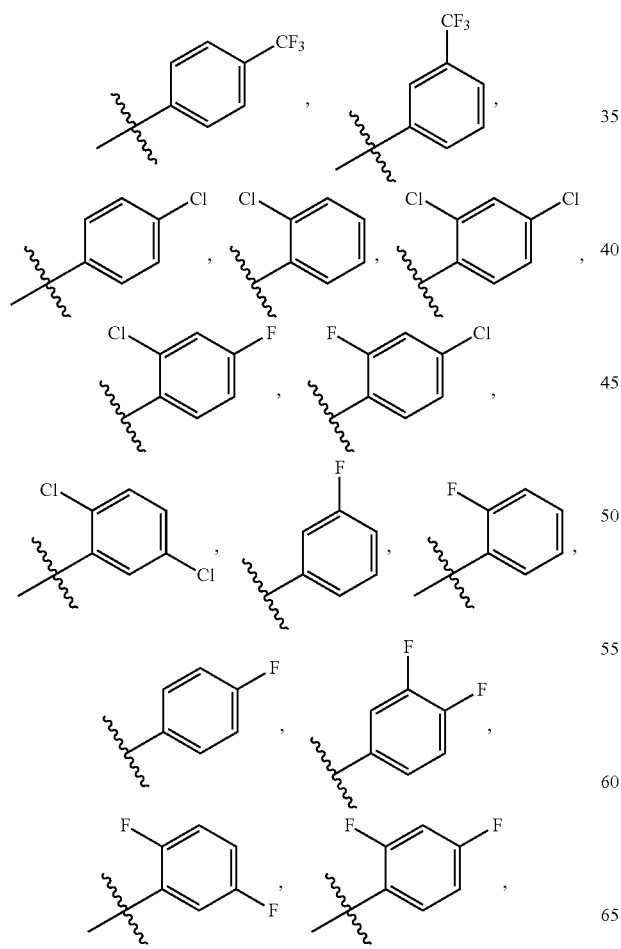

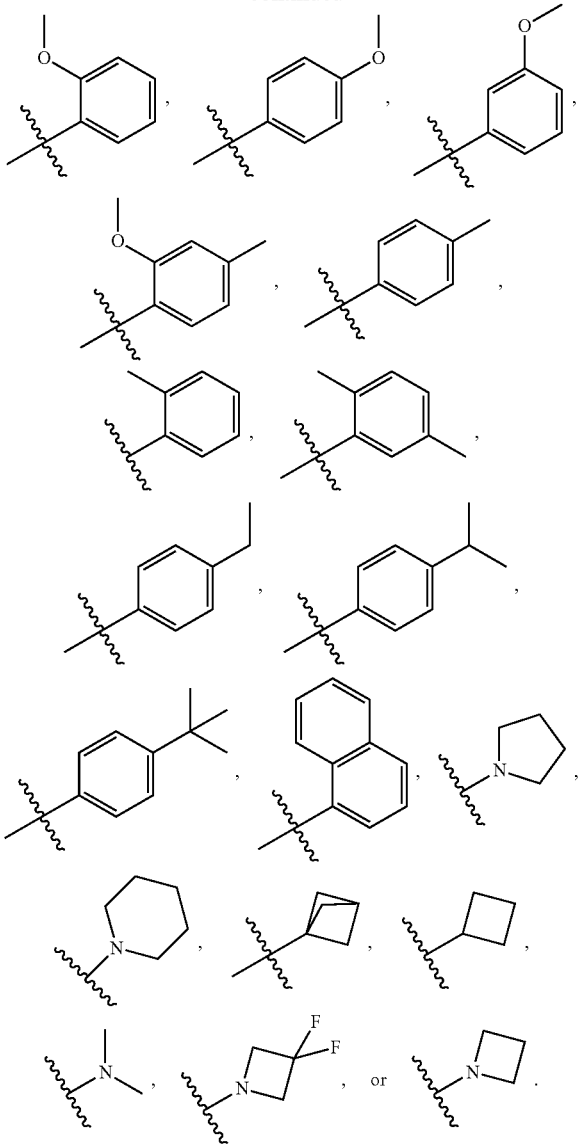

In other embodiments, R¹ is

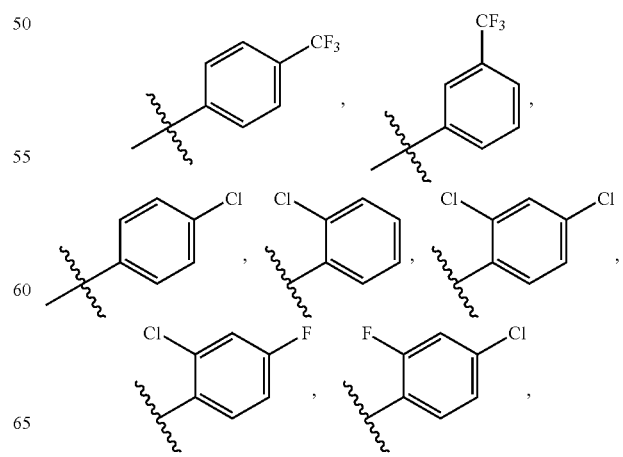

-continued

In other embodiments, R¹ is

-continued

In some embodiments, R¹ is a 3-, 4-, 5-, or 6-membered cycloaliphatic. In other embodiments, R¹ is a 5-to-10-membered bridged cycloaliphatic. In other embodiments, R¹ is a 3-, 4-, 5-, or 6-membered heterocyclyl having 1-4, 1-3, or 1-2 heteroatoms independently selected form nitrogen, oxygen, or sulfur. In other embodiments, R¹ is a 5-6-membered heteroaryl. In other embodiments, R¹ is phenyl. In other embodiments, R¹ is naphthyl.

In certain embodiments, R¹ is unsubstituted. In other embodiments, R¹ is substituted with 1, 2, 3, 4, or 5 R⁶ as described herein. In some embodiments, R¹ is optionally substituted with 1-3 R⁶ wherein each R⁶ independently is halo or -L³-R⁷. In some embodiments, L³ is a bond, $C_{1-3}$ alkylene. —O—, or —N(Rˣ)—. In other embodiments, R⁷ is hydrogen, 3-6-membered cycloaliphatic, phenyl, 3-6-membered heterocyclyl having 1-3 heteroatoms independently selected from nitrogen, oxygen or sulfur, or 5-6-membered heteroaryl having 1-3 heteroatoms independently selected from nitrogen, oxygen or sulfur. In other embodiments, R¹ is optionally substituted with 1-3 R⁶, wherein each R⁶ independently is fluoro, chloro, $C_{1-4}$ aliphatic, trifluoromethy, hydroxyl or —O—$C_{1-4}$ aliphatic.

In other embodiments, R¹ is optionally substituted cyclopropyl, methyl, ethyl, isopropyl, —(CH₂)₂OCH₂CH₃, optionally substituted phenyl (e.g., 2,4-difluorophenyl, 2,4-dichlorophenyl, 4-ethylphenyl, 2-methoxy-4-fluorophenyl, 3,4-difluorophenyl, 2,3-difluorophenyl, 2-trifluoromethylphenyl, 3-tert-butylphenyl, 2-methoxyphenyl, 3-methoxyphenyl, 2-fluoro-4-methylphenyl, 4-trifluoromethylphenyl, 3-trifluoromethylphenyl, 2,4-dimethylphenyl, 2,5-dimethylphenyl, 2,5-dichlorophenyl, 2-methoxy-4-methylphenyl, 2-chloro-4-methylphenyl, 2-fluoro-4-methylphenyl, 2-fluoro-4-trifluoromethylphenyl, 2,6-difluorophenyl, 4-chlorophenyl, 3-fluorophenyl, 2,5-difluoro-4-methoxyphenyl, or 4-(optionally substituted pyridyl)-phenyl), optionally substituted naphthyl, 3-fluorophenyl, optionally substituted pyrrolidyl, optionally substituted γ-sultam, optionally substituted piperidyl, optionally substituted piperizinyl, optionally substituted tetrahydrofuryl, optionally substituted morpholino, optionally substituted pyrrazolyl, optionally substituted imidazolyl, optionally substituted thienyl, optionally substituted oxazolyl, optionally substituted pyridyl, optionally substituted pyridazinyl, bicyclo[1.1.1]pentyl, —CH₂-(optionally substituted phenyl), —CH₂CH₂-(optionally substituted phenyl), —CH₂-(optionally substituted naphthyl), —CH₂-(optionally substituted pyridyl), optionally substituted bipyridyl, or —CH₂-(optionally substituted cyclopropyl). In some embodiments, $R^1$ is selected from those depicted in Table 1, below.

In some embodiments, $R^3$ is H. In other embodiments, $R^3$ is $C_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which is optionally substituted with 1-5 $R^6$. In other embodiments, $R^3$ is $C_{1-3}$ alkyl. In still other embodiments, $R^3$ is $C_{1-6}$ aliphatic, 3-6-membered cycloaliphatic, phenyl, naphthyl, 3-6-membered heterocyclyl having 1-4 heteroatoms independently selected from nitrogen, oxygen or sulfur, or 5-6-membered heteroaryl having 1-4 heteroatoms independently selected from nitrogen, oxygen or sulfur.

In some embodiments, $R^3$ is $C_{1-3}$ aliphatic, $C_{3-6}$ cycloaliphatic, or 5-10-membered heteroaryl having 1-4 heteroatoms independently selected from nitrogen, oxygen or sulfur, said cycloaliphatic or heteroaryl being optionally substituted with 1-5 $R^6$.

In other embodiments, $R^3$ is methyl, cyclopropyl, or 6-membered heteroaryl that is optionally substituted with 1-2 $R^6$.

In further embodiments, $R^3$ is 4-pyrimidinyl comprising optional substituents independently selected from methyl, methoxy, cyano, trifluoromethyl, and cyclopropyl (e.g., comprising 1, 2, or 3 optionally substituents independently selected from methyl, methoxy, cyano, trifluoromethyl, and cyclopropyl).

In some embodiments, $R^3$ is $C_{1-3}$ aliphatic. In other embodiments, $R^3$ is $C_{1-3}$ alkyl (e.g., methyl, ethyl, n-propyl, or iso-propyl). In other embodiments, $R^3$ is methyl.

In other embodiments, $R^3$ is $C_{3-6}$ cycloaliphatic (e.g., cyclopropyl).

In other embodiments, $R^3$ is 5-10-membered heteroaryl (e.g., 6-membered heteroaryl) having 1-4 heteroatoms independently selected from nitrogen, oxygen or sulfur. In other embodiments, $R^3$ is pyridinyl, pyrimidinyl, pyrazolyl, imidazolyl, benzoxazolyl, benzthiazolyl, 1,8-naphthyridinyl, quinolinyl, or isoquinolinyl. In other embodiments, $R^3$ is pyridyl or pyrimidinyl.

In some embodiments, $R^3$ is pyridinyl, pyrimidinyl, pyrazoly, imidazolyl, benzoxazolyl, benzthiazolyl, 1,8-naphthyridinyl, quinolinyl, or isoquinolinyl; each of which being optionally substituted with $C_{1-6}$ aliphatic, $C_{1-6}$ alkoxy, or cyano.

In certain embodiments, $R^3$ is unsubstituted. In other embodiments, $R^3$ is substituted with 1, 2, 3, 4, or 5 (e.g., 1 or 2) $R^6$ as described herein. For example, $R^6$ is $C_{1-6}$ aliphatic (e.g., methyl or trifluoromethyl), $C_{1-6}$ alkoxy (e.g., methoxy), cyano, or cyclopropyl.

In certain embodiments, $R^3$ is

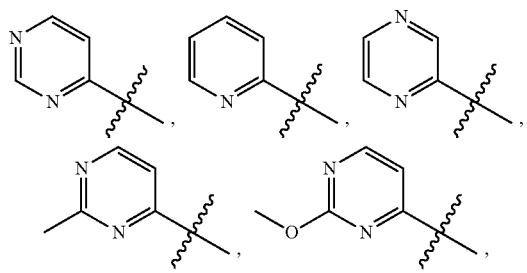

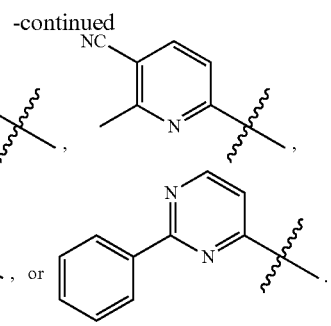

In some embodiments, $R^3$ is selected from those depicted in Table 1, below.

In some embodiments, each $R^6$ independently is halo or -$L^3$-$R^7$.

In some embodiments, $L^3$ is a bond. In other embodiments, $L^3$ is $C_{1-4}$ alkylene, —O—, —N($R^x$)—, —S—, —S(O)—, —S(O)$_2$—, —C(O)—, —CO$_2$—, —C(O)N$R^x$—, —N($R^x$)C(O)—, —N($R^x$)CO$_2$—, —S(O)$_2$N$R^x$—, —N($R^x$)S(O)$_2$—, —OC(O)N($R^x$)—, —N($R^x$)C(O)N($R^x$), —N($R^x$)S(O)$_2$N($R^x$)— or —OC(O)—. In still other embodiments, $L^3$ is a bond, $C_{1-3}$ alkylene, —O—, or —N($R^x$)—.

In some embodiments, $R^x$ is hydrogen. In other embodiments, $R^x$ is unsubstituted $C_{1-4}$ alkyl. In other embodiments, $R^x$ is substituted $C_{1-4}$ alkyl. In some embodiments, the substituent groups are selected from the exemplary substituent groups described herein for aliphatic groups; optionally, said substituted $C_{1-4}$ alkyl has 1, 2, 3, 4, or 5 substituents. In some embodiments, said alkyl includes a substituent selected from: a 3-, 4-, 5-, or 6-membered cycloaliphatic; 3-, 4-, 5-, or 6-membered heterocyclyl, —OH, —O—($C_{1-6}$ aliphatic), optionally substituted amino, and -halo.

In other embodiments, $R^7$ is hydrogen. In other embodiments, $R^7$ is $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur. In still other embodiments, $R^7$ is hydrogen, 3-6-membered cycloaliphatic, phenyl, 3-6-membered heterocyclyl having 1-3 heteroatoms independently selected from nitrogen, oxygen or sulfur, or 5-6-membered heteroaryl having 1-3 heteroatoms independently selected from nitrogen, oxygen or sulfur. In some embodiments, $R^7$ is unsubstituted. In some embodiments, the substituent groups are selected from the exemplary substituent groups described herein for aliphatic, cycloaliphatic, heterocyclyl, heteroaryl, and aryl moieties. For clarity, optional substituents for aryl also apply to phenyl and naphthyl. Optionally, said $R^7$ has 1, 2, 3, 4, or 5 substituents. In some embodiments, the substituent groups are selected from $C_{1-6}$ alkyl, —OH, optionally substituted amino, halo, and —O—($C_{1-6}$ aliphatic).

In some embodiments, each $R^6$ independently is halo or -$L^3$-$R^7$ wherein $L^3$ is a bond, $C_{1-3}$ alkylene, —O—, or —N($R^x$)— and $R^7$ is hydrogen, 3-6-membered cycloaliphatic, phenyl 3-6-membered heterocyclyl having 1-3 heteroatoms independently selected from nitrogen, oxygen or sulfur, or 5-6-membered heteroaryl having 1-3 heteroatoms independently selected from nitrogen, oxygen or sulfur.

In other embodiments, each $R^6$ independently is fluoro, chloro, $C_{1-4}$ aliphatic, trifluoromethyl, hydroxyl or —O—$C_{1-4}$ aliphatic. In some embodiments, $R^6$ is selected from those depicted in Table 1, below.

In some embodiments, X is a bond. In other embodiments, X is $C_{1-4}$ alkylene. In still other embodiments, X is methylene or ethylene. In some embodiments, X is selected from those depicted in Table 1, below.

In some embodiments, when one $R^4$ is substituted at the ring carbon between the ring nitrogen and the ring carbon to which —X-$L^1$-$R^1$ is substituted, X joins with said $R^4$ to form an optionally substituted 5-7-membered (e.g., 5-6-membered) heterocyclyl or an optionally substituted 5-6-membered heteroaryl. Said heterocyclyl and heteroaryl are as defined above (e.g., each can be optionally substituted as described above and e.g., each heteroaryl can contain heteroatom nitrogen, oxygen, or sulfur, including oxidized form of nitrogen or sulfur). In some embodiments, X joins with said $R^4$ to form an optionally substituted pyrazolyl, imidazolyl, pyrrolyl, triazolyl, oxazolyl, or thiazolyl. In other embodiments, X joins with said $R^4$ to form any of the embodiments in Table 1, below.

In other embodiments, X joins with $R^1$ to form an optionally substituted 5-6-membered heterocyclyl or 5-6-membered heteroaryl. In still other embodiments, X joins with $R^1$ to form an optionally substituted 5-6-membered heterocyclyl. In certain embodiments, X joins with $R^1$ to form an optionally substituted 5-6-membered heteroaryl. In each case mentioned above, said heterocyclyl and heteroaryl are as defined above (e.g., each can be optionally substituted as described above and e.g., each heteroaryl can contain heteroatom nitrogen, oxygen, or sulfur, including oxidized form of nitrogen or sulfur). In other embodiments, said 5-6-membered heterocyclyl or 5-6-membered heteroaryl is unsubstituted. In still other embodiments, said 5-6-membered heterocyclyl or 5-6-membered heteroaryl is substituted (e.g., comprises 1, 2, 3, 4, or 5 substituent groups such as those described for $R^6$ herein); in some embodiments, said substituents are independently -halo, —CN, —$C_{1-6}$ aliphatic, —OH, and —O—($C_{1-6}$ aliphatic). In certain embodiments, two substituent groups of said 5-6-membered heterocyclyl or 5-6-membered heteroaryl combine to form an optionally substituted phenyl group or an optionally substituted 5-6-membered heteroaryl group. In other embodiments, X joins with said $R^1$ to form any of the embodiments in Table 1, below.

In some embodiments, $L^1$ is —N($R^8$)C(O)—, —N($R^{10}$)S(O)$_2$—, —C(O)—, or —S(O)$_2$—. In some embodiments, $L^1$ is —N($R^8$)C(O)—, —N($R^{10}$)S(O)$_2$—, or —S(O)$_2$—. In some embodiments, $L^1$ is —N($R^{10}$)S(O)$_2$—. In some embodiments, $L^1$ is —C(O)—. In other embodiments, any of $R^8$, $R^9$, $R^{10}$, $R^{11}$, $R^{12}$, $R^{13}$, $R^{14}$, $R^{15}$, and $R^{16}$, independently, is hydrogen. In still other embodiments, any of $R^8$, $R^9$, $R^{10}$, $R^{11}$, $R^{12}$, $R^{13}$, $R^{14}$, $R^{15}$, and $R^{16}$, independently, is $C_{1-4}$ alkyl. In certain embodiments, each of $R^8$ and $R^{10}$, independently, is hydrogen, methyl or ethyl. In other embodiments, $R^{10}$ is hydrogen, methyl or ethyl. In other embodiments, any of $R^8$, $R^9$, $R^{10}$, $R^{11}$, $R^{12}$, $R^{13}$, $R^{14}$, $R^{15}$, and $R^{16}$, independently, is selected from those depicted in Table 1, below.

In further embodiments, $L^1$ is —N($R^{10}$)S(O)$_2$—, and $R^{10}$ is hydrogen, methyl or ethyl.

In certain embodiments, $L^1$ joins with $R^1$ to form an optionally substituted 5-6-membered heterocyclyl or optionally substituted 5-6-membered heteroaryl. In certain embodiments, $L^1$ joins with $R^1$ to form an optionally substituted 5-6-membered heterocyclyl. In certain embodiments, $L^1$ joins with $R^1$ to form an optionally substituted 5-6-membered heteroaryl. In some embodiments, $R^{10}$ and $R^1$ join together to form an optionally substituted 5-6-membered heterocyclyl. In some embodiments, $R^{11}$ and $R^1$ join together to form an optionally substituted 5-6-membered heteroaryl. In each case mentioned above, said heterocyclyl and heteroaryl are as defined above (e.g., each can be optionally substituted as described above and e.g., each heteroaryl can contain heteroatom nitrogen, oxygen, or sulfur, including oxidized form of nitrogen or sulfur). In other embodiments, said 5-6-membered heterocyclyl or 5-6-membered heteroaryl is unsubstituted. In still other embodiments, said 5-6-membered heterocyclyl or 5-6-membered heteroaryl is substituted (e.g., comprises 1, 2, 3, 4, or 5 substituent groups such as those described for $R^6$ herein): in some embodiments, said substituents are independently -halo, —CN, —$C_{1-6}$ aliphatic, —OH, and —O—($C_{1-6}$ aliphatic). In certain embodiments, two substituent groups of said 5-6-membered heterocyclyl or 5-6-membered heteroaryl combine to form an optionally substituted phenyl group or an optionally substituted 5-6-membered heteroaryl group.

In some embodiments, when one $R^4$ is substituted at the ring carbon between the ring nitrogen and the ring carbon to which —X-$L^1$-$R^1$ is substituted, $L^1$ joins with said $R^4$ to form an optionally substituted 5-6-membered heterocyclyl or an optionally substituted 5-6-membered heteroaryl. In some embodiments, $L^1$ joins with said $R^4$ to form an optionally substituted pyrazolyl, imidazolyl, pyrrolyl, triazolyl, oxazolyl, or thiazolyl. In other embodiments, X is a bond.

In some embodiments, $R^2$ is hydrogen. In other embodiments, $R^2$ is $C_{1-4}$ alkyl (e.g., methyl, ethyl, or cyclopropylmethyl). In certain embodiments, $R^2$ is hydrogen, methyl, ethyl, or cyclopropylmethyl. In some embodiments, $R^2$ is selected from those depicted in Table 1, below.

In some embodiments, $L^2$ is a bond. In some embodiments, when $L^2$ is a bond and $R^3$ is phenyl, naphthyl, or heteroaryl (e.g., pyridinyl or pyrimidinyl), $R^2$ can join with a substituent of $R^3$ to form an optionally substituted 5-7-membered heterocyclyl (e.g., piperidinyl or piperazinyl) or an optionally substituted 5-6-membered heteroaryl (e.g., imidazolyl, pyrazolyl, or pyridinyl). In other embodiments, $L^2$ is —C(O)—, —S(O)$_2$—, —C(O)—O—, —C(O)N($R^y$)—, or —S(O)$_2$N($R^y$)—. In other embodiments, $L^2$ is —C(O)— or —C(O)—O—. In certain embodiments, $L^2$ is —C(O)—. In other embodiments, $L^2$ is a bond, —C(O)— or —C(O)—O—. In still other embodiments, $L^2$ is a bond or —C(O)—. In some embodiments, $L^2$ is selected from those depicted in Table 1, below.

In other embodiments, any $R^y$ is hydrogen. In some embodiments, any $R^y$ is $C_{1-4}$ alkyl. In some embodiments, $R^y$ is selected from those depicted in Table 1, below.

In some embodiments, m is 0. In other embodiments, m is 1, 2, or 3. In some embodiments, m is 0, 1, or 2 (e.g., m is 1 or 2). For clarity, it is understood that when m is 1, 2, or 3, the $R^4$ groups may be located at any position of the pyridyl ring having the —X-$L^1$-$R^1$ moiety. That is, any $R^4$ can be located at either carbon ortho to the pyridyl nitrogen, as well as the carbon para to the pyridyl nitrogen.

In some embodiments, $R^4$ is —CN, halo or -$L^4$-$R^{17}$. In some embodiments, $R^4$ is halo or -$L^4$-$R^{17}$.

In some embodiments, $R^4$ is substituted at the ring carbon between the ring nitrogen and the ring carbon to which —X-$L^1$-$R^1$ is substituted. In certain embodiments' X or $L^1$ joins with said $R^4$ to form an optionally substituted 5-7-membered heterocyclyl or 5-6-membered heteroaryl. In other embodiments, X joins with said $R^4$ to form an optionally substituted 5-7-membered heterocyclyl. In other embodiments, X joins with said $R^4$ to form an optionally substituted 5-6-membered heteroaryl. In other embodiments, $L^1$ joins with said $R^4$ to form an optionally substituted 5-7-membered heterocyclyl. In other embodiments, $L^1$ joins with said R⁴ to form an optionally substituted 5-6-membered heteroaryl. In each case mentioned above, said heterocyclyl and heteroaryl are as defined above (e.g., each can be optionally substituted as described above and e.g., each heteroaryl can contain heteroatom nitrogen, oxygen, or sulfur, including oxidized form of nitrogen or sulfur). In other embodiments, said 5-7-membered heterocyclyl or 5-6-membered heteroaryl is unsubstituted. In still other embodiments, said 5-7-membered heterocyclyl or 5-6-membered heteroaryl is substituted (e.g., comprises 1, 2, 3, 4, or 5 substituent groups such as those described for R⁶ herein); in some embodiments, said substituents are independently -halo, —CN, —C₁₋₆ aliphatic, —OH, and —O—(C₁₋₆ aliphatic). In certain embodiments, two substituent groups of said 5-6-membered heterocyclyl or 5-6-membered heteroaryl combine to form an optionally substituted phenyl group or an optionally substituted 5-6-membered heteroaryl group.

In other embodiments, R⁴ is substituted at the ring carbon between the ring nitrogen and the ring carbon to which —X-L¹-R¹ is substituted, and a second R⁴ is substituted at the para position with respect to the ring nitrogen.

In other embodiments, R⁴ is halo or -L⁴-R¹⁷. In still other embodiments, L⁴ is C₁₋₄ alkylene chain, —O—, or —N(Rᶻ)—. In some embodiments, R⁴ is independently halo or C₁₋₃ alkyl. In some embodiments, Rᶻ is hydrogen. In other embodiments, Rᶻ is C₁₋₄ alkyl. In further embodiments, Rᶻ is hydrogen or methyl. In some embodiments, R¹⁷ is hydrogen. In other embodiments, R¹⁷ is C₁₋₆ aliphatic. In still other embodiments, R¹⁷ is hydrogen or C₁₋₃ alkyl. In other embodiments, R⁴ is fluoro, chloro, C₁₋₃ alkyl, trifluoromethyl, hydroxyl, —NH₂ or —NH—C₁₋₃ alkyl. In still other embodiments, R⁴ is fluoro, chloro, unsubstituted C₁₋₃ aliphatic, trifluoromethyl, hydroxyl, methoxy, —NH₂ or —NH—C₁₋₃ aliphatic. In some embodiments, R⁴ is selected from those depicted in Table 1, below. In further embodiments, m is 0-2. In some embodiments, one R⁴ is substituted at the ring carbon between the ring nitrogen and the ring carbon to which —X-L¹-R¹ is substituted. In still other embodiments, m is 2 and a second R⁴ is substituted at the para position with respect to the ring nitrogen. In certain embodiments, each of the two R⁴ (i.e., the R⁴ that is substituted at the ring carbon between the ring nitrogen and the ring carbon to which —X-L¹-R¹ is attached, and the second R⁴ substituted at the para position with respect to the ring nitrogen is independently fluoro, chloro, or methyl. In a further embodiment, said second R⁴ is fluoro, chloro, methyl, or methoxy.

In some embodiments, n is 0. In other embodiments, n is 1, 2, or 3. In other embodiments, n is 0, 1, or 2. For clarity, it is understood that when n is 1, 2, or 3, the R⁵ groups may be located at any position of the pyridyl ring having the —NR²-L²-R³ moiety. That is, any R⁵ can be located at either carbon meta to the pyridyl nitrogen, as well as the carbon ortho to the pyridyl nitrogen.

In some embodiments, R⁵ is halo or -L⁴-R¹⁷ wherein L⁴ is C₁₋₄ alkylene chain, —O—, or —N(Rᵃ)— where Rᵃ is hydrogen or methyl, and R¹⁷ is hydrogen or C₁₋₃ alkyl. In some embodiments, R⁵ is selected from those depicted in Table 1, below.

In certain embodiments,
X is a bond;
L is —N(R⁸)C(O)—, —N(R¹⁰)S(O)₂—, —C(O)—, or —S(O)₂— (e.g., L¹ is —N(R⁸)C(O)—, —N(R¹⁰)S(O)₂—, or —S(O)₂—);

R² is hydrogen, methyl, ethyl, or cyclopropylmethyl:
L² is a bond, —C(O)— or —C(O)—O—;
R³ is C₁₋₃ alkyl, cyclopropyl, or 6-membered heteroaryl (e.g., R³ is C₁₋₃ alkyl), each of which being optionally substituted with 1-2 R⁶;
R⁴ is fluoro, chloro, C₁₋₃ alkyl, trifluoromethyl, hydroxyl, methoxy, —NH₂ or —NH—C₁₋₃ aliphatic (e.g., R⁴ is fluoro, chloro, C₁₋₃ alkyl, trifluoromethyl, hydroxyl, —NH₂ or —NH—C₁₋₃ alkyl):
m is 0-2 (e.g., m is 1 or 2);
R⁴ is substituted at the ring carbon between the ring nitrogen and the ring carbon to which -L¹-R¹ is substituted;
n is 0 or 1; and
R¹ is

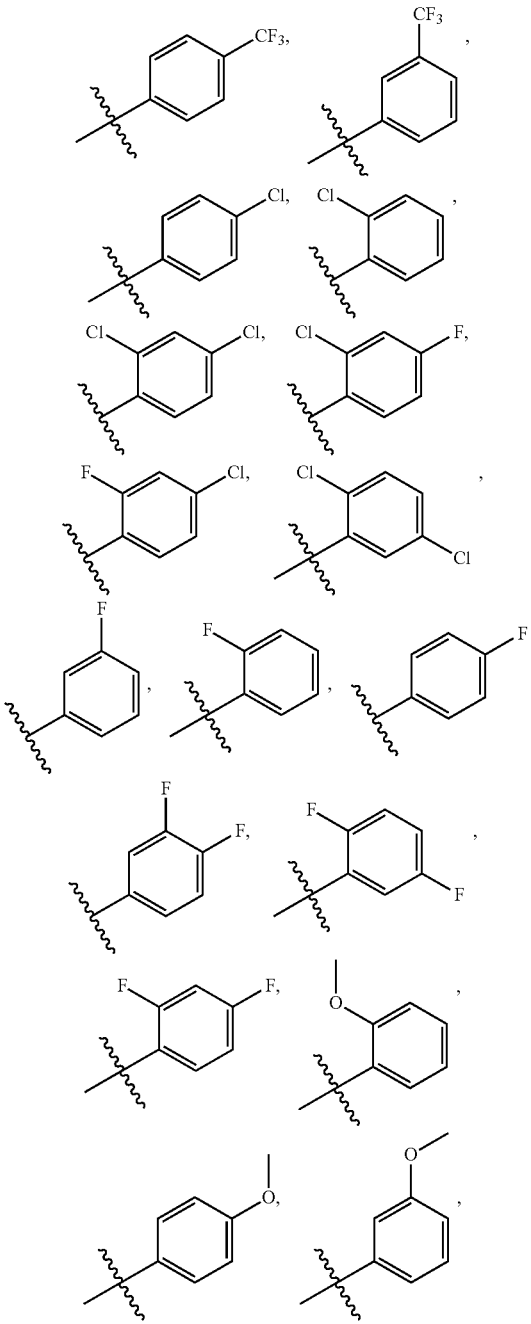

-continued
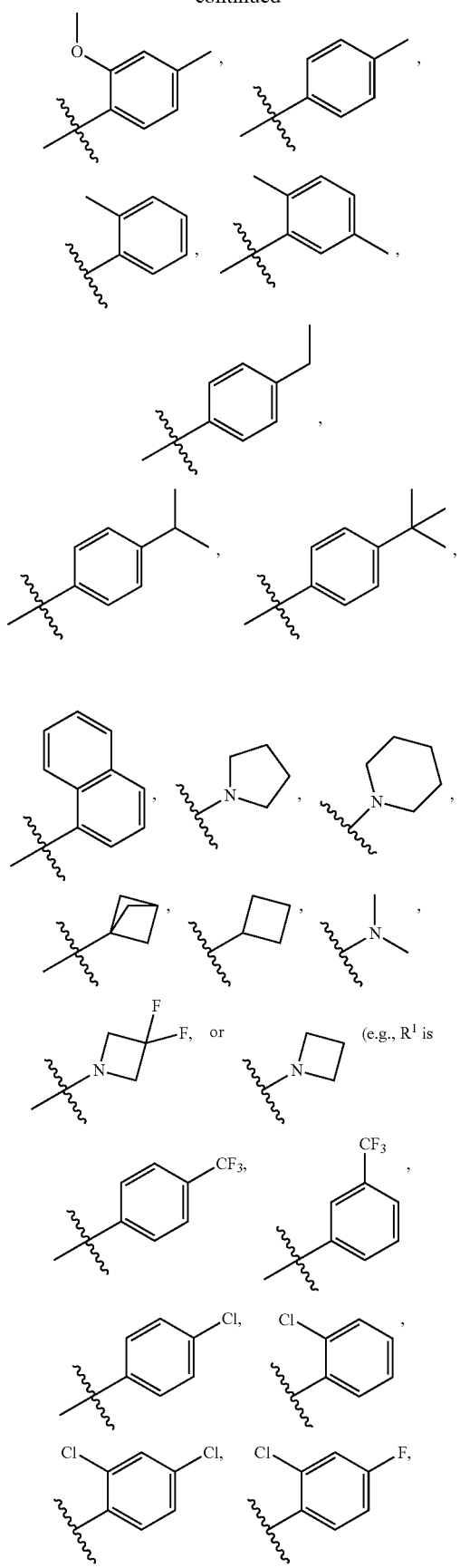
-continued
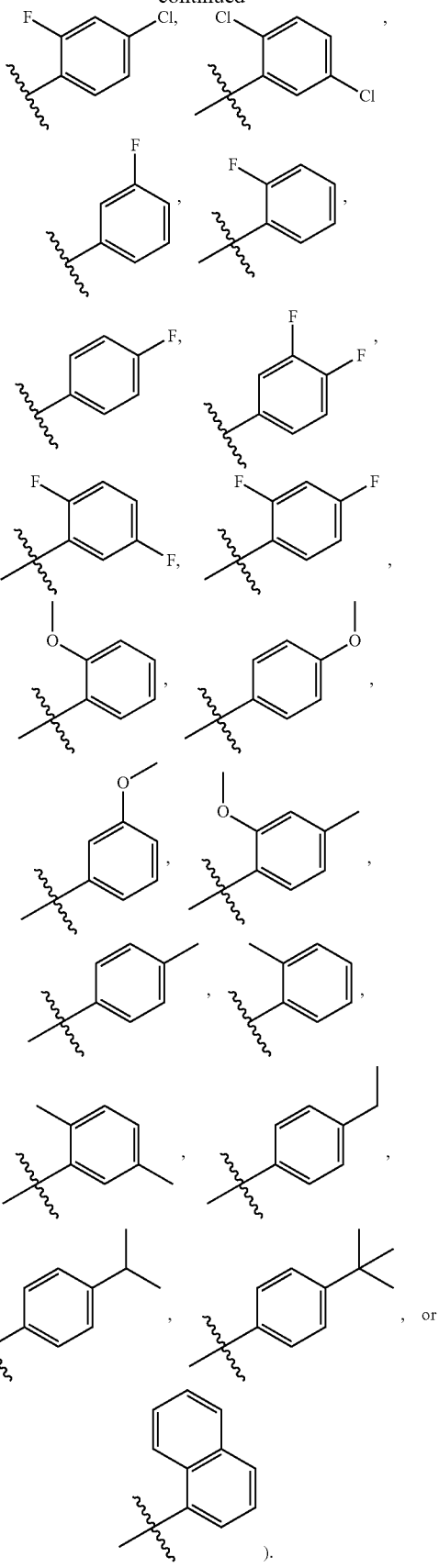

In some embodiments, m is 1 and $R^4$ is substituted at the ring carbon between the ring nitrogen and the ring carbon to which -$L^1$-$R^1$ is substituted. In some embodiments, m is 2 and one $R^4$ is substituted at the ring carbon between the ring nitrogen and the ring carbon to which $L^1$-$R^1$ is substituted whereas the other $R^4$ is substituted at the para position with respect to the ring nitrogen.

In some embodiments, $L^1$ is —N($R^8$)C(O)— or —N($R^{10}$)S(O)$_2$— where each of $R^8$ and $R^{10}$ independently, optionally join with $R^4$ to form an optionally substituted 5-7-membered heterocyclyl.

In other embodiments, $L^1$ is —N($R^8$)C(O)— or —N($R^{10}$)S(O)$_2$— where each of $R^8$ and $R^{10}$, independently, is hydrogen, methyl, or ethyl; $R^1$ is $C_{1-4}$ alkyl, phenyl, naphthyl 3-6-membered cycloaliphatic, 3-6-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur; $R^3$ is $C_{1-3}$ alkyl; and $R^4$ is halo or -$L^4$-$R^{17}$ wherein $L^4$ is $C_{1-4}$ alkylene chain, —O—, or —N($R^z$)— where $R^z$ is hydrogen or methyl, and $R^{17}$ is hydrogen or $C_{1-3}$ alkyl. In some embodiments, $R^4$ is methyl, ethyl, fluoro, chloro, —NH$_2$, methoxy, or ethoxy.

In other embodiments, $L^1$ is —C(O)— and $R^1$ is

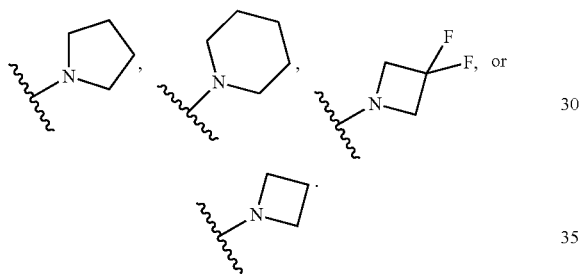

In some embodiments, the compound of formula I has a structure according to any of formulas I-A to I-Y as shown below:

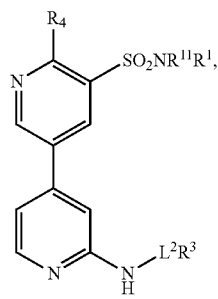

I-A

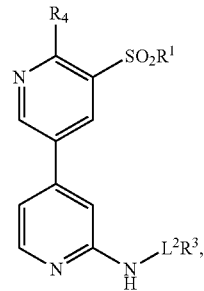

I-B

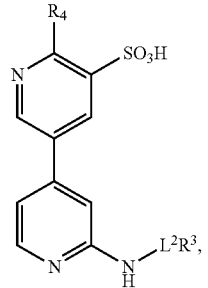

I-C

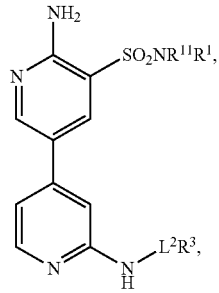

I-A'

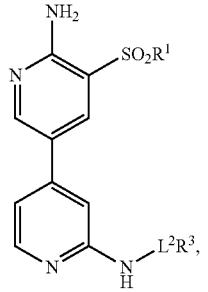

I-B'

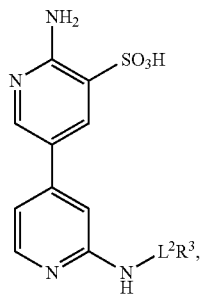

I-C'

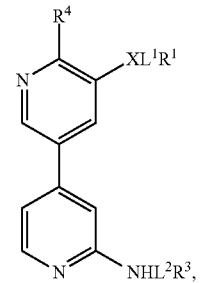

I-D

-continued
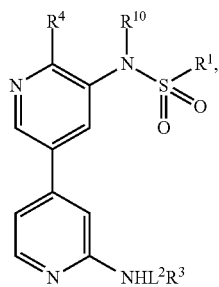
I-E
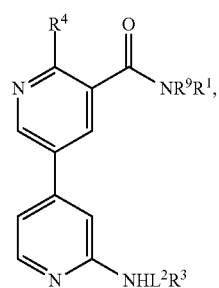
I-F
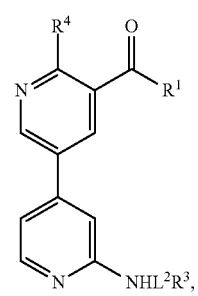
I-G
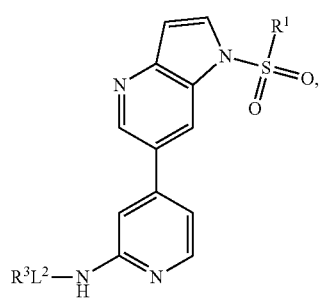
I-H
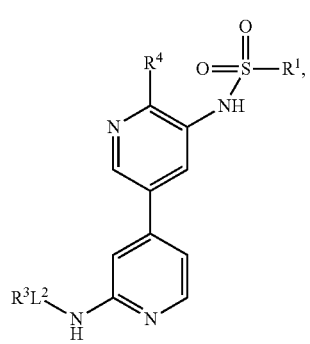
I-I
-continued
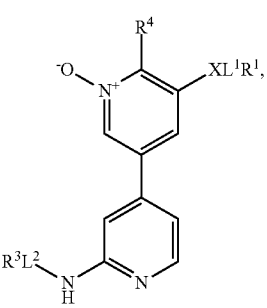
I-J
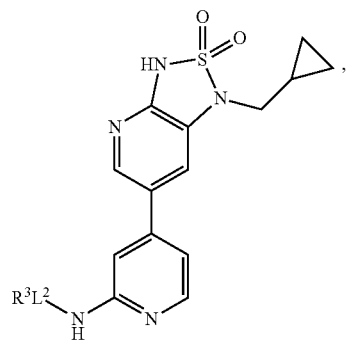
I-K
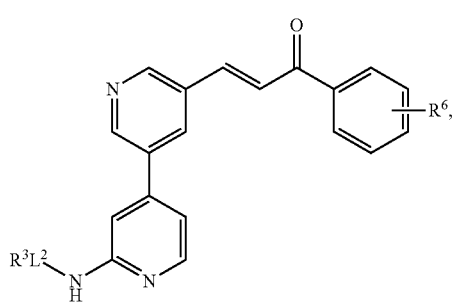
I-L
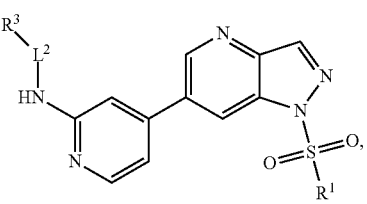
I-M
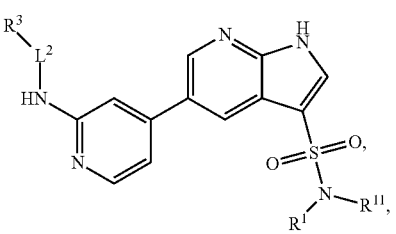
I-N
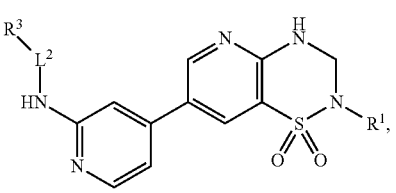
I-O I-P 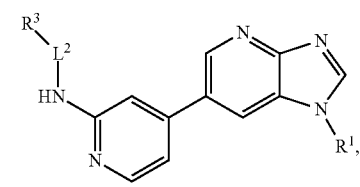
I-Q 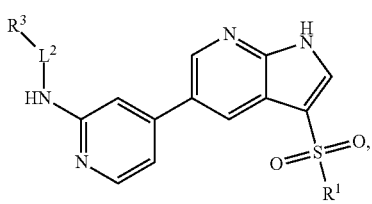
I-R 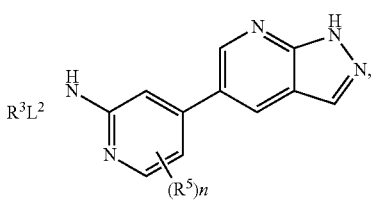
I-S 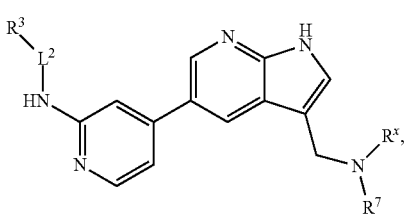
I-T 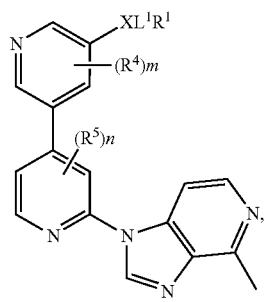
I-U 
I-U' 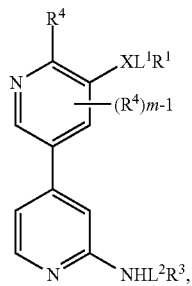
I-V 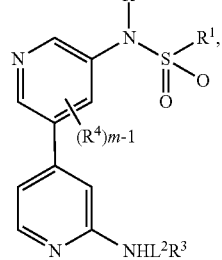
I-W 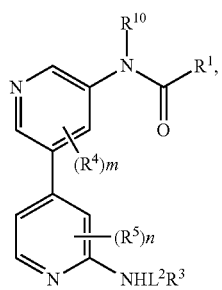
I-X 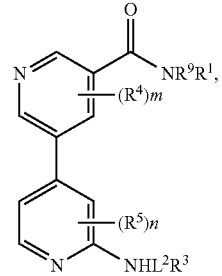
I-Y 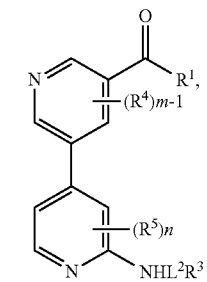
or a pharmaceutically acceptable salt thereof, wherein $L^2$, $R^x$, $R^1$, $R^3$, $R^4$, $R^5$, $R^6$, $R^7$, $R^9$, $R^{10}$, $R^{11}$, m, and n are as described herein.
In other embodiments, the compound of formula I has a structure according to formula II,

II

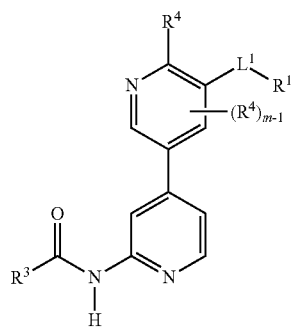

or a pharmaceutically acceptable salt thereof, where $R^1$, $L^1$, $R^3$, $R^4$, and m are as defined herein, wherein (m−1)≥0. In some embodiments, (m−1) is 0 or 1.

In some embodiments, (m−1) is 0. When (m−1) is 0, the pyridyl moiety comprises only the one $R^4$ group shown as shown in Formula II-a.

II-a

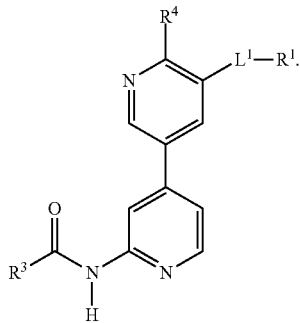

That is, there is only one $R^4$ and it is substituted at the ring carbon between the ring nitrogen and the ring carbon to which -$L^1$-$R^1$ is substituted.

In other embodiments, (m−1) is 1. That is, there are two $R^4$ and a first one is substituted at the ring carbon between the ring nitrogen and the ring carbon to which -$L^1$-$R^1$ is substituted whereas the other $R^4$ is substituted either at the para or ortho position with respect to the ring nitrogen as shown in Formulas II-b and II-c, II-b

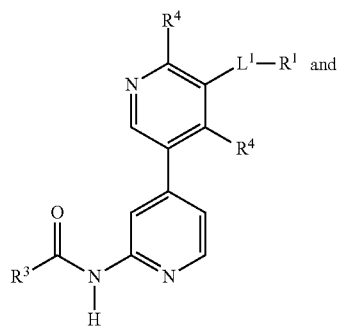

II-c

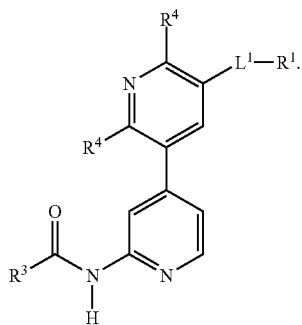

In further embodiments, the $R^4$ substituted at the para position with respect to the ring nitrogen is methyl. In still other embodiments, $L^1$ is —N($R^{10}$)S(O)$_2$—.

In still other embodiments, the compound of formula I has a structure according to any of formulas III, IV, IV', V, VI, and VI':

III

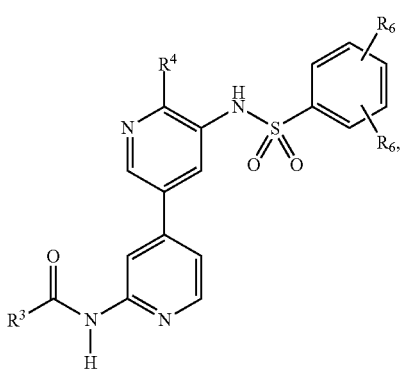

IV

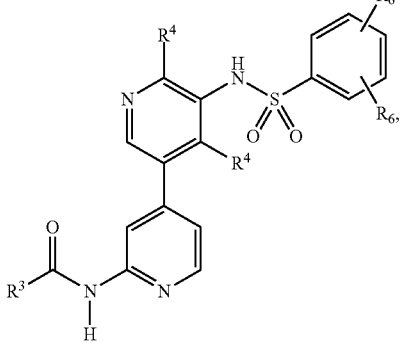

IV'

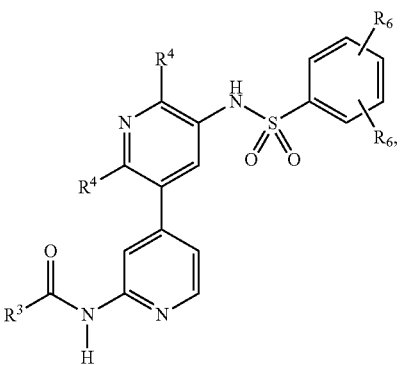

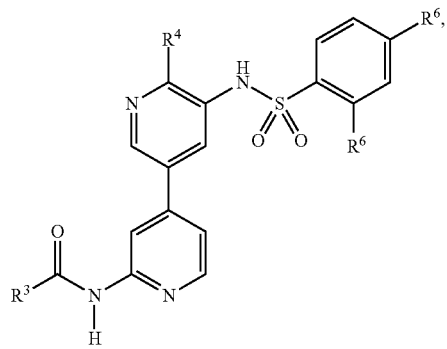

V

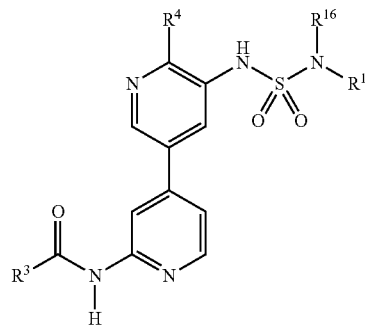

VII

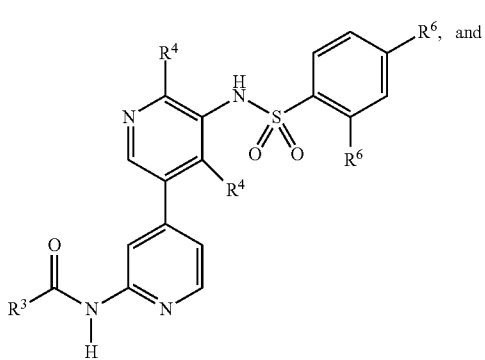

VI, and

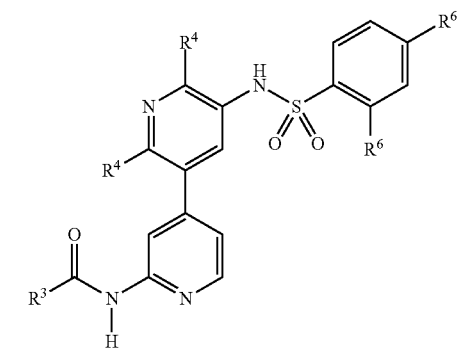

VI' or a pharmaceutically acceptable salt thereof, where $R^3$, $R^4$, and $R^6$ are as defined herein. In some embodiments, each $R^4$ is independently —$NH_2$, halo (e.g., F or Cl), optionally substituted $C_{1-3}$ alkyl, or —O-(optionally substituted $C_{1-3}$ alkyl). In other embodiments, each $R^6$ is independently halo (e.g., F or Cl), optionally substituted $C_{1-3}$ alkyl, or —O-(optionally substituted $C_{1-3}$ alkyl). In some embodiments, both $R^6$ are Cl. In other embodiments, both $R^6$ are F. In some embodiments, one $R^6$ is F and the other $R^6$ is Cl. In other embodiments, $R^3$ is optionally substituted $C_{1-3}$ alkyl.

In still other embodiments, the compound of formula I has a structure according to formula VII, or a pharmaceutically acceptable salt thereof, where $R^1$, $R^4$, $R^3$, and $R^{16}$ are as defined herein. In some embodiments, $R^1$ and $R^{16}$ are each optionally substituted $C_{1-4}$ alkyl.

In other embodiments, the compound of formula I has a structure according to formula VIII,

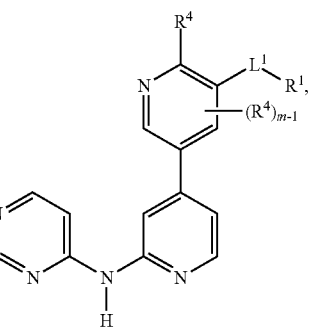

VIII or a pharmaceutically acceptable salt thereof, where (m–1) is 0 or 1 and $R^1$, $L^1$, $R^4$, and $R^6$ are as defined herein.

In other embodiments, $L^1$ is —C(O)— and $R^1$ is

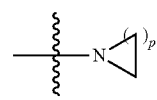

where p is 1-4. Further, $R^1$ can be substituted with 1-2 $R^6$ where $R^6$ is $C_{1-4}$ alkyl (e.g., methyl) or halo (e.g., fluoro). In other embodiments, $R^4$ is halo or -$L^4$-$R^{17}$ wherein $L^4$ is $C_{1-4}$ alkylene, —O—, or —N($R^z$)— where $R^z$ is hydrogen or methyl, and $R^{17}$ is hydrogen or $C_{1-3}$ aliphatic. For example, $R^4$ is methyl, ethyl, fluoro, chloro, —$NH_2$, methoxy, or ethoxy. In other embodiments, $R^6$ is cyano, fluoro, chloro, $C_{1-6}$ alkyl (e.g., methyl), 3-6-membered cycloalkyl, or phenyl.

In other embodiments, (m–1) is 0. That is, there is only one $R^4$ and it is substituted at the ring carbon between the ring nitrogen and the ring carbon to which -$L^1$-$R^1$ is substituted as shown in Formula VIII-A.

VIII-A

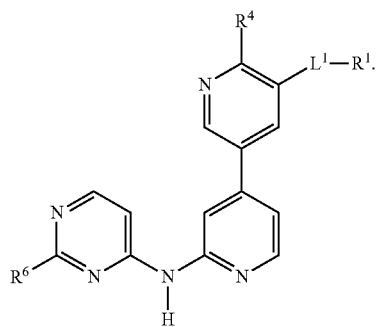

In other embodiments, (m−1) is 1. That is, there are two $R^4$ and a first one is substituted at the ring carbon between the ring nitrogen and the ring carbon to which -$L^1$-$R^1$ is substituted whereas a second $R^4$ is substituted either at the para (see Formula VIII-B) or ortho position (see Formula VIII-C) with respect to the ring nitrogen,

VIII-B

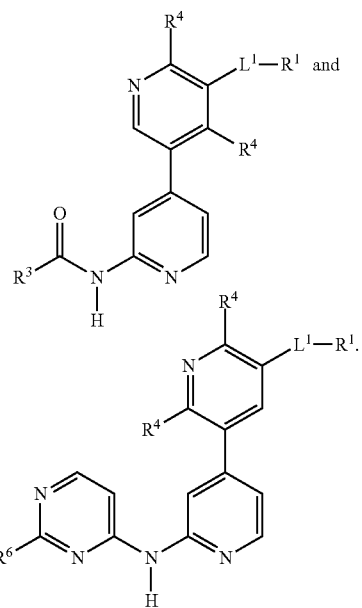

VIII-C

In some embodiments, the second $R^4$ is substituted at the para position with respect to the ring nitrogen. In some embodiments, the second $R^4$ is methyl.

In still other embodiments, the compound of formula I has a structure according to any of formulas VIII-D to VIII-O

VIII-D

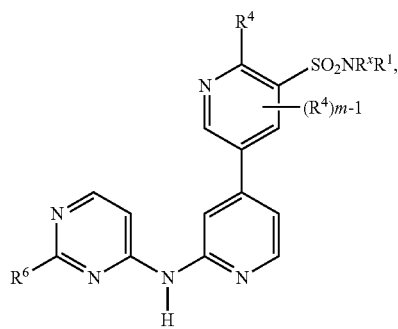

VIII-E

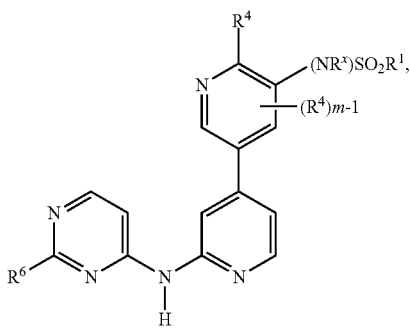

VIII-F

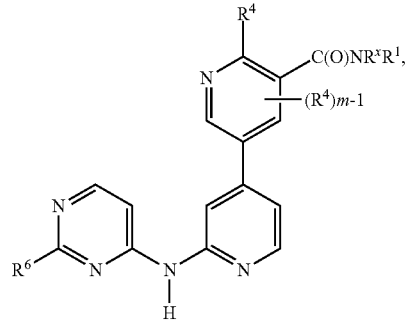

VIII-G

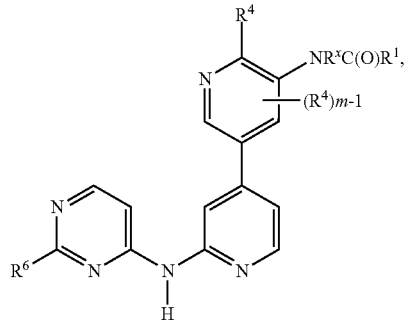

VIII-H

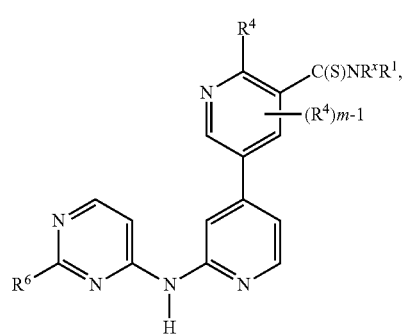

VIII-I

VIII-J

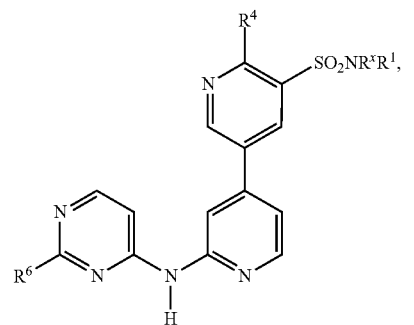

VIII-K

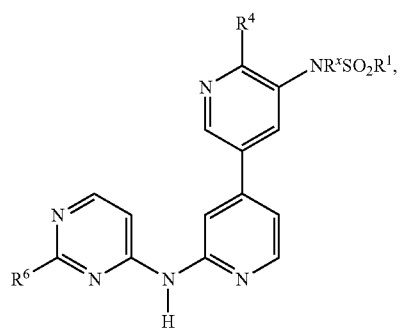

VIII-L

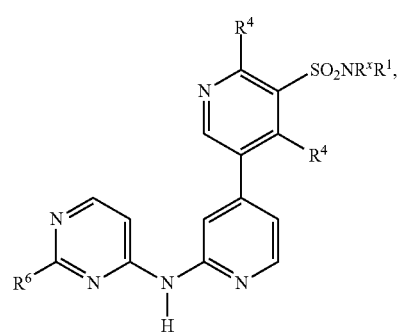

VIII-M

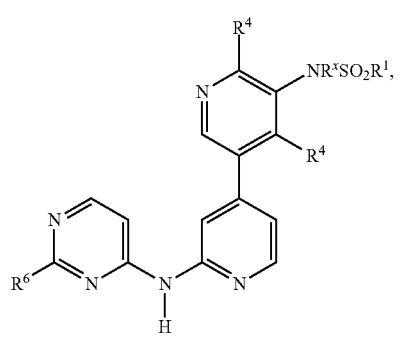

VIII-N

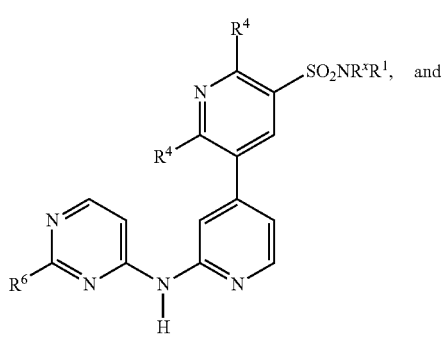

VIII-O

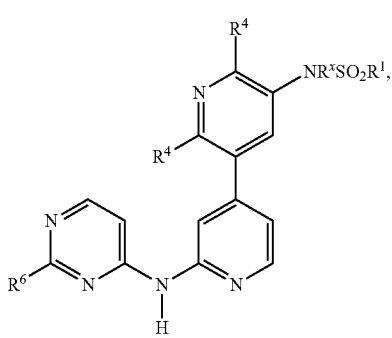

or a pharmaceutically acceptable salt thereof, where $R^x$, $R^1$, $R^4$, m, and $R^6$ are as described herein.

The present invention also provides compounds of formulas A and B:

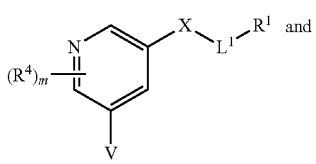

A

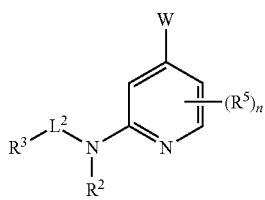

B where $R^1$, $L^1$, X, $R^4$, m, $R^5$, n, $L^2$, $R^2$, and $R^3$ are as defined herein and one of V and W is a halide group (e.g., bromo) or pseudohalide group (e.g., cyanide) and the other is a boronic acid or a derivative. For example, V can be bromo or iodo and W can be —B(OR$_a$)(OR$_b$) where each of R$_a$ and R$_b$ is independently hydrogen or $C_{1-3}$ alkyl, and R$_a$ and R$_b$ can join together to form an optionally substituted 5-6 membered heterocyclyl (together with B and O).

In some embodiments, the invention provides a composition comprising a compound according to formula A and a compound according to formula B.

The present invention also provides a method of coupling a compound of formula A to a compound of formula B to form a compound of formula I. The method comprises reacting a compound of formula A with a compound of formula B in the presence of a palladium catalyst (e.g., Pd(PPh$_3$)$_3$, Pd(dppf)Cl$_2$, or Pd$_2$(dba)$_3$) and a base (potassium carbonate or sodium carbonate) in an appropriate solvent (e.g., dioxane or THF).

Exemplary compounds of the present invention are set forth in Table 1, below.

TABLE 1

Exemplary Compounds

I-1

I-2

I-3

I-4

TABLE 1-continued
Exemplary Compounds
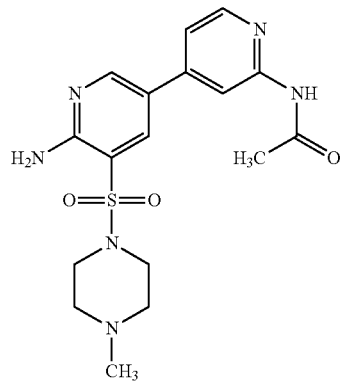 [SMILES: CC(=O)Nc1cc(-c2cnc(N)c(S(=O)(=O)N3CCN(C)CC3)c2)ccn1]
I-5
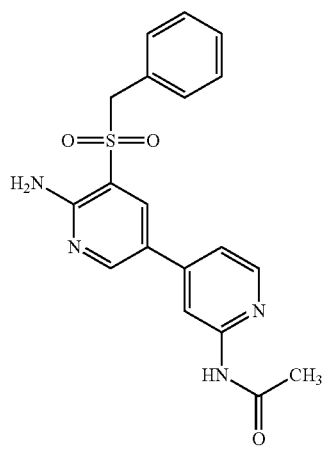 [SMILES: CC(=O)Nc1cc(-c2cnc(N)c(S(=O)(=O)Cc3ccccc3)c2)ccn1]
I-6
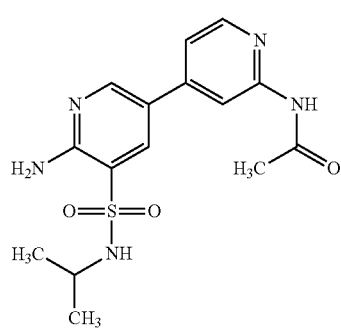 [SMILES: CC(=O)Nc1cc(-c2cnc(N)c(S(=O)(=O)NC(C)C)c2)ccn1]
I-7
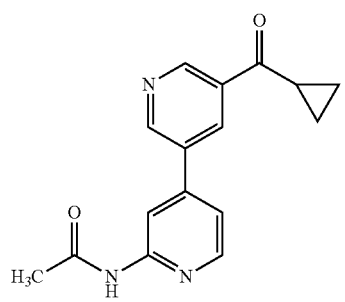 [SMILES: CC(=O)Nc1cc(-c2cncc(C(=O)C3CC3)c2)ccn1]
I-8

TABLE 1-continued

Exemplary Compounds

I-9

I-10

I-11

I-12

I-13

TABLE 1-continued
Exemplary Compounds
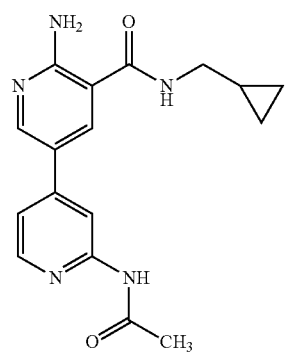 [SMILES: CC(=O)Nc1cc(-c2cnc(N)c(C(=O)NCC3CC3)c2)ccn1]
I-14
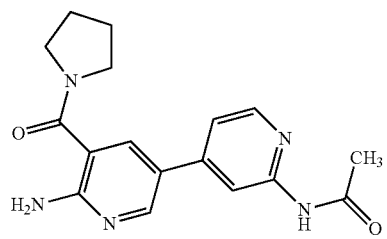 [SMILES: CC(=O)Nc1cc(-c2cnc(N)c(C(=O)N3CCCC3)c2)ccn1]
I-15
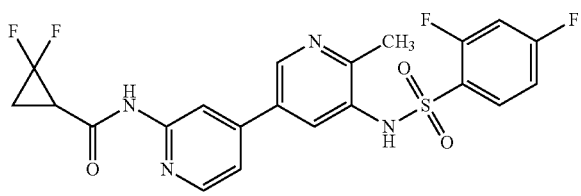 [SMILES: Cc1ncc(-c2ccnc(NC(=O)C3CC3(F)F)c2)cc1NS(=O)(=O)c1ccc(F)cc1F]
I-16
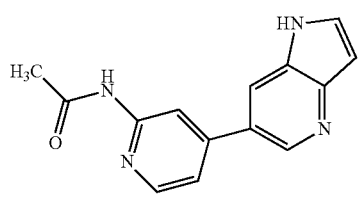 [SMILES: CC(=O)Nc1cc(-c2cnc3cc[nH]c3c2)ccn1]
I-17
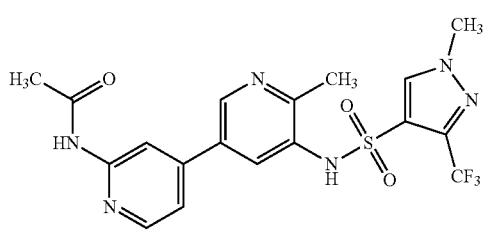 [SMILES: CC(=O)Nc1cc(-c2cnc(C)c(NS(=O)(=O)c3cn(C)nc3C(F)(F)F)c2)ccn1]
I-18
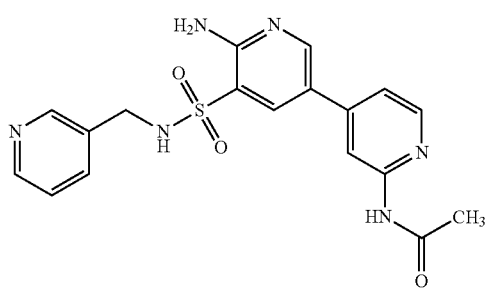 [SMILES: CC(=O)Nc1cc(-c2cnc(N)c(S(=O)(=O)NCc3cccnc3)c2)ccn1]
I-19

TABLE 1-continued
Exemplary Compounds
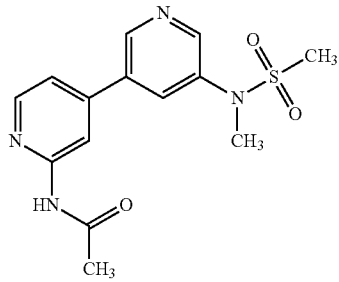 [SMILES: CC(=O)Nc1cc(-c2cncc(N(C)S(C)(=O)=O)c2)ccn1]
I-20
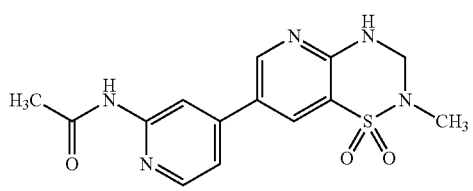 [SMILES: CC(=O)Nc1cc(-c2cnc3c(c2)S(=O)(=O)N(C)CN3)ccn1]
I-21
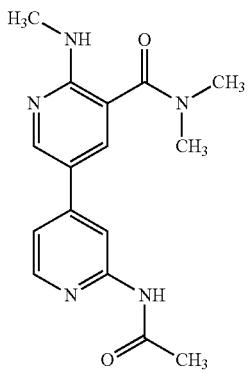 [SMILES: CNc1ncc(-c2ccnc(NC(C)=O)c2)cc1C(=O)N(C)C]
I-22
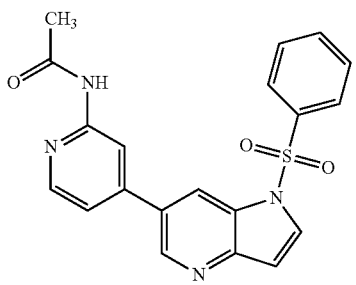 [SMILES: CC(=O)Nc1cc(-c2cnc3ccn(S(=O)(=O)c4ccccc4)c3c2)ccn1]
I-23
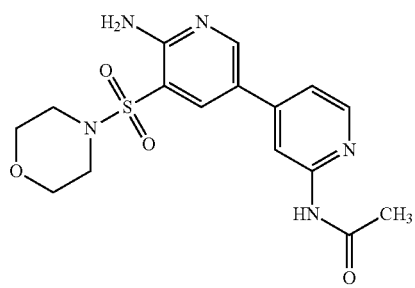 [SMILES: CC(=O)Nc1cc(-c2cnc(N)c(S(=O)(=O)N3CCOCC3)c2)ccn1]
I-24

TABLE 1-continued

Exemplary Compounds

I-25
I-26
I-27
I-28
I-29

TABLE 1-continued
Exemplary Compounds
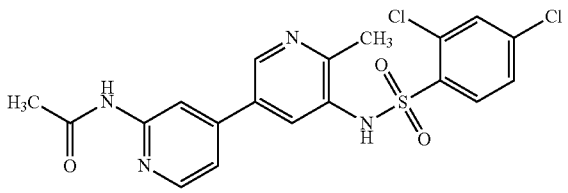 [SMILES: CC(=O)Nc1cc(-c2cnc(C)c(NS(=O)(=O)c3ccc(Cl)cc3Cl)c2)ccn1]
I-30
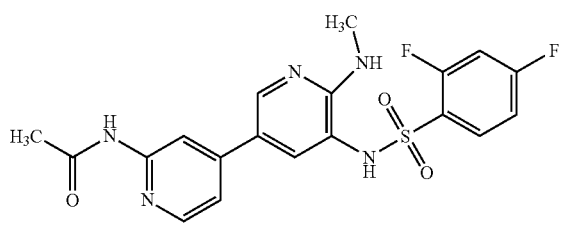 [SMILES: CNc1ncc(-c2ccnc(NC(C)=O)c2)cc1NS(=O)(=O)c1ccc(F)cc1F]
I-31
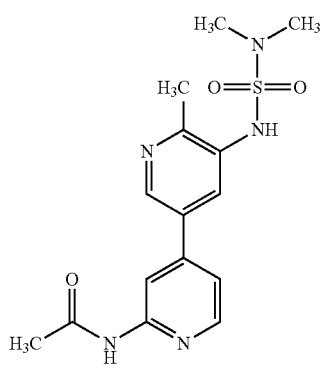 [SMILES: CC(=O)Nc1cc(-c2cnc(C)c(NS(=O)(=O)N(C)C)c2)ccn1]
I-32
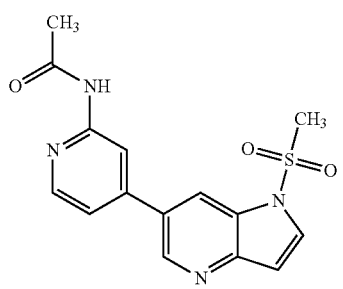 [SMILES: CC(=O)Nc1cc(-c2cnc3ccn(S(C)(=O)=O)c3c2)ccn1]
I-33
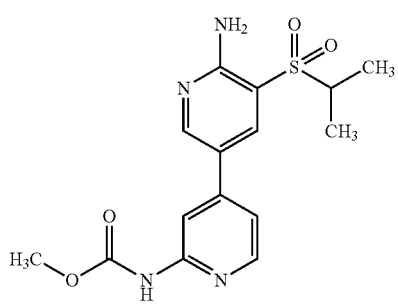
I-34
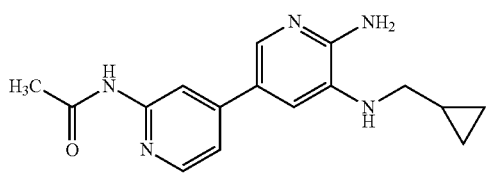 [SMILES: CC(=O)Nc1cc(-c2cnc(N)c(NCC3CC3)c2)ccn1]
I-35

TABLE 1-continued
Exemplary Compounds
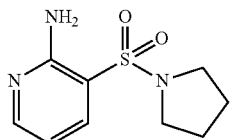
I-36
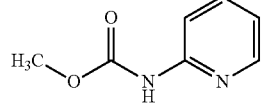
I-37
I-38
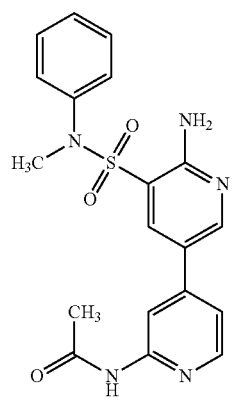 [SMILES: CC(=O)Nc1cc(-c2cnc(N)c(S(=O)(=O)N(C)c3ccccc3)c2)ccn1]
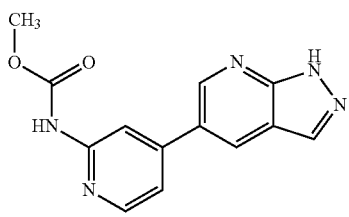 [SMILES: COC(=O)Nc1cc(-c2cnc3[nH]ncc3c2)ccn1]
I-39
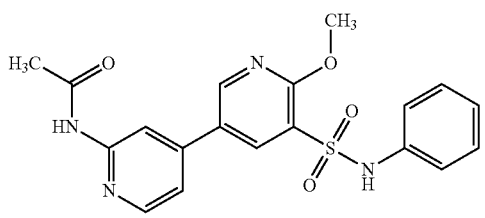 [SMILES: COc1ncc(-c2ccnc(NC(C)=O)c2)cc1S(=O)(=O)Nc1ccccc1]
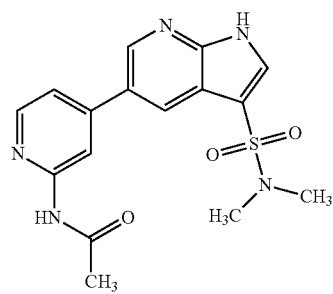 [SMILES: CC(=O)Nc1cc(-c2cnc3[nH]cc(S(=O)(=O)N(C)C)c3c2)ccn1]
I-40

TABLE 1-continued

Exemplary Compounds

I-41
I-42
I-43
I-44
I-45
I-46

TABLE 1-continued

Exemplary Compounds

I-47

I-48

I-49

I-50

I-51

TABLE 1-continued
Exemplary Compounds
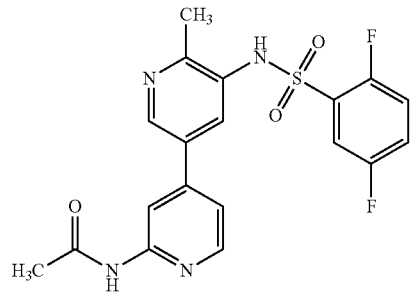 [SMILES: CC(=O)Nc1cc(-c2cnc(C)c(NS(=O)(=O)c3cc(F)ccc3F)c2)ccn1]
I-52
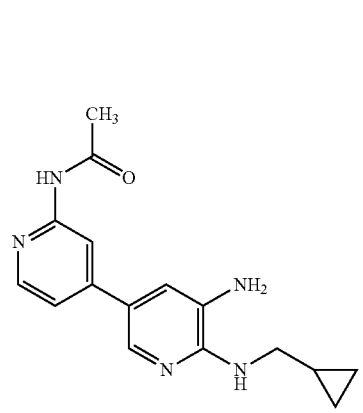 [SMILES: CC(=O)Nc1cc(-c2cnc(NCC3CC3)c(N)c2)ccn1]
I-53
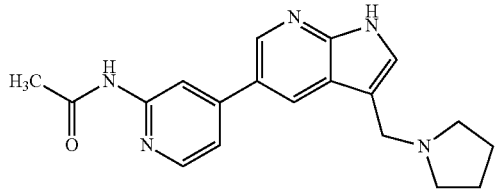 [SMILES: CC(=O)Nc1cc(-c2cnc3[nH]cc(CN4CCCC4)c3c2)ccn1]
I-54
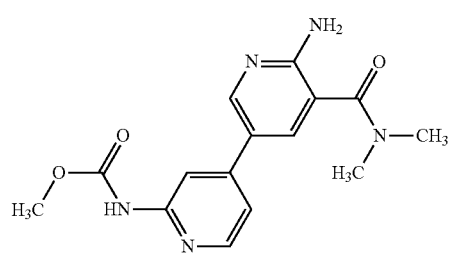
I-55
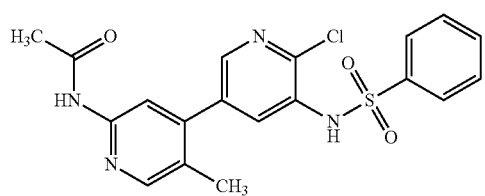 [SMILES: CC(=O)Nc1cc(-c2cnc(Cl)c(NS(=O)(=O)c3ccccc3)c2)c(C)cn1]
I-56

TABLE 1-continued

Exemplary Compounds

I-57

I-58

I-59

I-60

I-61

I-62

US 10,538,533 B2
TABLE 1-continued
Exemplary Compounds
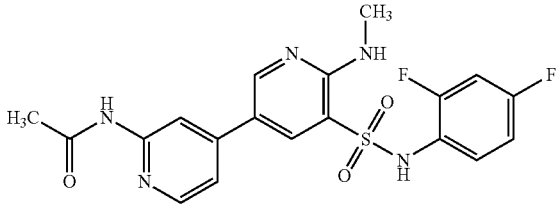 [SMILES: CNc1ncc(-c2ccnc(NC(C)=O)c2)cc1S(=O)(=O)Nc1ccc(F)cc1F] I-63
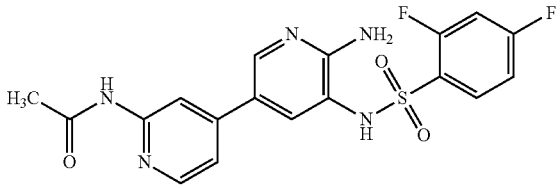 [SMILES: CC(=O)Nc1cc(-c2cnc(N)c(NS(=O)(=O)c3ccc(F)cc3F)c2)ccn1] I-64
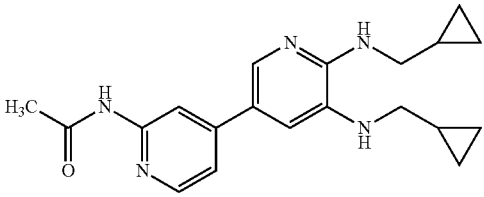 [SMILES: CC(=O)Nc1cc(-c2cnc(NCC3CC3)c(NCC3CC3)c2)ccn1] I-65
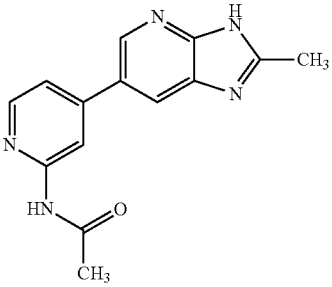 [SMILES: CC(=O)Nc1cc(-c2cnc3[nH]c(C)nc3c2)ccn1] I-66
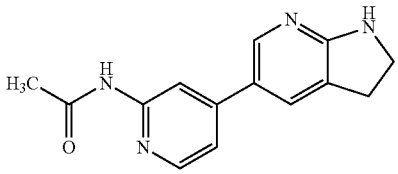 [SMILES: CC(=O)Nc1cc(-c2cnc3c(c2)CCN3)ccn1] I-67
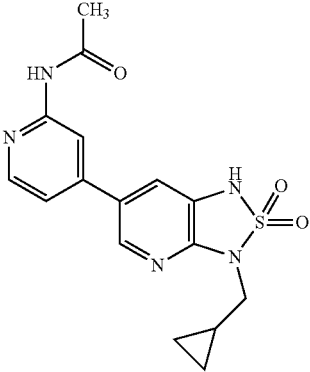 [SMILES: CC(=O)Nc1cc(-c2cnc3c(c2)NS(=O)(=O)N3CC2CC2)ccn1] I-68

TABLE 1-continued

Exemplary Compounds

I-69

I-70

I-71

I-72

I-73

I-74

TABLE 1-continued
Exemplary Compounds
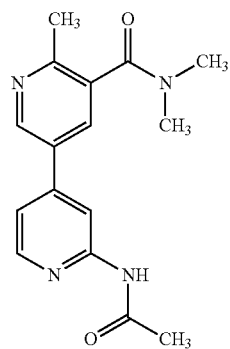 [SMILES: CC(=O)Nc1cc(-c2cnc(C)c(C(=O)N(C)C)c2)ccn1]
I-75
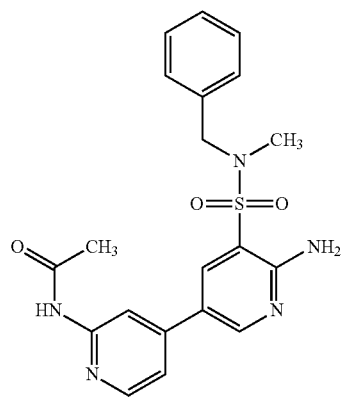 [SMILES: CC(=O)Nc1cc(-c2cnc(N)c(S(=O)(=O)N(C)Cc3ccccc3)c2)ccn1]
I-76
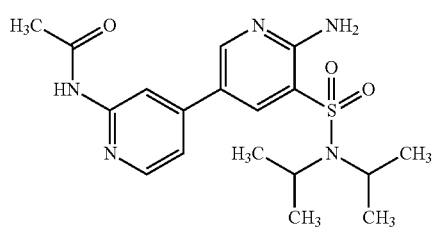 [SMILES: CC(=O)Nc1cc(-c2cnc(N)c(S(=O)(=O)N(C(C)C)C(C)C)c2)ccn1]
I-77
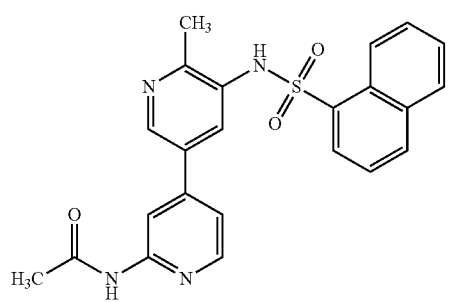 [SMILES: CC(=O)Nc1cc(-c2cnc(C)c(NS(=O)(=O)c3cccc4ccccc34)c2)ccn1]
I-78

TABLE 1-continued
Exemplary Compounds
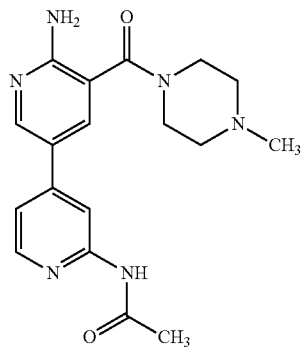 [SMILES: CC(=O)Nc1cc(-c2cnc(N)c(C(=O)N3CCN(C)CC3)c2)ccn1]
I-79
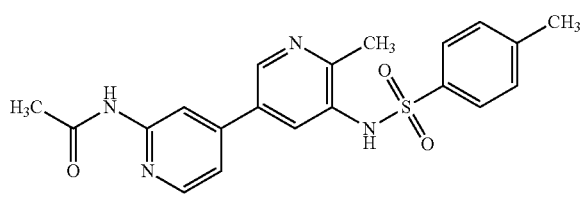 [SMILES: CC(=O)Nc1cc(-c2cnc(C)c(NS(=O)(=O)c3ccc(C)cc3)c2)ccn1]
I-80
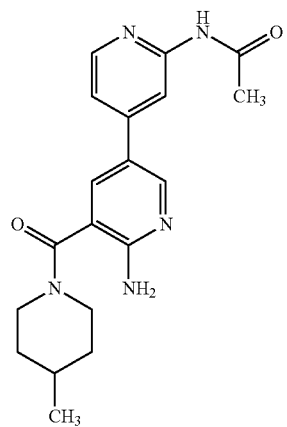 [SMILES: CC(=O)Nc1cc(-c2cnc(N)c(C(=O)N3CCC(C)CC3)c2)ccn1]
I-81
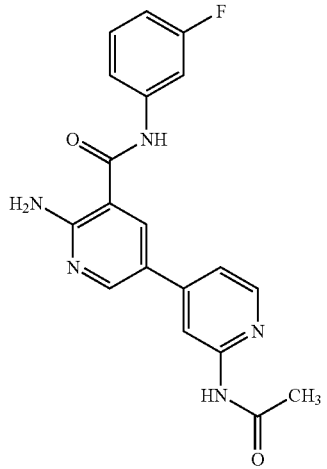 [SMILES: CC(=O)Nc1cc(-c2cnc(N)c(C(=O)Nc3cccc(F)c3)c2)ccn1]
I-82

TABLE 1-continued
Exemplary Compounds
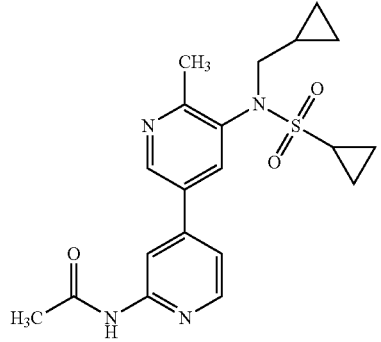 [SMILES: CC(=O)Nc1cc(-c2cnc(C)c(N(CC3CC3)S(=O)(=O)C3CC3)c2)ccn1]
I-83
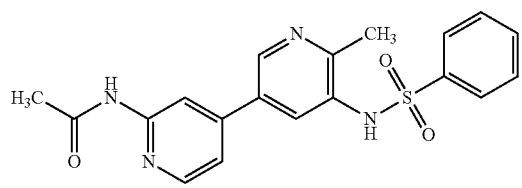 [SMILES: CC(=O)Nc1cc(-c2cnc(C)c(NS(=O)(=O)c3ccccc3)c2)ccn1]
I-84
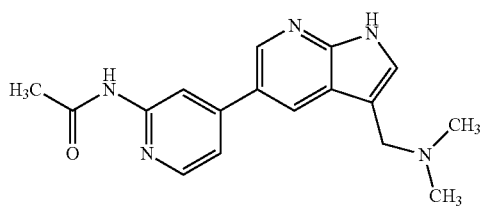 [SMILES: CC(=O)Nc1cc(-c2cnc3[nH]cc(CN(C)C)c3c2)ccn1]
I-85
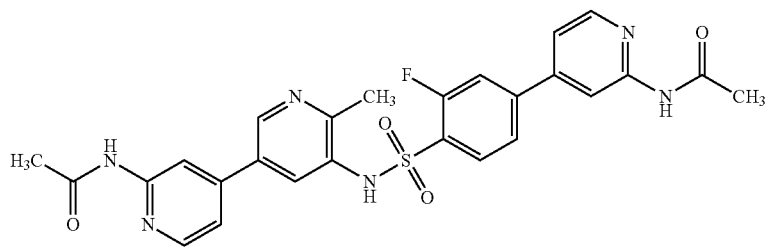 [SMILES: CC(=O)Nc1cc(-c2ccc(S(=O)(=O)Nc3cc(-c4ccnc(NC(C)=O)c4)cnc3C)c(F)c2)ccn1]
I-86
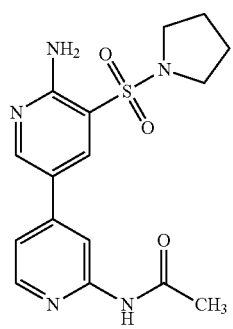 [SMILES: CC(=O)Nc1cc(-c2cnc(N)c(S(=O)(=O)N3CCCC3)c2)ccn1]
I-87

TABLE 1-continued

Exemplary Compounds

I-88

I-89

I-90

I-91

I-92

I-93

TABLE 1-continued
Exemplary Compounds
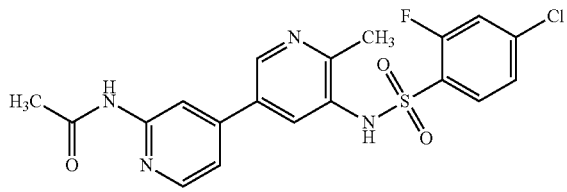
I-94
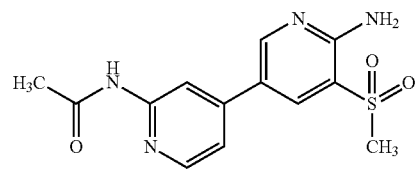 [SMILES: CC(=O)Nc1cc(-c2cnc(N)c(S(C)(=O)=O)c2)ccn1]
I-95
I-96
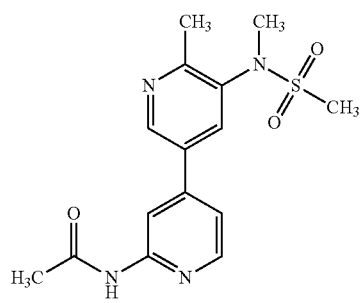 [SMILES: CC(=O)Nc1cc(-c2cnc(C)c(N(C)S(C)(=O)=O)c2)ccn1]
I-97
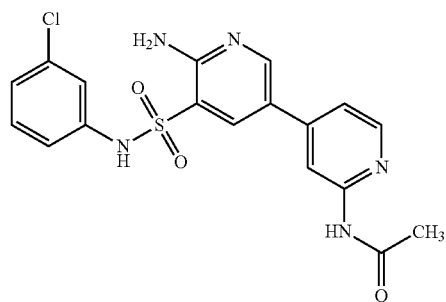 [SMILES: CC(=O)Nc1cc(-c2cnc(N)c(S(=O)(=O)Nc3cccc(Cl)c3)c2)ccn1]
I-98
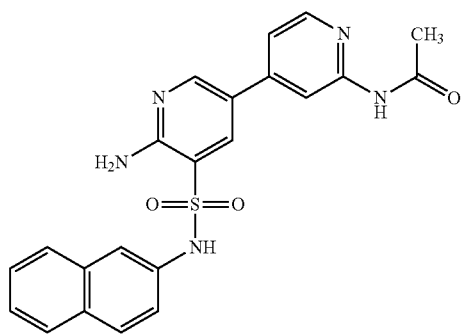 [SMILES: CC(=O)Nc1cc(-c2cnc(N)c(S(=O)(=O)Nc3ccc4ccccc4c3)c2)ccn1]

TABLE 1-continued
Exemplary Compounds
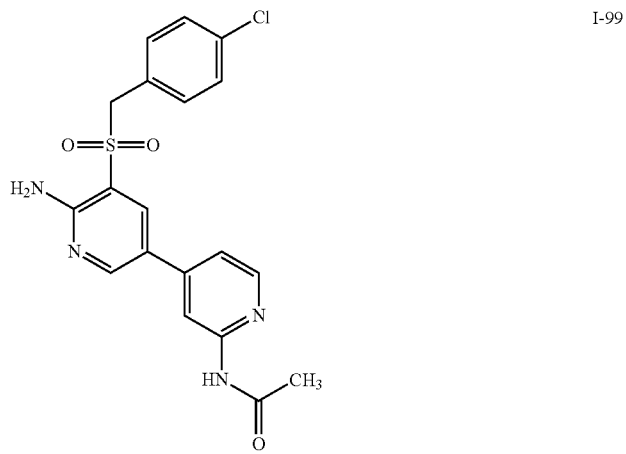
I-99
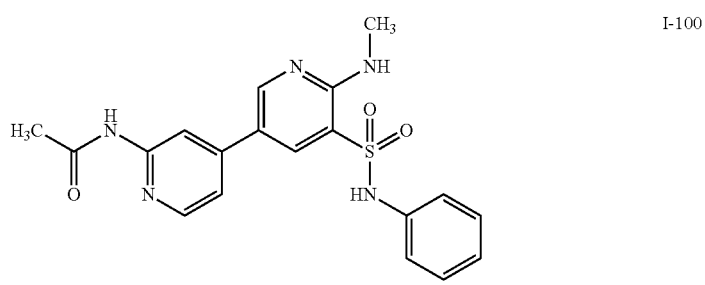
I-100
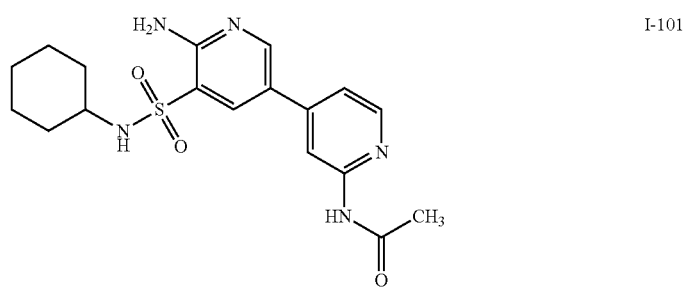
I-101
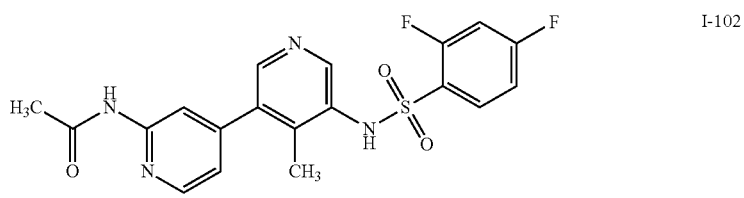
I-102
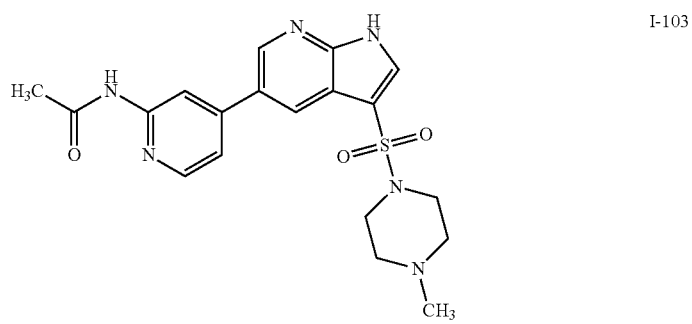
I-103

TABLE 1-continued
Exemplary Compounds
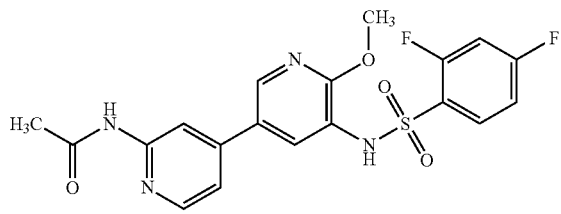 [SMILES: COc1ncc(-c2ccnc(NC(C)=O)c2)cc1NS(=O)(=O)c1ccc(F)cc1F]
I-104
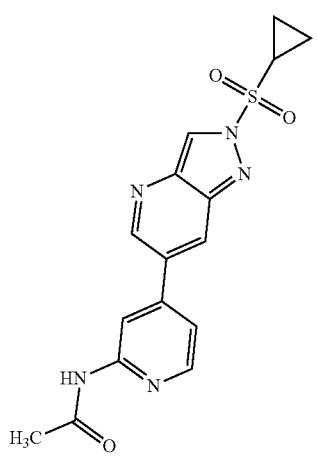 [SMILES: CC(=O)Nc1cc(-c2cnc3cn(S(=O)(=O)C4CC4)nc3c2)ccn1]
I-105
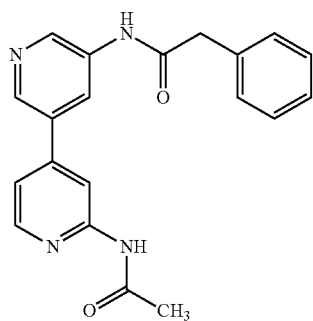 [SMILES: CC(=O)Nc1cc(-c2cncc(NC(=O)Cc3ccccc3)c2)ccn1]
I-106
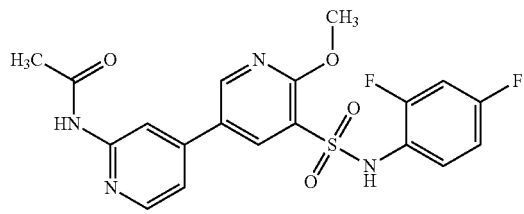 [SMILES: COc1ncc(-c2ccnc(NC(C)=O)c2)cc1S(=O)(=O)Nc1ccc(F)cc1F]
I-107
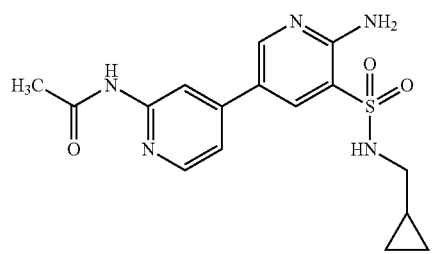 [SMILES: CC(=O)Nc1cc(-c2cnc(N)c(S(=O)(=O)NCC3CC3)c2)ccn1]
I-108

TABLE 1-continued
Exemplary Compounds
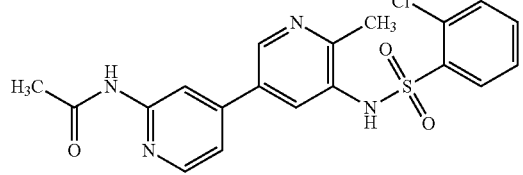
I-109
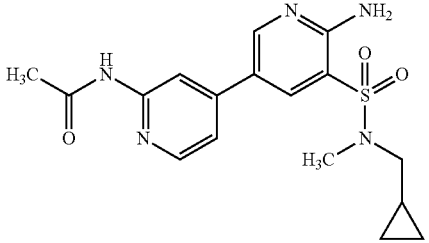 [SMILES: CC(=O)Nc1cc(-c2cnc(N)c(S(=O)(=O)N(C)CC3CC3)c2)ccn1]
I-110
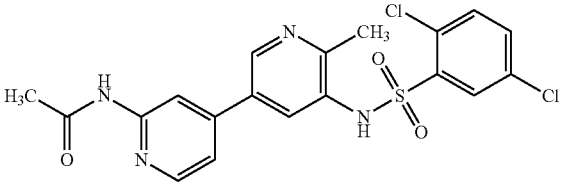 [SMILES: CC(=O)Nc1cc(-c2cnc(C)c(NS(=O)(=O)c3cc(Cl)ccc3Cl)c2)ccn1]
I-111
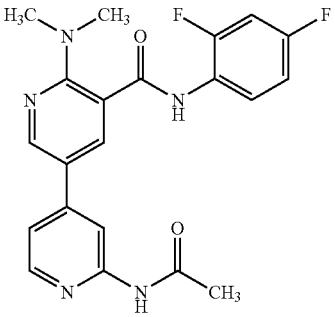 [SMILES: CC(=O)Nc1cc(-c2cnc(N(C)C)c(C(=O)Nc3ccc(F)cc3F)c2)ccn1]
I-112
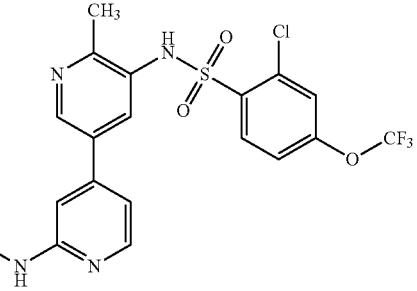
I-113
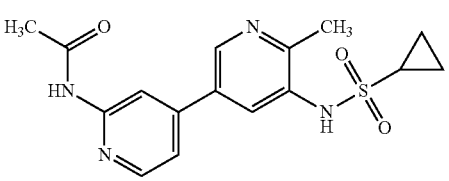 [SMILES: CC(=O)Nc1cc(-c2cnc(C)c(NS(=O)(=O)C3CC3)c2)ccn1]
I-114

TABLE 1-continued

Exemplary Compounds

I-115

I-116

I-117

I-118

I-119

I-120

TABLE 1-continued
Exemplary Compounds
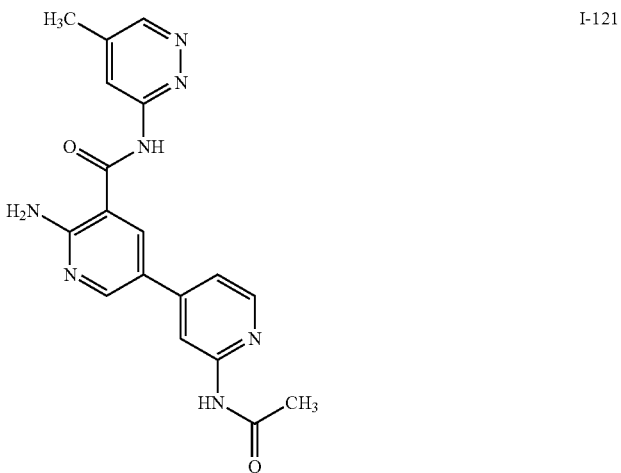 I-121
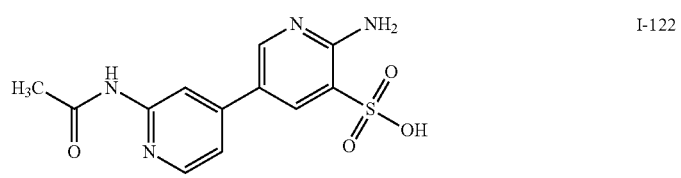 I-122
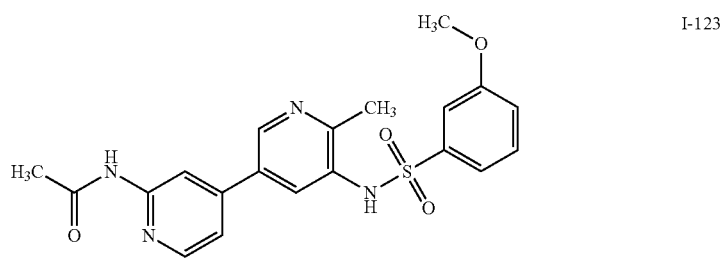 I-123
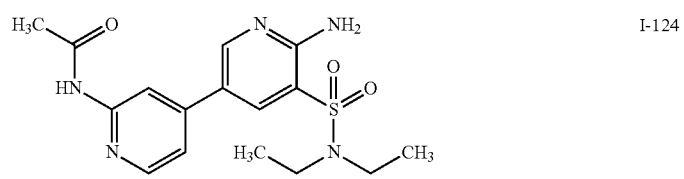 I-124
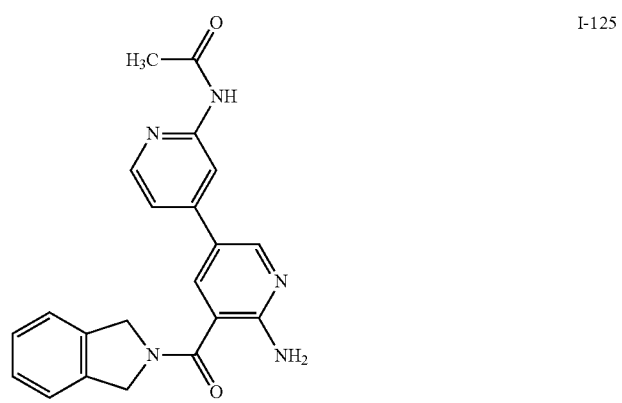 I-125

TABLE 1-continued

Exemplary Compounds

I-126

I-127

I-128

I-129

I-130

TABLE 1-continued
Exemplary Compounds
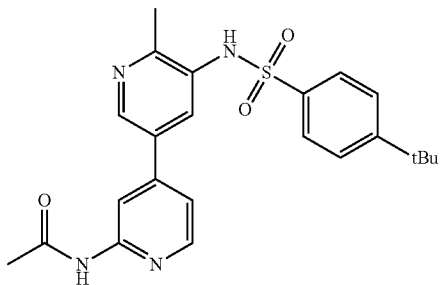 [SMILES: CC(=O)Nc1cc(-c2cnc(C)c(NS(=O)(=O)c3ccc(C(C)(C)C)cc3)c2)ccn1]
I-131
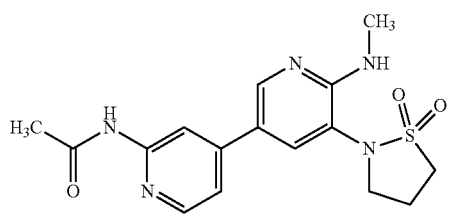 [SMILES: CNc1ncc(-c2ccnc(NC(C)=O)c2)cc1N1CCCS1(=O)=O]
I-132
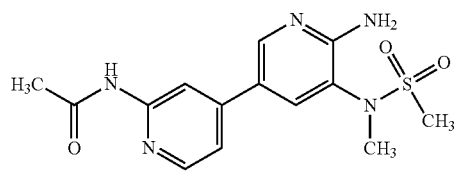 [SMILES: CC(=O)Nc1cc(-c2cnc(N)c(N(C)S(C)(=O)=O)c2)ccn1]
I-133
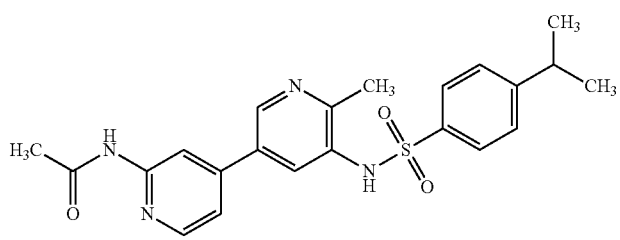 [SMILES: CC(=O)Nc1cc(-c2cnc(C)c(NS(=O)(=O)c3ccc(C(C)C)cc3)c2)ccn1]
I-134
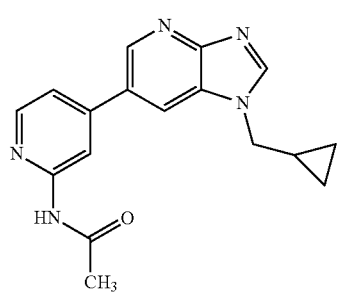 [SMILES: CC(=O)Nc1cc(-c2cnc3ncn(CC4CC4)c3c2)ccn1]
I-135

TABLE 1-continued
Exemplary Compounds
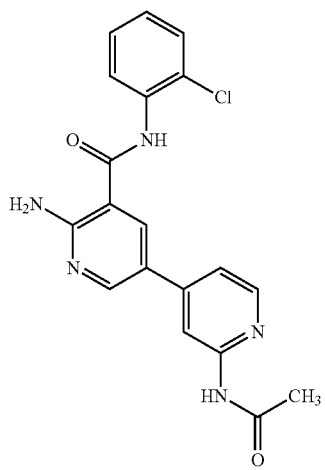 [SMILES: CC(=O)Nc1cc(-c2cnc(N)c(C(=O)Nc3ccccc3Cl)c2)ccn1]
I-136
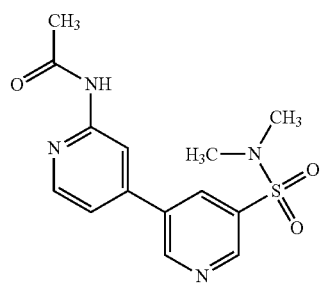 [SMILES: CC(=O)Nc1cc(-c2cncc(S(=O)(=O)N(C)C)c2)ccn1]
I-137
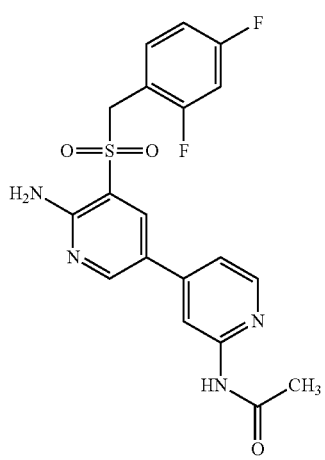 [SMILES: CC(=O)Nc1cc(-c2cnc(N)c(S(=O)(=O)Cc3ccc(F)cc3F)c2)ccn1]
I-138
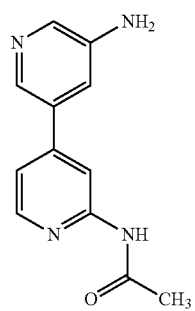
I-139

TABLE 1-continued
Exemplary Compounds
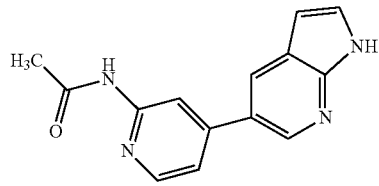 [SMILES: CC(=O)Nc1cc(-c2cnc3[nH]ccc3c2)ccn1]
I-140
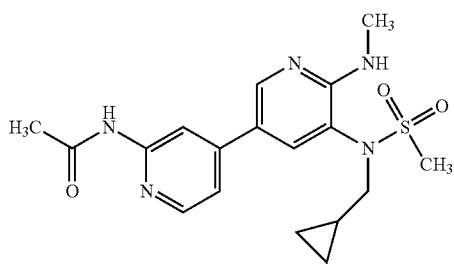 [SMILES: CNc1ncc(-c2ccnc(NC(C)=O)c2)cc1N(CC1CC1)S(C)(=O)=O]
I-141
I-142
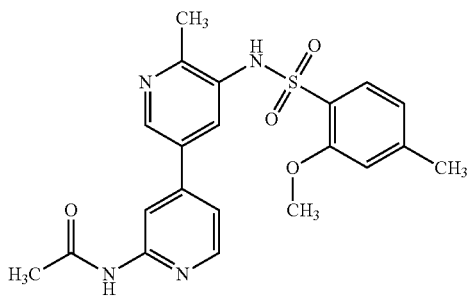 [SMILES: COc1cc(C)ccc1S(=O)(=O)Nc1cc(-c2ccnc(NC(C)=O)c2)cnc1C]
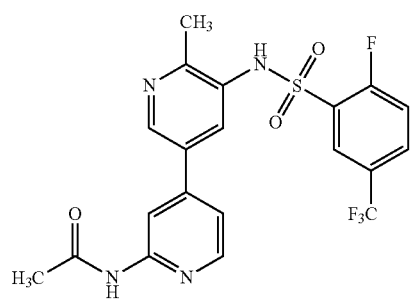 [SMILES: CC(=O)Nc1cc(-c2cnc(C)c(NS(=O)(=O)c3cc(C(F)(F)F)ccc3F)c2)ccn1]
I-143
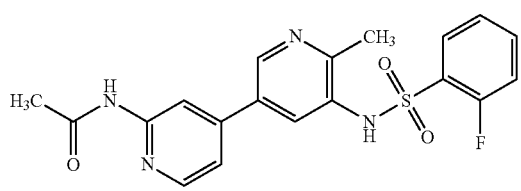 [SMILES: CC(=O)Nc1cc(-c2cnc(C)c(NS(=O)(=O)c3ccccc3F)c2)ccn1]
I-144

TABLE 1-continued
Exemplary Compounds
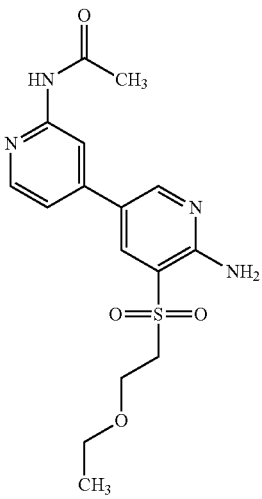 [SMILES: CCOCCS(=O)(=O)c1cc(-c2ccnc(NC(C)=O)c2)cnc1N]
I-145
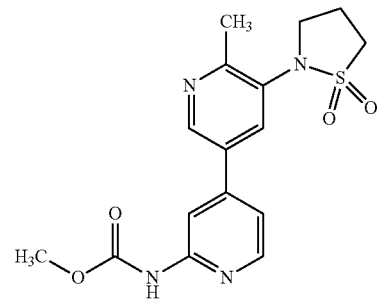 [SMILES: COC(=O)Nc1cc(-c2cnc(C)c(N3CCCS3(=O)=O)c2)ccn1]
I-146
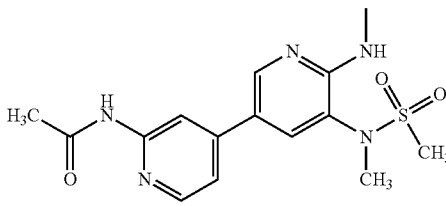
I-147
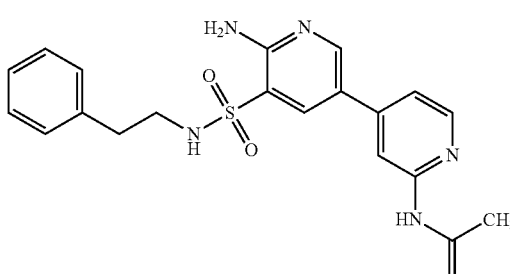
I-148
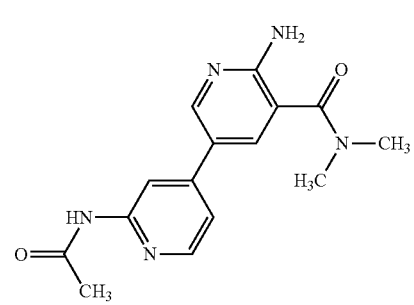 [SMILES: CC(=O)Nc1cc(-c2cnc(N)c(C(=O)N(C)C)c2)ccn1]
I-149

TABLE 1-continued

Exemplary Compounds

| Compound | 
|---|
| I-150 |
| I-151 |
| I-152 |
| I-153 |
| I-154 |
| I-155 |

US 10,538,533 B2
TABLE 1-continued
Exemplary Compounds
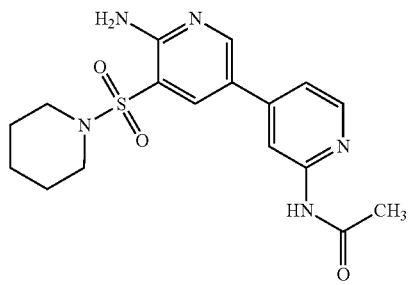 [SMILES: CC(=O)Nc1cc(-c2cnc(N)c(S(=O)(=O)N3CCCCC3)c2)ccn1]
I-156
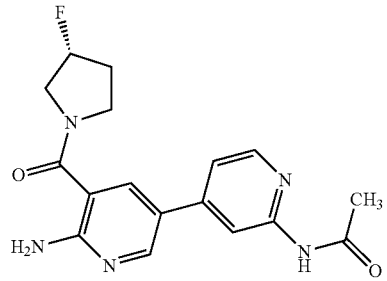 [SMILES: CC(=O)Nc1cc(-c2cnc(N)c(C(=O)N3CC[C@@H](F)C3)c2)ccn1]
I-157
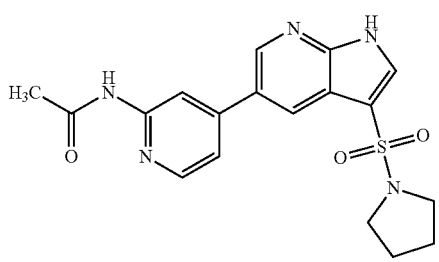 [SMILES: CC(=O)Nc1cc(-c2cnc3[nH]cc(S(=O)(=O)N4CCCC4)c3c2)ccn1]
I-158
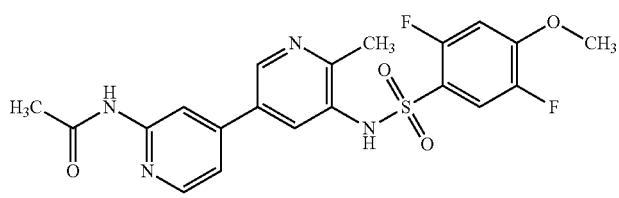 [SMILES: COc1cc(F)c(S(=O)(=O)Nc2cc(-c3ccnc(NC(C)=O)c3)cnc2C)cc1F]
I-159
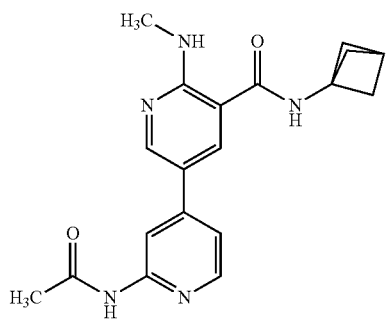 [SMILES: CNc1ncc(-c2ccnc(NC(C)=O)c2)cc1C(=O)NC12CC(C1)C2]
I-160

TABLE 1-continued

Exemplary Compounds

| Compound |
|---|
| I-161 |
| I-162 |
| I-163 |
| I-164 |
| I-165 |
| I-166 |

TABLE 1-continued
Exemplary Compounds
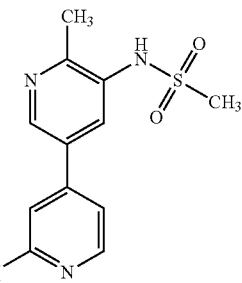
I-167
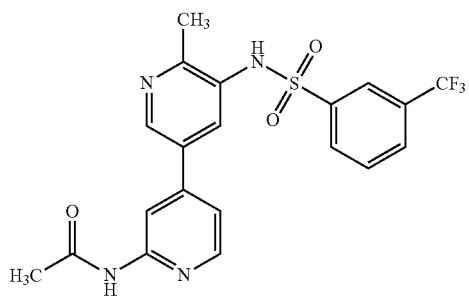 [SMILES: CC(=O)Nc1cc(-c2cnc(C)c(NS(=O)(=O)c3cccc(C(F)(F)F)c3)c2)ccn1]
I-168
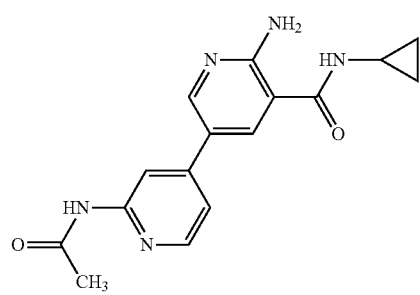 [SMILES: CC(=O)Nc1cc(-c2cnc(N)c(C(=O)NC3CC3)c2)ccn1]
I-169
I-170
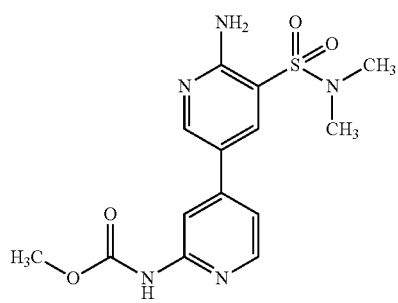
I-171

TABLE 1-continued
Exemplary Compounds
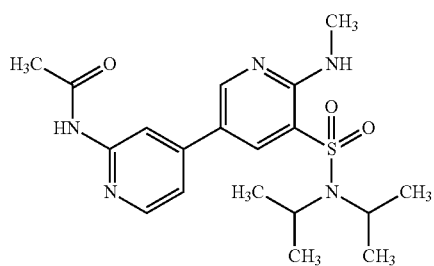 [SMILES: CNc1ncc(-c2ccnc(NC(C)=O)c2)cc1S(=O)(=O)N(C(C)C)C(C)C]
I-172
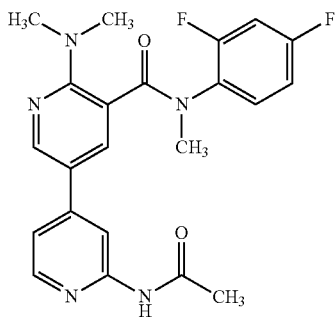 [SMILES: CC(=O)Nc1cc(-c2cnc(N(C)C)c(C(=O)N(C)c3ccc(F)cc3F)c2)ccn1]
I-173
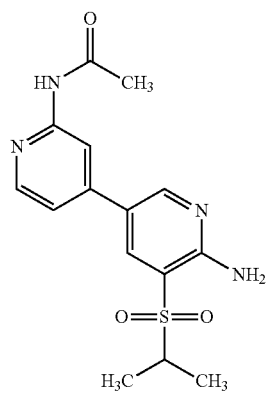 [SMILES: CC(=O)Nc1cc(-c2cnc(N)c(S(=O)(=O)C(C)C)c2)ccn1]
I-174
I-175

TABLE 1-continued
Exemplary Compounds
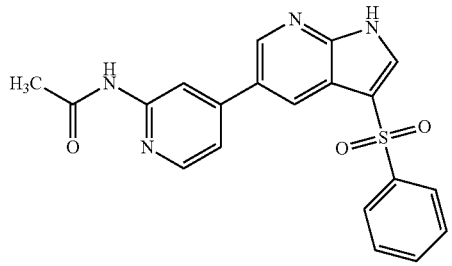 [SMILES: CC(=O)Nc1cc(-c2cnc3[nH]cc(S(=O)(=O)c4ccccc4)c3c2)ccn1]
I-176
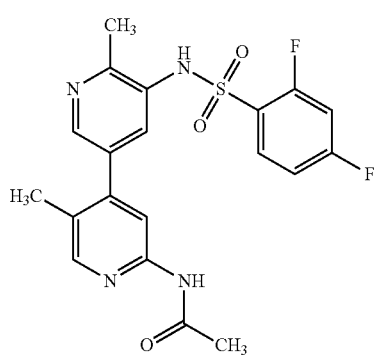 [SMILES: CC(=O)Nc1cc(-c2cnc(C)c(NS(=O)(=O)c3ccc(F)cc3F)c2)c(C)cn1]
I-177
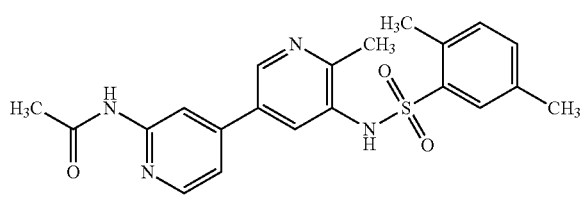 [SMILES: CC(=O)Nc1cc(-c2cnc(C)c(NS(=O)(=O)c3cc(C)ccc3C)c2)ccn1]
I-178
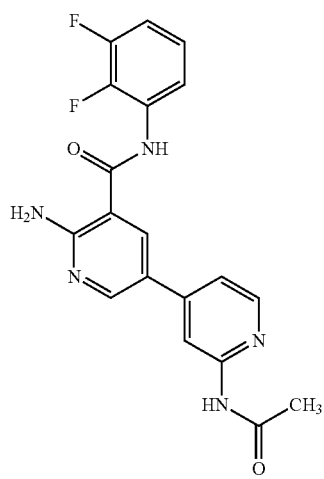 [SMILES: CC(=O)Nc1cc(-c2cnc(N)c(C(=O)Nc3cccc(F)c3F)c2)ccn1]
I-179
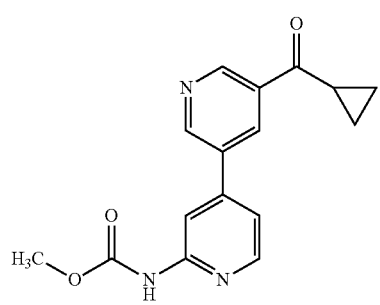 [SMILES: COC(=O)Nc1cc(-c2cncc(C(=O)C3CC3)c2)ccn1]
I-180

TABLE 1-continued

Exemplary Compounds

| | |
|---|---|
| (structure) | I-181 |
| (structure) | I-182 |
| (structure) | I-183 |
| (structure) | I-184 |
| (structure) | I-185 |
| (structure) | I-186 |

TABLE 1-continued

Exemplary Compounds

I-187

I-188

I-189

I-190

I-191

TABLE 1-continued
Exemplary Compounds
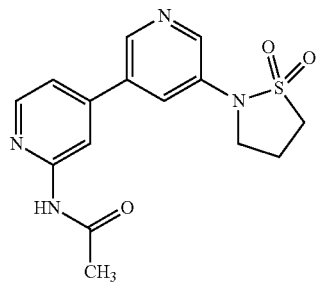 [SMILES: CC(=O)Nc1cc(-c2cncc(N3CCCS3(=O)=O)c2)ccn1]
I-192
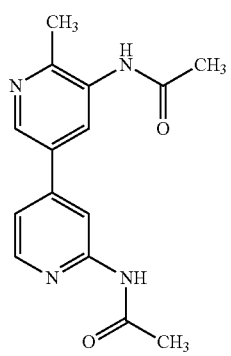 [SMILES: CC(=O)Nc1cc(-c2cnc(C)c(NC(C)=O)c2)ccn1]
I-193
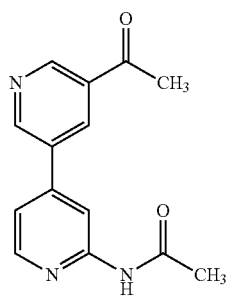 [SMILES: CC(=O)Nc1cc(-c2cncc(C(C)=O)c2)ccn1]
I-194
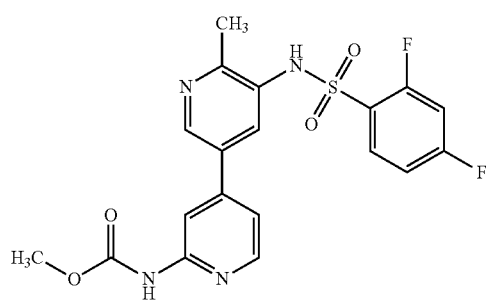 [SMILES: COC(=O)Nc1cc(-c2cnc(C)c(NS(=O)(=O)c3ccc(F)cc3F)c2)ccn1]
I-195
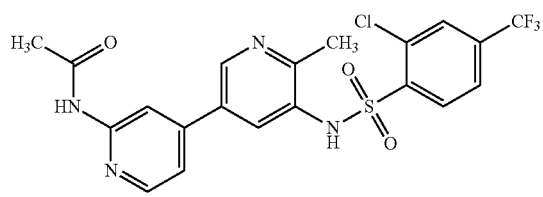 [SMILES: CC(=O)Nc1cc(-c2cnc(C)c(NS(=O)(=O)c3ccc(C(F)(F)F)cc3Cl)c2)ccn1]
I-196

115 116
TABLE 1-continued
Exemplary Compounds
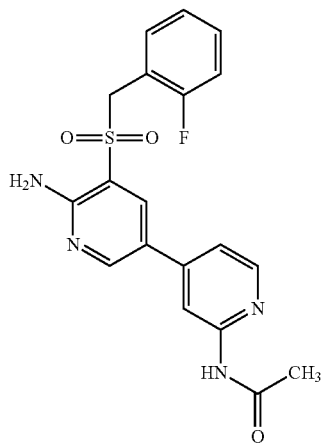 [SMILES: CC(=O)Nc1cc(-c2cnc(N)c(S(=O)(=O)Cc3ccccc3F)c2)ccn1]
I-197
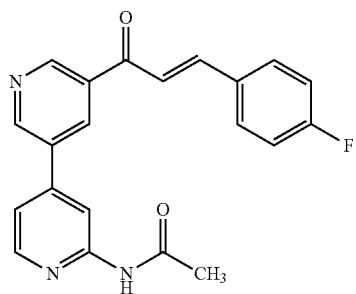 [SMILES: CC(=O)Nc1cc(-c2cncc(C(=O)/C=C/c3ccc(F)cc3)c2)ccn1]
I-198
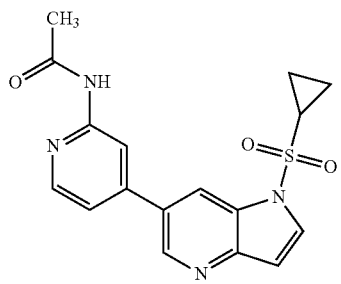 [SMILES: CC(=O)Nc1cc(-c2cnc3ccn(S(=O)(=O)C4CC4)c3c2)ccn1]
I-199
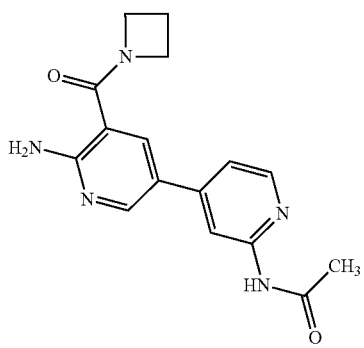 [SMILES: CC(=O)Nc1cc(-c2cnc(N)c(C(=O)N3CCC3)c2)ccn1]
I-200
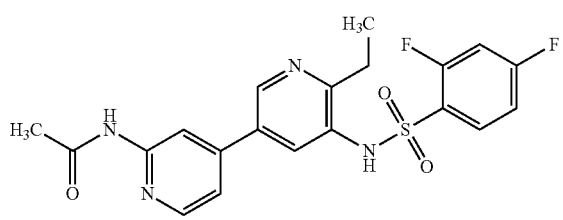 [SMILES: CCc1ncc(-c2ccnc(NC(C)=O)c2)cc1NS(=O)(=O)c1ccc(F)cc1F]
I-201

TABLE 1-continued
Exemplary Compounds
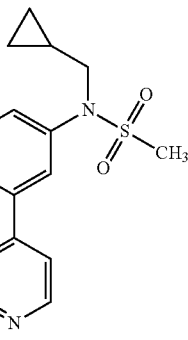 I-202
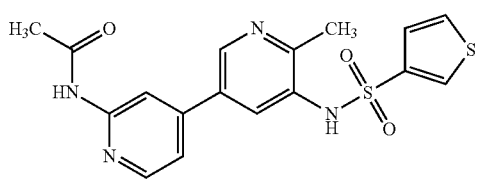 [SMILES: CC(=O)Nc1cc(-c2cnc(C)c(NS(=O)(=O)c3ccsc3)c2)ccn1] I-203
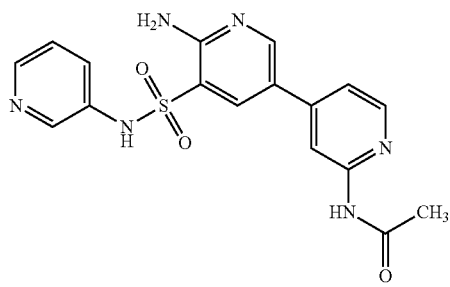 [SMILES: CC(=O)Nc1cc(-c2cnc(N)c(S(=O)(=O)Nc3cccnc3)c2)ccn1] I-204
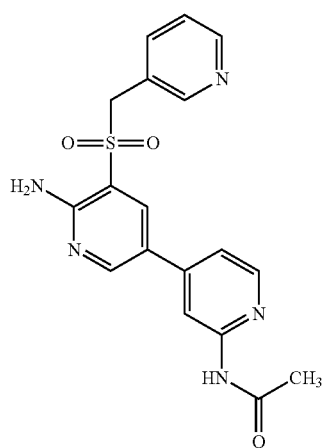 [SMILES: CC(=O)Nc1cc(-c2cnc(N)c(S(=O)(=O)Cc3cccnc3)c2)ccn1] I-205
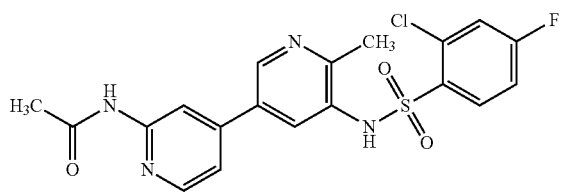 [SMILES: CC(=O)Nc1cc(-c2cnc(C)c(NS(=O)(=O)c3ccc(F)cc3Cl)c2)ccn1] I-206

TABLE 1-continued

Exemplary Compounds

I-207

I-208

I-209

I-210

I-211

TABLE 1-continued

Exemplary Compounds

| | |
|---|---|
| (structure) | I-212 |
| (structure) | I-213 |
| (structure) | I-214 |
| (structure) | I-215 |
| (structure) | I-216 |

TABLE 1-continued
Exemplary Compounds
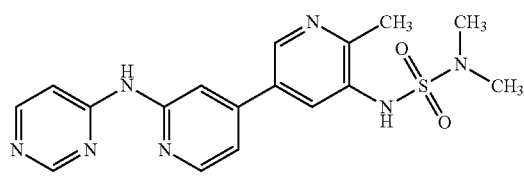 [SMILES: Cc1ncc(-c2ccnc(Nc3ccncn3)c2)cc1NS(=O)(=O)N(C)C]
I-217
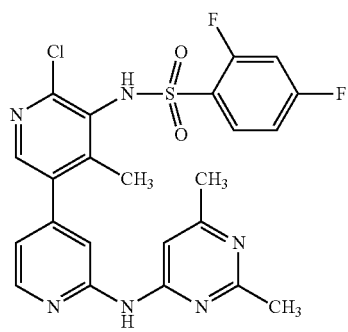 [SMILES: Cc1cc(Nc2cc(-c3cnc(Cl)c(NS(=O)(=O)c4ccc(F)cc4F)c3C)ccn2)nc(C)n1]
I-218
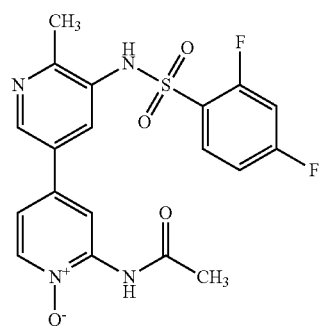 [SMILES: CC(=O)Nc1cc(-c2cnc(C)c(NS(=O)(=O)c3ccc(F)cc3F)c2)cc[n+]1[O-]]
I-219
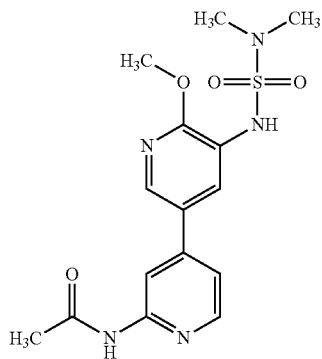 [SMILES: COc1ncc(-c2ccnc(NC(C)=O)c2)cc1NS(=O)(=O)N(C)C]
I-220
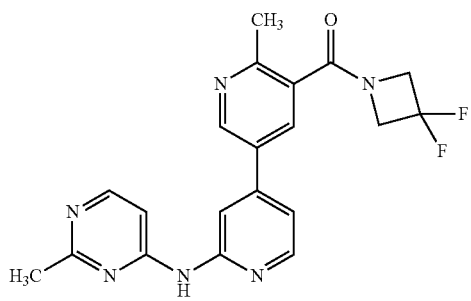 [SMILES: Cc1nccc(Nc2cc(-c3cnc(C)c(C(=O)N4CC(F)(F)C4)c3)ccn2)n1]
I-221

TABLE 1-continued

Exemplary Compounds

| Compound | ID |
|---|---|
| (structure) | I-222 |
| (structure) | I-223 |
| (structure) | I-224 |
| (structure) | I-225 |
| (structure) | I-226 |

TABLE 1-continued
Exemplary Compounds
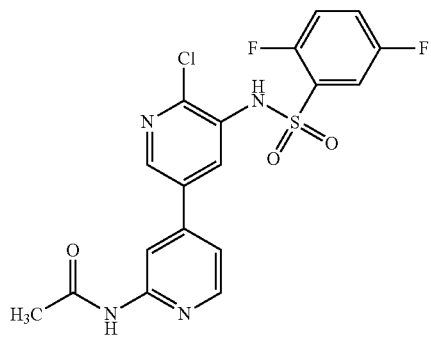 [SMILES: CC(=O)Nc1cc(-c2cnc(Cl)c(NS(=O)(=O)c3cc(F)ccc3F)c2)ccn1]
I-227
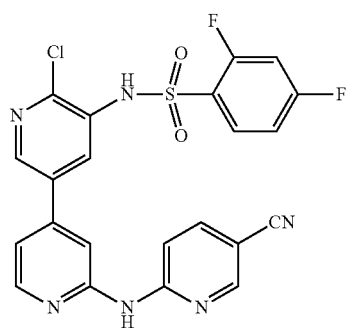 [SMILES: N#Cc1ccc(Nc2cc(-c3cnc(Cl)c(NS(=O)(=O)c4ccc(F)cc4F)c3)ccn2)nc1]
I-228
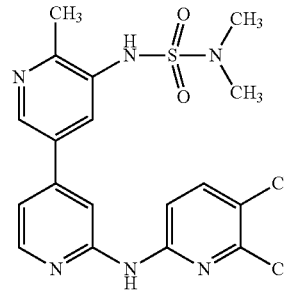
I-229
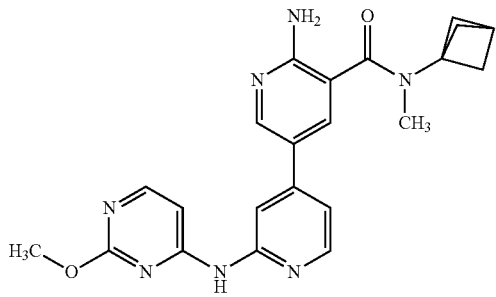 [SMILES: COc1nccc(Nc2cc(-c3cnc(N)c(C(=O)N(C)C45CC(C4)C5)c3)ccn2)n1]
I-230
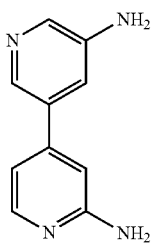
I-231

TABLE 1-continued
Exemplary Compounds
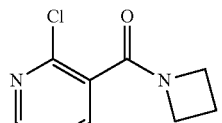
I-232
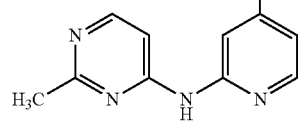
I-233
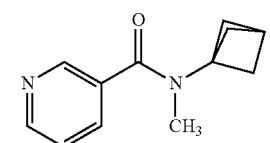
I-234
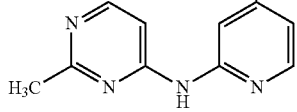
I-235
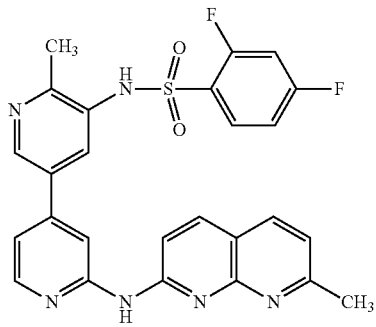 [SMILES: Cc1ccc2ccc(Nc3cc(-c4cnc(C)c(NS(=O)(=O)c5ccc(F)cc5F)c4)ccn3)nc2n1]
I-236

TABLE 1-continued
Exemplary Compounds
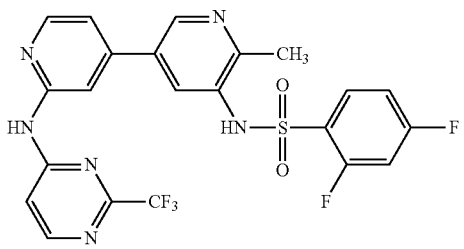 [SMILES: Cc1ncc(-c2ccnc(Nc3ccnc(C(F)(F)F)n3)c2)cc1NS(=O)(=O)c1ccc(F)cc1F]
I-237
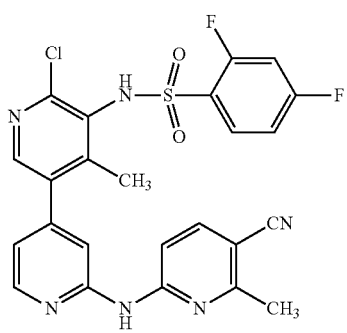 [SMILES: Cc1nc(Nc2cc(-c3cnc(Cl)c(NS(=O)(=O)c4ccc(F)cc4F)c3C)ccn2)ccc1C#N]
I-238
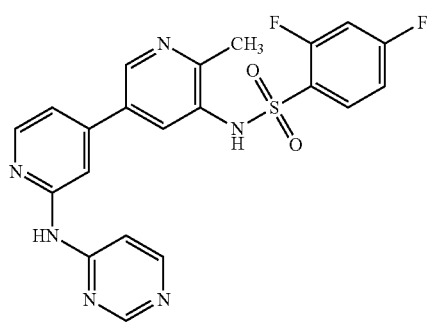 [SMILES: Cc1ncc(-c2ccnc(Nc3ccncn3)c2)cc1NS(=O)(=O)c1ccc(F)cc1F]
I-239
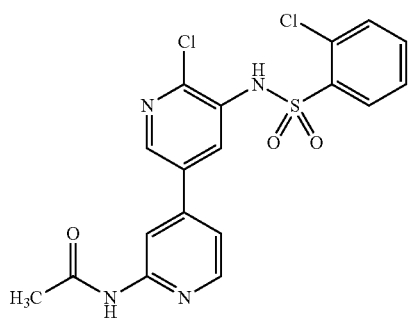 [SMILES: CC(=O)Nc1cc(-c2cnc(Cl)c(NS(=O)(=O)c3ccccc3Cl)c2)ccn1]
I-240
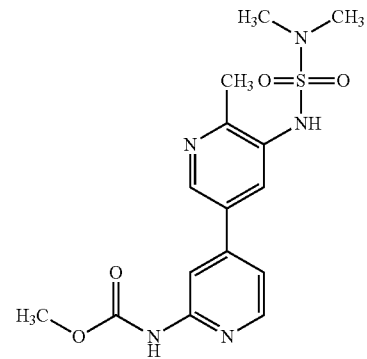 [SMILES: COC(=O)Nc1cc(-c2cnc(C)c(NS(=O)(=O)N(C)C)c2)ccn1]
I-241

TABLE 1-continued
Exemplary Compounds
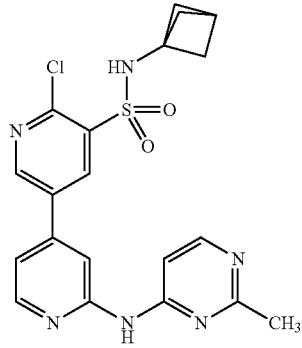 [SMILES: Cc1nccc(Nc2cc(-c3cnc(Cl)c(S(=O)(=O)NC45CC(C4)C5)c3)ccn2)n1]
I-242
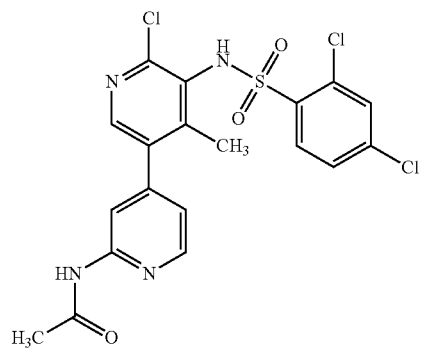 [SMILES: CC(=O)Nc1cc(-c2cnc(Cl)c(NS(=O)(=O)c3ccc(Cl)cc3Cl)c2C)ccn1]
I-243
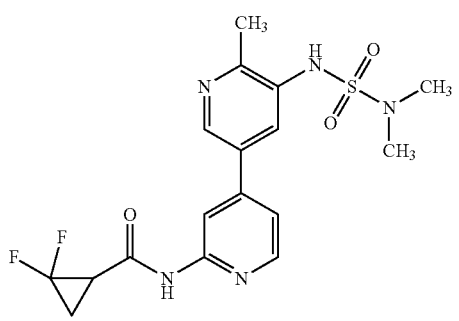 [SMILES: Cc1ncc(-c2ccnc(NC(=O)C3CC3(F)F)c2)cc1NS(=O)(=O)N(C)C]
I-244
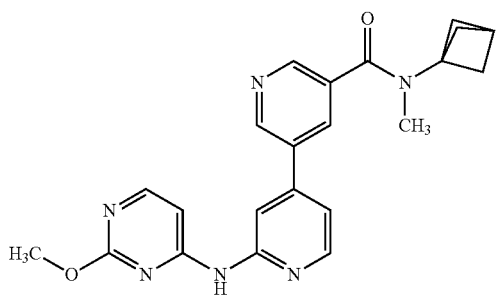 [SMILES: COc1nccc(Nc2cc(-c3cncc(C(=O)N(C)C45CC(C4)C5)c3)ccn2)n1]
I-245

TABLE 1-continued
Exemplary Compounds
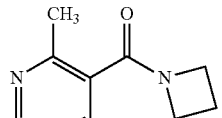
I-246
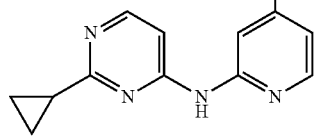
I-247
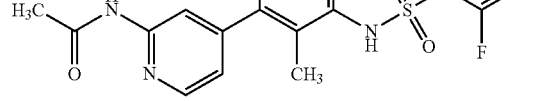
I-248
I-249
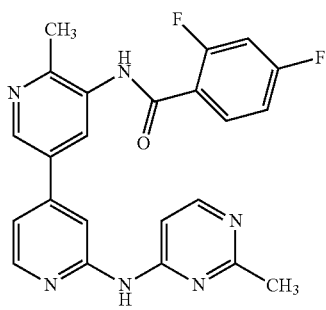 [SMILES: Cc1nccc(Nc2cc(-c3cnc(C)c(NC(=O)c4ccc(F)cc4F)c3)ccn2)n1]
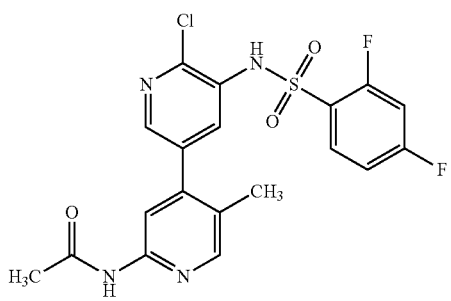 [SMILES: CC(=O)Nc1cc(-c2cnc(Cl)c(NS(=O)(=O)c3ccc(F)cc3F)c2)c(C)cn1]
I-250

TABLE 1-continued

Exemplary Compounds

I-251

I-252

I-253

I-254

I-255

TABLE 1-continued
Exemplary Compounds
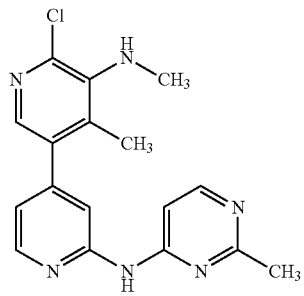 [SMILES: CNc1c(Cl)ncc(-c2ccnc(Nc3ccnc(C)n3)c2)c1C]
I-256
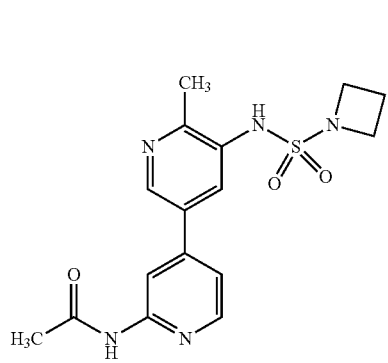 [SMILES: CC(=O)Nc1cc(-c2cnc(C)c(NS(=O)(=O)N3CCC3)c2)ccn1]
I-257
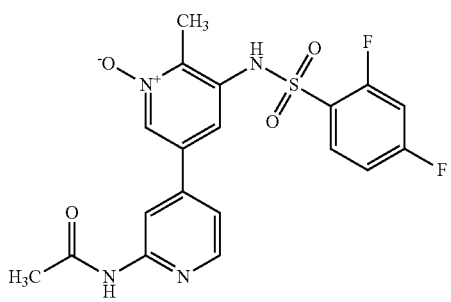 [SMILES: CC(=O)Nc1cc(-c2cc(NS(=O)(=O)c3ccc(F)cc3F)c(C)[n+]([O-])c2)ccn1]
I-258
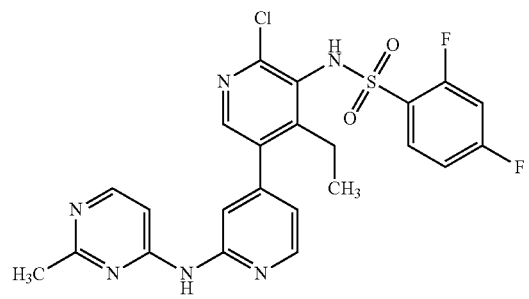 [SMILES: CCc1c(-c2ccnc(Nc3ccnc(C)n3)c2)cnc(Cl)c1NS(=O)(=O)c1ccc(F)cc1F]
I-259
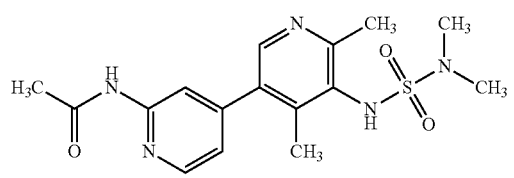 [SMILES: CC(=O)Nc1cc(-c2cnc(C)c(NS(=O)(=O)N(C)C)c2C)ccn1]
I-260

TABLE 1-continued
Exemplary Compounds
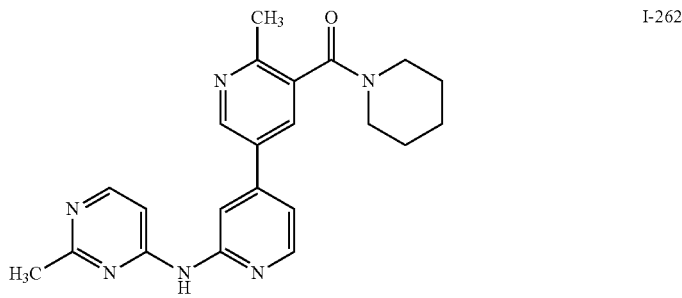
I-262
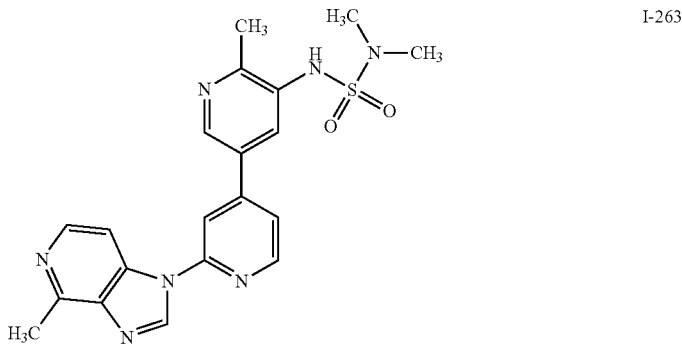
I-263
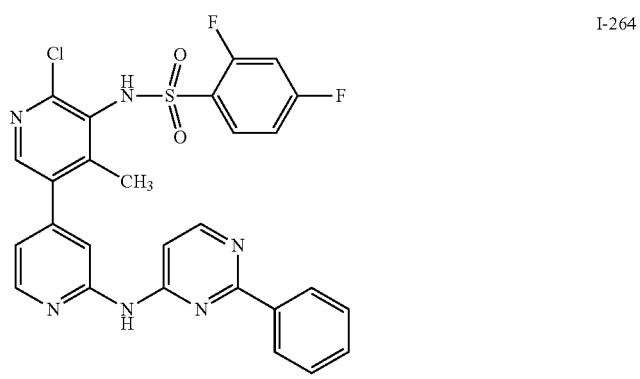
I-264
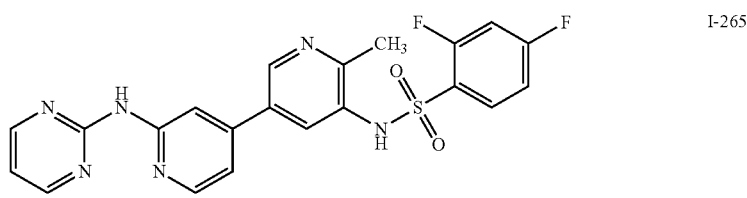
I-265
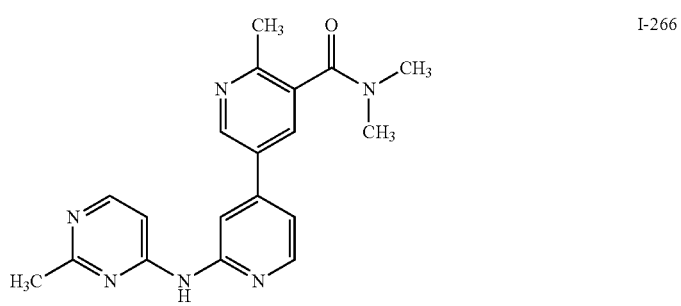
I-266

TABLE 1-continued
Exemplary Compounds
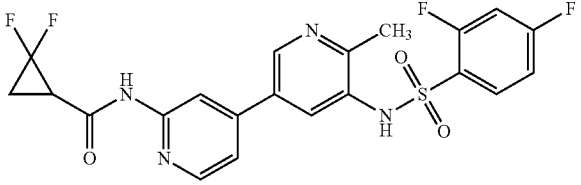
(Chiral Sep Peak1)
I-267a
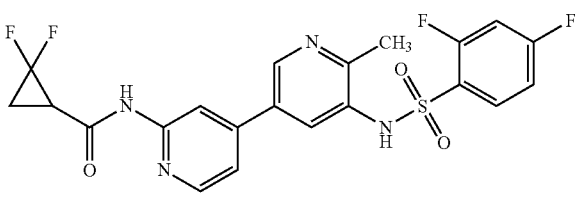
(Chiral Sep Peak2)
I-267b
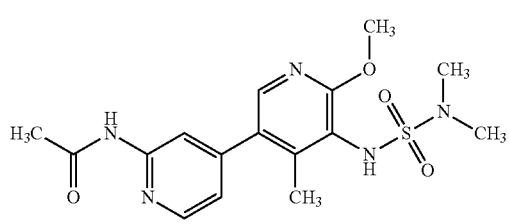 [SMILES: COc1ncc(-c2ccnc(NC(C)=O)c2)c(C)c1NS(=O)(=O)N(C)C]
I-268
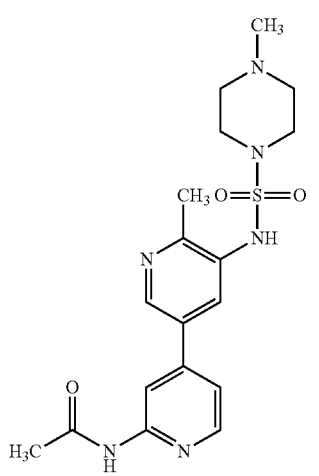 [SMILES: CC(=O)Nc1cc(-c2cnc(C)c(NS(=O)(=O)N3CCN(C)CC3)c2)ccn1]
I-269
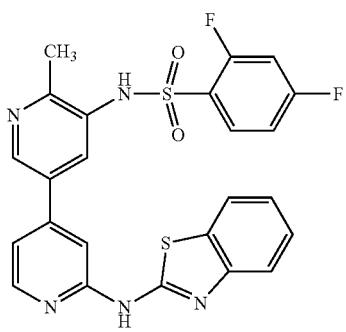 [SMILES: Cc1ncc(-c2ccnc(Nc3nc4ccccc4s3)c2)cc1NS(=O)(=O)c1ccc(F)cc1F]
I-271

TABLE 1-continued
Exemplary Compounds
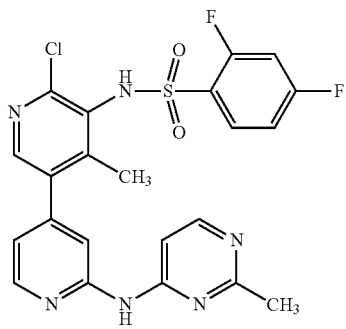 [SMILES: Cc1nccc(Nc2cc(-c3cnc(Cl)c(NS(=O)(=O)c4ccc(F)cc4F)c3C)ccn2)n1]
I-272
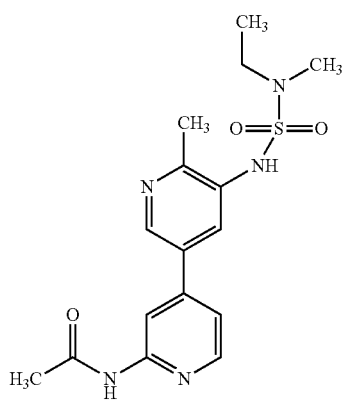 [SMILES: CCN(C)S(=O)(=O)Nc1cc(-c2ccnc(NC(C)=O)c2)cnc1C]
I-273
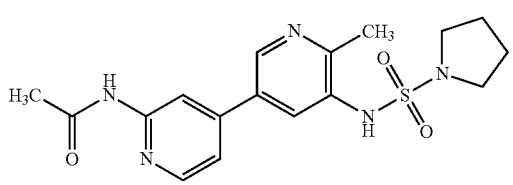 [SMILES: CC(=O)Nc1cc(-c2cnc(C)c(NS(=O)(=O)N3CCCC3)c2)ccn1]
I-274
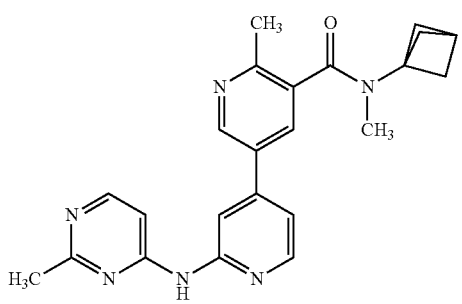 [SMILES: Cc1nccc(Nc2cc(-c3cnc(C)c(C(=O)N(C)C45CC(C4)C5)c3)ccn2)n1]
I-275
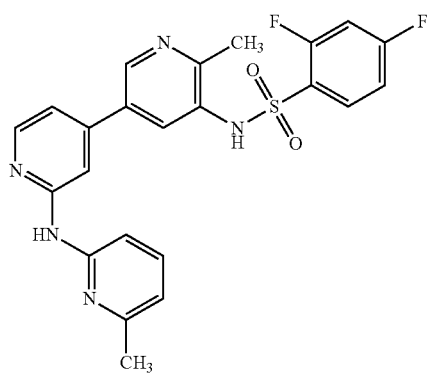 [SMILES: Cc1cccc(Nc2cc(-c3cnc(C)c(NS(=O)(=O)c4ccc(F)cc4F)c3)ccn2)n1]
I-276

TABLE 1-continued
Exemplary Compounds
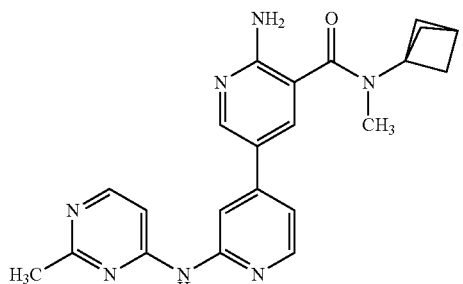
I-277
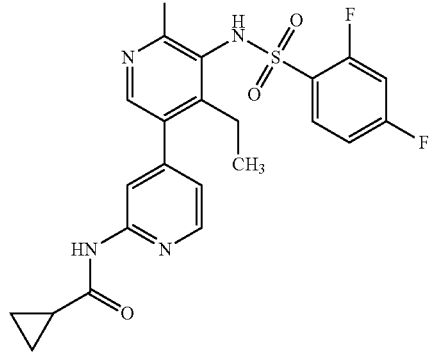
I-278
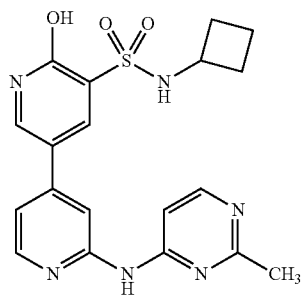 [SMILES: Cc1nccc(Nc2cc(-c3cnc(O)c(S(=O)(=O)NC4CCC4)c3)ccn2)n1]
I-279
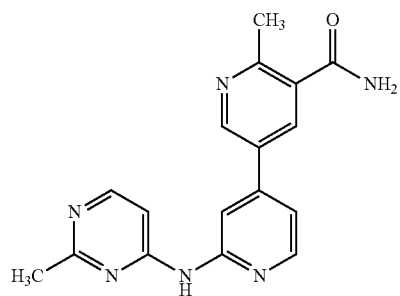 [SMILES: Cc1nccc(Nc2cc(-c3cnc(C)c(C(N)=O)c3)ccn2)n1]
I-280

TABLE 1-continued
Exemplary Compounds
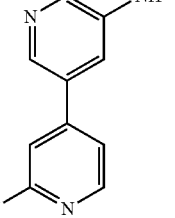 I-281
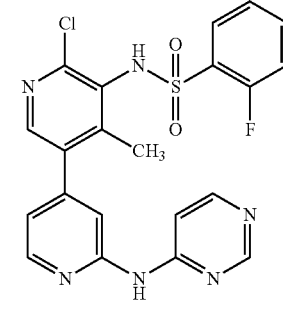 I-282
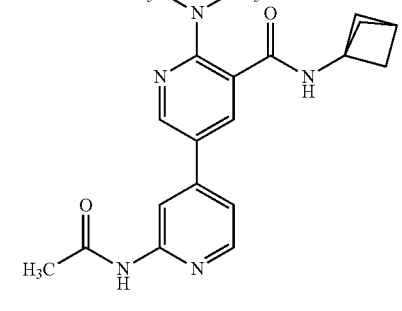 I-283
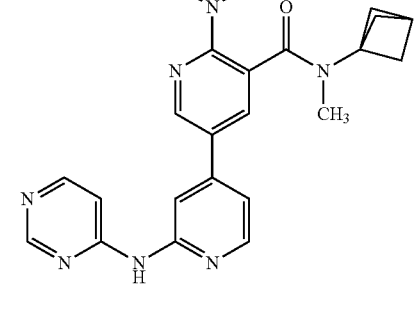 I-284
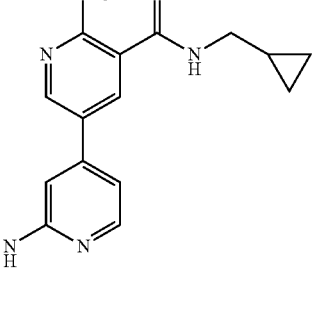 I-285

TABLE 1-continued
Exemplary Compounds
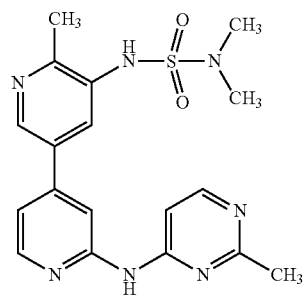 [SMILES: Cc1nccc(Nc2cc(-c3cnc(C)c(NS(=O)(=O)N(C)C)c3)ccn2)n1]
I-286
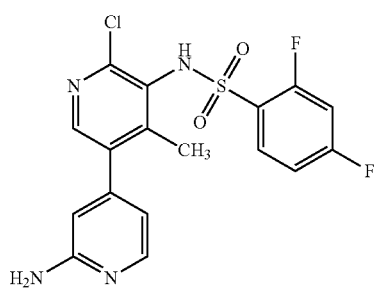 [SMILES: Cc1c(-c2ccnc(N)c2)cnc(Cl)c1NS(=O)(=O)c1ccc(F)cc1F]
I-287
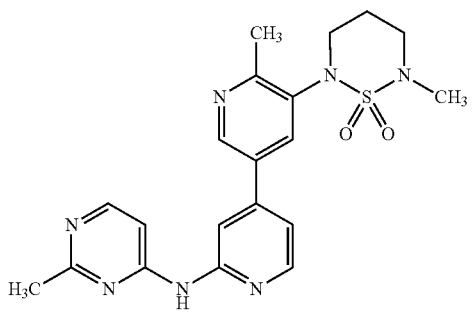
I-288
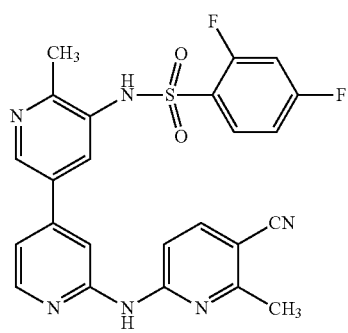 [SMILES: Cc1nc(Nc2cc(-c3cnc(C)c(NS(=O)(=O)c4ccc(F)cc4F)c3)ccn2)ccc1C#N]
I-289
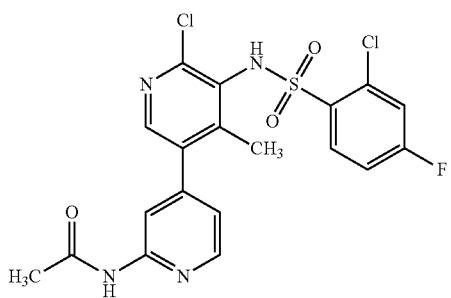 [SMILES: CC(=O)Nc1cc(-c2cnc(Cl)c(NS(=O)(=O)c3ccc(F)cc3Cl)c2C)ccn1]
I-290

TABLE 1-continued
Exemplary Compounds
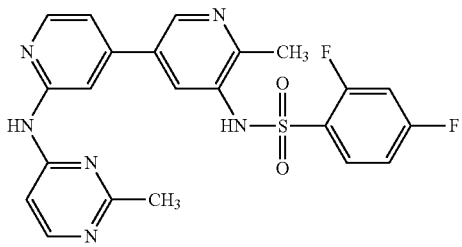 [SMILES: Cc1nccc(Nc2cc(-c3cnc(C)c(NS(=O)(=O)c4ccc(F)cc4F)c3)ccn2)n1] I-291
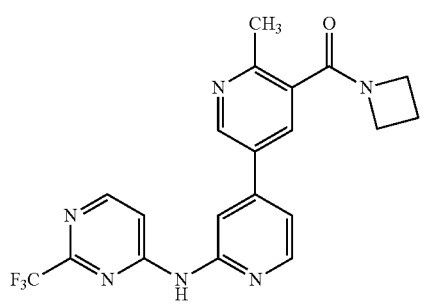 [SMILES: Cc1ncc(-c2ccnc(Nc3ccnc(C(F)(F)F)n3)c2)cc1C(=O)N1CCC1] I-292
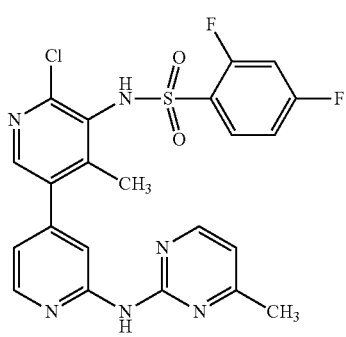 [SMILES: Cc1ccnc(Nc2cc(-c3cnc(Cl)c(NS(=O)(=O)c4ccc(F)cc4F)c3C)ccn2)n1] I-293
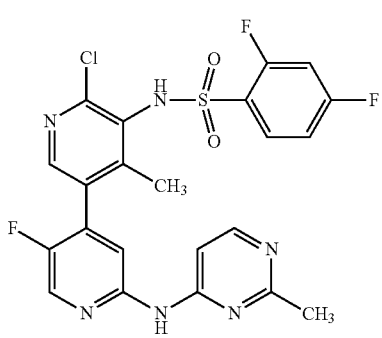 [SMILES: Cc1nccc(Nc2cc(-c3cnc(Cl)c(NS(=O)(=O)c4ccc(F)cc4F)c3C)c(F)cn2)n1] I-294
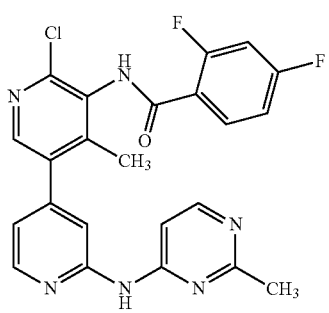 [SMILES: Cc1nccc(Nc2cc(-c3cnc(Cl)c(NC(=O)c4ccc(F)cc4F)c3C)ccn2)n1] I-295

TABLE 1-continued
Exemplary Compounds
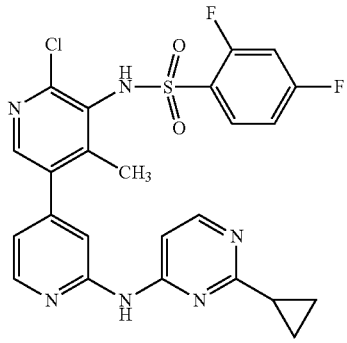 [SMILES: Cc1c(-c2ccnc(Nc3ccnc(C4CC4)n3)c2)cnc(Cl)c1NS(=O)(=O)c1ccc(F)cc1F]
I-296
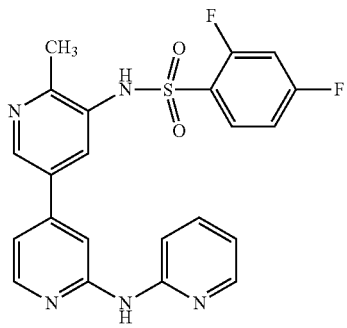 [SMILES: Cc1ncc(-c2ccnc(Nc3ccccn3)c2)cc1NS(=O)(=O)c1ccc(F)cc1F]
I-297
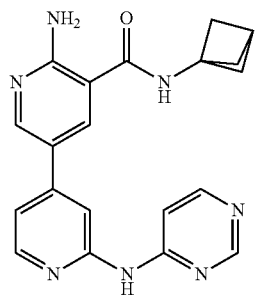 [SMILES: Nc1ncc(-c2ccnc(Nc3ccncn3)c2)cc1C(=O)NC12CC(C1)C2]
I-298
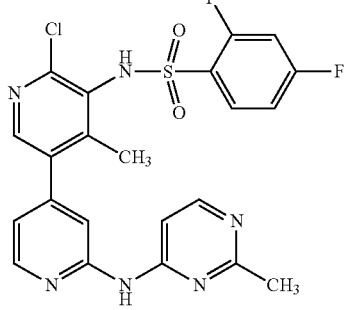
I-299

TABLE 1-continued
Exemplary Compounds
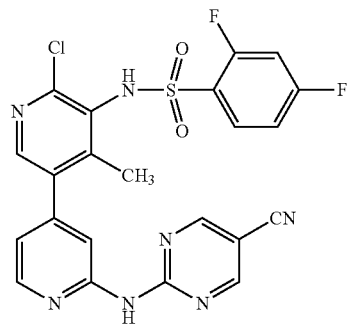 [SMILES: Cc1c(-c2ccnc(Nc3ncc(C#N)cn3)c2)cnc(Cl)c1NS(=O)(=O)c1ccc(F)cc1F]
I-300
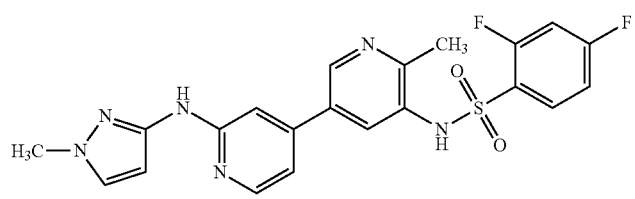 [SMILES: Cc1ncc(-c2ccnc(Nc3ccn(C)n3)c2)cc1NS(=O)(=O)c1ccc(F)cc1F]
I-301
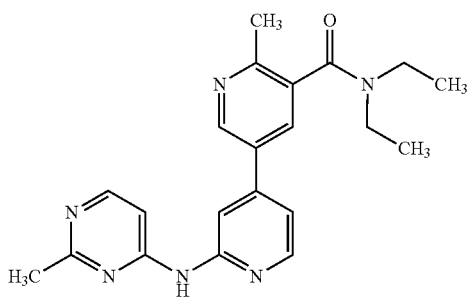 [SMILES: CCN(CC)C(=O)c1cc(-c2ccnc(Nc3ccnc(C)n3)c2)cnc1C]
I-302
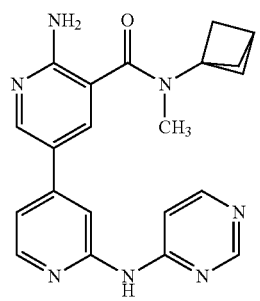 [SMILES: CN(C(=O)c1cc(-c2ccnc(Nc3ccncn3)c2)cnc1N)C12CC(C1)C2]
I-303
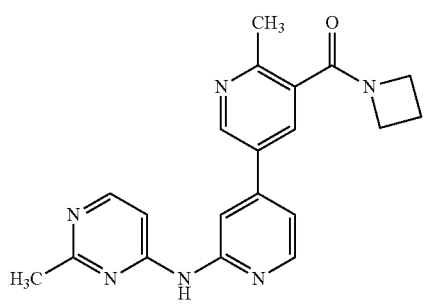
I-304

US 10,538,533 B2
TABLE 1-continued
Exemplary Compounds
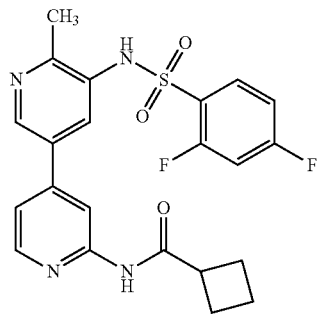 [SMILES: Cc1ncc(-c2ccnc(NC(=O)C3CCC3)c2)cc1NS(=O)(=O)c1ccc(F)cc1F]
I-305
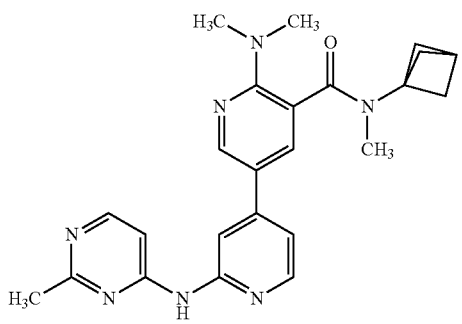 [SMILES: Cc1nccc(Nc2cc(-c3cnc(N(C)C)c(C(=O)N(C)C45CC(C4)C5)c3)ccn2)n1]
I-306
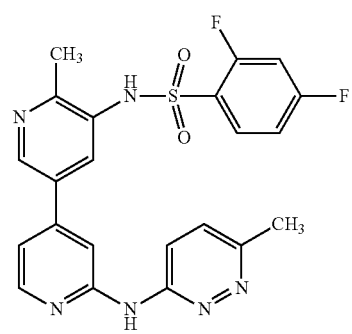 [SMILES: Cc1ccc(Nc2cc(-c3cnc(C)c(NS(=O)(=O)c4ccc(F)cc4F)c3)ccn2)nn1]
I-307
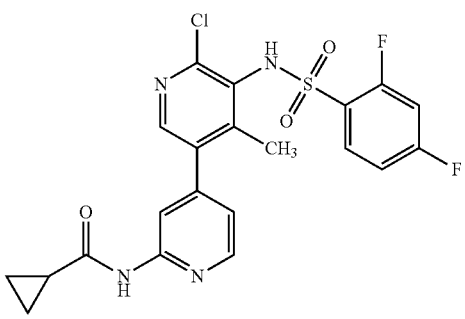 [SMILES: Cc1c(-c2ccnc(NC(=O)C3CC3)c2)cnc(Cl)c1NS(=O)(=O)c1ccc(F)cc1F]
I-308
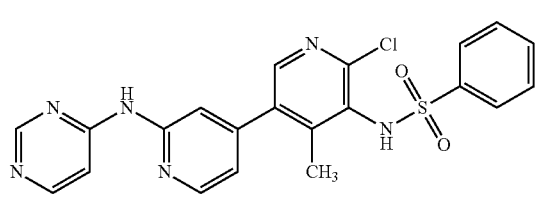 [SMILES: Cc1c(-c2ccnc(Nc3ccncn3)c2)cnc(Cl)c1NS(=O)(=O)c1ccccc1]
I-309

TABLE 1-continued
Exemplary Compounds
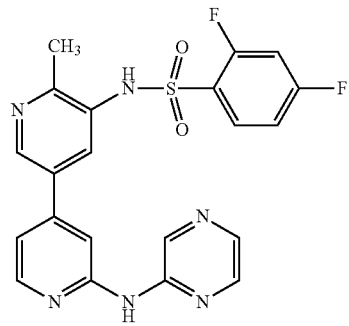 [SMILES: Cc1ncc(-c2ccnc(Nc3cnccn3)c2)cc1NS(=O)(=O)c1ccc(F)cc1F]
I-310
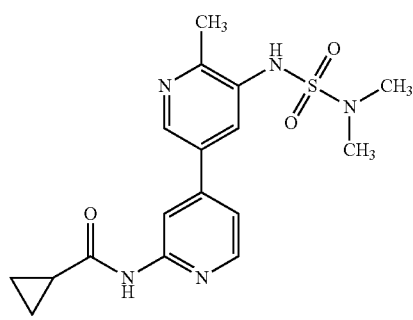 [SMILES: Cc1ncc(-c2ccnc(NC(=O)C3CC3)c2)cc1NS(=O)(=O)N(C)C]
I-311
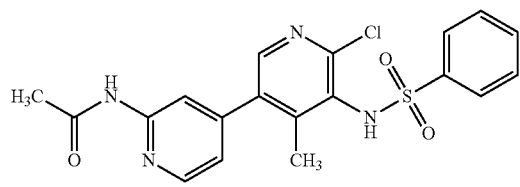 [SMILES: CC(=O)Nc1cc(-c2cnc(Cl)c(NS(=O)(=O)c3ccccc3)c2C)ccn1]
I-312
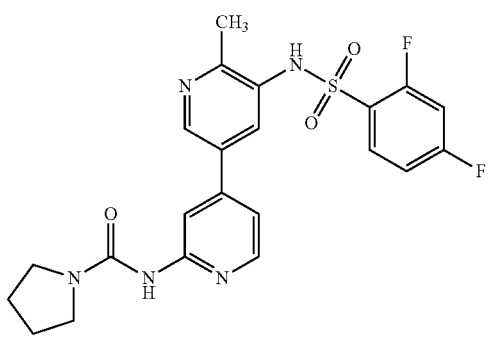 [SMILES: Cc1ncc(-c2ccnc(NC(=O)N3CCCC3)c2)cc1NS(=O)(=O)c1ccc(F)cc1F]
I-313
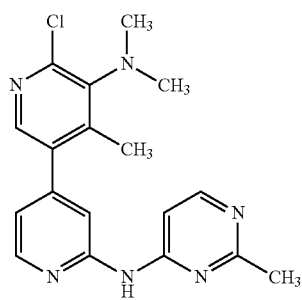 [SMILES: Cc1nccc(Nc2cc(-c3cnc(Cl)c(N(C)C)c3C)ccn2)n1]
I-314

TABLE 1-continued
Exemplary Compounds
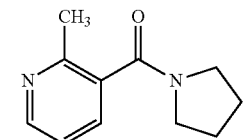
I-315
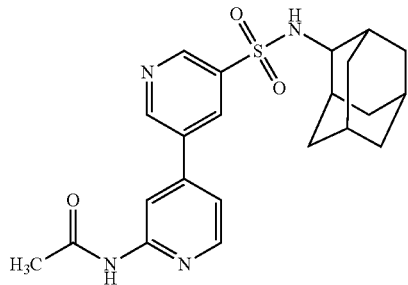 [SMILES: CC(=O)Nc1cc(-c2cncc(S(=O)(=O)NC3C4CC5CC(C4)CC3C5)c2)ccn1]
I-318
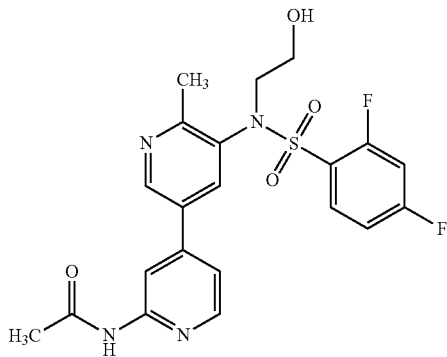 [SMILES: CC(=O)Nc1cc(-c2cnc(C)c(N(CCO)S(=O)(=O)c3ccc(F)cc3F)c2)ccn1]
I-319
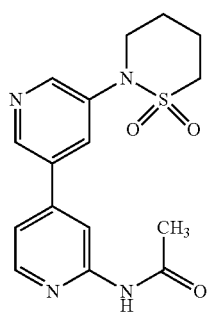 [SMILES: CC(=O)Nc1cc(-c2cncc(N3CCCCS3(=O)=O)c2)ccn1]
I-320

US 10,538,533 B2
165
TABLE 1-continued
Exemplary Compounds
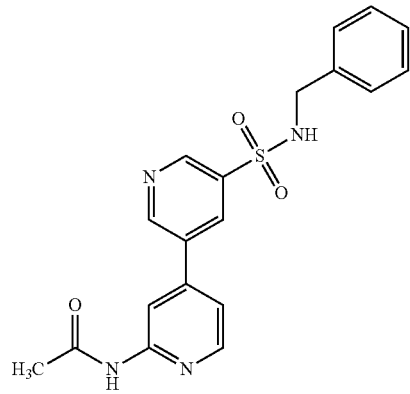 [SMILES: CC(=O)Nc1cc(-c2cncc(S(=O)(=O)NCc3ccccc3)c2)ccn1]
I-321
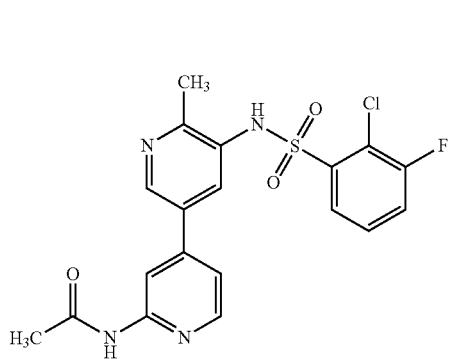 [SMILES: CC(=O)Nc1cc(-c2cnc(C)c(NS(=O)(=O)c3cccc(F)c3Cl)c2)ccn1]
I-322
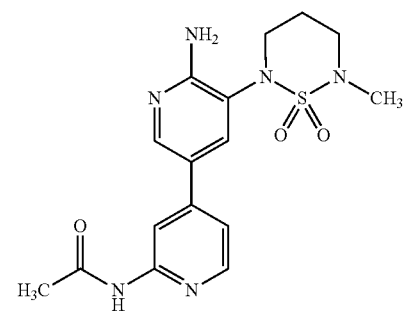 [SMILES: CC(=O)Nc1cc(-c2cnc(N)c(N3CCCN(C)S3(=O)=O)c2)ccn1]
I-323
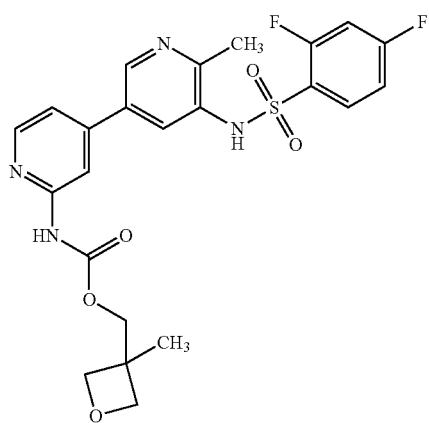 [SMILES: Cc1ncc(-c2ccnc(NC(=O)OCC3(C)COC3)c2)cc1NS(=O)(=O)c1ccc(F)cc1F]
I-324

TABLE 1-continued
Exemplary Compounds
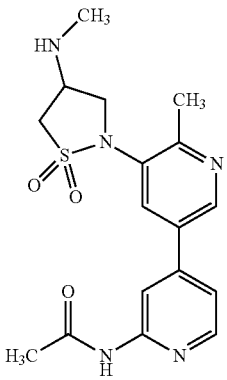 [SMILES: CNC1CN(c2cc(-c3ccnc(NC(C)=O)c3)cnc2C)S(=O)(=O)C1]
I-325
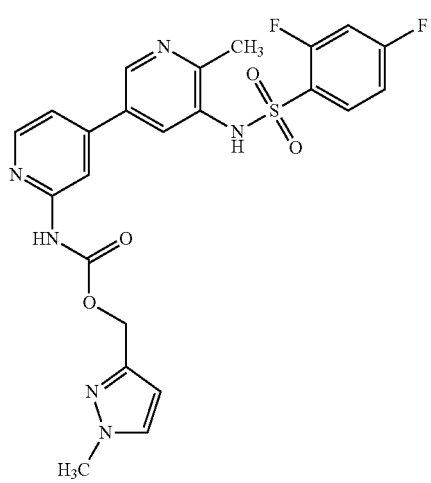 [SMILES: Cc1ncc(-c2ccnc(NC(=O)OCc3ccn(C)n3)c2)cc1NS(=O)(=O)c1ccc(F)cc1F]
I-326
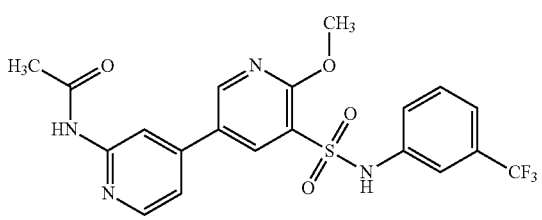 [SMILES: COc1ncc(-c2ccnc(NC(C)=O)c2)cc1S(=O)(=O)Nc1cccc(C(F)(F)F)c1]
I-329
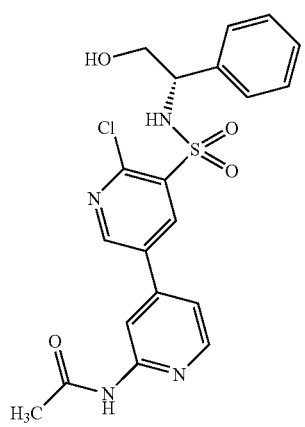 [SMILES: CC(=O)Nc1cc(-c2cnc(Cl)c(S(=O)(=O)N[C@H](CO)c3ccccc3)c2)ccn1]
I-330

TABLE 1-continued
Exemplary Compounds
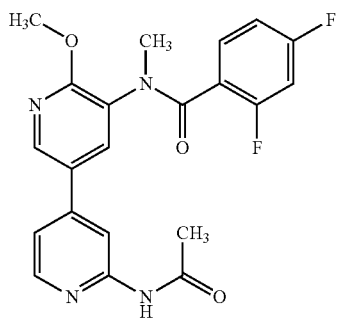 [SMILES: COc1ncc(-c2ccnc(NC(C)=O)c2)cc1N(C)C(=O)c1ccc(F)cc1F]
I-331
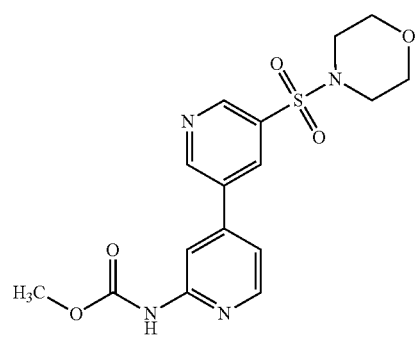 [SMILES: COC(=O)Nc1cc(-c2cncc(S(=O)(=O)N3CCOCC3)c2)ccn1]
I-332
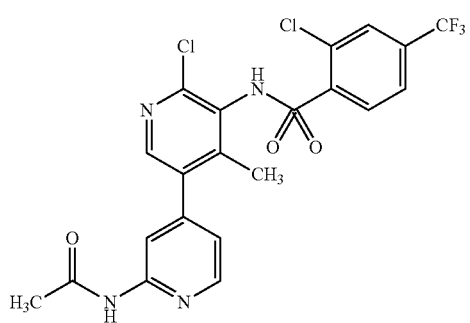
I-333
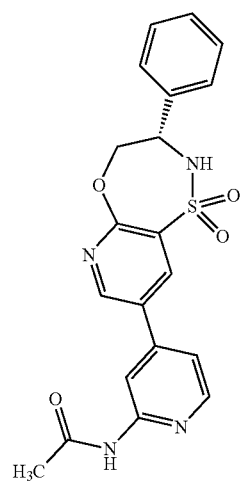 [SMILES: CC(=O)Nc1cc(-c2cnc3c(c2)S(=O)(=O)N[C@@H](c2ccccc2)CO3)ccn1]
I-334

TABLE 1-continued
Exemplary Compounds
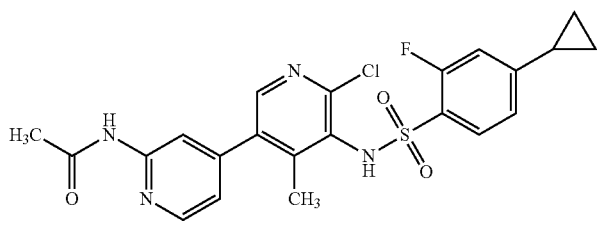 [SMILES: CC(=O)Nc1cc(-c2cnc(Cl)c(NS(=O)(=O)c3ccc(C4CC4)cc3F)c2C)ccn1]
I-335
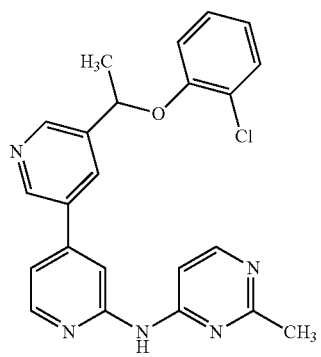 [SMILES: Cc1nccc(Nc2cc(-c3cncc(C(C)Oc4ccccc4Cl)c3)ccn2)n1]
I-336
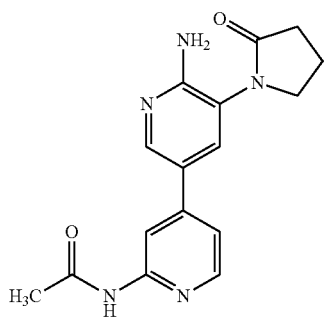 [SMILES: CC(=O)Nc1cc(-c2cnc(N)c(N3CCCC3=O)c2)ccn1]
I-337
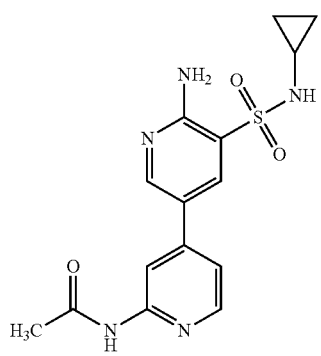 [SMILES: CC(=O)Nc1cc(-c2cnc(N)c(S(=O)(=O)NC3CC3)c2)ccn1]
I-338
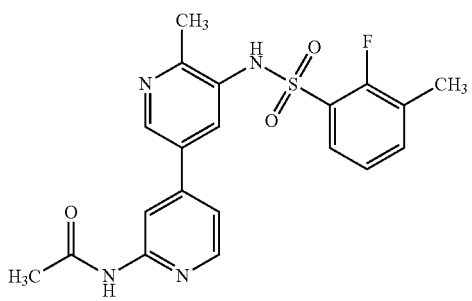 [SMILES: CC(=O)Nc1cc(-c2cnc(C)c(NS(=O)(=O)c3cccc(C)c3F)c2)ccn1]
I-339

TABLE 1-continued

Exemplary Compounds

| | |
|---|---|
| [chemical structure] | I-340 |
| [chemical structure] | I-341 |
| [chemical structure] | I-342 |
| [chemical structure] | I-343 |
| [chemical structure] | I-344 |

TABLE 1-continued
Exemplary Compounds
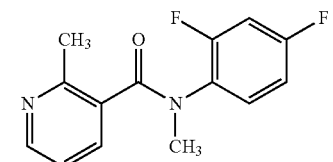
I-346
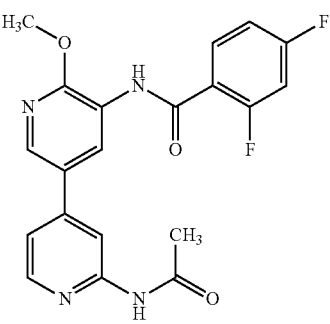 [SMILES: COc1ncc(-c2ccnc(NC(C)=O)c2)cc1NC(=O)c1ccc(F)cc1F]
I-347
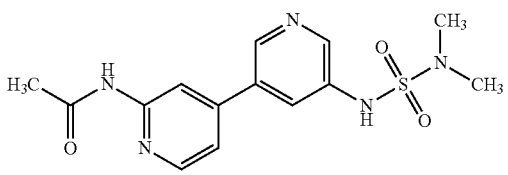 [SMILES: CC(=O)Nc1cc(-c2cncc(NS(=O)(=O)N(C)C)c2)ccn1]
I-348
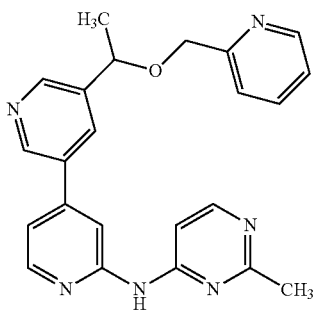 [SMILES: Cc1nccc(Nc2cc(-c3cncc(C(C)OCc4ccccn4)c3)ccn2)n1]
I-349
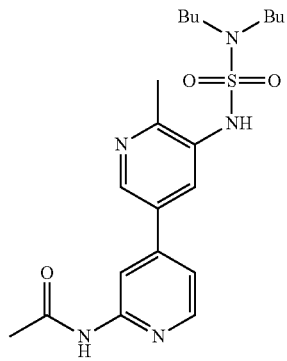
I-350

TABLE 1-continued
Exemplary Compounds
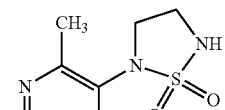
I-352
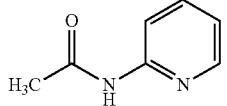
I-353
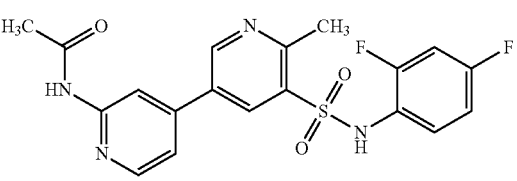 [SMILES: CC(=O)Nc1cc(-c2cnc(C)c(S(=O)(=O)Nc3ccc(F)cc3F)c2)ccn1]
I-354
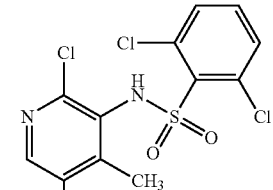
I-355
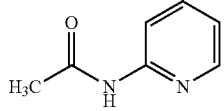
I-356

US 10,538,533 B2
179                                                                                                      180
TABLE 1-continued
Exemplary Compounds
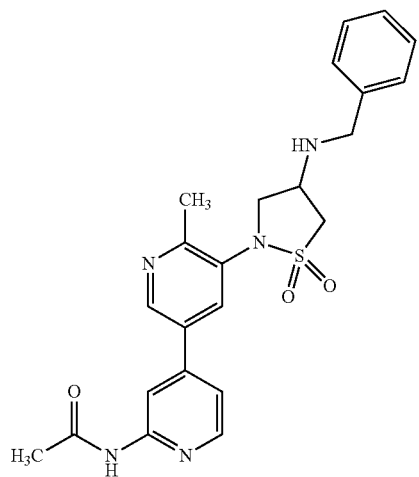 [SMILES: CC(=O)Nc1cc(-c2cnc(C)c(N3CC(NCc4ccccc4)CS3(=O)=O)c2)ccn1]
I-357
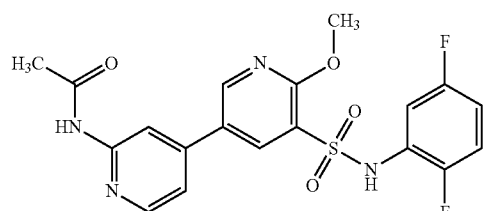
I-358
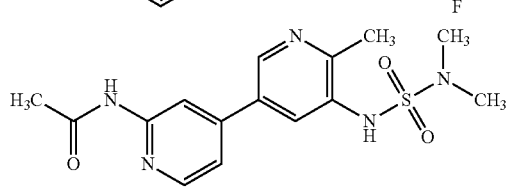
I-359
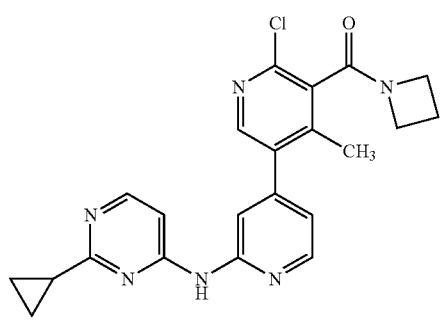 [SMILES: Cc1c(-c2ccnc(Nc3ccnc(C4CC4)n3)c2)cnc(Cl)c1C(=O)N1CCC1]
I-361
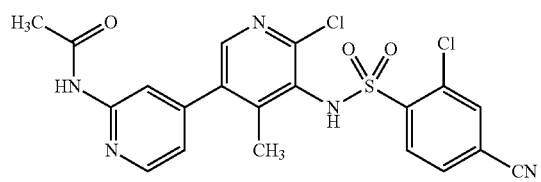 [SMILES: CC(=O)Nc1cc(-c2cnc(Cl)c(NS(=O)(=O)c3ccc(C#N)cc3Cl)c2C)ccn1]
I-362

TABLE 1-continued
Exemplary Compounds
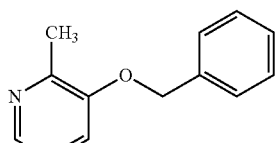
I-363
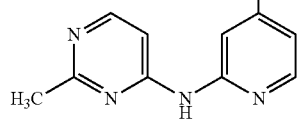
I-364
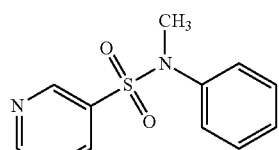
I-365
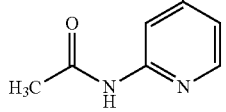
I-366
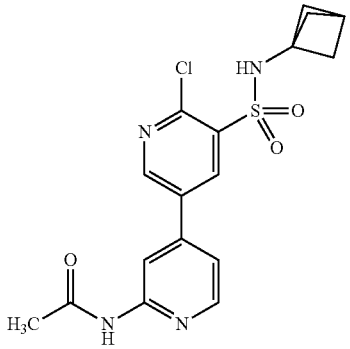 [SMILES: CC(=O)Nc1cc(-c2cnc(Cl)c(S(=O)(=O)NC34CC(C3)C4)c2)ccn1]
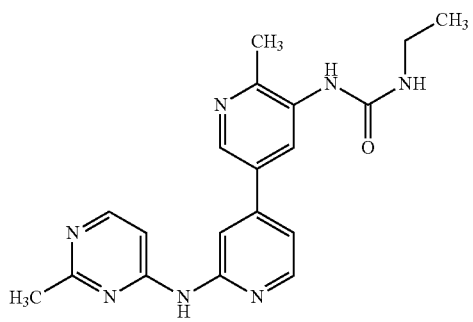 [SMILES: CCNC(=O)Nc1cc(-c2ccnc(Nc3ccnc(C)n3)c2)cnc1C]
I-367

TABLE 1-continued

Exemplary Compounds

I-368

I-369

I-370

I-371

I-372

TABLE 1-continued
Exemplary Compounds
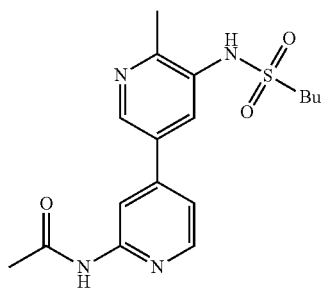
I-373
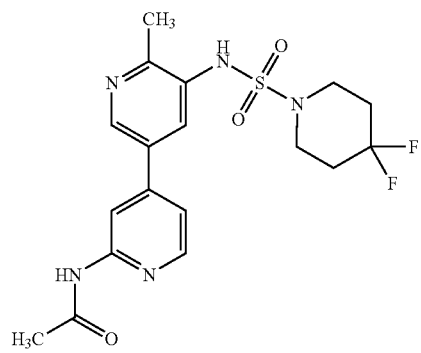 [SMILES: CC(=O)Nc1cc(-c2cnc(C)c(NS(=O)(=O)N3CCC(F)(F)CC3)c2)ccn1]
I-374
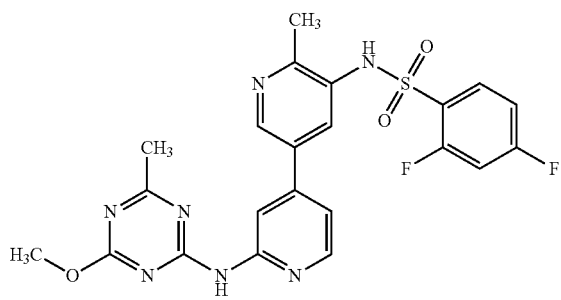 [SMILES: COc1nc(C)nc(Nc2cc(-c3cnc(C)c(NS(=O)(=O)c4ccc(F)cc4F)c3)ccn2)n1]
I-375
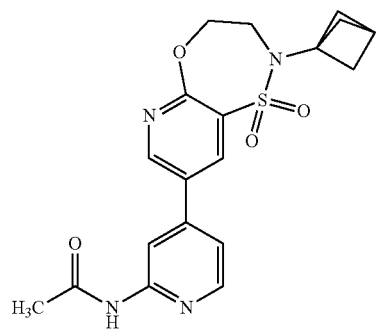 [SMILES: CC(=O)Nc1cc(-c2cnc3c(c2)S(=O)(=O)N(C24CC(C2)C4)CCO3)ccn1]
I-376
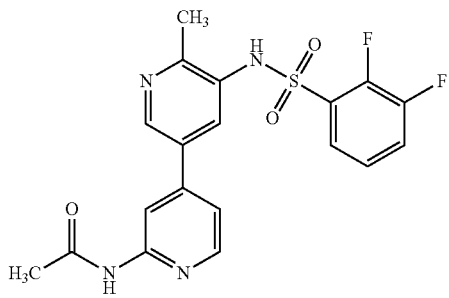 [SMILES: CC(=O)Nc1cc(-c2cnc(C)c(NS(=O)(=O)c3cccc(F)c3F)c2)ccn1]
I-377

TABLE 1-continued
Exemplary Compounds
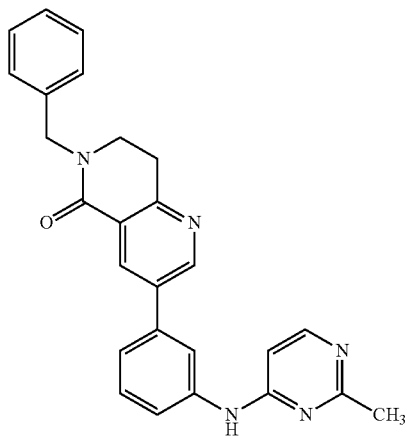 [SMILES: Cc1nccc(Nc2cccc(-c3cnc4c(c3)C(=O)N(Cc3ccccc3)CC4)c2)n1]
I-378
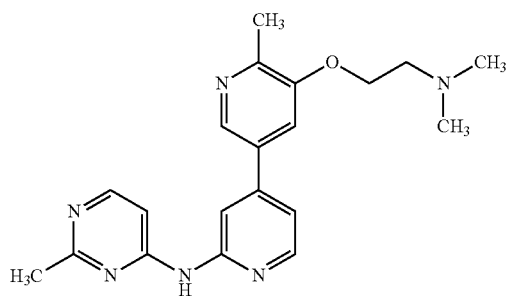
I-379
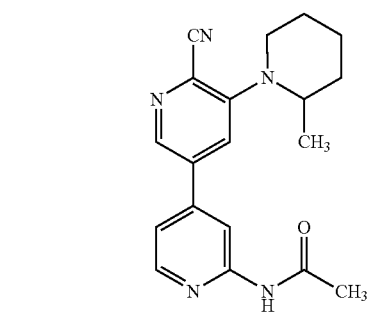 [SMILES: CC(=O)Nc1cc(-c2cnc(C#N)c(N3CCCCC3C)c2)ccn1]
I-380
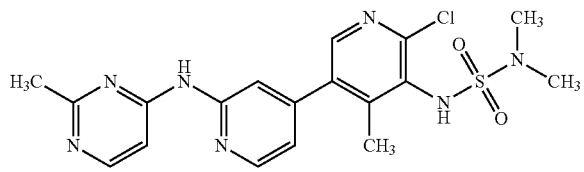
I-381
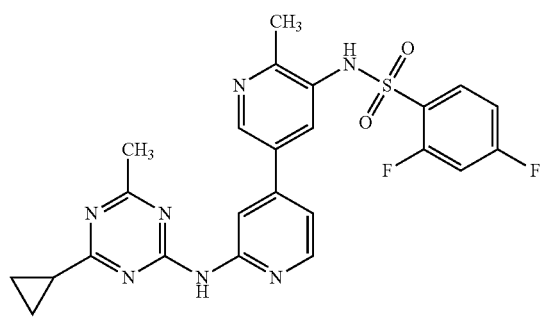 [SMILES: Cc1nc(Nc2cc(-c3cnc(C)c(NS(=O)(=O)c4ccc(F)cc4F)c3)ccn2)nc(C2CC2)n1]
I-382

TABLE 1-continued

Exemplary Compounds

I-383

I-384

I-386

I-387

I-388

TABLE 1-continued
Exemplary Compounds
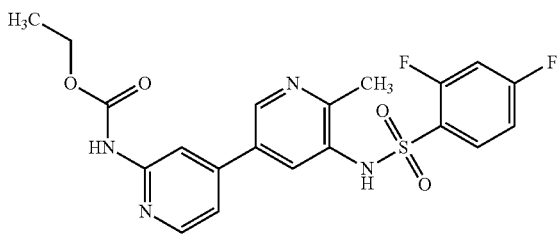 [SMILES: CCOC(=O)Nc1cc(-c2cnc(C)c(NS(=O)(=O)c3ccc(F)cc3F)c2)ccn1]
I-389
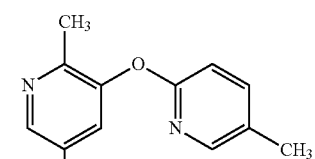
I-390
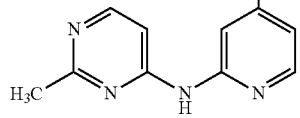
I-391
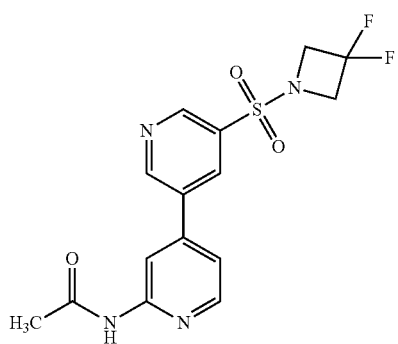 [SMILES: CC(=O)Nc1cc(-c2cncc(S(=O)(=O)N3CC(F)(F)C3)c2)ccn1]
I-392
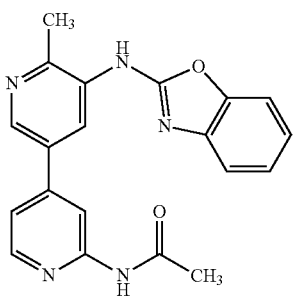 [SMILES: CC(=O)Nc1cc(-c2cnc(C)c(Nc3nc4ccccc4o3)c2)ccn1]
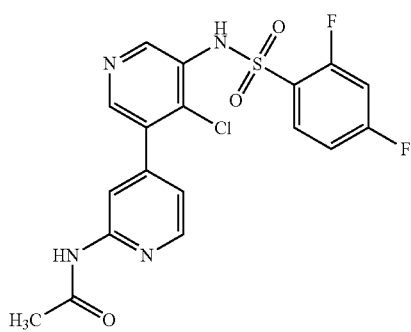 [SMILES: CC(=O)Nc1cc(-c2cncc(NS(=O)(=O)c3ccc(F)cc3F)c2Cl)ccn1]
I-394

TABLE 1-continued
Exemplary Compounds
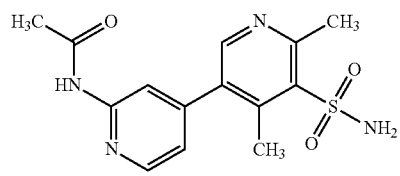 [SMILES: CC(=O)Nc1cc(-c2cnc(C)c(S(N)(=O)=O)c2C)ccn1]  I-395
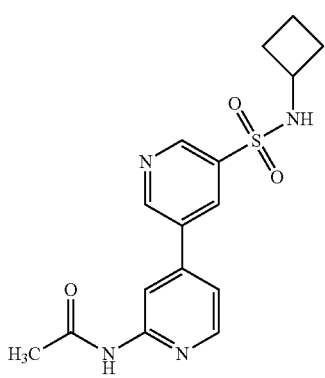 [SMILES: CC(=O)Nc1cc(-c2cncc(S(=O)(=O)NC3CCC3)c2)ccn1]  I-396
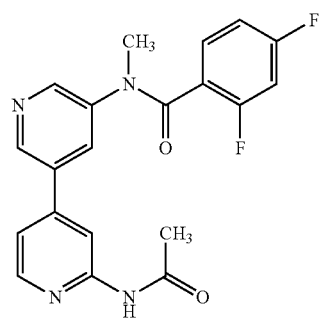 [SMILES: CC(=O)Nc1cc(-c2cncc(N(C)C(=O)c3ccc(F)cc3F)c2)ccn1]  I-397
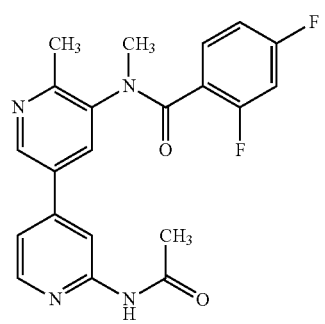 [SMILES: CC(=O)Nc1cc(-c2cnc(C)c(N(C)C(=O)c3ccc(F)cc3F)c2)ccn1]  I-398
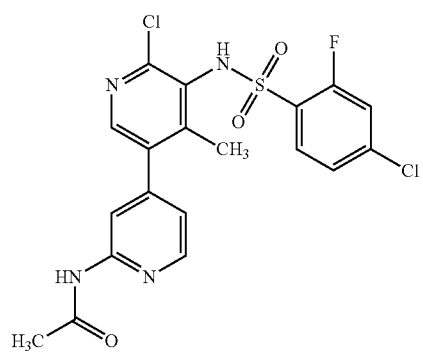 [SMILES: CC(=O)Nc1cc(-c2cnc(Cl)c(NS(=O)(=O)c3ccc(Cl)cc3F)c2C)ccn1]  I-399

TABLE 1-continued
Exemplary Compounds
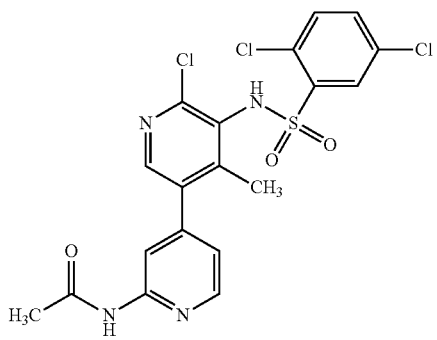 [SMILES: CC(=O)Nc1cc(-c2cnc(Cl)c(NS(=O)(=O)c3cc(Cl)ccc3Cl)c2C)ccn1]
I-401
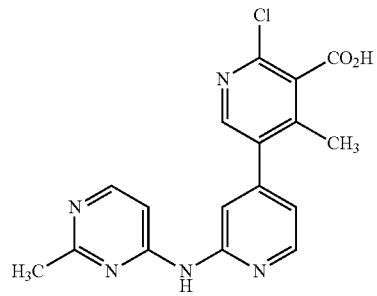 [SMILES: Cc1nccc(Nc2cc(-c3cnc(Cl)c(C(=O)O)c3C)ccn2)n1]
I-402
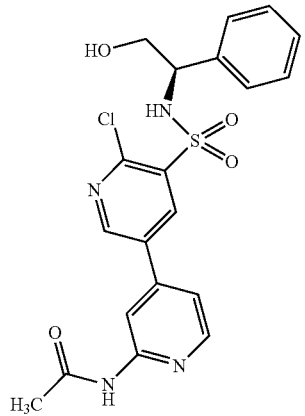 [SMILES: CC(=O)Nc1cc(-c2cnc(Cl)c(S(=O)(=O)N[C@@H](CO)c3ccccc3)c2)ccn1]
I-403
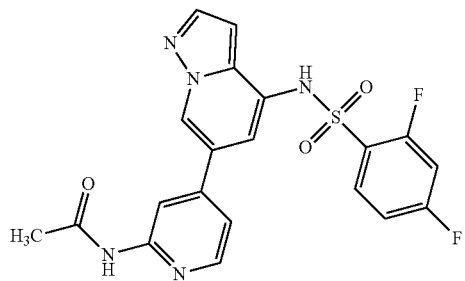 [SMILES: CC(=O)Nc1cc(-c2cc(NS(=O)(=O)c3ccc(F)cc3F)c3ccnn3c2)ccn1]
I-404

TABLE 1-continued

Exemplary Compounds

I-405

I-406

I-407

I-408

I-409

TABLE 1-continued

Exemplary Compounds

| | |
|---|---|
| (structure) | I-410 |
| (structure) | I-411 |
| (structure) | I-412 |
| (structure) | I-413 |
| (structure) | I-414 |

US 10,538,533 B2
TABLE 1-continued
Exemplary Compounds
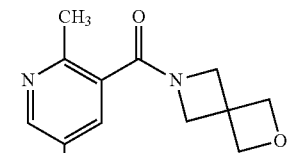
I-415
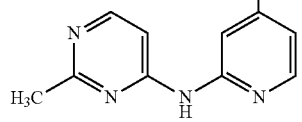
I-416
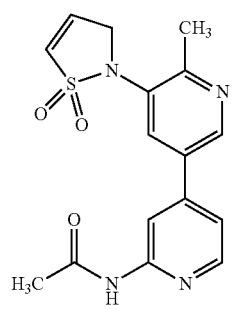 [SMILES: CC(=O)Nc1cc(-c2cnc(C)c(N3CC=CS3(=O)=O)c2)ccn1]
I-417
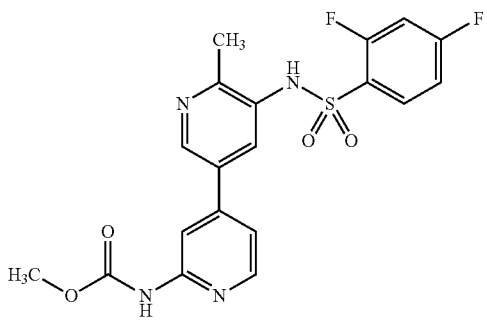 [SMILES: COC(=O)Nc1cc(-c2cnc(C)c(NS(=O)(=O)c3ccc(F)cc3F)c2)ccn1]
I-418
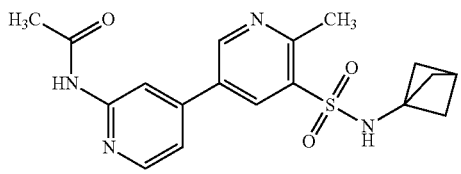 [SMILES: CC(=O)Nc1cc(-c2cnc(C)c(S(=O)(=O)NC34CC(C3)C4)c2)ccn1]
I-419
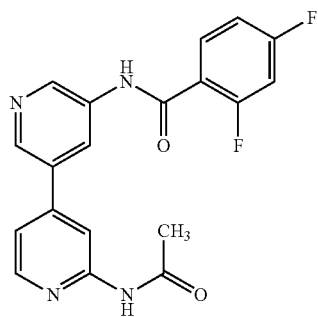 [SMILES: CC(=O)Nc1cc(-c2cncc(NC(=O)c3ccc(F)cc3F)c2)ccn1]

TABLE 1-continued
Exemplary Compounds
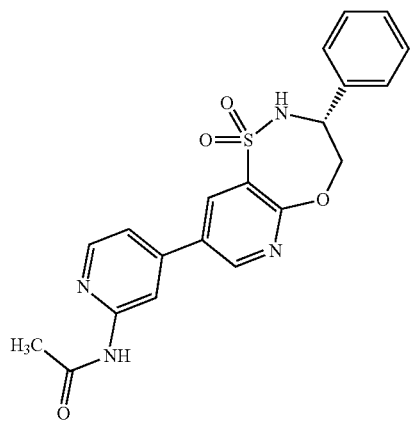 [SMILES: CC(=O)Nc1cc(-c2cnc3c(c2)S(=O)(=O)N[C@H](c2ccccc2)CO3)ccn1]
I-420
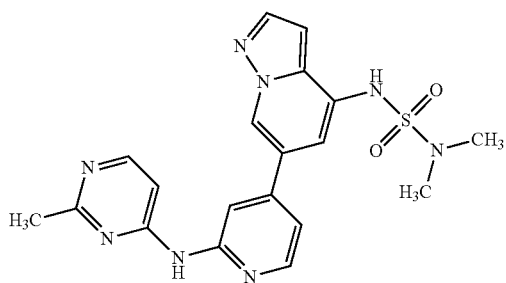
I-421
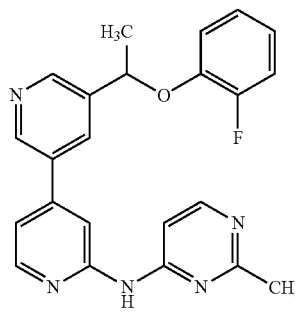
I-422
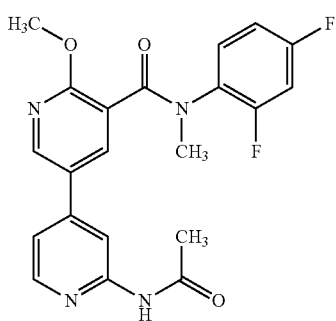 [SMILES: COc1ncc(-c2ccnc(NC(C)=O)c2)cc1C(=O)N(C)c1ccc(F)cc1F]
I-423

TABLE 1-continued
Exemplary Compounds
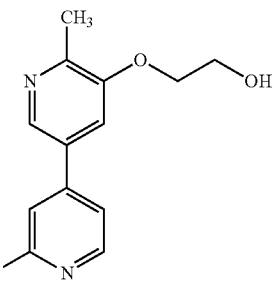 I-424
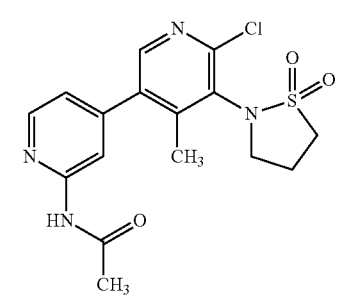 [SMILES: CC(=O)Nc1cc(-c2cnc(Cl)c(N3CCCS3(=O)=O)c2C)ccn1] I-425
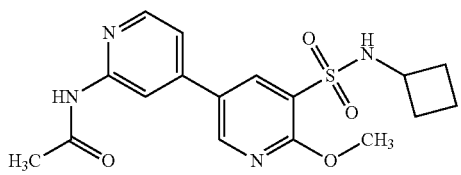 [SMILES: COc1ncc(-c2ccnc(NC(C)=O)c2)cc1S(=O)(=O)NC1CCC1] I-426
I-427
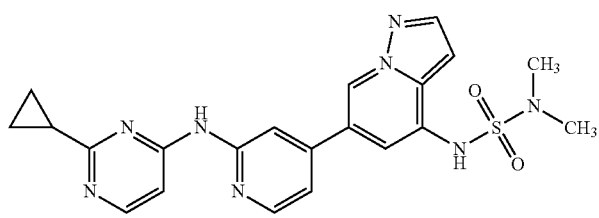
I-428
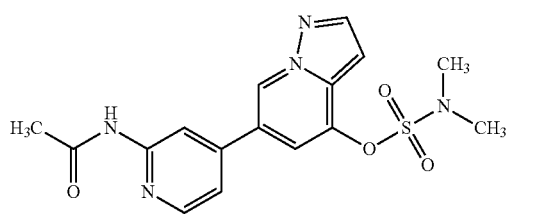
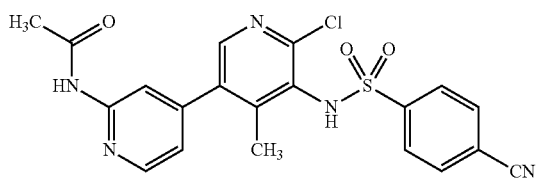 [SMILES: CC(=O)Nc1cc(-c2cnc(Cl)c(NS(=O)(=O)c3ccc(C#N)cc3)c2C)ccn1] I-429

TABLE 1-continued
Exemplary Compounds
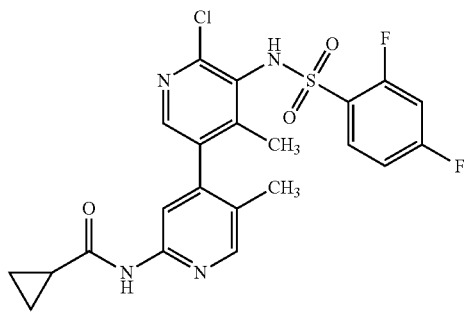 [SMILES: Cc1cnc(NC(=O)C2CC2)cc1-c1cnc(Cl)c(NS(=O)(=O)c2ccc(F)cc2F)c1C]
I-430
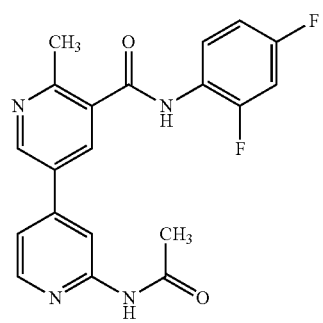 [SMILES: CC(=O)Nc1cc(-c2cnc(C)c(C(=O)Nc3ccc(F)cc3F)c2)ccn1]
I-431
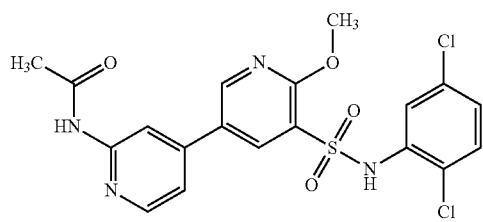 [SMILES: COc1ncc(-c2ccnc(NC(C)=O)c2)cc1S(=O)(=O)Nc1cc(Cl)ccc1Cl]
I-432
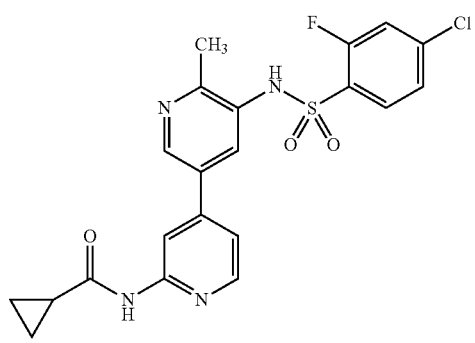 [SMILES: Cc1ncc(-c2ccnc(NC(=O)C3CC3)c2)cc1NS(=O)(=O)c1ccc(Cl)cc1F]
I-433
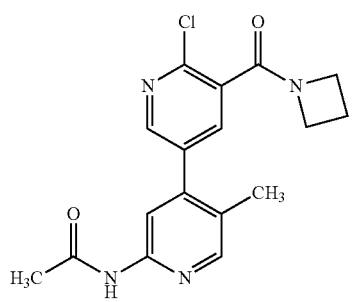 [SMILES: CC(=O)Nc1cc(-c2cnc(Cl)c(C(=O)N3CCC3)c2)c(C)cn1]
I-434

TABLE 1-continued
Exemplary Compounds
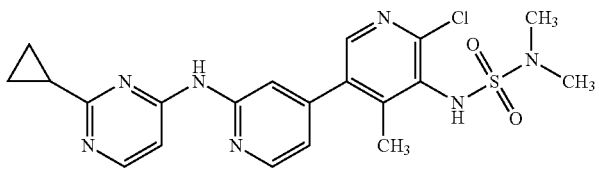 [SMILES: Cc1c(-c2ccnc(Nc3ccnc(C4CC4)n3)c2)cnc(Cl)c1NS(=O)(=O)N(C)C] I-435
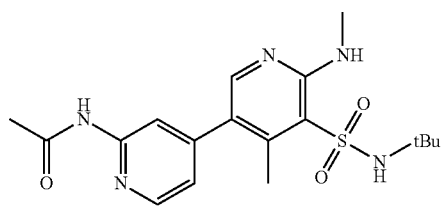 [SMILES: CNc1ncc(-c2ccnc(NC(C)=O)c2)c(C)c1S(=O)(=O)NC(C)(C)C] I-436
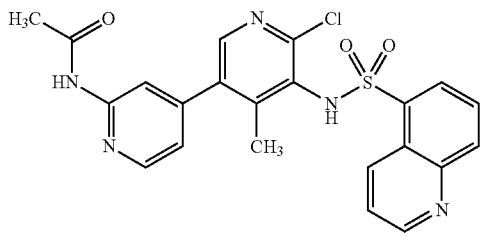 [SMILES: CC(=O)Nc1cc(-c2cnc(Cl)c(NS(=O)(=O)c3cccc4ncccc34)c2C)ccn1] I-437
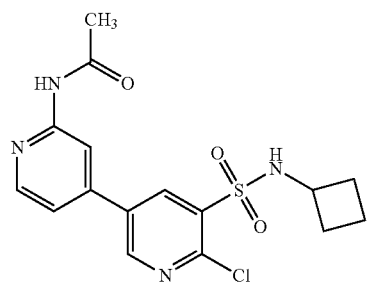 [SMILES: CC(=O)Nc1cc(-c2cnc(Cl)c(S(=O)(=O)NC3CCC3)c2)ccn1] I-438
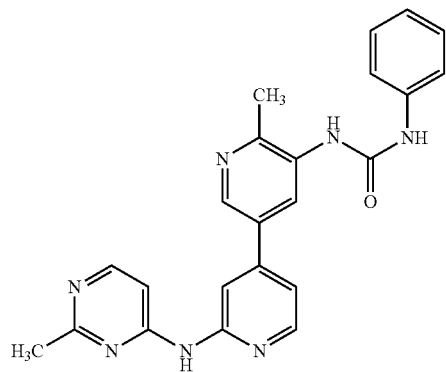 [SMILES: Cc1nccc(Nc2cc(-c3cnc(C)c(NC(=O)Nc4ccccc4)c3)ccn2)n1] I-439

TABLE 1-continued
Exemplary Compounds
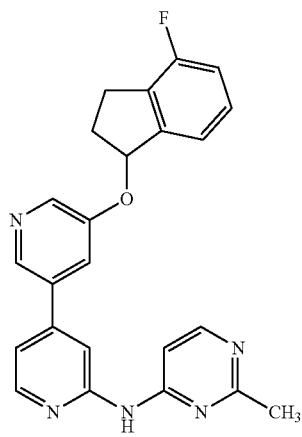 [SMILES: Cc1nccc(Nc2cc(-c3cncc(OC4CCc5c(F)cccc54)c3)ccn2)n1]
I-440
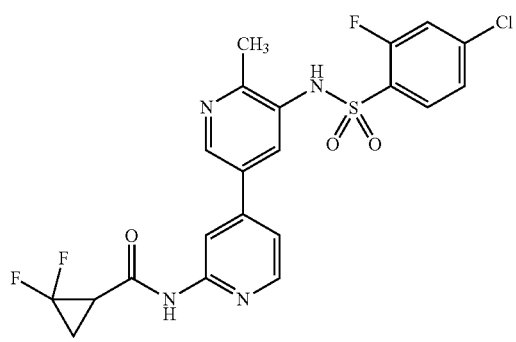 [SMILES: Cc1ncc(-c2ccnc(NC(=O)C3CC3(F)F)c2)cc1NS(=O)(=O)c1ccc(Cl)cc1F]
I-441
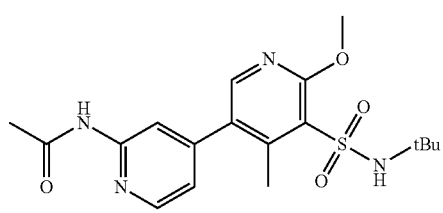 [SMILES: COc1ncc(-c2ccnc(NC(C)=O)c2)c(C)c1S(=O)(=O)NC(C)(C)C]
I-442
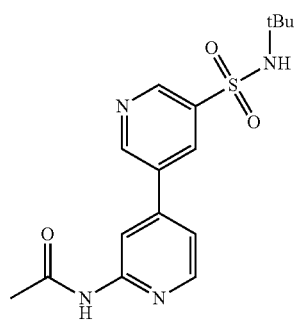 [SMILES: CC(=O)Nc1cc(-c2cncc(S(=O)(=O)NC(C)(C)C)c2)ccn1]
I-443
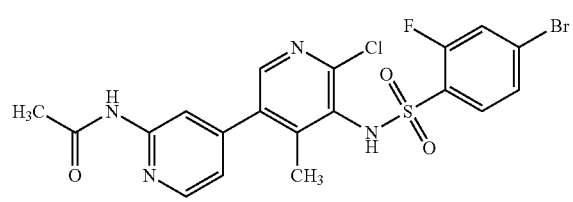 [SMILES: CC(=O)Nc1cc(-c2cnc(Cl)c(NS(=O)(=O)c3ccc(Br)cc3F)c2C)ccn1]
I-444

TABLE 1-continued
Exemplary Compounds
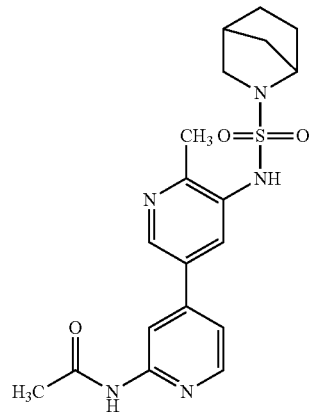 [SMILES: CC(=O)Nc1cc(-c2cnc(C)c(NS(=O)(=O)N3CC4CCC3C4)c2)ccn1]
I-445
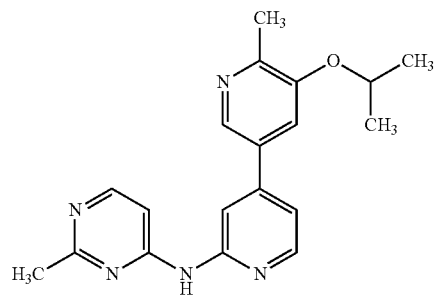 [SMILES: Cc1nccc(Nc2cc(-c3cnc(C)c(OC(C)C)c3)ccn2)n1]
I-446
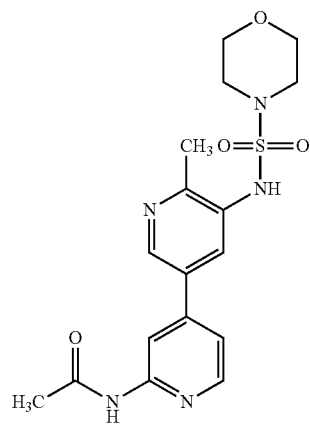 [SMILES: CC(=O)Nc1cc(-c2cnc(C)c(NS(=O)(=O)N3CCOCC3)c2)ccn1]
I-447
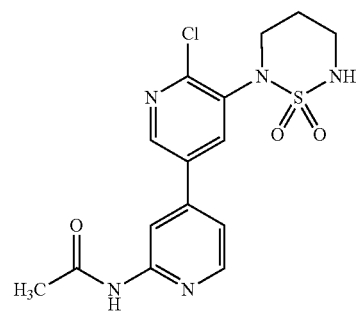 [SMILES: CC(=O)Nc1cc(-c2cnc(Cl)c(N3CCCNS3(=O)=O)c2)ccn1]
I-448

TABLE 1-continued
Exemplary Compounds
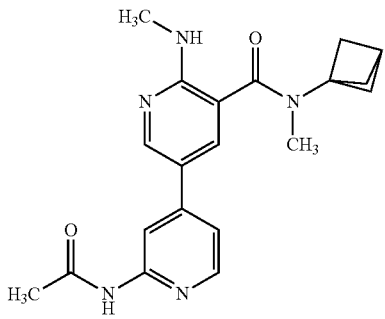 [SMILES: CNc1ncc(-c2ccnc(NC(C)=O)c2)cc1C(=O)N(C)C12CC(C1)C2]
I-449
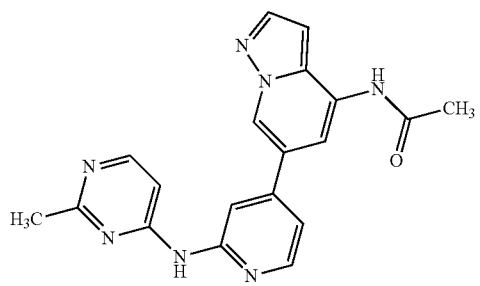 [SMILES: CC(=O)Nc1cc(-c2ccnc(Nc3ccnc(C)n3)c2)cn2nccc12]
I-450
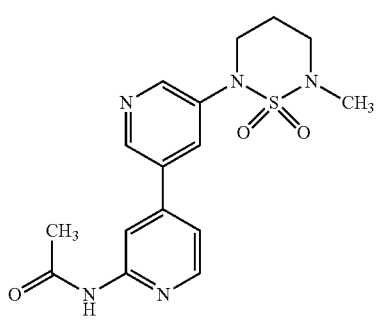 [SMILES: CC(=O)Nc1cc(-c2cncc(N3CCCN(C)S3(=O)=O)c2)ccn1]
I-452
I-454
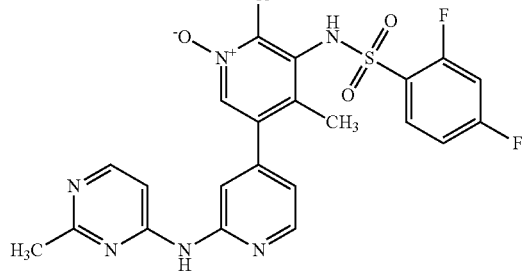
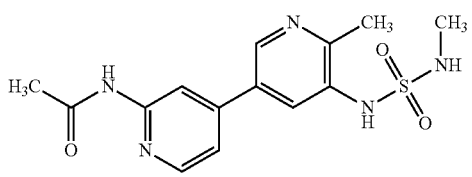 [SMILES: CNS(=O)(=O)Nc1cc(-c2ccnc(NC(C)=O)c2)cnc1C]
I-455

TABLE 1-continued
Exemplary Compounds
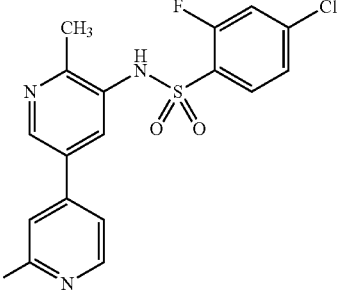
I-456
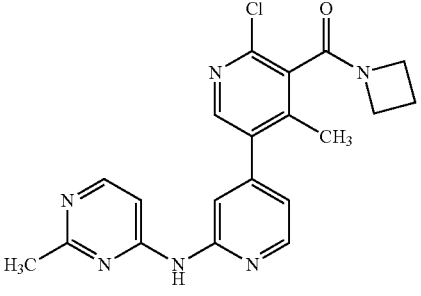 [SMILES: Cc1nccc(Nc2cc(-c3cnc(Cl)c(C(=O)N4CCC4)c3C)ccn2)n1]
I-457
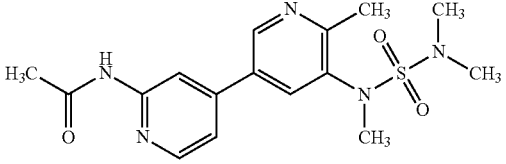 [SMILES: CC(=O)Nc1cc(-c2cnc(C)c(N(C)S(=O)(=O)N(C)C)c2)ccn1]
I-458
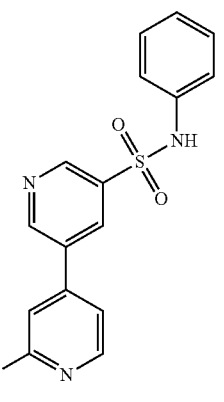
I-459
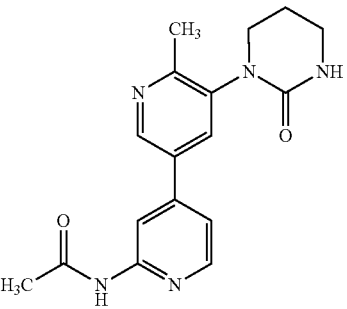 [SMILES: CC(=O)Nc1cc(-c2cnc(C)c(N3CCCNC3=O)c2)ccn1]
I-460

TABLE 1-continued
Exemplary Compounds
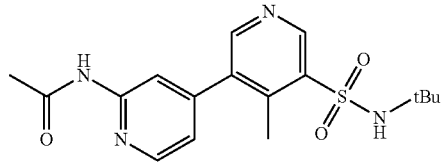 [SMILES: CC(=O)Nc1cc(-c2cncc(S(=O)(=O)NC(C)(C)C)c2C)ccn1]
I-462
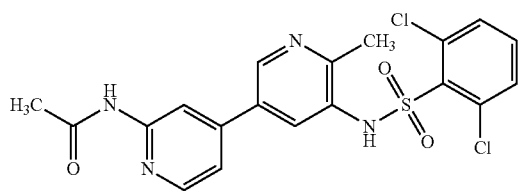 [SMILES: CC(=O)Nc1cc(-c2cnc(C)c(NS(=O)(=O)c3c(Cl)cccc3Cl)c2)ccn1]
I-463
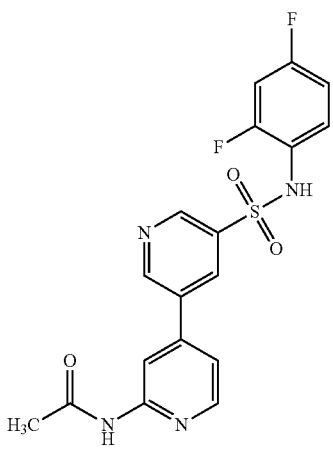 [SMILES: CC(=O)Nc1cc(-c2cncc(S(=O)(=O)Nc3ccc(F)cc3F)c2)ccn1]
I-464
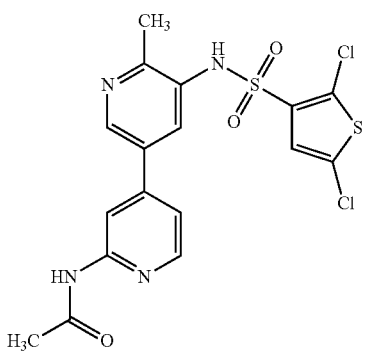 [SMILES: CC(=O)Nc1cc(-c2cnc(C)c(NS(=O)(=O)c3cc(Cl)sc3Cl)c2)ccn1]
I-465
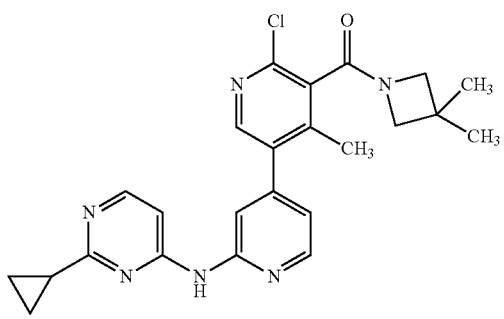 [SMILES: Cc1c(-c2ccnc(Nc3ccnc(C4CC4)n3)c2)cnc(Cl)c1C(=O)N1CC(C)(C)C1]
I-466

TABLE 1-continued

Exemplary Compounds

I-467

I-468

I-469

I-470

I-471

TABLE 1-continued
Exemplary Compounds
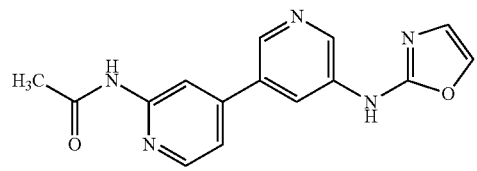 [SMILES: CC(=O)Nc1cc(-c2cncc(Nc3ncco3)c2)ccn1] I-472
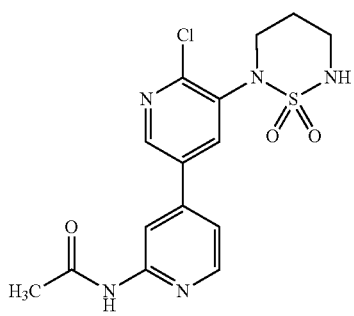 [SMILES: CC(=O)Nc1cc(-c2cnc(Cl)c(N3CCCNS3(=O)=O)c2)ccn1] I-473
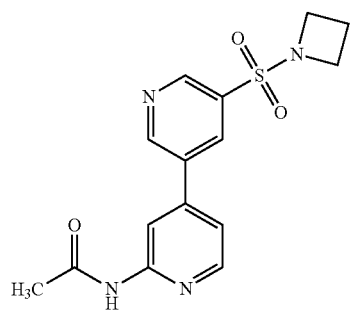 [SMILES: CC(=O)Nc1cc(-c2cncc(S(=O)(=O)N3CCC3)c2)ccn1] I-474
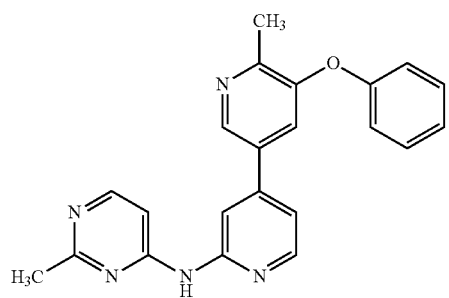 [SMILES: Cc1nccc(Nc2cc(-c3cnc(C)c(Oc4ccccc4)c3)ccn2)n1] I-475
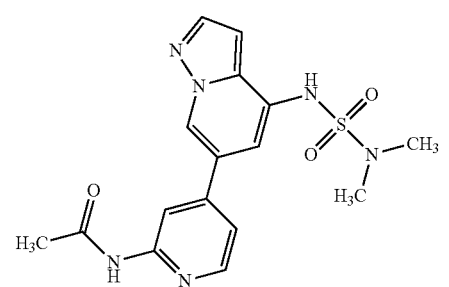 [SMILES: CC(=O)Nc1cc(-c2cc(NS(=O)(=O)N(C)C)c3ccnn3c2)ccn1] I-476

TABLE 1-continued
Exemplary Compounds
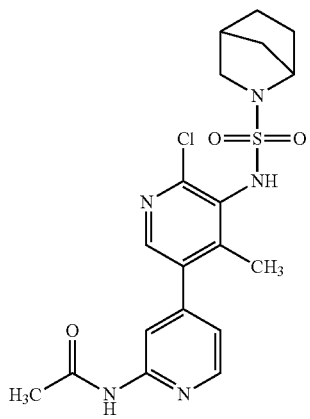 [SMILES: CC(=O)Nc1cc(-c2cnc(Cl)c(NS(=O)(=O)N3CC4CCC3C4)c2C)ccn1]
I-477
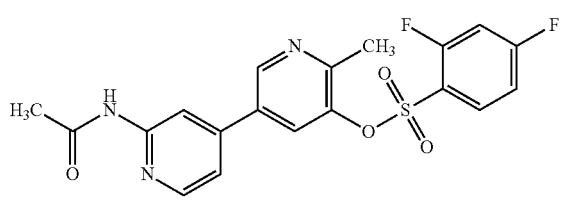 [SMILES: CC(=O)Nc1cc(-c2cnc(C)c(OS(=O)(=O)c3ccc(F)cc3F)c2)ccn1]
I-478
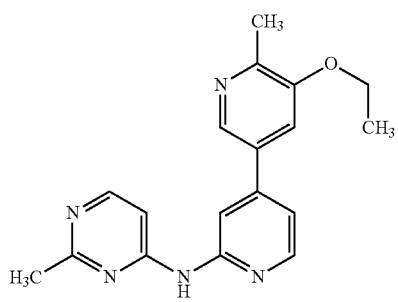 [SMILES: CCOc1cc(-c2ccnc(Nc3ccnc(C)n3)c2)cnc1C]
I-479
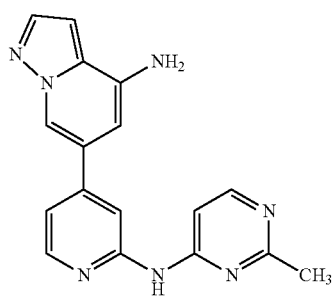 [SMILES: Cc1nccc(Nc2cc(-c3cc(N)c4ccnn4c3)ccn2)n1]
I-480
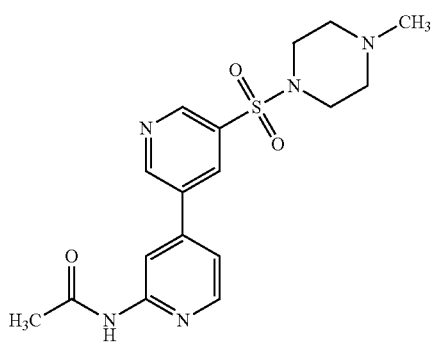 [SMILES: CC(=O)Nc1cc(-c2cncc(S(=O)(=O)N3CCN(C)CC3)c2)ccn1]
I-481

TABLE 1-continued
Exemplary Compounds
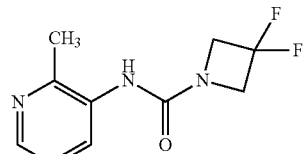
I-482
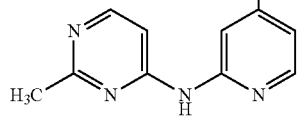
I-483
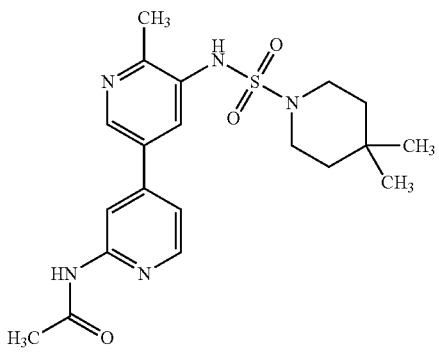 [SMILES: CC(=O)Nc1cc(-c2cnc(C)c(NS(=O)(=O)N3CCC(C)(C)CC3)c2)ccn1]
I-484
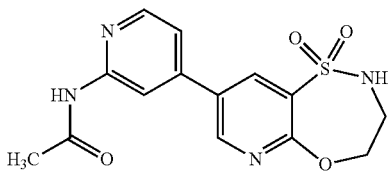 [SMILES: CC(=O)Nc1cc(-c2cnc3c(c2)S(=O)(=O)NCCO3)ccn1]
I-485
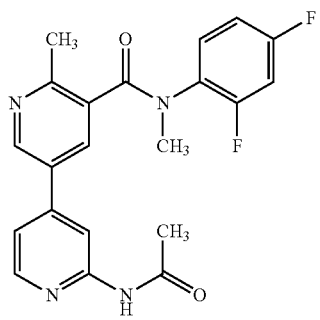 [SMILES: CC(=O)Nc1cc(-c2cnc(C)c(C(=O)N(C)c3ccc(F)cc3F)c2)ccn1]
I-486

TABLE 1-continued
Exemplary Compounds
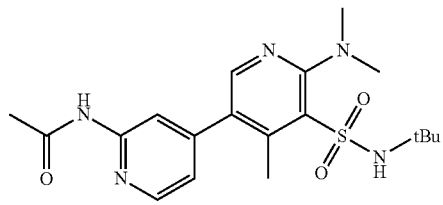 [SMILES: CC(=O)Nc1cc(-c2cnc(N(C)C)c(S(=O)(=O)NC(C)(C)C)c2C)ccn1]
I-487
I-488
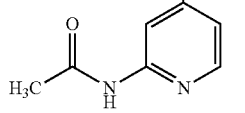
I-490
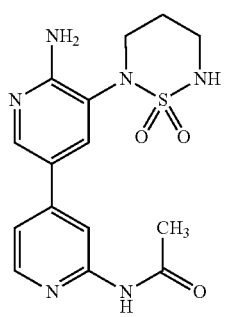 [SMILES: CC(=O)Nc1cc(-c2cnc(N)c(N3CCCNS3(=O)=O)c2)ccn1]
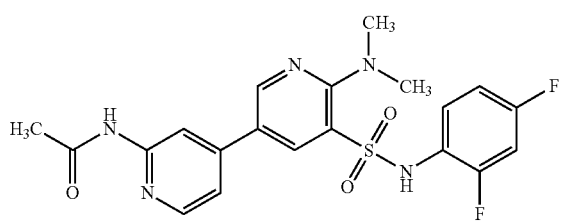 [SMILES: CC(=O)Nc1cc(-c2cnc(N(C)C)c(S(=O)(=O)Nc3ccc(F)cc3F)c2)ccn1]
I-491
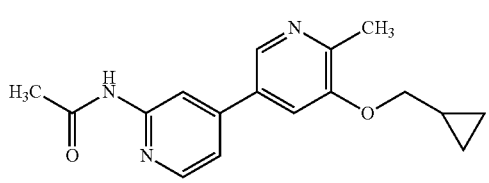 [SMILES: CC(=O)Nc1cc(-c2cnc(C)c(OCC3CC3)c2)ccn1]
I-492

TABLE 1-continued
Exemplary Compounds
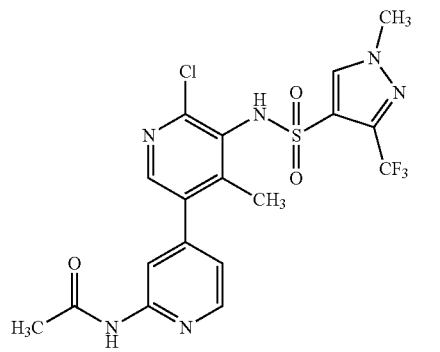 [SMILES: CC(=O)Nc1cc(-c2cnc(Cl)c(NS(=O)(=O)c3cn(C)nc3C(F)(F)F)c2C)ccn1]
I-493
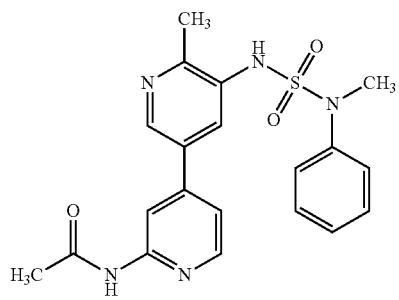 [SMILES: CC(=O)Nc1cc(-c2cnc(C)c(NS(=O)(=O)N(C)c3ccccc3)c2)ccn1]
I-494
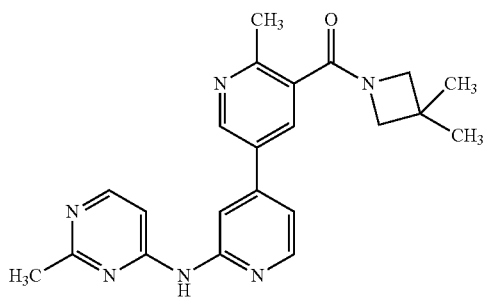
I-495
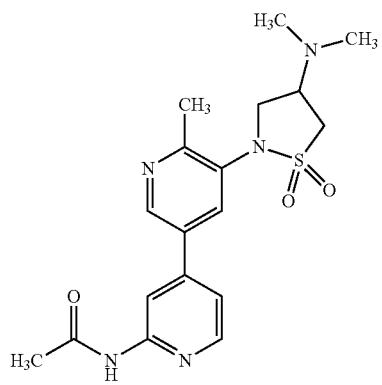
I-496
(peak 1)

TABLE 1-continued

Exemplary Compounds

I-497

(peak 2)

I-498

(peak 1)

I-499

(peak 2)

In certain embodiments, the present invention provides a compound depicted in Table 1, above, or a pharmaceutically acceptable salt thereof. In other embodiments, the compound is I-30, I-32, I-41, I-94, I-153, I-214, I-218, I-225, I-237, I-246, I-291, I-292, I-293, I-294, I-296, I-299, I-304 or I-308 or a pharmaceutically acceptable salt thereof. In other embodiments, the compound is I-41, I-94, I-153, I-299, or I-308 or a pharmaceutically acceptable salt thereof.

The compounds of Table 1 above may also be identified by the chemical names provided in Table 2. This table also references exemplary synthetic protocols that can be used to prepare the indicated compound.

TABLE 2

Chemical Names and Synthetic Protocols

| Compound | Synthetic Example | Chemical Name |
|---|---|---|
| I-1 | 9V | N-[6-methyl-5-({[6-(trifluoromethyl)pyridin-3-yl]sulfonyl}amino)-3,4'-bipyridin-2'-yl]acetamide |
| I-2 | 23 | N-{4-[1-(cyclopropylsulfonyl)-1H-pyrazolo[4,3-b]pyridin-6-yl]pyridin-2-yl}acetamide |
| I-3 | 7C | N-{6-amino-5-[(2-naphthylmethyl)sulfonyl]-3,4'-bipyridin-2'-yl}acetamide |

TABLE 2-continued

Chemical Names and Synthetic Protocols

| Compound | Synthetic Example | Chemical Name |
|---|---|---|
| I-4 | 9AV | N-(5-{[(2,4-difluorophenyl)sulfonyl]amino}-5',6-dimethyl-3,4'-bipyridin-2'-yl)cyclopropanecarboxamide |
| I-5 | 5C | N-{6-amino-5-[(4-methylpiperazin-1-yl)sulfonyl]-3,4'-bipyridin-2'-yl}acetamide |
| I-6 | 7H | N-[6-amino-5-(benzylsulfonyl)-3,4'-bipyridin-2'-yl]acetamide |
| I-7 | 5R | N-[6-amino-5-(isopropylsulfamoyl)-3,4'-bipyridin-2'-yl]acetamide |
| I-8 | 15 | N-[5-(cyclopropylcarbonyl)-3,4'-bipyridin-2'-yl]acetamide |
| I-9 | 5AM | N-{5-[(4,4-difluoropiperidin-1-yl)sulfonyl]-3,4'-bipyridin-2'-yl}acetamide |
| I-10 | 20E | N-[6-amino-5-(piperidin-1-ylcarbonyl)-3,4'-bipyridin-2'-yl]acetamide |
| I-11 | 5AK | N-[6-amino-5-(bicyclo[1.1.1]pent-1-ylsulfamoyl)-3,4'-bipyridin-2'-yl]acetamide |
| I-12 | 9AK | N-(5-{[(2,4-difluorophenyl)sulfonyl]amino}-3,4'-bipyridin-2'-yl)acetamide |
| I-13 | 21 | N-(2'-acetamido-3,4'-bipyridin-5-yl)benzamide |
| I-14 | 20K | 2'-acetamido-6-amino-N-(cyclopropylmethyl)-3,4'-bipyridine-5-carboxamide |
| I-15 | 20F | N-[6-amino-5-(pyrrlidin-1-ylcarbonyl)-3,4'-bipyridin-2'-yl]acetamide |
| I-16 | 9AP | (rac)-N-(5-{[(2,4-difluorophenyl)sulfonyl]amino}-6-methyl-3,4'-bipyridin-2'-yl)-2,2-difluorocyclopropanecarboxamide |
| I-17 | 8K | N-[4-(1H-pyrrolo[3,2-b]pyridin-6-yl)pyridin-2-yl]acetamide |
| I-18 | 10G | N-[6-methyl-5-({[1-methyl-3-(trifluoromethyl)-1H-pyrazol-4-yl]sulfonyl}amino)-3,4'-bipyridin-2'-yl]acetamide |
| I-19 | 5Q | N-{6-amino-5-[(pyridin-3-ylmethyl)sulfamoyl]-3,4'-bipyridin-2'-yl}acetamide |
| I-20 | 11A | N-{5-[methyl(methylsulfonyl)amino]-3,4'-bipyridin-2'-yl}acetamide |
| I-21 | 25 | N-[4-(2-methyl-1,1-dioxido-3,4-dihydro-2H-pyrido[2,3-e][1,2,4]thiadiazin-7-yl)pyridin-2-yl]acetamide |
| I-22 | 20V | 2'-acetamido-N,N-dimethyl-6-(methylamino)-3,4'-bipyridine-5-carboxamide |
| I-23 | 8B | N-{4-[1-(phenylsulfonyl)-1H-pyrrolo[3,2-b]pyridin-6-yl]pyridin-2-yl}acetamide |
| I-24 | 5L | N-[6-amino-5-(morpholin-4-ylsulfonyl)-3,4'-bipyridin-2'-yl]acetamide |
| I-25 | 9AQ | N-[5-{[(2,4-difluorophenyl)sulfonyl]amino}-6-(dimethylamino)-3,4'-bipyridin-2'-yl]acetamide |
| I-26 | 8D | N-{5-[(cyclopropylsulfonyl)(ethyl)amino]-6-methyl-3,4'-bipyridin-2'-yl}acetamide |
| I-27 | 20B | 2'-acetamido-6-amino-N,N-diethyl-3,4'-bipyridine-5-carboxamide |
| I-28 | 10H | N-(5-{[(2-fluoro-5-methylphenyl)sulfonyl]amino}-6-methyl-3,4'-bipyridin-2'-yl)acetamide |
| I-29 | 18 | N-{4-[1-(cyclopropylmethyl)-2,2-dioxido-1,3-dihydro[1,2,5]thiadiazolo[3,4-b]pyridin-6-yl]pyridin-2-yl}acetamide |
| I-30 | 9B | N-(5-{[(2,4-dichlorophenyl)sulfonyl]amino}-6-methyl-3,4'-bipyridin-2'-yl)acetamide |
| I-31 | 9AR | N-[5-{[(2,4-difluorophenyl)sulfonyl]amino}-6-(methylamino)-3,4'-bipyridin-2'-yl]acetamide |
| I-32 | 9G | N-{5-[(dimethylsulfamoyl)amino]-6-methyl-3,4'-bipyridin-2'-yl}acetamide |
| I-33 | 8M | N-{4-[1-(methylsulfonyl)-1H-pyrrolo[3,2-b]pyridin-6-yl]pyridin-2-yl}acetamide |
| I-34 | 6B | methyl[6-amino-5-(isopropylsulfonyl)-3,4'-bipyridin-2'-yl]carbamate |
| I-35 | 17 | N-{6-amino-5-[(cyclopropylmethyl)amino]-3,4'-bipyridin-2'-yl}acetamide |
| I-36 | 6A | methyl [6-amino-5-(pyrrolidin-1-ylsulfonyl)-3,4'-bipyridin-2'-yl]carbamate |
| I-37 | 5F | N-{6-amino-5-[methyl(phenyl)sulfamoyl]-3,4'-bipyridin-2'-yl}acetamide |
| I-38 | 30 | methyl [4-(1H-pyrazolo[3,4-b]pyridin-5-yl)pyridin-2-yl]carbamate |
| I-39 | 5AH | N-[6-methoxy-5-(phenylsulfamoyl)-3,4'-bipyridin-2'-yl]acetamide |
| I-40 | 24 | N-{4-[3-(dimethylsulfamoyl)-1H-pyrrolo[2,3-b]pyridin-5-yl]pyridin-2-yl}acetamide |
| I-41 | 9 | N-(5-{[(2,4-difluorophenyl)sulfonyl]amino}-6-methyl-3,4'-bipyridin-2'-yl)acetamide |
| I-42 | 28 | methyl {4-[1-(cyclopropylmethyl)-1H-pyrrolo[3,2-b]pyridin-6-yl]pyridin-2-yl}carbamate |
| I-43 | 5I | N-[6-amino-5-(phenylsulfamoyl)-3,4'-bipyridin-2'-yl]acetamide |
| I-44 | 9AG | N-(5-{[(4-ethylphenyl)sulfonyl]amino}-6-methyl-3,4'-bipyridin-2'-yl)acetamide |
| I-45 | 9AN | N-{6-methyl-5-[(pyridin-3-ylsulfonyl)amino]-3,4'-bipyridin-2'-yl}acetamide |
| I-46 | 8F | N-{6-methyl-5-[methyl(phenylsulfonyl)amino]-3,4'-bipyridin-2'-yl}acetamide |
| I-47 | 5Y | N-[5-(pyrrolidin-1-ylsulfonyl)-3,4'-bipyridin-2'-yl]acetamide |
| I-48 | 20AA | 2'-acetamido-N,N-dimethyl-3,4'-bipyridine-5-carboxamide |
| I-49 | 5X | N-{6-amino-5-[(cyclopropylmethyl)sulfamoyl]-4-methyl-3,4'-bipyridin-2'-yl}acetamide |
| I-50 | 7K | N-(6-amino-5-{[2-(trifluoromethyl)benzyl]sulfonyl}-3,4'-bipyridin-2'-yl)acetamide |
| I-51 | 7N | N-[5-(methylsulfonyl)-3,4'-bipyridin-2'-yl]acetamide |
| I-52 | 9H | N-(5-{[(2,5-difluorophenyl)sulfonyl]amino}-6-methyl-3,4'-bipyridin-2'-yl)acetamide |
| I-53 | 17A | N-{5-amino-6-[(cyclopropylmethyl)amino]-3,4'-bipyridin-2'-yl}acetamide |
| I-54 | 32 | N-{4-[3-(pyrrolidin-1-ylmethyl)-1H-pyrrolo[2,3-b]pyridin-5-yl]pyridin-2-yl}acetamide |
| I-55 | 6C | methyl [6-amino-5-(dimethylcarbamoyl)-3,4'-bipyridin-2'-yl]carbamate |
| I-56 | 16B | N-{6-chloro-5'-methyl-5-[(phenylsulfonyl)amino]-3,4'-bipyridin-2'-yl}acetamide |
| I-57 | 20I | 2'-acetamido-6-amino-N-methyl-3,4'-bipyridine-5-carboxamide |
| I-58 | 9Y | N-(5-{[(4-fluoro-2-methoxyphenyl)sulfonyl]amino}-6-methyl-3,4'-bipyridin-2'-yl)acetamide |
| I-59 | 9J | N-(5-{[(3,4-difluorophenyl)sulfonyl]amino}-6-methyl-3,4'-bipyridin-2'-yl)acetamide |
| I-60 | 20Q | N-{6-amino-5-[(3,3-difluoropyrrolidin-1-yl)carbonyl]-3,4'-bipyridin-2'-yl}acetamide |
| I-61 | 5J | N-(6-amino-5-sulfamoyl-3,4'-bipyridin-2'-yl)acetamide |
| I-62 | 10A | N-[6-methyl-5-({[2-(trifluoromethyl)phenyl]sulfonyl}amino)-3,4'-bipyridin-2'-yl]acetamide |
| I-63 | 5AF | N-{5-[(2,4-difluorophenyl)sulfamoyl]-6-(methylamino)-3,4'-bipyridin-2'-yl}acetamide |
| I-64 | 12B | N-(6-amino-5-{[(2,4-difluorophenyl)sulfonyl]amino}-3,4'-bipyridin-2'-yl)acetamide |
| I-65 | 17B | N-{5,6-bis[(cyclopropylmethyl)amino]-3,4'-bipyridin-2'-yl}acetamide |
| I-66 | 27 | N-[4-(2-methyl-3H-imidazo[4,5-b]pyridin-6-yl)pyridin-2-yl]acetamide |
| I-67 | 8H | N-[4-(2,3-dihydro-1H-pyrrolo[2,3-b]pyridin-5-yl)pyridin-2-yl]acetamide |
| I-68 | 18A | N-{4-[3-(cyclopropylmethyl)-2,2-dioxido-1,3-dihydro[1,2,5]thiadiazolo[3,4-b]pyridin-6-yl]pyridin-2-yl}acetamide |
| I-69 | 7M | N-[6-amino-5-(ethylsulfonyl)-3,4'-bipyridin-2'-yl]acetamide |
| I-70 | 9W | N-(5-{[(3-tert-butylphenyl)sulfonyl]amino}-6-methyl-3,4'-bipyridin-2'-yl)acetamide |
| I-71 | 20O | N-[6-amino-5-(2,3-dihydro-1H-indol-1-ylcarbonyl)-3,4'-bipyridin-2'-yl]acetamide |
| I-72 | 9AI | N-{5-[(cyclohexylsulfonyl)amino]-6-methyl-3,4'-bipyridin-2'-yl}acetamide |
| I-73 | 5O | N-[6-amino-5-(isobutylsulfamoyl)-3,4'-bipyridin-2'-yl]acetamide |

TABLE 2-continued

Chemical Names and Synthetic Protocols

| Compound | Synthetic Example | Chemical Name |
|---|---|---|
| I-74 | 9K | N-(5-{[(2-methoxyphenyl)sulfonyl]amino}-6-methyl-3,4'-bipyridin-2'-yl)acetamide |
| I-75 | 20Z | 2'-acetamido-N,N,6-trimethyl-3,4'-bipyridine-5-carboxamide |
| I-76 | 5K | N-{6-amino-5-[benzyl(methyl)sulfamoyl]-3,4'-bipyridin-2'-yl}acetamide |
| I-77 | 5AB | N-[6-amino-5-(diisopropylsulfamoyl)-3,4'-bipyridin-2'-yl]acetamide |
| I-78 | 9R | N-{6-methyl-5-[(1-naphthylsulfonyl)amino]-3,4'-bipyridin-2'-yl}acetamide |
| I-79 | 20J | N-{6-amino-5-[(4-methylpiperazin-1-yl)carbonyl]-3,4'-bipyridin-2'-yl}acetamide |
| I-80 | 9P | N-(6-methyl-5-{[(4-methylphenyl)sulfonyl]amino}-3,4'-bipyridin-2'-yl)acetamide |
| I-81 | 20C | N-{6-amino-5-[(4-methylpiperidin-1-yl)carbonyl]-3,4'-bipyridin-2'-yl}acetamide |
| I-82 | 20N | 2'-acetamido-6-amino-N-(3-fluorophenyl)-3,4'-bipyridine-5-carboxamide |
| I-83 | 8C | N-{5-[(cyclopropylmethyl)(cyclopropylsulfonyl)amino]-6-methyl-3,4'-bipyridin-2'-yl}acetamide |
| I-84 | 9A | N-{6-methyl-5-[(phenylsulfonyl)amino]-3,4'-bipyridin-2'-yl}acetamide |
| I-85 | 32B | N-(4-{3-[(dimethylamino)methyl]-1H-pyrrolo[2,3-b]pyridin-5-yl}pyridin-2-yl)acetamide |
| I-86 | 9AO | N-(4-{4-[(2'-acetamido-6-methyl-3,4'-bipyridin-5-yl)sulfamoyl]-3-fluorophenyl}pyridin-2-yl)acetamide |
| I-87 | 5V | N-[6-amino-5-(pyrrolidin-1-ylsulfonyl)-3,4'-bipyridin-2'-yl]acetamide |
| I-88 | 11B | N-[5-(1,1-dioxidoisothiazolidin-2-yl)-6-methyl-3,4'-bipyridin-2'-yl]acetamide |
| I-89 | 5T | N-[6-amino-5-(methylsulfamoyl)-3,4'-bipyridin-2'-yl]acetamide |
| I-90 | 9AD | N-(6-methyl-5-({[4-(trifluoromethyl)phenyl]sulfonyl}amino)-3,4'-bipyridin-2'-yl)acetamide |
| I-91 | 20H | 2'-acetamido-6-amino-N-(pyridin-3-yl)-3,4'-bipyridine-5-carboxamide |
| I-92 | 10D | N-(6-methyl-5-{[(1-methyl-1H-imidazol-2-yl)sulfonyl]amino}-3,4'-bipyridin-2'-yl)acetamide |
| I-93 | 8L | N-{4-[1-(cyclopropylmethyl)-1H-pyrrolo[3,2-b]pyridin-6-yl]pyridin-2-yl}acetamide |
| I-94 | 9S | N-(5-{[(4-chloro-2-fluorophenyl)sulfonyl]amino}-6-methyl-3,4'-bipyridin-2'-yl)acetamide |
| I-95 | 7 | N-[6-amino-5-(methylsulfonyl)-3,4'-bipyridin-2'-yl]acetamide |
| I-96 | 8E | N-{6-methyl-5-[methyl(methylsulfonyl)amino]-3,4'-bipyridin-2'-yl}acetamide |
| I-97 | 5B | N-{6-amino-5-[(3-chlorophenyl)sulfamoyl]-3,4'-bipyridin-2'-yl}acetamide |
| I-98 | 5G | N-[6-amino-5-(2-naphthylsulfamoyl)-3,4'-bipyridin-2'-yl]acetamide |
| I-99 | 7B | N-{6-amino-5-[(4-chlorobenzyl)sulfonyl]-3,4'-bipyridin-2'-yl}acetamide |
| I-100 | 5AG | N-[6-(methylamino)-5-(phenylsulfamoyl)-3,4'-bipyridin-2'-yl]acetamide |
| I-101 | 5E | N-[6-amino-5-(cyclohexylsulfamoyl)-3,4'-bipyridin-2'-yl]acetamide |
| I-102 | 9AL | N-(5-{[(2,4-difluorophenyl)sulfonyl]amino}-4-methyl-3,4'-bipyridin-2'-yl)acetamide |
| I-103 | 24C | N-(4-{3-[(4-methylpiperazin-1-yl)sulfonyl]-1H-pyrrolo[2,3-b]pyridin-5-yl}pyridin-2-yl)acetamide |
| I-104 | 9AS | N-(5-{[(2,4-difluorophenyl)sulfonyl]amino}-6-methoxy-3,4'-bipyridin-2'-yl)acetamide |
| I-105 | 23 | N-{4-[2-(cyclopropylsulfonyl)-2H-pyrazolo[4,3-b]pyridin-6-yl]pyridin-2-yl}acetamide |
| I-106 | 21A | N-(2'-acetamido-3,4'-bipyridin-5-yl)-2-phenylacetamide |
| I-107 | 5AI | N-[5-[(2,4-difluorophenyl)sulfamoyl]-6-methoxy-3,4'-bipyridin-2'-yl]acetamide |
| I-108 | 5A | N-[6-amino-5-[(cyclopropylmethyl)sulfamoyl]-3,4'-bipyridin-2'-yl]acetamide |
| I-109 | 9C | N-(5-{[(2-chlorophenyl)sulfonyl]amino}-6-methyl-3,4'-bipyridin-2'-yl)acetamide |
| I-110 | 5S | N-{6-amino-5-[(cyclopropylmethyl)(methyl)sulfamoyl]-3,4'-bipyridin-2'-yl}acetamide |
| I-111 | 9F | N-(5-{[(2,5-dichlorophenyl)sulfonyl]amino}-6-methyl-3,4'-bipyridin-2'-yl)acetamide |
| I-112 | 22A | 2'-acetamido-N-(2,4-difluorophenyl)-6-(dimethylamino)-3,4'-bipyridine-5-carboxamide |
| I-113 | 9AA | N-[5-({[2-chloro-4-(trifluoromethoxy)phenyl]sulfonyl}amino)-6-methyl-3,4'-bipyridin-2'-yl]acetamide |
| I-114 | 10C | N-{5-[(cyclopropylsulfonyl)amino]-6-methyl-3,4'-bipyridin-2'-yl}acetamide |
| I-115 | 21B | N-(2'-acetamido-6-methyl-3,4'-bipyridin-5-yl)-2,4-difluorobenzamide |
| I-116 | 8J | N-[4-(1H-pyrazolo[4,3-b]pyridin-6-yl)pyridin-2-yl]acetamide |
| I-117 | 30A | N-[4-(1H-pyrazolo[3,4-b]pyridin-5-yl)pyridin-2-yl]cyclopropanecarboxamide |
| I-118 | 5AN | N-{5-[(3,3-difluoropyrrolidin-1-yl)sulfonyl]-3,4'-bipyridin-2'-yl}acetamide |
| I-119 | 5 | N-[6-amino-5-(dimethylsulfamoyl)-3,4'-bipyridin-2'-yl]acetamide |
| I-120 | 5Z | N-[5-(diethylsulfamoyl)-3,4'-bipyridin-2'-yl]acetamide |
| I-121 | 20M | 2'-acetamido-6-amino-N-(5-methylpyridazin-3-yl)-3,4'-bipyridine-5-carboxamide |
| I-122 | 7P | 2'-acetamido-6-amino-3,4'-bipyridine-5-sulfonic acid |
| I-123 | 9E | N-(5-{[(3-methoxyphenyl)sulfonyl]amino}-6-methyl-3,4'-bipyridin-2'-yl)acetamide |
| I-124 | 5U | N-[6-amino-5-(diethylsulfamoyl)-3,4'-bipyridin-2'-yl]acetamide |
| I-125 | 20D | N-[6-amino-5-(1,3-dihydro-2H-isoindol-2-ylcarbonyl)-3,4'-bipyridin-2'-yl]acetamide |
| I-126 | 7D | N-{6-amino-5-[(2-phenylethyl)sulfonyl]-3,4'-bipyridin-2'-yl}acetamide |
| I-127 | 20X | 2'-acetamido-6-methoxy-N,N-dimethyl-3,4'-bipyridine-5-carboxamide |
| I-128 | 10E | N-(5-{[(2-chloro-4-methylphenyl)sulfonyl]amino}-6-methyl-3,4'-bipyridin-2'-yl)acetamide |
| I-129 | 14A | N-(4-{6-methyl-5-[methyl(methylsulfonyl)amino]-1-oxidopyridin-3-yl}pyridin-2-yl)acetamide |
| I-130 | 9AB | N-(5-{[(2-fluoro-4-methylphenyl)sulfonyl]amino}-5',6-dimethyl-3,4'-bipyridin-2'-yl)acetamide |
| I-131 | 9Q | N-(5-{[(4-tert-butylphenyl)sulfonyl]amino}-6-methyl-3,4'-bipyridin-2'-yl)acetamide |
| I-132 | 13A | N-[5-(1,1-dioxidoisothiazolidin-2-yl)-6-(methylamino)-3,4'-bipyridin-2'-yl]acetamide |
| I-133 | 12 | N-{6-amino-5-[methyl(methylsulfonyl)amino]-3,4'-bipyridin-2'-yl}acetamide |
| I-134 | 9AJ | N-(5-{[(4-isopropylphenyl)sulfonyl]amino}-6-methyl-3,4'-bipyridin-2'-yl)acetamide |
| I-135 | 26 | N-{4-[1-(cyclopropylmethyl)-1H-imidazo[4,5-b]pyridin-6-yl]pyridin-2-yl}acetamide |
| I-136 | 20P | 2'-acetamido-6-amino-N-(2-chlorophenyl)-3,4'-bipyridine-5-carboxamide |
| I-137 | 5W | N-[5-(dimethylsulfamoyl)-3,4'-bipyridin-2'-yl]acetamide |
| I-138 | 7A | N-{6-amino-5-[(2,4-difluorobenzyl)sulfonyl]-3,4'-bipyridin-2'-yl}acetamide |
| I-139 | 7O | N-(5-amino-3,4'-bipyridin-2'-yl)acetamide |
| I-140 | 8I | N-[4-(1H-pyrrolo[2,3-b]pyridin-5-yl)pyridin-2-yl]acetamide |
| I-141 | 13B | N-{5-[(cyclopropylmethyl)(methylsulfonyl)amino]-6-(methylamino)-3,4'-bipyridin-2'-yl}acetamide |
| I-142 | 9AC | N-(5-{[(2-methoxy-4-methylphenyl)sulfonyl]amino}-6-methyl-3,4'-bipyridin-2'-yl)acetamide |
| I-143 | 9U | N-[5-({[2-fluoro-5-(trifluoromethyl)phenyl]sulfonyl}amino)-6-methyl-3,4'-bipyridin-2'-yl]acetamide |

TABLE 2-continued

Chemical Names and Synthetic Protocols

| Compound | Synthetic Example | Chemical Name |
|---|---|---|
| I-144 | 9M | N-(5-{[(2-fluorophenyl)sulfonyl]amino}-6-methyl-3,4'-bipyridin-2-yl)acetamide |
| I-145 | 7J | N-{6-amino-5-[(2-ethoxyethyl)sulfonyl]-3,4'-bipyridin-2'-yl}acetamide |
| I-146 | 16A | methyl [5-(1,1-dioxidoisothiazolidin-2-yl)-6-methyl-3,4'-bipyridin-2'-yl]carbamate |
| I-147 | 13 | N-{6-(methylamino)-5-[methyl(methylsulfonyl)amino]-3,4'-bipyridin-2'-yl}acetamide |
| I-148 | 5D | N-{6-amino-5-[(2-phenylethyl)sulfamoyl]-3,4'-bipyridin-2'-yl}acetamide |
| I-149 | 20 | 2'-acetamido-6-amino-N,N-dimethyl-3,4'-bipyridine-5-carboxamide |
| I-150 | 9X | N-(5-{[(2,6-difluorophenyl)sulfonyl]amino}-6-methyl-3,4'-bipyridin-2'-yl)acetamide |
| I-151 | 24B | N-{4-[1-methyl-3-(pyrrolidin-1-ylsulfonyl)-1H-pyrrolo[2,3-b]pyridin-5-yl]pyridin-2-yl}acetamide |
| I-152 | 20S | N-[6-amino-5-(morpholin-4-ylcarbonyl)-3,4'-bipyridin-2'-yl]acetamide |
| I-153 | 9AX | N-(6-chloro-5-{[(2,4-difluorophenyl)sulfonyl]amino}-4-methyl-3,4'-bipyridin-2'-yl)acetamide |
| I-154 | 9AE | N-(5-{[(4-chlorophenyl)sulfonyl]amino}-6-methyl-3,4'-bipyridin-2'-yl)acetamide |
| I-155 | 9N | N-(5-{[(3-fluorophenyl)sulfonyl]amino}-6-methyl-3,4'-bipyridin-2'-yl)acetamide |
| I-156 | 5N | N-[6-amino-5-(piperidin-1-ylsulfonyl)-3,4'-bipyridin-2'-yl]acetamide |
| I-157 | 20T | N-(6-amino-5-{[(3R)-3-fluoropyrrolidin-1-yl]carbonyl}-3,4'-bipyridin-2'-yl)acetamide |
| I-158 | 24A | N-{4-[3-(pyrrolidin-1-ylsulfonyl)-1H-pyrrolo[2,3-b]pyridin-5-yl]pyridin-2-yl}acetamide |
| I-159 | 9T | N-(5-{[(2,5-difluoro-4-methoxyphenyl)sulfonyl]amino}-6-methyl-3,4'-bipyridin-2'-yl)acetamide |
| I-160 | 20AB | 2'-acetamido-N-(bicyclo[1.1.1]pent-1-yl)-6-(methylamino)-3,4'-bipyridine-5-carboxamide |
| I-161 | 9AU | N-(5-{[(2,4-difluorophenyl)sulfonyl]amino}-5'-fluoro-6-methyl-3,4'-bipyridin-2'-yl)acetamide |
| I-162 | 20W | 2'-acetamido-6-(dimethylamino)-N,N-dimethyl-3,4'-bipyridine-5-carboxamide |
| I-163 | 9Z | N-(5-{[(2-fluoro-4-methoxyphenyl)sulfonyl]amino}-6-methyl-3,4'-bipyridin-2'-yl)acetamide |
| I-164 | 9I | N-(5-{[(2,4-difluorophenyl)sulfonyl]amino}-6-fluoro-3,4'-bipyridin-2'-yl)acetamide |
| I-165 | 9AF | N-(5-{[(4-methoxyphenyl)sulfonyl]amino}-6-methyl-3,4'-bipyridin-2'-yl)acetamide |
| I-166 | 5AA | 6-amino-N,N-dimethyl-2'-(1,3-oxazol-2-ylamino)-3,4'-bipyridine-5-sulfonamide |
| I-167 | 9AM | N-{6-methyl-5-[(methylsulfonyl)amino]-3,4'-bipyridin-2'-yl}acetamide |
| I-168 | 9L | N-(6-methyl-5-({[3-(trifluoromethyl)phenyl]sulfonyl}amino)-3,4'-bipyridin-2'-yl)acetamide |
| I-169 | 20L | 2'-acetamido-6-amino-N-cyclopropyl-3,4'-bipyridine-5-carboxamide |
| I-170 | 5AE | N-{6-amino-5-[(2,4-difluorophenyl)sulfamoyl]-3,4'-bipyridin-2'-yl}acetamide |
| I-171 | 6 | methyl [6-amino-5-(dimethylsulfamoyl)-3,4'-bipyridin-2'-yl]carbamate |
| I-172 | 7E | N-{6-amino-5-[(2-chlorobenzyl)sulfonyl]-3,4'-bipyridin-2'-yl}acetamide |
| I-173 | 5AJ | N-[5-(diisopropylsulfamoyl)-6-(methylamino)-3,4'-bipyridin-2'-yl]acetamide |
| I-174 | 22 | 2'-acetamido-N-(2,4-difluorophenyl)-6-(dimethylamino)-N-methyl-3,4'-bipyridine-5-carboxamide |
| I-175 | 7G | N-[6-amino-5-(isopropylsulfonyl)-3,4'-bipyridin-2'-yl]acetamide |
| I-176 | 29 | N-{4-[3-(phenylsulfonyl)-1H-pyrrolo[2,3-b]pyridin-5-yl]pyridin-2-yl}acetamide |
| I-177 | 9AW | N-(5-{[(2,4-difluorophenyl)sulfonyl]amino}-5',6-dimethyl-3,4'-bipyridin-2'-yl)acetamide |
| I-178 | 9O | N-(5-{[(2,5-dimethylphenyl)sulfonyl]amino}-6-methyl-3,4'-bipyridin-2'-yl)acetamide |
| I-179 | 20U | 2'-acetamido-6-amino-N-(2,3-difluorophenyl)-3,4'-bipyridine-5-carboxamide |
| I-180 | 16C | methyl [5-(cyclopropylcarbonyl)-3,4'-bipyridin-2'-yl]carbamate |
| I-181 | 12A | N-[6-amino-5-(1,1-dioxidoisothiazolidin-2-yl)-3,4'-bipyridin-2'-yl]acetamide |
| I-182 | 10B | N-(5-{[(2-fluoro-4-methylphenyl)sulfonyl]amino}-6-methyl-3,4'-bipyridin-2'-yl)acetamide |
| I-183 | 5M | N-{6-amino-5-[(cyclohexylmethyl)sulfamoyl]-3,4'-bipyridin-2'-yl}acetamide |
| I-184 | 5AC | N-(5-formyl-3,4'-bipyridin-2'-yl)acetamide |
| I-185 | 9AH | N-(5-{[(4-fluorophenyl)sulfonyl]amino}-6-methyl-3,4'-bipyridin-2'-yl)acetamide |
| I-186 | 4 | N-[6-amino-5-(dimethylsulfamoyl)-5'-fluoro-3,4'-bipyridin-2'-yl]acetamide |
| I-187 | 20G | 2'-acetamido-6-amino-N-(bicyclo[1.1.1]pent-1-yl)-3,4'-bipyridine-5-carboxamide |
| I-188 | 19 | N-{5-[(1E)-3-(4-fluorophenyl)-3-oxoprop-1-en-1-yl]-3,4'-bipyridin-2'-yl}acetamide |
| I-189 | 33 | N-[4-(1H-pyrazolo[3,4-b]pyridin-5-yl)pyridin-2-yl]acetamide |
| I-190 | 5AL | N-[5-(bicyclo[1.1.1]pent-1-ylsulfamoyl)-3,4'-bipyridin-2'-yl]acetamide |
| I-191 | 14 | N-{4-[5-(methylsulfonyl)-1-oxidopyridin-3-yl]pyridin-2-yl}acetamide |
| I-192 | 11 | N-[5-(1,1-dioxidoisothiazolidin-2-yl)-3,4'-bipyridin-2'-yl]acetamide |
| I-193 | 21C | N,N'-(6-methyl-3,4'-bipyridine-2',5-diyl)diacetamide |
| I-194 | 5AD | N-(5-acetyl-3,4'-bipyridin-2'-yl)acetamide |
| I-195 | 16 | methyl (5-{[(2,4-difluorophenyl)sulfonyl]amino}-6-methyl-3,4'-bipyridin-2'-yl)carbamate |
| I-196 | 10F | N-[5-({[2-chloro-4-(trifluoromethyl)phenyl]sulfonyl}amino)-6-methyl-3,4'-bipyridin-2'-yl]acetamide |
| I-197 | 7F | N-{6-amino-5-[(2-fluorobenzyl)sulfonyl]-3,4'-bipyridin-2'-yl}acetamide |
| I-198 | 19A | N-{5-[(2E)-3-(4-fluorophenyl)prop-2-enoyl]-3,4'-bipyridin-2'-yl}acetamide |
| I-199 | 8N | N-{4-[1-(cyclopropylsulfonyl)-1H-pyrrolo[3,2-b]pyridin-6-yl]pyridin-2-yl}acetamide |
| I-200 | 20A | N-[6-amino-5-(azetidin-1-ylcarbonyl)-3,4'-bipyridin-2'-yl]acetamide |
| I-201 | 9AT | N-(5-{[(2,4-difluorophenyl)sulfonyl]amino}-6-ethyl-3,4'-bipyridin-2'-yl)acetamide |
| I-202 | 8G | N-{5-[(cyclopropylmethyl)(methylsulfonyl)amino]-3,4'-bipyridin-2'-yl}acetamide |
| I-203 | 10I | N-{6-methyl-5-[(3-thienylsulfonyl)amino]-3,4'-bipyridin-2'-yl}acetamide |
| I-204 | 5H | N-[6-amino-5-(pyridin-3-ylsulfamoyl)-3,4'-bipyridin-2'-yl]acetamide |
| I-205 | 7I | N-{6-amino-5-[(pyridin-3-ylmethyl)sulfonyl]-3,4'-bipyridin-2'-yl}acetamide |
| I-206 | 10 | N-(5-{[(2-chloro-4-fluorophenyl)sulfonyl]amino}-6-methyl-3,4'-bipyridin-2'-yl)acetamide |
| I-207 | 5P | N-{6-amino-5-[(4-chlorophenyl)sulfamoyl]-3,4'-bipyridin-2'-yl}acetamide |
| I-208 | 7L | N-{6-amino-5-[(cyclopropylmethyl)sulfonyl]-3,4'-bipyridin-2'-yl}acetamide |
| I-209 | 31 | N-[5-methyl-4-(1H-pyrazolo[3,4-b]pyridin-5-yl)pyridin-2-yl]acetamide |
| I-210 | 20R | 2'-acetamido-6-amino-N-(tetrahydro-2H-pyran-4-yl)-3,4'-bipyridine-5-carboxamide |
| I-211 | 9D | N-(6-methyl-5-{[(2-methylphenyl)sulfonyl]amino}-3,4'-bipyridin-2'-yl)acetamide |
| I-212 | 8 | N-[5-[(cyclopropylsulfonyl)(methyl)amino]-6-methyl-3,4'-bipyridin-2'-yl]acetamide |
| I-213 | 20Y | 2'-acetamido-6-chloro-N,N-dimethyl-3,4'-bipyridine-5-carboxamide |
| I-214 | 9AY | N-{6-methyl-5-[(piperidin-1-ylsulfonyl)amino]-3,4'-bipyridin-2'-yl}acetamide |

TABLE 2-continued

Chemical Names and Synthetic Protocols

| Compound | Synthetic Example | Chemical Name |
|---|---|---|
| I-215 | 43 | 6-chloro-N-cyclobutyl-2'-[(2-methylpyrimidin-4-yl)amino]-3,4'-bipyridine-5-sulfonamide |
| I-216 | 20AF | 6-amino-N-carbamimidoyl-2'-(pyrimidin-4-ylamino)-3,4'-bipyridine-5-carboxamide |
| I-217 | 35F | N,N-dimethyl-N'-[6-methyl-2'-(pyrimidin-4-ylamino)-3,4'-bipyridin-5-yl]sulfuric diamide |
| I-218 | 35D | N-{6-chloro-2'-[(2,6-dimethylpyrimidin-4-yl)amino]-4-methyl-3,4'-bipyridin-5-yl}-2,4-difluorobenzenesulfonamide |
| I-219 | 35AE | N-[4-(5-{[(2,4-difluorophenyl)sulfonyl]amino}-6-methylpyridin-3-yl)-1-oxidopyridin-2-yl]acetamide |
| I-220 | 9BI | N-{5-[(dimethylsulfamoyl)amino]-6-methoxy-3,4'-bipyridin-2'-yl}acetamide |
| I-221 | 39A | (3,3-difluoroazetidin-1-yl){6-methyl-2'-[(2-methylpyrimidin-4-yl)amino]-3,4'-bipyridin-5-yl}methanone |
| I-222 | 22E | N-(bicyclo[1.1.1]pent-1-yl)-N-methyl-6-(methylamino)-2'-(pyrimidin-4-ylamino)-3,4'-bipyridine-5-carboxamide |
| I-223 | 40 | azetidin-1-yl{6-methyl-2'-[(2-methylpyrimidin-4-yl)amino]-3,4'-bipyridin-5-yl}methanethione |
| I-224 | 43B | N-cyclobutyl-6-methoxy-2'-[(2-methylpyrimidin-4-yl)amino]-3,4'-bipyridine-5-sulfonamide |
| I-225 | 35E | N-{6-chloro-2'-[(2-methoxypyrimidin-4-yl)amino]-4-methyl-3,4'-bipyridin-5-yl}-2,4-difluorobenzenesulfonamide |
| I-226 | 34H | 6-chloro-4-methyl-N~2~'-(2-methylpyrimidin-4-yl)-3,4'-bipyridine-2',5-diamine |
| I-227 | 36C | N-(6-chloro-5-{[(2,5-difluorophenyl)sulfonyl]amino}-4-methyl-3,4'-bipyridin-2'-yl)acetamide |
| I-228 | 35Q | N-{2'-[(5-cyanopyridin-2-yl)amino]-6-methyl-3,4'-bipyridin-5-yl}-2,4-difluorobenzenesulfonamide |
| I-229 | 35M | N'-{2'-[(5-cyano-6-methylpyridin-2-yl)amino]-6-methyl-3,4'-bipyridin-5-yl}-N,N-dimethylsulfuric diamide |
| I-230 | 37 | 6-amino-N-(bicyclo[1.1.1]pent-1-yl)-2'-[(2-methoxypyrimidin-4-yl)amino]-N-methyl-3,4'-bipyridine-5-carboxamide |
| I-231 | 35AB | 3,4'-bipyridine-2',5-diamine |
| I-232 | 20AE | azetidin-1-yl{6-chloro-2'-[(2-methylpyrimidin-4-yl)amino]-3,4'-bipyridin-5-yl}methanone |
| I-233 | 35V | N-[2'-(1,3-benzoxazol-2-ylamino)-6-methyl-3,4'-bipyridin-5-yl]-2,4-difluorobenzenesulfonamide |
| I-234 | 37B | N-(bicyclo[1.1.1]pent-1-yl)-N-methyl-2'-[(2-methylpyrimidin-4-yl)amino]-3,4'-bipyridine-carboxamide |
| I-235 | 35Y | 2,4-difluoro-N-{6-methyl-2'-[(7-methyl-1,8-naphthyridin-2-yl)amino]-3,4'-bipyridin-5-yl}benzenesulfonamide |
| I-236 | 36I | N-{6-chloro-5-[(dimethylsulfamoyl)amino]-4-methyl-3,4'-bipyridin-2'-yl}acetamide |
| I-237 | 35B | 2,4-difluoro-N-(6-methyl-2'-{[2-(trifluoromethyl)pyrimidin-4-yl]amino}-3,4'-bipyridin-5-yl)benzenesulfonamide |
| I-238 | 35L | N-{6-chloro-2'-[(5-cyano-6-methylpyridin-2-yl)amino]-4-methyl-3,4'-bipyridin-5-yl}-2,4-difluorobenzenesulfonamide |
| I-239 | 35H | 2,4-difluoro-N-[6-methyl-2'-(pyrimidin-4-ylamino)-3,4'-bipyridin-5-yl]benzenesulfonamide |
| I-240 | 36E | N-(6-chloro-5-{[(2-chlorophenyl)sulfonyl]amino}-4-methyl-3,4'-bipyridin-2'-yl)acetamide |
| I-241 | 35AI | methyl {5-[(dimethylsulfamoyl)amino]-6-methyl-3,4'-bipyridin-2'-yl}carbamate |
| I-242 | 43C | N-(bicyclo[1.1.1]pent-1-yl)-6-chloro-2'-[(2-methylpyrimidin-4-yl)amino]-3,4'-bipyridine-5-sulfonamide |
| I-243 | 36F | N-(6-chloro-5-{[(2,4-dichlorophenyl)sulfonyl]amino}-4-methyl-3,4'-bipyridin-2'-yl)acetamide |
| I-244 | 9AZ | N-{5-[(dimethylsulfamoyl)amino]-6-methyl-3,4'-bipyridin-2'-yl}-2,2-difluorocyclopropanecarboxamide |
| I-245 | 37A | N-(bicyclo[1.1.1]pent-1-yl)-2'-[(2-methoxypyrimidin-4-yl)amino]-N-methyl-3,4'-bipyridine-5-carboxamide |
| I-246 | 38A | azetidin-1-yl{2'-[(2-cyclopropylpyrimidin-4-yl)amino]-6-methyl-3,4'-bipyridin-5-yl}methanone |
| I-247 | 34D | N-(5-{[(2,4-difluorophenyl)sulfonyl]amino}-4,6-dimethyl-3,4'-bipyridin-2'-yl)acetamide |
| I-248 | 34E | N-(5-{[(2,4-difluorophenyl)sulfonyl]amino}-6-methoxy-4-methyl-3,4'-bipyridin-2'-yl)acetamide |
| I-249 | 41A | 2,4-difluoro-N-{6-methyl-2'-[(2-methylpyrimidin-4-yl)amino]-3,4'-bipyridin-5-yl}benzamide |
| I-250 | 36H | N-(6-chloro-5-{[(2,4-difluorophenyl)sulfonyl]amino}-4,5'-dimethyl-3,4'-bipyridin-2'-yl)acetamide |
| I-251 | 36B | N-(6-chloro-5-{[(2-fluorophenyl)sulfonyl]amino}-4-methyl-3,4'-bipyridin-2'-yl)acetamide |
| I-252 | 38D | N-(2,4-difluorophenyl)-6-methoxy-N-methyl-2'-[(2-methylpyrimidin-4-yl)amino]-3,4'-bipyridine-5-carboxamide |
| I-253 | 39 | 6-methyl-2'-[(2-methylpyrimidin-4-yl)amino]-3,4'-bipyridine-5-carboxylic acid |
| I-254 | 36A | N-(6-chloro-5-{[(2,4-difluorophenyl)sulfonyl]amino}-4-methyl-3,4'-bipyridin-2'-yl)-2,2-difluorocyclopropanecarboxamide |
| I-255 | 35AG | methyl (6-chloro-5-{[(2,4-difluorophenyl)sulfonyl]amino}-4-methyl-3,4'-bipyridin-2'-yl)carbamate |
| I-256 | 34I | 6-chloro-N~5~,4-dimethyl-N~2~'-(2-methylpyrimidin-4-yl)-3,4'-bipyridine-2',5-diamine |
| I-257 | 9BF | N-{5-[(azetidin-1-ylsulfonyl)amino]-6-methyl-3,4'-bipyridin-2'-yl}acetamide |
| I-258 | 9BH | N-[4-(5-{[(2,4-difluorophenyl)sulfonyl]amino}-6-methyl-1-oxidopyridin-3-yl)pyridin-2-yl]acetamide |
| I-259 | 34A | N-{6-chloro-4-ethyl-2'-[(2-methylpyrimidin-4-yl)amino]-3,4'-bipyridin-5-yl}-2,4-difluorobenzenesulfonamide |
| I-260 | 34F | N-{5-[(dimethylsulfamoyl)amino]-4,6-dimethyl-3,4'-bipyridin-2'-yl}acetamide |
| I-262 | 20AJ | {6-methyl-2'-[(2-methylpyrimidin-4-yl)amino]-3,4'-bipyridin-5-yl}(piperidin-1-yl)methanone |
| I-263 | 35AC | N,N-dimethyl-N'-{6-methyl-2'-(4-methyl-1H-imidazo[4,5-c]pyridin-1-yl)-3,4'-bipyridin-5-yl}sulfuric diamide |
| I-264 | 35A | N-{6-chloro-4-methyl-2'-[(2-phenylpyrimidin-4-yl)amino]-3,4'-bipyridin-5-yl}-2,4-difluorobenzenesulfonamide |
| I-265 | 35U | 2,4-difluoro-N-[6-methyl-2'-(pyrimidin-2-ylamino)-3,4'-bipyridin-5-yl]benzenesulfonamide |
| I-266 | 38C | N,N,6-trimethyl-2'-[(2-methylpyrimidin-4-yl)amino]-3,4'-bipyridine-5-carboxamide |
| I-267a | 9BC | N-(5-{[(2,4-difluorophenyl)sulfonyl]amino}-6-methyl-3,4'-bipyridin-2'-yl)-2,2-difluorocyclopropanecarboxamide (Chiral Sep Peak1) |
| I-267b | 9BB | N-(5-{[(2,4-difluorophenyl)sulfonyl]amino}-6-methyl-3,4'-bipyridin-2'-yl)-2,2-difluorocyclopropanecarboxamide (Chiral Sep Peak2) |
| I-268 | 34G | N-{5-[(dimethylsulfamoyl)amino]-6-methoxy-4-methyl-3,4'-bipyridin-2'-yl}acetamide |
| I-269 | 9BE | N-(6-methyl-5-{[(4-methylpiperazin-1-yl)sulfonyl]amino}-3,4'-bipyridin-2'-yl)acetamide |
| I-271 | 35Z | N-[2'-(1,3-benzothiazol-2-ylamino)-6-methyl-3,4'-bipyridin-5-yl]-2,4-difluorobenzenesulfonamide |
| I-272 | 35K | N-{6-chloro-4-methyl-2'-[(2-methylpyridin-4-yl)amino]-3,4'-bipyridin-5-yl}-2,4-difluorobenzenesulfonamide |
| I-273 | 9BD | N-(5-{[ethyl(methyl)sulfamoyl]amino}-6-methyl-3,4'-bipyridin-2'-yl)acetamide |
| I-274 | 9BG | N-{6-methyl-5-[(pyrrolidin-1-ylsulfonyl)amino]-3,4'-bipyridin-2'-yl}acetamide |
| I-275 | 37C | N-(bicyclo[1.1.1]pent-1-yl)-N,6-dimethyl-2'-[(2-methylpyrimidin-4-yl)amino]-3,4'-bipyridine-5-carboxamide |

TABLE 2-continued

Chemical Names and Synthetic Protocols

| Compound | Synthetic Example | Chemical Name |
|---|---|---|
| I-276 | 35T | 2,4-difluoro-N-{6-methyl-2'-[(6-methylpyridin-2-yl)amino]-3,4'-bipyridin-5-yl}benzenesulfonamide |
| I-277 | 37D | 6-amino-N-(bicyclo[1.1.1]pent-1-yl)-N-methyl-2'-[(2-methylpyrimidin-4-yl)amino]-3,4'-bipyridine-5-carboxamide |
| I-278 | 34C | N-(6-chloro-5-{[(2,4-difluorophenyl)sulfonyl]amino}-4-ethyl-3,4'-bipyridin-2'-yl)cyclopropanecarboxamide |
| I-279 | 43A | N-cyclobutyl-6-hydroxy-2'-[(2-methylpyrimidin-4-yl)amino]-3,4'-bipyridine-5-sulfonamide |
| I-280 | 20AH | 6-methyl-2'-[(2-methylpyrimidin-4-yl)amino]-3,4'-bipyridine-5-carboxamide |
| I-281 | 35AA | N'-(2'-amino-6-methyl-3,4'-bipyridin-5-yl)-N,N-dimethylsulfuric diamide |
| I-282 | 34B | N-[6-chloro-4-methyl-2'-(pyrimidin-4-ylamino)-3,4'-bipyridin-5-yl]-2,4-difluorobenzenesulfonamide |
| I-283 | 22B | 2'-acetamido-N-(bicyclo[1.1.1]pent-1-yl)-6-(dimethylamino)-3,4'-bipyridine-5-carboxamide |
| I-284 | 22D | N-(bicyclo[1.1.1]pent-1-yl)-6-(dimethylamino)-N-methyl-2'-(pyrimidin-4-ylamino)-3,4'-bipyridine-5-carboxamide |
| I-285 | 39 | N-(cyclopropylmethyl)-6-methyl-2'-[(2-methylpyrimidin-4-yl)amino]-3,4'-bipyridine-5-carboxamide |
| I-286 | 35I | N,N-dimethyl-N'-{6-methyl-2'-[(2-methylpyrimidin-4-yl)amino]-3,4'-bipyridin-5-yl}sulfuric diamide |
| I-287 | 35AD | N-(2'-amino-6-chloro-4-methyl-3,4'-bipyridin-5-yl)-2,4-difluorobenzenesulfonamide |
| I-288 | 42 | 6-methyl-5-(6-methyl-1,1-dioxido-1,2,6-thiadiazinan-2-yl)-N-(2-methylpyrimidin-4-yl)-3,4'-bipyridin-2'-amine |
| I-289 | 35N | N-{2'-[(5-cyano-6-methylpyridin-2-yl)amino]-6-methyl-3,4'-bipyridin-5-yl}-2,4-difluorobenzenesulfonamide |
| I-290 | 36D | N-(6-chloro-5-{[(2-chloro-4-fluorophenyl)sulfonyl]amino}-4-methyl-3,4'-bipyridin-2'-yl)acetamide |
| I-291 | 35J | 2,4-difluoro-N-{6-methyl-2'-[(2-methylpyrimidin-4-yl)amino]-3,4'-bipyridin-5-yl}benzenesulfonamide |
| I-292 | 38B | azetidin-1-yl(6-methyl-2'-{[2-(trifluoromethyl)pyrimidin-4-yl]amino}-3,4'-bipyridin-5-yl)methanone |
| I-293 | 35P | N-{6-chloro-4-methyl-2'-[(4-methylpyrimidin-2-yl)amino]-3,4'-bipyridin-5-y}-2,4-difluorobenzenesulfonamide |
| I-294 | 35 | N-{6-chloro-5'-fluoro-4-methyl-2'-[(2-methylpyrimidin-4-yl)amino]-3,4'-bipyridin-5-yl}-2,4-difluorobenzenesulfonamide |
| I-295 | 41 | N-{6-chloro-4-methyl-2'-[(2-methylpyrimidin-4-yl)amino]-3,4'-bipyridin-5-yl}-2,4-difluorobenzenesulfonamide |
| I-296 | 35C | N-{6-chloro-2'-[(2-cyclopropylpyrimidin-4-yl)amino]-4-methyl-3,4'-bipyridin-5-yl}-2,4-difluorobenzenesulfonamide |
| I-297 | 35W | 2,4-difluoro-N-[6-methyl-2'-(pyridin-2-ylamino)-3,4'-bipyridin-5-yl]benzenesulfonamide |
| I-298 | 20AG | 6-amino-N-(bicyclo[1.1.1]pent-1-yl)-2'-(pyrimidin-4-ylamino)-3,4'-bipyridine-5-carboxamide |
| I-299 | 34 | N-{6-chloro-4-methyl-2'-[(2-methylpyrimidin-4-yl)amino]-3,4'-bipyridin-5-yl}-2,4-difluorobenzenesulfonamide |
| I-300 | 35O | N-{6-chloro-2'-[(5-cyanopyrimidin-2-yl)amino]-4-methyl-3,4'-bipyridin-5-yl}-2,4-difluorobenzenesulfonamide |
| I-301 | 35R | 2,4-difluoro-N-{6-methyl-2'-[(1-methyl-1H-pyrazol-3-yl)amino]-3,4'-bipyridin-5-yl}benzenesulfonamide |
| I-302 | 20AI | N,N-diethyl-6-methyl-2'-[(2-methylpyrimidin-4-yl)amino]-3,4'-bipyridine-5-carboxamide |
| I-303 | 20AC | 6-amino-N-(bicyclo[1.1.1]pent-1-yl)-N-methyl-2'-(pyrimidin-4-ylamino)-3,4'-bipyridine-5-carboxamide |
| I-304 | 38 | azetidin-1-yl{6-methyl-2'-[(2-methylpyrimidin-4-yl)amino]-3,4'-bipyridin-5-yl}methanone |
| I-305 | 35AF | N-(5-{[(2,4-difluorophenyl)sulfonyl]amino}-6-methyl-3,4'-bipyridin-2'-yl)cyclobutanecarboxamide |
| I-306 | 22C | N-(bicyclo[1.1.1]pent-1-yl)-6-(dimethylamino)-N-methyl-2'-[(2-methylpyrimidin-4-yl)amino]-3,4'-bipyridine-5-carboxamide |
| I-307 | 35S | 2,4-difluoro-N-{6-methyl-2'-[(6-methylpyridazin-3-yl)amino]-3,4'-bipyridin-5-yl}benzenesulfonamide |
| I-308 | 36 | N-(6-chloro-5-{[(2,4-difluorophenyl)sulfonyl]amino}-4-methyl-3,4'-bipyridin-2'-yl)cyclopropanecarboxamide |
| I-309 | 35G | N-[6-chloro-4-methyl-2'-(pyrimidin-4-ylamino)-3,4'-bipyridin-5-yl]benzenesulfonamide |
| I-310 | 35X | 2,4-difluoro-N-[6-methyl-2'-(pyrazin-2-ylamino)-3,4'-bipyridin-5-yl]benzenesulfonamide |
| I-311 | 9BA | N-(5-[(dimethylsulfamoyl)amino]-6-methyl-3,4'-bipyridin-2'-yl)cyclopropanecarboxamide |
| I-312 | 36G | N-{6-chloro-4-methyl-5-[(phenylsulfonyl)amino]-3,4'-bipyridin-2'-yl}acetamide |
| I-313 | 35AH | N-(5-{[(2,4-difluorophenyl)sulfonyl]amino}-6-methyl-3,4'-bipyridin-2'-yl)pyrrolidine-1-carboxamide |
| I-314 | 34J | 6-chloro-N5,N5,4-trimethyl-N2'-(2-methylpyrimidin-4-yl)-3,4'-bipyridine-2',5-diamine |
| I-315 | 20AD | {6-methyl-2'-[(2-methylpyrimidin-4-yl)amino]-3,4'-bipyridin-5-yl}(pyrrolidin-1-yl)methanone |
| I-318 | 5AW | N-[5-(adamantan-2-ylsulfamoyl)-3,4'-bipyridin-2'-yl]acetamide |
| I-319 | 9DB | N-(5-{[(2,4-difluorophenyl)sulfonyl](2-hydroxyethyl)amino}-6-methyl-3,4'-bipyridin-2'-yl)acetamide |
| I-320 | 47A | N-[5-(1,1-dioxido-1,2-thiazinan-2-yl)-3,4'-bipyridin-2'-yl]acetamide |
| I-321 | 5AR | N-[5-(benzylsulfamoyl)-3,4'-bipyridin-2'-yl]acetamide |
| I-322 | 9CS | N-(5-{[(2-chloro-3-fluorophenyl)sulfonyl]amino}-6-methyl-3,4'-bipyridin-2'-yl)acetamide |
| I-323 | 11J | N-[6-amino-5-(6-methyl-1,1-dioxido-1,2,6-thiadiazinan-2-yl)-3,4'-bipyridin-2'-yl]acetamide |
| I-324 | 35AK | (3-methyloxetan-3-yl)methyl (5-{[(2,4-difluorophenyl)sulfonyl]amino}-6-methyl-3,4'-bipyridin-2'-yl)carbamate |
| I-325 | 57A | N-{6-methyl-5-[4-(methylamino)-1,1-dioxidoisothiazolidin-2-yl]-3,4'-bipyridin-2'-yl}acetamide |
| I-326 | 35AM | (1-methyl-1H-pyrazol-3-yl)methyl(5-{[(2,4-difluorophenyl)sulfonyl]amino}-6-methyl-3,4'-bipyridin-2'-yl)carbamate |
| I-329 | 43K | N-(6-methoxy-5-{[3-(trifluoromethyl)phenyl]sulfamoyl}-3,4'-bipyridin-2'-yl)acetamide |
| I-330 | 43O | N-(6-chloro-5-{[(1S)-2-hydroxy-1-phenylethyl]sulfamoyl}-3,4'-bipyridin-2'-yl)acetamide |
| I-331 | 52A | N-(2'-acetamido-6-methoxy-3,4'-bipyridin-5-yl)-2,4-difluoro-N-methylbenzamide |
| I-332 | 35AQ | methyl [5-(morpholin-4-ylsulfonyl)-3,4'-bipyridin-2'-yl]carbamate |
| I-333 | 9CB | N-(6-chloro-5-(2-chloro-4-(trifluoromethyl)phenylsulfonamido)-4-methyl-[3,4'-bipyridin]-2'-yl)acetamide |
| I-334 | 43U | (S)—N-[4-(1,1-dioxido-3-phenyl-3,4-dihydro-2H-pyrido[2,3-b][1,4,5]oxathiazepin-8-yl)pyridin-2-yl]acetamide |
| I-335 | 10M | N-(6-chloro-5-{[(4-cyclopropyl-2-fluorophenyl)sulfonyl]amino}-4-methyl-3,4'-bipyridin-2'-yl)acetamide |
| I-336 | 34AC | 5-[1-(2-chlorophenoxy)ethyl]-N-(2-methylpyrimidin-4-yl)-3,4'-bipyridin-2'-amine |
| I-337 | 49 | N-[6-amino-5-(2-oxopyrrolidin-1-yl)-3,4'-bipyridin-2'-yl]acetamide |

TABLE 2-continued

Chemical Names and Synthetic Protocols

| Compound | Synthetic Example | Chemical Name |
|---|---|---|
| I-338 | 5AT | N-[5-(cyclopropylsulfamoyl)-3,4'-bipyridin-2'-yl]acetamide |
| I-339 | 9CU | N-(5-{[(2-fluoro-3-methylphenyl)sulfonyl]amino}-6-methyl-3,4'-bipyridin-2'-yl)acetamide |
| I-340 | 45 | N-[4-(8-{[(2,4-difluorophenyl)sulfonyl]amino}[1,2,4]triazolo[1,5-a]pyridin-6-yl)pyridin-2-yl]acetamide |
| I-341 | 9BS | N-{5-[(azepan-1-ylsulfonyl)amino]-6-methyl-3,4'-bipyridin-2'-yl}acetamide |
| I-342 | 9CT | N-(5-{[(2,3-dichlorophenyl)sulfonyl]amino}-6-methyl-3,4'-bipyridin-2'-yl)acetamide |
| I-343 | 11H | N-[6-methyl-5-(6-methyl-1,1-dioxido-1,2,6-thiadiazinan-2-yl)-3,4'-bipyridin-2'-yl]acetamide |
| I-344 | 43J | N-{5-[(2,4-dichlorophenyl)sulfamoyl]-6-methoxy-3,4'-bipyridin-2'-yl}acetamide |
| I-346 | 20AQ | N-(2,4-difluorophenyl)-N,6-dimethyl-2'-[(2-methylpyrimidin-4-yl)amino]-3,4'-bipyridine-5-carboxamide |
| I-347 | 21E | N-(2'-acetamido-6-methoxy-3,4'-bipyridin-5-yl)-2,4-difluorobenzenesulfonamide |
| I-348 | 9BN | N-{5-[(dimethylsulfamoyl)amino]-3,4'-bipyridin-2'-yl}acetamide |
| I-349 | 34AE | N-(2-methylpyrimidin-4-yl)-5-[1-(pyridin-2-ylmethoxy)ethyl]-3,4'-bipyridin-2'-amine |
| I-350 | 9CQ | N-{5-[(dibutylsulfamoyl)amino]-6-methyl-3,4'-bipyridin-2'-yl}acetamide |
| I-352 | 11E | N-[5-(1,1-dioxido-1,2,5-thiadiazolidin-2-yl)-6-methyl-3,4'-bipyridin-2'-yl]acetamide |
| I-353 | 43M | N-(5-(N-(2,4-difluorophenyl)sulfamoyl)-6-methyl-[3,4'-bipyridin]-2'-yl)acetamide |
| I-354 | 9CA | N-(6-chloro-5-{[(2,6-dichlorophenyl)sulfonyl]amino}-4-methyl-3,4'-bipyridin-2'-yl)acetamide |
| I-355 | 34S | 6-chloro-N~2~'-(2-cyclopropylpyrimidin-4-yl)-4-methyl-3,4'-bipyridine-2',5-diamine |
| I-356 | 9CW | N-(5-{[(4-cyano-2-fluorophenyl)sulfonyl]amino}-6-methyl-3,4'-bipyridin-2'-yl)acetamide |
| I-357 | 53B | N-{5-[4-(benzylamino)-1,1-dioxidoisothiazolidin-2-yl]-6-methyl-3,4'-bipyridin-2'-yl}acetamide |
| I-358 | 43I | N-{5-[(2,5-difluorophenyl)sulfamoyl]-6-methoxy-3,4'-bipyridin-2'-yl}acetamide |
| I-359 | 9BU | 2'-acetamido-6-methyl-3,4'-bipyridin-5-yl dimethylsulfamate |
| I-361 | 50 | azetidin-1-yl{6-chloro-2'-[(2-cyclopropylpyrimidin-4-yl)amino]-4-methyl-3,4'-bipyridin-5-yl}methanone |
| I-362 | 9BR | N-(6-chloro-5-{[(2-chloro-4-cyanophenyl)sulfonyl]amino}-4-methyl-3,4'-bipyridin-2'-yl)acetamide |
| I-363 | 34V | 5-(benzyloxy)-6-methyl-N-(2-methylpyrimidin-4-yl)-3,4'-bipyridin-2-amine |
| I-364 | 35AO | ethyl {5-[(dimethylsulfamoyl)amino]-3,4'-bipyridin-2'-yl}carbamate |
| I-365 | 5AU | N-{5-[methyl(phenyl)sulfamoyl]-3,4'-bipyridin-2'-yl}acetamide |
| I-366 | 43G | N-[5-(bicyclo[1.1.1]pent-1-ylsulfamoyl)-6-chloro-3,4'-bipyridin-2'-yl]acetamide |
| I-367 | 53B | 1-ethyl-3-{6-methyl-2'-[(2-methylpyrimidin-4-yl)amino]-3,4'-bipyridin-5-yl}urea |
| I-368 | 53 | N-{2'-[(2-cyclopropylpyrimidin-4-yl)amino]-6-methyl-3,4'-bipyridin-5-yl}-3,3-difluoroazetidine-1-carboxamide |
| I-369 | 50 | 6-chloro-2'-[(2-cyclopropylpyrimidin-4-yl)amino]-4-methyl-3,4'-bipyridine-5-carboxylic acid |
| I-370 | 43N | N-[5-(diethylsulfamoyl)-6-methyl-3,4'-bipyridin-2'-yl]acetamide |
| I-371 | 21G | N-(6-{2-[(2-cyclopropylpyrimidin-4-yl)amino]pyridin-4-yl}pyrazolo[1,5-a]pyridin-4-yl)acetamide |
| I-372 | 9BP | N-{6-chloro-5-[(dimethylsulfamoyl)amino]-3,4'-bipyridin-2'-yl}acetamide |
| I-373 | 10J | N-{5-[(butylsulfonyl)amino]-6-methyl-3,4'-bipyridin-2'-yl}acetamide |
| I-374 | 9CD | N-(5-{[(4,4-difluoropiperidin-1-yl)sulfonyl]amino}-6-methyl-3,4'-bipyridin-2'-yl)acetamide |
| I-375 | 35AU | 2,4-difluoro-N-{2'-[(4-methoxy-6-methyl-1,3,5-triazin-2-yl)amino]-6-methyl-3,4'-bipyridin-5-yl}benzenesulfonamide |
| I-376 | 9CZ | N-{4-[2-(bicyclo[1.1.1]pent-1-yl)-1,1-dioxido-3,4-dihydro-2H-pyrido[2,3-b][1,4,5]oxathiazepin-8-yl]pyridin-2-yl}acetamide |
| I-377 | 9CR | N-(5-{[(2,3-difluorophenyl)sulfonyl]amino}-6-methyl-3,4'-bipyridin-2'-yl)acetamide |
| I-378 | 54a | 6-benzyl-3-{2-[(2-methylpyrimidin-4-yl)amino]pyridin-4-yl}-7,8-dihydro-1,6-naphthyridin-5(6H)-one |
| I-379 | 34Z | 5-[2-(dimethylamino)ethoxy]-6-methyl-N-(2-methylpyrimidin-4-yl)-3,4'-bipyridin-2'-amine |
| I-380 | 9BK | N-[6-cyano-5-(2-methylpiperidin-1-yl)-3,4'-bipyridin-2'-yl]acetamide |
| I-381 | 34L | N'-{6-chloro-4-methyl-2'-[(2-methylpyrimidin-4-yl)amino]-3,4'-bipyridin-5-yl}-N,N-dimethylsulfuric diamide |
| I-382 | 35AV | N-{2'-[(4-cyclopropyl-6-methyl-1,3,5-triazin-2-yl)amino]-6-methyl-3,4'-bipyridin-5-yl}-2,4-difluorobenzenesulfonamide |
| I-383 | 35AR | ethyl (6-chloro-5-{[(2,4-difluorophenyl)sulfonyl]amino}-4-methyl-3,4'-bipyridin-2'-yl)carbamate |
| I-384 | 9DA | N-(5-{[(2,4-difluorophenyl)sulfonyl](2-hydroxyethyl)amino}-3,4'-bipyridin-2'-yl)acetamide |
| I-386 | 11G | N-[6-methyl-5-(5-methyl-1,1-dioxido-1,2,5-thiadiazolidin-2-yl)-3,4'-bipyridin-2'-yl]acetamide |
| I-387 | 11F | N-[5-(1,1-dioxido-1,2,6-thiadiazinan-2-yl)-6-methyl-3,4'-bipyridin-2'-yl]acetamide |
| I-388 | 20AL | N-(bicyclo[1.1.1]pent-1-yl)-2'-[(cyclopropylcarbonyl)amino]-N,6-dimethyl-3,4'-bipyridine-5-carboxamide |
| I-389 | 35AN | ethyl (5-{[(2,4-difluorophenyl)sulfonyl]amino}-6-methyl-3,4'-bipyridin-2'-yl)carbamate |
| I-390 | 34U | 6-methyl-5-[(5-methylpyridin-2-yl)oxy]-N-(2-methylpyrimidin-4-yl)-3,4'-bipyridin-2'-amine |
| I-391 | 5AZ | N-{5-[(3,3-difluoroazetidin-1-yl)sulfonyl]-3,4'-bipyridin-2'-yl}acetamide |
| I-392 | 51 | N-[5-(1,3-benzoxazol-2-ylamino)-6-methyl-3,4'-bipyridin-2'-yl]acetamide |
| I-394 | 9BM | N-(4-chloro-5-{[(2,4-difluorophenyl)sulfonyl]amino}-3,4'-bipyridin-2'-yl)acetamide |
| I-395 | 44 | N-(6-methyl-5-sulfamoyl-3,4'-bipyridin-2'-yl)acetamide |
| I-396 | 5AV | N-[5-(cyclobutylsulfamoyl)-3,4'-bipyridin-2'-yl]acetamide |
| I-397 | 52 | N-(2'-acetamido-3,4'-bipyridin-5-yl)-2,4-difluoro-N-methylbenzamide |
| I-398 | 52B | N-(2'-acetamido-6-methyl-3,4'-bipyridin-5-yl)-2,4-difluoro-N-methylbenzamide |
| I-399 | 9BY | N-(6-chloro-5-{[(4-chloro-2-fluorophenyl)sulfonyl]amino}-4-methyl-3,4'-bipyridin-2'-yl)acetamide |
| I-401 | 9CC | N-(6-chloro-5-{[(2,5-dichlorophenyl)sulfonyl]amino}-4-methyl-3,4'-bipyridin-2'-yl)acetamide |
| I-402 | 50B | 6-chloro-4-methyl-2'-[(2-methylpyrimidin-4-yl)amino]-3,4'-bipyridine-5-carboxylic acid |
| I-403 | 43P | N-(6-chloro-5-{[(1R)-2-hydroxy-1-phenylethyl]sulfamoyl}-3,4'-bipyridin-2'-yl)acetamide |
| I-404 | 9CK | N-[4-(4-{[(2,4-difluorophenyl)sulfonyl]amino}pyrazolo[1,5-a]pyridin-6-yl)pyridin-2-yl]acetamide |
| I-405 | 9DC | N-[5-(7-fluoro-1,1-dioxido-3,4-dihydro-2H-5,1,2-benzoxathiazepin-2-yl)-3,4'-bipyridin-2'-yl]acetamide |
| I-406 | 54b | 3-{2-[(2-methylpyrimidin-4-yl)amino]pyridin-4-yl}-7,8-dihydro-1,6-naphthyridin-5(6H)-one |

TABLE 2-continued

Chemical Names and Synthetic Protocols

| Compound | Synthetic Example | Chemical Name |
|---|---|---|
| I-407 | 53E | 3,3-difluoro-N-(6-{2-[(2-methylpyrimidin-4-yl)amino]pyridin-4-yl}pyrazolo[1,5-a]pyridin-4-yl)azetidine-1-carboxamide |
| I-408 | 20AS | (3,3-difluoroazetidin-1-yl){2'-[(2-methylpyrimidin-4-yl)amino]-3,4'-bipyridin-5-yl}methanone |
| I-409 | 20AO | 2'-acetamido-6-amino-N-carbamimidoyl-3,4'-bipyridine-5-carboxamide |
| I-410 | 43D | N-[5-(tert-butylsulfamoyl)-6-chloro-4-methyl-3,4'-bipyridin-2'-yl]acetamide |
| I-411 | 9BJ | N-(6-cyano-5-{[(2,4-difluorophenyl)sulfonyl]amino}-3,4'-bipyridin-2'-yl)acetamide |
| I-412 | 10K | N-(5-{[(2,2-difluoroethyl)sulfonyl]amino}-6-methyl-3,4'-bipyridin-2'-yl)acetamide |
| I-413 | 20AU | {2'-[(2-cyclopropylpyrimidin-4-yl)amino]-3,4'-bipyridin-5-yl}(3,3-difluoroazetidin-1-yl)methanone |
| I-414 | 35AP | N-(5-{[(2,4-difluorophenyl)sulfonyl]amino}-6,6'-dimethyl-3,4'-bipyridin-2'-yl)acetamide |
| I-415 | 20AT | {6-methyl-2'-[(2-methylpyrimidin-4-yl)amino]-3,4'-bipyridin-5-yl}(2-oxa-6-azaspiro[3.3]hept-6-yl)methanone |
| I-416 | 9CY | N-[5-(1,1-dioxidoisothiazol-2(3H)-yl)-6-methyl-3,4'-bipyridin-2'-yl]acetamide |
| I-417 | 35AX | methyl (5-{[(4-chloro-2-fluorophenyl)sulfonyl]amino}-6-methyl-3,4'-bipyridin-2'-yl)carbamate |
| I-418 | 44 | N-[5-(bicyclo[1.1.1]pent-1-ylsulfamoyl)-6-methyl-3,4'-bipyridin-2'-yl]acetamide |
| I-419 | 21D | N-(2'-acetamido-3,4'-bipyridin-5-yl)-2,4-difluorobenzamide |
| I-420 | 43V | (R)—N-(4-(1,1-dioxido-3-phenyl-3,4-dihydro-2H-pyrido[2,3-b][1,4,5]oxathiazepin-8-yl)pyridin-2-yl)acetamide |
| I-421 | 34P | N,N-dimethyl-N'-(6-{2-[(2-methylpyrimidin-4-yl)amino]pyridin-4-yl}pyrazolo[1,5-a]pyridin-4-yl)sulfuric diamide |
| I-422 | 34AD | 5-[1-(2-fluorophenoxy)ethyl]-N-(2-methylpyrimidin-4-yl)-3,4'-bipyridin-2'-amine |
| I-423 | 20AM | 2'-acetamido-N-(2,4-difluorophenyl)-6-methoxy-N-methyl-3,4'-bipyridine-5-carboxamide |
| I-424 | 34Y | 2-({6-methyl-2'-[(2-methylpyrimidin-4-yl)amino]-3,4'-bipyridin-5-yl}oxy)ethanol |
| I-425 | 11C | N-[6-chloro-5-(1,1-dioxidoisothiazolidin-2-yl)-4-methyl-3,4'-bipyridin-2'-yl]acetamide |
| I-426 | 43F | N-[5-(cyclobutylsulfamoyl)-6-methoxy-3,4'-bipyridin-2'-yl]acetamide |
| I-427 | 34R | N'-(6-{2-[(2-cyclopropylpyrimidin-4-yl)amino]pyridin-4-yl}pyrazolo[1,5-a]pyridin-4-yl)-N,N-dimethylsulfuric diamide |
| I-428 | 9BX | 6-(2-acetamidopyridin-4-yl)pyrazolo[1,5-a]pyridin-4-yl dimethylsulfamate |
| I-429 | 9BQ | N-(6-chloro-5-{[(4-cyanophenyl)sulfonyl]amino}-4-methyl-3,4'-bipyridin-2'-yl)acetamide |
| I-430 | 9CV | N-(6-chloro-5-{[(2,4-difluorophenyl)sulfonyl]amino}-4,5'-dimethyl-3,4'-bipyridin-2'-yl)cyclopropanecarboxamide |
| I-431 | 20AN | 2'-acetamido-N-(2,4-difluorophenyl)-6-methyl-3,4'-bipyridine-5-carboxamide |
| I-432 | 43H | N-{5-[(2,5-dichlorophenyl)sulfamoyl]-6-methoxy-3,4'-bipyridin-2'-yl}acetamide |
| I-433 | 9CG | N-(5-{[(4-chloro-2-fluorophenyl)sulfonyl]amino}-6-methyl-3,4'-bipyridin-2'-yl)cyclopropanecarboxamide |
| I-434 | 20AP | N-[5-(azetidin-1-ylcarbonyl)-6-chloro-5'-methyl-3,4'-bipyridin-2'-yl]acetamide |
| I-435 | 34N | N'-{6-chloro-2'-[(2-cyclopropylpyrimidin-4-yl)amino]-4-methyl-3,4'-bipyridin-5-yl}-N,N-dimethylsulfuric diamide |
| I-436 | 43R | N-[5-(tert-butylsulfamoyl)-4-methyl-6-(methylamino)-3,4'-bipyridin-2'-yl]acetamide |
| I-437 | 9CE | N-{6-chloro-4-methyl-5-[(quinolin-5-ylsulfonyl)amino]-3,4'-bipyridin-2'-yl}acetamide |
| I-438 | 5BA | N-[6-chloro-5-(cyclobutylsulfamoyl)-3,4'-bipyridin-2'-yl]acetamide |
| I-439 | 53C | 1-{6-methyl-2'-[(2-methylpyrimidin-4-yl)amino]-3,4'-bipyridin-5-yl}-3-phenylurea |
| I-440 | 34AF | 5-[(4-fluoro-2,3-dihydro-1H-inden-1-yl)oxy]-N-(2-methylpyrimidin-4-yl)-3,4'-bipyridin-2'-amine |
| I-441 | 9CF | N-(5-{[(4-chloro-2-fluorophenyl)sulfonyl]amino}-6-methyl-3,4'-bipyridin-2'-yl)-2,2-difluorocyclopropanecarboxamide |
| I-442 | 43L | N-[5-(tert-butylsulfamoyl)-6-methoxy-4-methyl-3,4'-bipyridin-2'-yl]acetamide |
| I-443 | 5AQ | N-[5-(tert-butylsulfamoyl)-3,4'-bipyridin-2'-yl]acetamide |
| I-444 | 10L | N-(5-{[(4-bromo-2-fluorophenyl)sulfonyl]amino}-6-chloro-4-methyl-3,4'-bipyridin-2'-yl)acetamide |
| I-445 | 9CN | N-{5-[(2-azabicyclo[2.2.1]hept-2-ylsulfonyl)amino]-6-methyl-3,4'-bipyridin-2'-yl}acetamide |
| I-446 | 34X | 5-isopropoxy-6-methyl-N-(2-methylpyrimidin-4-yl)-3,4'-bipyridin-2-amine |
| I-447 | 9BT | N-{6-methyl-5-[(morpholin-4-ylsulfonyl)amino]-3,4'-bipyridin-2'-yl}acetamide |
| I-448 | 11L | N-[6-chloro-5-(1,1-dioxido-1,2,6-thiadiazinan-2-yl)-3,4'-bipyridin-2'-yl]acetamide |
| I-449 | 22F | 2'-acetamido-N-(bicyclo[1.1.1]pent-1-yl)-N-methyl-6-(methylamino)-3,4'-bipyridine-5-carboxamide |
| I-450 | 21F | N-(6-{2-[(2-methylpyrimidin-4-yl)amino]pyridin-4-yl}pyrazolo[1,5-a]pyridin-4-yl)acetamide |
| I-452 | 47 | N-[5-(6-methyl-1,1-dioxido-1,2,6-thiadiazinan-2-yl)-3,4'-bipyridin-2'-yl]acetamide |
| I-454 | 34AB | N-(2-chloro-4-methyl-5-{2-[(2-methylpyrimidin-4-yl)amino]pyridin-4-yl}-1-oxidopyridin-3-yl)-2,4-difluorobenzenesulfonamide |
| I-455 | 9BL | N-{6-methyl-5-[(methylsulfamoyl)amino]-3,4'-bipyridin-2'-yl}acetamide |
| I-456 | 35AW | ethyl (5-{[(4-chloro-2-fluorophenyl)sulfonyl]amino}-6-methyl-3,4'-bipyridin-2'-yl)carbamate |
| I-457 | 50A | azetidin-1-yl{6-chloro-4-methyl-2'-[(2-methylpyrimidin-4-yl)amino]-3,4'-bipyridin-5-yl}methanone |
| I-458 | 8O | N-{5-[(dimethylsulfamoyl)(methyl)amino]-3,4'-bipyridin-2'-yl}acetamide |
| I-459 | 5AS | N-[5-(phenylsulfamoyl)-3,4'-bipyridin-2'-yl]acetamide |
| I-460 | 48 | N-[6-methyl-5-(2-oxotetrahydropyrimidin-1(2H)-yl)-3,4'-bipyridin-2'-yl]acetamide |
| I-462 | 43W | N-[5-(tert-butylsulfamoyl)-4-methyl-3,4'-bipyridin-2'-yl]acetamide |
| I-463 | 9BO | N-(5-{[(2,6-dichlorophenyl)sulfonyl]amino}-6-methyl-3,4'-bipyridin-2'-yl)acetamide |
| I-464 | 5AO | N-{5-[(2,4-difluorophenyl)sulfamoyl]-3,4'-bipyridin-2'-yl}acetamide |
| I-465 | 9CH | N-(5-{[(2,5-dichloro-3-thienyl)sulfonyl]amino}-6-methyl-3,4'-bipyridin-2'-yl)acetamide |
| I-466 | 50C | {6-chloro-2'-[(2-cyclopropylpyrimidin-4-yl)amino]-4-methyl-3,4'-bipyridin-5-yl}(3,3-dimethylazetidin-1-yl)methanone |
| I-467 | 11K | N-[6-chloro-5-(6-methyl-1,1-dioxido-1,2,6-thiadiazinan-2-yl)-3,4'-bipyridin-2'-yl]acetamide |
| I-468 | 5AX | N-[5-(adamantan-1-ylsulfamoyl)-3,4'-bipyridin-2'-yl]acetamide |
| I-469 | 34K | N-(6-chloro-5-{[(2,4-difluorophenyl)sulfonyl]amino}-4-ethyl-3,4'-bipyridin-2'-yl)acetamide |
| I-470 | 43E | N-[5-(bicyclo[1.1.1]pent-1-ylsulfamoyl)-6-methoxy-3,4'-bipyridin-2'-yl]acetamide |
| I-471 | 34W | 5-(cyclopentyloxy)-6-methyl-N-(2-methylpyrimidin-4-yl)-3,4'-bipyridin-2'-amine |
| I-472 | 46 | N-[5-(1,3-oxazol-2-ylamino)-3,4'-bipyridin-2'-yl]acetamide |
| I-473 | 11D | N-[6-chloro-5-(1,1-dioxido-1,2,6-thiadiazinan-2-yl)-4-methyl-3,4'-bipyridin-2'-yl]acetamide |
| I-474 | 5AY | N-[5-(azetidin-1-ylsulfonyl)-3,4'-bipyridin-2'-yl]acetamide |

TABLE 2-continued

Chemical Names and Synthetic Protocols

| Compound | Synthetic Example | Chemical Name |
|---|---|---|
| I-475 | 34AA | 6-methyl-N-(2-methylpyrimidin-4-yl)-5-phenoxy-3,4'-bipyridin-2'-amine |
| I-476 | 9CI | N-(4-{4-[(dimethylsulfamoyl)amino]pyrazolo[1,5-a]pyridin-6-yl}pyridin-2-yl)acetamide |
| I-477 | 9CP | N-{5-[(2-azabicyclo[2.2.1]hept-2-ylsulfonyl)amino]-6-chloro-4-methyl-3,4'-bipyridin-2'-yl}acetamide |
| I-478 | 9BW | 2'-acetamido-6-methyl-3,4'-bipyridin-5-yl 2,4-difluorobenzenesulfonate |
| I-479 | 34T | 5-ethoxy-6-methyl-N-(2-methylpyrimidin-4-yl)-3,4'-bipyridin-2'-amine |
| I-480 | 34Q | 6-{2-[(2-methylpyrimidin-4-yl)amino]pyridin-4-yl}pyrazolo[1,5-a]pyridin-4-amine |
| I-481 | 5AP | N-{5-[(4-methylpiperazin-1-yl)sulfonyl]-3,4'-bipyridin-2'-yl}acetamide |
| I-482 | 53A | 3,3-difluoro-N-{6-methyl-2'-[(2-methylpyrimidin-4-yl)amino]-3,4'-bipyridin-5-yl}azetidine-1-carboxamide |
| I-483 | 9BZ | N-(5-{[(4,4-dimethylpiperidin-1-yl)sulfonyl]amino}-6-methyl-3,4'-bipyridin-2'-yl)acetamide |
| I-484 | 43T | N-[4-(1,1-dioxido-3,4-dihydro-2H-pyrido[2,3-b][1,4,5]oxathiazepin-8-yl)pyridin-2-yl]acetamide |
| I-485 | 20AK | 2'-acetamido-N-(2,4-difluorophenyl)-N,6-dimethyl-3,4'-bipyridine-5-carboxamide |
| I-486 | 34O | 2,4-difluoro-N-(6-{2-[(2-methylpyrimidin-4-yl)amino]pyridin-4-yl}pyrazolo[1,5-a]pyridin-4-yl)benzenesulfonamide |
| I-487 | 43S | N-[5-(tert-butylsulfamoyl)-6-(dimethylamino)-4-methyl-3,4'-bipyridin-2'-yl]acetamide |
| I-488 | 9CO | N-{6-chloro-4-methyl-5-[(pyrrolidin-1-ylsulfonyl)amino]-3,4'-bipyridin-2'-yl}acetamide |
| I-490 | 11I | N-[6-amino-5-(1,1-dioxido-1,2,6-thiadiazinan-2-yl)-3,4'-bipyridin-2'-yl]acetamide |
| I-491 | 43Q | N-{5-[(2,4-difluorophenyl)sulfamoyl]-6-(dimethylamino)-3,4'-bipyridin-2'-yl}acetamide |
| I-492 | 9BV | N-[5-(cyclopropylmethoxy)-6-methyl-3,4'-bipyridin-2'-yl]acetamide |
| I-493 | 9CJ | N-[6-chloro-4-methyl-5-({[1-methyl-3-(trifluoromethyl)-1H-pyrazol-4-yl]sulfonyl}amino)-3,4'-bipyridin-2'-yl]acetamide |
| I-494 | 9CX | N-(6-methyl-5-{[methyl(phenyl)sulfamoyl]amino}-3,4'-bipyridin-2'-yl)acetamide |
| I-495 | 20AR | (3,3-dimethylazetidin-1-yl){6-methyl-2'-[(2-methylpyrimidin-4-yl)amino]-3,4'-bipyridin-5-yl}methanone |
| I-496 | 55a | N-{5-[4-(dimethylamino)-1,1-dioxidoisothiazolidin-2-yl]-6-methyl-3,4'-bipyridin-2'-yl}acetamide (peak 1) |
| I-497 | 55b | N-{5-[4-(dimethylamino)-1,1-dioxidoisothiazolidin-2-yl]-6-methyl-3,4'-bipyridin-2'-yl}acetamide (peak 2) |
| I-498 | 9CL | N-{5-[(dimethylsulfamoyl)amino]-6-methyl-3,4'-bipyridin-2'-yl}-2,2-difluorocyclopropanecarboxamide (peak 1) |
| I-499 | 9CM | N-{5-[(dimethylsulfamoyl)amino]-6-methyl-3,4'-bipyridin-2'-yl}-2,2-difluorocyclopropanecarboxamide (peak 2) |

General Synthetic Methods and Intermediates:

The compounds of the present invention can be prepared by methods known to one of ordinary skill in the art and/or by reference to the schemes shown below and the synthetic examples that follow. Exemplary synthetic routes are set forth in the Schemes below, and in the Examples. The person skilled in the art will understand that the synthetic schemes presented herein can be adapted for the preparation of regioisomeric compounds (e.g., compounds where, for example an $R^4$ group is located at a different position on the ring than that depicted in the exemplary schemes) or compounds comprising a different number of substituent groups (e.g., additional $R^4$ groups).

One of ordinary skill in the art will recognize that numerous variations in reaction conditions including variations in solvent, reagents, catalysts, reaction temperatures and times are possible for each of the reactions described. Variation of order of synthetic steps and alternative synthetic routes are also possible.

Scheme 1: General method for the preparation of N-(6-amino-5-(N-substituted-sulfamoyl)-[3,4'-bipyridines] and N-(6-amino-5-(sulfonyl)-[3,4'-bipyridines] I-A, I-B, and I-C

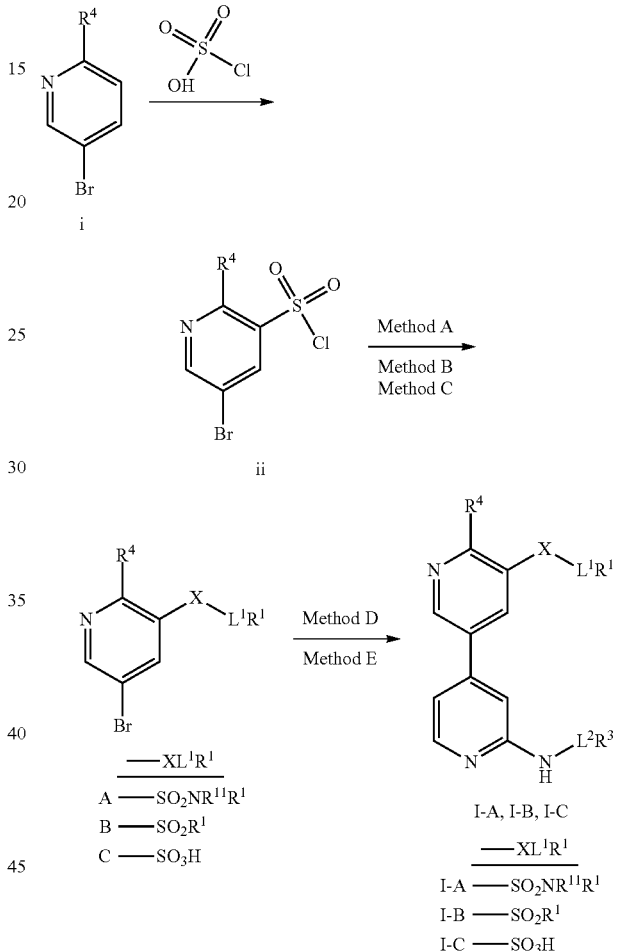

Scheme 1 shows a general route for the preparation of compounds of formula I-A, I-B, or I-C (e.g., compounds of formula I-A', I-B', or I-C') starting from $R^4$-substituted 5-bromopyridine-3-sulfonyl chloride ii (e.g., 2-amino-5-bromopyridine-3-sulfonyl chloride). See Banka et al., Intl. App. Pub. No. WO 2012/037108. Treatment of ii with an amine in the presence of an appropriate base provides access to sulfonamide containing material iii where $R^1$ is a variously substituted nitrogen (Method A). Alternatively, treatment of ii with hydrazine followed by base and an alkyl or benzyl halide provides variously substituted sulfones of iii (Method B). Additionally, treatment of ii with aqueous acid can provide the sulfonic acid (Method C). The resulting sulfonamides or sulfones can undergo Suzuki coupling with a suitable boron reagent (Method D) using, for example, Pd(dppf)Cl$_2$, Pd(amphos)Cl$_2$, XPhosG3/XPhos (see Buchwald, S. L. et. Al, *Chem. Sci.,* 2013, 4, 916-920), Pd(PPh$_3$)$_4$ or SiliaCat DPP-Pd as a catalyst, K$_2$CO$_3$, Cs$_2$CO$_3$ or K$_3$PO$_4$ as base in suitable solvent such as dioxane at elevated temperatures to afford compounds of formula I-A, I-B, or I-C (for similar procedures, see A. Suzuki, J. *Organometallic Chem.* 1999, 576, 147-168; Pagliaro et al., *Org. Process Res. Dev.* 2012, 16, 117-122). Stille coupling with an organotin species using conditions such asPd(PPh$_3$)$_4$, CuI and LiCl in a suitable solvent such as dioxane (Method E) can also be used to generate compounds I-A, I-B, or I-C (for a review of the Stille reaction, see W. J. Scott et al., "The Stille Reaction" Organic Reations, 2004, Wiley: Online). Note that compounds similar to I-A, I-B, or I-C wherein R$^4$ is substituted at a different position on the pyridine ring can be prepared using the reaction as shown in Scheme 1.

Scheme 2: General method for the preparation of substituted bipyridyls I-D

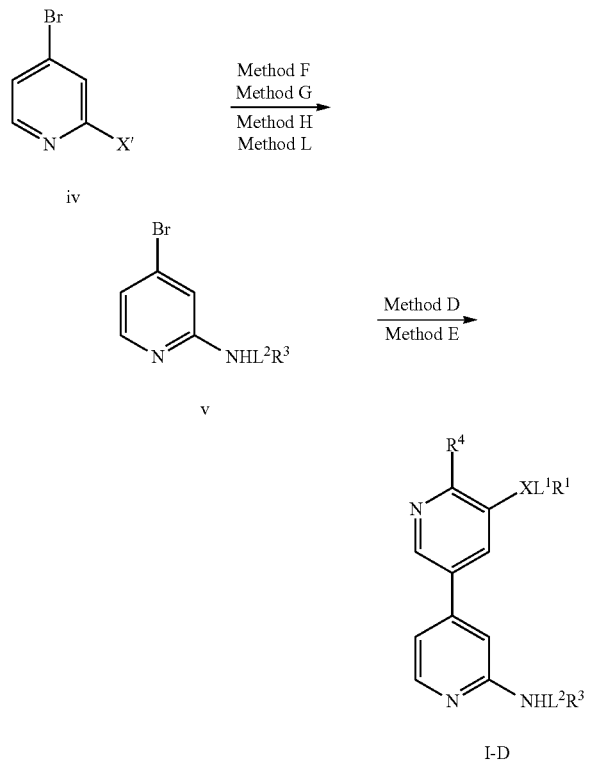

Scheme 2 shows a general route for the preparation of compounds of formula I-D starting from 2-substituted-4-bromopyridines iv. Other suitable 2-substituted pyridines (e.g., 2-substituted-4-chloropyridines or 2-substituted-4-iodopyridines) can also be used. Compounds of formula v can be obtained by displacement with an appropriate amine when X'=halogen (Method F), acylation when X'=NH$_2$ (Method G) or Curtius rearrangement when X'=carboxylic acid (Method H). Alternatively, when X'=halogen, Buchwald-Hartwig amination using an appropriate amine with a suitable catalyst system such as Pd$_2$(dba)$_3$/xantphos or Pd(dppf)Cl$_2$, and a suitable base such as Cs$_2$CO$_3$ or t-BuOK in an appropriate solvent can be employed to obtain compounds of formula v (Method L) (for similar procedures, see Driver, M. S., Hartwig, J. F., *J. Am. Chem. Soc.* 1996, 118, 7217-7218 and Yin, J., et. al., *Org. Lett.* 2002, 4, 3481). The coupling of compound v with the appropriately substituted boron reagent (Method D) or organotin species (Method E) affords compounds of formula I-D. Note that compounds similar to I-D wherein R$^4$ is substituted at a different position on the pyridine ring can be prepared using the reaction as shown in Scheme 2.

Scheme 3: General method for the preparation of substituted sulfonamido bipyridyls I-E

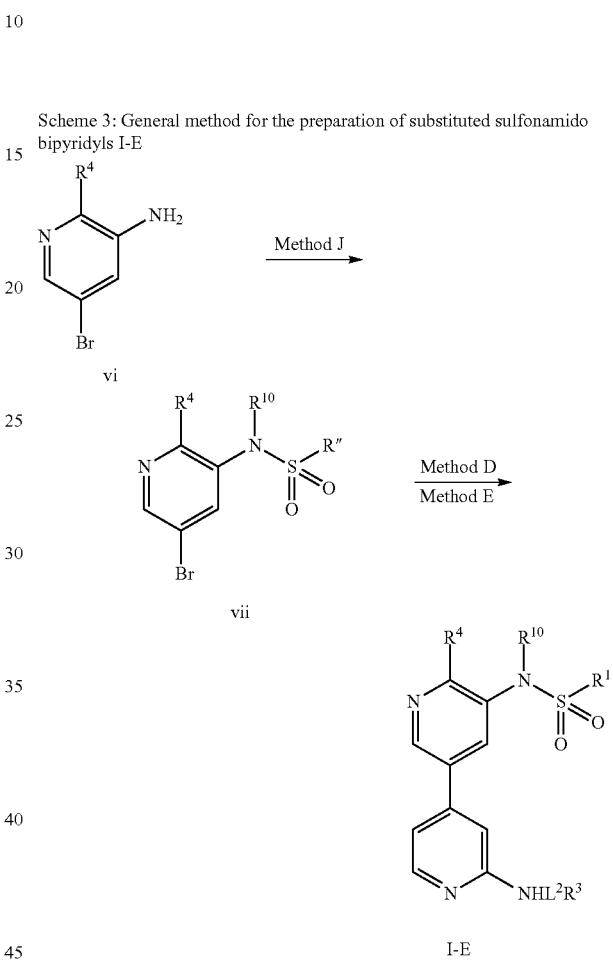

Scheme 3 shows a general route for the preparation of compounds of formula I-E starting from variously substituted 3-amino-pyridines vi. Treatment of vi with an appropriately substituted sulfonyl chloride in the presence of a suitable base such as pyridine provides access to compounds of the formula vii where R$^{10}$=H (Method J; see: Lebegue, N. et. al. *J. Med. Chem.* 2005, 48, 7363-7373). These intermediates can be coupled with the appropriately substituted boron reagent (Method D) or organotin species (Method E) to afford compounds of formula I-E. Alternatively, compounds of the formula vii where R$^{10}$=H can be further reacted in the presence of a base and an electrophile such as an alkyl halide, acyl halide or sulfonyl chloride to afford di-substituted sulfonamides of the formula vii where R$^{10}$ is as defined herein. These intermediates can be coupled with the appropriately substituted boron reagent (Method D) or organotin species (Method E) to afford compounds of formula I-E.

Scheme 4: General method for the preparation of substituted amido or keto bipyridyls I-F and I-G

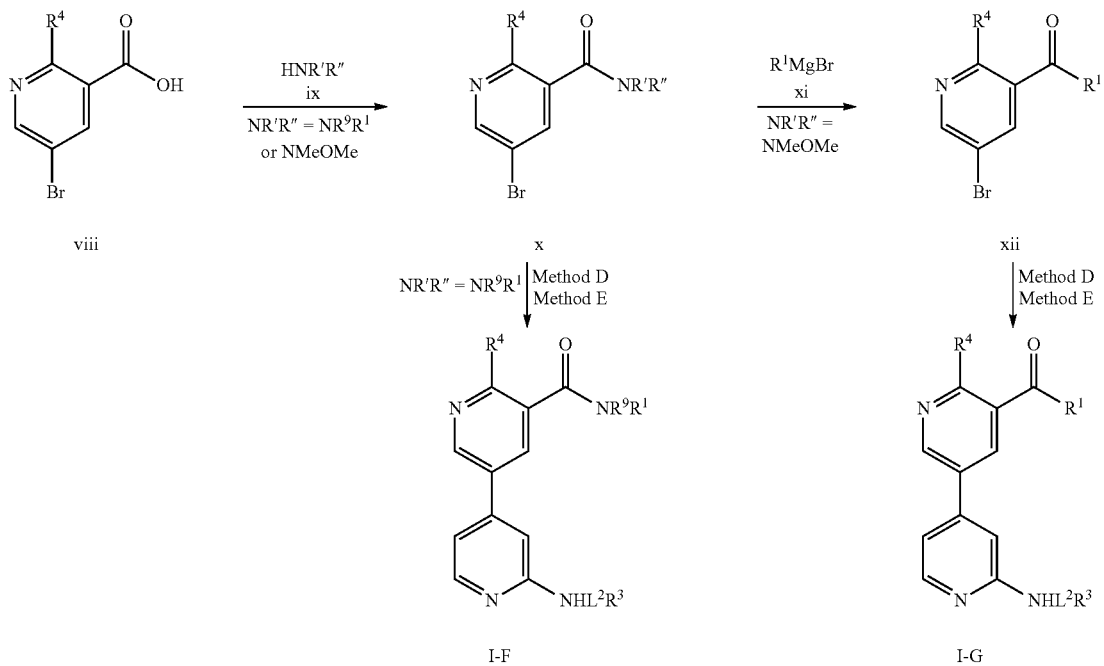

Scheme 4 shows a general route for the preparation of compounds of formula I-F and I-G starting from variously substituted pyridines with a carboxylic acid moiety at the 3-position. Treatment of viii with an amine ix and an appropriate coupling reagent such as TBTU in an appropriate solvent such as DCM affords amides of the formula x. These intermediates can be coupled with the appropriately substituted boron reagent (Method D) or organotin species (Method E) to afford compounds of formula I-F. Alternatively, compounds of the formula x where $R^9$=H can be further reacted in the presence of a base and an electrophile such as an alkyl halide to afford di-substituted amides of the formula x where $R^9$ is as defined herein. These intermediates can be coupled with the appropriately substituted boron reagent (Method D) or organotin species (Method E) to afford compounds of formula I-F. Alternatively, if intermediate x is a Weinreb amide (for an example of Weinreb amide preparation, see: Sun, X. et. al. Intl. App. Pub. No. WO 2012/009227 A1), treatment with an appropriately substituted Grignard reagent in a solvent such as THF is a method that can be used to generate compounds of the formula xii which can be coupled with the appropriately substituted boron reagent (Method D) or organotin species (Method E) to afford compounds of formula I-G.

Scheme 5: General method for the preparation of substituted 1H-pyrrolo[3,2-b]pyridines I-H

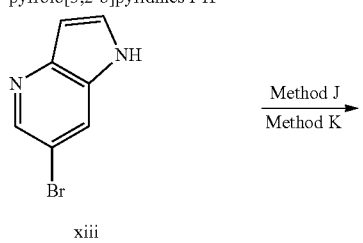

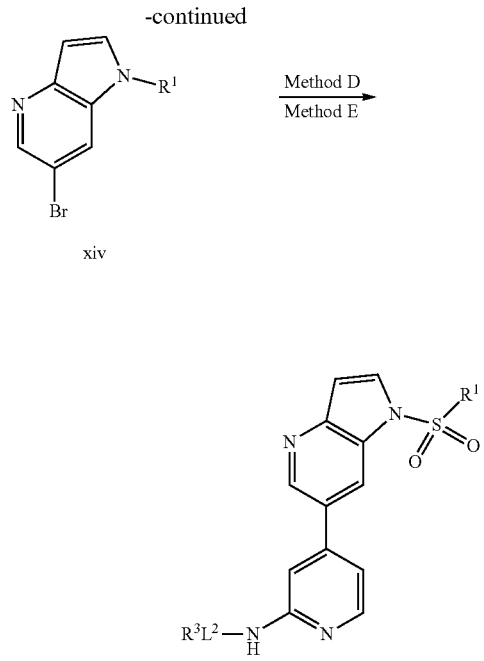

Scheme 5 shows a general route for the preparation of compounds I-H from starting materials xiii. Reaction with sulfonyl halides (Method J) or alkyl halides (Method K) under basic conditions in an appropriate solvent such as THF or DCM can provide compounds xiv. Further treatment with the appropriately substituted boron reagent (Method D) or organotin species (Method E) affords compounds of formula I-H.

Scheme 6: General method for the preparation of substituted sulfonamido bipyridyls I-I

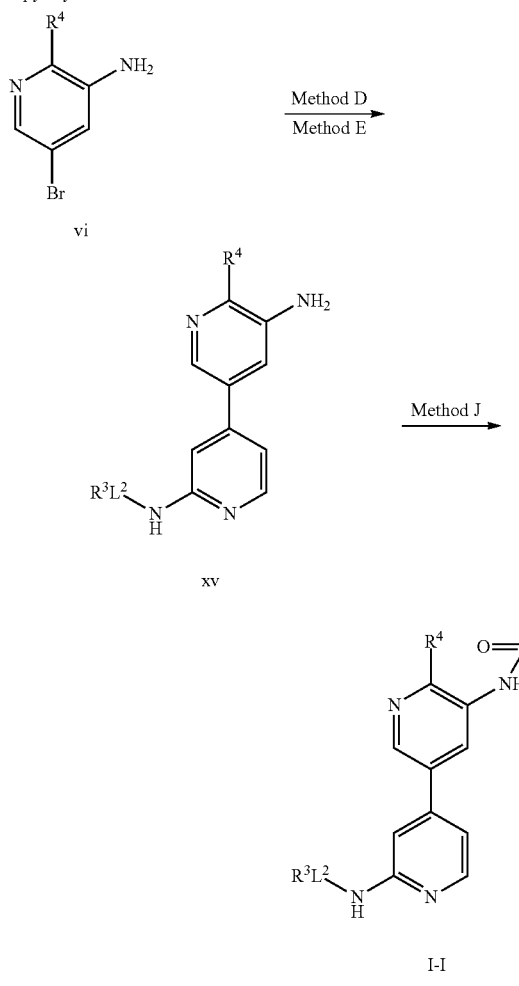

Scheme 6 shows a general route for the preparation of compounds I-I from starting materials vi (see, e.g., Scheme 3). Treatment of compounds vi with the appropriately substituted boron reagent (Method D) or organotin species (Method E) affords compounds of formula xv. Further treatment using Method J leads to the final compounds I-I.

Scheme 7: General method for the preparation of substituted bipyridyls I-J

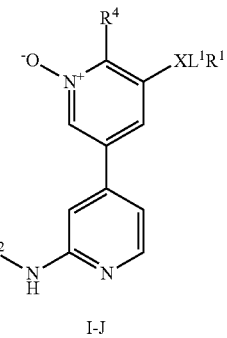

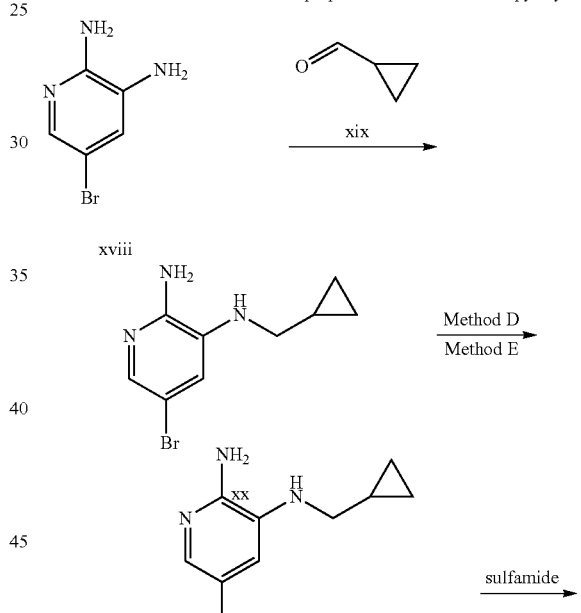

Scheme 7 shows a general route for the preparation of substituted bipyridyls I-J from starting materials xvi. Treatment of xvi with an oxidant such as mCPBA leads to the intermediates xvii. Further treatment with the appropriately substituted boron reagent (Method D) or organotin species (Method E) affords compounds of formula I-J.

Scheme 8: General method for the preparation of substituted bipyridyls I-K

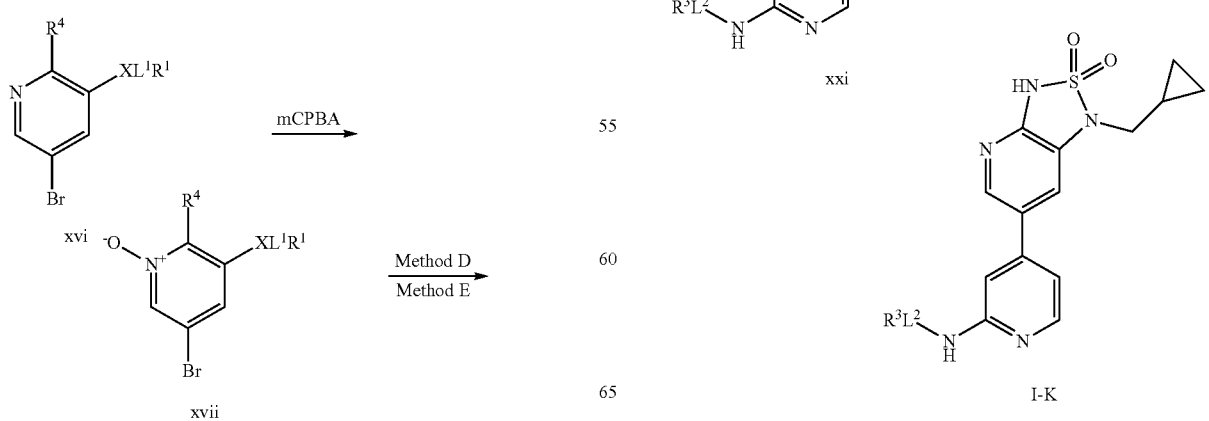

Scheme 8 shows a general route for the preparation of compounds I-K from starting material xviii. Reaction of the amine in the 3-position in xviii with cyclopropanecarboxaldehyde xix under acidic conditions in a suitable solvent such as DCM provides the intermediate imine, which can then be reduced with an appropriate reagent such as NaBH(OAc)$_3$ in a suitable solvent such as DCM to provide intermediate xx. Intermdiate xxi can be generated from xx by treatment with the appropriately substituted boron reagent (Method D) or organotin species (Method E). Compounds xxi can be further transformed by reaction with sulfamide under basic conditions to provide compounds of formula I-K.

Scheme 9: General method for the preparation of substituted bipyridyls I-L

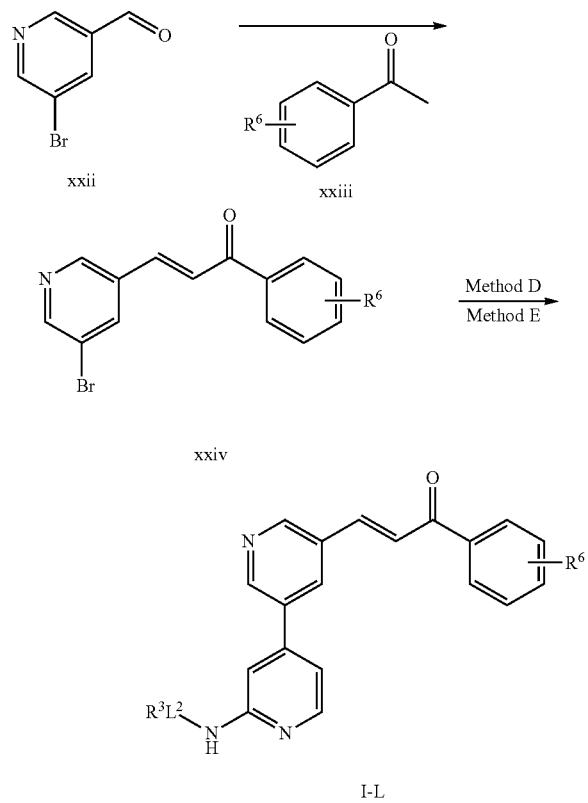

Scheme 9 shows a general route for formation of compounds I-L from starting materials xxii. Aldehyde xxii can be treated with a ketone under basic conditions in a suitable solvent, such as methanol, to provide the intermediates xxiv. Compounds xxiv can undergo further treatment with the appropriately substituted boron reagent (Method D) or organotin species (Method E) to afford compounds of formula I-L.

Scheme 10: General method for the preparation of substituted 1H-pyrazolo[4,3-b]pyridines I-M

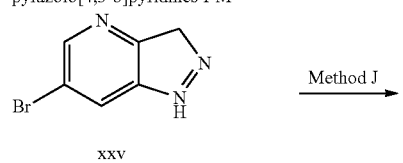

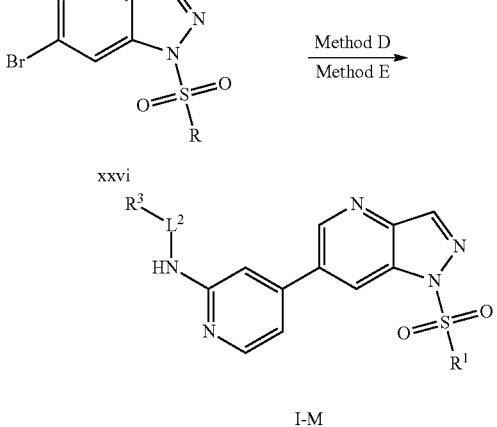

Scheme 10 shows a general route for the formation of compounds I-M from starting materials xxv. Compound xxv can be treated under Method J to provide the sulfonamides xxvi, which can undergo further treatment with the appropriately substituted boron reagent (Method D) or organotin species (Method E) to afford compounds of formula I-M.

Scheme 11: General method of the preparation of substituted 1H-pyrrolo[2,3-b]pyridines I-N

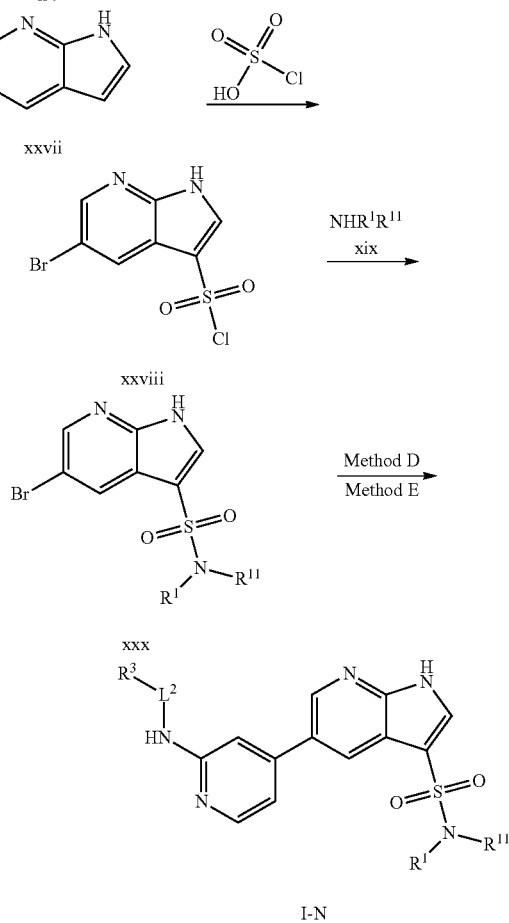

Scheme 11 shows a general route for the preparation of compounds I-N from starting material xxvii. Compound xxvii can be treated with chlorosulfonic acid to provide the sulfonyl chloride xxviii. Treatment of xxviii with disubstituted amines in a suitable solvent such as DCM provides intermediates xxx. Compounds xxx can undergo further treatment with the appropriately substituted boron reagent (Method D) or organotin species (Method E) to afford compounds of formula I-N.

Scheme 12: General method of the preparation of substituted 3,4-dihydro-2H-pyrido[2,3-e][1,2,4]thiadiazine 1,1-dioxides I-O

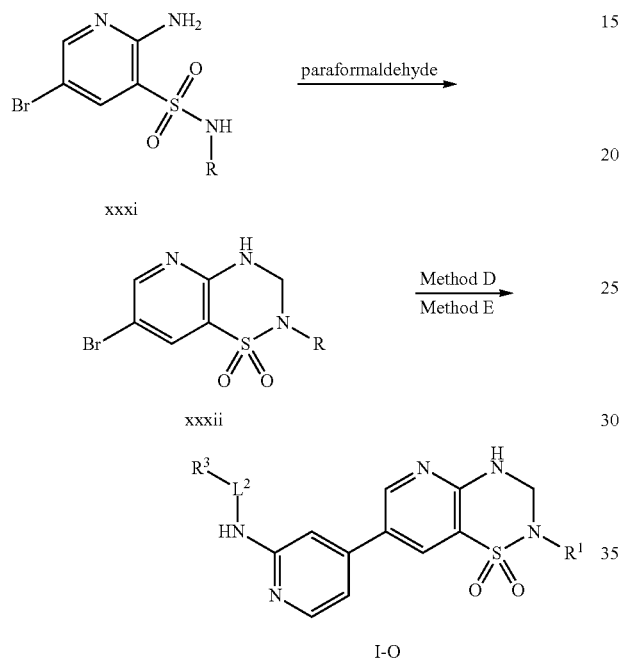

Scheme 12 shows a general route for the preparation of compounds I-O from starting materials xxxi. Treatment of xxxi with paraformaldehyde under acidic conditions in a suitable solvent such as iPrOH provides intermediates xxxii. Compounds xxxii can be further treated with the appropriately substituted boron reagent (Method D) or organotin species (Method E) to afford compounds of formula I-O.

Scheme 13: General method of the preparation of substituted 3H-imidazo[4,5-b]pyridines I-P

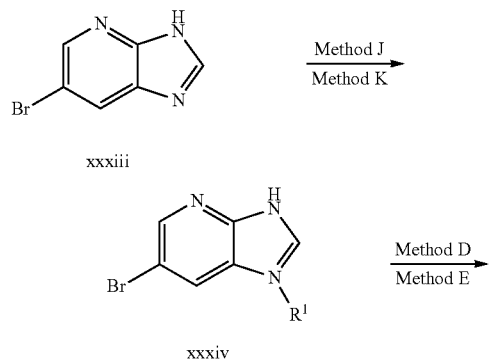

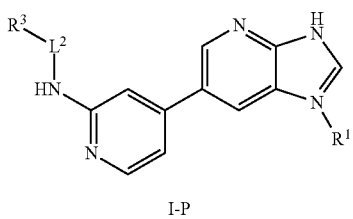

Scheme 13 shows a general route for the preparation of compounds I-P from starting materials xxxiii. Compound xxxiii can be treated under Method J or Method K to provide intermediates xxxiv, which can be further transformed by treatment with the appropriately substituted boron reagent (Method D) or organotin species (Method E) to afford compounds of formula I-P.

Scheme 14: General method of the preparation of substituted 1H-pyrrolo[2,3-b]pyridines I-Q

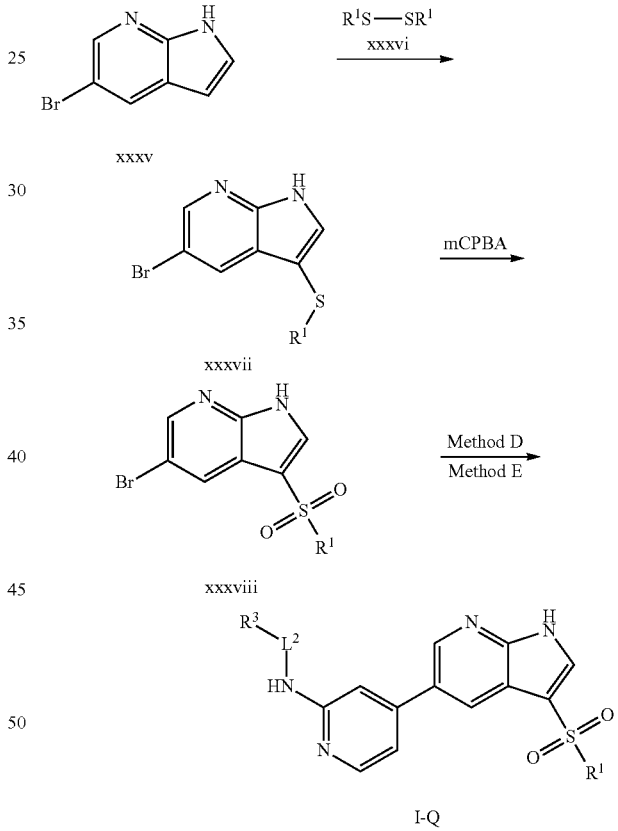

Scheme 14 shows a general route for the preparation of compounds I-Q from starting materials xxxv. Compound xxxv can be treated with disubstituted disulfides under basic conditions such as sodium hydride in an appropriate solvent such as DMF to provide sulfide intermediates xxxvii, which can be further transformed by oxidation with mCPBA in a suitable solvent such as DMF to provide intermediates xxxviii. Compounds xxxviii can be further transformed by treatment with the appropriately substituted boron reagent (Method D) or organotin species (Method E) to afford compounds of formula I-Q.

Scheme 15: General method of the preparation of substituted 1H-pyrazolo[3,4-b]pyridines I-R

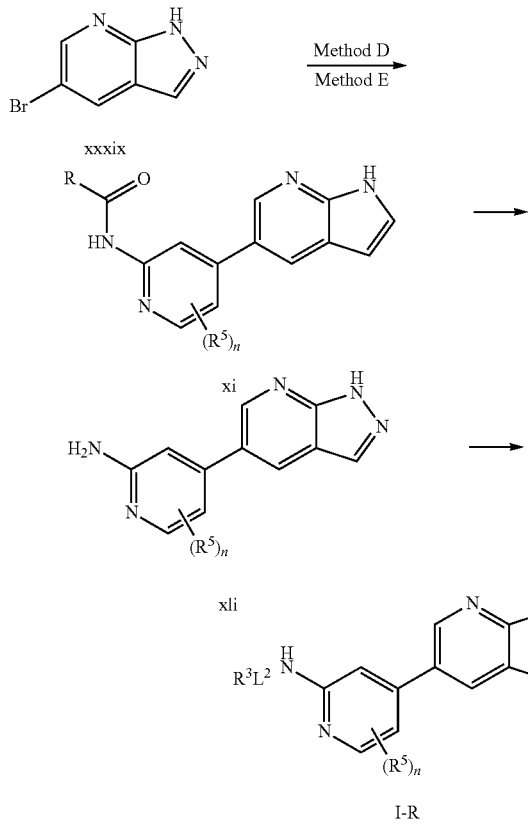

Scheme 15 shows a general route for the preparation of compounds I-R from starting material xxxix. Compound xxxix can be transformed by treatment with the appropriately substituted boron reagent (Method D) or organotin species (Method E) to afford intermediates xl. The acyl group of compounds xl can be removed under basic conditions in an appropriate solvent such as methanol to provide intermediates xli. This intermediate can be further transformed by reaction with an acyl or alkyl halide under basic conditions in an appropriate solvent such as THF or DCM to provide compounds of the formula I-R.

Scheme 16: General method of the preparation of substituted 1H-pyrrolo[2,3-b]pyridines I-S

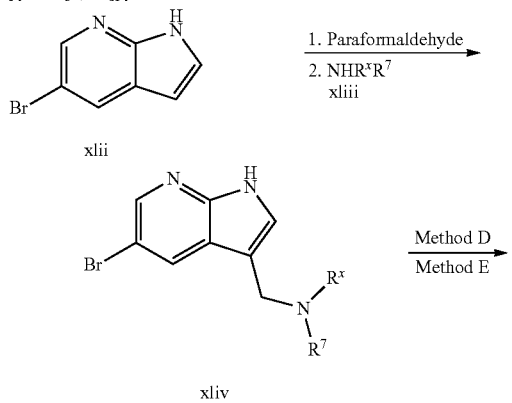

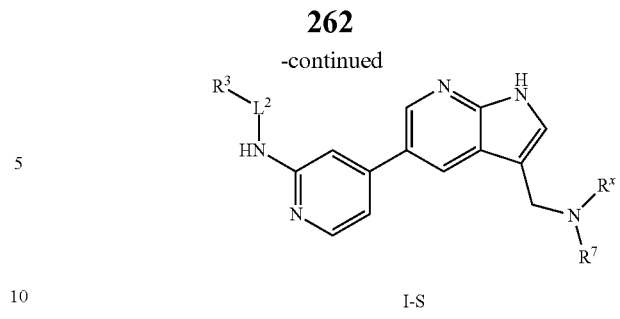

Scheme 16 shows a general route for the preparation of compounds I-S from starting materials xlii. Compound xlii can be treated with paraformaldehyde in a suitable solvent, such as butanol, followed by treatment with a disubstituted amine at elevated temperature to provide intermediates xliv. Compounds xliv can undergo treatment with the appropriately substituted boron reagent (Method D) or organotin species (Method E) affords compounds of formula I-S.

Scheme 17: General method for the preparation of substituted bipyridyls I-T

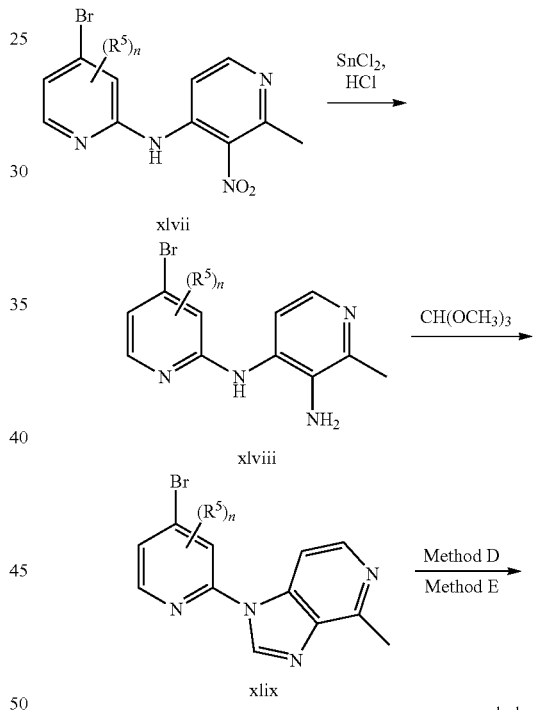

Scheme 17 shows a general route for the preparation of compounds of formula I-T starting from 2-substituted 4-bromo-pyridines xlvii. Treatment of compound xlvii with tin chloride provides compound xlviii, which reacts with trimethoxymethane to provide compounds xlix. The coupling of compound xlix with the appropriately substituted boron reagent (Method D) or organotin species (Method E) affords compounds of formula I-T.

Scheme 18: General method for the preparation of substituted bipyridyls I-U

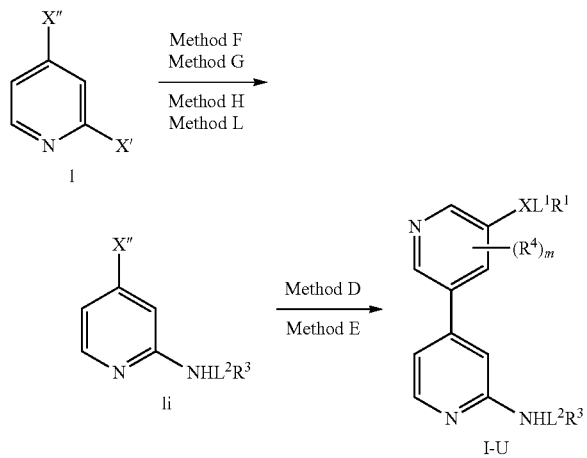

Scheme 18 shows a general route for the preparation of compounds of formula I-U using starting materials I, where X' and X" can be various groups. For example, starting from 2,4-halo-substituted pyridines 1 (X' and X" are both independently halo), compounds of formula li can be obtained by acylation when X'=NH$_2$ (Method G) or Curtius rearrangement when X'=carboxylic acid (Method H). The coupling of compound ii with the appropriately substituted boron reagent (Method D) or organotin species (Method E) affords compounds of formula I-U. Compounds of formula ii can be obtained by displacement with an appropriate amine when X'=halogen (Method F), acylation when X'=NH$_2$ (Method G) or Curtius rearrangement when X'=carboxylic acid (Method H). Alternatively, when X'=halogen, Buchwald-Hartwig amination using an appropriate amine with a suitable catalyst system such as Pd$_2$(dba)$_3$/xantphos or Pd(dpp)Cl$_2$, and a suitable base such as Cs$_2$CO$_3$ or t-BuOK in an appropriate solvent can be employed to obtain compounds of formula li (Method L) (for similar procedures, see Driver, M. S., Hartwig, J. F., J. Am. Chem. Soc. 1996, 118, 7217-7218 and Yin, J., et. al., Org. Lett. 2002, 4, 3481). The coupling of compound ii with the appropriately substituted boron reagent (Method D) or organotin species (Method E) affords compounds of formula I-U.

Scheme 19: General method for the preparation of substituted sulfonamido bipyridyls I-V

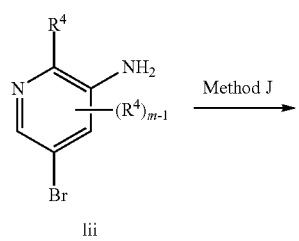

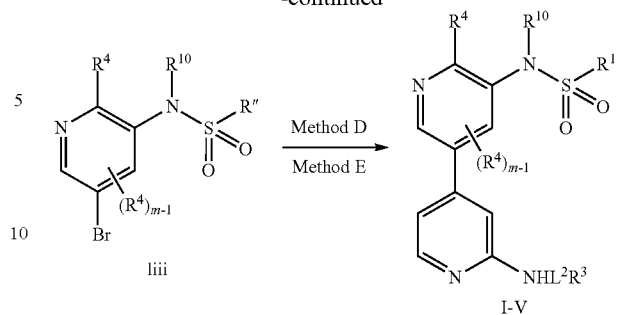

Scheme 19 shows a general route for the preparation of compounds of formula I-V starting from variously substituted 3-amino-pyridines lii. Treatment of lii with an appropriately substituted sulfonyl chloride in the presence of a suitable base such as pyridine or LiHMDS provides access to compounds of the formula liii where $R^{10}$=H (Method J). These intermediates can be coupled with the appropriately substituted boron reagent (Method D) or organotin species (Method E) to afford compounds of formula I-V. Alternatively, compounds of the formula liii where $R^{10}$=H can be further reacted in the presence of a base and an electrophile such as an alkyl halide, acyl halide or sulfonyl chloride to afford di-substituted sulfonamides of the formula liii where $R^{10}$ is as defined herein. These intermediates can be coupled with the appropriately substituted boron reagent (Method D) or organotin species (Method E) to afford compounds of formula I-V.

Scheme 20: General method for the preparation of substituted amido bipyridyls I-W

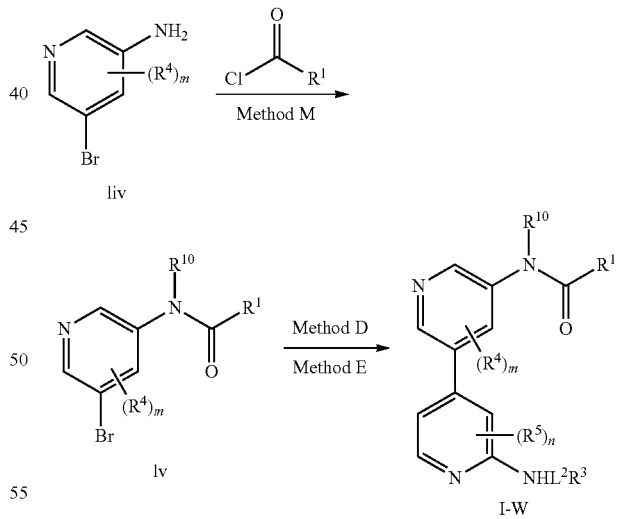

Scheme 20 shows a general route for the preparation of compounds of formula I-W starting from variously substituted 3-amino-pyridines liv. Treatment of liv with an appropriately substituted acid chloride in the presence of a suitable base such as pyridine provides compounds of the formula lv where $R^{10}$=H (Method M). These intermediates can be coupled with the appropriately substituted boron reagent (Method D) or organotin species (Method E) to afford compounds of formula I-W. Alternatively, compounds of the formula lv where $R^{10}$=H can be further reacted in the presence of a base and an electrophile such as an alkyl halide, acyl halide or sulfonyl chloride to afford di-substituted sulfonamides of the formula Iv where $R^{10}$ is as defined herein. These intermediates can be coupled with the appropriately substituted boron reagent (Method D) or organotin species (Method E) to afford compounds of formula I-W.

formula lvii where $R^9$ is as defined herein. These intermediates can be coupled with the appropriately substituted boron reagent (Method D) or organotin species (Method E) to afford compounds of formula I-X. Alternatively, halides of formula lvii can be converted to boronic esters and/or boronic acids lviii by reaction with bis(pinacolato)diboron in Scheme 21: General method for the preparation of substituted amido or keto bipyridyls I-X and I-Y

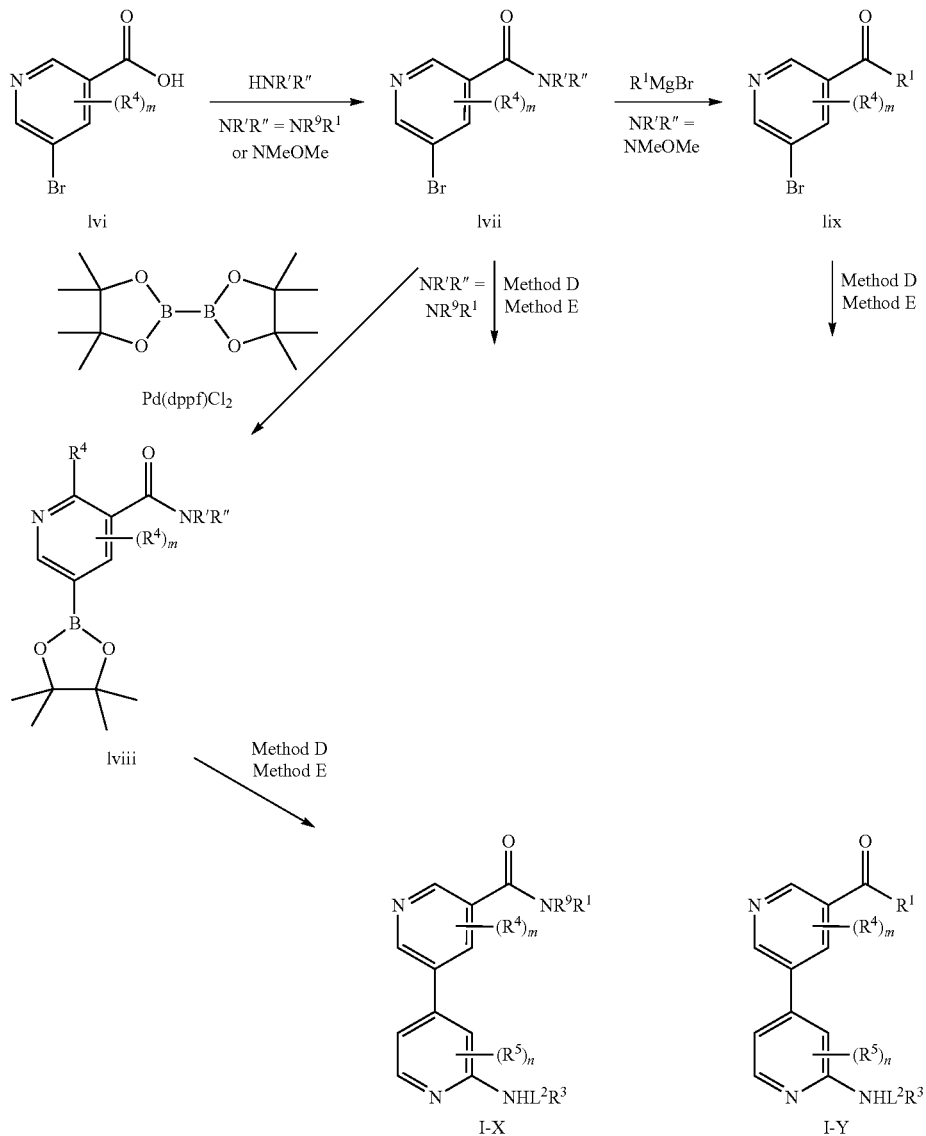

Scheme 21 shows a general route for the preparation of compounds of formula I-X and I-Y starting from variously substituted pyridines lvi with a carboxylic acid moiety at the 3-position. Treatment of lvi with an amine and an appropriate coupling reagent such as TBTU in an appropriate solvent such as DCM affords amides of the formula lvii. These intermediates can be coupled with the appropriately substituted boron reagent (Method D) or organotin species (Method E) to afford compounds of formula I-X. Alternatively, compounds of the formula lvii where $R^9$=H can be further reacted in the presence of a base and an electrophile such as an alkyl halide to afford di-substituted amides of the the presence of a catalyst such as Pd(dppf)Cl$_2$ and a base such as KOAc. The intermediates lviii can be coupled with the appropriately substituted halogen reagent (Method D) to afford compounds of formula I-X. Alternatively, if intermediate lvii is a Weinreb amide (for an example of Weinreb amide preparation, see: Sun, X. et. al. Intl. App. Pub. No. WO 2012/009227 A1), treatment with an appropriately substituted Grignard reagent in a solvent such as THF generates compounds of the formula lix which can be coupled with the appropriately substituted boron reagent (Method D) or organotin species (Method E) to afford compounds of formula I-Y.

The compounds of the present invention can be prepared by methods known to one of ordinary skill in the art and/or by reference to the schemes shown below and the synthetic examples that follow.

4. USES, FORMULATION AND ADMINISTRATION

As discussed above, the present invention provides compounds that can be useful as inhibitors of VPS34, and thus the present compounds can be useful for treating proliferative, inflammatory, cardiovascular, or proliferative disorders (such as tumor and/or cancerous cell growth) mediated by VPS34. In particular, the compounds can be useful in the treatment of cancers in a subject, including, but not limited to, lung and bronchus, including non-small cell lung cancer (NSCLC), squamous lung cancer, brochioloalveolar carcinoma (BAC), adenocarcinoma of the lung, and small cell lung cancer (SCLC); prostate, including androgen-dependent and androgen-independent prostate cancer; breast, including metastatic breast cancer; pancreas; colon and rectum; thyroid; liver and intrahepatic bile duct; hepatocellular; gastric; endometrial; melanoma; kidney; and renal pelvis, urinary bladder; uterine corpus; uterine cervix; ovary, including progressive epithelial or primary peritoneal cancer; multiple myeloma; esophagus; acute myelogenous leukemia (AML); chronic myelogenous leukemia (CML), including accelerated CML and CML blast phase (CML-BP); lymphocytic leukemia; myeloid leukemia; acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma, including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS). (refractory anemia with excess blasts (RAEB), and RAEB in transformation (RAEB-T); and myeloproliferative syndromes; brain, including glioma/glioblastoma, anaplastic oligodendroglioma, and adult anaplastic astrocytoma; neuroendocrine, including metastatic neuroendocrine tumors; head and neck, including, e.g., squamous cell carcinoma of the head and neck, and nasopharyngeal cancer; oral cavity; and pharynx; small intestine; bone; soft tissue sarcoma; and villous colon adenoma.

In some embodiments, compounds of the invention can be suitable for the treatment of breast cancer, bladder cancer, colon cancer, glioma, glioblastoma, lung cancer, hepatocellular cancer, gastric cancer, melanoma, squamous cell carcinoma, head and neck cancer, thyroid cancer, endometrial cancer, renal cancer, cervical cancer, pancreatic cancer, esophageal cancer, prostate cancer, brain cancer, or ovarian cancer.

In other embodiments, compounds of the invention can be suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. For clarity, the present invention can also include the corresponding N-oxide of the compounds of formula I.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of VPS34.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentancpropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate: powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound of formula I, or a pharmaceutical composition containing the same to a subject in need thereof. In certain embodiments of the present invention an "effective amount" of the compound of formula I or pharmaceutical composition containing the same is that amount effective for treating a proliferative, inflammatory, or cardiovascular disorder, or is that amount effective for treating cancer. In other embodiments, an "effective amount" of a compound of formula I is an amount which inhibits enzymatic activity of VPS34 and thereby blocks the resulting signaling cascades that lead to the abnormal activity of members of such cascades (e.g., growth factors, receptor tyrosine kinases, protein serine/threonine kinases, G protein coupled receptors, transmembrane receptors and phospholipid kinases and phosphatases). Still in other embodiments, an "effective amount" of a compound of formula I is an amount which inhibits enzymatic activity of VPS34 and thereby leads to abnormal activity of degradation pathways mediated by the proteasome or lysosome.

The compounds and compositions, according to the method of the present invention, may be administered using any amount and any route of administration effective for treating the disease. The exact amount required will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment: drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 200 mg/kg (e.g., from about 0.1 mg/kg to about 50 mg/kg or from about 1 mg/kg to about 25 mg/kg), of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol. 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Compounds of this invention can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the compounds of this invention may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents. In some embodiments, the additional therapeutic agent is selected from other inhibitors of VPS34. In other embodiments, a compound of the invention is administered in conjunction with a therapeutic agent selected from the group consisting of cytotoxic agents, radiotherapy, and immunotherapy. It is understood that other combinations may be undertaken while remaining within the scope of the invention. For example, any compound of this invention or pharmaceutically acceptable salt described herein can be administered in conjunction with a second therapeutic agent (e.g., an autophagy inducer, an EGFR inhibitor, a tyrosine kinase inhibitor (TKI), a receptor tyrosine kinase inhibitor (RTKI), or a PI3K pathway inhibitor such as an mTOR inhibitor). The combination therapy can be assayed using the tumor xenograft model described below.

In some embodiments, the therapeutic agent is gefitinib (Iressa™), erlotinib (Tarceva®), cetuximab (Erbitux®), afatinib (Gilotrif™), lapatinib (Tykerb®), panitumumab (Vectibix®), vandetanib (Caprelsa®), CO-1686 (N-(3-((2-((4-(4-acetylpiperazin-1-yl)-2-methoxyphenyl)amino)-5-(trifluoro methyl)pyrimidin-4-yl)amino)phenyl)acrylamide; Clovis Oncology), AZD9291 (AstraZeneca), axitinib (Inlyta®), dasatinib (Sprycel®), imatinib (Gleevec®), nilotinib (Tasigna®), pazopanib (Votrient®), sorafenib (Nexavar®), or sunitinib (Sutent®). In some embodiments, the additional therapeutic agent for use in combination therapy is erlotinib, afatinib, lapatinib, or CO-1686. In other embodiments, the additional therapeutic agent is selected from gefitinib, vandetanib, and panitumumab. In still other embodiments, the additional therapeutic agent is cetuximab.

Combination therapy can be administered with any of the compounds of the invention described herein, or a pharmaceutically acceptable salt thereof. In some embodiments, the compound is selected from the compounds of Table 1, or pharmaceutically acceptable salts thereof. In other embodiments, the compound is I-30, or a pharmaceutically acceptable salt thereof. In other embodiments, the compound is I-32, or a pharmaceutically acceptable salt thereof. In other embodiments, the compound is I-41, or a pharmaceutically acceptable salt thereof. In other embodiments, the compound is I-94, or a pharmaceutically acceptable salt thereof. In other embodiments, the compound is I-153, or a pharmaceutically acceptable salt thereof. In other embodiments, the compound is I-214, or a pharmaceutically acceptable salt thereof. In other embodiments, the compound is I-299, or a pharmaceutically acceptable salt thereof. In other embodiments, the compound is I-308, or a pharmaceutically acceptable salt thereof.

The additional agents may be administered separately from a provided combination therapy, as part of a multiple dosage regimen. Alternatively, those agents may be part of a single dosage form, mixed together with a compound of this invention in a single composition. If administered as part of a combination therapy, the two therapeutic agents may be submitted simultaneously, sequentially or intermittently.

Combination therapy can be used for any of the therapeutic indications described herein. In some embodiments, the combination therapy is for the treatment of a proliferative disorder (e.g., cancer) in a patient. In some embodiments, the proliferative disorder is breast cancer, bladder cancer, colon cancer, glioma, glioblastoma, lung cancer, hepatocellular cancer, gastric cancer, melanoma, squamous cell carcinoma, head and neck cancer, thyroid cancer, endometrial cancer, renal cancer, cervical cancer, pancreatic cancer, esophageal cancer, prostate cancer, brain cancer, or ovarian cancer. In some embodiments, the proliferative disorder is breast cancer, pancreatic cancer, head and neck cancer, non-small-cell lung carcinoma (NSCLC), colon cancer, renal cell carcinoma, squamous cell carcinoma, or thyroid cancer. In other embodiments, the proliferative disorder is breast cancer, pancreatic cancer, head and neck cancer, non-small-cell lung carcinoma (NSCLC), or colon cancer.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

Another aspect of the invention relates to inhibiting VPS34 activity in a biological sample or a patient, which method comprises administering to the patient, or contacting said biological sample with a compound as described herein, or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where VPS34 kinase plays a role.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Definitions

AA LCMS method using ammonium acetate
Ac acetyl
ACN acetonitrile
AcOH acetic acid
amphos bis(di-tert-butyl(4-dimethylaminophenyl)phosphine)
BOC tert-butoxycarbonyl
Bu butyl
t-Bu tert-butyl
C Celsius
CDI carbonyldiimidazole
dba dibenzylideneacetone
DCE dichloroethane
DCM dichloromethane
DIAD diisopropyl azodicarboxylate
DIEA N,N-diisopropylethylamine
DMAP 4-dimethylaminopyridine
DME 1,2-dimethoxyethane
DMF N,N-dimethylformamide
DMF-DMA N,N-dimethylformamide dimethyl acetal
dppf 1,1'-bis(diphenylphosphino)ferrocene
DMSO dimethylsulfoxide
EDC N-(3-dimethylaminopropyl)-N'-ethylcarbodiimide hydrochloride
Et ethyl
EtOAc ethyl acetate
EtOH ethanol
FA LCMS method using formic acid
h hours
HATU 1-[Bis(dimethylamino)methylene]-1H-1,2,3-triazolo[4,5-b]pyridinium 3-oxide hexafluorophosphate
HMDS hexamethyldisilazane
HMPT hexamethylphosphorous triamide
HPLC high pressure liquid chromatography IC$_{50}$ inhibitory concentration 50%
LCMS liquid chromoatography mass spectrometry
m/z mass to charge
mCPBA m-chloroperbenzoic acid
MHz mega hertz
Me methyl
MeOH methanol
min minutes
mpk mg per kg
MS mass spectrum
MTBE methyl tert-butyl ether
NaOAc sodium acetate
NB S N-bromosuccinimide
NMP N-methylpyrrolidinone
NMR nuclear magnetic resonance
po per os (by mouth or orally)
Pr propyl
i-Pr isopropyl
psi pounds per square inch
qd quaque die (every day)
rac racemic
rt room temperature
SiliaCat DPP-Pd diphenylphosphine palladium (II) heterogeneous silica-based catalyst
STAB sodium triacetoxyborohydride
T3P I-propanephosphonic acid cyclic anhydride
Tf trifluoromethanesulfonyl
TEA triethylamine
TFA trifluoroacetic acid
THF tetrahydrofuran
TBTU O-(benzotriazol-1-yl)-N,N,N',N'-tetramethyluronium tetrafluoroborate
UPLC ultra performance liquid chromatography
Xantphos 4,5-bis(diphenylphosphino)-9,9-dimethylxanthene
Xphos 2-dicyclohexylphosphino-2',4',6'-triisopropylbiphenyl
XPhosG3 (2-dicyclohexylphosphino-2',4',6'-triisopropyl-1,1'-biphenyl) [2-(2'-amino-1,1'-biphenyl)]palladium(II) methanesulfonate Analytical Methods NMR Conditions:

$^1$H NMR spectra are run on a 400 MHz Bruker or Varian spectrometer unless otherwise stated.

LCMS Conditions:

LCMS spectra were recorded on a Hewlett-Packard HP1100 or Agilent 1100 Series LC system connected to a Micromass mass spectromteter using reverse phase C18 columns. Various gradients and run times were selected in order to best characterize the compounds. Mobile phases were based on ACN/water gradients and contained either 0.1% formic acid (methods indicated as FA) or 10 mM ammonium acetate (methods indicated as AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run.

In some cases, LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase C18 columns. Various gradients and run times were selected in order to best characterize the compounds. Mobile phases were based on ACN/water gradients and contained either 0.1% formic acid (methods indicated as FA) or 10 mM ammonium acetate (methods indicated as AA). One example of a solvent gradient that was used was 95% mobile phase A (mobile phase A=99% water+1% ACN+0.1% formic acid) to 100% mobile phase B (mobile phase B=95% ACN+5% water+0.1% formic acid) at a flow rate of 0.5 mL/min for a 5 min run.

Preparative HPLC:

Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

One of ordinary skill in the art will recognize that modifications of the gradient, column length, and flow rate are possible and that some conditions may be suitable for compound characterization than others, depending on the chemical species being analyzed.

Preparative SFC:

Preparative SFC is conducted using 10, 20 or 30 mm×250 mm ChiralPak columns (typically IA, IB, IC, ID, IE and IF) eluting with appropriate percentages of supercritical carbon dioxide and alcohol containing 0.3% diethyl amine or 0.3% triethylamine or 0.3% formic acid or without any acid or base additives. Isocratic conditions with flow rates in the range of 10-100 mL/min and a column temperature of 40° C. are typical. A Jasco SFC prep purification system with UV/visible triggered fraction collection set to between 200 nm and 400 nm and back pressure regulation set to 10 MPa.

One of ordinary skill in the art will recognize that modifications of the gradient, column length, and flow rate are possible and that some conditions may be suitable for compound characterization than others, depending on the chemical species being analyzed.

X-Ray Powder Diffraction (XRPD) Conditions:

XRPD is performed using a Bruker AXS D8 Advance X-ray Diffractometer using CuKa radiation (40 kV, 40 mA), θ-2 θ goniometer, and divergence of V4 and receiving slits, a Ge monochormator and a Lynxeye detector. Samples are run under ambient conditions as flat plate specimens using powder. The sample is gently packed into a cavity cut into polished, zero-background (510) silicon wafer. The sample is rotated in its own plane during analysis. The data are collected on an angular range of 2 to 42° 2θ, with a step size of 0.05° 2θ and a collection time of 0.5 s/step. Data collection is performed using Diffrac Plus XRD Commander v2.6.1 software. Data analysis and presentation is performed using Diffrac Plus EVA v13.0.0.2 or v15.0.0.0 software.

Example 1: Synthesis of Intermediate Boronic Acids and Stannanes

N-[4-(4,4,5,5-tetramethyl-1,3,2-dioxaborolan-2-yl)pyridin-2-yl]acetamide

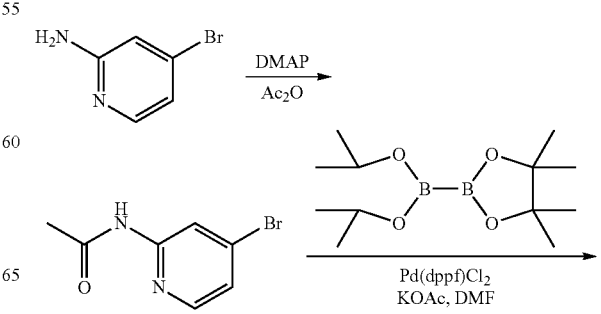

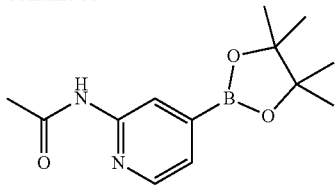

Step 1: N-(4-bromopyridin-2-yl)acetamide

To a solution of 4-bromopyridin-2-amine (12.0 g, 69.4 mmol) in acetic anhydride (240 mL) was added DMAP (0.0847 g, 0.694 mmol). The reaction mixture was allowed to stir at 140° C. for 3 h and then allowed to cool to rt. Ice water was added and the pH of the mixture was adjusted to 8.5 by the addition of concentrated NH$_4$OH. The solid which precipitated was filtered, washed with cold water and hexanes, and dried to give N-(4-bromopyridin-2-yl)acetamide (13.3 g, 89%) as a white solid.

Step 2: N-[4-(4,4,5,5-tetramethyl-1,3,2-dioxaborolan-2-yl)pyridin-2-yl]acetamide To a mixture of N-(4-bromopyridin-2-yl)acetamide (17.2 g, 80 mmol), 4,4,4',4',5,5,5',5'-octamethyl-2,2'-bi-1,3,2-dioxaborolane (26.4 g, 104 mmol), Pd(dppf)Cl$_2$ (11.7 g, 16 mmol) and KOAc (23.6 g, 240 mmol) under an atmosphere of nitrogen was added anhydrous DMF (1500 mL). The mixture was allowed to stir at 80° C. for 3.5 h. The solvent was removed and the residue was diluted with EtOAc (1000 mL). Activated carbon (100 g) was added. The slurry was heated at reflux for 5 min and then filtered. The organic solution was concentrated and the residue was recrystallized from EtOAc to give N-[4-(4,4,5,5-tetramethyl-1,3,2-dioxaborolan-2-yl)pyridin-2-yl]acetamide (6.1 g, 29%) as a white solid. $^1$H NMR (400 MHz, DMSO-d$_6$): δ 1.29 (s, 12H), 2.09 (s, 3H), 7.24 (dd, J=6.0, 1.2 Hz, 1H), 8.30-8.33 (m, 2H), 10.47 (br s, 1H).

N-[4-(4,4,5,5-tetramethyl-1,3,2-dioxaborolan-2-yl)pyridin-2-yl]cyclopropanecarboxamide

Step 1: N-(4-bromopyridin-2-yl)cyclopropanecarboxamide

To a stirring solution of 4-bromopyridin-2-amine (200 g, 1160 mmol) in DCM (2000 mL) and pyridine (183 g, 2310 mmol) was added cyclopropanecarbonyl chloride (157 mL, 1500 mmol) dropwise at 0° C. under a nitrogen atmosphere. The reaction mixture was allowed to stir at 0° C. for 12 h then the reaction mixture was allowed to warm to rt. The reaction mixture was washed with 1N HCl solution (3×500 mL) and brine (500 mL). The organic solution was dried over Na$_2$SO$_4$, filtered and concentrated to give N-(4-bromopyridin-2-yl)cyclopropanecarboxamide (224 g, 80% yield) as a white solid. LCMS (FA): m/z=241.0 (M+H).

Step 2: N-[4-(4,4,5,5-tetramethyl-1,3,2-dioxaborolan-2-yl)pyridin-2-yl]cyclopropanecarboxamide A mixture of N-(4-bromopyridin-2-yl)cyclopropanecarboxamide (100 g, 415 mmol), 4,4,4',4',5,5,5',5'-octamethyl-2,2'-bi-1,3,2-dioxaborolane (105 g, 415 mmol), potassium acetate (81.4 g, 830 mmol), and Pd(dppf)Cl$_2$ (30.4 g, 42 mmol) in 1,4-dioxane (1000 mL) was allowed to stir at 100° C. under an atmosphere of nitrogen for 12 h. The reaction mixture was allowed to cool to rt and was filtered through celite. The filtrate was concentrated and the residue was dissolved in EtOAc (1500 mL). Activated charcoal (400 g) was added and the mixture was allowed to stir at reflux for 2 h then allowed to cool to rt. The mixture was filtered and the filtrate was concentrated under vacuum. The residue was recrystallized from EtOAc: petroleum ether (1:1, 800 mL) to give N-[4-(4,4,5,5-tetramethyl-1,3,2-dioxaborolan-2-yl)pyridin-2-yl]cyclopropanecarboxamide (111 g, 47% yield) as a white solid. $^1$H NMR (400 MHz, DMSO-d$_6$) δ 10.79 (s, 1H), 8.36 (s, 1H), 8.34 (d, J=4.35 Hz, 1H), 7.25 (br d, J=4.02 Hz, 1H), 2.01 (m, 1H), 1.31 (s, 12H), 0.83 (br s, 4H).

N-[5-methyl-4-(4,4,5,5-tetramethyl-1,3,2-dioxaborolan-2-yl)pyridin-2-yl]cyclopropanecarboxamide

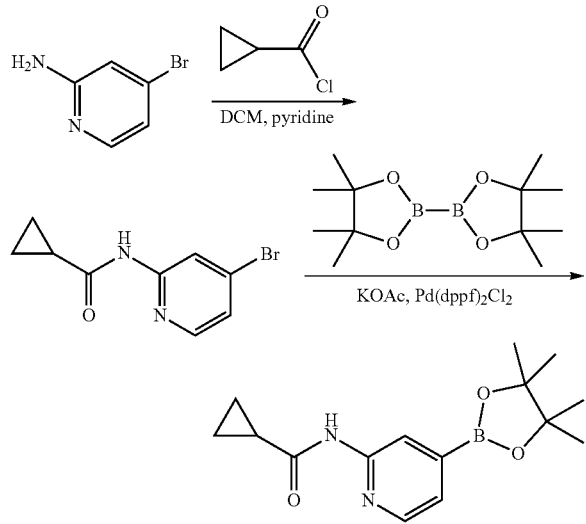

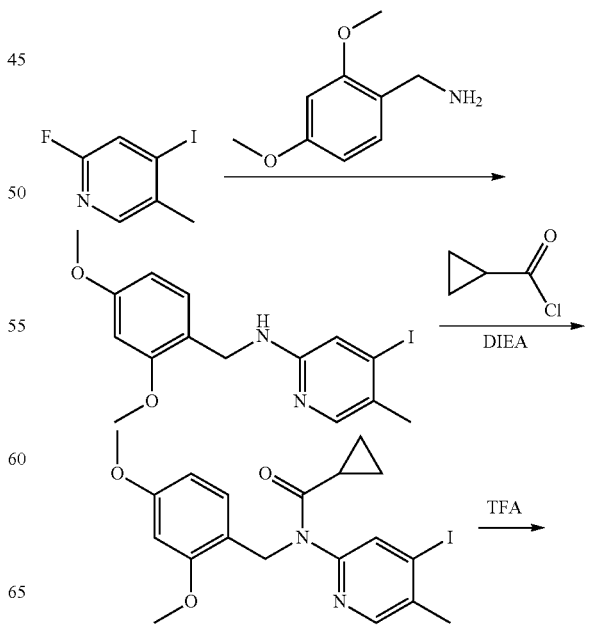

-continued

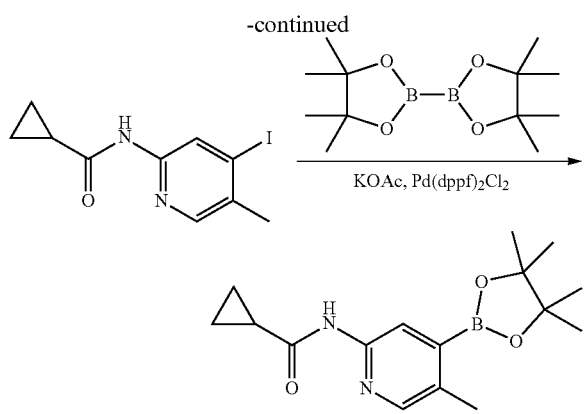

Step 1: N-(2,4-dimethoxybenzyl)-4-iodo-5-methyl-pyridin-2-amine

A solution of 2-fluoro-4-iodo-5-methylpyridine (85 g, 340 mmol) in 1-(2,4-dimethoxyphenyl)methanamine (270 mL, 1.68 mol) was allowed to stir at 110° C. overnight. The reaction mixture was allowed to cool to rt and diluted with EtOAc. A precipitate formed and was filtered and then washed with EtOAc. The solid was purified further by column chromatography to give N-(2,4-dimethoxybenzyl)-4-iodo-5-methylpyridin-2-amine (138 g, 50%).

Step 2: N-(2,4-dimethoxybenzyl)-N-(4-iodo-5-methylpyridin-2-yl)cyclopropanecarboxamide To a solution of DIEA (76 mL, 440 mmol) in THF (1700 mL) was added N-(2,4-dimethoxybenzyl)-4-iodo-5-methylpyridin-2-amine (85 g, 220 mmol) and cyclopropanecarbonyl chloride (27.9 mL, 310 mmol). The reaction mixture was allowed to stir at 70° C. for 12 h and then concentrated. The residue was diluted with aqueous saturated ammonium chloride and extracted with DCM. The organic solutions were combined, dried over $Na_2SO_4$, filtered and concentrated to give N-(2,4-dimethoxybenzyl)-N-(4-iodo-5-methylpyridin-2-yl)cyclopropanecarboxamide (130 g, 80%) which was used in the next step without purification.

Step 3: N-(4-iodo-5-methylpyridin-2-yl)cyclopropanecarboxamide

A solution of N-(2,4-dimethoxybenzyl)-N-(4-iodo-5-methylpyridin-2-yl)cyclopropanecarboxamide (65 g, 144 mmol) and TFA (833 mL, 4.13 mol) in DCM (850 mL) was allowed to stir at rt overnight. The reaction mixture was concentrated and the residue was redissolved in DCM. Aqueous sodium bicarbonate was added and the solution was extracted with DCM. The organic solutions were combined, dried over $Na_2SO_4$, filtered and concentrated. The residue was purified by column chromatography to give N-(4-iodo-5-methylpyridin-2-yl)cyclopropanecarboxamide (60 g, 70%).

Step 4: N-[5-methyl-4-(4,4,5,5-tetramethyl-1,3,2-dioxaborolan-2-yl)pyridin-2-yl]cyclopropanecarboxamide A mixture of N-(4-iodo-5-methylpyridin-2-yl)cyclopropanecarboxamide (20 g, 66 mmol). 4,4,4',4',5,5,5',5'-octamethyl-2,2'-bi-1,3,2-dioxaborolane (33.6 g, 132 mmol) and potassium acetate (19.4 g, 198 mmol) in DMSO (200 mL) was degassed with nitrogen for 20 min. $Pd(dppf)Cl_2$ (5.4 g, 7 mmol) was added and the mixture was again degassed with nitrogen for 20 min. The reaction mixture was allowed to stir at 60° C. overnight and was then allowed to cool to rt and filtered. The filtrate was diluted with EtOAc and the solution was washed with water and brine. Activated charcoal was added to the organic solution and the mixture was heated at reflux for 3 h. The mixture was filtered and the filtrate was concentrated. The residue was taken up in tert-butyl dimethylether and the resulting solid was filtered. The filtrate was concentrated and the resulting solid was washed with petroleum ether to give pure N-[5-methyl-4-(4,4,5,5-tetramethyl-1,3,2-dioxaborolan-2-yl)pyridin-2-yl]cyclopropanecarboxamide (7.4 g, 37%).

methyl [4-(trimethylstannyl)pyridin-2-yl]carbamate

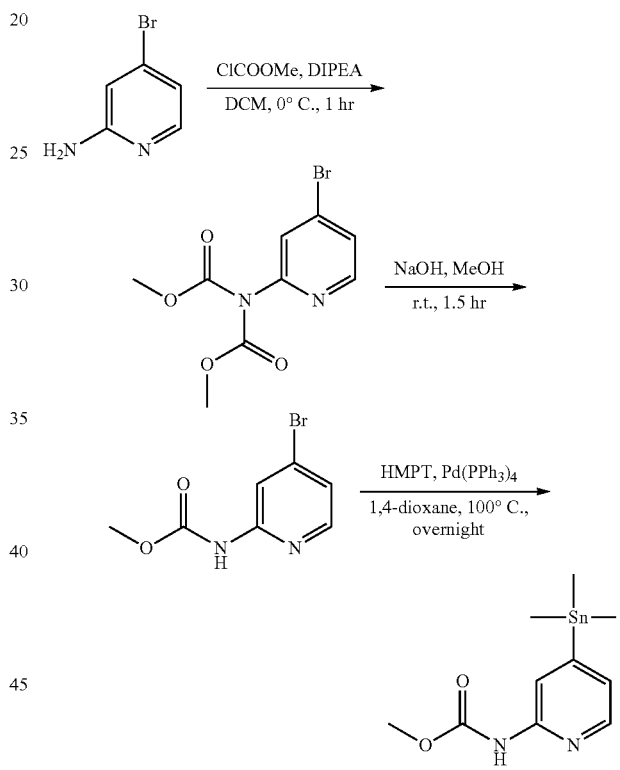

Step 1: dimethyl (4-bromopyridin-2-yl)imidodicarbonate

To a solution of 2-amino-4-bromopyridine (14.0 g, 81.0 mmol) in DCM (800 mL) was added DIEA (35.0 mL, 202 mmol) and methyl chloroformate (15.0 g, 162 mmol) at 0° C. The reaction mixture was stirred at 0° C. for 1 h. Saturated aqueous $NH_4Cl$ was added and the aqueous layer was extracted with DCM. The combined organic layers were washed with brine, and concentrated by rotary evaporation to give a brown solid which was taken on without further purification.

Step 2: methyl (4-bromopyridin-2-yl)carbamate

To a solution of (4-bromopyridin-2-yl)imidodicarbonate (8.0 g, 27.7 mmol) in MeOH (150 mL) was added NaOH (2.21 g, 55.4 mmol). The reaction mixture was stirred at rt for 15 h. The reaction mixture was concentrated and then EtOAc and water were added. The aqueous layer was extracted with EtOAc. The combined organic layers were washed with brine, dried over $Na_2SO_4$ and concentrated by rotary evaporation to give methyl (4-bromopyridin-2-yl) carbamate (5.15 g, 81%) which was used without purification.

Step 3: methyl [4-(trimethylstannyl)pyridin-2-yl] carbamate

Under an atmosphere of nitrogen, a solution of methyl (4-bromopyridin-2-yl)carbamate (22 g, 95.2 mmol), HMPT (37.5 g, 115 mmol), $Pd(PPh_3)_4$ (3.3 g, 2.86 mmol) and $NH_4Cl$ (225 mg, 4.77 mmol) in 1,4-dioxane (500 mL) was heated at 100° C. for 10 h. The mixture was filtered and concentrated. The crude compound was purified by column chromatography to give methyl [4-(trimethylstannyl)pyridin-2-yl]carbamate (13.5 g, 40%). $^1H$ NMR (400 MHz, $CDCl_3$): δ 0.34 (s, 9H) 3.09 (s, 3H), 7.10 (d, J=4.6 Hz, 2H), 7.66 (br s, 1H), 8.116 (s, 1H), 8.16 (d, J=4.6 Hz, 2H).

N-[5-methyl-4-(4,4,5,5-tetramethyl-1,3,2-dioxaborolan-2-yl)pyridin-2-yl]acetamide

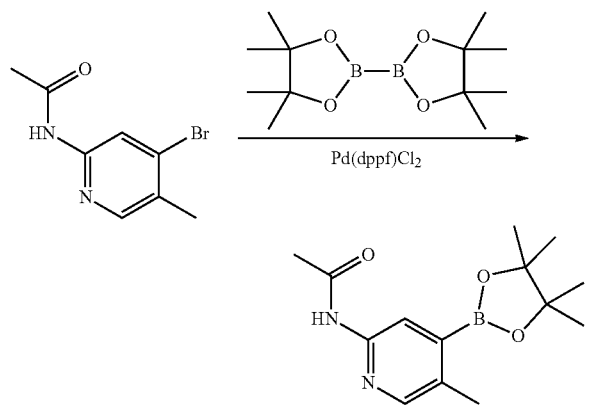

A mixture of N-(4-bromo-5-methylpyridin-2-yl)acetamide (30 g, 131 mmol), 4,4,4',4',5,5,5',5'-octamethyl-2,2'-bi-1,3,2-dioxaborolane (40 g, 157 mmol), potassium acetate (45.2 g, 459 mmol) and $Pd(dppf)Cl_2$ (10.6 g, 13 mmol) in 1,4-dioxane (900 mL) was allowed to stir under an atmosphere of nitrogen at 90° C. for 18 h. The reaction mixture was diluted with EtOAc and filtered while hot. The filtrate was concentrated to give N-[5-methyl-4-(4,4,5,5-tetramethyl-1,3,2-dioxaborolan-2-yl)pyridin-2-yl]acetamide (18.3 g, 51%).

(rac)-2,2-difluoro-N-(4-(4,4,5,5-tetramethyl-1,3,2-dioxaborolan-2-yl)pyridin-2-yl) cyclopropanecarboxamide

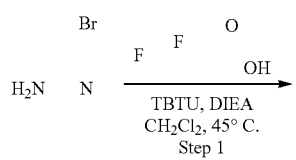

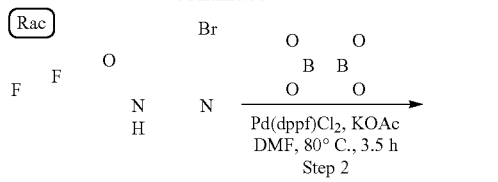

Step 1: (rac)-N-(4-bromopyridin-2-yl)-2,2-difluorocyclopropanecarboxamide

To a solution of (rac)-2,2-difluorocyclopropanecarboxylic acid (10.0 g, 82 mmol) in DCM (250 mL) was added DIEA (53 g, 409 mmol), TBTU (60 g, 185 mmol) and 4-bromopyridin-2-amine (18.4 g, 106 mmol). The reaction mixture was heated at 45° C. for 17 h. To the reaction mixture was added water (500 mL) and the aqueous layer was extracted with EtOAc (3×300 mL). The organic layers were combined and washed with brine, dried, and concentrated in vacuo. The residue was purified by column chromatography (petroleum ether/EtOAc) to give (rac)-N-(4-bromopyridin-2-yl)-2,2-difluorocyclopropanecarboxamide as a white solid (10 g, 44%).

Step 2: (rac)-2,2-difluoro-N-(4-(4,4,5,5-tetramethyl-1,3,2-dioxaborolan-2-yl)pyridin-2-yl) cyclopropanecarboxamide To a solution of (rac)-N-(4-bromopyridin-2-yl)-2,2-difluorocyclopropanecarboxamide (8.0 g, 28.9 mmol) in 1,4-dioxane (85 mL) under an atmosphere of nitrogen was added bis(pinacolato)diboron (9.5 g, 37.5 mmol), KOAc (8.4 g, 87.0 mmol) and $Pd(dppf)Cl_2$. The reaction mixture was heated at 75° C. for 12 h. The reaction mixture was filtered and washed with EtOAc (2×100 mL). To the filtrate was added water (500 mL) and the aqueous layer was extracted with EtOAc (2×200 mL). The combined organic layers were dried over $Na_2SO_4$ and concentrated by rotary evaporation. To the residue was added EtOAc (200 mL) and activated carbon (25.5 g). The mixture was stirred at 90° C. for 1 h and then filtered, rinsing with hot EtOAc (2×50 mL). The filtrated was concentrated by rotary evaporation, then taken up in EtOAc (10 mL) and petrolelum ether (50 mL). The mixture was stirred for 5 min, filtered and concentrated. The residue was again taken up in EtOAc (5 mL) and petroleum ether (25 mL), stirred for 5 min, filtered and concentrated to provide (rac)-2,2-difluoro-N-(4-(4,4,5,5-tetramethyl-1,3,2-dioxaborolan-2-yl)pyridin-2-yl) cyclopropanecarboxamide as a white solid (5.4 g, 57%). $^1H$ NMR (400 MHz, $CDCl_3$): δ 1.34 (s, 12H), 1.77 (m, 1H), 2.25 (m, 1H), 2.46 (m, 1H), 7.42 (d, J=4.8 Hz, 1H), 8.31 (d, J=4.8 Hz, 1H), 8.54 (s, 1H), 8.99 (s, 1H).

283

N-(1,3-oxazol-2-yl)-4-(4,4,5,5-tetramethyl-1,3,2-dioxaborolan-2-yl)pyridin-2-amine

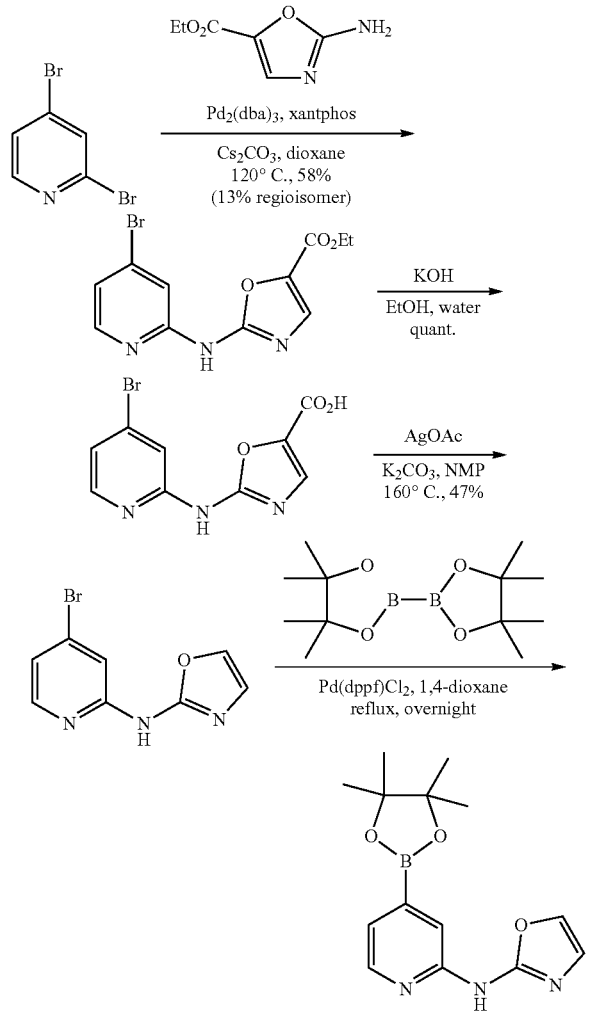

Step 1: ethyl 2-[(4-bromopyridin-2-yl)amino]-1,3-oxazole-5-carboxylate

To a mixture of 2-amino-oxazole-5-carboxylic acid ethyl ester (0.483 g, 3.09 mmol), tris(dba)dipalladium (0) (0.070 g, 0.077 mmol), xantphos (0.120 g, 0.208 mmol) and cesium carbonate (1.95 g, 5.98 mmol) in 1,4-dioxane (15.0 mL, 192 mmol) was added 2,4-dibromopyridine (1.078 g, 4.55 mmol). The reaction was heated in the microwave at 115° C. for 1 h. The reaction was diluted with DCM (30 mL), silica gel was added to the mixture (11 g) and the solvents were removed to absorb material onto the silica. Purification of sample by column chromatography to afford ethyl 2-[(4-bromopyridin-2-yl)amino]-1,3-oxazole-5-carboxylate (0.561 g, 58%). $^1$H NMR (400 MHz, DMSO-$d_6$) δ 11.64 (s, 1H), 8.34 (s, 1H), 8.21 (d, J=5.3 Hz, 1H), 7.90 (s. 1H), 7.32 (dd, J=5.3, 1.6 Hz, 1H), 4.29 (q, J=7.1 Hz, 2H), 1.29 (t, J=7.1 Hz, 3H) and ethyl 2-[(2-bromopyridin-4-yl)amino]-1,3-oxazole-5-carboxylate (0.13 g, 14%). $^1$H NMR (400 MHz, DMSO-$d_6$) δ 11.63 (s, 1H), 8.23 (d, J=5.7 Hz, 1H), 8.01-7.84 (m, 2H), 7.47 (dd, J=5.7, 2.0 Hz, 1H), 4.29 (q, J=7.1 Hz, 2H), 1.29 (t, J=7.1 Hz, 3H).

284

Step 2: 2-[(4-bromopyridin-2-yl)amino]-1,3-oxazole-5-carboxylic acid

A mixture of ethyl 2-[(4-bromopyridin-2-yl)amino]-1,3-oxazole-5-carboxylate (0.547 g, 1.75 mmol) and 0.50 M of potassium hydroxide in water (10.0 mL, 5.00 mmol) in reagent grade EtOH (35.0 mL, 599 mmol) was heated at 50° C. for 3 h. The reaction was cooled to rt and neutralized with the addition of 6.0 M of hydrochloric acid in water (0.880 mL, 5.28 mmol) resulting in the formation of a thick white precipitate. Collection by filtration and drying under vacuum afforded 2-[(4-bromopyridin-2-yl)amino]-1,3-oxazole-5-carboxylic acid as a white solid (0.48 g, 97%). $^1$H NMR (400 MHz, DMSO-$d_6$) δ 13.23 (s, 1H), 11.57 (s, 1H), 8.34 (d, J=1.4 Hz, 1H), 8.20 (d, J=5.3 Hz, 1H), 7.80 (s, 1H), 7.30 (dd, J=5.3, 1.7 Hz, 1H).

Step 3: 4-bromo-N-(1,3-oxazol-2-yl)pyridin-2-amine

A mixture of 2-[(4-bromopyridin-2-yl)amino]-1,3-oxazole-5-carboxylic acid (0.481 g, 1.69 mmol), potassium carbonate (351 mg, 2.54 mmol) and silver acetate (27.3 mg, 0.164 mmol) in degassed NMP (7.7 mL, 80.0 mmol) was heated at 170° C. in the microwave for 7 min. The reaction was cooled to rt and neutralized with the addition of 6.0 M of hydrochloric acid in water (0.880 mL, 5.28 mmol) resulting in the formation of a thick white precipitate. The solvent was evaporated under reduced pressure and the residue obtained was taken up in MeOH, insolubles removed by filtration and the solution purified by column chromatography to afford 4-bromo-N-(1,3-oxazol-2-yl)pyridin-2-amine as a yellow solid (0.18 g, 43%). $^1$H NMR (400 MHz, DMSO-$d_6$) δ 11.06 (s, 1H), 8.34 (s, 1H), 8.16 (d, J=5.3 Hz, 1H), 7.75 (s, 1H), 7.22 (dd, J=5.3, 1.4 Hz, 1H), 7.08 (d, J=0.8 Hz, 1H).

Step 4: N-(4-(4,4,5,5-tetramethyl-1,3,2-dioxaborolan-2-yl)pyridin-2-yl)oxazol-2-amine The procedure from example 1 for N-[5-methyl-4-(4,4,5,5-tetramethyl-1,3,2-dioxaborolan-2-yl)pyridine-2-yl]acetamide was followed to provide N-(4-(4,4,5,5-tetramethyl-1,3,2-dioxaborolan-2-yl)pyridin-2-yl)oxazol-2-amine (0.71 g, 36%). $^1$H NMR (400 MHz, CDCl$_3$) δ 9.0 (s, 1H), 8.35-8.40 (m, 1H), 8.34 (s, 1H), 7.35 (s, 1H), 7.25-7.30 (m, 1H), 7.00 (s, 1H), 1.34 (s, 12H).

2-methyl-N-(4-(4,4,5,5-tetramethyl-1,3,2-dioxaborolan-2-yl)pyridin-2-yl)pyrimidin-4-amine

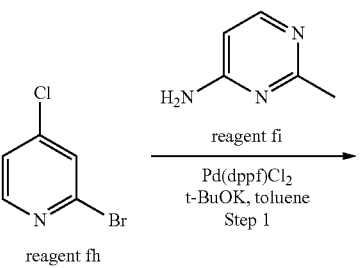

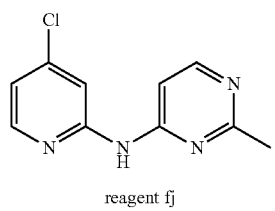 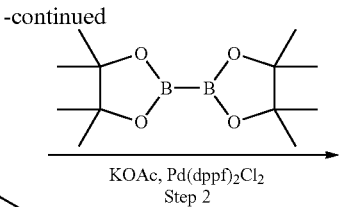

KOAc, Pd(dppf)$_2$Cl$_2$
Step 2 reagent fj

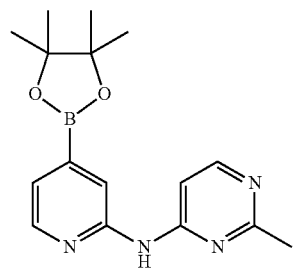

Step 1:
N-(4-chloropyridin-2-yl)-2-methylpyrimidin-4-amine t-BuOK (1.00 M in THF, 84 mL, 84 mmol) was added to a stirring mixture of 2-bromo-4 chloropyridine (14.0 g, 72.7 mmol), 2-methylpyrimidin-4-amine (6.1 g, 55.9 mmol), Pd(dppf)Cl$_2$ (0.82 g, 1.12 mmol), and dppf (2.48 g, 4.47 mmol) in toluene (204 mL). The reaction mixture was allowed to stir at 110° C. for 16 h under a nitrogen atmosphere then was allowed to cool to rt and then concentrated. The crude compound was purified by column chromatography to provide N-(4-chloropyridin-2-yl)-2-methyl-pyrimidin-4-amine (10 g, 81% yield). LCMS (FA): m/z=221.0 (M+H).

Step 2: 2-methyl-N-(4-(4,4,5,5-tetramethyl-1,3,2-dioxaborolan-2-yl)pyridin-2-yl)pyrimidin-4-amine A solution of N-(4-chloropyridin-2-yl)-2-methylpyrimidin-4-amine (50 g, 226.6 mmol), 4,4,4',4',5,5,5',5'-octamethyl-2,2'-bi-1,3,2-dioxaborolane (63.3 g, 249 mmol), and KOAc (66.7 g, 680 mmol) in anhydrous dioxane (1340 mL) was evacuated/purged with nitrogen three times. Pd(dppf)Cl$_2$ (24.9 g, 34.0 mmol) was added, and the resulting mixture was allowed to stir under an atmosphere of nitrogen at 110° C. for 16 h. The reaction mixture was allowed to cool to rt then the mixture was filtered through celite. The filtrate was concentrated under vacuum. The residue was washed with MTBE (300 mL) and filtered. The solid residue was added to a mixture of MTBE (2500 mL) and EtOAc (500 mL), stirred for 1 h, then filtered through celite. The filtrate was concentrated to give a residue which was washed with MTBE (300 mL) and then azeotropically coevaporated from EtOAc (1000 mL) twice to afford 2-methyl-N-(4-(4,4,5,5-tetramethyl-1,3,2-dioxaborolan-2-yl)pyridin-2-yl)pyrimidin-4-amine (49.5 g, 35% yield) as a grey solid. $^1$H NMR (400 MHz, DMSO-d$_6$): δ 10.47 (br s, 1H). 8.34 (br t, J=6.34 Hz, 2H), 7.80 (m, 2H), 7.15 (br d, J=4.52 Hz, 1H), 2.49 (s, 3H), 1.33 (s, 12H).

The reagents fj listed in the table below (Table 3) were prepared in an analogous fashion to that described above for Step 1 from the appropriate starting materials.

TABLE 3

| Reagent fj | Starting Material Reagent | Chemical Structure | LCMS Data |
|---|---|---|---|
| (structure: 5-F, 4-Cl pyridine linked via NH to 2-methylpyrimidine) | fh | (structure: 5-F, 4-Cl, 2-Br pyridine) | LCMS (FA): m/z = 239.5 (M + H) |
|  | fi | (structure: 4-amino-2-methylpyrimidine) |  |
| (structure: 4-Cl pyridine linked via NH to 2-phenylpyrimidine) | fh | (structure: 4-Cl-2-Br pyridine) | LCMS (FA): m/z = 283.1 (M + H) |

TABLE 3-continued

| Reagent fj | Starting Material | | |
|---|---|---|---|
| | Reagent | Chemical Structure | LCMS Data |
| | fi | 4-amino-2-phenylpyrimidine | |
| 4-chloro-N-(4-chloropyridin-2-yl)-2-(trifluoromethyl)pyrimidin-... | fh | 4-chloro-2-bromopyridine | LCMS (FA): m/z = 275.0 (M + H) |
| | fi | 4-amino-2-(trifluoromethyl)pyrimidine | |
| 4-chloro-N-(4-chloropyridin-2-yl)-2-cyclopropylpyrimidin-... | fh | 4-chloro-2-bromopyridine | LCMS (FA): m/z = 247.5 (M + H) |
| | fi | 4-amino-2-cyclopropylpyrimidine | |
| 4-chloro-N-(4-chloropyridin-2-yl)-2,6-dimethylpyrimidin-... | fh | 4-chloro-2-bromopyridine | LCMS (FA): m/z = 235.4 (M + H) |
| | fi | 4-amino-2,6-dimethylpyrimidine | |
| 4-chloro-N-(4-chloropyridin-2-yl)-2-methoxypyrimidin-... | fh | 4-chloro-2-bromopyridine | LCMS (FA): m/z = 237.1 (M + H) |

TABLE 3-continued

| Reagent fj | Reagent | Starting Material Chemical Structure | LCMS Data |
|---|---|---|---|
| | fi | H₂N-pyrimidine-OMe | |
| 4-chloro-2-(pyrimidin-4-ylamino)pyridine | fh | 4-bromo-2-chloropyridine | LCMS (FA): m/z = 207.1 (M + H) |
| | fi | 4-aminopyrimidine | |
| 4-chloro-2-((2-methylpyridin-4-yl)amino)pyridine | fh | 4-bromo-2-chloropyridine | LCMS (FA): m/z = 220.1 (M + H) |
| | fi | 4-amino-2-methylpyridine | |
| 6-((4-chloropyridin-2-yl)amino)-2-methylnicotinonitrile | fh | 4-bromo-2-chloropyridine | LCMS (FA): m/z = 245.2 (M + H) |
| | fi | 6-amino-2-methylnicotinonitrile | |
| 2-((4-chloropyridin-2-yl)amino)pyrimidine-5-carbonitrile | fh | 4-bromo-2-chloropyridine | LCMS (FA): m/z = 232.1 (M + H) |
| | fi | 2-aminopyrimidine-5-carbonitrile | |
| 4-chloro-2-((4-methylpyrimidin-2-yl)amino)pyridine | fh | 4-bromo-2-chloropyridine | LCMS (FA): m/z = 221.4 (M + H) |

TABLE 3-continued

| Reagent fj | Reagent fi | Starting Material Chemical Structure | LCMS Data |
|---|---|---|---|
| [4-chloro-N-(5-cyanopyridin-2-yl)pyridin-2-amine structure] | fh | [4-chloro-2-bromopyridine structure] | LCMS (FA): m/z = 231.1 (M + H) |
|  | fi | [2-amino-5-cyanopyridine structure] |  |
| [4-chloro-N-(1-methyl-1H-pyrazol-3-yl)pyridin-2-amine structure] | fh* | [4-chloro-2-bromopyridine structure] | LCMS (FA): m/z = 209.0 (M + H) |
|  | fi | [3-amino-1-methyl-1H-pyrazole structure] |  |
| [4-chloro-N-(6-methylpyridazin-3-yl)pyridin-2-amine structure] | fh | [4-chloro-2-bromopyridine structure] | LCMS (FA): m/z = 221.1 (M + H) |
|  | fi | [3-amino-6-methylpyridazine structure] |  |
| [4-chloro-N-(6-methylpyridin-2-yl)pyridin-2-amine structure] | fh | [4-chloro-2-bromopyridine structure] | LCMS (FA): m/z = 220.0 (M + H) |
|  | fi | [2-amino-6-methylpyridine structure] |  |
| [4-chloro-N-(pyrimidin-2-yl)pyridin-2-amine structure] | fh* | [4-chloro-2-bromopyridine structure] | LCMS (FA): m/z = 207.0 (M + H) |

TABLE 3-continued

| Reagent fj | Starting Material | | LCMS Data |
| --- | --- | --- | --- |
| | Reagent | Chemical Structure | |
| | fi | 2-aminopyrimidine | |
| 4-chloro-N-(benzo[d]oxazol-2-yl)pyridin-2-amine | fh | 4-chloro-2-bromopyridine | LCMS (FA): m/z = 246.1 (M + H) |
| | fi | 2-aminobenzo[d]oxazole | |
| 4-chloro-N-(pyridin-2-yl)pyridin-2-amine | fh | 4-chloro-2-bromopyridine | LCMS (FA): m/z = 206.4 (M + H) |
| | fi | 2-aminopyridine | |
| 4-chloro-N-(pyrazin-2-yl)pyridin-2-amine | fh | 4-chloro-2-bromopyridine | LCMS (FA): m/z = 207.1 (M + H) |
| | fi | 2-aminopyrazine | |
| 4-chloro-N-(7-methyl-1,8-naphthyridin-2-yl)pyridin-2-amine | fh | 4-chloro-2-bromopyridine | LCMS (FA): m/z = 271.2 (M + H) |
| | fi | 7-methyl-1,8-naphthyridin-2-amine | |
| 4-chloro-N-(benzo[d]thiazol-2-yl)pyridin-2-amine | fh** | 4-chloro-2-bromopyridine | LCMS (FA): m/z = 262.0 (M + H) |

TABLE 3-continued

| Reagent fj | Starting Material | | LCMS Data |
| --- | --- | --- | --- |
| | Reagent | Chemical Structure | |
| | fi | benzothiazol-2-amine | |
| 4-chloro-N-(2-methoxypyrimidin-4-yl)pyridin-2-amine | fh | 4-chloro-2-bromopyridine | LCMS (FA): m/z = 237.0 (M + H) |
| | fi | 2-methoxypyrimidin-4-amine | |
| N-(4-chloropyridin-2-yl)-4-methoxy-6-methyl-1,3,5-triazin-2-amine | fh | 4-chloro-2-bromopyridine | LCMS (FA): m/z = 252.1 (M + H) |
| | fi | 4-methoxy-6-methyl-1,3,5-triazin-2-amine | |
| N-(4-chloropyridin-2-yl)-4-cyclopropyl-6-methyl-1,3,5-triazin-2-amine | fh | 4-chloro-2-bromopyridine | LCMS (FA): m/z = 262.1 (M + H) |
| | fi | 4-cyclopropyl-6-methyl-1,3,5-triazin-2-amine | |
| N-(4-chloropyridin-2-yl)-4-methoxy-6-methyl-1,3,5-triazin-2-amine | fh | 4-chloro-2-bromopyridine | LCMS (FA): m/z = 252.1 (M + H) |
| | fi | 4-methoxy-6-methyl-1,3,5-triazin-2-amine | |

TABLE 3-continued

| Reagent fj | Starting Material Reagent | Chemical Structure | LCMS Data |
|---|---|---|---|
| (structure: 4-methyl-6-cyclopropyl-1,3,5-triazin-2-yl-NH-pyridine-Cl) | fh | (4-chloro-2-bromopyridine) | LCMS (FA): m/z = 262.1 (M + H) |
| | fi | (2-cyclopropyl-6-methyl-1,3,5-triazin-4-amine) | |

*Pd₂(dba)₃ used instead of Pd(dppf)Cl₂ in Step 1
**Pd₂(dba)₃ used instead of Pd(dppf)Cl₂ and xantphos used instead of dppf in Step 1

2-Cyclopropylpyrimidin-4-amine

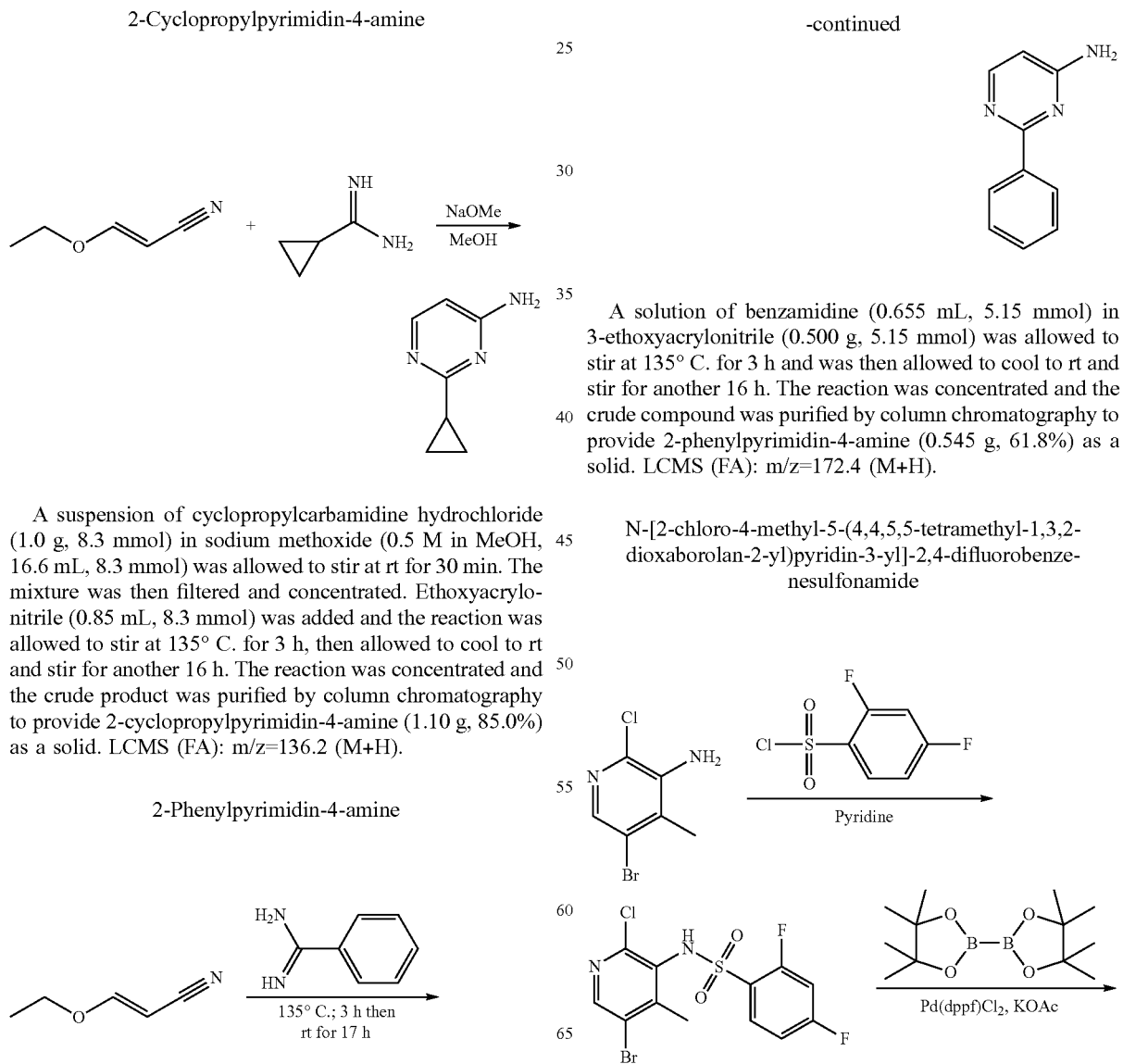

A suspension of cyclopropylcarbamidine hydrochloride (1.0 g, 8.3 mmol) in sodium methoxide (0.5 M in MeOH, 16.6 mL, 8.3 mmol) was allowed to stir at rt for 30 min. The mixture was then filtered and concentrated. Ethoxyacrylonitrile (0.85 mL, 8.3 mmol) was added and the reaction was allowed to stir at 135° C. for 3 h, then allowed to cool to rt and stir for another 16 h. The reaction was concentrated and the crude product was purified by column chromatography to provide 2-cyclopropylpyrimidin-4-amine (1.10 g, 85.0%) as a solid. LCMS (FA): m/z=136.2 (M+H).

2-Phenylpyrimidin-4-amine

A solution of benzamidine (0.655 mL, 5.15 mmol) in 3-ethoxyacrylonitrile (0.500 g, 5.15 mmol) was allowed to stir at 135° C. for 3 h and was then allowed to cool to rt and stir for another 16 h. The reaction was concentrated and the crude compound was purified by column chromatography to provide 2-phenylpyrimidin-4-amine (0.545 g, 61.8%) as a solid. LCMS (FA): m/z=172.4 (M+H).

N-[2-chloro-4-methyl-5-(4,4,5,5-tetramethyl-1,3,2-dioxaborolan-2-yl)pyridin-3-yl]-2,4-difluorobenzenesulfonamide

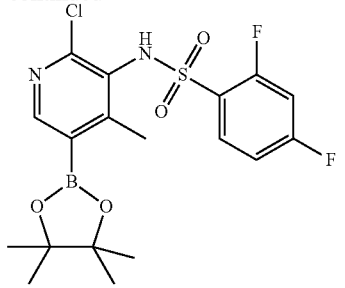

Step 1: N-(5-bromo-2-chloro-4-methylpyridin-3-yl)-2,4-difluorobenzenesulfonamide To a solution of 5-bromo-2-chloro-4-methylpyridin-3-amine (12 g, 54 mmol) in THF (360 mL) was added a 1.0 M solution of LiHMDS in THF (108 mL, 108 mmol) at −5° C. The reaction mixture was allowed to stir at −5° C. for 10 min. To the reaction mixture was then added 2,4-difluorobenzenesulfonyl chloride (17.3 g, 81 mmol). The reaction mixture was allowed to stir at rt for 12 h. The reaction mixture was diluted with saturated NH$_4$Cl solution (200 mL) and extracted with EtOAc. The organic solutions were combined, dried over Na$_2$SO$_4$, filtered and concentrated. The crude compound was purified by column chromatography to provide N-(5-bromo-2-chloro-4-methylpyridin-3-yl)-2,4-difluorobenzenesulfonamide (11.5 g, 53%). $^1$H NMR (400 MHz, CDCl$_3$) δ 8.37 (s, 1H), 7.72 (m, 1H), 7.00 (m, 2H), 6.70 (s, 1H), 2.64 (s, 3H).

Step 2: N-[2-chloro-4-methyl-5-(4,4,5,5-tetramethyl-1,3,2-dioxaborolan-2-yl)pyridin-3-yl]-2,4-difluorobenzenesulfonamide A mixture of N-(5-bromo-2-chloro-4-methylpyridin-3-yl)-2,4-difluorobenzenesulfonamide (6.0 g, 15.1 mmol), 4,4,4',4',5,5,5',5'-octamethyl-2,2'-bi-1,3,2-dioxaborolane (4.6 g, 18.1 mmol), KOAc (4.4 g, 45.3 mmol) and Pd(dppf)Cl$_2$ (3.3 g, 4.5 mmol) in 1,4-dioxane (80 mL) was degassed for 10 min. The reaction mixture was allowed to stir under an atmosphere of nitrogen at reflux for 12 h. The reaction mixture was cooled to rt and then filtered and concentrated. The crude compound was purified by recrystallization (EtOAc and pentane) to provide N-[2-chloro-4-methyl-5-(4,4,5,5-tetramethyl-1,3,2-dioxaborolan-2-yl)pyridin-3-yl]-2,4-difluorobenzenesulfonamide (1.1 g, 16%). $^1$H NMR (400 MHz, CDCl$_3$) δ 8.50 (s, 1H), 7.70 (m, 1H), 6.97 (s, 2H), 6.59 (s, 1H), 2.71 (s, 3H), 1.36 (s, 12H).

2,4-difluoro-N-[2-methyl-5-(4,4,5,5-tetramethyl-1,3,2-dioxaborolan-2-yl)pyridin-3-yl]benzenesulfonamide

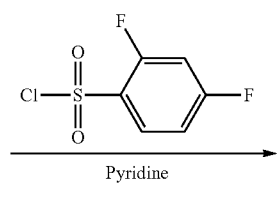

Step 1: N-(5-bromo-2-methylpyridin-3-yl)-2,4-difluorobenzenesulfonamide

A mixture of 5-bromo-2-methylpyridin-3-amine (35 g, 187 mmol) and 2,4-difluorobenzenesulfonyl chloride (47.7 g, 225 mmol) in pyridine (200 mL) was allowed to stir at 80° C. for 2 h. The reaction mixture was poured into water (1000 mL) and allowed to stir at rt for 30 min. The solid was collected by filtration, washed with water (3×100 mL) and then added into a mixture of EtOAc (150 mL) and MeOH (150 mL). The mixture was allowed to stir at rt for 30 min. The suspension was filtered and the solid was dried to provide N-(5-bromo-2-methylpyridin-3-yl)-2,4-difluorobenzenesulfonamide (56 g, 82%). $^1$H NMR (400 MHz, DMSO-d$_6$) δ 10.66 (s, 1H), 8.45 (s, 1H), 7.81 (m, 1H), 7.69 (s, 1H), 7.60 (m, 1H), 7.27 (m, 1H), 2.23 (s, 3H).

Step 2: 2,4-difluoro-N-[2-methyl-5-(4,4,5,5-tetramethyl-1,3,2-dioxaborolan-2-yl)pyridin-3-yl]benzenesulfonamide

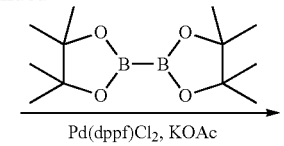

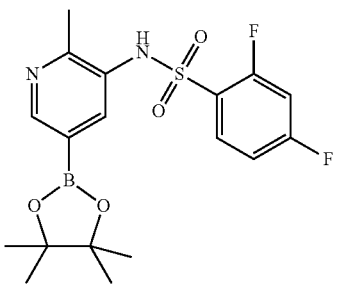

A mixture of N-(5-bromo-2-methylpyridin-3-yl)-2,4-difluorobenzenesulfonamide (56 g, 154 mmol), 4,4,4',4',5,5,5',5'-octamethyl-2,2'-bi-1,3,2-dioxaborolane (45 g, 177 mmol), KOAc (45.4 g, 463 mmol) and Pd(dppf)Cl$_2$ (11.3 g, 15.4 mmol) in 1,4-dioxane (600 mL) was degased for 10 min, then refilled with nitrogen gas. The reaction mixture was allowed to stir at 100° C. for 3 h. The reaction mixture was cooled to rt and then filtered. The filtrate was concentrated, then diluted with EtOAc (1500 mL). Active carbon (50 g) was added to the mixture and allowed to stir at reflux for 1 h. The mixture was filtered and concentrated again. The crude compound was washed with hot EtOAc (3×500 mL) and recrystallized in EtOAc and pentane to provide 2,4-difluoro-N-[2-methyl-5-(4,4,5,5-tetramethyl-1,3,2-dioxaborolan-2-yl)pyridin-3-yl]benzenesulfonamide (30 g, 47%). $^1$H NMR (400 MHz, CDCl$_3$) δ 8.61 (s, 1H), 7.85 (s, 1H), 7.81 (m, 1H), 6.95 (m, 2H), 6.73 (m, 1H), 2.46 (s, 3H), 1.32 (s, 12H).

N,N-dimethyl-N'-[2-methyl-5-(4,4,5,5-tetramethyl-1,3,2-dioxaborolan-2-yl)pyridin-3-yl]sulfuric diamide

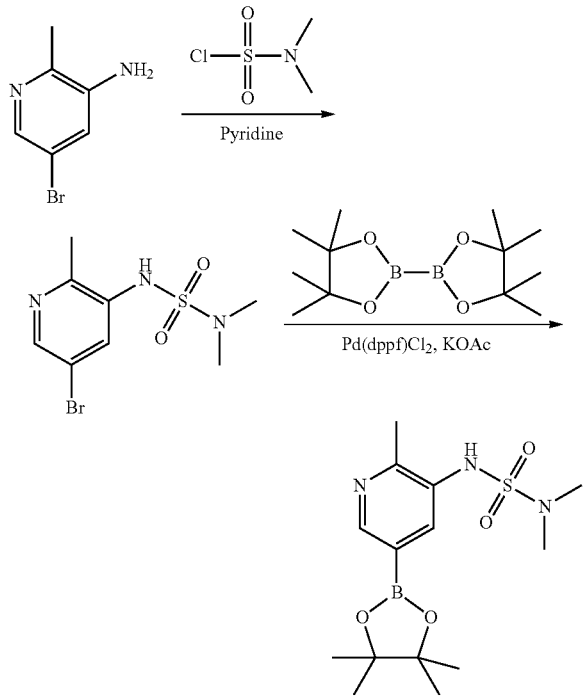

Step 1: N'-(5-bromo-2-methylpyridin-3-yl)-N,N-dimethylsulfuric diamide

A mixture of 5-bromo-2-methylpyridin-3-amine (40 g, 214 mmol) and dimethylsulfamyl chloride (46.1 g, 321 mmol) in pyridine (600 mL) was allowed to stir at 40° C. for 72 h. The reaction mixture was concentrated. Then the residue was diluted with DCM and filtered to remove the solid. The filtrate was concentrated. The crude compound was purified by column chromatography to provide N'-(5-bromo-2-methylpyridin-3-yl)-N,N-dimethylsulfuric diamide (30 g, 47.7%). $^1$H NMR (400 MHz, DMSO-$d_6$) δ 9.59 (s, 1H), 8.39 (s, 1H), 7.84 (s, 1H), 2.74 (s, 6H), 2.49 (s, 3H).

Step 2: N,N-dimethyl-N'-[2-methyl-5-(4,4,5,5-tetramethyl-1,3,2-dioxaborolan-2-yl)pyridin-3-yl]sulfuric diamide A mixture of N'-(5-bromo-2-methylpyridin-3-yl)-N,N-dimethylsulfuric diamide (20 g, 68 mmol). 4,4,4',4',5,5,5',5'-octamethyl-2,2'-bi-1,3,2-dioxaborolane (20.7 g, 81.6 mmol), KOAc (20.0 g, 204 mmol) and Pd(dppf)Cl$_2$ (9.95 g, 13.6 mmol) in 1,4-dioxane (224 mL) was degased for 10 min, then refilled with nitrogen gas. The reaction mixture was allowed to stir at 100° C. for 1 h. The reaction mixture was cooled to rt and then filtered. The filtrate was concentrated, then diluted with EtOAc (700 mL). Active carbon (120 g) was added to the mixture and allowed to stir at reflux for 40 min. The mixture was filtered and concentrated again. The crude compound was purified by recrystallization (EtOAc and pentane) to provide N,N-dimethyl-N'-[2-methyl-5-(4,4,5,5-tetramethyl-1,3,2-dioxaborolan-2-yl)pyridin-3-yl]sulfuric diamide (27.5 g, 40%). $^1$H NMR (400 MHz, CDCl$_3$) δ 8.61 (s, 1H), 8.03 (s, 1H), 6.32 (s, 1H), 2.88 (s, 6H), 2.59 (s, 3H), 1.27 (s, 12H).

Example 2: 5-bromo-2-(methylamino)pyridine-3-sulfonyl chloride

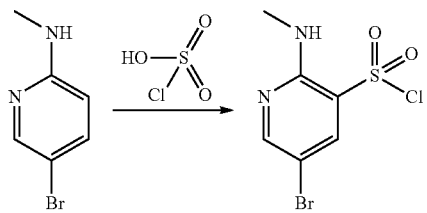

To chlorosulfonic acid (3.58 mL, 53.8 mmol) in a flask at 0° C. was added 5-bromo-N-methylpyridin-2-amine (1.00 g, 5.35 mmol). The reaction mixture was allowed to stir at rt for 2 h, then heated at 150° C. for 3 h. The crude reaction mixture was added dropwise into a flask containing ice. The resulting precipitate was collected by filtration and dried under vacuum to afford a light yellow solid determined to be 5-bromo-2-(methylamino)pyridine-3-sulfonyl chloride (0.828 g, 54%). LCMS (FA): m/z=287.1 (M+H).

Example 3: 6-bromo-1-(cyclopropylmethyl)-H-pyrrolo[3,2-b]pyridine

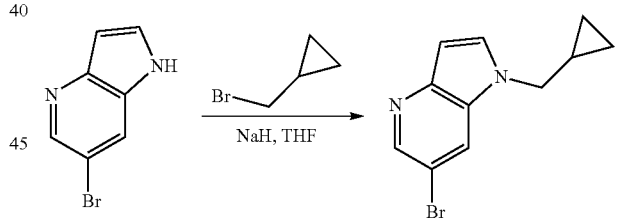

To a flask was added NaH (60% in mineral oil, 58.9 mg, 1.47 mmol) suspended in THF (7.17 mL, 88.4 mmol) and cooled to 0° C. 6-Bromo-1H-pyrrolo[3,2-b]pyridine (0.15 g, 0.74 mmol) was added and the resulting mixture was stirred at 0° C. for 30 min. Then cyclopropylmethyl bromide (0.10 mL, 1.10 mmol) was added and the reaction was stirred warming to rt overnight. The crude reaction mixture was partitioned between EtOAc and water, and extracted with EtOAc. The combined organic layers were then washed with water, followed by brine, dried using Na$_2$SO$_4$, filtered and concentrated. The residue was purified by column chromatography to afford 6-bromo-1-(cyclopropylmethyl)-1H-pyrrolo[3,2-b]pyridine (77 mg, 42%). LCMS (FA): m/z=253.0 (M+H). The intermediates listed in the table below (Table 4) were prepared in an analogous fashion to that described above starting from the appropriate starting materials:

TABLE 4

| Intermediate | LCMS Data |
|---|---|
| ![structure] 6-bromo-1-(methylsulfonyl)pyrrolo[3,2-b]pyridine | LCMS (FA): m/z = 277.0 (M + H) |
| ![structure] 6-bromo-1-(cyclopropylsulfonyl)pyrrolo[3,2-b]pyridine | LCMS (FA): m/z = 351.3 (M + H) |
| ![structure] 6-bromo-1-(phenylsulfonyl)pyrrolo[3,2-b]pyridine | LCMS (FA): m/z = 316.3 (M + H) |

Example 4: Methyl [6-amino-5-(dimethylsulfamoyl)-3,4'-bipyridin-2'-yl]carbamate I-186

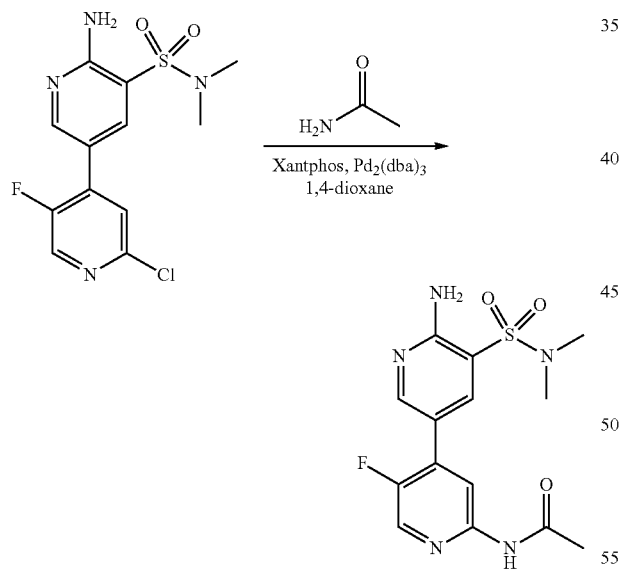

To a microwave vial was added acetamide (0.382 g, 6.47 mmol), tris(dba)dipalladium(0) (59.3 mg, 0.065 mmol), xantphos (112 mg, 0.194 mmol), cesium carbonate (591 mg, 1.81 mmol) and 1,4-dioxane (12.8 mL, 164 mmol). The reaction mixture was flushed with nitrogen and heated in the microwave at 130° C. for 60 min. The reaction mixture was concentrated in vacuo and then purified by column chromatography followed by prep HPLC to yield methyl [6-amino-5-(dimethylsulfamoyl)-3,4'-bipyridin-2'-yl]carbamate (7.0 mg, 5.7%). LCMS (AA): m/z=354.2 (M+H).

Example 5: N-[6-amino-5-(dimethylsulfamoyl)-3,4'-bipyridin-2'-yl]acetamide I-119

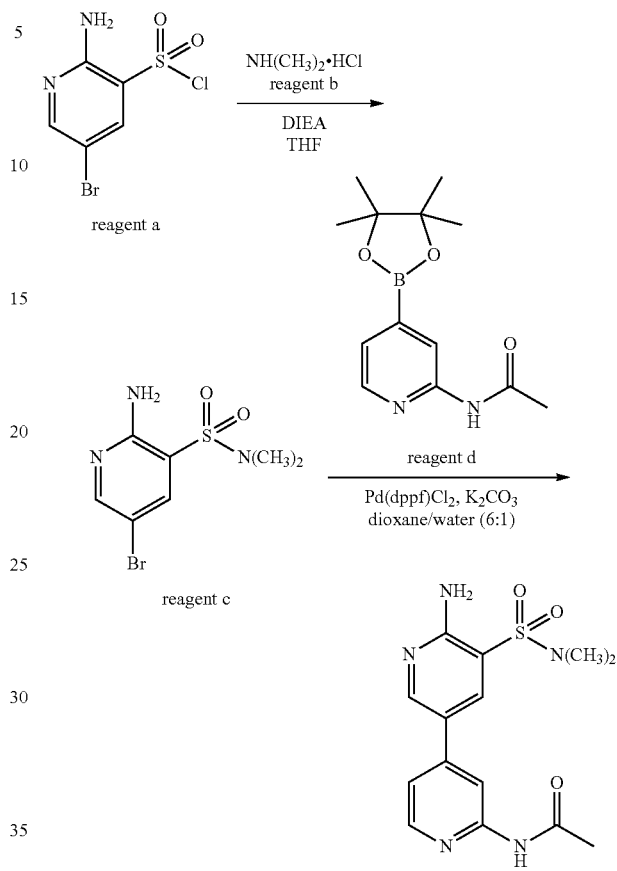

Step 1: 2-Amino-5-bromo-N,N-dimethylpyridine-3-sulfonamide

To a solution of 2-amino-5-bromopyridine-3-sulfonyl chloride (0.500 g, 1.84 mmol; prepared according to the procedure described in Banka et al., Intl. App. Pub. No. WO 2012/037108) and dimethylamine hydrochloride (1.59 g, 19.4 mmol) in THF (9.30 mL) was added DIEA (3.40 mL, 19.5 mmol). The reaction mixture was allowed to stir at rt overnight. The crude reaction mixture was adsorbed to silica gel and purified by column chromatography to yield 2-amino-5-bromo-N,N-dimethylpyridine-3-sulfonamide (0.446 g, 86%). LCMS (AA): m/z=280.1 (M+H).

Step 2: N-[6-amino-5-(dimethylsulfamoyl)-3,4'-bipyridin-2'-yl]acetamide

N-[4-(4,4,5,5-tetramethyl-1,3,2-dioxaborolan-2-yl)pyridin-2-yl]acetamide (0.127 g, 0.483 mmol), 2-amino-5-bromo-N,N-dimethylpyridine-3-sulfonamide (0.176 g, 0.628 mmol), potassium carbonate (134 mg, 0.966 mmol), 1,4-dioxane:water (4.26 mL, 6:1 mixture) and Pd(dppf)Cl$_2$ (19.9 mg, 0.024 mmol) were combined in a reaction vial, flushed with nitrogen and sealed. The reaction mixture was heated at 120° C. in an oil bath for 18 h. The reaction mixture was cooled to rt, filtered through celite and washed with DCM. The crude material was purified by prep HPLC to yield N-[6-amino-5-(dimethylsulfamoyl)-3,4'-bipyridin-2'-yl]acetamide (0.047 g, 26%). LCMS (AA): nm/z=336.0 (M+H).

The compounds listed in the table below (Table 5) were prepared in an analogous fashion to that described above starting from the appropriate starting materials:

TABLE 5

| Example | Starting Material Reagent | Starting Material Structure | Compound No. | LCMS Data |
|---|---|---|---|---|
| 5A | b | H₂N-CH₂-cyclopropyl | I-108 | LCMS (AA): m/z = 362.0 (M + H) |
| 5B | b | 3-chloroaniline | I-97 | LCMS (FA): m/z = 418.8 (M + H) |
| 5C | b | 1-methylpiperazine | I-5 | LCMS (FA): m/z = 391.3 (M + H) |
| 5D | b | phenethylamine | I-148 | LCMS (FA): m/z = 412.8 (M + H) |
| 5E | b | cyclohexylamine | I-101 | LCMS (FA): m/z = 390.3 (M + H) |
| 5F | b | N-methylaniline | I-37 | LCMS (FA): m/z = 398.8 (M + H) |
| 5G | b | 2-aminonaphthalene | I-98 | LCMS (FA): m/z = 434.3 (M + H) |
| 5H | b | 3-aminopyridine | I-204 | LCMS (FA): m/z = 385.3 (M + H) |
| 5I | b | aniline | I-43 | LCMS (FA): m/z = 384.2 (M + H) |
| 5J | b | $NH_3$ | I-61 | LCMS (FA): m/z = 308.3 (M + H) |
| 5K | b | N-methylbenzylamine | I-76 | LCMS (FA): m/z = 412.8 (M + H) |
| 5L | b | morpholine | I-24 | LCMS (FA): m/z = 378.7 (M + H) |
| 5M | b | cyclohexylmethylamine | I-183 | LCMS (FA): m/z = 404.8 (M + H) |

TABLE 5-continued

| Example | Starting Material Reagent | Starting Material Structure | Compound No. | LCMS Data |
|---|---|---|---|---|
| 5N | b | piperidine (NH) | I-156 | LCMS (FA): m/z = 376.7 (M + H) |
| 5O | b | H2N-CH2-CH(CH3)2 | I-73 | LCMS (FA): m/z = 364.3 (M + H) |
| 5P | b | 4-chloro-2-aminobenzene (Cl-C6H3-NH2) | I-207 | LCMS (FA): m/z = 418.3 (M + H) |
| 5Q | b | 3-(aminomethyl)pyridine | I-19 | LCMS (FA): m/z = 399.3 (M + H) |
| 5R | b | isopropylamine (CH(CH3)2-NH2) | I-7 | LCMS (FA): m/z = 350.6 (M + H) |
| 5S | b | N-methyl-cyclopropylmethylamine (HN(CH3)-CH2-cyclopropyl) | I-110 | LCMS (FA): m/z = 376.3 (M + H) |
| 5T | b | methylamine (CH3-NH2) | I-89 | LCMS (FA): m/z = 322.0 (M + H) |
| 5U* | b | diethylamine (Et-NH-Et) | I-124 | LCMS (FA): m/z = 364.0 (M + H) |
| 5V* | b | pyrrolidine (HN) | I-87 | LCMS (AA): m/z = 362.4 (M + H) |
| 5W | a | 5-bromo-pyridine-3-sulfonyl chloride | I-137 | LCMS (AA): m/z = 321.2 (M + H) |
|  | b | methylamine (CH3-NH-) |  |  |
| 5X | a | 2-amino-5-bromo-4-methylpyridine-3-sulfonyl chloride | I-49 | LCMS (FA): m/z = 376.3 (M + H) |
|  | b | cyclopropylmethylamine (H2N-CH2-cyclopropyl) |  |  |

TABLE 5-continued

| Example | Starting Material | | Compound No. | LCMS Data |
|---|---|---|---|---|
| | Reagent | Structure | | |
| 5Y** | a | 5-bromopyridine-3-sulfonyl chloride | I-47 | LCMS (FA): m/z = 347.2 (M + H) |
| | b | pyrrolidine | | |
| 5Z** | c | 5-bromo-N,N-diethylpyridine-3-sulfonamide | I-120 | LCMS (AA): m/z = 349.0 (M + H) |
| 5AA | b | dimethylamine | I-166 | LCMS (FA): m/z = 361.1 (M + H) |
| | d | N-(4-(4,4,5,5-tetramethyl-1,3,2-dioxaborolan-2-yl)pyridin-2-yl)oxazol-2-amine | | |
| 5AB | b | diisopropylamine | I-77 | LCMS (FA): m/z = 392.3 (M + H) |
| 5AC*** | c | 5-bromonicotinaldehyde | I-184 | LCMS (AA): m/z = 242.0 (M + H) |
| 5AD*** | c | 1-(5-bromopyridin-3-yl)ethanone | I-194 | LCMS (AA): m/z = 256.2 (M + H) |
| 5AE | b | 2,4-difluoroaniline | I-170 | LCMS (FA): m/z = 421.1 (M + H) |

TABLE 5-continued

| Example | Starting Material Reagent | Starting Material Structure | Compound No. | LCMS Data |
|---|---|---|---|---|
| 5AF | a | (5-bromo-2-(methylamino)pyridine-3-sulfonyl chloride) | I-63 | LCMS (FA): m/z = 434.1 (M + H) |
| | b | 2,4-difluoroaniline | | |
| 5AG | a | (5-bromo-2-(methylamino)pyridine-3-sulfonyl chloride) | I-100 | LCMS (FA): m/z = 398.3 (M + H) |
| | b | aniline | | |
| 5AH**** | c | (5-bromo-2-methoxy-N-phenylpyridine-3-sulfonamide) | I-39 | LCMS (FA): m/z = 399.4 (M + H) |
| 5AI**** | c | (5-bromo-N-(2,4-difluorophenyl)-2-methoxypyridine-3-sulfonamide) | I-107 | LCMS (FA): m/z = 435.3 (M + H) |
| 5AJ | a | (5-bromo-2-(methylamino)pyridine-3-sulfonyl chloride) | I-173 | LCMS (AA): m/z = 406.5 (M + H) |
| | b | diisopropylamine | | |
| 5AK | b | 1-aminobicyclo[1.1.1]pentane | I-11 | LCMS (FA): m/z = 374.4 (M + H) |

TABLE 5-continued

| Example | Reagent | Starting Material Structure | Compound No. | LCMS Data |
|---|---|---|---|---|
| 5AL | a | 3-bromo-5-pyridinesulfonyl chloride | I-190 | LCMS (FA): m/z = 359.1 (M + H) |
| | b | 1-aminobicyclobutane | | |
| 5AM | a | 3-bromo-5-pyridinesulfonyl chloride | I-9 | LCMS (FA): m/z = 397.4 (M + H) |
| | b | 4,4-difluoropiperidine | | |
| 5AN | a | 3-bromo-5-pyridinesulfonyl chloride | I-118 | LCMS (FA): m/z = 383.5 (M + H) |
| | b | 3,3-difluoropyrrolidine | | |
| 5AO*** | a | 5-bromopyridine-3-sulfonyl chloride | I-464 | LCMS (FA): m/z = 405.0 (M + H) |
| | b | 2,4-difluoroaniline | | |
| 5AP*** | a | 5-bromopyridine-3-sulfonyl chloride | I-481 | LCMS (FA): m/z = 376.1 (M + H) |
| | b | 1-methylpiperazine | | |

TABLE 5-continued

| Example | Starting Material Reagent | Structure | Compound No. | LCMS Data |
|---|---|---|---|---|
| 5AQ*** | a | 5-bromopyridine-3-sulfonyl chloride | I-443 | LCMS (FA): m/z = 349.1 (M + H) |
| | b | 2-amino-2-methylpropane (tert-butylamine) | | |
| 5AR*** | a | 5-bromopyridine-3-sulfonyl chloride | I-321 | LCMS (FA): m/z = 383.1 (M + H) |
| | b | benzylamine | | |
| 5AS*** | a | 5-bromopyridine-3-sulfonyl chloride | I-459 | LCMS (FA): m/z = 369.1 (M + H) |
| | b | aniline | | |
| 5AT*** | a | 5-bromopyridine-3-sulfonyl chloride | I-338 | LCMS (FA): m/z = 333.2 (M + H) |
| | b | cyclopropylamine | | |
| 5AU*** | a | 5-bromopyridine-3-sulfonyl chloride | I-365 | LCMS (FA): m/z = 383.1 (M + H) |

TABLE 5-continued

| | Starting Material | | Compound | LCMS |
|---|---|---|---|---|
| Example | Reagent | Structure | No. | Data |

| | b | N-methylaniline | | |
|---|---|---|---|---|

| 5AV*** | a | 5-bromopyridine-3-sulfonyl chloride | I-396 | LCMS (FA): m/z = 347.1 (M + H) |
| | b | cyclobutylamine | | |

| 5AW*** | a | 5-bromopyridine-3-sulfonyl chloride | I-318 | LCMS (FA): m/z = 427.1 (M + H) |
| | b | 2-adamantylamine | | |

| 5AX*** | a | 5-bromopyridine-3-sulfonyl chloride | I-468 | LCMS (FA): m/z = 427.1 (M + H) |
| | b | 1-adamantylamine | | |

| 5AY*** | a | 5-bromopyridine-3-sulfonyl chloride | I-474 | LCMS (FA): m/z = 333.1 (M + H) |
| | b | azetidine | | |

TABLE 5-continued

| Example | Reagent | Starting Material Structure | Compound No. | LCMS Data |
|---|---|---|---|---|
| 5AZ*** | a | [5-bromopyridine-3-sulfonyl chloride structure] | I-391 | LCMS (FA): m/z = 369.1 (M + H) |
| | b | [3,3-difluoroazetidine structure] | | |
| 5BA | a | [5-bromo-2-chloropyridine-3-sulfonyl chloride structure] | I-438 | LCMS (FA): m/z = 380.7 (M + H) |
| | b | [cyclobutylamine structure] | | |

*DIEA was not added in Step 1 of Example 5.
**In Step 2, tetrakis(triphenylphosphine)palladium(O) and cesium carbonate were used instead of Pd(dppf)Cl₂ and potassium carbonate.
***In Step 2, the reaction mixture was heated in the microwave (120° C., 35 min).
****Starting material for step 2 was prepared from 5-bromo-2-chloro-N-phenylpyridine-3-sulfonamide according to the procedure in WO2012/037108, p. 268.

Example 6: Methyl [6-amino-5-(dimethylsulfamoyl)-3,4'-bipyridin-2'-yl]carbamate I-171

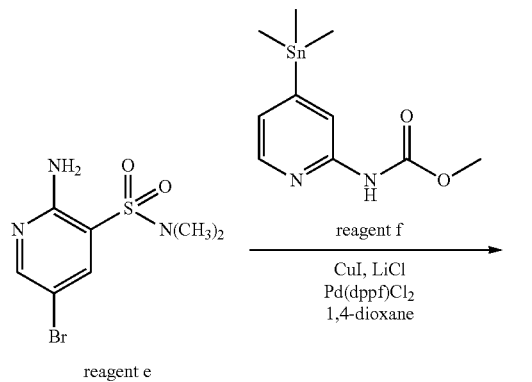

Step 1: [6-amino-5-(dimethylsulfamoyl)-3,4'-bipyridin-2'-yl]carbamate

To a microwave vial was added 2-amino-5-bromo-N,N-dimethylpyridine-3-sulfonamide (0.098 g, 0.35 mmol), methyl [4-(trimethylstannyl)pyridin-2-yl]carbamate (0.220 g, 0.700 mmol), lithium chloride (52.2 mg, 1.23 mmol), CuI (33.3 mg, 0.175 mmol) and 1,4-dioxane (3.87 mL, 49.6 mmol). The reaction mixture was flushed with argon and heated in the microwave at 110° C. for 30 min and then filtered through a short plug of celite. The celite was washed with MeOH and the supernatant concentrated by rotary evaporation. EtOAc was added to the residue and the resulting precipitate was collected in a buchner funnel. The material was purified by prep HPLC to yield methyl [6-amino-5-(dimethylsulfamoyl)-3,4'-bipyridin-2'-yl]carbamate (7.0 mg, 5.7%). LCMS (AA): m/z=352.4 (M+H).

The compounds listed in the table below (Table 6) were prepared in an analogous fashion to that described above starting from the appropriate starting materials:

TABLE 6

| Example | Reagent e | Compound No. | LCMS Data |
|---|---|---|---|
| 6A | 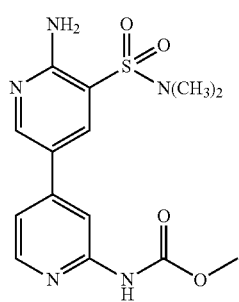 | I-36 | LCMS (AA): m/z = 378.3 (M + H) |

TABLE 6-continued

| Example | Reagent e | Compound No. | LCMS Data |
|---|---|---|---|
| 6B | ![structure: 2-amino-3-(isopropylsulfonyl)-5-bromopyridine] | I-34 | LCMS (AA): m/z = 351.3 (M + H) |
| 6C | ![structure: 2-amino-5-bromo-N,N-dimethylpyridine-3-carboxamide] | I-55 | LCMS (FA): m/z = 316.3 (M + H) |

Example 7: N-[6-amino-5-(methylsulfonyl)-3,4'-bipyridin-2'-yl]acetamide I-95

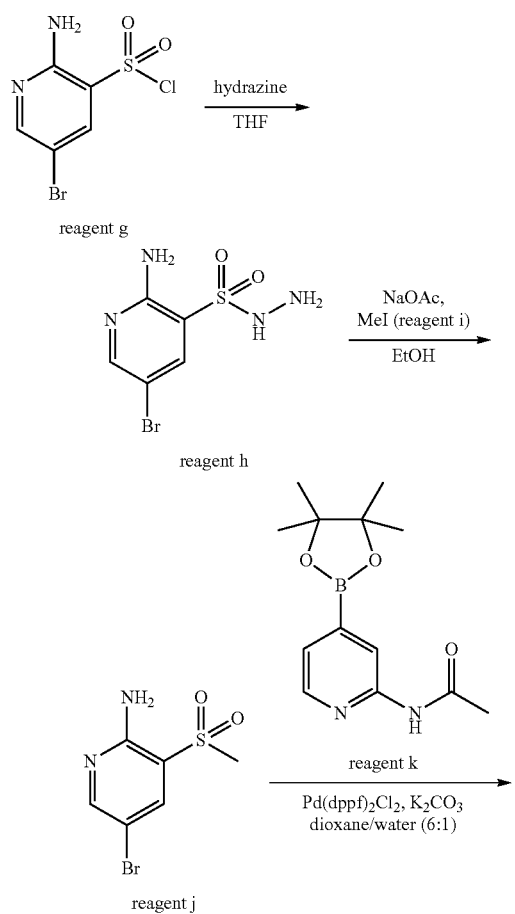

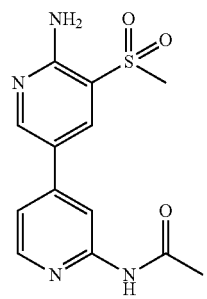

Step 1: 2-amino-5-bromopyridine-3-sulfonohydrazide

To a solution of 2-amino-5-bromopyridine-3-sulfonyl chloride (1.41 g, 5.19 mmol) in THF (30.0 mL) was added hydrazine (0.659 mL, 21.0 mmol) and the mixture was allowed to stir at rt for 10 min. The solvent was removed by rotary evaporation to give 2-amino-5-bromopyridine-3-sulfonohydrazide which was used in the next step without purification. LCMS (AA): m/z=267/269 (M+H).

Step 2: 5-bromo-3-(methylsulfonyl)pyridin-2-amine

To 2-amino-5-bromopyridine-3-sulfonohydrazide (1.00 g, 3.74 mmol) in EtOH (21.3 mL, 364 mmol) was added sodium acetate (3.40 g, 41.5 mmol) and the mixture was refluxed for 24 h and then cooled to rt. Solvent was removed by rotary evaporation and the residue was diluted with EtOAc and water, and washed with brine. The organic layer was dried over sodium sulfate and concentrated by rotary evaporation. The crude material was purified by column chromatography to yield 5-bromo-3-(methylsulfonyl)pyridine-2-amine (0.404 g, 43.0%).

Step 3: N-[6-amino-5-(methylsulfonyl)-3,4'-bipyridin-2'-yl]acetamide

The procedure from Example 5, Step 2 was followed to yield N-[6-amino-5-(methylsulfonyl)-3,4'-bipyridin-2'-yl]acetamide (5.0 mg, 1.5%). LCMS (FA): m/z=307.2 (M+H).

The compounds listed in the table below (Table 7) were prepared in an analogous fashion to that described above starting from the appropriate starting materials:

TABLE 7

| Example | Starting material | | Compound | |
|---|---|---|---|---|
| | Reagent | Chemical Structure | No. | Data |
| 7A | i | ![F-CH2-C6H3(F)-CH2-Br] | I-138 | LCMS (FA): m/z = 419.3 (M + H) |
| 7B | i | ![Cl-C6H4-CH2-Br] | I-99 | LCMS (FA): m/z = 417.3 (M + H) |

TABLE 7-continued

| Example | Reagent | Starting material Chemical Structure | Compound No. | Data |
|---|---|---|---|---|
| 7C | i | 2-(bromomethyl)naphthalene | I-3 | LCMS (FA): m/z = 433.8 (M + H) |
| 7D | i | (2-bromoethyl)benzene | I-126 | LCMS (FA): m/z = 397.3 (M + H) |
| 7E | i | 1-(bromomethyl)-2-chlorobenzene | I-172 | LCMS (FA): m/z = 417.3 (M + H) |
| 7F | i | 1-(bromomethyl)-2-fluorobenzene | I-197 | LCMS (FA): m/z = 401.3 (M + H) |
| 7G | i | isopropyl bromide | I-175 | LCMS (FA): m/z = 335.3 (M + H) |
| 7H | i | benzyl bromide | I-6 | LCMS (FA): m/z = 383.4 (M + H) |
| 7I | i | 3-(bromomethyl)pyridine | I-205 | LCMS (FA): m/z = 384.3 (M + H) |
| 7J | i | 1-bromo-2-ethoxyethane | I-145 | LCMS (FA): m/z = 365.3 (M + H) |
| 7K | i | 1-(bromomethyl)-2-(trifluoromethyl)benzene | I-50 | LCMS (FA): m/z = 451.7 (M + H) |
| 7L | i | (bromomethyl)cyclopropane | I-208 | LCMS (FA): m/z = 347.3 (M + H) |
| 7M | i | ethyl iodide | I-69 | LCMS (AA): m/z = 321.0 (M + H) |
| 7N | j | 3-bromo-5-(methylsulfonyl)pyridine | I-51 | LCMS (AA): m/z = 292.2 (M + H) |
| 7O | j | N-(4-bromopyridin-2-yl)acetamide | I-139 | LCMS (FA): m/z = 229.2 (M + H) |
| | k | 5-(4,4,5,5-tetramethyl-1,3,2-dioxaborolan-2-yl)pyridin-3-amine | | |

Example 7P: 2'-acetamido-6-amino-3,4'-bipyridine-5-sulfonic acid I-122

Step 1: 2-amino-5-bromopyridine-3-sulfonic acid 2-amino-5-bromopyridine-3-sulfonyl chloride (92 mg, 0.34 mmol) was allowed to stir in HCl (6 M in water: 6.1 mL, 37 mmol) and ACN (2.0 mL, 38 mmol) at rt overnight. The reaction mixture was concentrated by rotary evaporation to yield 2-amino-5-bromopyridine-3-sulfonic acid (64.0 mg, 75%). LCMS (FA): m/z 253/255 (M+H).

Step 2: 2'-acetamido-6-amino-3,4'-bipyridine-5-sulfonic acid

Followed the procedure described in Step 2 of Example 5 with the following modification: Used 3.5 equivalents of 2M $K_2CO_3$ instead of solid potassium carbonate. No additional water was added. The reaction yielded 2'-acetamido-6-amino-3,4'-bipyridine-5-sulfonic acid (40 mg, 40.0%). LCMS (AA): m/z=309.0 (M+H).

Example 8: N-{5-[(cyclopropylsulfonyl)(methyl)amino]-6-methyl-3,4'-bipyridin-2'-yl}acetamide I-212

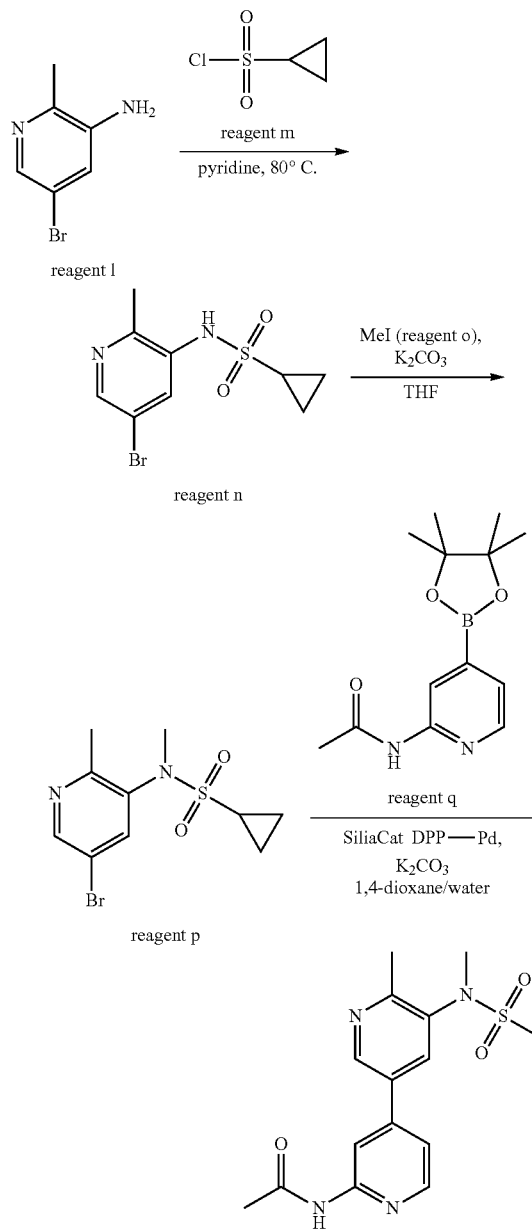

Step 1: N-(5-bromo-2-methylpyridin-3-yl)cyclopropanesulfonamide

A mixture of cyclopropanesulfonylchloride (372 mg, 2.65 mmol), pyridine (2.86 mL, 35.4 mmol) and 5-bromo-2-methylpyridin-3-amine (450 mg, 2.41 mmol) was allowed to stir at 80° C. overnight. Solvent was removed under reduced pressure and the residue was purified by column chromatography to yield N-(5-bromo-2-methylpyridin-3-yl)cyclopropanesulfonamide (468 mg, 66.8%). LCMS (FA): m/z=289.1; 291.1 (M+H).

Step 2: N-(5-bromo-2-methylpyridin-3-yl)-N-methylcyclopropanesulfonamide

A mixture of N-(5-bromo-2-methylpyridin-3-yl)cyclopropanesulfonamide (200 mg, 0.687 mmol), potassium carbonate (570 mg, 4.12 mmol) and methyl iodide (64.1 uL, 1.03 mmol) in THF (7.0 mL) was allowed to stir overnight at rt. The reaction mixture was filtered and the filtrate was concentrated under reduced pressure. The residue was purified by column chromatography to yield N-(5-bromo-2-methylpyridin-3-yl)-N-methylcyclopropanesulfonamide (40.0 mg, 15%) LCMS (FA): m/z=305/307 (M+H).

Step 3: N-{5-[(cyclopropylsulfonyl)(methyl)amino]-6-methyl-3,4'-bipyridin-2'-yl}acetamide To a microwave vial were added N-[4-(4,4,5,5-tetramethyl-1,3,2-dioxaborolan-2-yl)pyridin-2-yl]acetamide (45 mg, 0.17 mmol) and potassium carbonate (125 mg, 0.924 mmol) SiliaCat DPP-Pd (81.5 mg, 0.020 mmol) and 1,4-dioxane:water (3.1 mL, 7:1 mixture) The vial was flushed with nitrogen and the reaction was heated in the microwave at 150° C. for 40 min. The reaction mixture was cooled to rt and then filtered through celite and washed with MeOH. The solvent was removed under reduced pressure and the residue was purified by column chromatography to yield N-{5-[(cyclopropylsulfonyl)(methyl)amino]-6-methyl-3,4'-bipyridin-2'-yl}acetamide (37 mg, 77%). LCMS (FA): m/z=361.2 (M+H).

The compounds listed in the table below (Table 8) were prepared in an analogous fashion to that described above starting from the appropriate starting materials:

TABLE 8

| Example | Reagent | Starting material Chemical Structure | Compound No. | LCMS Data |
|---|---|---|---|---|
| 8C | m | ![structure] | I-83 | LCMS (FA): m/z = 401.3 (M + H) |
|  | o | ![structure] |  |  |
| 8D | m | ![structure] | I-26 | LCMS (FA): m/z = 375.5 (M + H) |
|  | o | ![structure] |  |  |

TABLE 8-continued

| Example | Reagent | Starting material Chemical Structure | Compound No. | LCMS Data |
|---|---|---|---|---|
| 8E | m | (methanesulfonyl chloride) | I-96 | LCMS (FA): m/z = 335.1 (M + H) |
|  | o | CH₃I |  |  |
| 8F | m | (benzenesulfonyl chloride) | I-46 | LCMS (FA): m/z = 397.0 (M + H) |
|  | o | CH₃I |  |  |
| 8G | o | (bromomethyl cyclopropane) | I-202 | LCMS (FA): m/z = 361.1 (M + H) |
|  | n | (N-(5-bromopyridin-3-yl)methanesulfonamide) |  |  |
| 8O* | l | H₂N—pyridine—Br | I-458 | LCMS (FA): m/z = 350.3 (M + H) |
|  | m | (dimethylsulfamoyl chloride) |  |  |
|  | o | CH₃I |  |  |

*In Step 2, LiHMDS was used in place of $K_2CO_3$. In Step 3, conditions used were $Pd_2(dba)_3$, XPhos, KOAc, Dioxane, water (110° C., 2 h).

Example 8B: N-{4-[1-(phenylsulfonyl)-1H-pyrrolo[3,2-b]pyridin-6-yl]pyridin-2-yl}acetamide I-23

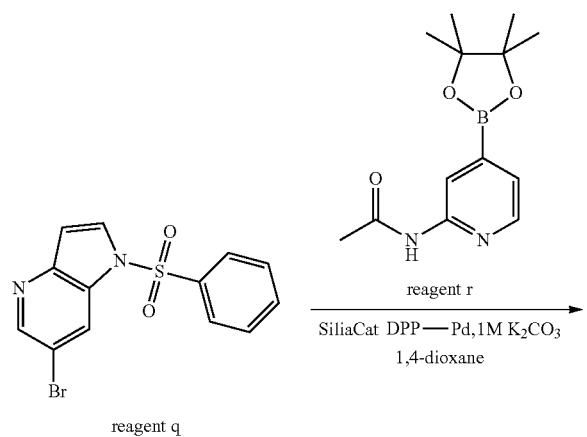

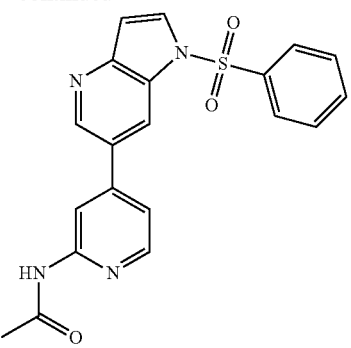

Following the procedure described in Step 3 of Example 8 starting from 6-bromo-1-(phenylsulfonyl)-1H-pyrrolo[3,2-b]pyridine to yield N-{4-[1-(phenylsulfonyl)-1H-pyrrolo[3,2-b]pyridin-6-yl]pyridin-2-yl}acetamide (85 mg, 81%). LCMS (FA): m/z=393.0 (M+H).

The compounds listed in the table below (Table 9) were prepared in an analogous fashion to that described above starting from the appropriate starting materials:

TABLE 9

| Example | Reagent q | Compound No. | LCMS Data |
|---|---|---|---|
| 8H | 5-bromo-2,3-dihydro-1H-pyrrolo[2,3-b]pyridine | I-67 | LCMS (FA): m/z = 255.2 (M + H) |
| 8I | 5-bromo-1H-pyrrolo[2,3-b]pyridine | I-140 | LCMS (FA): m/z = 253.1 (M + H) |
| 8J | 6-bromo-1H-pyrazolo[3,4-b]pyridine | I-116 | LCMS (FA): m/z = 254.1 (M − H) |
| 8K | 6-bromo-1H-pyrrolo[3,2-b]pyridine | I-17 | LCMS (FA): m/z = 253.1 (M + H) |
| 8L | 6-bromo-1-(cyclopropylmethyl)-1H-pyrrolo[3,2-b]pyridine | I-93 | LCMS (FA): m/z = 307.1 (M + H) |
| 8M | 6-bromo-1-(methylsulfonyl)-1H-pyrrolo[3,2-b]pyridine | I-33 | LCMS (FA): m/z = 331.5 (M + H) |

TABLE 9-continued

| Example | Reagent q | Compound No. | LCMS Data |
|---|---|---|---|
| 8N | 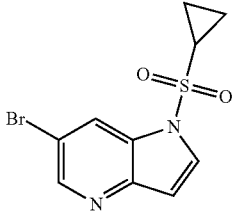 [SMILES: O=S(=O)(C1CC1)n1ccc2ncc(Br)cc21] | I-199 | LCMS (FA): m/z = 357.3 (M + H) |

Example 9: N-(5-bromo-2-methylpyridin-3-yl)-2,4-difluorobenzenesulfonamide I-41

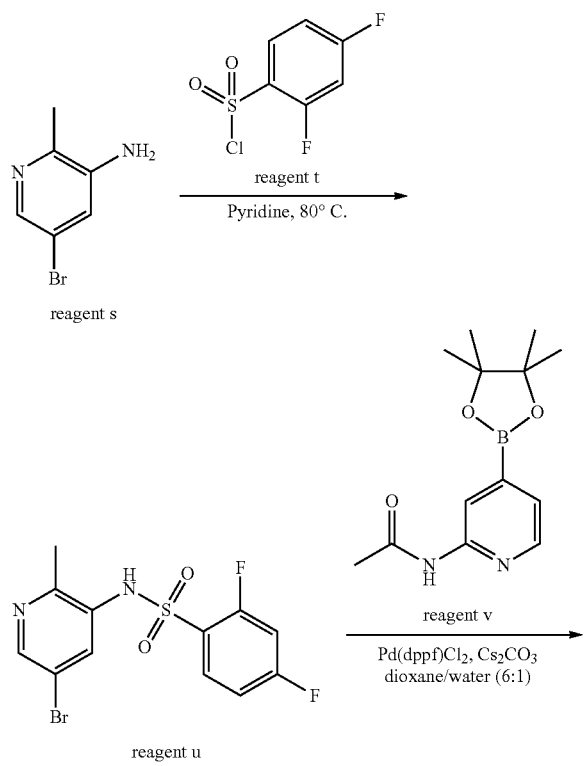

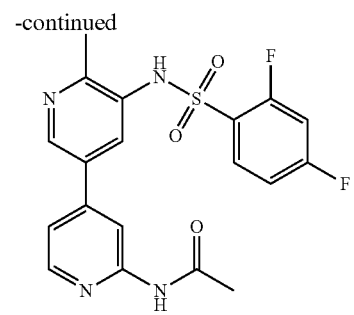

Step 1: N-(5-bromopyridin-3-yl)-3-chloropropane-1-sulfonamide

To a reaction vial were added 5-bromo-2-methylpyridin-3-amine (1.29 g, 6.91 mmol), pyridine (8.00 mL, 98.9 mmol) and 2,4-difluorobenzene-1-sulfonyl chloride (1.47 g, 6.91 mmol) and this reaction mixture was allowed to stir at 80° C. for 5 h. The pyridine was removed by rotary evaporation and EtOAc was added resulting in a dark yellow suspension. The solid was collected and dissolved in MeOH. A white solid precipitated out of solution upon standing. The solid was filtered and further washed with MeOH to yield N-(5-bromo-2-methylpyridin-3-yl)-2,4-difluorobenzenesulfonamide (1.84 g, 73.3%). LCMS (FA): m/z=318.9/321 (M+H).

Step 2: N-(5-{[(2,4-difluorophenyl)sulfonyl]amino}-6-methyl-3,4'-bipyridin-2'-yl)acetamide N-(5-bromopyridin-3-yl)-3-chloropropane-1-sulfonamide (0.29 g, 0.79 mmol), N-[4-(4,4,5,5-tetramethyl-1,3,2-dioxaborolan-2-yl)pyridin-2-yl]acetamide (0.27 g, 1.03 mmol), [1,1'-bis(diphenylphosphino)ferrocene]dichloropalladium (65 mg, 0.079 mmol) and cesium carbonate (0.77 g, 2.37 mmol) were taken up in 1,4-dioxane (2.16 mL) and water (0.37 mL) under an atmosphere of nitrogen. The reaction mixture was heated at 110° C. for 18 h. The reaction mixture was cooled to rt and water was added and extracted with EtOAc. The combined organic layers were washed with brine, dried over magnesium sulfate and concentrated by rotary evaporation. The crude compound was purified by column chromatography to provide N-(5-{[(2,4-difluorophenyl) sulfonyl]amino}-6-methyl-3,4'-bipyridin-2'-yl)acetamide (142 mg, 43%). LCMS (FA): m/z=419.3 (M+H). $^1$H NMR (500 MHz, DMSO-$d_6$) δ 10.65 (s, 1H), 10.60 (s, 1H), 8.67 (d, J=2.11 Hz, 1H), 8.39 (d, J=5.17 Hz, 1H), 8.28 (s, 1H), 7.83 (m, 1H), 7.73 (d, J=2.14 Hz, 1H), 7.59 (ddd, J=2.50, 9.06, 11.20 Hz, 1H), 7.38 (dd, J=1.67, 5.28 Hz, 1H), 7.24 (m, 1H), 2.36 (s, 3H), 2.14 (s, 3H).

The compounds listed in the table below (Table 10) were prepared in an analogous fashion to that described above from the appropriate starting materials:

TABLE 10

| Example | Reagent | Starting material Chemical Structure | Compound No. | LCMS Data |
|---|---|---|---|---|
| 9A | t | 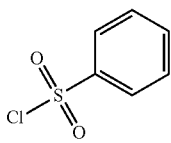 | I-84 | LCMS (AA): m/z = 383.0 (M + H) |

TABLE 10-continued

| Example | Starting material Reagent | Chemical Structure | Compound No. | LCMS Data |
|---|---|---|---|---|
| 9B | t | 2,4-dichlorobenzenesulfonyl chloride | I-30 | LCMS (FA): m/z = 451.2/453.2 (M + H) |
| 9C | t | 2-chlorobenzenesulfonyl chloride | I-109 | LCMS (FA): m/z = 417.2/419.1 (M + H) |
| 9D | t | 2-methylbenzenesulfonyl chloride | I-211 | LCMS (FA): m/z = 397.5 (M + H) |
| 9E | t | 3-methoxybenzenesulfonyl chloride | I-123 | LCMS (FA): m/z = 413.1 (M + H) |
| 9F | t | 2,5-dichlorobenzenesulfonyl chloride | I-111 | LCMS (AA): m/z = 451.4 (M + H) |
| 9G | t | dimethylsulfamoyl chloride | I-32 | LCMS (FA): m/z = 350.3 (M + H) |
| 9H | t | 2,5-difluorobenzenesulfonyl chloride | I-52 | LCMS (FA): m/z = 419.2 (M + H) |
| 9I | t | 2,4-difluorobenzenesulfonyl chloride | I-164 | LCMS (FA): m/z = 423.3 (M + H) |
|  | s | 5-bromo-2-fluoropyridin-3-amine |  |  |
| 9J | t | 3,4-difluorobenzenesulfonyl chloride | I-59 | LCMS (FA): m/z = 419.3 (M + H) |

TABLE 10-continued

| Example | Starting material | | Compound No. | LCMS Data |
|---|---|---|---|---|
| | Reagent | Chemical Structure | | |
| 9K | t | 2-methoxybenzenesulfonyl chloride | I-74 | LCMS (FA): m/z = 413.3 (M + H) |
| 9L | t | 3-(trifluoromethyl)benzenesulfonyl chloride | I-168 | LCMS (FA): m/z = 451.3 (M + H) |
| 9M | t | 2-fluorobenzenesulfonyl chloride | I-144 | LCMS (FA): m/z = 401.2 (M + H) |
| 9N | t | 3-fluorobenzenesulfonyl chloride | I-155 | LCMS (FA): m/z = 401.3 (M + H) |
| 9O | t | 2,5-dimethylbenzenesulfonyl chloride | I-178 | LCMS (FA): m/z = 411.1 (M + H) |
| 9P | t | 4-methylbenzenesulfonyl chloride | I-80 | LCMS (AA): m/z = 397.1 (M + H) |
| 9Q | t | 4-tert-butylbenzenesulfonyl chloride | I-131 | LCMS (FA): m/z = 439.4 (M + H) |
| 9R | t | naphthalene-1-sulfonyl chloride | I-78 | LCMS (FA): m/z = 433.5 (M + H) |

TABLE 10-continued

| Example | Starting material | | | LCMS |
| | Reagent | Chemical Structure | Compound No. | Data |
| --- | --- | --- | --- | --- |
| 9S | t | 2-F, 4-Cl benzenesulfonyl chloride | I-94 | LCMS (FA): m/z = 435.3 (M + H) |
| 9T | t | 2-F, 4-OMe, 5-F benzenesulfonyl chloride | I-159 | LCMS (FA): m/z = 449.4 (M + H) |
| 9U | t | 2-F, 5-CF$_3$ benzenesulfonyl chloride | I-143 | LCMS (FA): m/z = 469.3 (M + H) |
| 9V | t | 6-(trifluoromethyl)pyridine-3-sulfonyl chloride | I-1 | LCMS (FA): m/z = 452.3 (M + H) |
| 9W | t | 3-tert-butylbenzenesulfonyl chloride | I-70 | LCMS (FA): m/z = 439.8 (M + H) |
| 9X | t | 2,6-difluorobenzenesulfonyl chloride | I-150 | LCMS (FA): m/z = 419.3 (M + H) |
| 9Y | t | 2-OMe, 4-F benzenesulfonyl chloride | I-58 | LCMS (FA): m/z = 431.3 (M + H) |
| 9Z | t | 2-F, 4-OMe benzenesulfonyl chloride | I-163 | LCMS (FA): m/z = 431.3 (M + H) |

TABLE 10-continued

| | Starting material | | | LCMS |
|---|---|---|---|---|
| Example | Reagent | Chemical Structure | Compound No. | Data |
| 9AA | t | (2-chloro-4-(trifluoromethoxy)benzenesulfonyl chloride) | I-113 | LCMS (FA): m/z = 501.4 (M + H) |
| 9AB | t | (2-fluoro-4-methylbenzenesulfonyl chloride) | I-130 | LCMS (FA): m/z = 429.4 (M + H) |
| 9AC | t | (2-methoxy-4-methylbenzenesulfonyl chloride) | I-142 | LCMS (FA): m/z = 427.4 (M + H) |
| 9AD | t | (4-(trifluoromethyl)benzenesulfonyl chloride) | I-90 | LCMS (FA): m/z = 451.3 (M + H) |
| 9AE | t | (4-chlorobenzenesulfonyl chloride) | I-154 | LCMS (AA): m/z = 417.0 (M + H) |
| 9AF | t | (4-methoxybenzenesulfonyl chloride) | I-165 | LCMS (FA): m/z = 413.3 (M + H) |
| 9AG | t | (4-ethylbenzenesulfonyl chloride) | I-44 | LCMS (FA): m/z = 411.3 (M + H) |
| 9AH | t | (4-fluorobenzenesulfonyl chloride) | I-185 | LCMS (FA): m/z = 401.3 (M + H) |

TABLE 10-continued

| Example | Starting material | | | LCMS |
| | Reagent | Chemical Structure | Compound No. | Data |
|---|---|---|---|---|
| 9AI | t | cyclohexanesulfonyl chloride | I-72 | LCMS (FA): m/z = 389.3 (M + H) |
| 9AJ | t | 4-isopropylbenzenesulfonyl chloride | I-134 | LCMS (FA): m/z = 425.4 (M + H) |
| 9AK | t | 2,4-difluorobenzenesulfonyl chloride | I-12 | LCMS (FA): m/z = 405.3 (M + H) |
| | s | 5-bromopyridin-3-amine | | |
| 9AL | t | 2,4-difluorobenzenesulfonyl chloride | I-102 | LCMS (FA): m/z = 420.5 (M + H) |
| | s | 3-bromo-4-methylpyridin-5-amine | | |
| 9AM | t | methanesulfonyl chloride | I-167 | LCMS (FA): m/z = 321.2 (M + H) |
| 9AN | t | pyridine-3-sulfonyl chloride | I-45 | LCMS (FA): m/z = 384.2 (M + H) |
| 9AO | t | 4-chloro-2-fluorobenzenesulfonyl chloride | I-86 | LCMS (FA): m/z = 535.5 (M + H) |
| 9AP | t | 2,4-difluorobenzenesulfonyl chloride | I-16 | LCMS (AA): m/z = 481.1 (M + H) |

TABLE 10-continued
| Example | Starting material | | Compound No. | LCMS Data |
|---|---|---|---|---|
| | Reagent | Chemical Structure | | |
| | v | 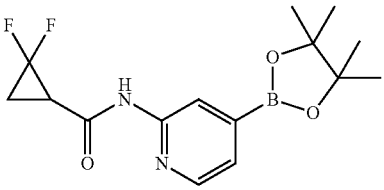 [SMILES: CC1(C)OB(c2ccnc(NC(=O)C3CC3(F)F)c2)OC1(C)C] | | |
| 9AQ | t | 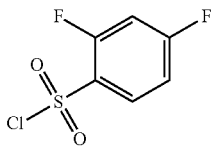 [SMILES: O=S(=O)(Cl)c1ccc(F)cc1F] | I-25 | LCMS (FA): m/z = 448.4 (M + H) |
| | s | 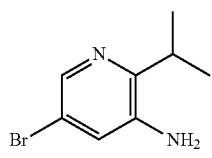 | | |
| 9AR | t | 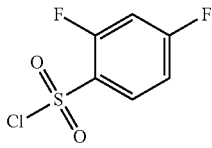 [SMILES: O=S(=O)(Cl)c1ccc(F)cc1F] | I-31 | LCMS (FA): m/z = 432.1 (M − H) |
| | s | 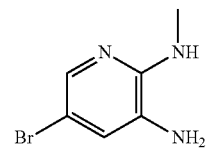 | | |
| 9AS | t | 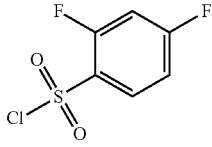 [SMILES: O=S(=O)(Cl)c1ccc(F)cc1F] | I-104 | LCMS (FA): m/z = 435.3 (M + H) |
| | s | 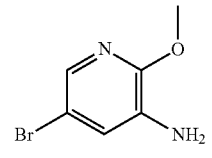 | | |
| 9AT | t | 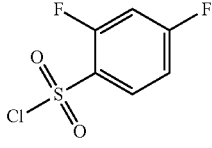 [SMILES: O=S(=O)(Cl)c1ccc(F)cc1F] | I-201 | LCMS (FA): m/z = 433.3 (M + H) |
| | s | 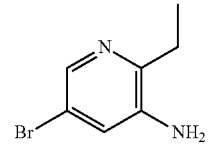 | | |

TABLE 10-continued

| | Starting material | | | LCMS |
|---|---|---|---|---|
| Example | Reagent | Chemical Structure | Compound No. | Data |
| 9AU | t | 2,4-difluorobenzenesulfonyl chloride | I-161 | LCMS (FA): m/z = 437.2 (M + H) |
| | v | 2-chloro-5-fluoro-4-(4,4,5,5-tetramethyl-1,3,2-dioxaborolan-2-yl)pyridine | | |
| 9AV | t | 2,4-difluorobenzenesulfonyl chloride | I-4 | LCMS (FA): m/z = 459.3 (M + H) |
| | v | N-(5-methyl-4-(4,4,5,5-tetramethyl-1,3,2-dioxaborolan-2-yl)pyridin-2-yl)cyclopropanecarboxamide | | |
| 9AW | t | 2,4-difluorobenzenesulfonyl chloride | I-177 | LCMS (AA): m/z = 433.4 (M + H) |
| | v | N-(5-methyl-4-(4,4,5,5-tetramethyl-1,3,2-dioxaborolan-2-yl)pyridin-2-yl)acetamide | | |
| 9AX | t | 2,4-difluorobenzenesulfonyl chloride | I-153 | LCMS (FA): m/z = 453.3 (M + H) |
| | s | 5-bromo-2-chloro-4-methylpyridin-3-amine | | |
| 9AY | t | piperidine-1-sulfonyl chloride | I-214 | LCMS (FA): m/z = 390.0 (M + H) |

TABLE 10-continued

| Example | Starting material | | Compound No. | LCMS Data |
|---|---|---|---|---|
| | Reagent | Chemical Structure | | |
| 9AZ | t | Cl-S(=O)(=O)-N(CH3)2 | I-244 | LCMS (FA): m/z = 412.4 (M + H) |
| | v* | 2,2-difluorocyclopropane carboxamide-pyridine-Bpin | | |
| 9BA | t | Cl-S(=O)(=O)-N(CH3)2 | I-311 | LCMS (FA): m/z = 376.0 (M + H) |
| | v* | cyclopropane carboxamide-pyridine-Bpin | | |
| 9BB | t | 2,4-difluorophenyl sulfamoyl chloride | I-267b | LCMS (FA): m/z = 481.0 (M + H) Chiral sep Peak2*** |
| | v** | 2,2-difluorocyclopropane carboxamide-pyridine-Bpin | | |
| 9BC | t | 2,4-difluorophenyl sulfamoyl chloride | I-267a | LCMS (FA): m/z = 481.1 (M + H) Chiral sep Peak1*** |
| | | 2,2-difluorocyclopropane carboxamide-pyridine-Bpin | | |
| 9BD | t* | Cl-S(=O)(=O)-N(Et)(Me) | I-273 | LCMS (FA): m/z = 364.1 (M + H) |

TABLE 10-continued

| Example | Reagent | Chemical Structure | Compound No. | LCMS Data |
|---|---|---|---|---|
| 9BE | t* | (4-methylpiperazine-1-sulfonyl chloride) | I-269 | LCMS (FA): m/z = 405.1 (M + H) |
| 9BF | t* | (azetidine-1-sulfonyl chloride) | I-257 | LCMS (FA): m/z = 362.1 (M + H) |
| 9BG | t* | (pyrrolidine-1-sulfonyl chloride) | I-274 | LCMS (FA): m/z = 376.3 (M + H) |
| 9BH | u** | (N-(5-bromo-2-methylpyridin-3-yl 1-oxide)-2,4-difluorobenzenesulfonamide) | I-258 | LCMS (FA): m/z = 435.0 (M + H) |
| 9BI | t | (N,N-dimethylsulfamoyl chloride) | I-220 | LCMS (FA): m/z = 366.8 (M + H) |
|  | s* | (5-bromo-2-methoxypyridin-3-amine) |  |  |
| 9BJ | s | (3-amino-5-bromopicolinonitrile) | I-411 | LCMS (FA): m/z = 430.6 (M + H) |
|  | u^^^ | (N-(5-bromo-2-cyanopyridin-3-yl)-2,4-difluorobenzenesulfonamide) |  |  |
| 9BK | s | (5-bromo-3-fluoropicolinonitrile) | I-380 | LCMS (FA): m/z = 336.4 (M + H) |

TABLE 10-continued

| Example | Starting material | | | LCMS |
|---|---|---|---|---|
| | Reagent | Chemical Structure | Compound No. | Data |
| | t | 2-methylpiperidine | | |
| | u^^^ | 5-bromo-2-cyano-3-(2-methylpiperidin-1-yl)pyridine | | |
| 9BL | t | N-methylsulfamoyl chloride | I-455 | LCMS (FA): m/z = 336.2 (M + H) |
| | u* | N-(5-bromo-2-methylpyridin-3-yl)-N'-methylsulfamide | | |
| 9BM | s | 5-bromo-4-chloropyridin-3-amine | I-394 | LCMS (FA): m/z = 439.2 (M + H) |
| | u^^^ | N-(5-bromo-4-chloropyridin-3-yl)-2,4-difluorobenzenesulfonamide | | |
| 9BN | s | 5-bromopyridin-3-amine | I-348 | LCMS (FA): m/z = 336.2 (M + H) |
| | t | N,N-dimethylsulfamoyl chloride | | |

TABLE 10-continued

| | Starting material | | | LCMS |
|---|---|---|---|---|
| Example | Reagent | Chemical Structure | Compound No. | Data |
| | u^^ | [structure: N,N-dimethylsulfamoyl-NH-(5-bromopyridin-3-yl)] | | |
| 9BO | t | [structure: 2,6-dichlorobenzenesulfonyl chloride] | I-463 | LCMS (FA): m/z = 451.0 (M + H) |
| | u* | [structure: N-(5-bromo-2-methylpyridin-3-yl)-2,6-dichlorobenzenesulfonamide] | | |
| 9BP | s | [structure: 5-bromo-2-chloro-3-aminopyridine] | I-372 | LCMS (FA): m/z = 470.2 (M + H) |
| | t | [structure: N,N-dimethylsulfamoyl chloride] | | |
| | u* | [structure: N-(5-bromo-2-chloropyridin-3-yl)-N',N'-dimethylsulfamide] | | |
| 9BQ | s | [structure: 5-bromo-2-chloro-4-methyl-3-aminopyridine] | I-429 | LCMS (FA): m/z = 441.6 (M + H) |
| | t | [structure: 4-cyanobenzenesulfonyl chloride] | | |

TABLE 10-continued

| Example | Starting material | | Compound No. | LCMS Data |
|---|---|---|---|---|
| | Reagent | Chemical Structure | | |
| | u* | [structure: 5-bromo-2-chloro-4-methyl-3-pyridyl sulfonamide with 4-cyanophenyl] | | |
| 9BR | s | [structure: 5-bromo-2-chloro-4-methyl-3-aminopyridine] | I-362 | LCMS (FA): m/z = 476.2 (M + H) |
| | t | [structure: 2-chloro-4-cyanobenzenesulfonyl chloride] | | |
| | u* | [structure: 5-bromo-2-chloro-4-methyl-3-pyridyl sulfonamide with 2-chloro-4-cyanophenyl] | | |
| 9BS | t | [structure: azepane-1-sulfonyl chloride] | I-341 | LCMS (FA): m/z = 404.1 (M + H) |
| | u* | [structure: 5-bromo-2-methyl-3-pyridyl azepane sulfonamide] | | |
| 9BT | t | [structure: morpholine-4-sulfonyl chloride] | I-447 | LCMS (FA): m/z = 392.1 (M + H) |
| | u* | [structure: 5-bromo-2-methyl-3-pyridyl morpholine sulfonamide] | | |

TABLE 10-continued
| Example | Starting material | | Compound No. | LCMS Data |
|---|---|---|---|---|
| | Reagent | Chemical Structure | | |
| 9BU | s | 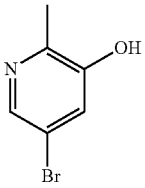 | I-359 | LCMS (FA): m/z = 351.2 (M + H) |
| | t | 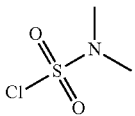 | | |
| | u^^^ | 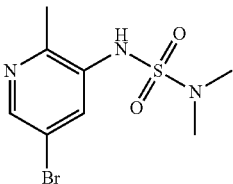 | | |
| 9BV | ^^ | 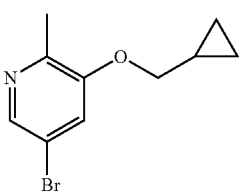 | I-492 | LCMS (FA): m/z = 298.1 (M + H) |
| 9BW | s | 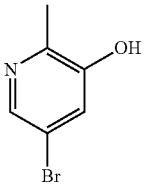 | I-478 | LCMS (FA): m/z = 419.9 (M + H) |
| | u^^^ | 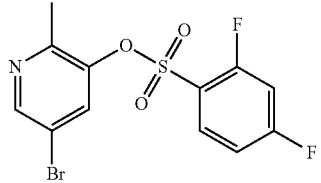 [SMILES: Cc1ncc(Br)cc1OS(=O)(=O)c1ccc(F)cc1F] | | |
| 9BX | s | 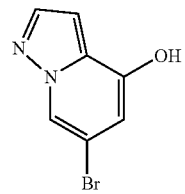 | I-428 | LCMS (FA): m/z = 376.4 (M + H) |
| | t | 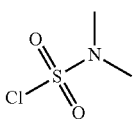 | | |

TABLE 10-continued

| | Starting material | | | LCMS |
|---|---|---|---|---|
| Example | Reagent | Chemical Structure | Compound No. | Data |
| | u^^^ | (pyrazolo[1,5-a]pyridine with O-SO2-N(CH3)2 and Br substituent) | | |
| 9BY | s | (2-chloro-5-bromo-4-methyl-3-aminopyridine) | I-399 | LCMS (FA): m/z = 470.9 (M + H) |
| | t | (4-chloro-2-fluorobenzenesulfonyl chloride) | | |
| | u^^^ | (2-chloro-5-bromo-4-methylpyridin-3-yl 4-chloro-2-fluorobenzenesulfonate) | | |
| 9BZ | t | (4,4-dimethylpiperidine-1-sulfonyl chloride) | I-483 | LCMS (FA): m/z = 418.1 (M + H) |
| | u^^^ | (2-methyl-5-bromopyridin-3-yl 4,4-dimethylpiperidine-1-sulfonate) | | |
| 9CA | s | (2-chloro-5-bromo-4-methyl-3-aminopyridine) | I-354 | LCMS (FA): m/z = 484.9 (M + H) |
| | t | (2,6-dichlorobenzenesulfonyl chloride) | | |

TABLE 10-continued

| | Starting material | | | LCMS |
|---|---|---|---|---|
| Example | Reagent | Chemical Structure | Compound No. | Data |
| | u^^^ | [structure: 2-Cl, 5-Br, 4-methyl pyridine-3-yl sulfonamide with 2,6-dichlorophenyl] | | |
| 9CB | s | [structure: 2-chloro-5-bromo-4-methylpyridin-3-amine] | I-333 | LCMS (FA): m/z = 518.9 (M + H) |
| | t | [structure: 2-chloro-4-(trifluoromethyl)benzenesulfonyl chloride] | | |
| | u^^^ | [structure: sulfonamide product with 2-Cl, 5-Br, 4-methyl pyridinyl and 2-chloro-4-trifluoromethylphenyl] | | |
| 9CC | s | [structure: 2-chloro-5-bromo-4-methylpyridin-3-amine] | I-401 | LCMS (FA): m/z = 485.0 (M + H) |
| | t | [structure: 2,5-dichlorobenzenesulfonyl chloride] | | |
| | u^^^ | [structure: sulfonamide product with 2-Cl, 5-Br, 4-methyl pyridinyl and 2,5-dichlorophenyl] | | |

TABLE 10-continued

| | Starting material | | | LCMS |
|---|---|---|---|---|
| Example | Reagent | Chemical Structure | Compound No. | Data |
| 9CD | t | [structure: 4,4-difluorocyclohexanesulfonyl chloride] | I-374 | LCMS (FA): m/z = 426.3 (M + H) |
| | u^^^ | [structure: N-(5-bromo-2,4-dimethylpyridin-3-yl)-4,4-difluoropiperidine-1-sulfonamide] | | |
| 9CE | s | [structure: 5-bromo-2-chloro-4-methylpyridin-3-amine] | I-437 | LCMS (FA): m/z = 468.0 (M + H) |
| | t' | [structure: quinoline-5-sulfonyl chloride] | | |
| | u* | [structure: N-(5-bromo-2-chloro-4-methylpyridin-3-yl)quinoline-5-sulfonamide] | | |
| 9CF | t | [structure: 4-chloro-2-fluorobenzenesulfonyl chloride] | I-441 | LCMS (FA): m/z = 497.0 (M + H) |
| | u^^^ | [structure: N-(5-bromo-2-methylpyridin-3-yl)-4-chloro-2-fluorobenzenesulfonamide] | | |

TABLE 10-continued

| Example | Starting material | | Compound No. | LCMS Data |
|---|---|---|---|---|
| | Reagent | Chemical Structure | | |
| | v | (pinacol boronate pyridine with 2,2-difluorocyclopropanecarboxamide) | | |
| 9CG | t | (4-chloro-2-fluorobenzenesulfonyl chloride) | I-433 | LCMS (FA): m/z = 461.1 (M + H) |
| | u^^^ | (N-(5-bromo-2,4-dimethylpyridin-3-yl)-4-chloro-2-fluorobenzenesulfonamide) | | |
| | v | (pinacol boronate pyridine with cyclopropanecarboxamide) | | |
| 9CH | t | (2,5-dichlorothiophene-3-sulfonyl chloride) | I-465 | LCMS (FA): m/z = 426.3 (M + H) |
| | u" | (N-(5-bromo-2-methylpyridin-3-yl)-2,5-dichlorothiophene-3-sulfonamide) | | |
| 9CI | s | (6-bromopyrazolo[1,5-a]pyridin-4-amine) | I-476 | LCMS (FA): m/z = 375.4 (M + H) |

TABLE 10-continued

| | Starting material | | | LCMS |
|---|---|---|---|---|
| Example | Reagent | Chemical Structure | Compound No. | Data |
| | t | (dimethylsulfamoyl chloride) | | |
| | u'' | (6-bromopyrazolo[1,5-a]pyridin-4-yl dimethylsulfamate) | | |
| 9CJ | s | (2-chloro-5-bromo-4-methylpyridin-3-amine) | I-493 | LCMS (FA): m/z = 489.1 (M + H) |
| | t | (4-chlorosulfonyl-3-(trifluoromethyl)-1-methylpyrazole) | | |
| | u'' | (N-(2-chloro-5-bromo-4-(trifluoromethyl)pyridin-3-yl)-1-methyl-3-(trifluoromethyl)pyrazole-4-sulfonamide) | | |
| 9CK | s | (6-bromopyrazolo[1,5-a]pyridin-4-amine) | I-404 | LCMS (FA): m/z = 444.4 (M + H) |
| | t' | (2,4-difluorobenzenesulfonyl chloride) | | |
| | u'' | (6-bromopyrazolo[1,5-a]pyridin-4-yl 2,4-difluorobenzenesulfonate) | | |

TABLE 10-continued

| Example | Starting material | | Compound No. | LCMS Data |
|---|---|---|---|---|
| | Reagent | Chemical Structure | | |
| 9CL**** | t | [structure: dimethylsulfamoyl chloride] | I-498 (Peak 1) | LCMS (FA): m/z = 412.4 (M + H) |
| | u^^^ | [structure: 5-bromo-2-methyl-3-(dimethylsulfamoylamino)pyridine] | | |
| | v | [structure: pinacol boronate pyridine with difluorocyclopropanecarboxamide] | | |
| 9CM**** | t | [structure: dimethylsulfamoyl chloride] | I-499 (Peak 2) | LCMS (FA): m/z = 412.4 (M + H) |
| | u^^^ | [structure: 5-bromo-2-methyl-3-(dimethylsulfamoylamino)pyridine] | | |
| | v | [structure: pinacol boronate pyridine with difluorocyclopropanecarboxamide] | | |
| 9CN | t | [structure: azabicyclic sulfonyl chloride] | I-445 | LCMS (FA): m/z = 402.1 (M + H) |

TABLE 10-continued
| | Starting material | | | LCMS |
|---|---|---|---|---|
| Example | Reagent | Chemical Structure | Compound No. | Data |
| | u* | 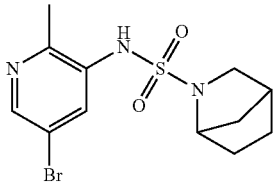 [SMILES: Cc1ncc(Br)cc1NS(=O)(=O)N1CC2CCC1C2] | | |
| 9CO | s | 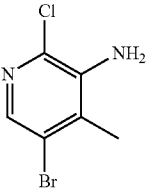 | I-488 | LCMS (FA): m/z = 410.1 (M + H) |
| | t | 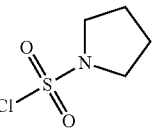 | | |
| | u^^^ | 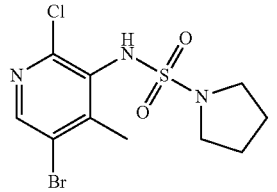 | | |
| 9CP | s | 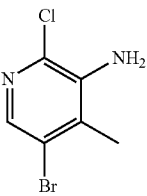 | I-477 | LCMS (FA): m/z = 436.1 (M + H) |
| | t | 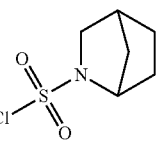 | | |
| | u^^^ | 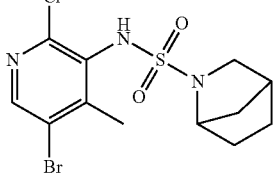 | | |
| 9CQ | t | 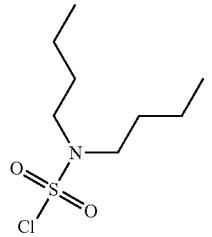 | I-350 | LCMS (FA): m/z = 434.2 (M + H) |

TABLE 10-continued
| | Starting material | | | LCMS |
|---|---|---|---|---|
| Example | Reagent | Chemical Structure | Compound No. | Data |
| | u^^^ | 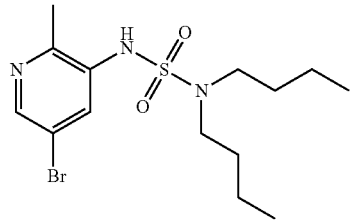 [SMILES: CCCCN(CCCC)S(=O)(=O)Nc1cc(Br)cnc1C] | | |
| 9CR | t | 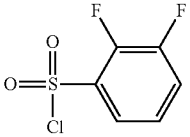 [SMILES: O=S(=O)(Cl)c1cccc(F)c1F] | I-377 | LCMS (FA): m/z = 419.1 (M + H) |
| | u^^^ | 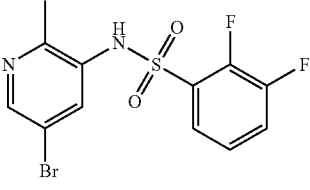 [SMILES: Cc1ncc(Br)cc1NS(=O)(=O)c1cccc(F)c1F] | | |
| 9CS | t | 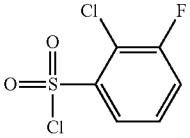 [SMILES: O=S(=O)(Cl)c1cccc(F)c1Cl] | I-322 | LCMS (FA): m/z = 435.0 (M + H) |
| | u^^^ | 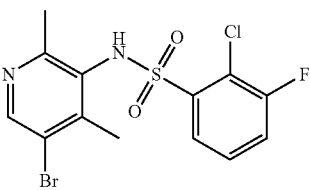 [SMILES: Cc1ncc(Br)c(C)c1NS(=O)(=O)c1cccc(F)c1Cl] | | |
| 9CT | t | 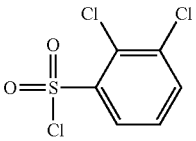 [SMILES: O=S(=O)(Cl)c1cccc(Cl)c1Cl] | I-342 | LCMS (FA): m/z = 451.0 (M + H) |
| | u^^^ | 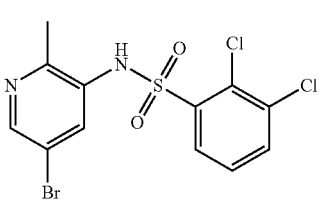 [SMILES: Cc1ncc(Br)cc1NS(=O)(=O)c1cccc(Cl)c1Cl] | | |
| 9CU | t | 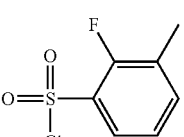 | I-339 | LCMS (FA): m/z = 415.1 (M + H) |

TABLE 10-continued

| Example | Starting material | | Compound No. | LCMS Data |
|---|---|---|---|---|
| | Reagent | Chemical Structure | | |
| | u^^^ | [structure: N-(5-bromo-2-methylpyridin-3-yl)-2-fluoro-3-methylbenzenesulfonamide] | | |
| 9CV | s | [structure: 2-chloro-4-methyl-5-bromo-3-aminopyridine] | I-430 | LCMS (FA): m/z = 493.1 (M + H) |
| | u^^^ | [structure: N-(2-chloro-5-bromo-4-methylpyridin-3-yl)-2,4-difluorobenzenesulfonamide] | | |
| | v | [structure: pinacol boronate pyridine with butyramide] | | |
| 9CW | t | [structure: 2-fluoro-4-cyanobenzenesulfonyl chloride] | I-356 | LCMS (FA): m/z = 426.1 (M + H) |
| | u^^^ | [structure: N-(5-bromo-2-methylpyridin-3-yl)-2-fluoro-4-cyanobenzenesulfonamide] | | |
| 9CX | u* | [structure: N-(5-bromo-2-methylpyridin-3-yl)-N'-methyl-N'-phenylsulfamide] | I-494 | LCMS (FA): m/z = 412.1 (M + H) |

TABLE 10-continued

| Example | Starting material | | Compound No. | LCMS Data |
|---|---|---|---|---|
| | Reagent | Chemical Structure | | |
| 9CY[1] | u* | | I-416 | LCMS (FA): m/z = 345.3 (M + H) |
| 9CZ | u* | | I-376 | LCMS (FA): m/z = 345.3 (M + H) |
| 9DA | u* | | I-384 | LCMS (AA): m/z = 449.1 (M + H) |
| 9DB | u* | | I-319 | LCMS (FA): m/z = 463.2 (M + H) |

*Aqueous $K_2CO_3$ or $Na_2CO_3$ used in Step 2 instead of $Cs_2CO_3$

[1]Step 1 conditions use LiHMDS in THF at rt

^Step 2 conditions use $Pd(PPh_3)_4$, 1.0 M $Na_2CO_3$; toluene, EtOH, microwave irradiation

Step 2 conditions use XPhosG3; 0.500 M of $K_3PO_4$, dioxane, microwave irradiation at 130° C.

^^Step 2 conditions use $Pd_2(dba)_3$,, XPhos, KOAC, dioxane, water, 110° C.

^^^Step 2 conditions use $K_2CO_3$ instead of $Cs_2CO_3$ and microwave irradiation ranging from 120-150° C.

**Step 2 conditions use SiliaCat DPP-Pd instead of $Pd(dppf)Cl_2$ and microwave irradiation

***Chiral Separation conditions

Column: 5 micron Chiralpak IF (250 × 10 mm); Back Pressure Regulator value: 15 mPa Solvent: 85% $CO_2$/15% (0.3% DEA in MeOH); Flow Rate: 10 mL/min; Temperature: 40° C.

****Chiral Separation conditions

Column: Chiralpak IF (250 × 30 mm) 5 micron column from Chiral Technologies

Solvent: Hexane/Ethanol/DEA (80/20/0.1); Flow Rate: 35 mL/min

[1]Reagent u prepared as shown in Example 57

Synthesis of Reagent (s) from Example 9AT: 5-bromo-2-ethylpyridin-3-amine

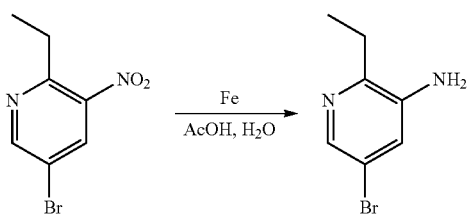

5-bromo-2-ethyl-3-nitropyridine (0.503 g, 2.18 mmol) was dissolved in acetic acid (4 mL, 70 mmol) and water (1 mL, 60 mmol), then iron (0.365 g, 6.53 mmol) was added and the reaction mixture was allowed to stir at rt for 3 h. Water and NaOH were added to adjust the reaction mixture to pH 8, then EtOAc was added and the mixture was filtered through celite and washed with more EtOAc. The combined organic layer was washed with water, concentrated, and the resulting residue was purified by column chromatography to yield 5-bromo-2-ethylpyridin-3-amine (0.4 g, 91%). LCMS (FA): m/z=201.1/203.1 (M+H).

Synthesis of Reagent (u) from Example 9BH: 5-bromo-3-(2,4-difluorophenylsulfonamido)-2-methylpyridine 1-oxide

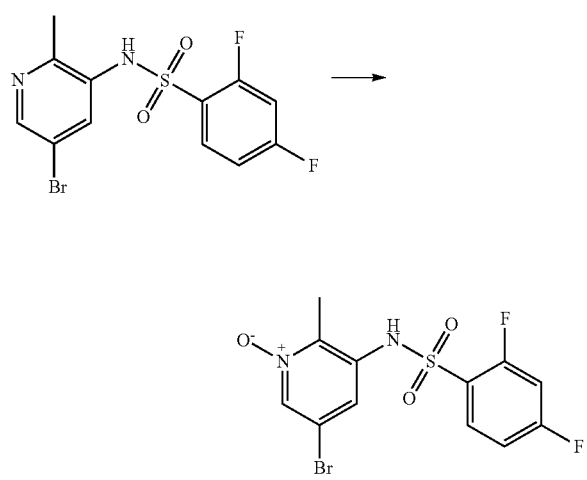

To N-(5-bromo-2-methylpyridin-3-yl)-2,4-difluorobenzenesulfonamide (400 mg, 1.10 mmol) was added DCM (2 mL). The reaction mixture was cooled in an ice-water bath and to this solution was added mCPBA (855 mg, 4.96 mmol) portion-wise. The reaction mixture was allowed to stir and warm to rt overnight. The reaction contents were purified by column chromatography and then vacuum dried to give 5-bromo-3-(2,4-difluorophenylsulfonamido)-2-methylpyridine 1-oxide as a white solid, (0.33 g, 78%). LCMS (FA): m/z=379.0 (M+H).

Synthesis of Reagent (u) from Example 9BI: N'-(5-bromo-2-methoxypyridin-3-yl)-N,N-dimethylsulfuric diamide

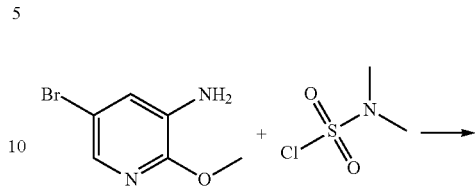

Dimethylsulfamoyl chloride (3.2 mL, 30 mmol) was added slowly to a solution of 3-amino-5-bromo-2-methoxypyridine (1.0 g, 4.9 mmol) in pyridine (20 mL) at −30° C. The reaction mixture was allowed to stir at rt for 16 h. The reaction mixture was concentrated and the crude compound was purified by column chromatography to provide N'-(5-bromo-2-methoxypyridin-3-yl)-N,N-dimethylsulfuric diamide (0.64 g, 42%). LCMS (FA): m/z=310.1 (M+H).

Synthesis of Reagent (u) from Example 9BK: 5-bromo-3-(2-methylpiperidin-1-yl)pyridine-2-carbonitrile

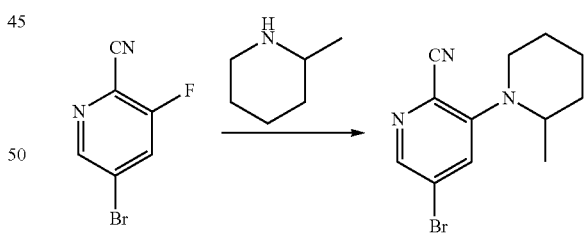

To a mixture of 5-bromo-3-fluoropyridine-2-carbonitrile (195 mg, 0.970 mmol) and 2-methylpiperidine (0.228 mL, 1.94 mmol) in THF (2.35 mL) was added DIEA (507 uL, 2.91 mmol). The reaction mixture was allowed to stir at rt overnight. The reaction mixture was diluted with water and extracted with EtOAc three times. The organic solutions were combined, dried over Na$_2$SO$_4$, filtered and concentrated. The crude compound was purified by column chromatography to provide 5-bromo-3-(2-methylpiperidin-1-yl)pyridine-2-carbonitrile (45 mg, 17%). LCMS (FA): m/z=280.2 (M+H).

Synthesis of Reagent (u) from Example 9CX: N'-(5-bromo-2-methylpyridin-3-yl)-N-methyl-N-phenylsulfuric diamide

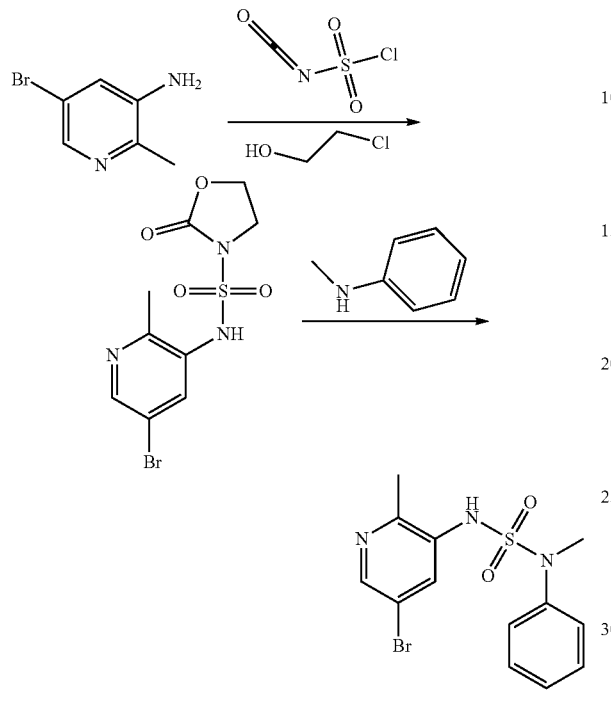

Step 1: N-(5-bromo-2-methylpyridin-3-yl)-2-oxooxazolidine-3-sulfonamide

To a solution of chlorosulfonyl isocyanate (0.140 mL, 1.60 mmol) in DCM (53.64 mL, 836.9 mmol) was added 2-chloroethanol (0.215 mL, 3.20 mmol. The reaction mixture was allowed to stir at rt for one h. To this mixture 5-bromo-2-methylpyridin-3-amine (300 mg, 1.60 mmol) and TEA (0.224 mL, 1.60 mmol) were added. The reaction mixture was allowed to stir at rt overnight. Excess DCM was removed under reduced pressure. The residue was co-evaporated with fresh DCM twice, and vacuum dried to give N-(5-bromo-2-methylpyridin-3-yl)-2-oxo-1,3-oxazolidine-3-sulfonamide, which was used without further purification. LCMS (FA): m/z=334.4 (M+) Ref: Austin; Joel, Sharma, Lisa, S.; et al
WO 2012/015723 PCT/US2011/045153 2012 I-195

Step 2: N'-(5-bromo-2-methylpyridin-3-yl)-N-methyl-N-phenylsulfuric diamide

To N-(5-bromo-2-methylpyridin-3-yl)-2-oxo-1,3-oxazolidine-3-sulfonamide (530 mg, 1.58 mmol) was added DCE (25 mL, 317 mmol). To this stirred solution N-methylaniline (0.172 mL, 1.58 mmol) and TEA (0.220 mL, 1.58 mmol) were added and the reaction mixture was allowed to stir at 80° C. After one h, additional N-methylaniline (0.25 mL) was added and the reaction mixture was allowed to stir for an additional h. Excess solvent was removed under reduced pressure and the residue was purified on a silica gel column using DCM-MeOH. Appropriate fractions were pooled together, excess solvent was removed under reduced pressure and this was vacuum dried to give N'-(5-bromo-2-methylpyridin-3-yl)-N-methyl-N-phenylsulfuric diamide in 80% purity. (70%, 0.516 mg) LCMS (FA): m/z=358.0 (M+2).

Synthesis of Precursor to Reagent (s) from Example 9CI:
6-bromopyrazolo[1,5-a]pyridin-4-amine

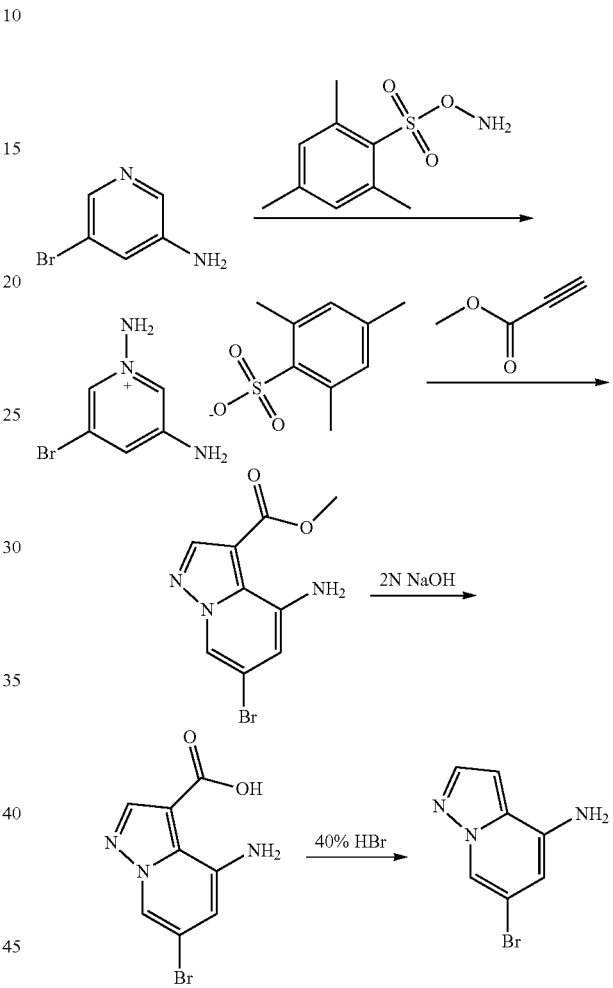

Step 1: 1,3-diamino-5-bromopyridinium 2,4,6-trimethylbenzenesulfonate

To a solution of 5-bromopyridin-3-amine (43.0 g, 249 mmol) in DCM (250 mL) at 0° C., 2-[(aminooxy)sulfonyl]-1,3,5-trimethylbenzene (64.0 g, 297 mmol; see procedure below) in DCM (250 mL) was added in a steady stream via cannula. The reaction mixture was allowed to stir at 0° C. for 1 h. To the reaction mixture, diethyl ether (600 mL) was added dropwise via addition funnel over 25 min. The reaction mixture was filtered and washed with cold diethyl ether. The solid was dried under vacuum for 30 mins to provide 1,3-diamino-5-bromopyridinium 2,4,6-trimethylbenzenesulfonate (90.0 g, 93.3%). $^1$H NMR (400 MHz, DMSO-$d_6$) δ 8.35 (s, br, 2H), 8.14 (s, 1H), 7.94 (s, 1H), 7.49 (s, 1H), 6.90 (s, br, 2H), 6.76 (s, 2H), 2.51 (s. 6H), 2.18 (s, 3H).

Step 2: methyl 4-amino-6-bromopyrazolo[1,5-a]pyridine-3-carboxylate

To a solution of 1,3-diamino-5-bromopyridinium 2,4,6-trimethylbenzenesulfonate (90.0 g, 232 mmol) in DMF (500 mL) at 0° C., potassium carbonate (64.1 g, 464 mmol) was added. The reaction mixture was allowed to stir for 10 mins. To the reaction mixture, methyl propiolate (39.0 g, 464 mmol) was then added dropwise. The reaction mixture was allowed to warm to rt and stir overnight. The reaction mixture was poured into water (2,500 mL). The solid was collected by filtration, washed with water (500 mL×3) and dried under vacuum to provide methyl 4-amino-6-bromopyrazolo[1,5-a]pyridine-3-carboxylate (20.0 g, 32.0%). $^1$H NMR (400 MHz, DMSO-$d_6$) δ 8.36 (s, 1H), 8.34 (s, 1H), 7.17 (s, br, 2H), 6.63 (s, 1H), 3.84 (s, 3H).

Step 3: 4-amino-6-bromopyrazolo[1,5-a]pyridine-3-carboxylic acid

A mixture of methyl 4-amino-6-bromopyrazolo[1,5-a]pyridine-3-carboxylate (20.0 g, 74.0 mmol) in aqueous sodium hydroxide solution (2.0 N, 150 mL) was allowed to stir at 60° C. for 12 h. The reaction mixture became a clear solution and was neutralized by the addition of 6N HCl to pH-3. The solid was collected by filtration and dried under vacuum to provide 4-amino-6-bromopyrazolo[1,5-a]pyridine-3-carboxylic acid (12.0 g, 63.3%). $^1$H NMR (400 MHz, DMSO-$d_6$) δ 8.29 (s, 1H), 8.26 (s, 1H), 6.57 (s, 1H).

Step 4: 6-bromopyrazolo[1,5-a]pyridin-4-amine

A mixture of 4-amino-6-bromopyrazolo[1,5-a]pyridine-3-carboxylic acid (12.0 g, 0.78 mmol) in HBr (40%, 150 mL) was allowed to stir at 100° C. for 12 h. The reaction mixture became a clear solution and was neutralized by the addition of 4N NaOH to pH-8. The reaction mixture was extracted with DCM (150 ml×3). The organic solutions were combined, dried over $Na_2SO_4$, filtered and concentrated to provide 6-bromopyrazolo[1,5-a]pyridin-4-amine (5.30 g, 53.3%). LCMS (FA): m/z=212.0 (M+H). $^1$H NMR (400 MHz, DMSO-$d_6$) δ 8.18 (s, 1H), 7.81 (m, 1H), 6.77 (m, 1H), 6.26 (m, 1H), 6.21 (s, 2H).

Synthesis of 2-[(aminooxy)sulfonyl]-1,3,5-trimethylbenzene

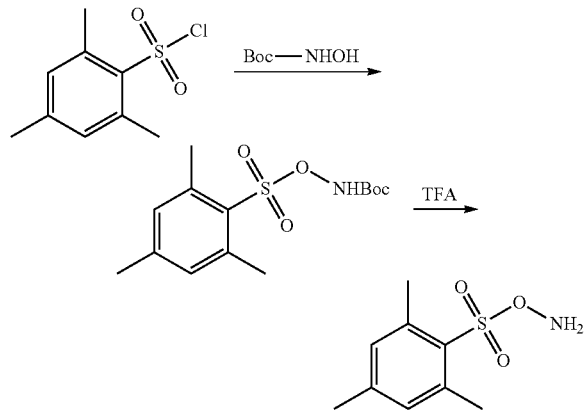

Step 1: tert-butyl [(mesitylsulfonyl)oxy]carbamate

To a mixture of 2,4,6-trimethylbenzenesulfonyl chloride (100 g, 457 mmol) and tert-butyl hydroxycarbamate (60.9 g, 457 mmol) in diethyl ether (1000 mL) was added TEA (46.3 g, 24.9 mmol) at 0° C. The reaction mixture was allowed to stir at 0° C. for 30 min. The reaction mixture was filtered and washed with MTBE (250 mL). The solution was concentrated at 20° C. at 150 mm Hg to remove the diethyl ether. The reaction mixture was then diluted with petroleum ether (1500 mL) and allowed to stir for 5 min. The reaction mixture was filtered and washed with petroleum ether (300 mL) to provide tert-butyl [(mesitylsulfonyl)oxy]carbamate (110 g, 76.3%). $^1$H NMR (400 MHz, DMSO-$d_6$) δ 11.19 (s, 1H), 7.14 (s, 2H), 2.54 (s. 6H), 2.30 (s, 3H), 1.25 (s, 9H).

Step 2: 2-[(aminooxy)sulfonyl]-1,3,5-trimethylbenzene

To a solution of TFA (500 mL) at 0° C., tert-butyl [(mesitylsulfonyl)oxy]carbamate (110 g, 349 mmol) was added portion-wise over 10 min and the mixture was allowed to stir at 0° C. for another 10 min. Crushed ice was added to the mixture followed by water (500 mL). The internal temperature increased to 8° C. while a white solid appeared. The reaction mixture was filtered after 15 min. The solid was collected and washed with water until pH~7. The crude compound was dried for 15 min to remove excess water to provide 2-[(aminooxy)sulfonyl]-1,3,5-trimethylbenzene (64.0 g, 85.2%). The compound was unstable in the air and was used for next step directly.

Synthesis of Reagent (u) from Example 9BV: 5-bromo-3-(cyclopropylmethoxy)-2-methylpyridine

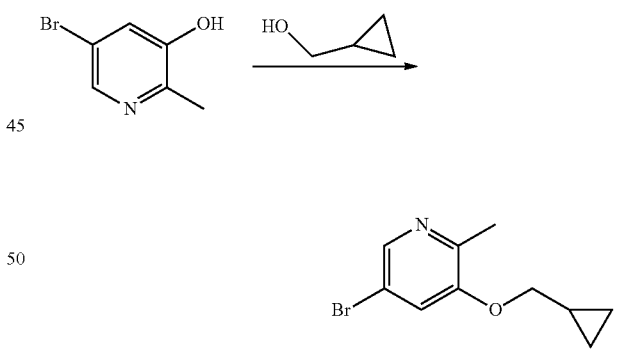

To a mixture of cyclopropylmethanol (131 uL, 1.66 mmol), 5-bromo-2-methylpyridin-3-ol (250 mg, 1.30 mmol) and triphenylphosphine (420 mg, 1.60 mmol) in THF (8.3 mL) at 0° C. was added diethyl azodicarboxylate (250 uL, 1.60 mmol) dropwise. The reaction mixture was allowed to stir at rt overnight. The reaction mixture was diluted with water and extracted with DCM three times. The organic solutions were combined, dried over $Na_2SO_4$, filtered and concentrated. The crude compound was purified by column chromatography to provide 5-bromo-3-(cyclopropylmethoxy)-2-methylpyridine (120 mg, 37%). LCMS (FA): m/z=242.1 (M+H).

383

Synthesis of Reagent (u) from Example 9CZ: 2-(bicyclo[1.1.1]pentan-1-yl)-8-bromo-3,4-dihydro-2H-pyrido[2,3-b][1,4,5]oxathiazepine 1,1-dioxide

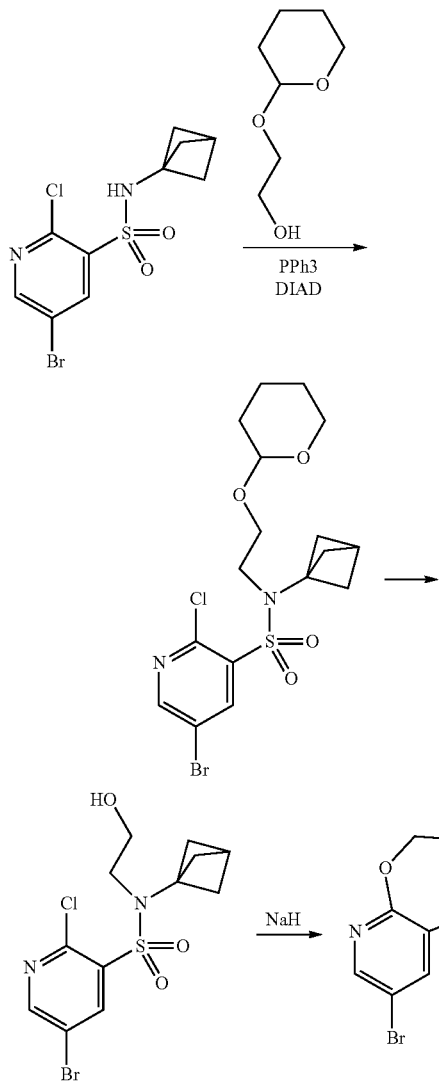

Step 1: N-(bicyclo[1.1.1]pentan-1-yl)-5-bromo-2-chloro-N-(2-((tetrahydro-2H-pyran-2-yl)oxy)ethyl)pyridine-3-sulfonamide A solution of N-(bicyclo[1.1.1]pent-1-yl)-5-bromo-2-chloropyridine-3-sulfonamide (450 mg, 1.3 mmol) in THF (9 mL) was treated with triphenylphosphine (524 mg, 2 mmol) and tetrahydropyranoylethylene glycol (390 mg, 2.6 mmol) followed by dropwise addition of diisopropylazodcarboxylate (404 mg, 2 mmol) and the mixture was stirred ar rt for 15 h. The solvent was evaporated under reduced pressure and the residue purified by column chromatography to give N-(bicyclo[1.1.1]pentan-1-yl)-5-bromo-2-chloro-N-(2-((tetrahydro-2H-pyran-2-yl)oxy)ethyl)pyridine-3-sulfonamide (1.2 g, 96%)

384

Step 2: N-(bicyclo[1.1.1]pentan-1-yl)-5-bromo-2-chloro-N-(2-hydroxyethyl)pyridine-3-sulfonamide A solution of N-(bicyclo[1.1.1]pentan-1-yl)-5-bromo-2-chloro-N-(2-((tetrahydro-2H-pyran-2-yl)oxy)ethyl)pyridine-3-sulfonamide (600 mg, 1.29 mmol) in MeOH (30 mL) was cooled in an ice bath and treated with p-toluenesulfonic acid (122 mg, 0.6 mmol). The reaction mixture was allowed to warm to rt and stirred for 15 h. A solution of NaHCO$_3$ in water was added until the pH was 7 and then the MeOH was evaporated under reduced pressure. The residue was extracted with DCM and the organic solution washed with water and brine, dried over MgSO$_4$, filtered and concentrated. The crude product purified by column chromatography to give N-(bicyclo[1.1.1]pentan-1-yl)-5-bromo-2-chloro-N-(2-hydroxyethyl)pyridine-3-sulfonamide (800 mg, 81%). LCMS: m/z=381.0.

Step 3: 2-(bicyclo[1.1.1]pentan-1-yl)-8-bromo-3,4-dihydro-2H-pyrido[2,3-b][1,4,5]oxathiazepine 1,1-dioxide A solution of N-(bicyclo[1.1.1]pentan-1-yl)-5-bromo-2-chloro-N-(2-hydroxyethyl)pyridine-3-sulfonamide (285 mg, 0.75 mmol) in DMF (2.85 mL) was treated with NaH (35.6 mg, 0.90 mmol) at 0° C. The reaction mixture was stirred at 0° C. for 0.5 h and then treated with water (2.8 mL) and extracted with EtOAc. The organinc solution was washed with water and brine, dried over Na$_2$SO$_4$ and the solvent removed under reduced pressure. The crude product was triturated with hexane-EtOAc (50:1) to give 2-(bicyclo[1.1.1]pentan-1-yl)-8-bromo-3,4-dihydro-2H-pyrido[2,3-b][1,4,5]oxathiazepine 1,1-dioxide (433 mg, 84%). LCMS: m/z=346.0.

Synthesis of Reagent (u) from Example 9DA: N-(5-bromo-2-methylpyridin-3-yl)-2,4-difluoro-N-(2-hydroxyethyl)benzenesulfonamide

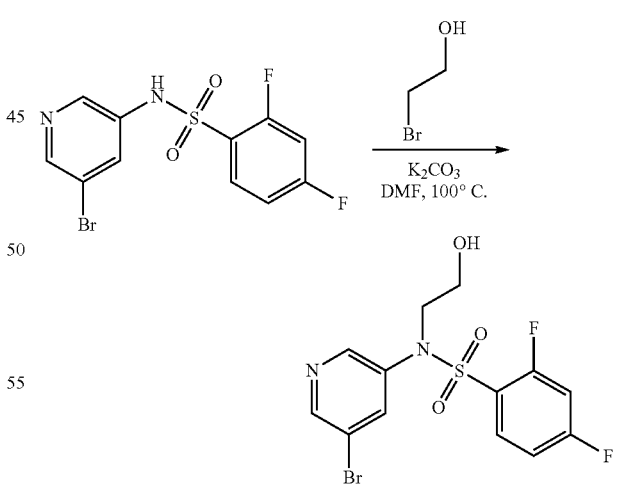

A solution of N-(5-bromo-2-methylpyridin-3-yl)-2,4-difluorobenzenesulfonamide (0.180 g, 0.496 mmol) in DMF (1.00 mL, 12.9 mmol) treated with 2-bromoethanol (105.4 uL, 1.487 mmol) and potassium carbonate (0.137 g, 0.991 mmol). The reaction mixture was heated in a sealed tube at 100° C. for 16 h. The reaction mixture was diluted with ice-water and the precipitate collected. The crude product was purified by column chromatography to give N-(5-bromo-2-methylpyridin-3-yl)-2,4-difluoro-N-(2-hydroxyethyl)benzenesulfonamide LCMS (FA): m/z=407.1 (M+H).

Example 9DC: N-(5-(8-fluoro-1,1-dioxido-3,4-dihydro-2H-benzo[b][1,4,5]oxathiazepin-2-yl)-[3,4'-bipyridin]-2'-yl)acetamide (I-405)

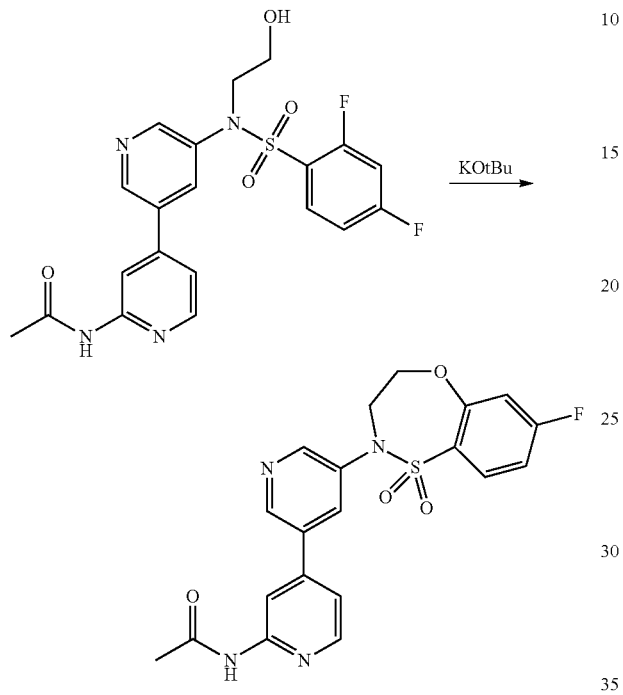

A solution of N-(5-{[(2,4-difluorophenyl)sulfonyl](2-hydroxyethyl)amino}-3,4'-bipyridin-2'-yl)acetamide in dry DMSO (0.50 mL) was treated dropwise with a 1M solution of KOt-Bu (7.71 mg, 0.0687 mmol) in THF and allowed to stir at rt. After 3 h, additional KOt-Bu (2 equivalents) was added and the mixture was allowed to stir for 72 h. The mixture was treated with AcOH (53.2 uL, 0.936 mmol) and the volatiles were evaporated under reduced pressure. The crude product was purified by column chromatography to give N-(5-(8-fluoro-1,1-dioxido-3,4-dihydro-2H-benzo[b][1,4,5]oxathiazepin-2-yl)-[3,4'-bipyridin]-2'-yl)acetamide. LCMS: m/z=429.3 (M+H).

Example 10: N-(5-{[(2-chloro-4-fluorophenyl)sulfonyl]amino}-6-methyl-3,4'-bipyridin-2'-yl)acetamide I-206

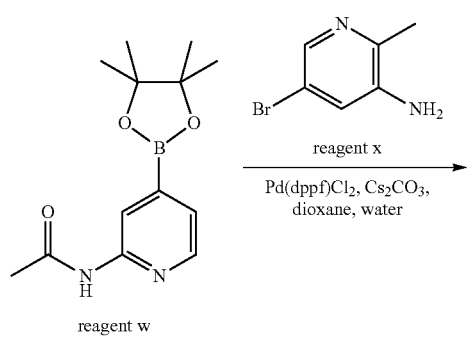

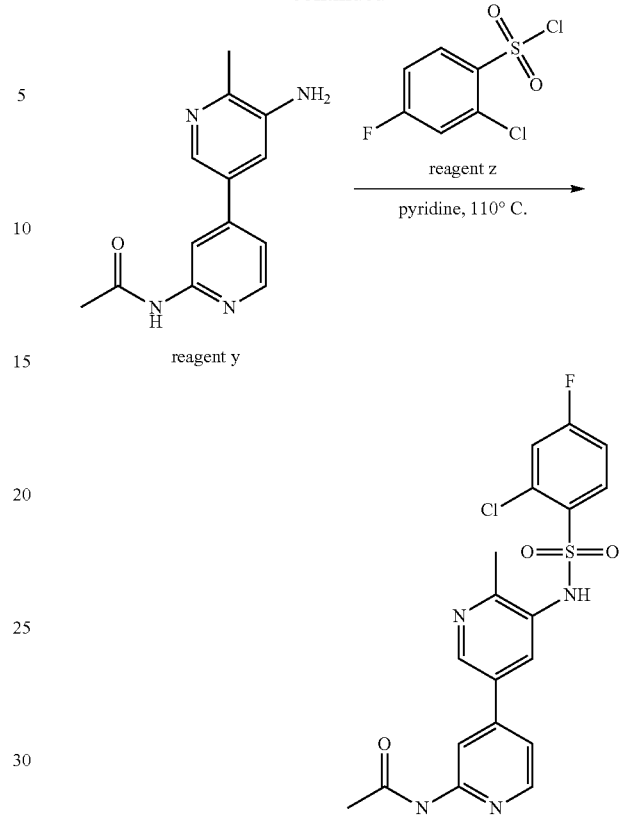

Step 1: N-(5-amino-6-methyl-3,4'-bipyridin-2'-yl)acetamide

A mixture of N-[4-(4,4,5,5-tetramethyl-1,3,2-dioxaborolan-2-yl)pyridin-2-yl]acetamide (4.20 g, 16.0 mmol), 5-bromo-2-methylpyridin-3-amine (2.00 g, 10.7 mmol), cesium carbonate (10.4 g, 32.1 mmol), Pd(dppf)Cl$_2$ (0.88 g, 1.1 mmol) in 1,4-dioxane (36.0 mL) and water (6.0 mL) was heated to reflux for 2.5 h. After cooling to rt, water was added and the mixture was extracted with EtOAc. The combined organic layers were dried over Na$_2$SO$_4$ and concentrated by rotary evaporation. The crude compound was purified by column chromatography to provide N-(5-amino-6-methyl-3,4'-bipyridin-2'-yl)acetamide (0.94 g, 36%). LCMS (FA): m/z=243.1 (M+H).

Step 2: N-(5-{[(2-chloro-4-fluorophenyl)sulfonyl]amino}-6-methyl-3,4'-bipyridin-2'-yl)acetamide N-(5-amino-6-methyl-3,4'-bipyridin-2'-yl)acetamide (125 mg, 0.52 mmol) and 2-chloro-4-fluorobenzenesulfonyl chloride (0.09 mL, 0.62 mmol) were suspended in pyridine (1.25 mL) and heated at 110° C. overnight. The reaction was cooled and concentrated. The crude compound was purified by column chromatography to provide N-(5-{[(2-chloro-4-fluorophenyl)sulfonyl]amino}-6-methyl-3,4'-bipyridin-2'-yl)acetamide (107 mg, 48%). LCMS (FA): m/z=435.1 (M+H).

The compounds listed in the table below (Table 11) were prepared in an analogous fashion to that described above starting from the appropriate starting materials:

TABLE 11

| Example | Reagent z | Compound No. | LCMS Data |
|---|---|---|---|
| 10A | 2-(trifluoromethyl)benzenesulfonyl chloride | I-62 | LCMS (FA): m/z = 451.1 (M + H) |
| 10B | 2-fluoro-4-methylbenzenesulfonyl chloride | I-182 | LCMS (FA): m/z = 415.4 (M + H) |
| 10C | cyclopropanesulfonyl chloride | I-114 | LCMS (FA): m/z = 347.4 (M + H) |
| 10D | 1-methyl-1H-imidazole-2-sulfonyl chloride | I-92 | LCMS (FA): m/z = 387.1 (M + H) |
| 10E | 2-chloro-4-methylbenzenesulfonyl chloride | I-128 | LCMS (FA): m/z = 432.1 (M + H) |
| 10F | 2-chloro-4-(trifluoromethyl)benzenesulfonyl chloride | I-196 | LCMS (FA): m/z = 485.0 (M + H) |
| 10G | 1-methyl-3-(trifluoromethyl)-1H-pyrazole-4-sulfonyl chloride | I-18 | LCMS (FA): m/z = 455.1 (M + H) |
| 10H | 2-fluoro-5-methylbenzenesulfonyl chloride | I-28 | LCMS (FA): m/z = 415.1 (M + H) |
| 10I | thiophene-3-sulfonyl chloride | I-203 | LCMS (FA): m/z = 389.1 (M + H) |
| 10J* | butane-1-sulfonyl chloride | I-373 | LCMS (FA): m/z = 363.1 (M + H) |
| 10K* | 2,2-difluoroethanesulfonyl chloride | I-412 | LCMS (FA): m/z = 371.2 (M + H) |

*Aqueous K₂CO₃ or Na₂CO₃ used in Step 2 instead of Cs₂CO₃

The compounds listed in the table below (Table 11A) were prepared in an analogous fashion to that described above starting from the appropriate starting materials:

TABLE 11A

| Example | Reagent x | Reagent y | Reagent z** | Compound No. | LCMS Data |
|---|---|---|---|---|---|
| 10L* | (structure) | (structure) | (structure) | I-444 | LCMS (FA): m/z = 514.9 (M + H) |

*Aqueous K₂CO₃ or Na₂CO₃ used in Step 1 instead of Cs₂CO₃
***1M LiHMDS and THF at rt used in Step 2

Example 10M: N-(6-chloro-5-{[(4-cyclopropyl-2-fluorophenyl)sulfonyl]amino}-4-methyl-3,4'-bipyridin-2'-yl)acetamide (I-335)

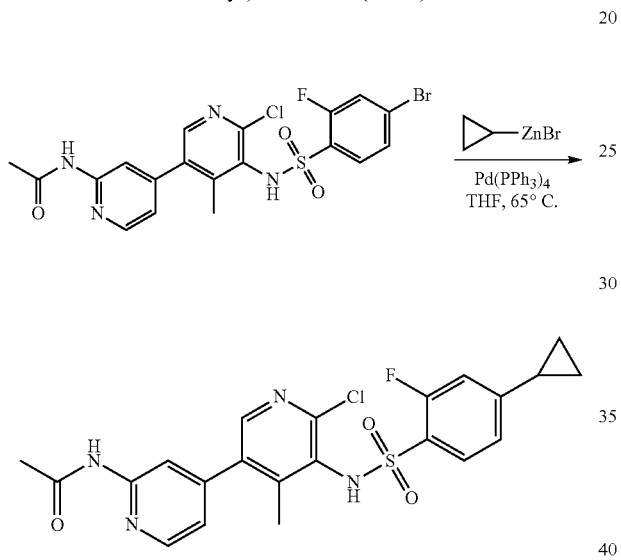

N-(6-chloro-5-{[(4-cyclopropyl-2-fluorophenyl)sulfonyl]amino}-4-methyl-3,4'-bipyridin-2'-yl)acetamide To a mixture of N-(5-{[(4-bromo-2-fluorophenyl)sulfonyl]amino}-6-chloro-4-methyl-3,4'-bipyridin-2'-yl)acetamide (0.07 g, 0.136 mmol) and tetrakis(triphenylphosphine) palladium(0) (0.004 g, 0.003 mmol;) under an atmosphere of nitrogen was added cyclopropylzinc bromide (0.50 M in THF, 3.00 mL, 1.50 mmol). The resulting solution was allowed to stir at 65° C. for 1 h. The reaction was allowed to cool to rt. The reaction mixture was diluted with EtOAc and washed with water then with brine. The organic solution was dried over Na₂SO₄, filtered, and concentrated. The crude compound was purified by HPLC to provide N-(6-chloro-5-{[(4-cyclopropyl-2-fluorophenyl)sulfonyl]amino}-4-methyl-3,4'-bipyridin-2'-yl)acetamide I-335 (0.031 g, 48.0%). LCMS (FA): m/z=475.1 (M+H). ¹H NMR (400 MHz, DMSO-d₆) δ 10.67 (s, 1H), 10.41 (s. 1H), 8.40 (d, J=5.0 Hz, 1H), 8.05 (s, 2H), 7.53 (t, J=7.9 Hz, 1H), 7.13-7.04 (m, 2H), 7.00 (d, J=7.9 Hz, 1H), 2.16 (s, 3H), 2.11 (s, 3H), 2.01 (tt, J=8.6, 5.1 Hz, 1H), 1.10-1.00 (m, 2H), 0.83-0.76 (m, 2H).

Example 11: N-[5-(1,1-dioxidoisothiazolidin-2-yl)-3,4'-bipyridin-2'-yl]acetamide I-192

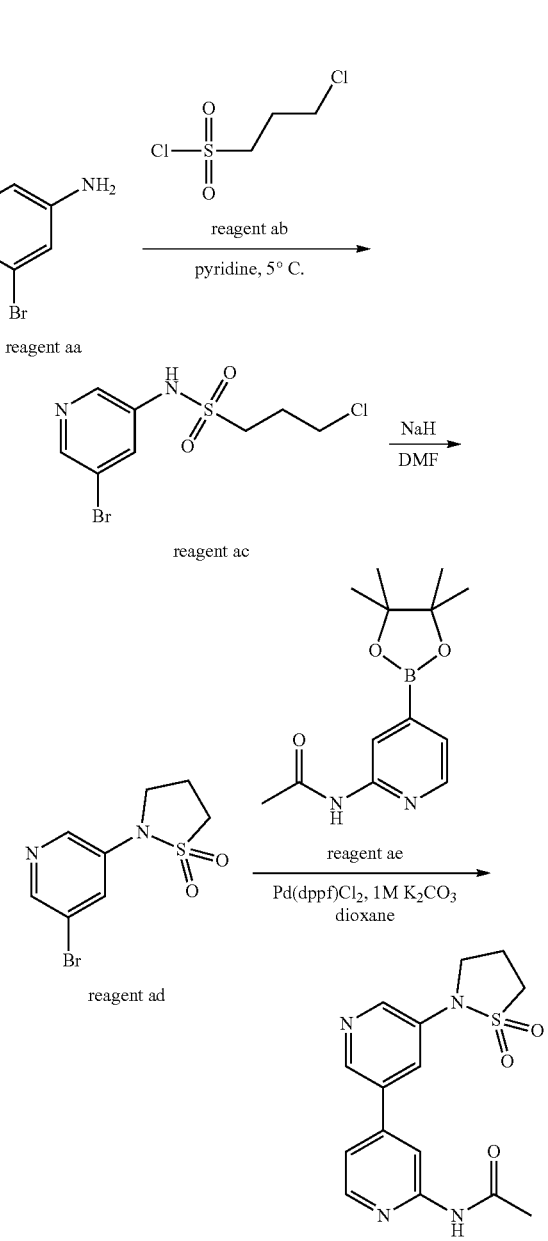

Step 1: N-(5-bromopyridin-3-yl)-3-chloropropane-1-sulfonamide

To a solution of 3-amino-5-bromopyridine (438 mg, 2.53 mmol) in pyridine (3.8 mL, 47 mmol) at 5° C. was added 3-chloropropane-1-sulfonyl chloride (0.339 mL, 2.78 mmol) dropwise. After 30 min the reaction mixture was warmed to rt and then poured into a aqueous solution of NaHCO$_3$. This was extracted with EtOAc and the organic layer washed with brine, dried over sodium sulfate and concentrated by rotary evaporation. The crude material residue was purified by column chromatography to yield N-(5-bromopyridin-3-yl)-3-chloropropane-1-sulfonamide (126 mg, 14.3%). LCMS (AA): m/z=312.8/314.8 (M+H).

Step 2: 3-bromo-5-(1,1-dioxidoisothiazolidin-2-yl)pyridine

To a solution of N-(5-bromopyridin-3-yl)-3-chloropropane-1-sulfonamide (126 mg, 0.402 mmol) in DMF (1.25 mL, 16.1 mmol) at rt was added NaH (60:40, sodium hydride:mineral oil, 20.1 mg, 0.502 mmol). The mixture was allowed to stir at rt for 10 min and then heated at 45° C. for 2.5 h. The mixture was partitioned between EtOAc and an aqueous solution of NaHCO$_3$. The aqueous layer was further extracted with EtOAc and the combined organic layers were washed with brine, dried over sodium sulfate and concentrated by rotary evaporation. The crude material residue was purified by column chromatography to yield 3-bromo-5-(1,1-dioxidoisothiazolidin-2-yl)pyridine (72 mg, 65%). LCMS (AA): nm/z=277/278.9 (M+H).

Step 3: N-[5-(1,1-dioxidoisothiazolidin-2-yl)-3,4'-bipyridin-2'-yl]acetamide Followed the procedure described in Step 2 of Example 5 with the following modification: Used 1.4 equivalents of 1M K$_2$CO$_3$ instead of solid potassium carbonate. No additional water was added. The reaction yielded N-[5-(1,1-dioxidoisothiazolidin-2-yl)-3,4'-bipyridin-2'-yl]acetamide (69.0 mg, 83.4%). LCMS (AA): m/z=333.1 (M+H).

The compounds listed in the table below (Table 12) were prepared in an analogous fashion to that described above starting from the appropriate starting materials

TABLE 12

| Example | Starting material | | Compound | |
|---|---|---|---|---|
| | Reagent | Chemical Structure | No. | LCMS Data |
| 11A* | ab | ![structure: Cl-S(=O)(=O)-CH3] | I-20 | LCMS (AA): m/z = 321.0 (M + H) |
| | ac' | CH$_3$I | | |
| 11B** | aa | ![structure: 5-bromo-2-methyl-3-aminopyridine] | I-88 | LCMS (FA): m/z = 347.2 (M + H) |
| 11C*** | aa | ![structure: 2-chloro-5-bromo-4-methyl-3-aminopyridine] | I-425 | LCMS (FA): m/z = 381.0 (M + H) |
| | ac | ![structure: bis-sulfonyl chloride adduct] | | |

TABLE 12-continued

| Example | Starting material | | Compound | |
|---|---|---|---|---|
| | Reagent | Chemical Structure | No. | LCMS Data |
| | ad | (2-chloro-5-bromo-4-methylpyridin-3-yl isothiazolidine 1,1-dioxide) | | |
| | ae | (4-trimethylstannyl-2-acetamidopyridine) | | |
| 11D^ | aa | (5-bromo-4-methyl-2-chloropyridin-3-amine) | I-473 | LCMS (FA): m/z = 396.0 (M + H) |
| | ab | (N-(3-chloropropyl)sulfamoyl chloride) | | |
| | ad | (2-chloro-5-bromo-4-methylpyridin-3-yl 1,2,6-thiadiazinane 1,1-dioxide) | | |
| | ae | (4-trimethylstannyl-2-acetamidopyridine) | | |
| 11E^ | aa | (5-bromo-2-methylpyridin-3-amine) | I-352 | LCMS (FA): m/z = 348.1 (M + H) |
| | ab | (N-(3-chloropropyl)sulfamoyl chloride) | | |
| | ad | (2-methyl-5-bromopyridin-3-yl isothiazolidine 1,1-dioxide) | | |

TABLE 12-continued

| Example | Starting material Reagent | Chemical Structure | Compound No. | LCMS Data |
|---|---|---|---|---|
| | ae | [trimethylstannyl pyridine acetamide] | | |
| 11F^ | aa | 5-bromo-3-amino-2-methylpyridine | I-387 | LCMS (FA): m/z = xxx.x (M + H) |
| | ab | 3-chloro-N-(3-chloropropyl)sulfamoyl chloride | | |
| | ad | [2-methyl-5-bromo-3-(1,1-dioxo-1,2,6-thiadiazinan-2-yl)pyridine] | | |
| | ae | [pinacol boronate pyridine acetamide] | | |
| 11G^^ | ab | 3-chloro-N-(3-chloropropyl)sulfamoyl chloride | I-386 | LCMS (FA): m/z = 362.2 (M + H) |
| | ad | [2-methyl-5-bromo-3-(1,1-dioxo-1,2,5-thiadiazolidin-2-yl)pyridine] | | |
| | ad' | [2-methyl-5-bromo-3-(5-methyl-1,1-dioxo-1,2,5-thiadiazolidin-2-yl)pyridine] | | |
| 11H^^ | ab | 3-chloro-N-(3-chloropropyl)sulfamoyl chloride | I-343 | LCMS (FA): m/z = 376.2 (M + H) |

TABLE 12-continued

| Example | Starting material | | Compound | |
|---|---|---|---|---|
| | Reagent | Chemical Structure | No. | LCMS Data |
| | ad | [2-methyl-5-bromopyridin-3-yl bound to 1,2,6-thiadiazinane 1,1-dioxide with NH] | | |
| | ad' | [2-methyl-5-bromopyridin-3-yl bound to 2-methyl-1,2,6-thiadiazinane 1,1-dioxide] | | |
| 11I^^^ | aa | [5-bromo-pyridine-2,3-diamine] | I-490 | LCMS (FA): m/z = 363.6 (M + H) |
| | ab | [N-(3-chloropropyl)sulfamoyl chloride] | | |
| | ad | [2-amino-5-bromopyridin-3-yl bound to 1,2,6-thiadiazinane 1,1-dioxide with NH] | | |
| 11J^^^ | aa | [5-bromo-pyridine-2,3-diamine] | I-323 | LCMS (FA): m/z = 377.1 (M + H) |
| | ab | [N-(3-chloropropyl)sulfamoyl chloride] | | |
| | ad | [2-amino-5-bromopyridin-3-yl bound to 1,2,6-thiadiazinane 1,1-dioxide with NH] | | |

TABLE 12-continued

| Example | Starting material | | Compound | |
|---|---|---|---|---|
| | Reagent | Chemical Structure | No. | LCMS Data |
| | ad' | [2-amino-5-bromo-pyridin-3-yl bound to N-methyl thiadiazinane 1,1-dioxide] | | |
| 11K^ | aa | [5-bromo-2-chloro-pyridin-3-amine] | I-467 | LCMS (FA): m/z = 396.0 (M + H) |
| | ab | [N-(3-chloropropyl)sulfamoyl chloride] | | |
| | ad' | [2-chloro-5-bromo-pyridin-3-yl bound to N-methyl thiadiazinane 1,1-dioxide] | | |
| | ae | [4-(trimethylstannyl)-2-acetamidopyridine] | | |
| 11L^ | aa | [5-bromo-2-chloro-pyridin-3-amine] | I-448 | LCMS (FA): m/z = 381.8 (M + H) |
| | ab | [N-(3-chloropropyl)sulfamoyl chloride] | | |

TABLE 12-continued

| Example | Starting material | | Compound | |
|---|---|---|---|---|
| | Reagent | Chemical Structure | No. | LCMS Data |
| | ad | 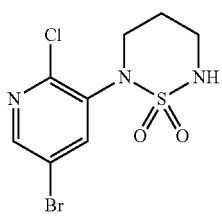 | | |
| | ae | 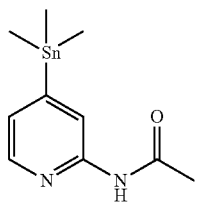 | | |

*In Step 2, methyl iodide was used as the electrophile, NaH as the base, and DMF as the solvent. In Step 3, two equivalents of 2M 1M $K_2CO_3$ was used instead of 1.4 equivalents of 1M $K_2CO_3$.

**In Step 3, the procedure described in Step 3 of Example 8 was used.

***In Step 1, Et3N was used as the base. In step 2, $K_2CO_3$ was used as the base, and MeOH as the solvent.

^In Step 2, $K_2CO_3$ was used as the base, and ACN as the solvent. Step 3 coupling conditions were Pd(PPh₃)₄; LiCl; CuI; 1,4-dioxane; 120° C.

^^In Step 2, $K_2CO_3$ was used as the base, and ACN as the solvent. Methylation of reagent ad to give reagent ad' is described below. Final coupling with reagent ad' used Pd(PPh₃)₄; $Na_2CO_3$, EtOH/Toluene; 120° C.

^^^In Step 2, $K_2CO_3$ was used as the base, and ACN as the solvent. Step 3 conditions used Pd(PPh₃)₄; $Na_2CO_3$, EtOH/Toluene; 120° C.

Synthesis of Reagent (ad') from Example 11H: 2-(5-bromo-2-methylpyridin-3-yl)-6-methyl-1,2,6-thiadiazinane 1,1-dioxide Example 12: N-{6-amino-5-[methyl(methylsulfonyl)amino]-3,4'-bipyridin-2'-yl}acetamide I-133

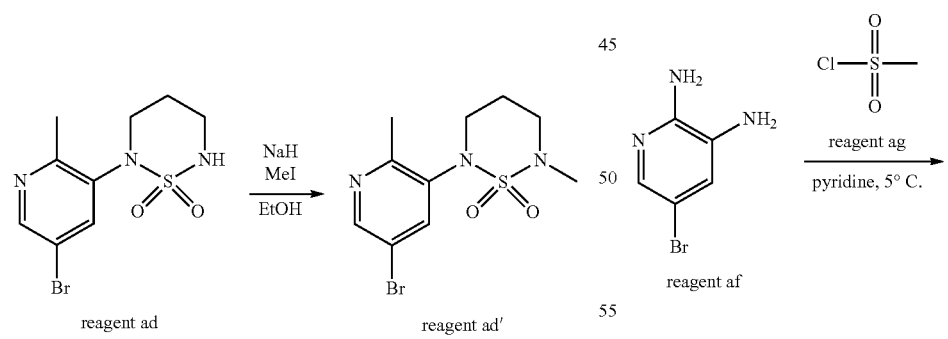

To a solution of 2-(5-bromo-2-methylpyridin-3-yl)-1,2,6-thiadiazinane 1,1-dioxide (0.773 g, 2.52 mmol), EtOH (30 mL), and MeI (0.63 mL, 10.1 mmol) was added sodium hydroxide (1M in water, 6.3 mL). The mixture was allowed stir at rt overnight. The reaction mixture was acidified with 1M HCl and then concentrated. The crude compound was purified by column chromatography to give 2-(5-bromo-2-methylpyridin-3-yl)-6-methyl-1,2,6-thiadiazinane 1,1-dioxide as an off white solid (0.81 g, 100%). LCMS (FA): m/z=320.0 (M+H).

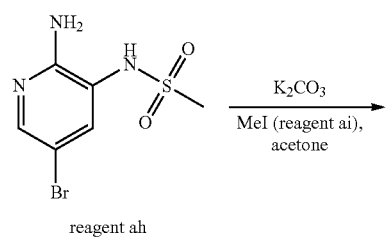

-continued

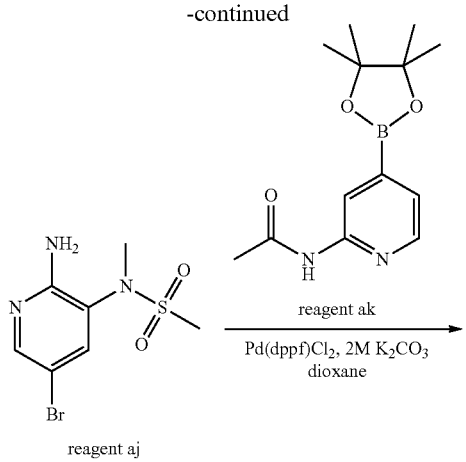

reagent aj reagent ak

Pd(dppf)Cl₂, 2M K₂CO₃
dioxane

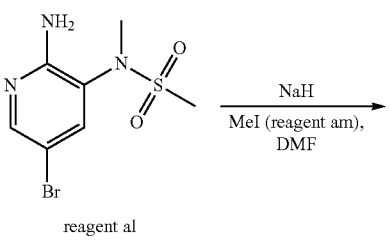

Step 1: N-(2-amino-5-bromopyridin-3-yl)methanesulfonamide

To a solution of 2,3-diamino-5-bromopyridine (631 mg, 3.36 mmol) in pyridine (11 mL, 140 mmol) cooled to −10° C. was added methanesulfonyl chloride (273 uL, 3.52 mmol) dropwise. After 30 min, the mixture was warmed to rt and allowed to stir for 4 h. The mixture was diluted with toluene and concentrated by rotary evaporation. The residue was allowed to stir in MeOH for 30 min and then concentrated again by rotary evaporation. The residue was partitioned between EtOAc and aqueous solution of NaHCO₃ and the aqueous layer further extracted with EtOAc. The combined organic layers were washed with brine dried over sodium sulfate and concentrated by rotary evaporation. The crude material was purified by column chromatography to yield N-(2-amino-5-bromopyridin-3-yl)methanesulfonamide (650 mg, 73%). LCMS (AA): m/z=266/268 (M+H).

Step 2: N-(2-amino-5-bromopyridin-3-yl)-N-methylmethanesulfonamide

To a mixture of N-(2-amino-5-bromopyridin-3-yl)methanesulfonamide (205 mg, 0.770 mmol) and potassium carbonate (165 mg, 1.19 mmol) in acetone (2.5 mL, 34 mmol) was added methyl iodide (59 uL, 0.95 mmol). The mixture was allowed to stir at rt overnight and then partitioned between EtOAc and water. The aqueous layer was further extracted with EtOAc. The combined organic layers were washed with brine dried over sodium sulfate and concentrated by rotary evaporation. The crude material was purified by column chromatography to yield N-(2-amino-5-bromopyridin-3-yl)-N-methylmethanesulfonamide (94 mg, 44%). LCMS (AA): m/z=280/282 (M+H).

Step 3: N-{6-amino-5-[methyl(methylsulfonyl)amino]-3,4'-bipyridin-2'-yl}acetamide Followed the procedure described in Step 2 of Example 5 with the following modification: Used 2.0 equivalents of 2 M K₂CO₃ instead of solid potassium carbonate. No additional water was added. The reaction yielded N-{6-amino-5-[methyl(methylsulfonyl)amino]-3,4'-bipyridin-2'-yl}acetamide (11 mg, 10.1%). LCMS (AA): m/z=336.5 (M+H).

The compounds listed in the table below (Table 13) were prepared in an analogous fashion to that described above starting from the appropriate starting materials:

TABLE 13

| Example | Reagent ag | Compound No. | LCMS Data |
|---|---|---|---|
| 12A | ![Cl-propyl-SO2-Cl] | I-181 | LCMS (AA): m/z = 348.3 (M + H) |
| 12B | ![2,4-difluorobenzenesulfonyl chloride] | I-64 | LCMS (FA): m/z = 420.3 (M − H) |

Example 13: N-{6-(methylamino)-5-[methyl(methylsulfonyl)amino]-3,4'-bipyridin-2'-yl}acetamide I-147

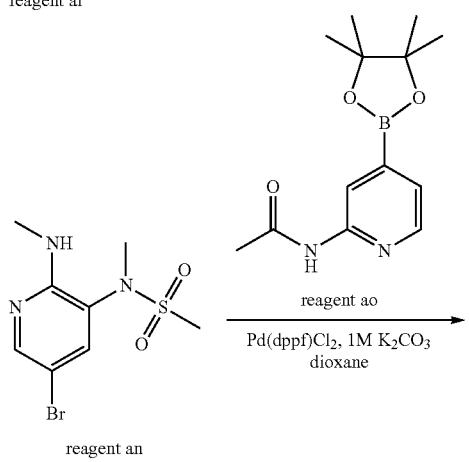

reagent al

NaH
MeI (reagent am),
DMF reagent an reagent ao

Pd(dppf)Cl₂, 1M K₂CO₃
dioxane

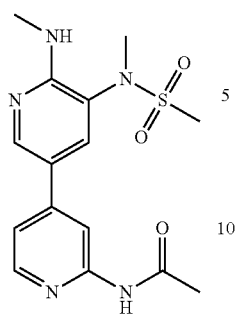

Step 1: N-[5-bromo-2-(methylamino)pyridin-3-yl]-N-methylmethanesulfonamide

To a mixture of N-(2-amino-5-bromopyridin-3-yl)-N-methylmethanesulfonamide (101 mg, 0.360 mmol) in DMF (1.2 mL) at 5° C. was added NaH (60% in mineral oil, 18.0 mg, 0.451 mmol). The mixture was allowed to stir at 5° C. for 20 min. Methyl iodide (28.0 uL, 0.451 mmol) was added and the mixture was allowed to stir at 5° C. for 1 h. The reaction was quenched with a saturated solution of NaHCO$_3$ and then partitioned between EtOAc and water. The aqueous layer was further extracted with EtOAc. The combined organic layers were washed with brine dried over sodium sulfate and concentrated by rotary evaporation. The crude material was purified by column chromatography to yield N-[5-bromo-2-(methylamino)pyridin-3-yl]-N-methylmethanesulfonamide (85 mg, 80.0%). LCMS (AA): m/z=294/296 (M+H).

Step 2: N-{6-(methylamino)-5-[methyl(methylsulfonyl)amino]-3,4'-bipyridin-2'-yl}acetamide Followed the procedure described in Step 2 of Example 5 with the following modification: 2.0 equivalents of 2M K$_2$CO$_3$ was used instead of solid potassium carbonate. No additional water was added. The reaction yielded N-{6-(methylamino)-5-[methyl(methylsulfonyl)amino]-3,4'-bipyridin-2'-yl}acetamide (82 mg, 82.2%). LCMS (AA): m/z=350.2 (M+H).

The compounds listed in the table below (Table 14) were prepared in an analogous fashion to that described above starting from the appropriate starting materials:

TABLE 14

| Example | Reagent an | Compound No. | LCMS Data |
|---|---|---|---|
| 13A | | I-132 | LCMS (AA): m/z = 362.3 (M + H) |
| 13B | | I-141 | LCMS (FA): m/z = 390.5 (M + H) |

Example 14: N-{4-[5-(methylsulfonyl)-1-oxidopyridin-3-yl]pyridin-2-yl}acetamide I-191

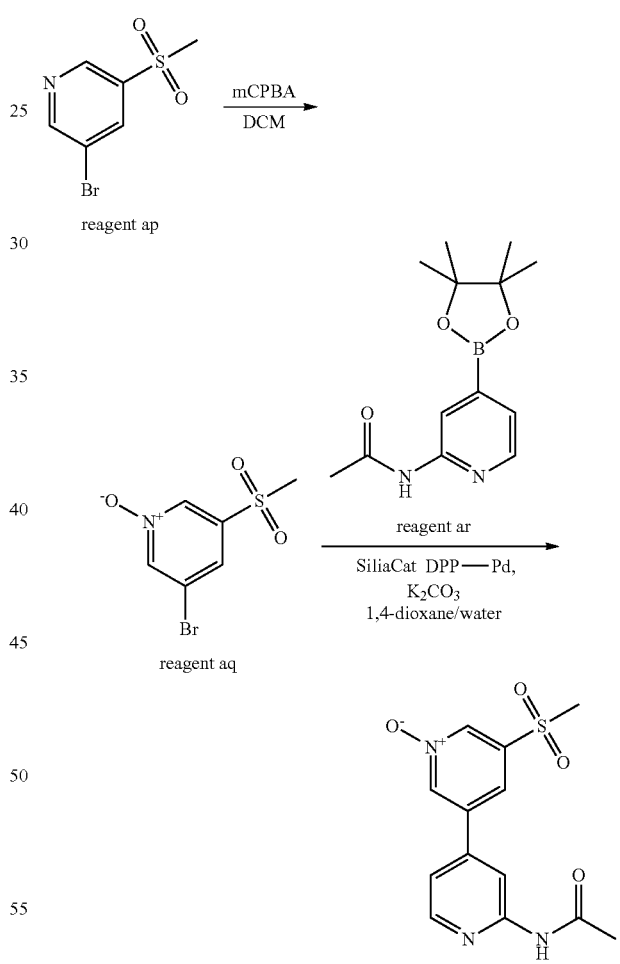

Step 1: 3-bromo-5-(methylsulfonyl)pyridine 1-oxide

A solution of 3-bromo-5-(methylsulfonyl)pyridine 1-oxide (250 mg, 1.06 mmol) was dissolved in DCM (1.8 mL) and cooled to 0° C. mCPBA (822 mg, 4.77 mmol) was added portionwise, and then allowed to warm to rt and stir overnight. The reaction mixture was concentrated and a 15% K$_2$CO$_3$ solution was added and extracted with EtOAc. The combined organic layers were washed with brine, dried over MgSO$_4$ and concentrated by rotary evaporation. The crude compound was used without further purification.

Step 2: N-{4-[5-(methylsulfonyl)-1-oxidopyridin-3-yl]pyridin-2-yl}acetamide 3-bromo-5-(methylsulfonyl)pyridine 1-oxide (240 mg, 0.19 mmol), N-[4-(4,4,5,5-tetramethyl-1,3,2-dioxaborolan-2-yl)pyridin-2-yl]acetamide (75 mg, 0.29 mmol), K$_2$CO$_3$ (132 mg, 0.95 mmol) and SiliaCat DPP-Pd (91 mg, 0.022 mmol) were suspended in dioxane (3.0 mL) and water (0.43 mL). The reaction mixture was heated at 150° C. in the microwave for 40 min. The solvent was removed by rotary evaporation, then the crude compound was purified by colum chromatography followed by prep HPLC to give N-{4-[5-(methylsulfonyl)-1-oxidopyridin-3-yl]pyridin-2-yl}acetamide (10 mg, 17%). LCMS (FA): m/z=308.1 (M+H).

The compounds listed in the table below (Table 15) were prepared in an analogous fashion to that described above starting from the appropriate starting materials:

TABLE 15

| Example | Reagent aq | Compound No. | LCMS Data |
|---|---|---|---|
| 14A | 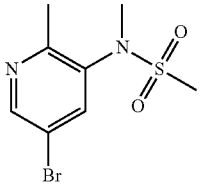 | I-129 | LCMS (FA): m/z = 351.3 (M + H) |

Example 15: N-[5-(cyclopropylcarbonyl)-3,4'-bipyridin-2'-yl]acetamide I-8

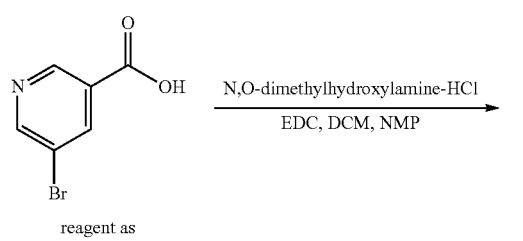

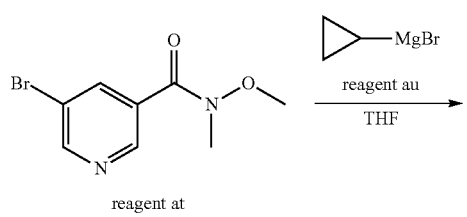

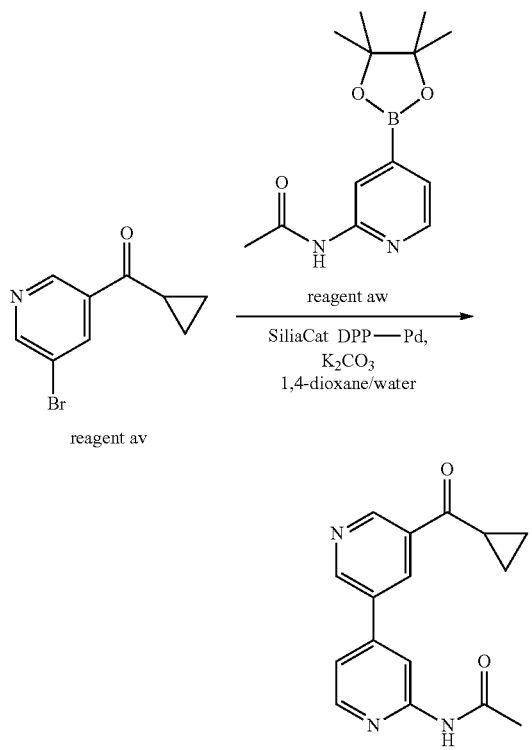

Step 1: 5-Bromo-N-methoxy-N-methylpyridine-3-carboxamide

To a suspension of 5-bromonicotinic acid (1.12 g, 5.54 mmol) in DCM (106 mL) at 0° C. were added NMP (0.588 mL, 6.10 mmol), N,O-dimethylhydroxylamine hydrochloride (0.595 g, 6.10 mmol) and EDC (1.17 g, 6.10 mmol). The reaction was warmed to rt and allowed to stir overnight. The reaction mixture was diluted with DCM and water. The organic layer was washed with 0.1 M HCl and brine, dried over magnesium sulfate, filtered and concentrated. The crude material was purified by column chromatography to yield 5-bromo-N-methoxy-N-methylpyridine-3-carboxamide (1.39 g, 51.1%). LCMS (FA): m/z=245/247 (M+H).

Step 2: (5-bromopyridin-3-yl)(cyclopropyl)methanone

5-Bromo-N-methoxy-N-methylpyridine-3-carboxamide (500 mg, 1.02 mmol) was allowed to stir in THF (4.8 mL) and cooled to 0° C. Cyclopropylmagnesium bromide (0.5 M in THF; 10.0 mL, 5.02 mmol) was added dropwise and the reaction mixture allowed to stir at 0° C. for 30 min and then allowed to warm to rt. The reaction mixture was then cooled in an ice/water bath and quenched with acid and then diluted with DCM. The organic layer was washed with brine, dried over magnesium sulfate, filtered and concentrated. The crude material was purified by column chromatography to yield (5-bromopyridin-3-yl)(cyclopropyl)methanone (218 mg, 56.8%). LCMS (FA): m/z=226/228 (M+H).

Step 3: N-[5-(1,1-dioxidoisothiazolidin-2-yl)-3,4'-bipyridin-2'-yl]acetamide Followed the procedure described in Step 2 of Example 14 to yield N-[5-(cyclopropylcarbonyl)-3,4'-bipyridin-2'-yl]acetamide (15.7 mg, 21.0%). LCMS (FA): m/z=282.3 (M+H).

Example 16: methyl (5-{[(2,4-difluorophenyl)sulfonyl]amino}-6-methyl-3,4'-bipyridin-2'-yl)carbamate I-195

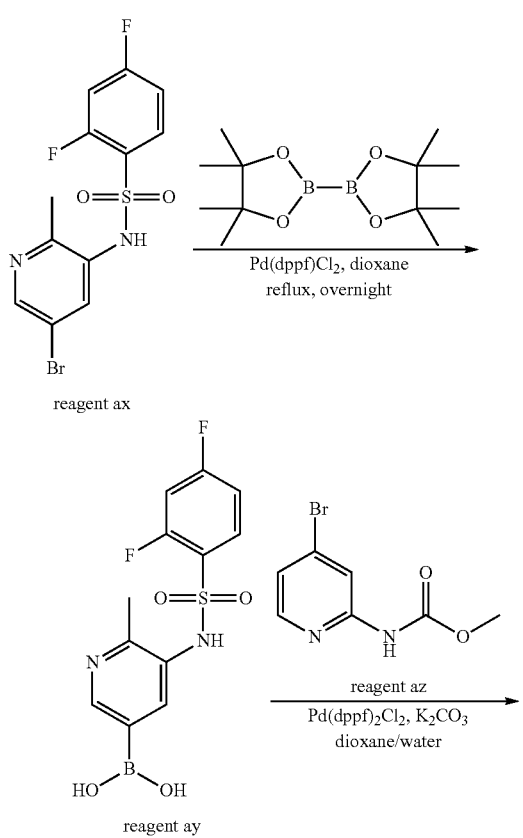

reagent ax reagent ay

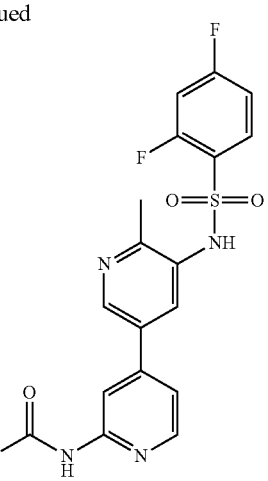

Step 1: (5-{[(2,4-difluorophenyl)sulfonyl]amino}-6-methylpyridin-3-yl)boronic acid The boronate was prepared in a similar manner as N-[4-(4,4,5,5-tetramethyl-1,3,2-dioxaborolan-2-yl)pyridin-2-yl]acetamide in Example 1 and used without further purification. LCMS (FA) m/z=329.4 (M+H).

Step 2: methyl (5-{[(2,4-difluorophenyl)sulfonyl]amino}-6-methyl-3,4'-bipyridin-2'-yl)carbamate Followed the procedure described in Step 2 of Example 5 to yield methyl (5-{[(2,4-difluorophenyl)sulfonyl]amino}-6-methyl-3,4'-bipyridin-2'-yl)carbamate (16 mg, 30%). LCMS (FA): m/z=435.2 (M+H).

The compounds listed in the table below (Table 16) were prepared in an analogous fashion to that described above starting from the appropriate starting materials:

TABLE 16

| Example | Starting material* Reagent | Chemical Structure | Compound No. | LCMS Data |
|---|---|---|---|---|
| 16A* | ax | (structure) | I-146 | LCMS (FA): m/z = 363.3 (M + H) |
| 16B | ax | (structure) | I-56 | LCMS (AA): m/z = 417.1 (M + H) |

TABLE 16-continued

| Example | Reagent | Starting material* Chemical Structure | Compound No. | LCMS Data |
|---|---|---|---|---|
| | az | 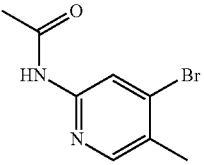 | | |
| 16C | az | 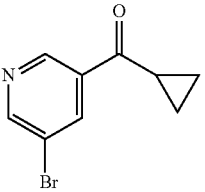 [SMILES: O=C(c1cncc(Br)c1)C1CC1] | I-180 | LCMS (FA): m/z = 298.2 (M + H) |

*The starting material for example 16A was prepared according to Example 11, steps 1 and 2.

Example 17: N-{6-amino-5-[(cyclopropylmethyl)amino]-3,4'-bipyridin-2'-yl}acetamide I-35

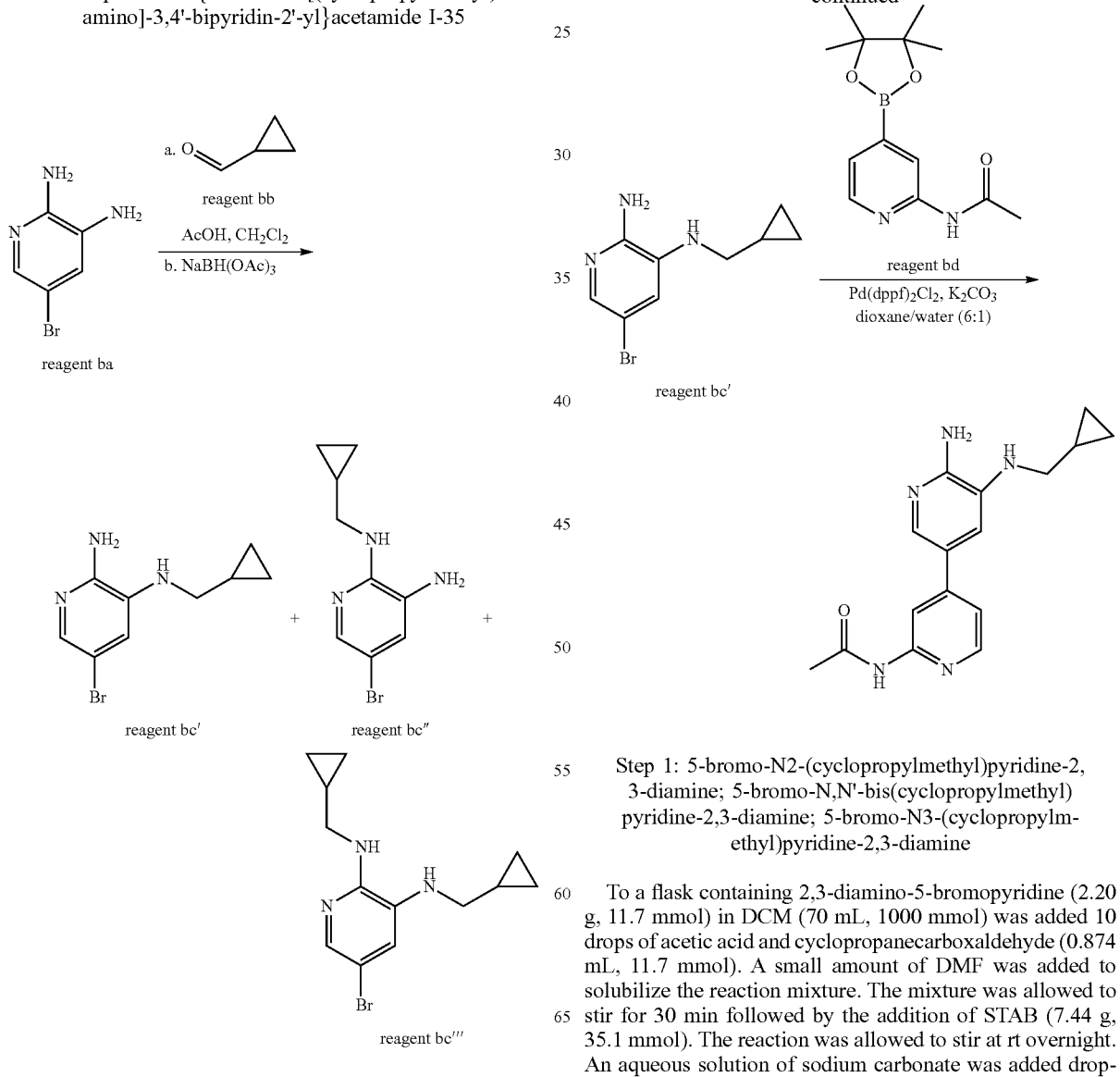

Step 1: 5-bromo-N2-(cyclopropylmethyl)pyridine-2,3-diamine; 5-bromo-N,N'-bis(cyclopropylmethyl)pyridine-2,3-diamine; 5-bromo-N3-(cyclopropylmethyl)pyridine-2,3-diamine To a flask containing 2,3-diamino-5-bromopyridine (2.20 g, 11.7 mmol) in DCM (70 mL, 1000 mmol) was added 10 drops of acetic acid and cyclopropanecarboxaldehyde (0.874 mL, 11.7 mmol). A small amount of DMF was added to solubilize the reaction mixture. The mixture was allowed to stir for 30 min followed by the addition of STAB (7.44 g, 35.1 mmol). The reaction was allowed to stir at rt overnight. An aqueous solution of sodium carbonate was added dropwise until gas evolution ceased. The residue was partitioned between DCM and water and the organic layer was dried over sodium sulfate, filtered and concentrated by rotary evaporation. The crude material was purified by column chromatography to yield 5-bromo-N-2-(cyclopropylmethyl) pyridine-2,3-diamine (355 mg, 12.5%) LCMS (FA): m/z=242/244 (M+H), 5-bromo-N-3-(cyclopropylmethyl) pyridine-2,3-diamine (763 mg, 26.9%) LCMS (FA): m/z=242/244 (M+H), and 5-bromo-N,N'-bis(cyclopropylmethyl)pyridine-2,3-diamine (596 mg, 17.2%). LCMS (FA): m/z=270/272 (M+H).

Step 2: N-{6-amino-5-[(cyclopropylmethyl)amino]-3,4'-bipyridin-2'-yl}acetamide

The procedure from Example 5. Step 2 was followed to provide N-{6-amino-5-[(cyclopropylmethyl)amino]-3,4'-bipyridin-2'-yl}acetamide (90 mg, 26%) LCMS (FA): m/z=298.2 (M+H).

The compounds listed in the table below (Table 17) were prepared in an analogous fashion to that described above starting from the appropriate starting materials:

TABLE 17

| Example | Starting material* | | Compound No. | LCMS Data |
|---|---|---|---|---|
| | Reagent | Chemical Structure | | |
| 17A | bc''' | 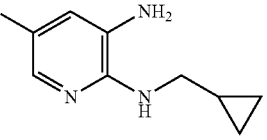 | I-53 | LCMS (FA): m/z = 298.2 (M + H) |
| 17B | bc''' | 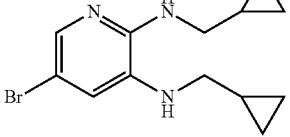 | I-65 | LCMS (AA): m/z = 352.4 (M + H) |

*Synthesized according to Step 1 of Example 17.

Example 18: N-{4-[1-(cyclopropylmethyl)-2,2-dioxido-1,3-dihydro[1,2,5]thiadiazolo[3,4-b]pyridin-6-yl]pyridin-2-yl}acetamide I-29

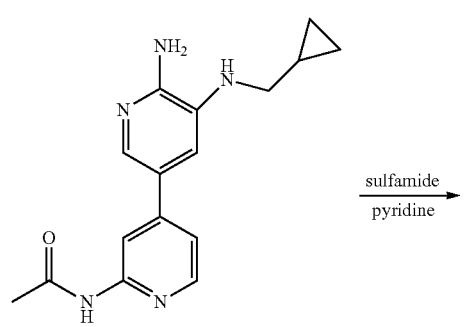

sulfamide
pyridine

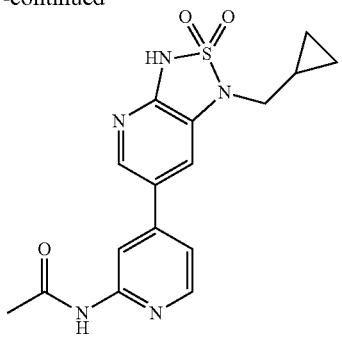

A mixture of N-{6-amino-5-[(cyclopropylmethyl)amino]-3,4'-bipyridin-2'-yl}acetamide (0.100 g, 0.336 mmol) and sulfamide (0.048 g, 0.504 mmol) in pyridine (0.71 mL, 8.8 mmol) was heated at reflux overnight. The reaction was cooled to rt and the pyridine removed by rotary evaporation. DMF was added and the mixture was filtered through celite. The supernatant was concentrated and purified by prep HPLC to yield N-{4-[1-(cyclopropylmethyl)-2,2-dioxido-1,3-dihydro[1,2,5]thiadiazolo[3,4-b]pyridin-6-yl]pyridin-2-yl}acetamide (76 mg, 62.9%). LCMS (FA): m/z=360.2 (M+H).

The compounds listed in the table below (Table 18) were prepared in an analogous fashion to that described above starting from the appropriate starting materials (i.e., I-53):

TABLE 18

| Example | Starting material | Compound No. | LCMS Data |
|---|---|---|---|
| 18A | 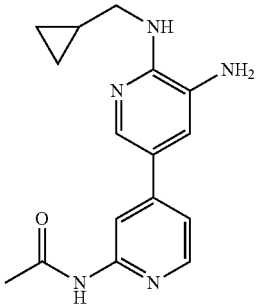 | I-68 | LCMS (FA): m/z = 360.2 (M + H) |

Example 19: N-{5-[(1E)-3-(4-fluorophenyl)-3-oxoprop-1-en-1-yl]-3,4'-bipyridin-2'-yl}acetamide I-188

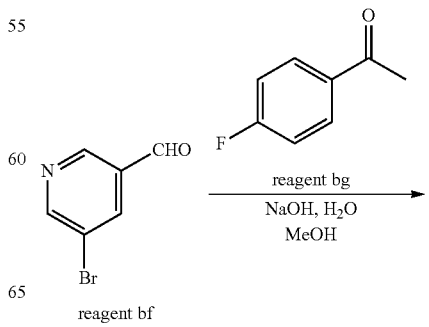

reagent bf reagent bg
NaOH, H₂O
MeOH

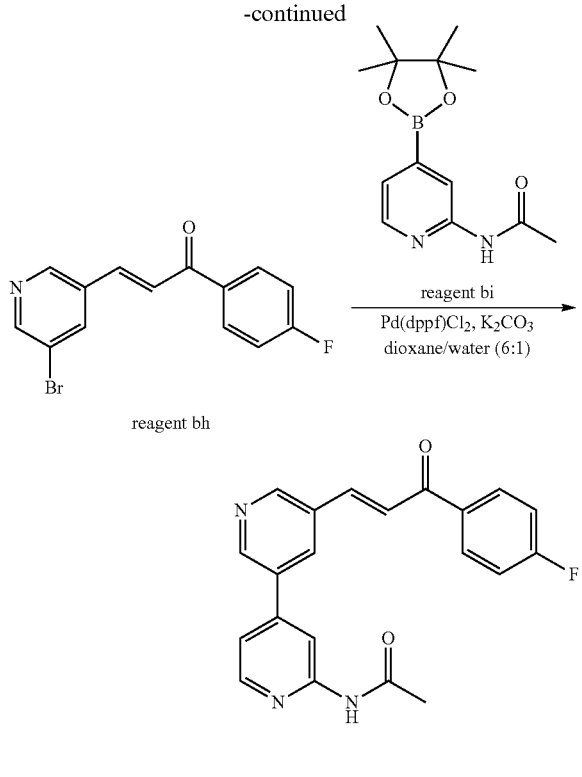

reagent bh

Step 1: (2E)-3-(5-bromopyridin-3-yl)-1-(4-fluorophenyl)prop-2-en-1-one

To a solution of 4'-fluoroacetophenone (0.302 mL, 2.49 mmol), 5-bromo-3-formylpyridine (0.500 g, 2.69 mmol) in water (7.5 mL) and MeOH (7.5 mL, 184 mmol) was added a solution of sodium hydroxide (0.075 g, 1.9 mmol) in water (0.747 mL, 41.4 mmol). A precipitate was observed within 2 min. After 2 h, the precipitate was filtered and collected to yield (2E)-3-(5-bromopyridin-3-yl)-1-(4-fluorophenyl)prop-2-en-1-one (67.4 mg, 88.4%). LCMS (AA): m/z=307.9 (M+H).

Step 2: N-{5-[(1E)-3-(4-fluorophenyl)-3-oxoprop-1-en-1-yl]-3,4'-bipyridin-2'-yl}acetamide The procedure described in Step 2 of Example 5 was followed with the following modification: The reaction was heated in the microwave at 120° C. for 30 min to yield N-{5-[(1E)-3-(4-fluorophenyl)-3-oxoprop-1-en-1-yl]-3,4'-bipyridin-2'-yl}acetamide (30 mg, 15.2%). LCMS (FA): m/z=362 (M+H).

The compound listed in the table below (Table 19) was prepared in an analogous fashion to that described above starting from the appropriate starting materials:

TABLE 19

| Example | Reagent | Starting material | Compound No. | LCMS Data |
|---|---|---|---|---|
| 19A | bf | ![F-phenyl-CHO] | I-198 | LCMS (AA): m/z = 362.2 (M + H) |

TABLE 19-continued

| Example | Reagent | Starting material | Compound No. | LCMS Data |
|---|---|---|---|---|
| | bg | ![Br-pyridyl ketone] | | |

Example 20: 2'-acetamido-6-amino-N,N-dimethyl-3,4'-bipyridine-5-carboxamide I-149

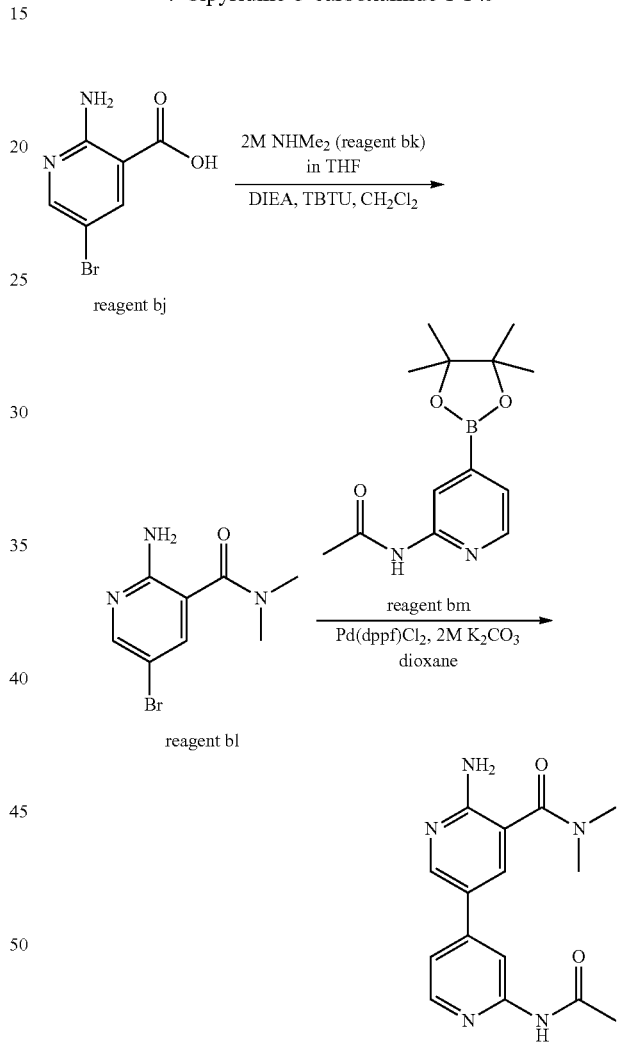

Step 1: 2-amino-5-bromo-N,N-dimethylnicotinamide

2-Amino-5-bromonicotinic acid (390 mg, 1.8 mmol) and DIEA (2.38 mL, 13.7 mmol) were allowed to stir in DCM (46.5 mL). TBTU (1.44 g, 4.49 mmol) was added and the reaction was allowed to stir at rt for 15 min. Dimethylamine (2 M in THF; 7.19 mL, 14.4 mmol) was added and the reaction was allowed to stir at rt overnight. The reaction mixture was diluted with water and extracted with DCM. The combined organic layers were washed with brine, dried over sodium sulfate and concentrated. The crude material residue was purified by column chromatography to yield 2-amino-5-bromo-N,N-dimethylnicotinamide (350 mg, 79.8%). LCMS (FA): m/z=244/246 (M+H).

Step 2: 2'-acetamido-6-amino-N,N-dimethyl-3,4'-bipyridine-5-carboxamide

A microwave tube was charged with N-[4-(4,4,5,5-tetramethyl-1,3,2-dioxaborolan-2-yl)pyridin-2-yl]acetamide (153 mg, 0.582 mmol), 2-amino-5-bromo-N,N-dimethylnicotinamide (115 mg, 0.471 mmol) and Pd(dppf)Cl$_2$ (24 mg, 0.030 mmol). 1,4-dioxane (3.7 mL, 47 mmol) and potassium carbonate (2 M in water; 0.471 mL, 0.942 mmol) were added. The tube was purged with nitrogen and heated at 130° C. for 30 min in the microwave. The mixture was partitioned between EtOAc and water. The aqueous layer was further extracted with EtOAc and the combined organic layers were washed with brine, dried over sodium sulfate and concentrated. The crude material was purified by prep HPLC to yield 2'-acetamido-6-amino-N,N-dimethyl-3,4'-bipyridine-5-carboxamide (75 mg, 53.2%). LCMS (AA): m/z=300.1 (M+H).

The compounds listed in the table below (Table 20) were prepared in an analogous fashion to that described above starting from the appropriate starting materials:

TABLE 20

| Example | Starting material | | Compound | |
|---|---|---|---|---|
| | Reagent | Chemical Structure | No. | LCMS Data |
| 20A | bk | HN-azetidine | I-200 | LCMS (FA): m/z = 312.4 (M + H) |
| 20B | bk | HN(Et)CH2CH= | I-27 | LCMS (AA): m/z = 328.5 (M + H) |
| 20C | bk | 4-methylpiperidine | I-81 | LCMS (FA): m/z = 354.5 (M + H) |
| 20D | bk | isoindoline | I-125 | LCMS (FA): m/z = 374.4 (M + H) |
| 20E | bk | piperidine | I-10 | LCMS (FA): m/z = 340.4 (M + H) |
| 20F | bk | pyrrolidine | I-15 | LCMS (FA): m/z = 326.4 (M + H) |
| 20G | bk | H$_2$N-bicyclopentyl | I-187 | LCMS (FA): m/z = 338.4 (M + H) |
| 20H | bk | H$_2$N-pyridyl | I-91 | LCMS (FA): m/z = 349.2 (M + H) |
| 20I | bk | H$_2$N— | I-57 | LCMS (AA): m/z = 286.3 (M + H) |
| 20J | bk | HN-piperazine-N— | I-79 | LCMS (AA): m/z = 355.4 (M + H) |
| 20K | bk | H$_2$N-CH$_2$-cyclopropyl | I-14 | LCMS (FA): m/z = 326.3 (M + H) |
| 20L | bk | H$_2$N-cyclopropyl | I-169 | LCMS (FA): m/z = 312.4 (M + H) |

TABLE 20-continued

| Example | Starting material | | Compound | |
|---|---|---|---|---|
| | Reagent | Chemical Structure | No. | LCMS Data |
| 20M | bk | 3-amino-4-methylpyridazine | I-121 | LCMS (FA): m/z = 364.4 (M + H) |
| 20N | bk | 3-fluoroaniline | I-82 | LCMS (FA): m/z = 366.4 (M + H) |
| 20O | bk | indoline | I-71 | LCMS (FA): m/z = 374.4 (M + H) |
| 20P | bk | 2-chloroaniline | I-136 | LCMS (FA): m/z = 382.4 (M + H) |
| 20Q | bk | 3,3-difluoropyrrolidine | I-60 | LCMS (FA): m/z = 362.4 (M + H) |
| 20R | bk | 4-aminotetrahydropyran | I-210 | LCMS (FA): m/z = 356.4 (M + H) |
| 20S | bk | morpholine | I-152 | LCMS (FA): m/z = 342.4 (M + H) |
| 20T | bk | (3S)-3-fluoropyrrolidine | I-157 | LCMS (FA): m/z = 344.4 (M + H) |
| 20U | bk | 2,3-difluoroaniline | I-179 | LCMS (FA): m/z = 384.3 (M + H) |
| 20V | bj | 5-bromo-2-(methylamino)nicotinic acid | I-22 | LCMS (AA): m/z = 314.4 (M + H) |
| | bk | dimethylamine | | |

TABLE 20-continued
| Example | Starting material Reagent | Chemical Structure | Compound No. | LCMS Data |
|---|---|---|---|---|
| 20W | bj | 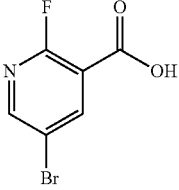 | I-162 | LCMS (FA): m/z = 328.3 (M + H) |
|  | bk |  |  |  |
| 20X | bj | 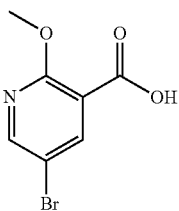 | I-127 | LCMS (FA): m/z = 315.4 (M + H) |
|  | bk |  |  |  |
| 20Y | bj | 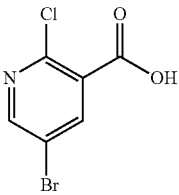 | I-213 | LCMS (FA): m/z = 319.4 (M + H) |
|  | bk |  |  |  |
| 20Z | bj | 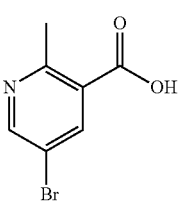 | I-75 | LCMS (FA): m/z = 299.3 (M + H) |
|  | bk |  |  |  |
| 20AA | bj | 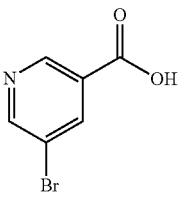 | I-48 | LCMS (AA): m/z = 285.3 (M + H) |
|  | bk |  |  |  |

TABLE 20-continued

| Example | Starting material Reagent | Starting material Chemical Structure | Compound No. | LCMS Data |
|---|---|---|---|---|
| 20AB | bj | 5-bromo-2-(methylamino)nicotinic acid | I-160 | LCMS (FA): m/z = 352.4 (M + H) |
|  | bk | 1-aminobicyclo[1.1.1]pentane (H2N-bicyclopentyl) |  |  |
| 20AC | bl | 2-amino-5-bromo-N-(bicyclo[1.1.1]pent-1-yl)-N-methylnicotinamide | I-303 | LCMS (FA): m/z = 388.3 (M + H) |
|  | bm | 4-(4,4,5,5-tetramethyl-1,3,2-dioxaborolan-2-yl)-N-(pyrimidin-4-yl)pyridin-2-amine |  |  |
| 20AD | bl | (5-bromo-2-methylpyridin-3-yl)(pyrrolidin-1-yl)methanone | I-315 | LCMS (FA): m/z = 375.2 (M + 1) |
|  | bm* | 4-(4,4,5,5-tetramethyl-1,3,2-dioxaborolan-2-yl)-N-(2-methylpyrimidin-4-yl)pyridin-2-amine |  |  |
| 20AE | bl | azetidin-1-yl(5-bromo-2-chloropyridin-3-yl)methanone | I-232 | LCMS (FA): m/z = 381.0 (M + H) |

TABLE 20-continued

| | | Starting material | Compound | |
|---|---|---|---|---|
| Example | Reagent | Chemical Structure | No. | LCMS Data |
| | bm* | [pyridine with pinacol boronate and NH-linked 2-methylpyrimidine] | | |
| 20AF** | bk | [H₂N-C(=NH)-NH-C(=O)-O-tBu] | I-216 | LCMS (AA): m/z = 350.1 (M + H) |
| | bm | [pyridine with pinacol boronate and NH-linked pyrimidine] | | |
| 20AG | bk | [H₂N-bicyclobutane] | I-298 | LCMS (FA): m/z = 374.3 (M + H) |
| | bm | [pyridine with pinacol boronate and NH-linked pyrimidine] | | |
| 20AH | bl | [2-methyl-5-bromo-nicotinamide] | I-280 | LCMS (FA): m/z = 321.2 (M + H) |
| | bm* | [pyridine with pinacol boronate and NH-linked 2-methylpyrimidine] | | |

TABLE 20-continued

| Example | Starting material Reagent | Chemical Structure | Compound No. | LCMS Data |
|---|---|---|---|---|
| 20AI | bl | 2-methyl-5-bromo-N,N-diethylnicotinamide | I-302 | LCMS (FA): m/z = 377.0 (M + H) |
| | bm* | 4-(4,4,5,5-tetramethyl-1,3,2-dioxaborolan-2-yl)-N-(2-methylpyrimidin-4-yl)pyridin-2-amine | | |
| 20AJ | bl | (5-bromo-2-methylpyridin-3-yl)(piperidin-1-yl)methanone | I-262 | LCMS (FA): m/z = 389.2 (M + H) |
| | bm* | 4-(4,4,5,5-tetramethyl-1,3,2-dioxaborolan-2-yl)-N-(2-methylpyrimidin-4-yl)pyridin-2-amine | | |
| 20AK^^ | bj | 5-bromo-2-methylnicotinic acid | I-485 | LCMS (FA): m/z = 397.2 (M + H) |
| | bk*** | 2,4-difluoroaniline | | |
| | bl | 5-bromo-N-(2,4-difluorophenyl)-2-methylnicotinamide | | |

TABLE 20-continued

| Example | Starting material Reagent | Chemical Structure | Compound No. | LCMS Data |
|---|---|---|---|---|
| | bl'^ | 5-bromo-2-methyl-N-(2,4-difluorophenyl)-N-methylnicotinamide | | |
| 20AL^^ | bj | 5-bromo-2-methylnicotinic acid | I-388 | LCMS (FA): m/z = 377.2 (M + H) |
| | bk | bicyclo[1.1.1]pentan-1-amine | | |
| | bl | 5-bromo-N-(bicyclo[1.1.1]pentan-1-yl)-2-methylnicotinamide | | |
| | bl'* | 5-bromo-N-(bicyclo[1.1.1]pentan-1-yl)-N,2-dimethylnicotinamide | | |
| | bm | N-(4-(4,4,5,5-tetramethyl-1,3,2-dioxaborolan-2-yl)pyridin-2-yl)cyclopropanecarboxamide | | |
| 20AM | bj | 5-bromo-4-methyl-2-methoxynicotinic acid | I-423 | LCMS (FA): m/z = 413.2 (M + H) |
| | bk*** | N-methyl-2,4-difluoroaniline | | |

TABLE 20-continued
| Example | Reagent | Starting material Chemical Structure | Compound No. | LCMS Data |
|---|---|---|---|---|
| | bl^ | 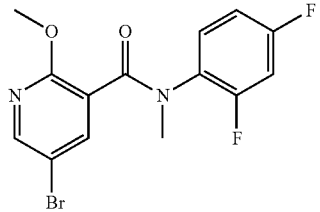 [SMILES: COc1ncc(Br)cc1C(=O)N(C)c1ccc(F)cc1F] | | |
| 20AN | bj | 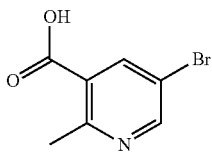 | I-431 | LCMS (FA): m/z = 383.2 (M + H) |
| | bk*** | 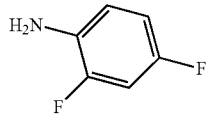 | | |
| | bl^ | 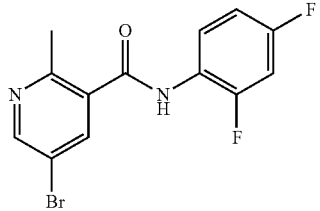 [SMILES: Cc1ncc(Br)cc1C(=O)Nc1ccc(F)cc1F] | | |
| 20AO** | bj | 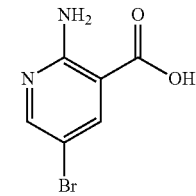 | I-409 | LCMS (FA): m/z = 314.1 (M + H) |
| | bk | 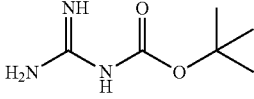 | | |
| | bl | 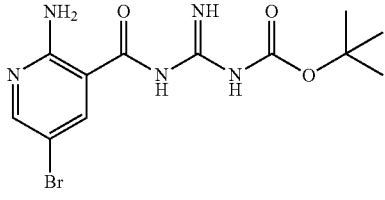 [SMILES: CC(C)(C)OC(=O)NC(=N)NC(=O)c1cc(Br)cnc1N] | | |
| 20AP | bj | 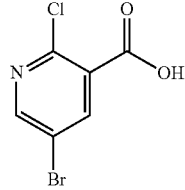 | I-434 | LCMS (FA): m/z = 345.0 (M + H) |
| | bk | 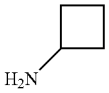 | | |

TABLE 20-continued

| Example | Reagent | Starting material Chemical Structure | Compound No. | LCMS Data |
|---|---|---|---|---|
| | bl* | 2-chloro-5-bromo-pyridine-3-carbonyl azetidine | | |
| | bm | 2-acetamido-5-methyl-4-(pinacolboronate)pyridine | | |
| 20AQ^^ | bj | 5-bromo-2-methylnicotinic acid | I-346 | LCMS (FA): m/z = 447.1 (M + H) |
| | bk | 2,4-difluoroaniline | | |
| | bl | 5-bromo-N-(2,4-difluorophenyl)-2-methylnicotinamide | | |
| | bl' | 5-bromo-N-(2,4-difluorophenyl)-N,2-dimethylnicotinamide | | |
| | bm* | N-(2-methylpyridin-4-yl)-4-(pinacolboronate)pyridin-2-amine | | |

TABLE 20-continued

| | Starting material | | Compound | |
|---|---|---|---|---|
| Example | Reagent | Chemical Structure | No. | LCMS Data |
| 20AR | bj | (2-methyl-5-bromo-nicotinic acid) | I-495 | LCMS (FA): m/z = 389.2 (M + H) |
| | bk | (3,3-dimethylazetidine) | | |
| | bl | (2-methyl-5-bromo-pyridine-3-carbonyl-3,3-dimethylazetidine) | | |
| | bm* | (pinacol boronate of 2-((2-methylpyrimidin-4-yl)amino)pyridine) | | |
| 20AS | bj | (5-bromonicotinic acid) | I-408 | LCMS (FA): m/z = 383.1 (M + H) |
| | bk | (3,3-difluoroazetidine) | | |
| | bl | (5-bromo-pyridine-3-carbonyl-3,3-difluoroazetidine) | | |

TABLE 20-continued
| Example | Reagent | Starting material Chemical Structure | Compound No. | LCMS Data |
|---|---|---|---|---|
| | bm* | 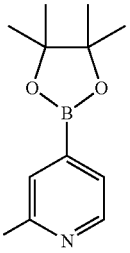 | | |
| 20AT | bj | 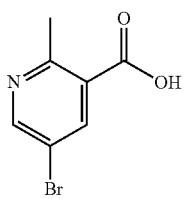 | I-415 | LCMS (FA): m/z = 403.1 (M + H) |
| | bk | 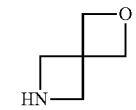 | | |
| | bl | 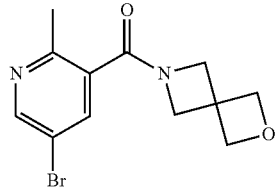 | | |
| | bm* | 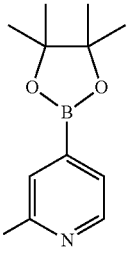 | | |
| 20AU | bj | 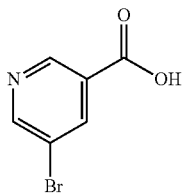 | I-413 | LCMS (FA): m/z = 409.2 (M + H) |
| | bk | 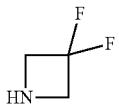 | | |

TABLE 20-continued

| | | Starting material | Compound | |
|---|---|---|---|---|
| Example | Reagent | Chemical Structure | No. | LCMS Data |
| | bl | (5-bromopyridin-3-yl)(3,3-difluoroazetidin-1-yl)methanone structure | | |
| | bm* | 2-cyclopropyl-N-(4-(4,4,5,5-tetramethyl-1,3,2-dioxaborolan-2-yl)pyridin-2-yl)pyrimidin-4-amine structure | | |

*Step 2 conditions use SiliaCat DPP-Pd instead of Pd(dppf)Cl$_2$ and microwave irradiation
**Deprotection of the BOC group according to Example 20AF (see below) employed to generate I-216 and I-XXX
***In Step 1, HATU, DIEA, and DMF were used with microwave irradiation (120° C.)
^Step 2 conditions use Pd(PPh$_3$)$_4$, 1.0 M Na$_2$CO$_3$; toluene, and EtOH under microwave irradiation
^^Synthesis of reagent bl' shown in Table 20a.

Example 20AF: 6-Amino-N-carbamimidoyl-2'-(pyrimidin-4-ylamino)-3,4'-bipyridine-5-carboxamide I-216

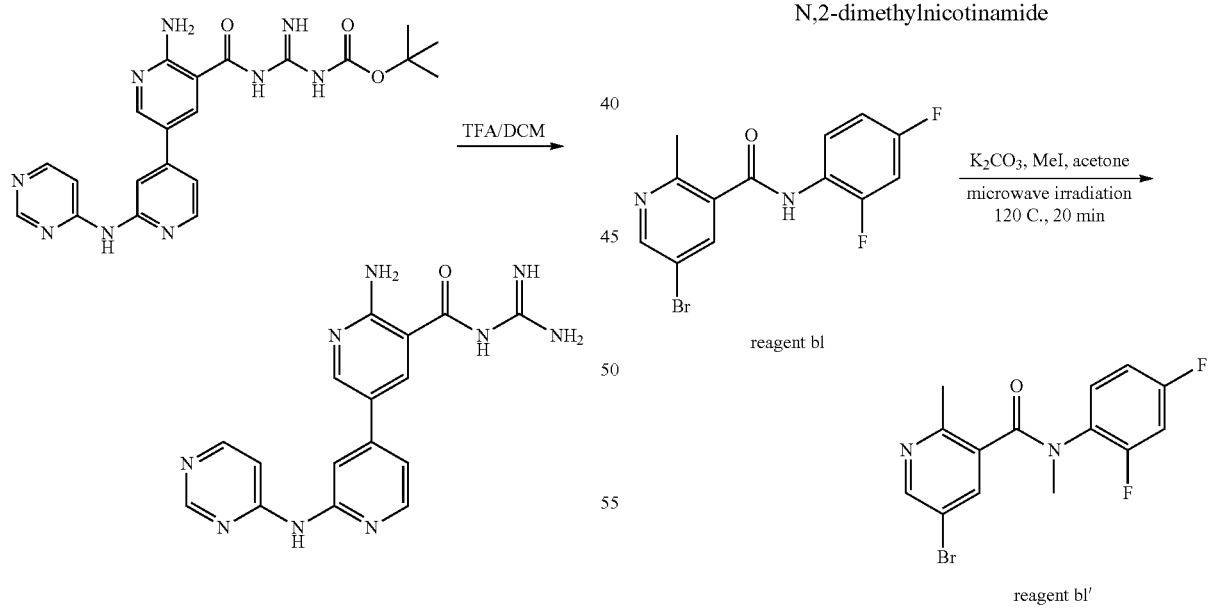

To a solution of crude tert-butyl (N-{[6-amino-2'-(pyrimidin-4-ylamino)-3,4'-bipyridin-5-yl]carbonyl}carbamimidoyl)carbamate (300 mg, 327.4 mmol) in DCM (5 mL) was added TFA (5 mL) at rt. The reaction mixture was allowed to stir for 12 h at rt. The reaction mixture was then concentrated. The crude compound was purified by column chromatography to provide 6-amino-N-carbamimidoyl-2'-(pyrimidin-4-ylamino)-3,4'-bipyridine-5-carboxamide I-216 (58 mg, 30%). LCMS (FA): m/z=350.1 (M+H).

Synthesis of Reagents bl' for Examples 20AK, 20AL and 20AX: 5-bromo-N-(2,4-difluorophenyl)-N,2-dimethylnicotinamide A mixture of 5-bromo-N-(2,4-difluorophenyl)-2-methylnicotinamide (0.110 g, 0.336 mmol) and K$_2$CO$_3$ (0.140 g, 1.01 mmol) were placed in a microwave vial and sealed. The reaction vessel was evacuated with argon, and acetone (6.0 mL) was added. The vessel was again evacuated with argon, methyl iodide (0.10 mL, 1.68 mmol) was added, and the reaction was subjected to microwave irradiation at 120° C.

for 20 min. The crude reaction material was mixed with 1 g of silica and the solvent was removed. The residue was purified by column chromatography to give 5-bromo-N-(2,4-difluorophenyl)-N,2-dimethylnicotinamide (51.8 mg, 45.2%). LCMS (FA): m/z=342.1 (M+H).

TABLE 20a

| Reagent bl' | | Starting Material | | LCMS Data for bl' | Intermediate |
|---|---|---|---|---|---|
| | Reagent | Reagent bl structure | | | |
| (structure) | bl | (structure) | | LCMS (FA): m/z = 342.1 (M + H) | From Examples 20AK (I-485) and 20AQ (I-346) |
| (structure) | bl | (structure) | | LCMS (FA): m/z = 297.0 (M + H) | From example 20BB |

Example 21: N-(2'-acetamido-3,4'-bipyridin-5-yl)benzamide I-13

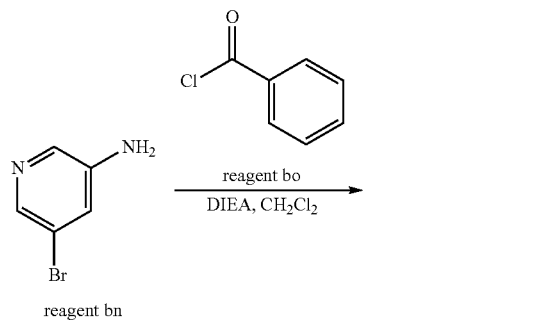

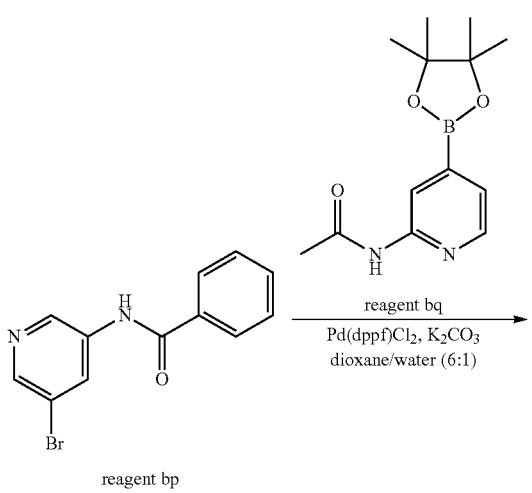

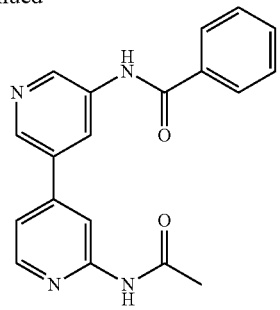

Step 1: N-(5-bromopyridin-3-yl)benzamide

3-Amino-5-bromopyridine (0.589 g, 3.40 mmol), DCM (33.1 mL), DIEA (1.18 mL, 6.81 mmol), and benzoyl chloride (0.593 mL, 5.11 mmol) were combined and allowed to stir at rt overnight. The reaction mixture was concentrated by rotary evaporation and diluted with EtOAc and 1 N NaOH (aq). The organic layer was washed with water and brine, dried over sodium sulfate and concentrated by rotary evaporation. The crude material was purified by column chromatography to yield N-(5-bromopyridin-3-yl)benzamide (0.679 g, 72.0%). LCMS (AA): m/z=277/279 (M+H).

Step 2: N-(2'-acetamido-3,4'-bipyridin-5-yl)benzamide

To a reaction vial were added N-[4-(4,4,5,5-tetramethyl-1,3,2-dioxaborolan-2-yl)pyridin-2-yl]acetamide (0.142 g, 0.544 mmol)), N-(5-bromopyridin-3-yl)benzamide (0.196 g, 0.707 mmol), potassium carbonate (150 mg, 1.09 mmol) and dioxane-water (6:1 mixture of 1,4-dioxane:water; 4.80 mL). The mixture was flushed with argon and Pd(dppf)Cl$_2$ (22.4 mg, 0.027 mmol) was added. The reaction was sealed and heated at 120° C. in an oil bath for 18 h. The reaction was filtered through celite and the celite was washed with DCM. The filtrate was concentrated and the residue was purified by column chromatography to yield N-(2'-acetamido-3,4'-bipyridin-5-yl)benzamide (60 mg, 33.3%). LCMS (FA): m/z=333.1 (M+H).

The compounds listed in the table below (Table 21) were prepared in an analogous fashion to that described above starting from the appropriate starting materials:

TABLE 21

| Example | Reagent | Starting material Chemical Structure | Compound No. | LCMS Data |
|---|---|---|---|---|
| 21A* | bo | phenylacetyl chloride | I-106 | LCMS (FA): m/z = 347.1 |
| 21B | bn | 3-amino-5-bromo-2-methylpyridazine | I-115 | LCMS (FA): m/z = 383.4 |
|  | bo | 2,4-difluorobenzoyl chloride |  |  |
| 21C | bn | 3-amino-5-bromo-2-methylpyridine | I-193 | LCMS (AA): m/z = 285.5 |
|  | bo | acetyl chloride |  |  |
| 21D^ | bo^^ | 2,4-difluorobenzoyl chloride | I-419 | LCMS (FA): m/z = 369.1 |
| 21E^ | bn | 3-amino-5-bromo-2-methoxypyridine | I-347 | LCMS (FA): m/z = 399.5 |
|  | bo^^ | 2,4-difluorobenzoyl chloride |  |  |
| 21F | bn | 5-amino-6-bromopyrazolo[1,5-a]pyridine | I-450 | LCMS (FA): m/z = 360.2 |

TABLE 21-continued

| Example | Reagent | Starting material Chemical Structure | Compound No. | LCMS Data |
|---|---|---|---|---|
| | bo | acetyl chloride | | |
| | bp | N-(6-bromopyrazolo[1,5-a]pyridin-4-yl)acetamide | | |
| | bq*** | 2-methyl-N-(4-(4,4,5,5-tetramethyl-1,3,2-dioxaborolan-2-yl)pyridin-2-yl)pyrimidin-4-amine | | |
| 21G | bn | 6-bromopyrazolo[1,5-a]pyridin-4-amine | I-371 | LCMS (FA): m/z = 386.4 |
| | bo | acetyl chloride | | |
| | bp | N-(6-bromopyrazolo[1,5-a]pyridin-4-yl)acetamide | | |
| | bq^^^ | 2-cyclopropyl-N-(4-(4,4,5,5-tetramethyl-1,3,2-dioxaborolan-2-yl)pyridin-2-yl)pyrimidin-4-amine | | |

*In Step 1, TEA was used instead of DIEA. The reaction was heated at 50° C. overnight instead of at rt.
**In Step 1, HATU, DIEA, and DMF were used with microwave irradiation (120° C.)
***In Step 2, XPhosG3 was used with K$_3$PO$_4$ in 1,4-dioxane; microwave irradiation (130° C.)
^Step 2 conditions use Pd(PPh$_3$)$_4$, 1.0 M Na$_2$CO$_3$; toluene, and EtOH under microwave irradiation
^^Step 1 conditions use pyridine instead of DIEA
^^^Step 2 conditions use microwave irradiation (150° C.)

Example 22: 2'-Acetamido-N-(2,4-difluorophenyl)-6-(dimethylamino)-N-methyl-[3,4'-bipyridine]-5-carboxamide I-174

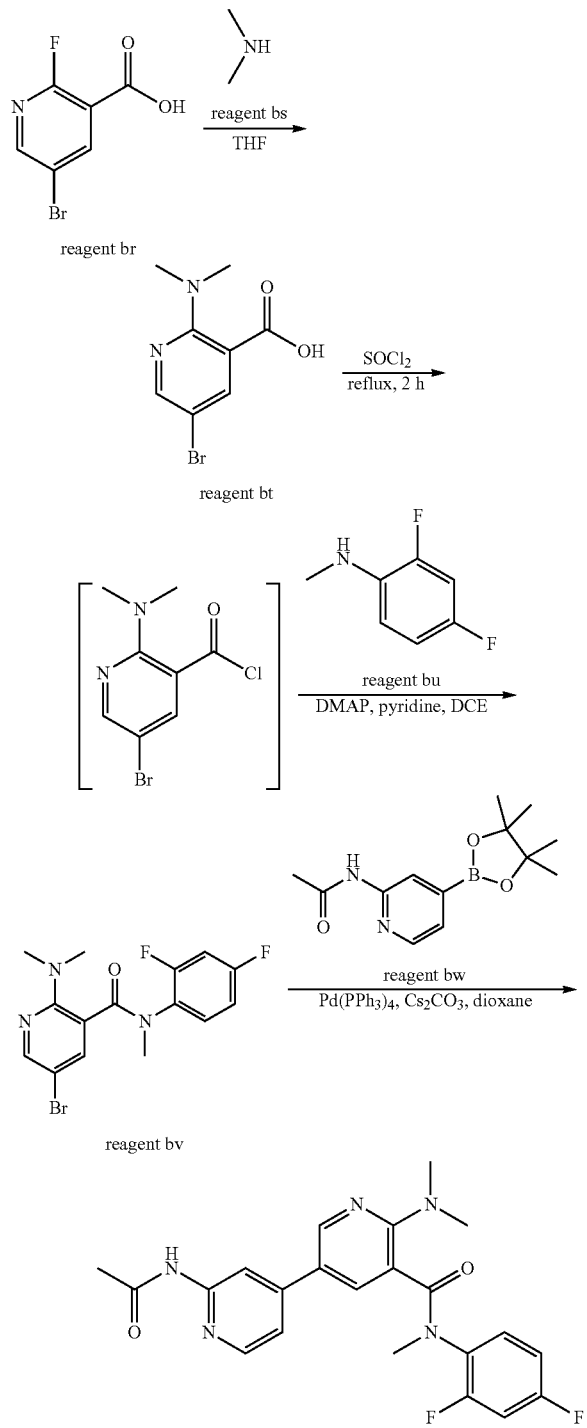

Step 1: 5-bromo-2-(dimethylamino)nicotinic acid

5-Bromo-2-fluoronicotinicacid (450 mg, 2.0 mmol) and DIEA (2.71 mL, 15.6 mmol) were dissolved in THF (67.0 mL). The reaction mixture was allowed to stir at rt for 15 min. Then, dimethylamine (2.0 M in THF, 8.18 mL, 16.4 mmol) was added and the reaction was allowed to stir at rt for 3 h. The reaction was concentrated to dryness and used in the next step without purification. LCMS (FA): m/z=245.1/247.2 (M+H).

Step 2: 5-bromo-N-(2,4-difluorophenyl)-2-(dimethylamino)-N-methylnicotinamide To a solution of 5-bromo-2-(dimethylamino)nicotinic acid (192 mg, 0.783 mmol) in thionyl chloride (10 mL) was added DMF (0.5 mL). The reaction mixture was allowed to stir at reflux for 2 h. Then, the mixture was evaporated to dryness and used without purification. To the mixture, N-1-methyl-2,4-difluoroaniline (168 mg, 1.18 mmol), DMAP (19.1 mg, 0.157 mmol), pyridine (317 uL, 3.92 mmol) and DCE (25.6 mL) were added. The reaction mixture was allowed to stir at 70° C. for 3 h. The reaction mixture was then quenched with water and then diluted with DCM. The organic layer was washed with brine, dried over magnesium sulfate, filtered and concentrated. The crude material was purified by column chromatography to yield 5-bromo-N-(2,4-difluorophenyl)-2-(dimethylamino)-N-methylnicotinamide (157 mg, 54.1%). LCMS (FA): m/z=370.3/372.3 (M+H).

Step 3: 2'-Acetamido-N-(2,4-difluorophenyl)-6-(dimethylamino)-N-methyl-[3,4'-bipyridine]-5-carboxamide To a solution of N-[4-(4,4,5,5-tetramethyl-1,3,2-dioxaborolan-2-yl)pyridin-2-yl]acetamide (164 mg, 0.628 mmol) in 1,4-dioxane (6.3 mL) and water (0.2 mL, 9 mmol) were added 5-bromo-N-(2,4-difluorophenyl)-2-(dimethylamino)-N-methylnicotinamide (155 mg, 0.418 mmol), tetrakis (triphenylphosphine) palladium (32.0 mg, 0.026 mmol) and cesium carbonate (409 mg, 1.26 mmol). The reaction mixture was heated at 140° C. for 30 min under microwave irradiation. Then, the reaction mixture was diluted with EtOAc. The organic layer was washed with brine, dried over magnesium sulfate, filtered and concentrated. The crude material was purified by prep HPLC to yield 2'-acetamido-N-(2,4-difluorophenyl)-6-(dimethylamino)-N-methyl-[3,4'-bipyridine]-5-carboxamide (91 mg, 51.0%). LCMS (FA): m/z=426.5 (M+H).

The compound listed in the table below (Table 22) were prepared in an analogous fashion to that described above starting from the appropriate starting materials:

TABLE 22

| Example | Reagent bu | Compound No. | LCMS Data |
|---|---|---|---|
| 22A | ![H2N-2,4-difluorophenyl] | I-112 | LCMS (FA): m/z = 412.5 (M + H) |

Example 22B: 2'-Acetamido-N-(bicyclo[1.1.1]pent-1-yl)-6-(dimethylamino)-3,4'-bipyridine-5-carboxamide (I-283)

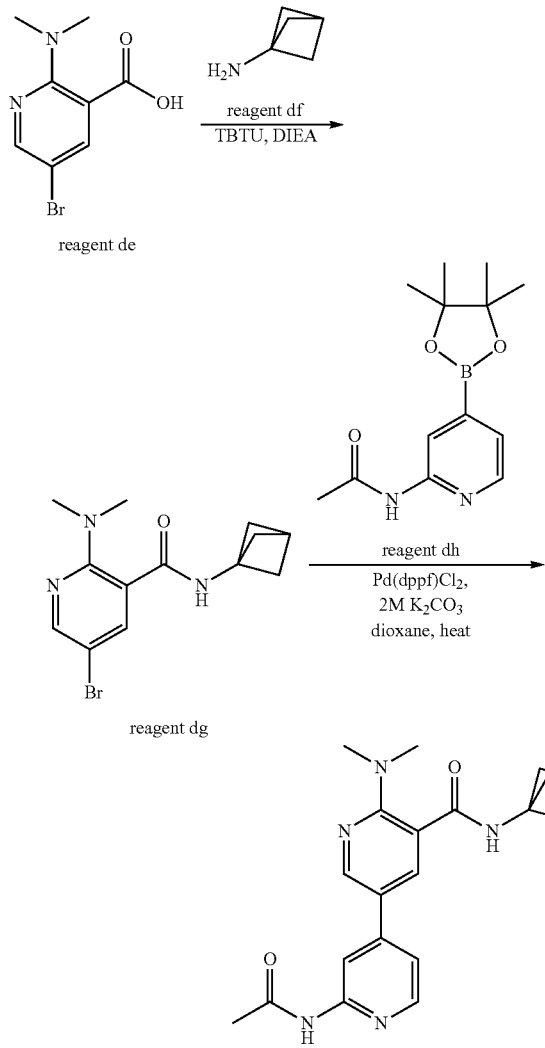

Step 1: N-(Bicyclo[1.1.1]pent-1-yl)-5-bromo-2-(dimethylamino)nicotinamide

To a solution of 5-bromo-2-(dimethylamino)nicotinic acid (0.20 g, 0.82 mmol) in DCM (8 mL) and DIEA (0.21 mL, 1.22 mmol) were added TBTU (0.76 g, 2.37 mmol) and bicyclo[1.1.1]pentan-1-amine hydrochloride salt (117 mg, 0.98 mmol). The reaction mixture was allowed to stir at rt overnight. The reaction mixture was partitioned into water and DCM. The organic solutions were separated, washed with brine, dried over MgSO$_4$, filtered and concentrated. The residue was purified by column chromatography to give N-(bicyclo[1.1.1]pent-1-yl)-5-bromo-2-(dimethylamino)nicotinamide (0.20 g, 77%). LCMS (FA): m/z=310.3/312.3 (M+H).

Step 2: 2'-Acetamido-N-(bicyclo[1.1.1]pent-1-yl)-6-(dimethylamino)-3,4'-bipyridine-5-carboxamide To a vial were added N-[4-(4,4,5,5-tetramethyl-1,3,2-dioxaborolan-2-yl)pyridin-2-yl]acetamide (198 mg, 0.75 mmol) and N-(bicyclo[1.1.1]pent-1-yl)-5-bromo-2-(dimethylamino)nicotinamide (0.195 g, 0.629 mmol), Pd(dppf)Cl$_2$, complex with DCM (1:1) (32 mg, 0.039 mmol), 2.0 M potassium carbonate in water (0.63 mL) and 1,4-dioxane (4.9 mL). The vial was thoroughly flushed with N$_2$ and then subjected to microwave irradiation at 130° C. for 30 min. The reaction mixture was partitioned into EtOAc and water. The aqueous solutions were extracted twice. The organic solutions were combined, washed with brine, dried over MgSO$_4$, filtered and concentrated. The residue was purified by column chromatography to give 2'-acetamido-N-(bicyclo[1.1.1]pent-1-yl)-6-(dimethylamino)-3,4'-bipyridine-5-carboxamide I-283 (0.20 g, 80%) LCMS (FA): m/z=366.2 (M+1).

Example 22C: N-(bicyclo[1.1.1]pent-1-yl)-6-(dimethylamino)-N-methyl-2'-((2-methylpyrimidin-4-yl)amino)-3,4'-bipyridine-5-carboxamide (I-306)

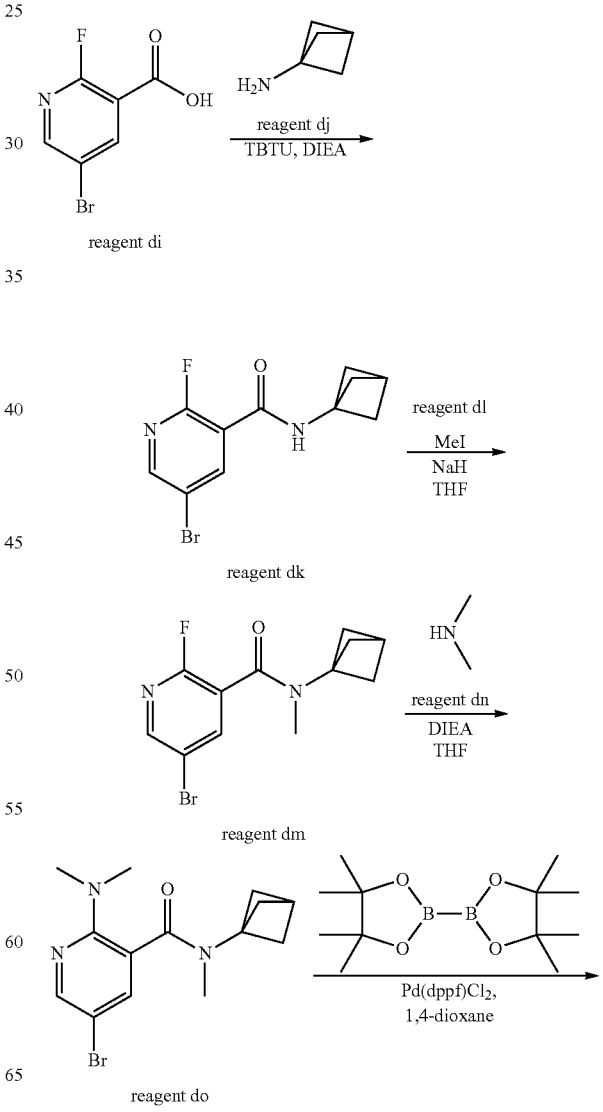

-continued

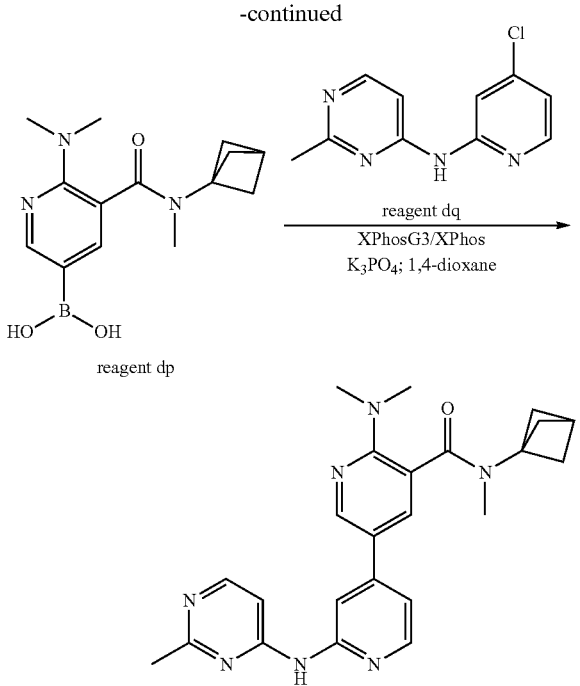

reagent dp

Step 1: N-(bicyclo[1.1.1]pent-1-yl)-5-bromo-2-fluoronicotinamide

To 5-bromo-2-fluoronicotinic acid (1.00 g, 4.55 mmol) in DCM (43 mL) were added DIEA (1.19 mL, 6.82 mmol), TBTU (4.23 g, 13.2 mmol) and bicyclo[1.1.1]pentan-1-amine hydrochloride salt (652 mg, 5.45 mmol). The reaction mixture was allowed to stir at rt overnight. The reaction mixture was diluted with DCM and water. The aqueous solution was extracted twice. The organic solutions were combined, washed with brine, dried over MgSO₄, filtered and concentrated under reduced pressure. The residue was purified by column chromatography to give N-(bicyclo[1.1.1]pent-1-yl)-5-bromo-2-fluoronicotinamide as a white solid (0.80 g, 62%). LCMS (FA): m/z=285.0/287.0 (M+H).

Step 2: N-(bicyclo[1.1.1]pent-1-yl)-5-bromo-2-fluoro-N-methylnicotinamide

N-(bicyclo[1.1.1]pent-1-yl)-5-bromo-2-fluoronicotinamide (500 mg, 1.75 mmol) was dissolved in THF (15 mL). The reaction mixture was cooled to 0° C. and sodium hydride (60% dispersion in mineral oil, 175 mg, 4.38 mmol) was added. To the reaction mixture, a solution of methyl iodide (0.33 mL, 5.27 mmol) in THF (0.1 mL) was added slowly. The reaction mixture was allowed to stir for 4 h. The reaction mixture was concentrated under reduced pressure and the residue was diluted with 1N HCl and extracted with Et₂O. The organic solutions were separated, washed with brine, dried over MgSO₄, filtered and concentrated under reduced pressure. The residue was purified by column chromatography to give N-(bicyclo[1.1.1]pent-1-yl)-5-bromo-2-fluoro-N-methylnicotinamide (0.44 g, 83%). LCMS (FA): m/z=299.0 (M+H).

Step 3: N-(bicyclo[1.1.1]pent-1-yl)-5-bromo-2-(dimethylamino)-N-methylnicotinamide To N-(bicyclo[1.1.1]pent-1-yl)-5-bromo-2-fluoro-N-methylnicotinamide (0.15 g, 0.50 mmol) were added THF (6.4 mL) and DIEA (0.26 mL, 1.50 mmol). To this stirred solution, 2.0 M of dimethylamine in THF (1.50 mL, 3.00 mmol) was added. The reaction mixture was allowed to stir overnight and was then concentrated. The residue was purified by column chromatography to give N-(bicyclo[1.1.1]pent-1-yl)-5-bromo-2-(dimethylamino)-N-methylnicotinamide (0.15 g, 78%). LCMS (FA): m/z=324.1/326.1 (M+H).

Step 4: (5-(bicyclo[1.1.1]pent-1-yl(methyl)carbamoyl)-6-(dimethylamino)pyridin-3-yl)boronic acid To a flask were added N-(bicyclo[1.1.1]pent-1-yl)-5-bromo-2-(dimethylamino)-N-methylnicotinamide (90 mg, 0.28 mmol), 4,4,4',4',5,5,5',5'-octamethyl-2,2'-bi-1,3,2-dioxaborolane (88 mg, 0.35 mmol), potassium acetate (80 mg, 0.82 mmol), Pd(dppf)Cl₂ (27 mg, 0.033 mmol) and 1,4-dioxane (3.1 mL). The flask was flushed with N₂ and the reaction mixture was allowed to stir at 90° C. overnight. The reaction mixture was filtered through celite. The filter cake was washed with fresh EtOAc. The filtrate was concentrated under reduced pressure to give a viscous dark brown oil which was used in the next step without purification. LCMS (FA): m/z=290.1 (M+H).

Step 5: N-(bicyclo[1.1.1]pent-1-yl)-6-(dimethylamino)-N-methyl-2'-((2-methylpyrimidin-4-yl)amino)-[3,4'-bipyridine]-5-carboxamide To a vial were added (5-(bicyclo[1.1.1]pent-1-yl(methyl)carbamoyl)-6-(dimethylamino)pyridin-3-yl)boronic acid (65 mg, 0.22 mmol), N-(4-chloropyridin-2-yl)-2-methylpyrimidin-4-amine (59 mg, 0.27 mmol), XPhos (3.3 mg, 0.007 mmol), XPhosG3 (6.4 mg, 0.007 mmol), 0.5 M potassium phosphate in water (0.91 mL, 0.45 mmol) and 1,4-dioxane (0.45 mL). The vial was thoroughly flushed with N₂ and then was subjected to microwave irradiation at 120° C. for 30 min. The reaction mixture was partitioned into EtOAc and water. The aqueous solution was extracted twice. The organic solutions were combined, washed with brine, dried over MgSO₄, filtered and concentrated under reduced pressure. The crude compound was purified by column chromatography to give N-(bicyclo[1.1.1]pent-1-yl)-6-(dimethylamino)-N-methyl-2'-((2-methylpyrimidin-4-yl)amino)-3,4'-bipyridine-5-carboxamide I-306 (0.042 g, 44%) with 90% purity. LCMS (FA): m/z=430.2 (M+H).

The compounds listed in the table below (Table 23) were prepared in an analogous fashion to that described above from the appropriate starting materials:

TABLE 23

| Example | Reagent | Starting Material Chemical Structure | Compound No. | LCMS Data |
|---|---|---|---|---|
| 22D | dq* | (structure with Cl) | I-284 | LCMS (FA): m/z = 416.2 (M + H) |
| 22E | dq* | (structure with Cl) | I-222 | LCMS (FA): m/z = 402.2 (M + H) |

TABLE 23-continued

| Example | Reagent | Starting Material Chemical Structure | Compound No. | LCMS Data |
|---|---|---|---|---|
| 22F | dn dq* | H₂N (structure); acetamide-pyridine-boronate pinacol ester | I-449 | LCMS (FA): m/z = 366.2 (M + H) |
| | dn do** | H₂N (structure); 2-(methylamino)-N-bicyclobutyl-N-methyl-5-bromopyridine-3-carboxamide | | |

*Step 5 conditions use Pd(dppf)Cl₂ and K₂CO₃ instead of XPhosG3/XPhos and K₃PO₄

**In Step 4, the final product for example 22F is generated from direct reaction of reagent do with reagent dq using Pd(dppf)Cl₂ and K₂CO₃ instead of XPhosG3/XPhos and K₃PO₄

Example 23: N-{4-[1-(cyclopropylsulfonyl)-1H-pyrazolo[4,3-b]pyridin-6-yl]pyridin-2-yl}acetamide and N-{4-[2-(cyclopropylsulfonyl)-2H-pyrazolo[4,3-b]pyridin-6-yl]pyridin-2-yl}acetamide I-2 and I-105

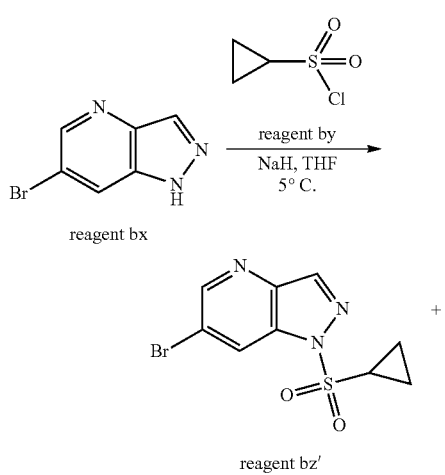

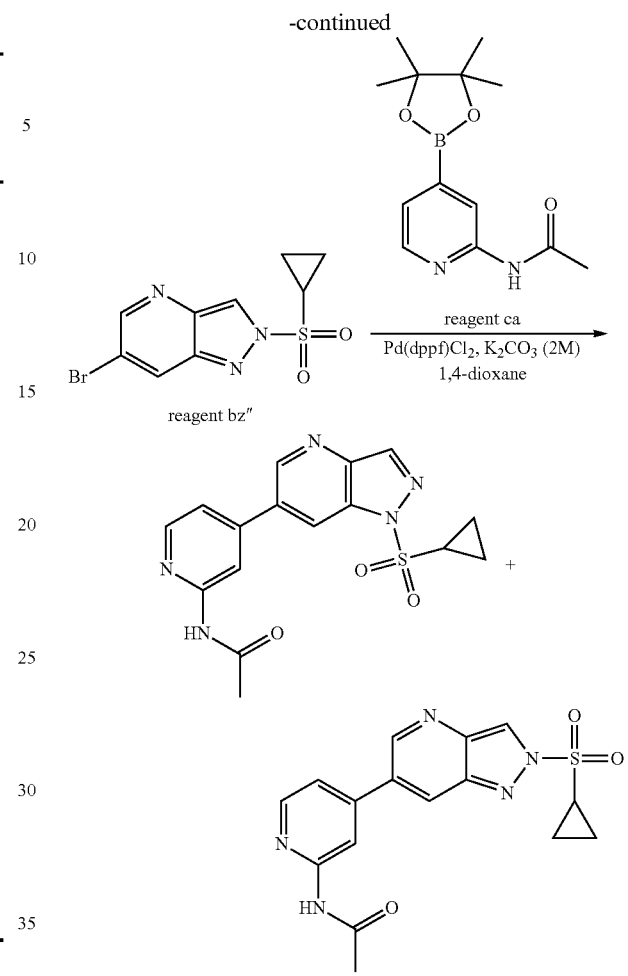

Step 1: 6-bromo-1-(cyclopropylsulfonyl)-1H-pyrazolo[4,3-b]pyridine and 6-bromo-2-(cyclopropylsulfonyl)-2H-pyrazolo[4,3-b]pyridine To a solution of 6-bromo-1H-pyrazolo[4,3-b]pyridine (145 mg, 0.732 mmol) in THF (4.1 mL) at rt was added NaH (60:40 sodium hydride:mineral oil, 37.0 mg, 0.925 mmol). The mixture was allowed to stir for 5 min and then cooled in ice bath. Cyclopropanesulfonylchloride (95.0 uL, 0.919 mmol) was added dropwise and the mixture was allowed to stir for 2 h while the bath temperature warmed to between 10-15° C. The reaction mixture was quenched with ammonium chloride (2M aq. solution, 5 mL) and was partitioned between EtOAc and water. The aqueous layer was further extracted with EtOAc and the combined organic layers were washed with brine, dried over sodium sulfate, filtered and concentrated by rotary evaporation. An LCMS of the crude material showed ~4:1 mixture of isomers. The residue was purified by column chromatography to provide a mixture of 6-bromo-1-(cyclopropylsulfonyl)-1H-pyrazolo[4,3-b]pyridine LCMS (AA): m/z=304.3 (M+H), second peak, and 6-bromo-2-(cyclopropylsulfonyl)-2H-pyrazolo[4,3-b]pyridine LCMS (AA): m/z=304.3 (M+H), first peak (combined yield 201 mg, 90.8%).

Step 2: N-{4-[1-(cyclopropylsulfonyl)-1H-pyrazolo[4,3-b]pyridin-6-yl]pyridin-2-yl}acetamide and N-{4-[2-(cyclopropylsulfony)-2H-pyrazolo[4,3-b]pyridin-6-yl]pyridin-2-yl}acetamide A microwave vial was charged with N-[4-(4,4,5,5-tetramethyl-1,3,2-dioxaborolan-2-yl)pyridin-2-yl]acetamide (208 mg, 0.794 mmol), Pd(dppf)Cl$_2$ (33 mg, 0.040 mmol) and purged with nitrogen. The mixture of 6-bromo-1-(cyclopropylsulfonyl)-1H-pyrazolo[4,3-b]pyridine and 6-bromo-2-(cyclopropylsulfonyl)-2H-pyrazolo[4,3-b]pyridine (194 mg, 0.642 mmol) in 1,4-dioxane (5.0 mL) was added followed by 2 M of potassium carbonate in water (0.642 mL, 1.28 mmol). The reaction mixture was heated in an oil bath at 90° C. for 20 min. The reaction mixture was partitioned between EtOAc and water. The aqueous layer was further extracted with EtOAc and the combined organic layers were washed with brine, dried over sodium sulfate, filtered and concentrated by rotary evaporation. The crude material was purified by prep HPLC to yield N-{4-[1-(cyclopropylsulfonyl)-1H-pyrazolo[4,3-b]pyridin-6-yl]pyridin-2-yl}acetamide (113 mg, 49.2%). LCMS (AA): nm/z=358.1 (M+H) and N-{4-[2-(cyclopropylsulfonyl)-2H-pyrazolo[4,3-b]pyridin-6-yl]pyridin-2-yl}acetamide (21 mg, 9.2%). LCMS (AA): m/z=358.1 (M+H).

Example 24: N-{4-[3-(dimethylsulfamoyl)-1H-pyrrolo[2,3-b]pyridin-5-yl]pyridin-2-yl}acetamide

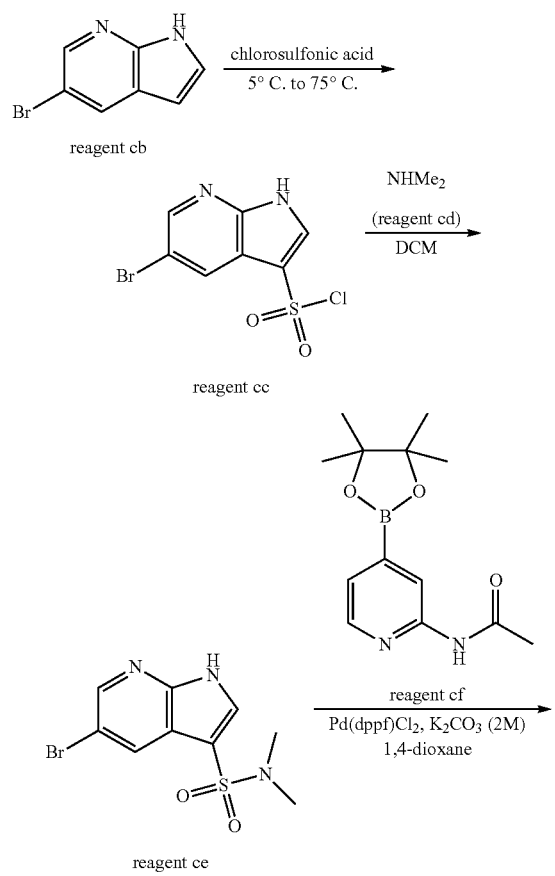

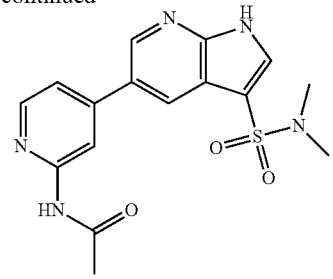

Step 1: 5-bromo-1H-pyrrolo[2,3-b]pyridine-3-sulfonyl chloride

To a flask containing chlorosulfonic acid (1.00 mL, 15.0 mmol) cooled to 5° C. was added 5-bromo-1H-pyrrolo[2,3-b]pyridine (255 mg, 1.29 mmol) portionwise. The mixture was allowed to warm to rt over the course of 1 h and then heated at 50° C. for 1 h and at 75° C. for 1 h. The reaction was cooled to rt and was quenched by adding the mixture dropwise to 20 mL of ice-water with good stirring. The resulting suspension was allowed to stir for 5 min. and the white solid was collected by filtration and dried under high vacuum to yield 5-bromo-1H-pyrrolo[2,3-b]pyridine-3-sulfonyl chloride (319 mg, 83.4%). LCMS (AA): nm/z=293.3 (M+H).

Step 2: 5-bromo-N,N-dimethyl-1H-pyrrolo[2,3-b]pyridine-3-sulfonamide

Dimethylamine (9 M in water, 6 mL, 50 mmol) was added to DCM (6 mL) and allowed to stir for 5 min. The organic layer was removed and dried over anhydrous sodium sulfate and then added to a suspension of 5-bromo-1H-pyrrolo[2,3-b]pyridine-3-sulfonyl chloride (267 mg, 0.903 mmol) in DCM (3.5 mL). The resulting solution was allowed to stir at rt for 2 h. The mixture was partitioned between water and DCM. The aqueous layer was further extracted with DCM and the combined organic layers were dried over sodium sulfate, filtered and concentrated by rotary evaporation to yield 5-bromo-N,N-dimethyl-1H-pyrrolo[2,3-b]pyridine-3-sulfonamide (273 mg, 99.3%). LCMS (AA): m/z=306.3 (M+H).

Step 3: N-{4-[3-(dimethylsulfamoyl)-1H-pyrrolo[2,3-b]pyridin-5-yl]pyridin-2-yl}acetamide Followed the procedure in Step 2 of Example 23 with the following modification: Heated at 100° C. for 2 h. LCMS (AA): m/z=360.1 (M+H).

The compounds listed in the table below (Table 24) were prepared in an analogous fashion to that described above starting from the list class of starting materials:

TABLE 24

| Example | Reagent ce | Compound No. | LCMS Data |
|---|---|---|---|
| 24A | 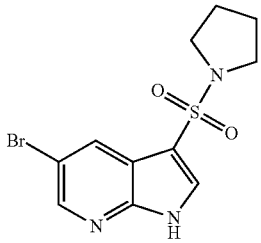 [SMILES: O=S(=O)(c1c[nH]c2ncc(Br)cc12)N1CCCC1] | I-158 | LCMS (FA): m/z = 386.5 (M + H) |
| 24B | 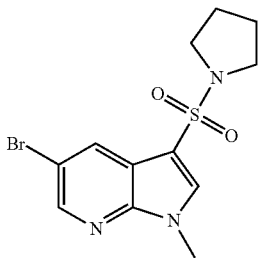 | I-151 | LCMS (FA): m/z = 400.5 (M + H) |
| 24C | 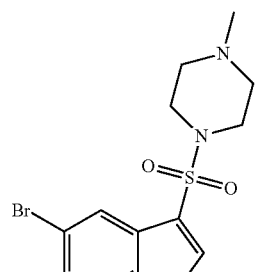 | I-103 | LCMS (FA): m/z = 415.5 (M + H) |

Example 25: N-[4-(2-methyl-1,1-dioxido-3,4-dihydro-2H-pyrido[2,3-e][1,2,4]thiadiazin-7-yl)pyridin-2-yl]acetamide I-21

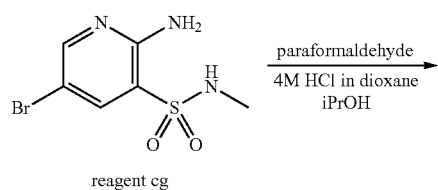

reagent cg

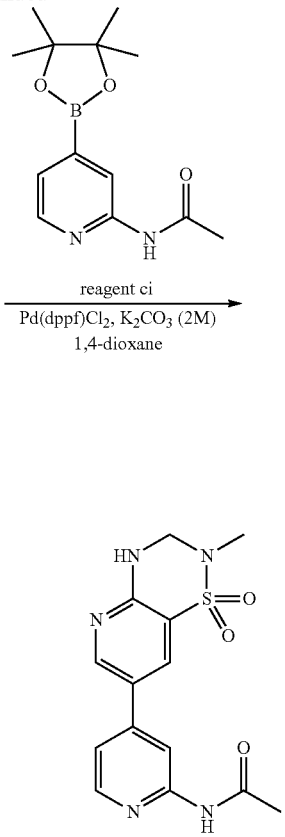

reagent ch

Step 1: 7-bromo-2-methyl-3,4-dihydro-2H-pyrido[2,3-e][1,2,4]thiadiazine 1,1-dioxide To a suspension of 2-amino-5-bromo-N-methylpyridine-3-sulfonamide (61 mg, 0.23 mmol) and paraformaldehyde (31.0 mg, 0.344 mmol) in isopropyl alcohol (2.7 mL) was added HCl (4 M in 1,4-dioxane, 61 uL, 0.24 mmol). The reaction mixture was allowed to stir at reflux for 2 h, cooled to rt and then placed in the refrigerator overnight. The resulting suspension was filtered and the solid was suspended in water. The pH was adjusted to 7-7.5 with saturated sodium bicarbonate solution. The mixture was allowed to stir for 1 h and filtered. The collected solid was further dried under vacuum to yield 7-bromo-2-methyl-3,4-dihydro-2H-pyrido[2,3-e][1,2,4]thiadiazine 1,1-dioxide (31 mg, 48.6%). LCMS (AA): m/z=280.2 (M+H).

Step 2: N-[4-(2-methyl-1,1-dioxido-3,4-dihydro-2H-pyrido[2,3-e][1,2,4]thiadiazin-7-yl)pyridin-2-yl]acetamide Followed the procedure in Step 2 of Example 23 to yield N-[4-(2-methyl-1,1-dioxido-3,4-dihydro-2H-pyrido[2,3-e][1,2,4]thiadiazin-7-yl)pyridin-2-yl]acetamide (20 mg, 54%). LCMS (AA): m/z=334.4 (M+H).

Example 26: N-{4-[1-(cyclopropylmethyl)-1H-imidazo[4,5-b]pyridin-6-yl]pyridin-2-yl}acetamide I-135

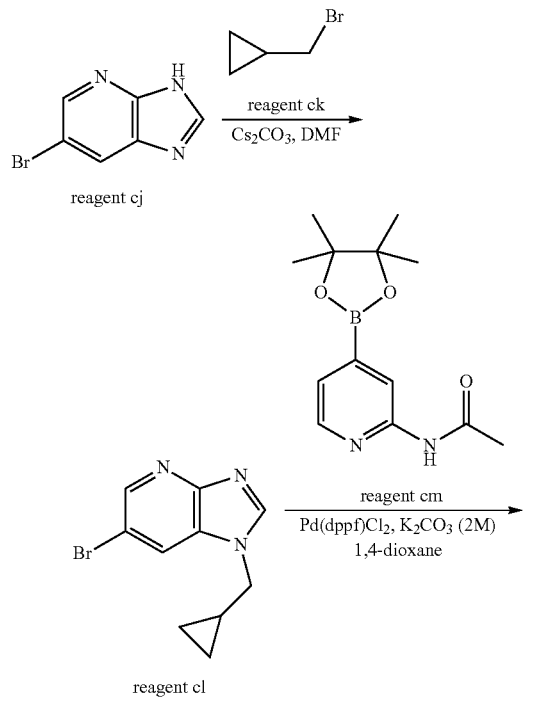

reagent cj reagent cl

Step 1: 6-bromo-1-(cyclopropylmethyl)-1H-imidazo[4,5-b]pyridine

To a mixture of 6-bromo-3H-imidazo[4,5-b]pyridine (99 mg, 0.50 mmol) and cesium carbonate (240 mg, 0.75 mmol) in DMF (1.4 mL) was added cyclopropylmethyl bromide (53 uL, 0.55 mmol). The reaction was allowed to stir at rt for 2.5 h and then partitionned between EtOAc and water. The aqueous layer was further extracted with EtOAc and the combined organics were washed with brine, dried over sodium sulfate and concentrated by rotary evaporation. The crude material was purified by column chromatography to yield 6-bromo-1-(cyclopropylmethyl)-1H-imidazo[4,5-b]pyridine (65 mg, 52%). LCMS (AA): m/z=252.2/254.3 (M+H).

Step 2: N-{4-[1-(cyclopropylmethyl)-1H-imidazo[4,5-b]pyridin-6-yl]pyridin-2-yl}acetamide Followed the procedure in Step 2 of Example 23 with the following modification: Heated at 120° C. for 5 h to yield N-{4-[1-(cyclopropylmethyl)-1H-imidazo[4,5-b]pyridin-6-yl]pyridin-2-yl}acetamide (62 mg, 83%). LCMS (AA): m/z=308.4 (M+H).

Example 27: N-[4-(2-methyl-3H-imidazo[4,5-b]pyridin-6-yl)pyridin-2-yl]acetamide I-66

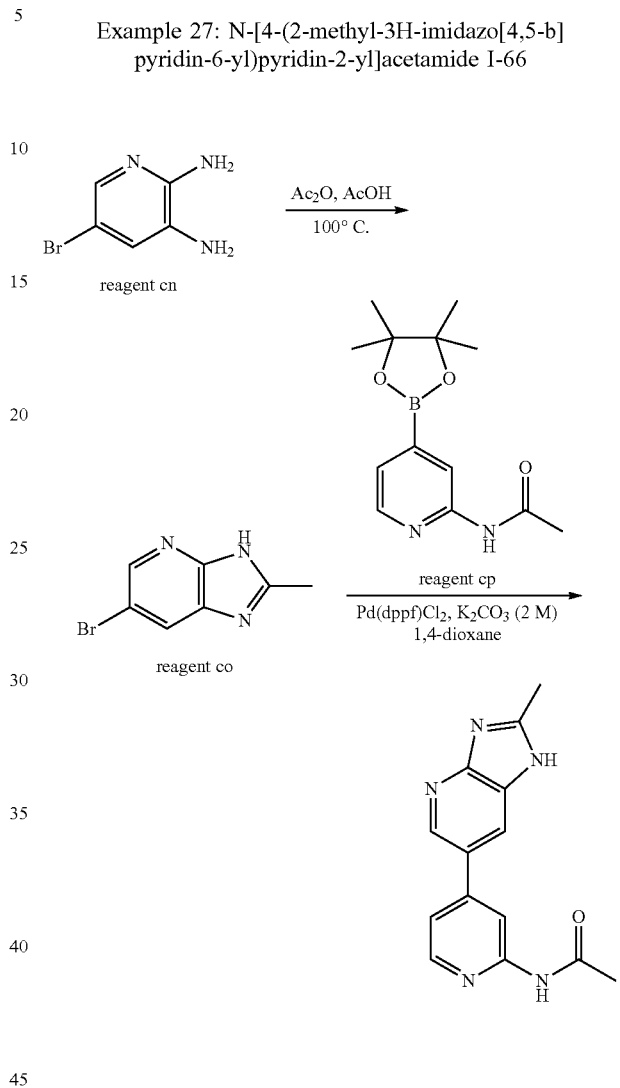

reagent cn reagent co

Step 1: 6-Bromo-2-methyl-3H-imidazo[4,5-b]pyridine

To a flask containing neat 2,3-diamino-5-bromopyridine (2.00 g, 10.6 mmol) was added acetic acid (6.05 mL, 106 mmol) and acetic anhydride (1.76 mL, 18.6 mmol). The resulting dark mixture was heated at 100° C. overnight. The mixture was diluted with EtOH and toluene and then concentrated to dryness. The residue was allowed to stir in 50 mL of EtOAc and 50 mL of saturated sodium bicarbonate for 1 h. The resulting suspension was filtered and the solid was dried under vacuum to provide a light brown solid. The supernatant contained desired product as well and was washed with brine, dried over sodium sulfate and concentrated by rotary evaporation. The light brown solid from the filtration was suspended in EtOAc (20 mL) and heated at reflux for 15 min. After cooling to rt, the solid was filtered and collected. This material and the material recovered from the supernatant in the filtration were purified by column to yield 6-bromo-2-methyl-3H-imidazo[4,5-b]pyridine (732 mg, 32.4%). LCMS (AA): m/z=211.9/213.9 (M+H).

Step 2: N-[4-(2-methyl-3H-imidazo[4,5-b]pyridin-6-yl)pyridin-2-yl]acetamide

Followed the procedure in Step 2 of Example 23 with the following modification: Heated at 120° C. for 15 h to yield N-[4-(2-methyl-3H-imidazo[4,5-b]pyridin-6-yl)pyridin-2-yl]acetamide (13 mg, 14%). LCMS (AA): m/z=268.1 (M+H).

Example 28: Methyl {4-[1-(cyclopropylmethyl)-1H-pyrrolo[3,2-b]pyridin-6-yl]pyridin-2-yl}carbamate I-42

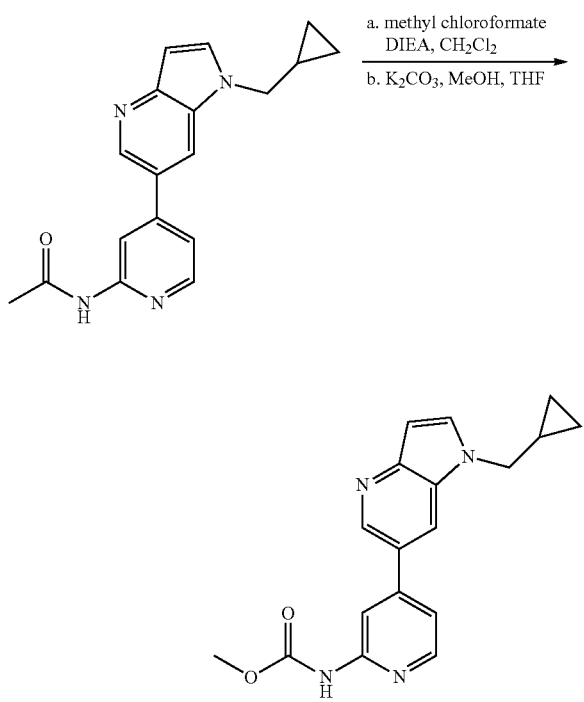 [SMILES: CC(=O)Nc1cc(-c2cnc3ccn(CC4CC4)c3c2)ccn1 ; COC(=O)Nc1cc(-c2cnc3ccn(CC4CC4)c3c2)ccn1]

To a flask containing N-{4-[1-(cyclopropylmethyl)-1H-pyrrolo[3,2-b]pyridin-6-yl]pyridin-2-yl}acetamide (I-93 of Example 8L: 179 mg, 0.584 mmol) in DCM (7.5 mL) was added DIEA (0.203 mL, 1.17 mmol). The reaction mixture was cooled to 0° C., methyl chloroformate (0.135 mL, 1.75 mmol) was added slowly and the reaction was stirred for 1 h. Additional methyl chloroformate (0.060 mL) was added and the reaction was stirred for 1 h. Solvent was removed by rotary evaporation followed by the addition of THF (1 mL), MeOH (1 mL) and K₂CO₃ (10 mg). The reaction mixture was allowed to stir for 1.5 h and the solvent was removed by rotary evaporation. The residue was partitioned between EtOAc and water, washed with brine, dried over magnesium sulfate and concentrated by rotary evaporation. The crude material was purified by prep HPLC to yield methyl {4-[1-(cyclopropylmethyl)-1H-pyrrolo[3,2-b]pyridin-6-yl]pyridin-2-yl}carbamate (107 mg, 56.5%). LCMS (FA): m/z=323.0 (M+H).

Example 29: N-{4-[3-(phenylsulfonyl)-1H-pyrrolo[2,3-b]pyridin-5-yl]pyridin-2-yl}acetamide I-176

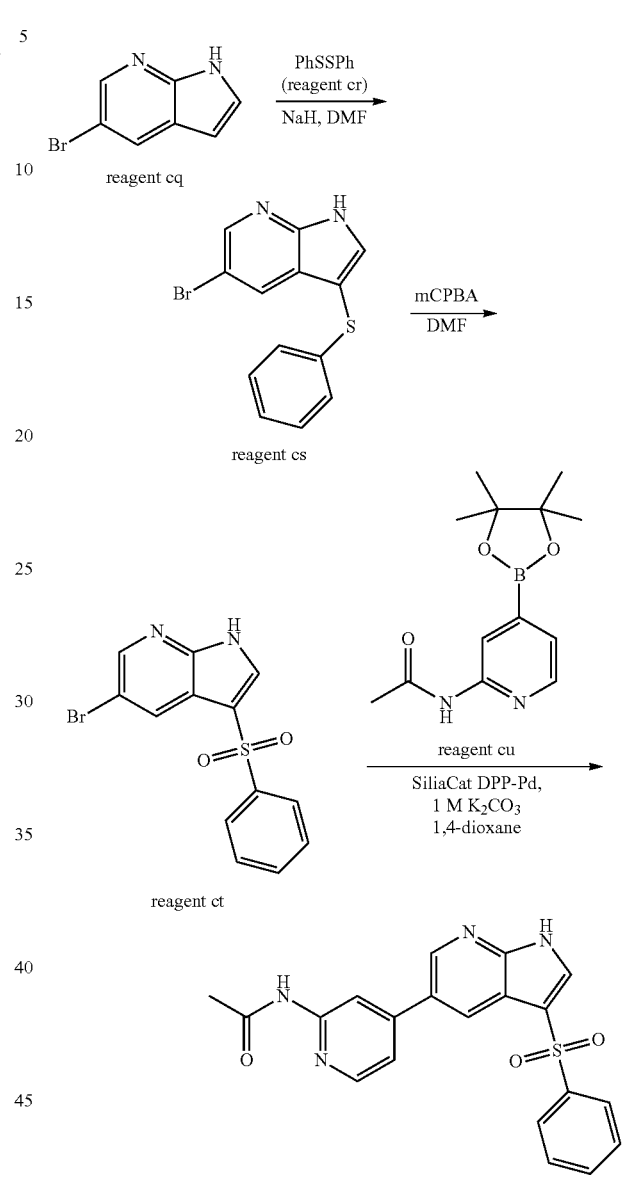

Step 1: 5-Bromo-3-(phenylsulfanyl)-1H-pyrrolo[2,3-b]pyridine

5-Bromo-1H-pyrrolo[2,3-b]pyridine (360 mg, 1.83 mmol) was dissolved in DMF (13.9 mL) and cooled to 0° C. Sodium hydride (60:40, sodium hydride:mineral oil, 89 mg, 2.23 mmol) was added and the reaction allowed to stir for 15 min followed by the addition of diphenyl disulfide (0.48 g, 2.23 mmol). The reaction mixture was allowed to stir at rt overnight. Water was added and a white solid precipitated out. The solid was filtered and further washed with ether to yield 5-bromo-3-(phenylsulfanyl)-1H-pyrrolo[2,3-b]pyridine (200 mg, 35.9%). LCMS (FA): m/z=306.8 (M+H).

Step 2: 5-Bromo-3-(phenylsulfonyl)-1H-pyrrolo[2,3-b]pyridine

To a solution of 5-bromo-3-(phenylsulfanyl)-1H-pyrrolo[2,3-b]pyridine (200 mg, 0.655 mmol) in DMF (6.0 mL) was added mCPBA (294 mg, 1.31 mmol). The reaction mixture was allowed to stir at rt and an additional 100 mg portion of mCPBA was added 1 h later, then another 100 mg 1 h later. Solid NaHCO₃ and water were added and the desired product precipitated out of solution and collected by filtration to yield 5-bromo-3-(phenylsulfonyl)-1H-pyrrolo[2,3-b]pyridine (220 mg, 100%). LCMS (FA): m/z=338.9 (M+H).

Step 3: N-{4-[3-(phenylsulfonyl)-H-pyrrolo[2,3-b]pyridin-5-yl]pyridin-2-yl}acetamide The procedure described in Step 2 of Example 14 was used with the following modification: 1 M K₂CO₃ was used in place of solid K₂CO₃. No additional water was added. The reaction yielded N-{4-[3-(phenylsulfonyl)-1H-pyrrolo[2,3-b]pyridin-5-yl]pyridin-2-yl}acetamide (62%). LCMS (FA): m/z=393.4 (M+H).

Example 30: Methyl [4-(1H-pyrazolo[3,4-b]pyridin-5-yl)pyridin-2-yl]carbamate I-38

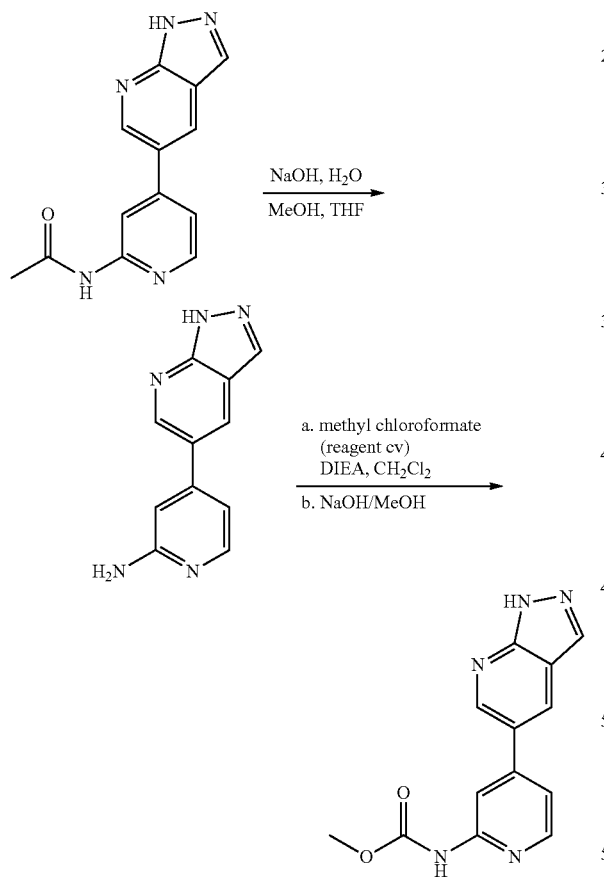

Step 1: 4-(1H-pyrazolo[3,4-b]pyridin-5-yl)pyridin-2-amine

A mixture of N-[4-(1H-pyrazolo[3,4-b]pyridin-5-yl)pyridin-2-yl]acetamide (380 mg, 1.50 mol) and sodium hydroxide (300 mg, 7.50 mmol) was allowed to stir in THF (30 mL), MeOH (30 mL) and water (30 mL) for 1 day at rt. Solvent was removed by rotary evaporation. The crude residue was diluted with EtOAc and MeOH and then washed with water and brine. The organic layer was dried over sodium sulfate, filtered and concentrated by rotary evaporation to yield 4-(1H-pyrazolo[3,4-b]pyridin-5-yl)pyridin-2-amine (123 mg, 38.8%). LCMS (FA): m/z=212.1 (M+H).

Step 2: Methyl [4-(1H-pyrazolo[3,4-b]pyridin-5-yl)pyridin-2-yl]carbamate 4-(1H-pyrazolo[3,4-b]pyridin-5-yl)pyridin-2-amine (73 mg, 0.35 mmol) was suspended in DCM (5.0 mL). DIEA (0.12 mL, 0.69 mmol) was added and the mixture was cooled to 0° C. followed by the addition of methyl chloroformate (0.040 mL, 0.52 mmol). The reaction mixture was allowed to stir for 1 h and then concentrated by rotary evaporation. MeOH (5.10 mL) and sodium hydroxide (1 M in water, 1.02 mL) were added and the reaction mixture allowed to stir at rt for 1 h. The mixture was partitioned between EtOAc and water. The aqueous layer was further extracted with EtOAc. The combined organic layers were washed with water and brine, dried over sodium sulfate, filtered and concentrated by rotary evaporation. The crude material was purified by prep HPLC to yield methyl [4-(1H-pyrazolo[3,4-b]pyridin-5-yl)pyridin-2-yl]carbamate (13.6 mg, 14.6%). LCMS (FA): m/z=270.1 (M+H).

The compounds listed in the table below (Table 25) were prepared in an analogous fashion to that described above starting from the list class of starting materials:

TABLE 25

| Example | Reagent cv | Compound No. | LCMS Data |
|---|---|---|---|
| 30A | 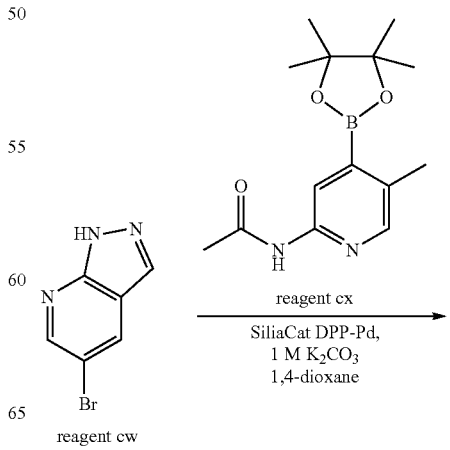 | I-117 | LCMS (FA): m/z = 280.1 (M + H) |

Example 31: N-[5-methyl-4-(1H-pyrazolo[3,4-b]pyridin-5-yl)pyridin-2-yl]acetamide I-209

-continued

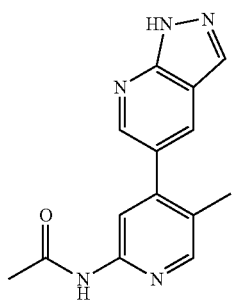

The procedure described in Step 2 of Example 14 was used with the following modification: 1 M K$_2$CO$_3$ was used in place of solid K$_2$CO$_3$. No additional water was added. The reaction yielded N-[5-methyl-4-(1H-pyrazolo[3,4-b]pyridin-5-yl)pyridin-2-yl]acetamide (26 mg, 19.3%). LCMS (FA): m/z=268.1 (M+H).

Example 32: N-{4-[3-(pyrrolidin-1-ylmethyl)-1H-pyrrolo[2,3-b]pyridin-5-yl]pyridin-2-yl}acetamide I-54

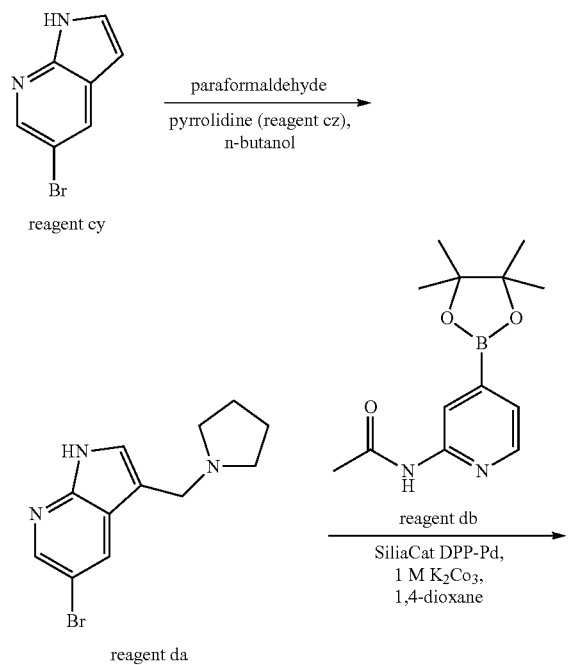

Step 1: 4-(2-chloro-5-fluoropyridin-4-yl)-1-(cyclopropylsulfonyl)-1H-pyrrolo[2,3-c]pyridine To a mixture of 5-bromo-1H-pyrrolo[2,3-b]pyridine (415 mg, 2.11 mmol), paraformaldehyde (70.8 mg, 2.36 mmol) in 1-butanol (8 mL, 90 mmol) was added pyrrolidine (0.19 mL, 2.3 mmol). The reaction was allowed to stir at 125° C. for 3 h and then concentrated by rotary evaporation. The crude residue was triturated with Et$_2$O. A solid precipitated out and was isolated by filtration to yield 5-bromo-3-(pyrrolidin-1-ylmethyl)-1H-pyrrolo[2,3-b]pyridine (270 mg, 45.8%). LCMS (FA): m/z=280.2/282.2 (M+H).

Step 2: N-{4-[3-(pyrrolidin-1-ylmethyl)-1H-pyrrolo[2,3-b]pyridin-5-yl]pyridin-2-yl}acetamide The procedure described in Step 2 of Example 14 was used with the following modification: 1 M K$_2$CO$_3$ was used in place of solid K$_2$CO$_3$. No additional water was added. The reaction yielded N-{4-[3-(pyrrolidin-1-ylmethyl)-H-pyrrolo[2,3-b]pyridin-5-yl]pyridin-2-yl}acetamide (65 mg, 57.5%). LCMS (FA): m/z=336.4 (M+H).

The compounds listed in the table below (Table 26) were prepared in an analogous fashion to that described above starting from the list class of starting materials:

TABLE 26

| Example | Starting material | | Compound | |
|---|---|---|---|---|
| | Reagent | Chemical Structure | No. | LCMS Data |
| 32A | cy | Br-[5-bromo-7-azaindole] | I-85 | LCMS (FA): m/z = 310.5 (M + H) |
| | cz | HN(CH$_3$)$_2$ | | |

Example 33: N-[4-(1H-pyrazolo[3,4-b]pyridin-5-yl)pyridin-2-yl]acetamide I-189

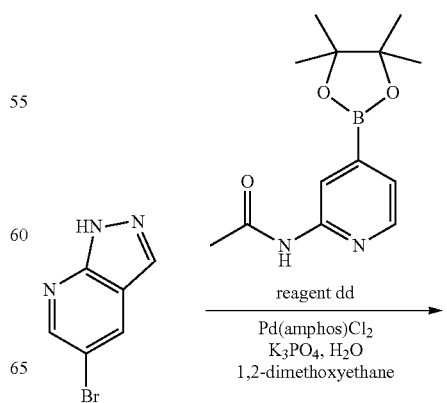

467

-continued

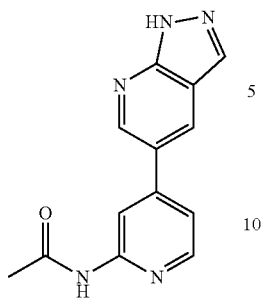

A mixture of 5-bromo-1H-pyrazolo[3,4-b]pyridine (0.100 g, 0.505 mmol), N-(4-(4,4,5,5-tetramethyl-1,3,2-dioxaborolan-2-yl)pyridin-2-yl)acetamide (0.199 g, 0.758 mmol), amphosdichloropalladium(II) (0.0718 g, 0.101 mmol) and potassium phosphate (0.323 g, 1.52 mmol) was allowed to stir in water (0.27 mL) and DME (4.6 mL) and heated in the microwave at 150° C. for 60 min. The reaction mixture was partitioned between water and EtOAc and the organic layer was washed with brine. The aqueous layer was further extracted with a DCM/MeOH mixture. The combined all organic layers were dried over magnesium sulfate, filtered and concentrated by rotary evaporation. Added MeOH and filtered to remove solids and concentrated the supernatant by rotary evaporation. Purified by prep HPLC to yield N-[4-(1H-pyrazolo[3,4-b]pyridin-5-yl)pyridin-2-yl]acetamide (1.5 mg, 1.2%). LCMS(FA): m/z=254.4 (M+H).

Example 34: N-{6-chloro-4-methyl-2'-[(2-methylpyrimidin-4-yl)amino]-3,4'-bipyridin-5-yl}-2,4-difluorobenzenesulfonamide (I-299)

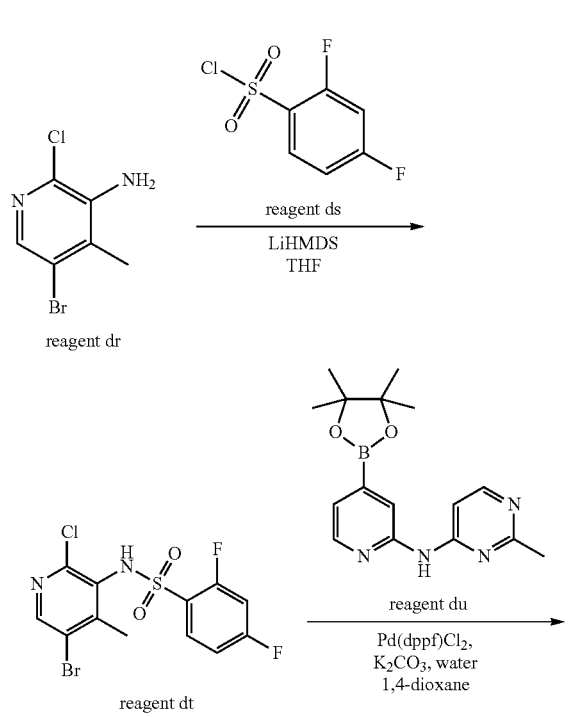

468

-continued

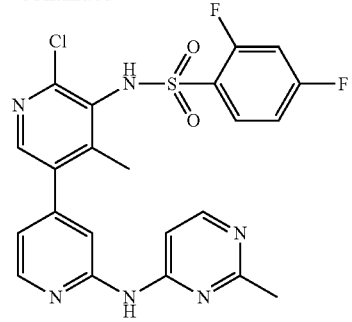

Step 1: N-(5-bromo-2-chloro-4-methylpyridin-3-yl)-2,4-difluorobenzenesulfonamide To a solution of 5-bromo-2-chloro-4-methylpyridin-3-amine (12 g, 54 mmol) in THF (360 mL) was added a solution of LiHMDS in THF (1.0 M, 108 mL, 108 mmol) at −5° C. The reaction mixture was allowed to stir at −5° C. for 10 min. To the reaction mixture, 2,4-difluorobenzenesulfonyl chloride (17.3 g, 81 mmol) was then added. The reaction mixture was allowed to stir at rt for 12 h. The reaction mixture was diluted with saturated aqueous $NH_4Cl$ (200 mL) and extracted with EtOAc. The organic solutions were combined, dried over $Na_2SO_4$, filtered and concentrated. The crude compound was purified by column chromatography to provide N-(5-bromo-2-chloro-4-methylpyridin-3-yl)-2,4-difluorobenzenesulfonamide (11.5 g, 53%). $^1$H NMR (400 MHz, $CDCl_3$) δ 8.37 (s, 1H), 7.72 (m, 1H), 7.00 (m, 2H), 6.70 (s, 1H), 2.64 (s, 3H).

Step 2: N-{6-Chloro-4-methyl-2'-[(2-methylpyrimidin-4-yl)amino]-3,4'-bipyridin-5-yl}-2,4-difluorobenzenesulfonamide (I-299)

N-(5-Bromo-2-chloro-4-methylpyridin-3-yl)-2,4-difluorobenzenesulfonamide (6.40 g, 16.1 mmol), 2-methyl-N-[4-(4,4,5,5-tetramethyl-1,3,2-dioxaborolan-2-yl)pyridin-2-yl]pyrimidin-4-amine (6.0 g, 19 mmol) and Pd(dppf)$Cl_2$ (431 mg, 0.524 mmol) were combined in a round bottomed flask equipped with a stirbar. Degassed 1,4-dioxane (125 mL) and degassed potassium carbonate in water (1.0 M, 32.2 mL, 32.2 mmol) were added. The flask was evacuated and refilled with argon three times and then the reaction mixture was allowed to stir overnight at 105° C. under an argon atmosphere. The reaction was allowed to cool to rt then filtered through a fritted funnel The filtrate was concentrated to ~one-half volume and then was slowly poured into stirring saline solution (750 mL). The resulting mixture was stirred and the pH was adjusted to ~6.5 via the slow addition of 1N HCl. The precipitate which formed was collected by filtration and air-dried to leave a gray solid. The crude product was purified by column chromatography to provide N-{6-chloro-4-methyl-2'-[(2-methylpyrimidin-4-yl)amino]-3,4'-bipyridin-5-yl}-2,4-difluorobenzenesulfonamide I-299 (4.3 g, 53%) as a white powder. LCMS (FA): m/z=503.1 (M+H). $^1$H NMR (400 MHz, DMSO-d6) δ ppm 10.66 (br s, 1H), 10.32 (s, 1H), 8.43 (d, J=5.09 Hz, 1H), 8.37 (d, J=5.74 Hz, 1H), 8.26 (s, 1H), 7.71-7.89 (m, 2H), 7.55-7.71 (m, 2H), 7.28 (m, 1H), 7.07 (br d, J=3.76 Hz, 1H), 2.48 (s, 3H), 2.35 (s, 3H).

The compounds listed in the table below (Table 27) were prepared in an analogous fashion to that described above from the appropriate starting materials:

TABLE 27
| Example | Starting Material | | Compound No. | LCMS Data |
|---|---|---|---|---|
| | Reagent | Chemical Structure | | |
| 34A | dr[1] | 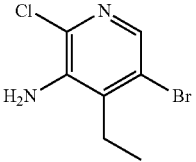 | I-259 | LCMS (FA): m/z = 517.1 (M + H) |
| 34B | du | 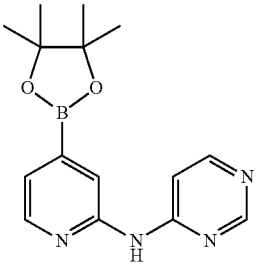 | I-282 | LCMS (FA): m/z = 489.2 (M + H) |
| 34C | dr[1] | 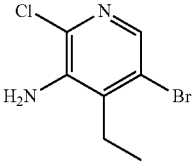 | I-278 | LCMS (FA): m/z = 493.1 (M + H) |
| | du | 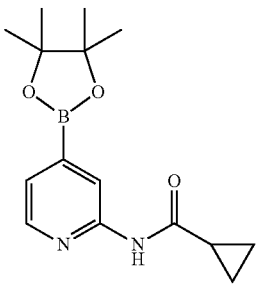 [SMILES: CC1(C)OB(c2ccnc(NC(=O)C3CC3)c2)OC1(C)C] | | |
| 34D* | dt[2] | 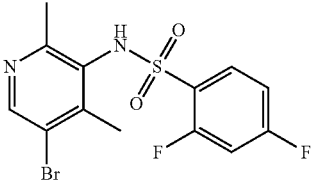 | I-247 | LCMS (FA): m/z = 433.1 (M + H) |
| | du | 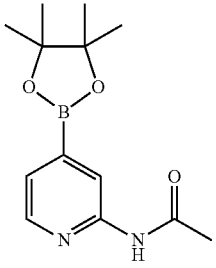 [SMILES: CC(=O)Nc1cc(B2OC(C)(C)C(C)(C)O2)ccn1] | | |

TABLE 27-continued

| Ex-ample | Starting Material | | Compound No. | LCMS Data |
|---|---|---|---|---|
| | Reagent | Chemical Structure | | |
| 34E* | dt² | (structure: 2-methoxy-5-bromo-4-methylpyridin-3-yl sulfonamide with 2,4-difluorophenyl) | I-248 | LCMS (FA): m/z = 449.1 (M + H) |
| | du | (structure: 2-acetamidopyridine-4-boronic acid pinacol ester) | | |
| 34F* | dt² | (structure: 2,4-dimethyl-5-bromopyridin-3-yl sulfamide with dimethylamino) | I-260 | LCMS (FA): m/z = 364.2 (M + H) |
| | du | (structure: 2-acetamidopyridine-4-boronic acid pinacol ester) | | |
| 34G* | dt² | (structure: 2-methoxy-5-bromo-4-methylpyridin-3-yl sulfamide with dimethylamino) | I-268 | LCMS (FA): m/z = 3580.2 (M + H) |
| | du | (structure: 2-acetamidopyridine-4-boronic acid pinacol ester) | | |

TABLE 27-continued

| Example | Starting Material | | Compound No. | LCMS Data |
|---|---|---|---|---|
| | Reagent | Chemical Structure | | |
| 34K | dr | 2-chloro-3-amino-5-bromo-4-ethylpyridine | I-469 | LCMS (FA): m/z = 467.0 (M + H) |
| | dt | N-(2-chloro-5-bromo-4-ethylpyridin-3-yl)-2,4-difluorobenzenesulfonamide | | |
| | du** | 2-acetamido-4-(pinacolboronate)pyridine | | |
| 34L | ds | dimethylsulfamoyl chloride | I-381 | LCMS (FA): m/z = 434.2 (M + H) |
| | dt** | N-(2-chloro-5-bromo-4-methylpyridin-3-yl)-N',N'-dimethylsulfamide | | |
| 34N | ds | dimethylsulfamoyl chloride | I-435 | LCMS (FA): m/z = 460.2 (M + H) |
| | dt** | N-(2-chloro-5-bromo-4-methylpyridin-3-yl)-N',N'-dimethylsulfamide | | |

TABLE 27-continued

| Example | Starting Material Reagent | Starting Material Chemical Structure | Compound No. | LCMS Data |
|---|---|---|---|---|
| | du** | [pinacol boronate-pyridine-NH-pyrimidine-cyclopropyl structure] | | |
| 34O | dr | [4-amino-6-bromopyrazolo[1,5-a]pyridine] | I-486 | LCMS (FA): m/z = 494.4 (M + H) |
| | dt*** | [N-(6-bromopyrazolo[1,5-a]pyridin-4-yl)-2,4-difluorobenzenesulfonamide] | | |
| 34P | dr | [4-amino-6-bromopyrazolo[1,5-a]pyridine] | I-421 | LCMS (FA): m/z = 425.4 (M + H) |
| | ds^^ | [dimethylsulfamoyl chloride] | | |
| | dt*** | [N-(6-bromopyrazolo[1,5-a]pyridin-4-yl)-N',N'-dimethylsulfamide] | | |
| 34R | dr | [5-amino-6-bromopyrazolo[1,5-a]pyridine] | I-427 | LCMS (FA): m/z = 451.4 (M + H) |
| | ds^^ | [dimethylsulfamoyl chloride] | | |

TABLE 27-continued

| Example | Starting Material Reagent | Chemical Structure | Compound No. | LCMS Data |
|---|---|---|---|---|
| dt** | | 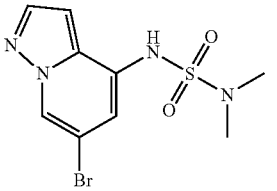 [SMILES: CN(C)S(=O)(=O)Nc1cc(Br)cn2nccc12] | | |
| du | | 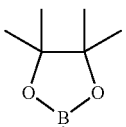 | | |

[1] See synthesis of reagent dr of Example 34A below.
[2] See synthesis of reagent dt of Example 34D-G below.
*In step 2, Cs₂CO₃ was used instead of K₂CO₃
**In step 2, microwave irradiation was used (140-150° C.)
^Step 2 conditions use SiliaCat DPP-Pd and microwave irradiation instead of Pd(dppf)Cl₂
^^In step 1, used pyridine at 80° C.
***In Step 2, XPhosG3 was used with K₃PO₄ in 1,4-dioxane; microwave irradiation (130° C.)

Synthesis of Reagent (dr) from Example 34A:
5-bromo-2-chloro-4-ethylpyridin-3-amine

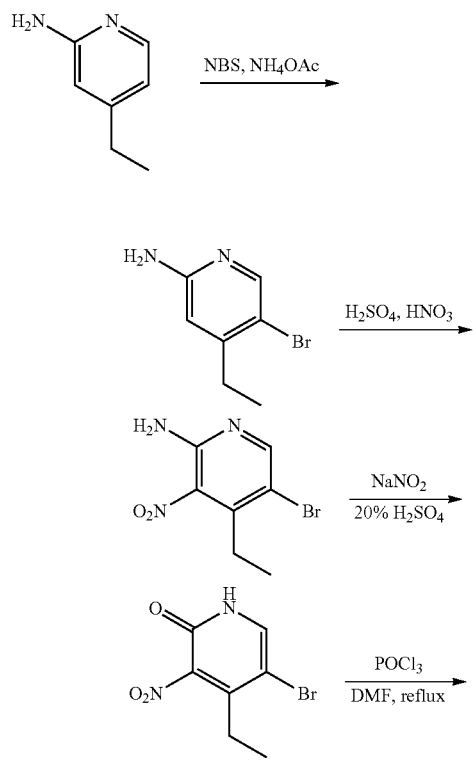

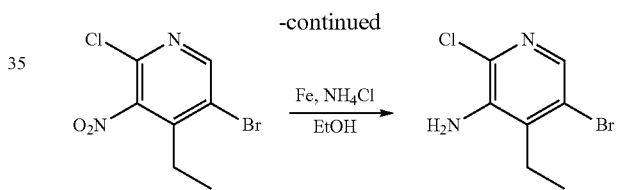

Step 1: 5-bromo-4-ethylpyridin-2-amine

To a mixture of 4-ethylpyridin-2-amine (40 g, 327.4 mmol) and ammonium acetate (2.5 g, 32 mmol) in ACN (1,200 mL) was added NBS (61.2 g, 343 mmol) at rt. The reaction mixture was allowed to stir for 1 min at rt. The reaction mixture was then diluted with water and extracted with EtOAc. The organic solutions were combined, dried over $Na_2SO_4$, filtered and concentrated. The crude compound was purified by column chromatography to provide 5-bromo-4-ethylpyridin-2-amine (60 g, 91%).

Step 2: 5-bromo-4-ethyl-3-nitropyridin-2-amine

To a solution of 5-bromo-4-ethylpyridin-2-amine (35 g, 174 mmol) in concentrated $H_2SO_4$ (520 mL) was added $HNO_3$ (18 mL, 261 mmol) dropwise at rt. The reaction mixture was allowed to stir for 3 h at rt. The reaction mixture was then poured into a mixture of ice (800 g) and water (800 g). The pH was adjusted to 10 by addition of aqueous NaOH solution. The resulting light yellow precipitate was collected by filtration and washed with water twice (200 mL). The filter cake was dissolved in THF (70 mL) at 45° C. Water (500 mL) was added and the mixture was allowed to stir for 1 h at −10° C. to 0° C. The crude compound was collected by filtration to provide 5-bromo-4-ethyl-3-nitropyridin-2-amine (50 g, 58%). $^1$H NMR (400 MHz, CDCl$_3$) δ 8.28 (s, 1H), 5.78 (s, 2H), 2.85 (q, J=7.6 Hz, 2H), 1.32 (t, J=7.6 Hz, 3H).

Step 3: 5-bromo-4-ethyl-3-nitropyridin-2(1H)-one

To a solution of 5-bromo-4-ethyl-3-nitropyridin-2-amine (53 g, 215 mmol) in H$_2$SO$_4$ (20 wt %, 1600 mL) was added a solution of NaNO$_2$ (29.7 g, 430 mmol) in water (140 mL) dropwise at −5° C. The reaction mixture was allowed to stir for 30 min at −5° C. The resulting pale yellow precipitate was collected by filtration and washed with water (200 mL). The crude compound was dried under vacuum to provide 5-bromo-4-ethyl-3-nitropyridin-2(1H)-one (41 g, 77%). $^1$H NMR (400 MHz, CDCl$_3$) δ 7.72 (s, 1H), 2.67 (q, J=7.6 Hz, 2H), 1.28 (t, J=7.6 Hz, 3H).

Step 4: 5-bromo-2-chloro-4-ethyl-3-nitropyridine

To a solution of 5-bromo-4-ethyl-3-nitropyridin-2(1H)-one (41 g, 166 mmol) in POCl$_3$ (200 mL) was added DMF (41 mL, 531 mmol) at rt. The reaction mixture was allowed to stir at 120° C. for 2 h. Then, POCl$_3$ was removed by distillation. The residue was poured into water slowly and the pH was adjusted to pH=6-8 by the addition of aqueous NaHCO$_3$. The aqueous layer was extracted with EtOAc, and the combined organic solutions were dried over Na$_2$SO$_4$, filtered and concentrated. The crude compound was purified by column chromatography to provide 5-bromo-2-chloro-4-ethyl-3-nitropyridine (34 g, 59%). $^1$H NMR (400 MHz, CDCl$_3$) δ 8.59 (s, 1H), 2.74 (q, J=7.6 Hz, 2H), 1.26 (t, J=7.6 Hz, 3H).

Step 5: 5-bromo-2-chloro-4-ethylpyridin-3-amine

To a solution of 5-bromo-2-chloro-4-ethyl-3-nitropyridine (32 g, 121 mmol) in EtOH (300 mL) and water (75 mL) was added NH$_4$Cl (19.4 g, 361 mmol) and Fe (20.2 g, 362 mmol) in portions at reflux. The reaction mixture was allowed to stir at reflux for 30 min. The reaction mixture was filtered through celite and concentrated. The aqueous solution was extracted with EtOAc, and the combined organic solutions were dried over Na$_2$SO$_4$, filtered and concentrated. The crude compound was purified by column chromatography to provide 5-bromo-2-chloro-4-ethylpyridin-3-amine (26 g, 91%). $^1$H NMR (400 MHz, CDCl$_3$) δ 7.90 (s, 1H), 4.12 (s, 2H), 2.75 (q, J=7.6 Hz, 2H), 1.18 (t, J=7.6 Hz, 3H). LCMS (FA): m/z=235.0 (M+H).

Synthesis of Reagent (dt) from Example 34D: N-(5-bromo-2,4-dimethylpyridin-3-yl)-2,4-difluorobenzenesulfonamide

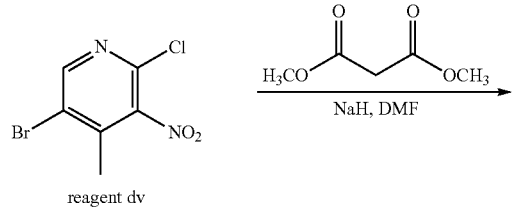

reagent dv

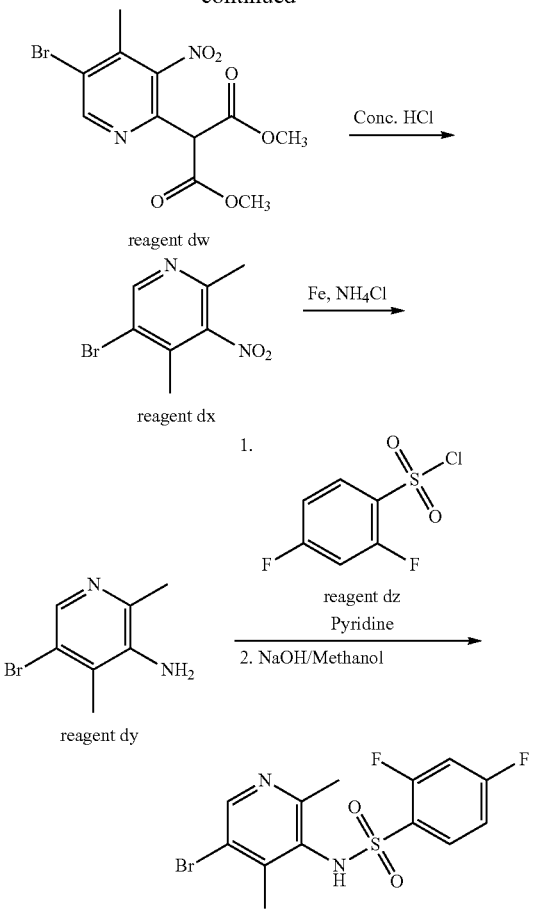

Step 1: Dimethyl 2-(5-bromo-4-methyl-3-nitropyridin-2-yl)malonate

To a suspension of NaH (60% in mineral oil, 0.64 g, 0.016 mol) in DMF (14 mL) was slowly added dimethyl malonate (1.70 mL, 0.0149 mol). After addition, the reaction mixture was allowed to stir for 10 min. 2-chloro-3-nitro-5-bromo-4-picoline (2.50 g, 9.90 mmol) in DMF (4.7 mL) was added. The resulting orange mixture was allowed to stir at 40° C. overnight. The mixture was carefully poured in 0.5M NaHCO$_3$ and extracted with Et$_2$O twice. The combined organic solutions were washed with brine, dried over Na$_2$SO$_4$, and concentrated to give dimethyl (5-bromo-4-methyl-3-nitropyridin-2-yl) malonate (3.17 g, 90%). LCMS (FA): m/z=347.3 (M+H).

Step 2: 5-Bromo-2,4-dimethyl-3-nitropyridine

To dimethyl (5-bromo-4-methyl-3-nitropyridin-2-yl)malonate (2.75 g, 7.92 mmol) was added 12.0 M of hydrochloric acid (15 mL, 0.18 mol). The reaction mixture was allowed to stir at 105° C. until LCMS showed complete conversion. The reaction mixture was diluted with 100 mL of brine and was extracted with Et$_2$O three times. The organic solutions were combined, washed with brine twice, dried over Na$_2$SO$_4$, filtered and concentrated. The crude product was purified by column chromatography to give 5-bromo-2,4-dimethyl-3-nitropyridine (1.15 g, 60%). LCMS (FA): m/z=231.0 (M+H).

Step 3: 5-Bromo-2,4-dimethylpyridin-3-amine

To a flask containing 5-bromo-2,4-dimethyl-3-nitropyridine (1.15 g, 4.98 mmol) was added EtOH (4.3 mL), water (4.3 mL), iron (1.17 g, 20.9 mmol) and ammonium chloride (1.17 g, 21.8 mmol). The reaction mixture was allowed to stir at reflux for 2 h. The reaction mixture was filtered through celite and the filtrate was concentrated to give a crude solid. The solid was triturated with water and filtered to give 5-bromo-2,4-dimethylpyridin-3-amine (630 mg, 69%). LCMS (FA): m/z=201.0 (M+H).

Step 4: N-(5-Bromo-2,4-dimethylpyridin-3-yl)-2,4-difluorobenzenesulfonamide

To a solution of 5-bromo-2,4-dimethylpyridin-3-amine (0.20 g, 0.99 mmol) in pyridine (1.04 mL, 12.9 mmol) was added 2,4-difluorobenzene-1-sulfonyl chloride (0.171 mL, 1.27 mmol) The mixture was allowed to stir at 80° C. for 3 h. The reaction mixture was concentrated and the crude product was purified by column chromatography to give product as a mixture of mono and bis sulfamate. The product mixture was dissolved in MeOH (10 mL) and 1N NaOH (10 mL) and allowed to heat at 50° C. overnight. The reaction mixture turned into clear solution, and LCMS showed complete reaction. The pH of the solution was adjusted to 5-6 by the addition of 1N HCl. The mixture was extracted with EtOAc. The organic solutions were combined and concentrated to give the crude product, which was purified by column chromatography to give N-(5-bromo-2,4-dimethylpyridin-3-yl)-2,4-difluorobenzenesulfonamide (187 mg, 50%). LCMS (FA): m/z=379.0 (M+H).

The intermediates listed in the table below (Table 28) were prepared in an analogous fashion to that described above from the appropriate starting materials:

TABLE 28

| Intermediate | Reagent | Starting Material Chemical Structure | LCMS Data |
|---|---|---|---|
| 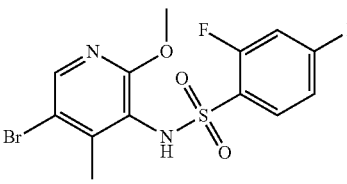<br>from Example 34E | dx | 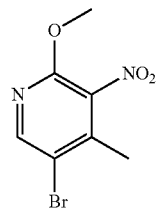 | LCMS (FA): m/z = 393.2 (M + H) |
| 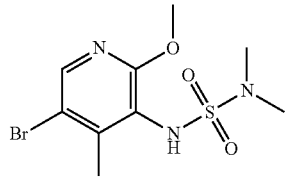<br>from Example 34G | dx<br><br>dz | 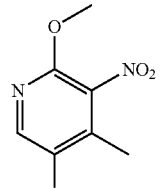 | LCMS (FA): m/z = 324.4 (M + H) |
| 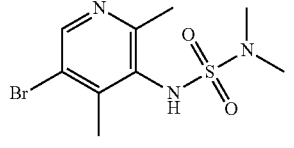<br>from Example 34F | dz | 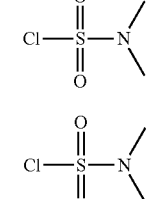 | LCMS (FA): m/z = 308.0 (M + H) |

Example 34H: 6-chloro-4-methyl-N-2'-(2-methylpyrimidin-4-yl)-3,4'-bipyridine-2',5-diamine (I-226)

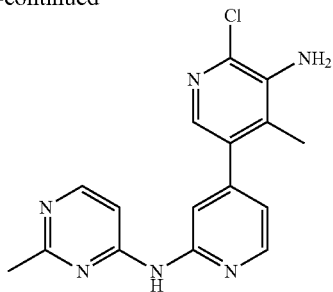

A mixture of 5-bromo-2-chloro-4-methylpyridin-3-amine (0.59 g, 2.67 mmol), 2-methyl-N-(4-(4,4,5,5-tetramethyl-1,3,2-dioxaborolan-2-yl)pyridin-2-yl)pyrimidin-4-amine (0.92 g, 2.94 mmol) and Pd(dppf)Cl$_2$, complex with DCM (1:1) (0.074 g, 0.090 mmol) in 1,4-dioxane (20 mL) and 1M aqueous K$_2$CO$_3$ (2.6 mL) was subjected to microwave irradiation for 30 min at 130° C. The reaction mixture was allowed to cool to rt and filtered through celite. The filtrate was diluted with EtOAc, and the solution was washed with water, dried over Na$_2$SO$_4$, filtered and concentrated. The crude compound was purified by column chromatography to provide 6-chloro-4-methyl-N-2'-(2-methylpyrimidin-4-yl)-3,4'-bipyridine-2',5-diamine I-226 (0.25 g, 29%). LCMS (FA): m/z=327.1 (M+H).

The compounds listed in the table below (Table 29) were prepared in an analogous fashion to that described above from the appropriate starting materials:

TABLE 29

| Example | Reagent | Starting Material Chemical Structure | Compound No. | LCMS Data |
|---|---|---|---|---|
| 34I | ea* | [structure] | I-256 | LCMS (FA): m/z = 341.2 (M + H) |
| 34J | ea* | [structure] | I-314 | LCMS (FA): m/z = 355.2 (M + H) |
| 34Q | ea^ | [structure] | I-480 | LCMS (FA): m/z = 318.0 (M + H) |
| 34S | ea^ eb | [structure] [structure] | I-355 | LCMS (FA): m/z = 353.0 (M + H) |

TABLE 29-continued

| Example | Starting Material Reagent | Starting Material Chemical Structure | Compound No. | LCMS Data |
|---|---|---|---|---|
| 34T[1] | ea^ | (5-bromo-2-methyl-3-ethoxypyridine) | I-479 | LCMS (FA): m/z = 322.1 (M + H) |
| 34U[2] | ea^ | (5-bromo-2-methyl-3-((5-methylpyridin-2-yl)oxy)pyridine) | I-390 | LCMS (FA): m/z = 385.2 (M + H) |
| 34V[1] | ea^ | (3-(benzyloxy)-5-bromo-2-methylpyridine) | I-363 | LCMS (FA): m/z = 384.2 (M + H) |
| 34W[1] | ea^ | (5-bromo-3-(cyclopentyloxy)-2-methylpyridine) | I-471 | LCMS (FA): m/z = 362.2 (M + H) |
| 34X[1] | ea^ | (5-bromo-3-isopropoxy-2-methylpyridine) | I-446 | LCMS (FA): m/z = 336.2 (M + H) |
| 34Y[1] | ea^ | (2-((5-bromo-2-methylpyridin-3-yl)oxy)ethanol) | I-424 | LCMS (FA): m/z = 338.2 (M + H) |

TABLE 29-continued

| | Starting Material | | Compound | |
|---|---|---|---|---|
| Example | Reagent | Chemical Structure | No. | LCMS Data |
| 34Z[1] | ea^ | (5-bromo-2-methylpyridin-3-yl) 2-(dimethylamino)ethyl ether | I-379 | LCMS (FA): m/z = 365.2 (M + H) |
| 34AA[3] | ea^ | 5-bromo-2-methyl-3-phenoxypyridine | I-475 | LCMS (FA): m/z = 370.1 (M + H) |
| 34AB[4] | ea^ | 5-bromo-2-chloro-N-(2,4-difluorophenylsulfonyl)-4-methylpyridin-3-amine 1-oxide | I-454 | LCMS (FA): m/z = 519.1 (M + H) |
| 34AC[5] | ea | 3-bromo-5-(1-(2-chlorophenoxy)ethyl)pyridine | I-336 | LCMS (FA): m/z = 418.2 (M + H) |
| 34AD[5] | ea | 3-bromo-5-(1-(2-fluorophenoxy)ethyl)pyridine | I-422 | LCMS (FA): m/z = 402.2 (M + H) |
| 34AE[5] | ea | 3-bromo-5-(1-(pyridin-3-ylmethoxy)ethyl)pyridine | I-349 | LCMS (FA): m/z = 399.2 (M + H) |

TABLE 29-continued

| | | Starting Material | Compound | |
|---|---|---|---|---|
| Example | Reagent | Chemical Structure | No. | LCMS Data |
| 34AF[5] | ea | 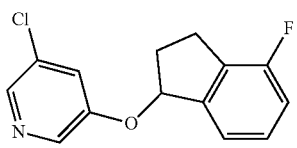 [SMILES: Fc1cccc2c1CCC2Oc1cncc(Cl)c1] | I-440 | LCMS (FA): m/z = 414.2 (M + H) |

*Conditions: XPhosG3 and XPhos instead of Pd(dppf)Cl$_2$ and K$_3$PO$_4$ instead of K$_2$CO$_3$
~SiliaCat DPP-Pd used instead of Pd(dppf)Cl$_2$
[1]Reagent ea is synthesized using the below procedure described for 5-bromo-3-ethoxy-2-methyl-pyridine by reacting an appropriate alkyl halide with 5-bromo-2-methyl-pyridin-3-ol
[2]Reagent ea is synthesized using K$_2$CO$_3$, DMSO, and MW irradiation at 170 C. by reacting 2-fluoro-5-methyl pyridine with 5-bromo-2-methyl-pyridin-3-ol
[3]Reagent ea is synthesized by reacting 5-bromo-2-methyl-pyridin-3-ol, diphenyliodonium trifluoromethanesulfonate and NaOtBu in THF at 70 C.
[4]Reagent ea is synthesized according to the procedure for reagent u from example 9BG
[5]Reagent ea is synthesized according to the below procedure described for intermediates of example 34AC, 34AD, 34AE, 34AF Synthesis of Reagent (ea) from Examples 34I and 34J: 5-bromo-2-chloro-N,4-dimethylpyridin-3-amine and 5-bromo-2-chloro-N,N,4-trimethylpyridin-3-amine

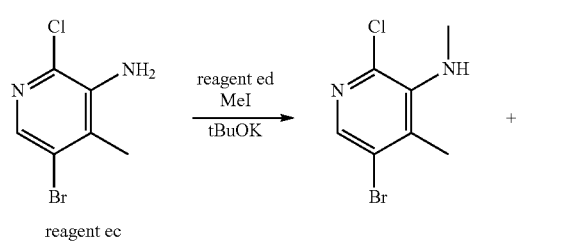

tBuOK (1.0 M in THF, 10.0 mL, 10.0 mmol) was added dropwise to a stirring solution of 5-bromo-2-chloro-4-methylpyridin-3-amine (0.74 g, 3.35 mmol) in THF (12 mL). The reaction mixture was allowed to stir at rt for 30 min then MeI (1.0 mL, 17 mmol) was added dropwise and the reaction mixture was allowed to stir at rt for 16 h. The reaction mixture was filtered and the filtrate was diluted with EtOAc and then washed with water. The organic solution was dried over Na$_2$SO$_4$, filtered, and concentrated. The crude compound was purified by column chromatography to provide 5-bromo-2-chloro-N,4-dimethylpyridin-3-amine (0.37 g, 46.5%). LCMS (FA): m/z=235.1 (M+H) and 5-bromo-2-chloro-N,N,4-trimethylpyridin-3-amine (0.36 g, 43.8%). LCMS (FA): m/z=249.1 (M+H).

Synthesis of Reagents (ea) from Example 34T: 5-bromo-3-ethoxy-2-methyl-pyridine

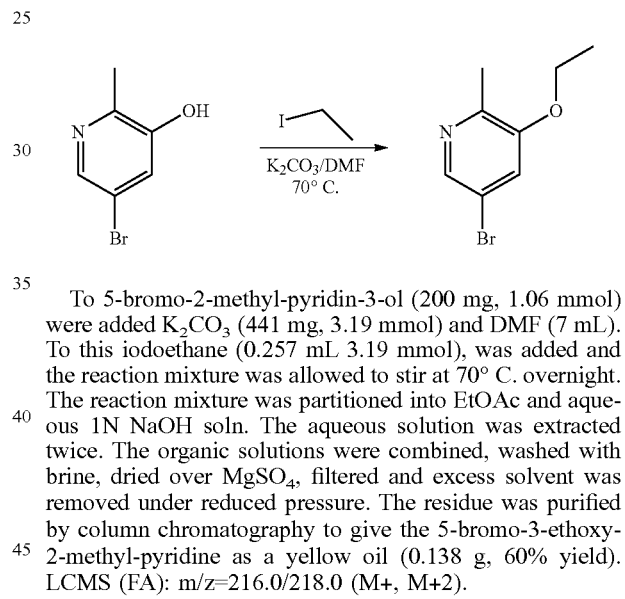

To 5-bromo-2-methyl-pyridin-3-ol (200 mg, 1.06 mmol) were added K$_2$CO$_3$ (441 mg, 3.19 mmol) and DMF (7 mL). To this iodoethane (0.257 mL, 3.19 mmol), was added and the reaction mixture was allowed to stir at 70° C. overnight. The reaction mixture was partitioned into EtOAc and aqueous 1N NaOH soln. The aqueous solution was extracted twice. The organic solutions were combined, washed with brine, dried over MgSO$_4$, filtered and excess solvent was removed under reduced pressure. The residue was purified by column chromatography to give the 5-bromo-3-ethoxy-2-methyl-pyridine as a yellow oil (0.138 g, 60% yield). LCMS (FA): m/z=216.0/218.0 (M+, M+2).

Synthesis of Reagent (ea) from Example 34AF: 3-Chloro-5-[(4-fluoro-2,3-dihydro-1H-inden-1-yl)oxy]pyridine

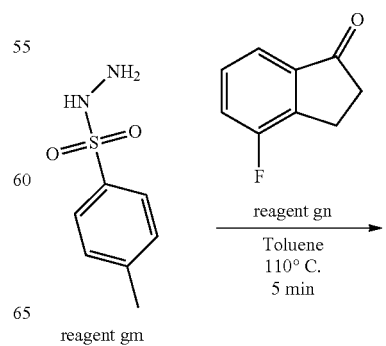

491

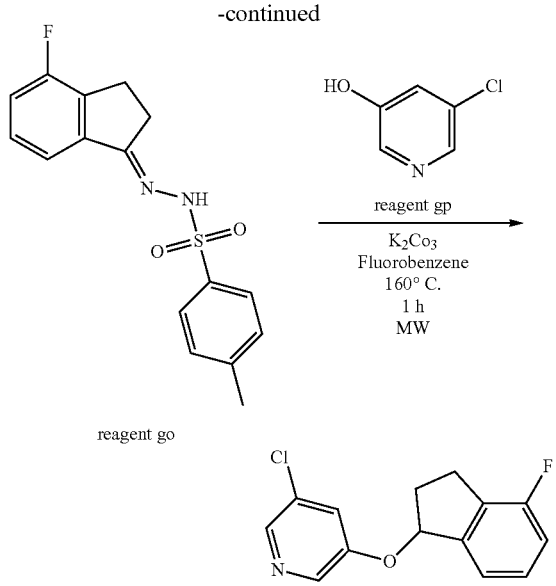

Step 1: N'-[(1E)-4-fluoro-2,3-dihydro-1H-inden-1-ylidene]-4-methylbenzenesulfonohydrazide A round bottomed flask equipped with a stir bar was charged with 4-fluoroindan-1-one (444 mg, 2.96 mmol), 4-methylbenzenesulfonohydrazide (551 mg, 2.96 mmol) and toluene (8 mL). The resulting mixture was allowed to stir at 110° C. for 10 min, then was cooled to rt. The precipitate which formed was collected by suction filtration and was dried under high vacuum to provide N-[(1E)-4-fluoro-2,3-dihydro-1H-inden-1-ylidene]-4-methylbenzenesulfonohydrazide (0.94 g, 72% yield) as an off-white solid. LCMS (FA): m/z=319.1 (M+H).

Step 2: 3-Chloro-5-[(4-fluoro-2,3-dihydro-1H-inden-1-yl)oxy]pyridine

A 5 mL microwave tube equipped with a stir bar was charged with 5-chloropyridin-3-ol (232 mg, 1.79 mmol), N'-[(1E)-4-fluoro-2,3-dihydro-1H-inden-1-ylidene]-4-methylbenzenesulfonohydrazide (285 mg, 0.895 mmol), potassium carbonate (433 mg, 3.13 mmol), and fluorobenzene (3 ml). The tube was sealed and the reaction mixture was subjected to microwave irradiation at 160° C. for 1 h. The reaction mixture was allowed to cool to rt, then the vial was opened and the reaction mixture was poured into stirring 1N NaOH. The resulting mixture was extracted with DCM. The organic solutions were combined, washed with 1 N NaOH and saline, dried with MgSO$_4$, filtered, and concentrated. The crude compound was purified by column chromatography to provide 3-chloro-5-[(4-fluoro-2,3-dihydro-1H-inden-1-yl)oxy]pyridine (0.236 g, 34%) as a white solid. LCMS (FA): m/z=264.0 (M+H). $^1$H NMR (400 MHz, DMSO-d6) δ ppm 8.34 (d, J=2.51 Hz, 1H), 8.26 (d, J=1.76 Hz, 1H), 7.78 (t. J=2.26 Hz, 1H), 7.26-7.36 (m, 2H), 7.18 (t, J=8.51 Hz, 1H), 6.06 (dd, J=6.53, 3.51 Hz, 1H), 3.02-3.12 (m, 1H), 2.93 (ddd, J=16.38, 8.72, 4.77 Hz, 1H), 2.59-2.70 (m, 1H), 2.10 (dddd, J=13.68, 8.66, 4.77, 3.76 Hz, 1H).

The compounds listed in the table below (Table 29a) were prepared in an analogous fashion to that described above from the appropriate starting materials:

TABLE 29a

| Intermediate | | Starting Material | | Compound | |
|---|---|---|---|---|---|
| ea | Reagent | Chemical Structure | | No. | LCMS Data |
| From example 34AC | gm | (structure of 4-methoxybenzenesulfonohydrazide) gn | | I-336 | LCMS (FA): m/z = 314.0 (M + H) |
| From example 34AD | gm | (structure of 4-methoxybenzenesulfonohydrazide) | | I-422 | LCMS (FA): m/z = 296.0 (M + H) |

US 10,538,533 B2

493                                                                                     494

TABLE 29a-continued

| Intermediate ea | Starting Material | | Compound No. | LCMS Data |
|---|---|---|---|---|
| | Reagent | Chemical Structure | | |
| | gn | 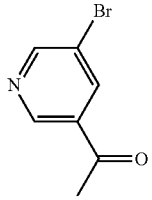 | | |
| From example 34AE | gp gm gn | 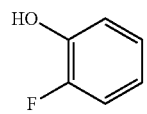 | I-349 | LCMS (FA): m/z = 294.2 (M + H) |
| | gp | 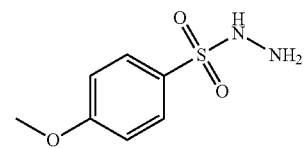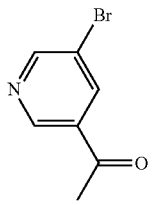 | | |

Example 35: N-{6-chloro-5'-fluoro-4-methyl-2'-[(2-methylpyrimidin-4-yl)amino]-3,4'-bipyridin-5-yl}-2,4-difluorobenzenesulfonamide (I-294)

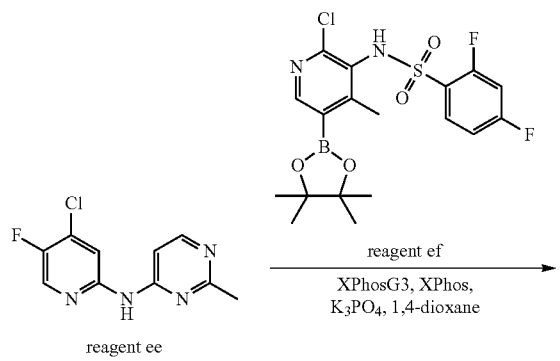

-continued

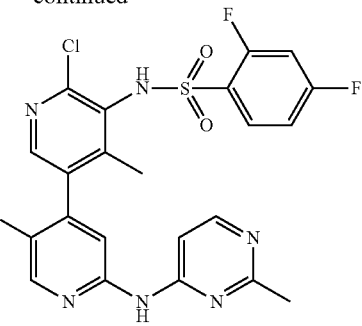

A mixture of N-(2-chloro-4-methyl-5-(4,4,5,5-tetramethyl-1,3,2-dioxaborolan-2-yl)pyridin-3-yl)-2,4-difluorobenzenesulfonamide (0.162 g, 0.364 mmol) (see Example 1 above), N-(4-chloro-5-fluoropyridin-2-yl)-2-methylpyrimidin-4-amine (0.067 g, 0.280 mmol) (see Example 1 above), XPhos (0.004 g, 0.008 mmol), XPhosG3 (0.007 g, 0.008 mmol), and degassed K₃PO₄ (0.50 M in water, 1.10 mL, 0.56 mmol) in degassed 1,4-dioxane (1.0 mL) was allowed to stir at 105° C. for 2 h. The reaction was allowed to cool to rt and then filtered through celite. The filtrate was diluted with EtOAc and then washed with water. The organic solution was dried over Na₂SO₄, filtered, and concentrated. The crude compound was purified by column chromatography to provide N-{6-chloro-5'-fluoro-4-methyl-2'-[(2-methylpyrimidin-4-yl)amino]-3,4'-bipyridin-5-yl}-2,4-difluorobenzenesulfonamide I-294 (0.11 g, 75%). LCMS (FA): m/z=521.1 (M+H). ¹H NMR (400 MHz, DMSO-d₆) δ 10.69 (s, 1H), 10.39 (s, 1H), 8.46 (d, J=0.9 Hz, 1H), 8.35 (d, J=5.9 Hz, 1H), 8.31 (s, 1H), 7.87-7.74 (m, 2H). 7.68-7.55 (m, 1H), 7.51 (d, J=5.9 Hz, 1H), 7.34-7.23 (m, 1H), 2.46 (s, 3H), 2.24 (s, 3H).

The compounds listed in the table below (Table 30) were prepared in an analogous fashion to that described above from the appropriate starting materials:

TABLE 30

| Example | Reagent | Starting Material Chemical Structure | Compound No. | LCMS Data |
|---|---|---|---|---|
| 35A | ee | (4-chloropyridin-2-yl)-(2-phenylpyrimidin-4-yl)amine structure | I-264 | LCMS (FA): m/z = 565.1 (M + H) |
| 35B | ef | 2-methyl-N-(2,4-difluorophenylsulfonyl)-5-(pinacolboronate)pyridine structure | I-237 | LCMS (FA): m/z = 523.1 (M + H) |
|  | ee | (4-chloropyridin-2-yl)-(2-trifluoromethylpyrimidin-4-yl)amine structure | | |
| 35C | ee | (4-chloropyridin-2-yl)-(2-cyclopropylpyrimidin-4-yl)amine structure | I-296 | LCMS (FA): m/z = 529.1 (M + H) |
| 35D | ee | (4-chloropyridin-2-yl)-(2,6-dimethylpyrimidin-4-yl)amine structure | I-218 | LCMS (FA): m/z = 517.1 (M + H) |
| 35E | ee | (4-chloropyridin-2-yl)-(2-methoxypyrimidin-4-yl)amine structure | I-225 | LCMS (FA): m/z = 519.1 (M + H) |

TABLE 30-continued
| Example | Starting Material Reagent | Chemical Structure | Compound No. | LCMS Data |
|---|---|---|---|---|
| 35F | ef | 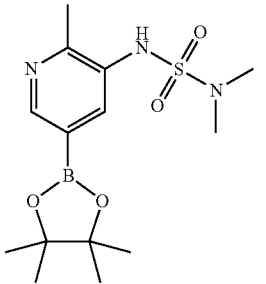 | I-217 | LCMS (FA): m/z = 386.1 (M + H) |
| | ee | 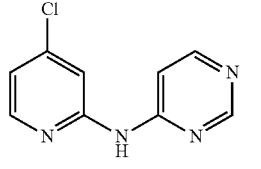 [SMILES: Clc1ccnc(Nc2ccncn2)c1] | | |
| 35G | ef | 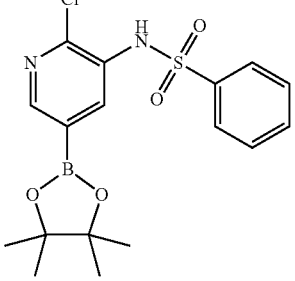 | I-309 | LCMS (FA): m/z = 453.1 (M + H) |
| | ee | 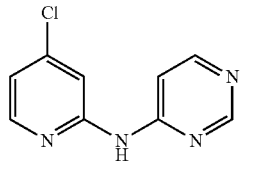 [SMILES: Clc1ccnc(Nc2ccncn2)c1] | | |
| 35H | ef | 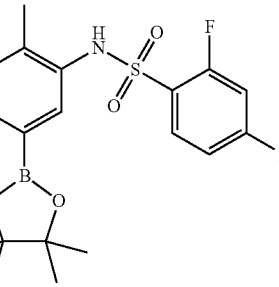 | I-239 | LCMS (FA): m/z = 455.1 (M + H) |
| | ee | 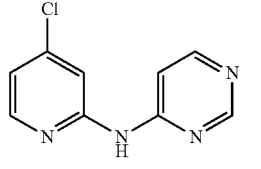 [SMILES: Clc1ccnc(Nc2ccncn2)c1] | | |

TABLE 30-continued
| Example | Starting Material Reagent | Starting Material Chemical Structure | Compound No. | LCMS Data |
|---|---|---|---|---|
| 35I | ef | 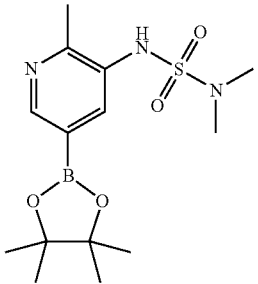 | I-286 | LCMS (FA): m/z = 400.1 (M + H) |
|  | ee | 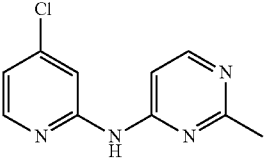 |  |  |
| 35J | ef | 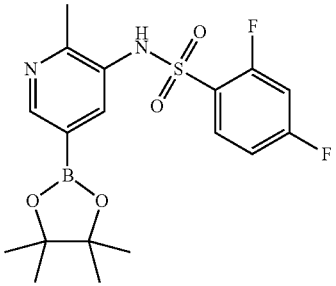 | I-291 | LCMS (FA): m/z = 469.1 (M + H) |
|  | ee | 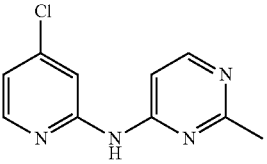 |  |  |
| 35K | ee | 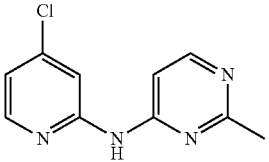 | I-272 | LCMS (FA): m/z = 502.1 (M + H) |
| 35L | ee | 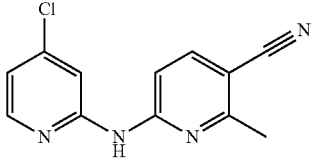 | I-238 | LCMS (FA): m/z = 527.3 (M + H) |

TABLE 30-continued

| | | Starting Material | Compound | LCMS |
|---|---|---|---|---|
| Example | Reagent | Chemical Structure | No. | Data |
| 35M | ef | (structure) | I-229 | LCMS (FA): m/z = 424.0 (M + H) |
| | ee | (structure) | | |
| 35N | ef | (structure) | I-289 | LCMS (FA): m/z = 493.0 (M + H) |
| | ee | (structure) | | |
| 35O | ee | (structure) | I-300 | LCMS (FA): m/z = 514.0 (M + H) |
| 35P | ee | (structure) | I-293 | LCMS (FA): m/z = 503.1 (M + H) |

TABLE 30-continued

| Example | Starting Material Reagent | Starting Material Chemical Structure | Compound No. | LCMS Data |
|---|---|---|---|---|
| 35Q | ef | (pyridine-sulfonamide-Bpin structure with 2,4-difluorophenyl) | I-228 | LCMS (FA): m/z = 479.2 (M + H) |
|  | ee | (4-chloro-2-((5-cyanopyridin-2-yl)amino)pyridine) | | |
| 35R | ef | (pyridine-sulfonamide-Bpin structure with 2,4-difluorophenyl) | I-301 | LCMS (FA): m/z = 457.1 (M + H) |
|  | ee | (4-chloro-2-((1-methyl-1H-pyrazol-3-yl)amino)pyridine) | | |
| 35S | ef | (pyridine-sulfonamide-Bpin structure with 2,4-difluorophenyl) | I-307 | LCMS (FA): m/z = 469.1 (M + H) |
|  | ee | (4-chloro-2-((6-methylpyridazin-3-yl)amino)pyridine) | | |

TABLE 30-continued

| Example | Reagent | Starting Material Chemical Structure | Compound No. | LCMS Data |
|---------|---------|--------------------------------------|--------------|-----------|
| 35T | ef | (pyridine-pinacol boronate sulfonamide with 2,4-difluorophenyl) | I-276 | LCMS (FA): m/z = 468.1 (M + H) |
| | ee | 4-chloro-N-(6-methylpyridin-2-yl)pyridin-2-amine | | |
| 35U | ef | (pyridine-pinacol boronate sulfonamide with 2,4-difluorophenyl) | I-265 | LCMS (FA): m/z = 455.1 (M + H) |
| | ee | 4-chloro-N-(pyridin-2-yl)pyridin-2-amine | | |
| 35V | ef* | (pyridine-pinacol boronate sulfonamide with 2,4-difluorophenyl) | I-233 | LCMS (FA): m/z = 494.1 (M + H) |
| | ee | 4-chloro-N-(benzo[d]oxazol-2-yl)pyridin-2-amine | | |

TABLE 30-continued
| | | Starting Material | Compound | LCMS |
|---|---|---|---|---|
| Example | Reagent | Chemical Structure | No. | Data |
| 35W | ef | 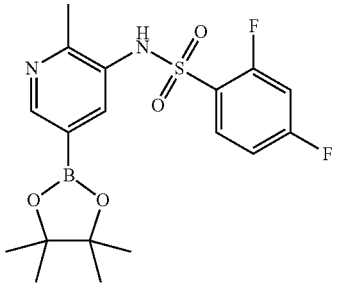 | I-297 | LCMS (FA): m/z = 454.2 (M + H) |
| | ee | 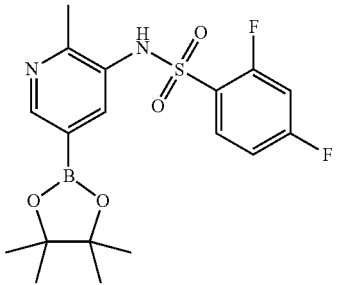 [SMILES: Cc1ncc(B2OC(C)(C)C(C)(C)O2)cc1NS(=O)(=O)c1ccc(F)cc1F] | | |
| 35X | ef | 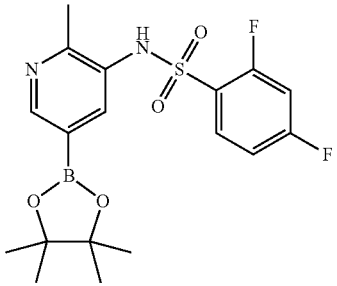 | I-310 | LCMS (FA): m/z = 455.2 (M + H) |
| | ee | | | |
| 35Y | ef* | 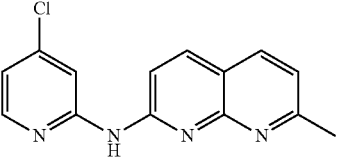 | I-235 | LCMS (FA): m/z = 519.6 (M + H) |
| | ee | | | |

TABLE 30-continued
| Example | Starting Material Reagent | Starting Material Chemical Structure | Compound No. | LCMS Data |
|---|---|---|---|---|
| 35Z | ef* | 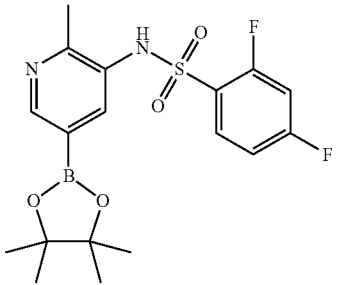 | I-271 | LCMS (FA): m/z = 510.2 (M + H) |
| | ee | 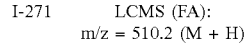 | | |
| 35AA | ef** | 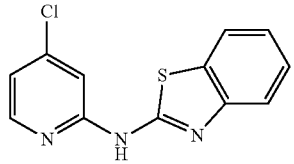 [SMILES: Clc1ccnc(Nc2nc3ccccc3s2)c1] | I-281 | LCMS (FA): m/z = 308.5 (M + H) |
| | ee | 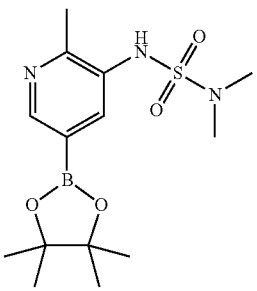 | | |
| 35AB | ef | 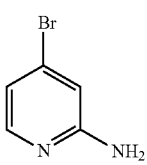 | I-231 | LCMS (FA): m/z = 187.1 (M + H) |
| | ee | 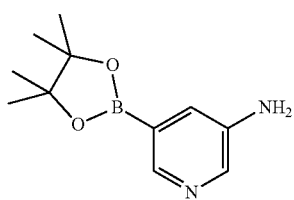 [SMILES: CC1(C)OB(c2cncc(N)c2)OC1(C)C] | | |

TABLE 30-continued
| Example | Starting Material Reagent | Chemical Structure | Compound No. | LCMS Data |
|---|---|---|---|---|
| 35AC | ef | 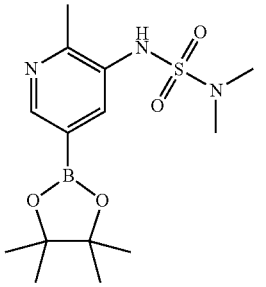 | I-263 | LCMS (FA): m/z = 424.1 (M + H) |
| | ee | 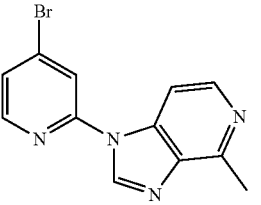 [SMILES: Cc1nccc2c1ncn2-c1cc(Br)ccn1] | | |
| 35AD | ee*** | 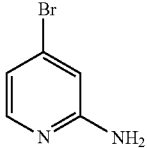 | I-287 | LCMS (FA): m/z = 411.0 (M + H) |
| 35AE | ef | 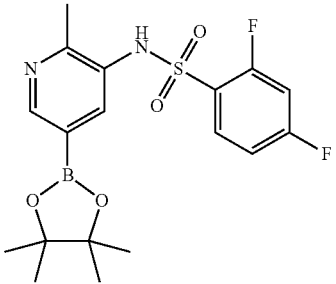 | I-219 | LCMS (FA): m/z = 435.2 (M + H) |
| | ee | 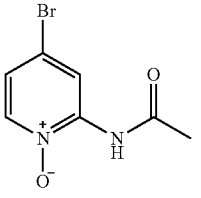 | | |
| 35AF | ef | 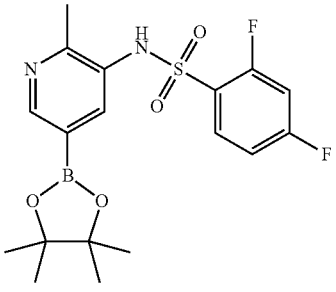 | I-305 | LCMS (FA): m/z = 459.1 (M + H) |

TABLE 30-continued

| Example | Starting Material Reagent | Chemical Structure | Compound No. | LCMS Data |
|---|---|---|---|---|
| | ee | 4-chloro-N-(cyclobutanecarbonyl)pyridin-2-amine | | |
| 35AG | ee** | methyl (4-bromopyridin-2-yl)carbamate | I-255 | LCMS (FA): m/z = 469.0 (M + H) |
| 35AH | ef** | N-(2-methyl-5-(4,4,5,5-tetramethyl-1,3,2-dioxaborolan-2-yl)pyridin-3-yl)-2,4-difluorobenzenesulfonamide | I-313 | LCMS (FA): m/z = 474.1 (M + H) |
| | ee | N-(4-bromopyridin-2-yl)pyrrolidine-1-carboxamide | | |
| 35AI | ef** | N-(2-methyl-5-(4,4,5,5-tetramethyl-1,3,2-dioxaborolan-2-yl)pyridin-3-yl)-N',N'-dimethylsulfamide | I-241 | LCMS (FA): m/z = 366.1 (M + H) |
| | ee | methyl (4-bromopyridin-2-yl)carbamate | | |
| 35AK | ef | N-(2-methyl-5-(4,4,5,5-tetramethyl-1,3,2-dioxaborolan-2-yl)pyridin-3-yl)-2,4-difluorobenzenesulfonamide | I-324 | LCMS (FA): m/z = 505.1 (M + H) |

TABLE 30-continued

| Example | Starting Material Reagent | Chemical Structure | Compound No. | LCMS Data |
|---|---|---|---|---|
| | ee | (4-bromopyridin-2-yl)carbamate of (3-methyloxetan-3-yl)methanol | | |
| 35AM | ef | N-(2-methyl-5-(4,4,5,5-tetramethyl-1,3,2-dioxaborolan-2-yl)pyridin-3-yl)-2,4-difluorobenzenesulfonamide | I-326 | LCMS (FA): m/z = 515.1 (M + H) |
| | ee | (4-bromopyridin-2-yl)carbamate of (1-methyl-1H-pyrazol-3-yl)methanol | | |
| 35AN | ef | N-(2-methyl-5-(4,4,5,5-tetramethyl-1,3,2-dioxaborolan-2-yl)pyridin-3-yl)-2,4-difluorobenzenesulfonamide | I-389 | LCMS (FA): m/z = 449.1 (M + H) |
| | ee | ethyl (4-chloropyridin-2-yl)carbamate | | |
| 35AO | ef | N,N-dimethyl sulfamide of 2-methyl-5-(4,4,5,5-tetramethyl-1,3,2-dioxaborolan-2-yl)pyridin-3-amine | I-364 | LCMS (FA): m/z = 380.1 (M + H) |

TABLE 30-continued

| Example | Starting Material Reagent | Chemical Structure | Compound No. | LCMS Data |
|---|---|---|---|---|
| | ee | 4-chloro-2-(ethoxycarbonylamino)pyridine | | |
| 35AP | ef | 2-methyl-3-(2,4-difluorophenylsulfonamido)-5-(pinacol boronate)pyridine | I-414 | LCMS (FA): m/z = 433.3 (M + H) |
| | ee | 4-chloro-6-methyl-2-acetamidopyridine | | |
| 35AQ | ef⁻¹ | 5-(morpholinosulfonyl)pyridine-3-boronic acid | I-332 | LCMS (FA): m/z = 379.1 (M + H) |
| | ee | 4-chloro-2-(methoxycarbonylamino)pyridine | | |
| 35AR | ee | 4-chloro-2-(ethoxycarbonylamino)pyridine | I-383 | LCMS (FA): m/z = 483.0 (M + H) |
| 35AU | ef | 2-methyl-3-(2,4-difluorophenylsulfonamido)-5-(pinacol boronate)pyridine | I-375 | LCMS (FA): m/z = 500.1 (M + H) |

TABLE 30-continued

| Example | Starting Material Reagent | Starting Material Chemical Structure | Compound No. | LCMS Data |
|---|---|---|---|---|
| | ee | (4-methyl-6-methoxy-1,3,5-triazin-2-yl)(4-chloropyridin-2-yl)amine | | |
| 35AV | ef | N-(2-methyl-5-(4,4,5,5-tetramethyl-1,3,2-dioxaborolan-2-yl)pyridin-3-yl)-2,4-difluorobenzenesulfonamide | I-382 | LCMS (FA): m/z = 510.1 (M + H) |
| | ee | (4-methyl-6-cyclopropyl-1,3,5-triazin-2-yl)(4-chloropyridin-2-yl)amine | | |
| 35AW | ee | ethyl (4-chloropyridin-2-yl)carbamate | I-456 | LCMS (FA): m/z = 465.1 (M + H) |
| | ef | N-(2-methyl-5-(4,4,5,5-tetramethyl-1,3,2-dioxaborolan-2-yl)pyridin-3-yl)-2-fluoro-4-chlorobenzenesulfonamide | | |
| 35AX | ee | methyl (4-chloropyridin-2-yl)carbamate | I-417 | LCMS (FA): m/z = 450.9 (M + H) |

TABLE 30-continued

| | | Starting Material | Compound | LCMS |
|---|---|---|---|---|
| Example | Reagent | Chemical Structure | No. | Data |
| | ef | 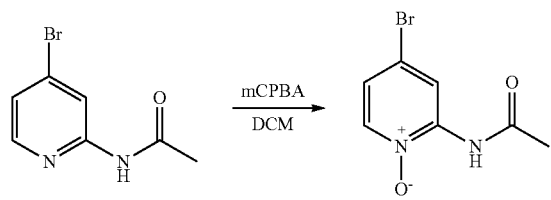 | | |

*Coupling using Pd(PPh₃)₄ and Cs₂CO₃
**Coupling using Pd(dppf)Cl₂ and K₂CO₃
***Coupling using Pd(PPh₃)₄ and K₂CO₃, subjected to microwave irradiation
˜Coupling using Pd(dppf)Cl₂ and K₂CO₃, subjected to microwave irradiation
˜˜Coupling using Pd₂(dba)₃, Xphos, KOAc/water
¹Reagent ef prepared according to standard procedures described for boronate synthesis in the intermediates section Synthesis of Reagent (ee) from Example 35AE:
N-(4-bromo-1-oxidopyridin-2-yl)acetamide

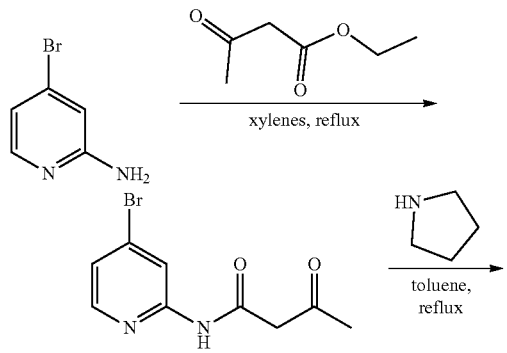

To a solution of N-(4-bromopyridin-2-yl)acetamide (350 mg, 1.6 mmol) in DCM (20 mL) was added mCPBA (1.26 g, 7.3 mmol) at 0° C. The reaction mixture was allowed to stir at rt for 3 h. The reaction mixture was then diluted with water and saturated K₂CO₃ solution, and extracted with DCM. The organic solutions were combined, dried over Na₂SO₄, filtered and concentrated. The crude compound was purified by column chromatography to provide N-(4-bromo-1-oxidopyridin-2-yl)acetamide (340 mg, 90%). LCMS (FA): m/z=231.3 (M+H).

Synthesis of Reagent (ee) from Example 35AH:
N-(4-bromopyridin-2-yl)pyrrolidine-1-carboxamide -continued

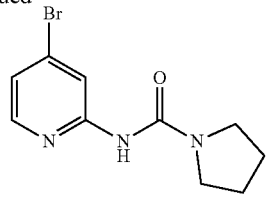

Step 1: N-(4-bromopyridin-2-yl)-3-oxobutanamide

2-Amino-4-bromopyridine (5.00 g, 29.0 mmol) was added portionwise to a refluxing solution of 3-oxobutanoic acid ethyl ester (3.70 mL, 29.0 mmol) in xylenes (15 mL) over 1 h. The reaction was allowed to cool to rt and was concentrated. DCM was added to the residue and the mixture was filtered. The filtrate was concentrated and the crude compound was purified by column chromatography to provide N-(4-bromopyridin-2-yl)-3-oxobutanamide (0.60 g, 8%). LCMS (FA): m/z=257.2 (M+H).

Step 2:
N-(4-bromopyridin-2-yl)pyrrolidine-1-carboxamide

A solution of N-(4-bromopyridin-2-yl)-3-oxobutanamide (0.13 mg, 0.52 mmol) and pyrrolidine (0.40 mL, 5.0 mmol) in toluene (10 mL) was allowed to stir at reflux for 3.5 h. The reaction was allowed to cool to rt and was concentrated. The crude compound was purified by column chromatography to give N-(4-bromopyridin-2-yl)pyrrolidine-1-carboxamide (0.07 g, 47%). LCMS (FA): m/z=270.1 (M+H).

Synthesis of Reagent (ee) from Example 35AF:
N-(4-chloropyridin-2-yl)cyclobutanecarboxamide

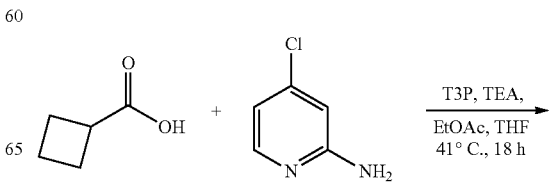

-continued

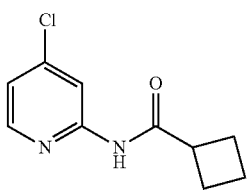

Cyclobutanecarboxylic acid (0.659 mL, 6.98 mmol) was added to a stirring solution of 2-amino-4-chloropyridine (0.833 g, 6.48 mmol), T3P (50% in EtOAc, 4.2 mL, 7.0 mmol), and TEA (1.95 mL, 14.0 mmol) in THF (10 mL). The resulting solution was allowed to stir in an oil bath at 41° C. overnight under an atmosphere of nitrogen. The reaction was allowed to cool to rt and was quenched by pouring into stirring saline (~30 mL). The reaction mixture was extracted with EtOAc. The organic solutions were combined, washed with saline, dried over MgSO$_4$, filtered, and concentrated to give the crude product. The crude product was purified by column chromatography to give N-(4-chloropyridin-2-yl)cyclobutanecarboxamide (0.892 g, 65% yield) as a white solid. LCMS (FA): m/z=211.1 (M+H).

Synthesis of Reagent (ee) from Example 35AC:
1-(4-bromopyridin-2-yl)-4-methyl-1H-imidazo[4,5-c]pyridine

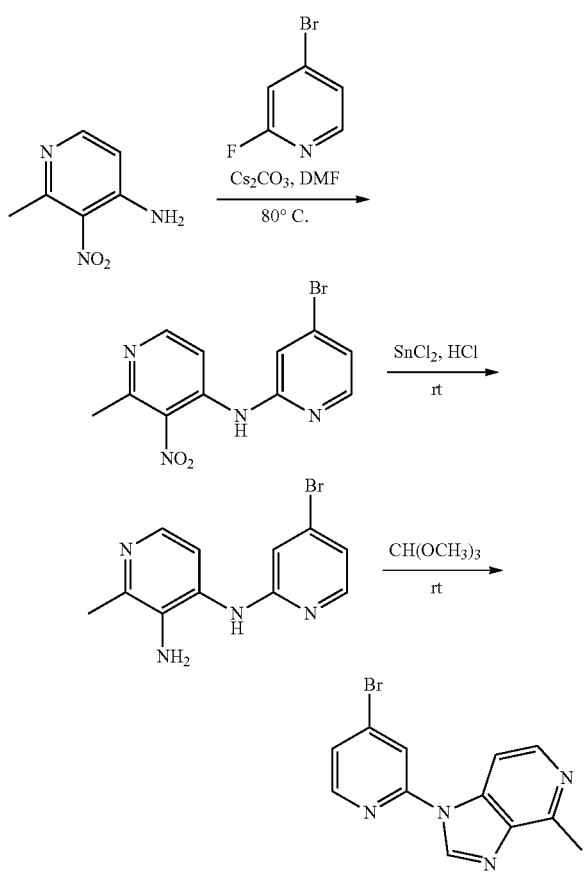

Step 1: 4-bromo-N-(2-methyl-3-nitropyridin-4-yl)pyridin-2-amine

A mixture of 4-amino-3-nitro-2-picoline (0.267 g, 1.74 mmol), 4-bromo-2-fluoropyridine (0.44 g, 2.50 mmol) and cesium carbonate (1.74 g, 5.33 mmol) in DMF (4.0 mL) was allowed to stir at 80° C. for 1.5 h. The reaction mixture was extracted with EtOAc. The organic solutions were combined, washed with 10% lithium chloride solution, dried over Na$_2$SO$_4$, filtered and concentrated to give crude 4-bromo-N-(2-methyl-3-nitropyridin-4-yl)pyridin-2-amine as a yellow solid which was used without purification.

Step 2: N$^4$-(4-bromopyridin-2-yl)-2-methylpyridine-3,4-diamine

To 4-bromo-N-(2-methyl-3-nitropyridin-4-yl)pyridin-2-amine in hydrochloric acid (12M, 4.36 mL, 52.3 mmol) was added tin(II) chloride dihydrate (1.19 g, 5.23 mmol) at 0° C. After addition, the reaction mixture was allowed to warm to rt and stir overnight. The reaction mixture was cooled to 0° C. and basified by the addition of concentrated sodium hydroxide solution to pH=9. The mixture was evaporated and the crude product was purified by chromatography to give N$^4$-(4-bromopyridin-2-yl)-2-methylpyridine-3,4-diamine (0.19 g, 39%), as a white powder. LCMS (FA): m/z=279.0 (M+H).

Step 3: 1-(4-bromopyridin-2-yl)-4-methyl-1H-imidazo[4,5-c]pyridine

To a mixture of N$^4$-(4-bromopyridin-2-yl)-2-methylpyridine-3,4-diamine (0.055 g, 0.20 mmol) and p-toluenesulfonic acid (0.0197 mmol) in a round bottom flask was added trimethyl orthoformate (3.00 g, 28.3 mmol) and the mixture was allowed to stir at 60° C. for 2 h. The reaction mixture was evaporated and the residue was purified by column chromatography to give 1-(4-bromopyridin-2-yl)-4-methyl-1H-imidazo[4,5-c]pyridine as a white powder (22 mg, 38%). LCMS (FA): m/z=289.0 (M+H).

Synthesis of Reagent (ee) from Example 35AW:
Ethyl (4-chloropyridin-2-yl)carbamate

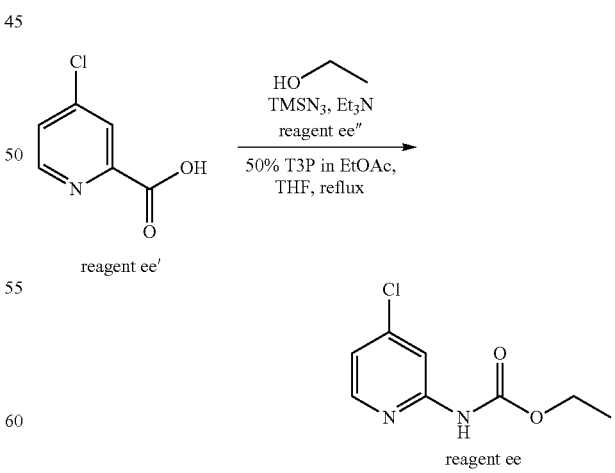

EtOH (0.741 mL, 12.7 mmol) was added to a stirring solution of 4-chloropicolinic acid (1.00 g, 6.35 mmol), 50% T3P in EtOAc (4.2 mL, 7.0 mmol), azidotrimethylsilane (0.93 mL, 7.0 mmol), and TEA (1.3 mL, 9.5 mmol) in THF (10 mL). The resulting solution was allowed to stir at reflux overnight under an atmosphere of nitrogen. After cooling to rt, the reaction mixture was poured into stirring saline (~30 mL). The precipitate which formed was collected on a fritted funnel, washed with water, and dried to give the crude product as a tan powder. The crude compound was purified by column chromatography to provide ethyl (4-chloropyridin-2-yl)carbamate (0.93 g, 73%) as a white powder. LCMS (FA): m/z=201.0 (M+H).

The compounds listed in the table below (Table 30a) were prepared in an analogous fashion to that described above from the appropriate starting materials:

TABLE 30a

| Intermediate | Starting Material | | Compound | |
| --- | --- | --- | --- | --- |
| ee | Reagent | Chemical Structure | No. | LCMS Data |
| From example 35AK | ee'' | (structure) | I-324 | LCMS (FA): m/z = 301.1 (M + H) |
| From example 35AM | ee'' | (structure) | I-326 | LCMS (FA): m/z = 311.1 (M + H) |

Synthesis of Reagent (ee) from Example 35AP: N-(4-chloro-6-methylpyridin-2-yl)acetamide

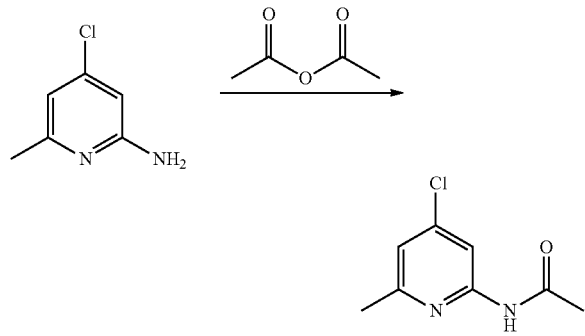

To a solution of 4-chloro-6-methylpyridin-2-amine (416 mg, 2.92 mmol) in acetic anhydride (5.89 mL) was added DMAP (3.6 mg, 0.029 mmol). The reaction mixture was allowed to stir at 140° C. for 3 h. The reaction mixture was concentrated and purified by column chromatography to provide N-(4-chloro-6-methylpyridin-2-yl)acetamide (420 mg, 78%). LCMS (FA): m/z=185.0 (M+H).

Example 36: N-(6-chloro-5-{[(2,4-difluorophenyl)sulfonyl]amino}-4-methyl-3,4'-bipyridin-2'-yl)cyclopropane carboxamide (I-308)

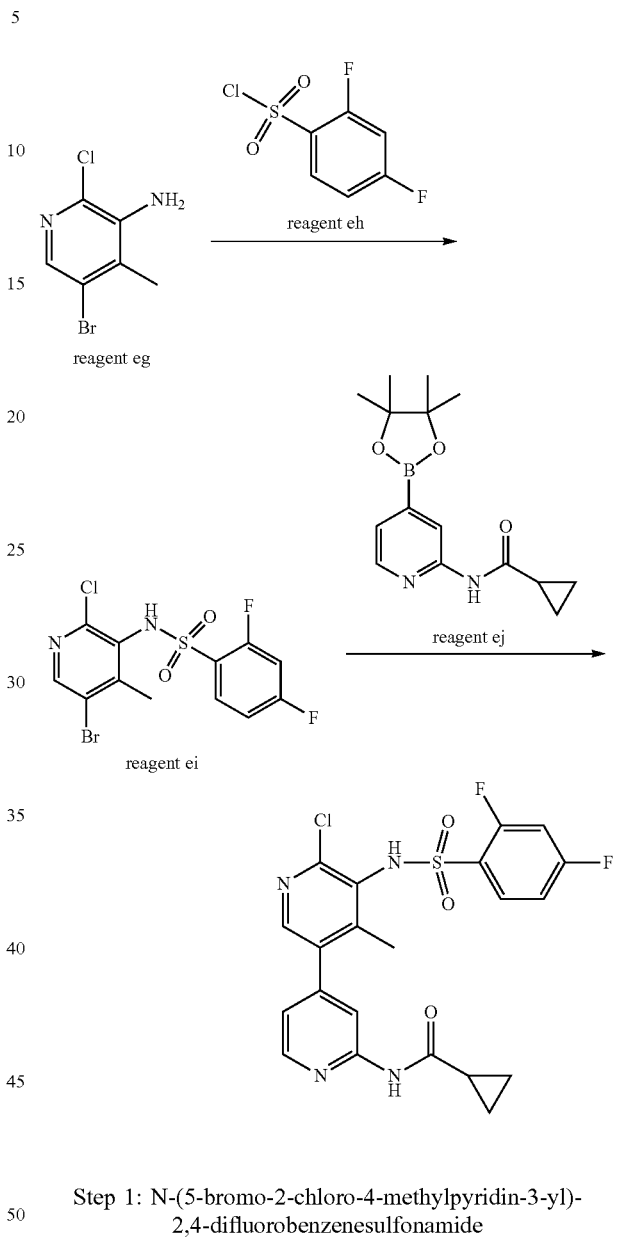

Step 1: N-(5-bromo-2-chloro-4-methylpyridin-3-yl)-2,4-difluorobenzenesulfonamide To a solution of 5-bromo-2-chloro-4-methylpyridin-3-amine (12 g, 54 mmol) in THF (360 mL) was added LiHMDS (1M in THF, 108 mL, 108 mmol) at −5° C. The reaction mixture was allowed to stir at −5° C. for 10 min. To the reaction mixture 2,4-difluorobenzenesulfonyl chloride (17.3 g, 81 mmol) was added. The reaction mixture was allowed to stir at rt for 12 h. The reaction mixture was diluted with water and extracted with EtOAc. The organic solutions were combined, dried over Na$_2$SO$_4$, filtered and concentrated. The crude compound was purified by column chromatography to provide N-(5-bromo-2-chloro-4-methylpyridin-3-yl)-2,4-difluorobenzenesulfonamide (11.5 g, 53%). LCMS (FA): m/z=396.9 (M+H). $^1$H NMR (400 MHz, CDCl$_3$) δ 8.37 (s, 1H), 7.71 (m, 1H), 7.00 (m, 2H), 6.70 (s, 1H), 2.64 (s, 3H).

Step 2: N-(6-chloro-5-{[(2,4-difluorophenyl)sulfonyl]amino}-4-methyl-3,4'-bipyridin-2'-yl)cyclopropane carboxamide (I-308)

A mixture of N-(5-bromo-2-chloro-4-methylpyridin-3-yl)-2,4-difluorobenzenesulfonamide (6.75 g, 17 mmol), N-[4-(4,4,5,5-tetramethyl-1,3,2-dioxaborolan-2-yl)pyridin-2-yl]cyclopropanecarboxamide (5.87 g, 20.4 mmol) and Pd(dppf)Cl$_2$, complex with DCM (1:1) (470 mg, 0.57 mmol) in 1,4-dioxane (133 mL) and K$_2$CO$_3$ (1M in water, 34 mL) was allowed to stir at 105° C. overnight. The reaction mixture was diluted with water and extracted with EtOAc. The organic solutions were combined, dried over Na$_2$SO$_4$, filtered and concentrated. The crude product was purified by column chromatography to provide N-(6-chloro-5-{[(2,4-difluorophenyl)sulfonyl]amino}-4-methyl-3,4'-bipyridin-2'-yl)cyclopropanecarboxamide I-308 (6.5 g, 80%). LCMS (FA): m/z=479.3 (M+H). H NMR (400 MHz, DMSO-d$_6$) δ 11.01 (s, 1H), 10.63 (s, 1H), 8.42 (d, J=5.2 Hz, 1H), 8.20 (s, 1H), 8.06 (s, 1H), 7.79 (m, 1H), 7.62 (m, 1H), 7.25 (m, 1H), 7.13 (dd, J=5.2, 1.6 Hz, 1H), 2.23 (s, 3H), 2.03 (m, 1H), 0.82 (m, 4H).

The compounds listed in the table below (Table 31) were prepared in an analogous fashion to that described above from the appropriate starting materials:

TABLE 31

| Example | Starting Material Reagent | Starting Material Chemical Structure | Compound No. | LCMS Data |
|---|---|---|---|---|
| 36A | eh | | I-254 | LCMS (FA): m/z = 515.0 (M + H) |
| | ej* | | | |
| 36B | eh | | I-251 | LCMS (FA): m/z = 435.1 (M + H) |
| | ej | | | |
| 36C | eh | | I-227 | LCMS (FA): m/z = 453.1 (M + H) |

TABLE 31-continued

| | Starting Material | | Compound | |
|---|---|---|---|---|
| Example | Reagent | Chemical Structure | No. | LCMS Data |
| | ej | *pyridine with pinacol boronate and NHAc* | | |
| 36D | eh | *2-chloro-4-fluorobenzenesulfonyl chloride* | I-290 | LCMS (FA): m/z = 469.3 (M + H) |
| | ej | *pyridine with pinacol boronate and NHAc* | | |
| 36E | eh | *2-chlorobenzenesulfonyl chloride* | I-240 | LCMS (FA): m/z = 450.9 (M + H) |
| | ej | *pyridine with pinacol boronate and NHAc* | | |
| 36F | eh | *2,4-dichlorobenzenesulfonyl chloride* | I-243 | LCMS (FA): m/z = 484.9 (M + H) |
| | ej | *pyridine with pinacol boronate and NHAc* | | |

TABLE 31-continued

| | Starting Material | | Compound | |
|---|---|---|---|---|
| Example | Reagent | Chemical Structure | No. | LCMS Data |
| 36G | eh | (benzenesulfonyl chloride) | I-312 | LCMS (FA): m/z = 417.1 (M + H) |
| | ej | (4-(4,4,5,5-tetramethyl-1,3,2-dioxaborolan-2-yl)pyridin-2-yl acetamide) | | |
| 36H | ej* | (5-methyl-4-(4,4,5,5-tetramethyl-1,3,2-dioxaborolan-2-yl)pyridin-2-yl acetamide) | I-250 | LCMS (FA): m/z = 467.0 (M + H) |
| 36I | eh | (N,N-dimethylsulfamoyl chloride) | I-236 | LCMS (FA): m/z = 384.1 (M + H) |
| | ej | (4-(4,4,5,5-tetramethyl-1,3,2-dioxaborolan-2-yl)pyridin-2-yl acetamide) | | |

*SiliaCat DPP-Pd and $K_2CO_3$ were used instead of Pd(dppf)$Cl_2$ and $K_2CO_3$

Example 37: 6-amino-N-(bicyclo[1.1.1]pent-1-yl)-2'-((2-methoxypyrimidin-4-yl)amino)-N-methyl-[3,4'-bipyridine]-5-carboxamide (I-230)

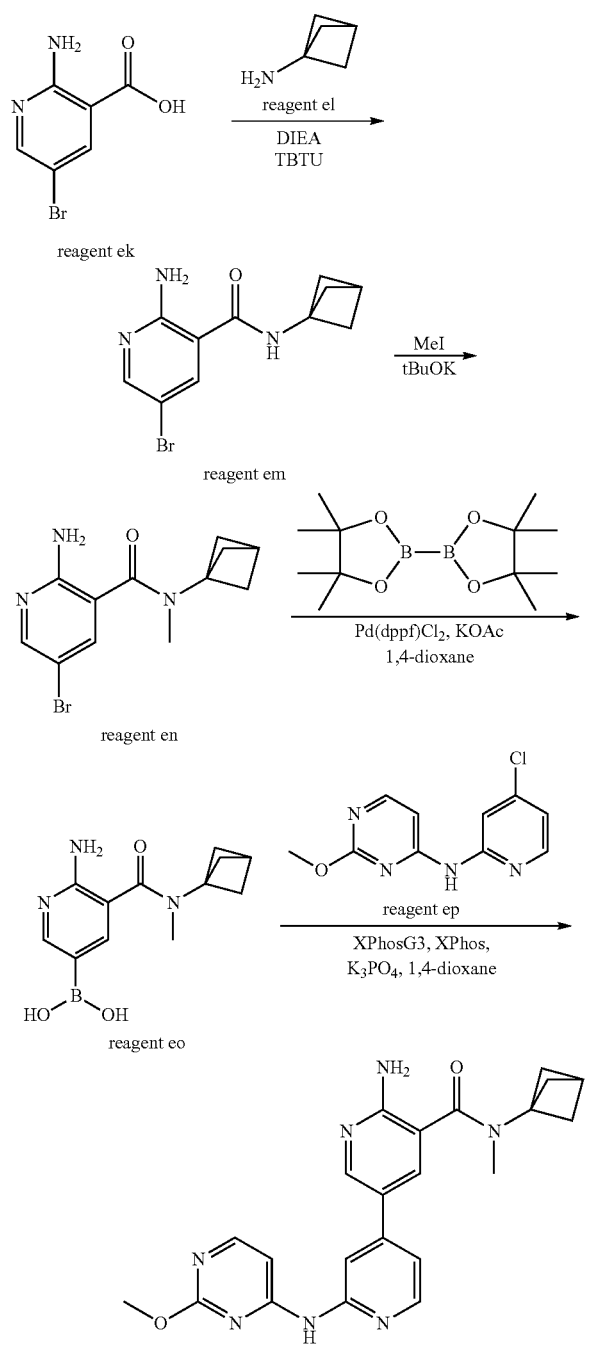

Step 1: 2-Amino-N-(bicyclo[1.1.1]pentan-1-yl)-5-bromonicotinamide

To 2-amino-5-bromonicotinicacid (2.00 g, 9.22 mmol) in DCM (87 mL) were added DIEA (4.5 mL, 25 mmol) and TBTU (4.4 g, 13.8 mmol). The reaction mixture was allowed to stir at rt for 20 min. To the reaction mixture was added bicyclo[1.1.1]pent-1-amine hydrochloride salt (0.73 g, 6.14 mmol). The reaction mixture was allowed to stir overnight at rt and was then diluted with water and DCM. The organic solution was separated, washed with brine, dried over $MgSO_4$, filtered and concentrated. The crude product was purified by column chromatography to give 2-amino-N-(bicyclo[1.1.1]pent-1-yl)-5-bromonicotinamide (0.67 g, 39%) as a white solid. LCMS (FA): m/z=282.0 (M+H).

Step 2: 2-amino-N-(bicyclo[1.1.1]pent-1-yl)-5-bromo-N-methylnicotinamide

To a flask under an atmosphere of $N_2$ were added 2-amino-N-(bicyclo[1.1.1]pent-1-yl)-5-bromonicotinamide (0.66 g, 2.34 mmol) and THF (19 mL). The reaction mixture was allowed to stir at 0° C. To this cooled solution, tBuOK (1M in THF, 2.11 mL, 2.11 mmol) was added drop wise. The reaction mixture was allowed to stir for 1 h. Methyl iodide (0.73 mL, 11.70 mmol) was added at 0° C. and the reaction mixture was allowed to stir for 5 h. The reaction mixture was filtered. The filtrate was concentrated and the residue was purified by column chromatography to give 2-amino-N-(bicyclo[1.1.1]pent-1-yl)-5-bromo-N-methylnicotinamide as a white foamy solid. (0.46 g, 66%). LCMS (FA): m/z=296.0 (M+H).

Step 3: (6-amino-5-(bicyclo[1.1.1]pent-1-yl(methyl)carbamoyl)pyridin-3-yl)boronic acid A mixture of 2-amino-N-(bicyclo[1.1.1]pent-1-yl)-5-bromo-N-methylnicotinamide (0.393 g, 1.33 mmol), bis(pinacolato)diboron (0.404 g, 1.59 mmol), $Pd(dppf)Cl_2$ (0.131 g, 0.159 mmol) and potassium acetate (0.384 g, 3.91 mmol) in 1,4-dioxane (15 mL) was allowed to stir between 82-85° C. under an atmosphere of nitrogen for 8 h. The reaction mixture was filtered through celite. The filter cake was washed with EtOAc. The filtrate was concentrated to give crude (6-amino-5-(bicyclo[1.1.1]pent-1-yl(methyl)carbamoyl)pyridin-3-yl)boronic acid, which was used without further purification. (0.34 g, 98%). LCMS (FA): m/z=262.1 (M+H).

Step 4: 6-amino-N-(bicyclo[1.1.1]pent-1-yl)-2'-((2-methoxypyrimidin-4-yl)amino)-N-methyl-[3,4'-bipyridine]-5-carboxamide A mixture of N-(4-chloropyridin-2-yl)-2-methoxypyrimidin-4-amine (0.141 g, 0.596 mmol), (6-amino-5-(bicyclo[1.1.1]pent-1-yl(methyl)carbamoyl)pyridin-3-yl)boronic acid (0.115 g, 0.442 mmol) in 1,4-dioxane (1.3 mL), XPhos (0.0092 g, 0.019 mmol), XPhosG3 (0.018 mg, 0.021 mmol) and potassium phosphate (0.05M in water, 2.55 mL, 1.27 mmol) under an atmosphere of nitrogen was allowed to stir at 90° C. for 2.5 h. The reaction mixture was filtered through celite. The filter cake was washed with MeOH and the filtrate was concentrated. The residue was purified by column chromatography to give 6-amino-N-(bicyclo[1.1.1]pent-1-yl)-2'-((2-methoxypyrimidin-4-yl)amino)-N-methyl-[3,4'-bipyridine]-5-carboxamide I-230 (0.080 g, 43%) as a yellow solid. LCMS (FA): m/Z=418.1 (M+H).

The compounds listed in the table below (Table 32) were prepared in an analogous fashion to that described above from the appropriate starting materials:

TABLE 32

| Example | Starting Material Reagent | Chemical Structure | Compound No. | LCMS Data |
|---|---|---|---|---|
| 37A | ek* | 5-bromonicotinic acid | I-245 | LCMS (FA): m/z = 403.1 (M + H) |
| 37B | ek* | 5-bromopyridine-3-carboxylic acid | I-234 | |
| | ep | 4-chloro-N-(2-methylpyrimidin-4-yl)pyridin-2-amine | | LCMS (FA): m/z = 387.2 (M + H) |
| 37C | ek* | 5-bromo-2-methylnicotinic acid | I-275 | LCMS (FA): m/z = 401.2 (M + H) |
| | ep | 4-chloro-N-(2-methylpyrimidin-4-yl)pyridin-2-amine | | |
| 37D | ep | 4-chloro-N-(2-methylpyrimidin-4-yl)pyridin-2-amine | I-277 | LCMS (FA): m/z = 402.2 (M + H) |

*NaH was used instead of tBuOK in Step 2

**HATU was used instead of TBTU in Step 1

***Final coupling with reagent en using Pd(PPh$_3$)$_4$, 1M Na$_2$CO$_3$, EtOH, Toluene, MW at 120° C.

Example 38: Azetidin-1-yl(6-methyl-2'-((2-methyl-pyrimidin-4-yl)amino)-3,4'-bipyridin-5-yl)methanone (I-304)

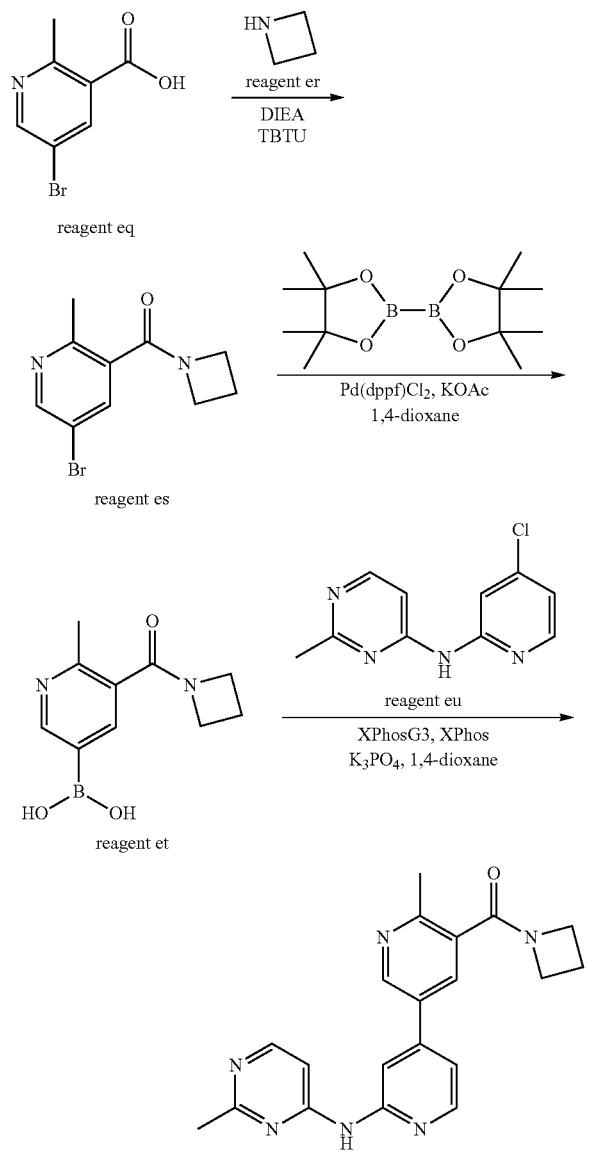

Step 1: Azetidin-1-yl(5-bromo-2-methylpyridin-3-yl)methanone

To 5-bromo-2-methylnicotinic acid (0.420 g, 1.94 mmol) in DCM (12.3 mL) were added DIEA (0.34 mL, 1.94 mmol), TBTU (1.25 g, 3.89 mmol) and azetidine (0.087 mL, 1.30 mmol). The reaction mixture was allowed to stir at rt. Excess solvent was removed under reduced pressure. The reaction mixture was diluted with EtOAc, washed with aqueous saturated NaHCO$_3$ solution, washed with brine, dried over MgSO$_4$, filtered and concentrated under reduced pressure. The residue was purified by column chromatography to give azetidin-1-yl(5-bromo-2-methylpyridin-3-yl)methanone (0.35 g, 80%). LCMS (FA): m/z=255.0 (M+H)

Step 2: (5-(Azetidine-1-carbonyl)-6-methylpyridin-3-yl)boronic acid

To azetidin-1-yl(5-bromo-2-methylpyridin-3-yl)methanone (0.20 g. 0.78 mmol) and bis(pinacolato)diboron (239 mg, 0.94 mmol) were added Pd(dppf)Cl$_2$ (77 mg, 0.094 mmol), potassium acetate (227 mg, 2.31 mmol) and 1,4-dioxane (8.63 mL). The flask was flushed with N$_2$ and then allowed to stir at 90° C. for 6.5 h. The reaction mixture was filtered through celite. The filter cake was washed with EtOAc. The filtrate was concentrated to give (5-(azetidine-1-carbonyl)-6-methylpyridin-3-yl)boronic acid. The crude material was used without purification. (0.17 g, 84%). LCMS (FA): m/z=221.0 (M+H).

Step 3: Azetidin-1-yl(6-methyl-2'-((2-methylpyrimidin-4-yl)amino)-3,4'-bipyridin-5-yl)methanone To a vial were added N-(4-chloropyridin-2-yl)-2-methylpyrimidin-4-amine (230.15 mg, 1.04 mmol), a solution of [5-(azetidin-1-ylcarbonyl)-6-methylpyridin-3-yl]boronic acid (170 mg, 0.77 mmol) in 1,4-dioxane (2.2 mL), XPhos (16.04 mg, 0.034 mmol), XPhosG3 (31.18 mg, 0.037 mmol) and 0.500 M of potassium phosphate in water (4.45 mL, 2.23 mmol). The vial was thoroughly flushed with N$_2$ and allowed to stir at 90° C. for 2.5 h. The reaction mixture was filtered through celite. The filter cake was washed with MeOH and the filtrate was concentrated. The residue was partitioned into EtOAc and water. The aqueous solution was extracted twice with EtOAc. The combined organic solutions were washed with brine, dried over MgSO$_4$, filtered and concentrated. The crude product was purified by column chromatography to give azetidin-1-yl(6-methyl-2'-((2-methylpyrimidin-4-yl)amino)-3,4'-bipyridin-5-yl)methanone I-304 (0.16 g, 58%). LCMS (FA): m/z=361.2 (M+H).

The compounds listed in the table below (Table 33) were prepared in an analogous fashion to that described above from the appropriate starting materials:

TABLE 33

| | | Starting Material | Compound | |
|---|---|---|---|---|
| Example | Reagent | Chemical Structure | No. | LCMS Data |
| 38A | eu* | (2-cyclopropyl-pyrimidin-4-yl)-(4-chloropyridin-2-yl)amine structure | I-246 | LCMS (FA): m/z = 387.2 (M + H) |

TABLE 33-continued

| | Starting Material | | Compound | |
|---|---|---|---|---|
| Example | Reagent | Chemical Structure | No. | LCMS Data |
| 38B | eu* | 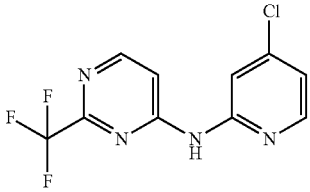 [SMILES: FC(F)(F)c1nccc(Nc2cc(Cl)ccn2)n1] | I-292 | LCMS (FA): m/z = 415.1 (M + H) |
| 38C | er |  | I-266 | LCMS (FA): m/z = 349.1 (M + H) |
| 38D | eq er | 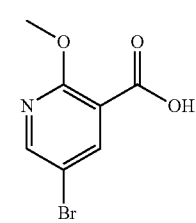 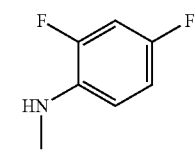 | I-252 | LCMS (FA): m/z = 463.2 (M + H) |

*Step 3: microwave irradiation was used instead of conventional heating

Example 39: 6-methyl-2'-((2-methylpyrimidin-4-yl)amino)-[3,4'-bipyridine]-5-carboxylic acid (I-253) and N-(cyclopropylmethyl)-6-methyl-2'-((2-methylpyrimidin-4-yl)amino)-[3,4'-bipyridine]-5-carboxamide (I-285)

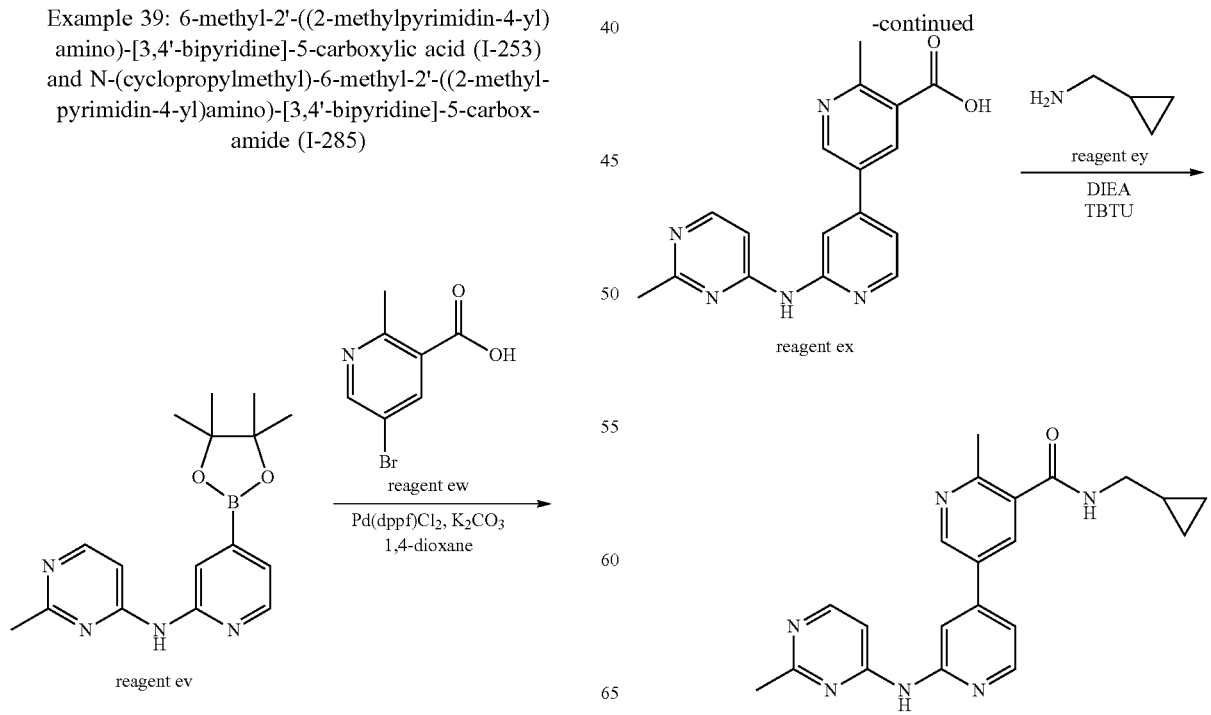

Step 1: 6-Methyl-2'-((2-methylpyrimidin-4-yl)amino)-3,4'-bipyridine-5-carboxylic acid To a microwave vial were added 2-methyl-N-[4-(4,4,5,5-tetramethyl-1,3,2-dioxaborolan-2-yl)pyridin-2-yl]pyrimidin-4-amine (101 mg, 0.325 mmol), 5-bromo-2-methylnicotinicacid (70.19 mg, 0.325 mmol), Pd(dppf)Cl$_2$ (7.43 mg, 0.0090 mmol), potassium carbonate (61.07 mg, 0.44 mmol), 1,4-dioxane (2.2 mL, 28 mmol) and water (0.053 mL, 2.92 mmol). The vial was thoroughly flushed with N$_2$ and then subjected to microwave irradiation at 125° C. for 40 min. The reaction mixture was filtered and the solid obtained was dried and purified by column chromatography to give 6-methyl-2'-((2-methylpyrimidin-4-yl)amino)-[3,4'-bipyridine]-5-carboxylic acid I-253 (0.036 g, 34%). LCMS (FA): m/z=322.0 (M+H).

Step 2: N-(Cyclopropylmethyl)-6-methyl-2'-((2-methylpyrimidin-4-yl)amino)-3,4'-bipyridine-5-carboxamide To 6-methyl-2'-[(2-methylpyrimidin-4-yl)amino]-3,4'-bipyridine-5-carboxylic acid (50.00 mg, 0.156 mmol) were added DCM (1.48 mL, 23.03 mmol) and DIEA (0.081 mL, 0.48 mmol) and TBTU (74.94 mg, 0.23 mmol). To this stirred reaction mixture, cyclopropylmethylamine (0.068 mL, 0.78 mmol) was added and the reaction mixture was allowed to stir at rt for 5 h. The reaction mixture was partitioned into EtOAc and water. The aqueous solution was extracted twice with EtOAc. The combined organic solutions were washed with brine, dried over MgSO$_4$, filtered and concentrated. The crude product was purified by column chromatography to give N-(cyclopropylmethyl)-6-methyl-2'-((2-methylpyrimidin-4-yl)amino)-3,4'-bipyridine-5-carboxamide as a white solid I-285 (0.021 g, 36%). LCMS (FA): m/z=375.2 (M+1).

The compounds listed in the table below (Table 34) were prepared in an analogous fashion to that described above from the appropriate starting materials:

TABLE 34

| Example | Starting Material Reagent | Chemical Structure | Compound No. | LCMS Data |
|---|---|---|---|---|
| 39A | ey | 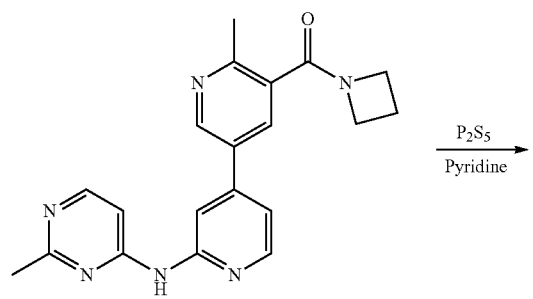 | I-221 | LCMS (FA): m/z = 397.1 (M + H) |

Example 40: Azetidin-1-yl{6-methyl-2'-[(2-methylpyrimidin-4-yl)amino]-3,4'-bipyridin-5-yl}methanethione (I-223)

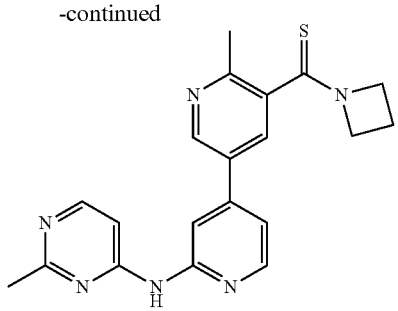

A mixture of azetidin-1-yl{6-methyl-2'-[(2-methylpyrimidin-4-yl)amino]-3,4'-bipyridin-5-yl}methanone (110 mg, 0.30 mmol) and P$_2$S$_5$ (170 mg, 0.76 mmol) in pyridine (10 mL) was allowed to stir for 12 h at 65° C. The reaction mixture was then added to a mixture of NaHCO$_3$ solution (1.0 M, 10 mL) and water (10 mL). The reaction mixture was allowed to stir for 30 min at rt, then was diluted with water and extracted with EtOAc. The organic solutions were combined, dried over Na$_2$SO$_4$, filtered and concentrated. The crude compound was purified by column chromatography to provide azetidin-1-yl {6-methyl-2'-[(2-methylpyrimidin-4-yl)amino]-3,4'-bipyridin-5-yl}methanethione I-223 (95 mg, 83%). LCMS (FA): m/z=377.5 (M+H). $^1$H NMR (400 MHz, DMSO-d$_6$) δ 10.24 (s, 1H), 8.83 (d, J=3.0 Hz, 1H), 8.39 (d, J=6.0 Hz, 1H), 8.37 (d, J=6.0 Hz, 1H), 8.10 (s, 1H), 7.92 (d, J=2.4 Hz, 1H), 7.63 (d, J=6.0 Hz, 1H), 7.40 (dd, J=5.2, 1.6 Hz, 1H), 4.30 (m, 2H), 4.06 (m, 2H), 2.54 (s, 3H), 2.49 (s, 3H), 2.30 (m, 2H).

Example 41: N-{6-chloro-4-methyl-2'-[(2-methylpyrimidin-4-yl)amino]-3,4'-bipyridin-5-yl}-2,4-difluorobenzamide (I-295)

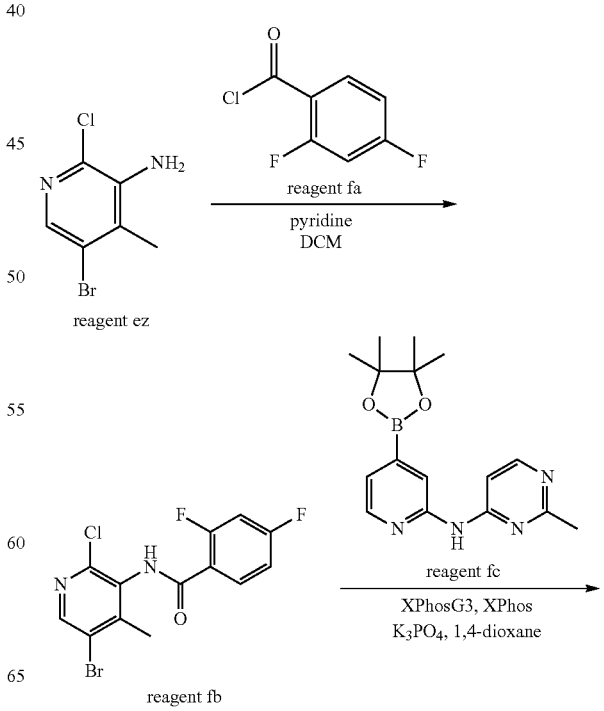

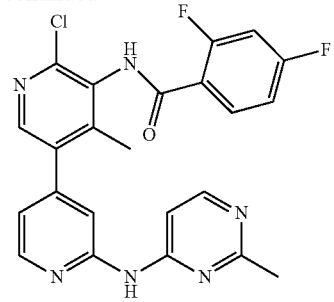

Step 1: N-(5-bromo-2-chloro-4-methylpyridin-3-yl)-2,4-difluorobenzamide

To a solution of 5-bromo-2-chloro-4-methylpyridin-3-amine (0.50 g, 2.26 mmol) in DCM (6.76 mL) and pyridine (0.54 mL, 6.77 mmol) at 0° C. was added dropwise a solution of 2,4-difluorobenzoyl chloride (0.47 g, 2.67 mmol) in DCM (2.5 mL). The reaction mixture was allowed to stir in an ice bath for 5 h. The resulting white precipitate was collected by filtration and dried under vacuum to give N-(5-bromo-2-chloro-4-methylpyridin-3-yl)-2,4-difluorobenzamide as a white solid (0.576 g, 70.5%). LCMS (FA): m/z=361.0 (M+H).

Step 2: N-{6-chloro-4-methyl-2'-[(2-methylpyrimidin-4-yl)amino]-3,4'-bipyridin-5-yl}-2,4-difluorobenzamide A mixture of N-(5-bromo-2-chloro-4-methylpyridin-3-yl)-2,4-difluorobenzamide (0.22 g, 0.61 mmol), 2-methyl-N-[4-(4,4,5,5-tetramethyl-1,3,2-dioxaborolan-2-yl)pyridin-2-yl]pyrimidin-4-amine (0.23 g, 0.75 mmol), XPhos (0.09 g, 0.02 mmol), XPhosG3 (0.02 g, 0.02 mmol), degassed K₃PO₄ (0.50 M in water, 2.43 mL, 1.21 mmol) and degassed 1,4-dioxane (2.13 mL) was allowed to stir at 105° C. for 2 h. The reaction was allowed to cool to rt and then filtered through celite. The filtrate was diluted with EtOAc and then washed with water. The organic solution was dried over Na₂SO₄, filtered, and concentrated. The crude compound was purified by column chromatography to provide N-{6-chloro-4-methyl-2'-[(2-methylpyrimidin-4-yl)amino]-3,4'-bipyridin-5-yl}-2,4-difluorobenzamide I-295 (0.03 g, 6%). LCMS (FA): m/z=467.2 (M+H).

The compounds listed in the table below (Table 35) were prepared in an analogous fashion to that described above from the appropriate starting materials:

TABLE 35

| Example | Starting Material Reagent | Chemical Structure | Compound No. | LCMS Data |
|---|---|---|---|---|
| 41A | ez | ![structure] | I-249 | LCMS (FA): m/z = 433.2 (M + H) |

Example 42: 6-methyl-5-(6-methyl-1,1-dioxido-1,2,6-thiadiazinan-2-yl)-N-(2-methylpyrimidin-4-yl)-3,4'-bipyridin-2'-amine (I-288)

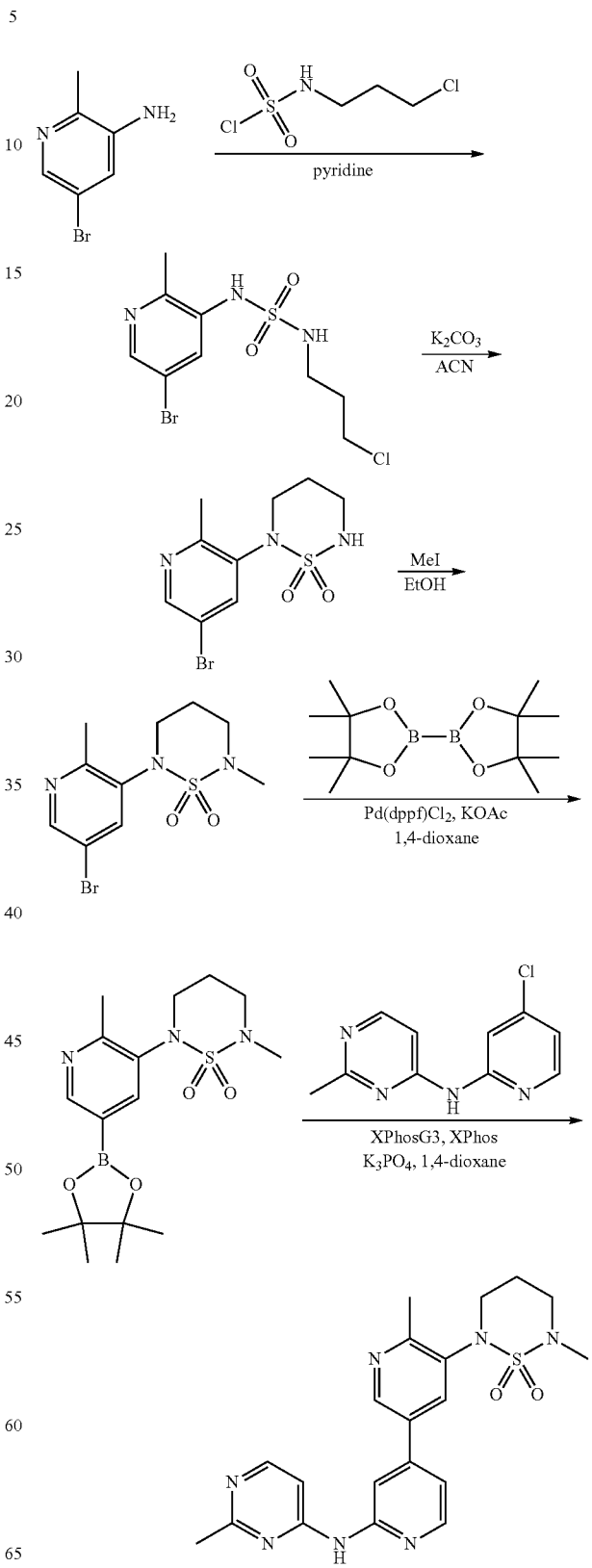

Step 1: N-(5-bromo-2-methylpyridin-3-yl)-N'-(3-chloropropyl)sulfuric diamide To a mixture of 5-bromo-2-methylpyridin-3-amine (0.874 g, 4.67 mmol) and (3-chloropropyl)sulfamyl chloride (2.567 g, 13.37 mmol) in an ice bath was added pyridine (8.65 mL). The mixture was allowed to stir at rt overnight. Additional (3-chloropropyl)sulfamyl chloride (2.0 g, 10.0 mmol) was added and the mixture was allowed to continue stirring at rt for another 24 h. The reaction mixture was extracted with EtOAc. The organic solutions were combined, washed with brine, dried over $Na_2SO_4$, filtered and concentrated. The crude compound was purified by column chromatography to give N-(5-bromo-2-methylpyridin-3-yl)-N'-(3-chloropropyl)sulfuric diamide as a white solid (0.83 g, 52%). LCMS (FA): m/z=342.1 (M+H).

Step 2: 2-(5-bromo-2-methylpyridin-3-yl)-1,2,6-thiadiazinane 1,1-dioxide

To a round bottomed flask was added N-(5-bromo-2-methylpyridin-3-yl)-N'-(3-chloropropyl)sulfuric diamide (0.83 g, 2.43 mmol), potassium carbonate (0.672 g, 4.86 mmol), and ACN (40 mL). The reaction mixture was allowed to stir at 65° C. overnight. The reaction mixture was allowed to cool to rt, concentrated and the residue purified by column chromatography to give 2-(5-bromo-2-methylpyridin-3-yl)-1,2,6-thiadiazinane 1,1-dioxide as a solid (0.74 g, 100%). LCMS (FA): m/z=306.0 (M+H).

Step 3: 2-(5-bromo-2-methylpyridin-3-yl)-6-methyl-1,2,6-thiadiazinane 1,1-dioxide To a solution of 2-(5-bromo-2-methylpyridin-3-yl)-1,2,6-thiadiazinane 1,1-dioxide (0.773 g, 2.52 mmol), EtOH (30 mL), and MeI (0.63 mL, 10.1 mmol) was added sodium hydroxide (1M in water, 6.3 mL). The mixture was allowed stir at rt overnight. The reaction mixture was acidified with 1M HCl and then concentrated. The crude compound was purified by column chromatography to give 2-(5-bromo-2-methylpyridin-3-yl)-6-methyl-1,2,6-thiadiazinane 1,1-dioxide as an off white solid (0.81 g, 100%). LCMS (FA): m/z=320.0 (M+H).

Step 4: 2-methyl-6-[2-methyl-5-(4,4,5,5-tetramethyl-1,3,2-dioxaborolan-2-yl)pyridin-3-yl]-1,2,6-thiadiazinane 1,1-dioxide A mixture of 2-(5-bromo-2-methylpyridin-3-yl)-6-methyl-1,2,6-thiadiazinane 1,1-dioxide (0.333 g, 1.04 mmol), bis(pinacolato)diboron (0.290 g, 1.14 mmol), [Pd(dppf)Cl$_2$, complex with DCM (1:1) (85 mg, 0.10 mmol) and potassium acetate (0.31 g, 3.18 mmol) in 1,4-dioxane (4 mL) was allowed to stir at 90° C. for 3 days. The reaction mixture was filtered through celite. The filtrate was mixed with charcoal (0.97 g) and the mixture was allowed to stir at 80° C. for 1 h. The mixture was then filtered and the filtrate was concentrated to give 2-methyl-6-[2-methyl-5-(4,4,5,5-tetramethyl-1,3,2-dioxaborolan-2-yl)pyridin-3-yl]-1,2,6-thiadiazinane 1,1-dioxide as off white solid.

Step 5: 6-methyl-5-(6-methyl-1,1-dioxido-1,2,6-thiadiazinan-2-yl)-N-(2-methylpyrimidin-4-yl)-3,4'-bipyridin-2'-amine To a mixture of 2-methyl-6-[2-methyl-5-(4,4,5,5-tetramethyl-1,3,2-dioxaborolan-2-yl)pyridin-3-yl]-1,2,6-thiadiazinane 1,1-dioxide (0.150 g, 0.327 mmol), 4-chloro-N-(2-methylpyrimidin-4-yl)pyrimidin-2-amine (0.056 g, 0.25 mmol), XPhosG3 (8.5 mg, 0.0091 mmol), and XPhos (4.3 mg, 0.0091 mmol) were added 1,4-dioxane (1 mL) and potassium phosphate (0.50 M in water, 1 mL). The reaction mixture was subjected to microwave irradiation at 100° C. for 30 min. The reaction mixture was concentrated and the crude compound was purified by column chromatography to give 6-methyl-5-(6-methyl-1,1-dioxido-1,2,6-thiadiazinan-2-yl)-N-(2-methylpyrimidin-4-yl)-3,4'-bipyridin-2'-amine I-288 (0.045 g, 42%). LCMS (FA): m/z=425.9 (M+H).

Example 43: 6-chloro-N-cyclobutyl-2'-((2-methylpyrimidin-4-yl)amino)-[3,4'-bipyridine]-5-sulfonamide (I-215)

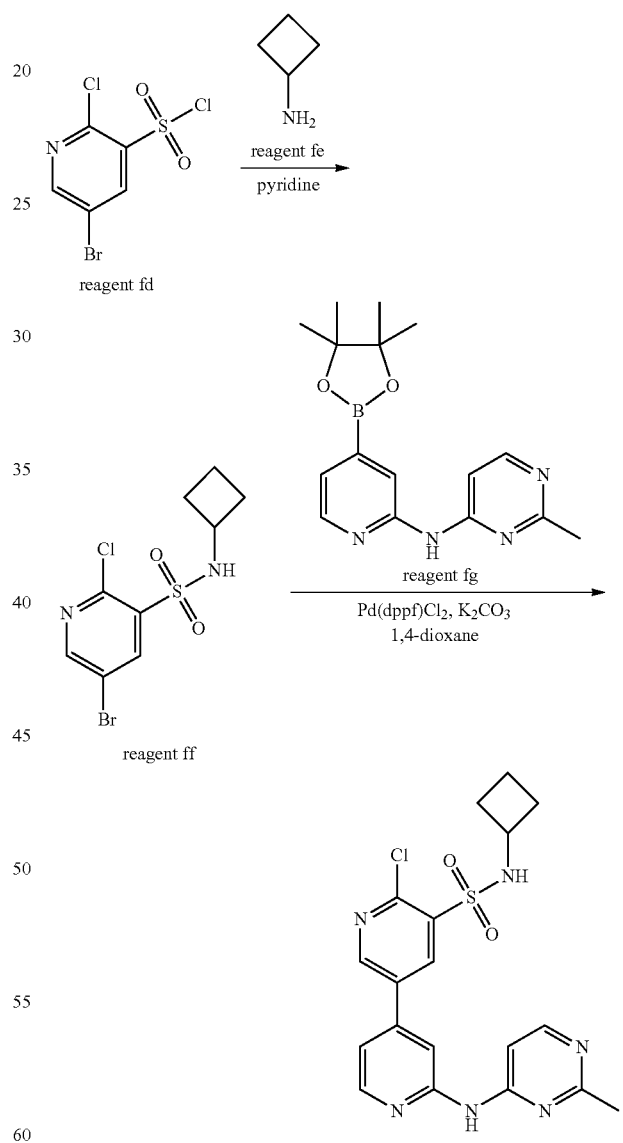

Step 1: 5-bromo-2-chloro-N-cyclobutylpyridine-3-sulfonamide

A partial suspension of cyclobutylamine hydrochloride salt (0.39 g, 3.64 mmol) in pyridine (0.8 mL) was treated dropwise with a solution of 5-bromo-2-chloropyridine-3-sulfonyl chloride (0.52 g, 1.79 mmol) in DCM (1 mL) and the mixture was allowed to stir at rt for 16 h. The solvent was evaporated under reduced pressure and the residue was treated with ice cold 1N HCl and extracted with EtOAc. The organic solution was washed with water and dried over MgSO$_4$, filtered and the solvent was evaporated. The crude product was purified by column chromatography to give 5-bromo-2-chloro-N-cyclobutylpyridine-3-sulfonamide (0.58 g, 58%). LCMS (FA): m/z=325.1 (M+H).

Step 2: 6-chloro-N-cyclobutyl-2'-((2-methylpyrimidin-4-yl)amino)-[3,4'-bipyridine]-5-sulfonamide A partial suspension of 5-bromo-2-chloro-N-cyclobutylpyridine-3-sulfonamide (0.050 g, 0.15 mmol) and 2-methyl-N-[4-(4,4,5,5-tetramethyl-1,3,2-dioxaborolan-2-yl)pyridin-2-yl]pyrimidin-4-amine (0.052 g, 0.166 mmol) in 1,4-dioxane (2.0 mL) was treated with potassium carbonate (0.042 g, 0.30 mmol) in water (0.20 mL) and purged with nitrogen gas. Pd(dppf)Cl$_2$ (40 mg, 0.05 mmol) was added and the mixture was allowed to stir in a sealed tube at 100° C. for 0.5 h. The solvents were evaporated under reduced pressure and the residue was diluted with water and the precipitate collected. The crude product was purified by column chromatography to give 6-chloro-N-cyclobutyl-2'-((2-methylpyrimidin-4-yl)amino)-[3,4'-bipyridine]-5-sulfonamide I-215 (30 mg, 46%). LCMS (FA): m/z=431.1 (M+H). $^1$H NMR (400 MHz, MeOH-d$_4$) δ 8.96 (d, J=4.0 Hz, 1H), 8.74 (d, J=4.0 Hz, 1H), 8.44 (d, J=4.0 Hz, 1H), 8.30 (m, 2H), 7.50 (d, J=4.0 Hz, 1H), 7.41 (dd, J=8.0, 4.0 Hz, 1H), 3.83 (m, 1H), 2.61 (s, 3H), 2.04 (m, 4H), 1.60 (m, 2H).

The compounds listed in the table below (Table 36) were prepared in an analogous fashion to that described above from the appropriate starting materials:

TABLE 36

| Example | Starting Material Reagent | Chemical Structure | Compound No. | LCMS Data |
|---|---|---|---|---|
| 43A | ff | (5-bromo-2-hydroxy-N-cyclobutylpyridine-3-sulfonamide) | I-279 | LCMS (AA): m/z = 413.0 (M + H) |
| 43B | ff | (5-bromo-2-methoxy-N-cyclobutylpyridine-3-sulfonamide) | I-224 | LCMS (AA): m/z = 427.1 (M + H) |
| 43C | fe | (cyclobutylamine, H$_2$N-cyclobutyl) | I-242 | LCMS (FA): m/z = 442.6 (M + H) |
| | ff | (5-bromo-2-chloro-N-cyclobutylpyridine-3-sulfonamide) | | |

TABLE 36-continued

| | Starting Material | | Compound | |
|---|---|---|---|---|
| Example | Reagent | Chemical Structure | No. | LCMS Data |
| 43D | fd | (2-chloro-5-bromo-4-methylpyridine-3-sulfonyl chloride) | I-410 | LCMS (FA): m/z = 397.2 (M + H) |
| | fe | (tert-butylamine) | | |
| | ff | (N-tert-butyl 2-chloro-5-bromo-4-methylpyridine-3-sulfonamide) | | |
| | fg* | (N-(4-(4,4,5,5-tetramethyl-1,3,2-dioxaborolan-2-yl)pyridin-2-yl)acetamide) | | |
| 43E | ff' | (N-cyclobutyl 5-bromo-2-methoxypyridine-3-sulfonamide) | I-470 | LCMS (FA): m/z = 388.7 (M + H) |
| | fg** | (N-(4-(4,4,5,5-tetramethyl-1,3,2-dioxaborolan-2-yl)pyridin-2-yl)acetamide) | | |

TABLE 36-continued
| | Starting Material | | Compound | |
|---|---|---|---|---|
| Example | Reagent | Chemical Structure | No. | LCMS Data |
| 43F | ff' | 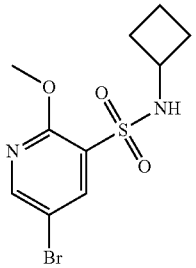 | I-426 | LCMS (FA): m/z = 376.7 (M + H) |
| | fg** | 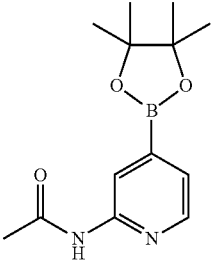 [SMILES: CC(=O)Nc1cc(B2OC(C)(C)C(C)(C)O2)ccn1] | | |
| 43G | ff | 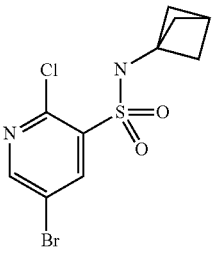 [SMILES: O=S(=O)(NC12CC(C1)C2)c1cc(Br)cnc1Cl] | I-366 | LCMS (FA): m/z = 392.7 (M + H) |
| | fg** | 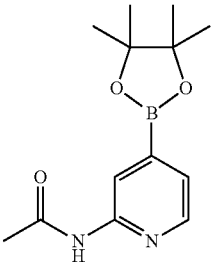 [SMILES: CC(=O)Nc1cc(B2OC(C)(C)C(C)(C)O2)ccn1] | | |
| 43H | fe | 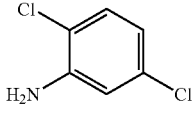 | I-432 | LCMS (FA): m/z = 467.3 (M + H) |
| | ff' | 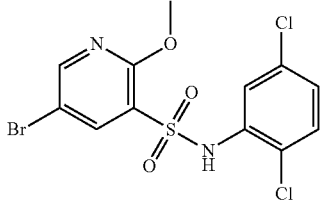 [SMILES: COc1ncc(Br)cc1S(=O)(=O)Nc1cc(Cl)ccc1Cl] | | |

TABLE 36-continued
| | Starting Material | | Compound | |
|---|---|---|---|---|
| Example | Reagent | Chemical Structure | No. | LCMS Data |
| | fg* | 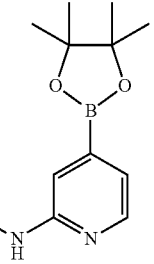 | | |
| 43I | fe | 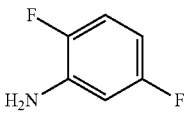 | I-358 | LCMS (FA): m/z = 435.2 (M + H) |
| | ff' | 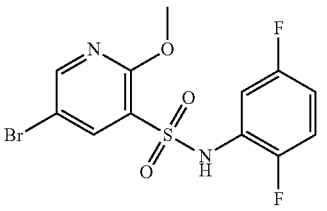 | | |
| | fg | 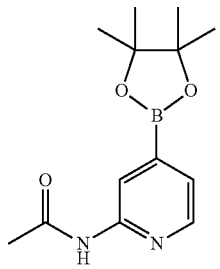 [SMILES: CC(=O)Nc1cc(B2OC(C)(C)C(C)(C)O2)ccn1] | | |
| 43J | fe | 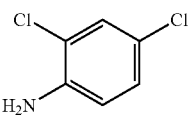 | I-344 | LCMS (FA): m/z = 467.3 (M + H) |
| | ff' | 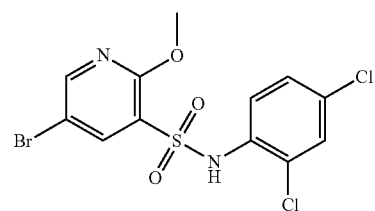 [SMILES: COc1ncc(Br)cc1S(=O)(=O)Nc1ccc(Cl)cc1Cl] | | |
| | fg | 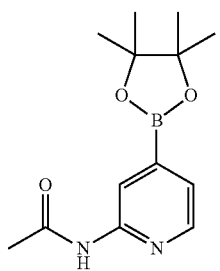 [SMILES: CC(=O)Nc1cc(B2OC(C)(C)C(C)(C)O2)ccn1] | | |

TABLE 36-continued

| | Starting Material | | Compound | |
|---|---|---|---|---|
| Example | Reagent | Chemical Structure | No. | LCMS Data |
| 43K | fe | 3-(trifluoromethyl)aniline | I-329 | LCMS (FA): m/z = 467.4 (M + H) |
| | ff' | 5-bromo-2-methoxy-N-(3-(trifluoromethyl)phenyl)pyridine-3-sulfonamide | | |
| | fg*** | N-(4-(4,4,5,5-tetramethyl-1,3,2-dioxaborolan-2-yl)pyridin-2-yl)acetamide | | |
| 43L | fd | 5-bromo-2-chloro-4-methylpyridine-3-sulfonyl chloride | I-442 | LCMS (FA): m/z = 393.4 (M + H) |
| | fe | tert-butylamine | | |
| | ff' | 5-bromo-N-tert-butyl-2-methoxy-4-methylpyridine-3-sulfonamide | | |
| | fg* | N-(4-(4,4,5,5-tetramethyl-1,3,2-dioxaborolan-2-yl)pyridin-2-yl)acetamide | | |

TABLE 36-continued

| | Starting Material | | Compound | |
|---|---|---|---|---|
| Example | Reagent | Chemical Structure | No. | LCMS Data |
| 43M | fd | Br, O, Cl, S, O, N, Cl (2-bromo-5-chloropyridine-3-sulfonyl chloride) | I-353 | LCMS (FA): m/z = 419.4 (M + H) |
| | fe | 2,5-difluoroaniline | | |
| | ff′′′ | Me, HN-(2,4-difluorophenyl), S, O, O, N, Cl (5-chloro-2-methyl-N-(2,4-difluorophenyl)pyridine-3-sulfonamide) | | |
| | fg^ | pinacol boronate, acetamido pyridine | | |
| 43N | fd | Br, O, Cl, S, O, N, Cl | I-370 | LCMS (FA): m/z = 363.3 (M + H) |
| | fe | HN(Et)₂ (diethylamine) | | |
| | ff′′′ | Me, N(Et)₂, S, O, O, N, Cl | | |

TABLE 36-continued

| | Starting Material | | Compound | |
|---|---|---|---|---|
| Example | Reagent | Chemical Structure | No. | LCMS Data |
| | fg^ | (pinacol boronate pyridine with NHAc) | | |
| 43O | fd | 2-chloro-5-bromo-pyridine-3-sulfonyl chloride | I-330 | LCMS (FA): m/z = 447.3 (M + H) |
| | fe | (S)-2-amino-2-phenylethanol | | |
| | fg^ | (pinacol boronate pyridine with NHAc) | | |
| 43P | fd | 2-chloro-5-bromo-pyridine-3-sulfonyl chloride | I-403 | LCMS (FA): m/z = 447.3 (M + H) |
| | fe | (R)-2-amino-2-phenylethanol | | |
| | fg^ | (pinacol boronate pyridine with NHAc) | | |

TABLE 36-continued

| Example | Reagent | Starting Material Chemical Structure | Compound No. | LCMS Data |
|---|---|---|---|---|
| 43Q | ff | (5-bromo-2-(dimethylamino)-N-(2,4-difluorophenyl)pyridine-3-sulfonamide) | I-491 | LCMS (FA): m/z = 448.5 (M + H) |
| | fg* | (N-(4-(4,4,5,5-tetramethyl-1,3,2-dioxaborolan-2-yl)pyridin-2-yl)acetamide) | | |
| 43R | ff | (5-bromo-N-tert-butyl-4-methyl-2-(methylamino)pyridine-3-sulfonamide) | I-436 | LCMS (FA): m/z = 392.2 (M + H) |
| | fg* | (N-(4-(4,4,5,5-tetramethyl-1,3,2-dioxaborolan-2-yl)pyridin-2-yl)acetamide) | | |
| 43S | ff | (5-bromo-N-tert-butyl-2-(dimethylamino)-4-methylpyridine-3-sulfonamide) | I-487 | LCMS (FA): m/z = 406.2 (M + H) |
| | fg* | (N-(4-(4,4,5,5-tetramethyl-1,3,2-dioxaborolan-2-yl)pyridin-2-yl)acetamide) | | |

*Step 2: Cs$_2$CO$_3$ was used instead of K$_2$CO$_3$, and microwave irradiation was used instead of conventional heating
**Step 2: Cs$_2$CO$_3$ was used instead of K$_2$CO$_3$
***Step 2: microwave irradiation was used instead of conventional heating
^Step 2: Pd$_2$(dba)$_3$, Xphos, KOAc/water, dioxane, 110° C.

Example 43T: N-(4-(1,1-dioxido-3,4-dihydro-2H-pyrido[2,3-b][1,4,5]oxathiazepin-8-yl)pyridin-2-yl)acetamide (I-484)

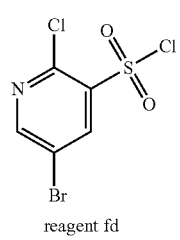
reagent fd

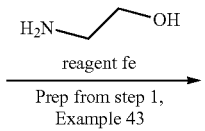
reagent fe

Prep from step 1, Example 43

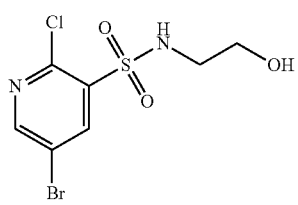
reagent ff

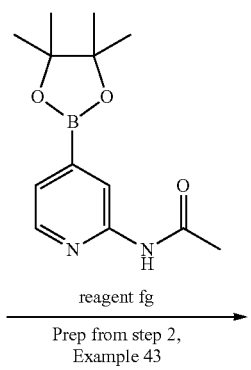
reagent fg

Prep from step 2, Example 43

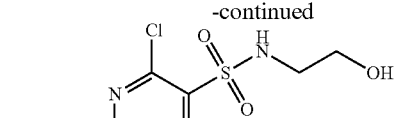
reagent fh

DMSO, KOtBu THF, rt

Step 3: N-(4-(1,1-dioxido-3,4-dihydro-2H-pyrido[2,3-b][1,4,5]oxathiazepin-8-yl)pyridin-2-yl)acetamide A solution of N-{6-chloro-5-[(2-hydroxyethyl)sulfamoyl]-3,4'-bipyridin-2'-yl}acetamide (0.033 g, 0.089 mmol) in DMSO (0.6 mL, 8 mmol) was treated with KOt-Bu (0.0210 g, 0.187 mmol) as a solution in THF, The reaction mixture was allowed to stir at rt for 3 h and then concentrated. The crude product was purified by column chromatography to give N-(4-(1,1-dioxido-3,4-dihydro-2H-pyrido[2,3-b][1,4,5]oxathiazepin-8-yl)pyridin-2-yl)acetamide (I-484). LCMS (FA): m/z=335.1 (M+H).

The compounds listed in the table below (Table 36a) were prepared in an analogous fashion to that described above from the appropriate starting materials:

TABLE 36a

| Example | Reagent | Starting Material Chemical Structure | Compound No. | LCMS Data |
|---|---|---|---|---|
| 43U | fe, fh | (structures shown) | I-334 | LCMS (AA): m/z = 411.3 (M + H) |

TABLE 36a-continued

| | Starting Material | | Compound | |
|---|---|---|---|---|
| Example | Reagent | Chemical Structure | No. | LCMS Data |
| 43V | fe | (structure shown) | I-420 | LCMS (FA): m/z = 410.6 (M + H) |
| | fh | (structure shown) | | |

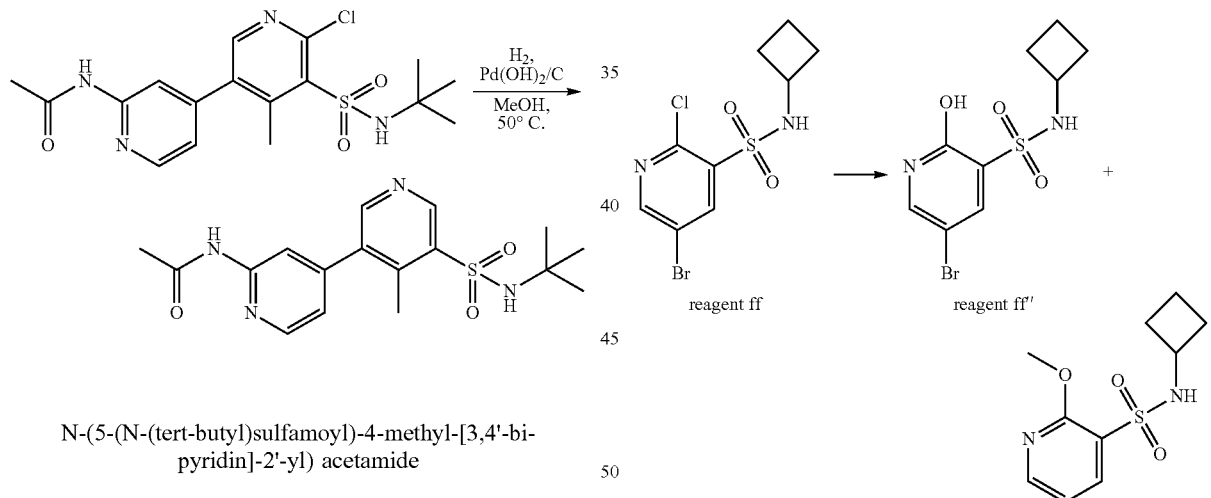

Example 43W: N-(5-(N-(tert-butyl)sulfamoyl)-4-methyl-[3,4'-bipyridin]-2'-yl)acetamide (I-462)

N-(5-(N-(tert-butyl)sulfamoyl)-4-methyl-[3,4'-bipyridin]-2'-yl) acetamide

To a flask containing N-[5-(tert-butylsulfamoyl)-6-chloro-4-methyl-3,4'-bipyridin-2'-yl]acetamide (60 mg, 0.2 mmol) in MeOH (1.5 mL) was added 10% palladium hydroxide on carbon (6 mg) under nitrogen. After the flask was flushed with hydrogen a few times, then the reaction mixture was allowed to stir at 40° C. for 2 h under hydrogen. The reaction mixture was filtered through celite. The filtrate was evaporated to dryness and purified by HPLC to afford N-(5-(N-(tert-butyl)sulfamoyl)-4-methyl-[3,4'-bipyridin]-2'-yl)acetamide (20 mg, 40%) LCMS (FA): m/z=363.2 (M+H). $^1$H NMR (400 MHz, DMSO-$d_6$) δ ppm 10.70 (s, 1H) 9.02 (s, 1H) 8.61 (s, 1H) 8.44 (d, J=5.02 Hz, 1H) 8.08 (s, 1H) 7.92 (s, 1H) 7.20 (dd, J=5.02, 1.51 Hz, 1H) 2.46-2.56 (m, 3H) 2.12 (s, 3H) 1.18 (s, 9H).

Synthesis of Reagents (ff') from Examples 43A and 43B: 5-bromo-N-cyclobutyl-2-methoxypyridine-3-sulfonamide and 5-bromo-N-cyclobutyl-2-hydroxypyridine-3-sulfonamide A solution of 5-bromo-2-chloro-N-cyclobutylpyridine-3-sulfonamide (0.12 g, 0.37 mmol) in THF (3.0 mL) was treated with a solution of sodium methoxide (0.08 g, 1.50 mmol) in MeOH (1.5 mL) and allowed to stir at 85° C. in a sealed tube for 16 h. The reaction mixture containing starting material and methoxy displacement product was treated with 25% sodium methoxide in MeOH (2 mL) and allowed to stir at 85° C. in sealed tube for 16 h. The solvents were evaporated and the residue diluted with 1 N HCl and extracted with EtOAc. The organic solution was dried over MgSO$_4$, filtered and evaporated to give the crude product which was purified by chromatography to give 5-bromo-N-cyclobutyl-2-methoxypyridine-3-sulfonamide (67 mg, 56%)

LCMS (FA): m/z=321.1 (M+H) and 5-bromo-N-cyclobutyl-2-hydroxypyridine-3-sulfonamide (32 mg, 28%) LCMS (FA): m/z=307.1 (M+H).

The compounds listed in the table below (Table 36b.) were prepared in an analogous fashion to that described above from the appropriate starting materials:

TABLE 36b

| Starting Material | Reagent ff | Reagent ff' | LCMS Data |
|---|---|---|---|
| From Ex 43L | 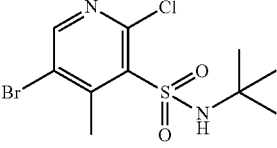 | 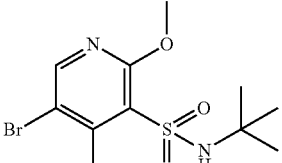 | LCMS (FA): m/z = 339.2 (M + H) |
| From Ex 43E | 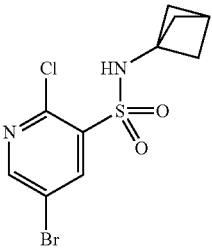 [SMILES: O=S(=O)(NC12CC(C1)C2)c1cc(Br)cnc1Cl] | 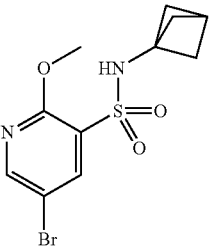 [SMILES: COc1ncc(Br)cc1S(=O)(=O)NC12CC(C1)C2] | LCMS (FA): m/z = 333.3 (M − 1) |
| From Ex 43F | 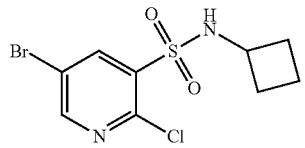 [SMILES: O=S(=O)(NC1CCC1)c1cc(Br)cnc1Cl] | 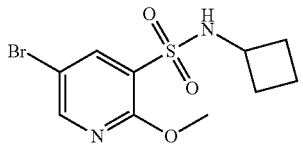 [SMILES: COc1ncc(Br)cc1S(=O)(=O)NC1CCC1] | LCMS (FA): m/z = 323.1 (M + H) |
| From Ex 43K | 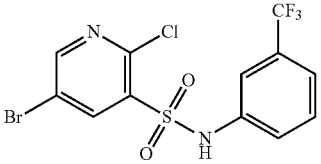 [SMILES: O=S(=O)(Nc1cccc(C(F)(F)F)c1)c1cc(Br)cnc1Cl] | 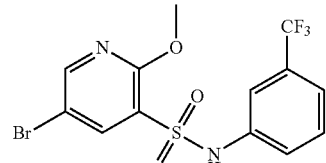 | LCMS (FA): m/z = 411.1 (M + H) |
| From Ex 43J | 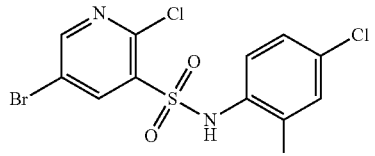 | 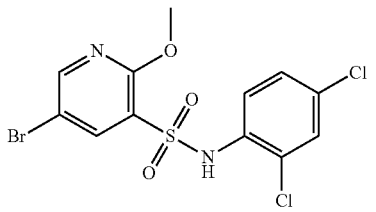 [SMILES: COc1ncc(Br)cc1S(=O)(=O)Nc1ccc(Cl)cc1Cl] | LCMS (FA): m/z = 413.2 (M + H) |
| From Ex 43I | 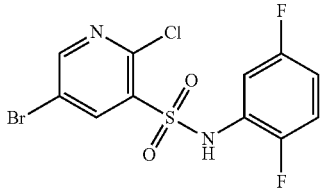 [SMILES: O=S(=O)(Nc1cc(F)ccc1F)c1cc(Br)cnc1Cl] | 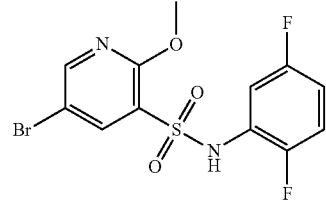 [SMILES: COc1ncc(Br)cc1S(=O)(=O)Nc1cc(F)ccc1F] | LCMS (FA): m/z = 379.1 (M + H) |

TABLE 36b-continued

| Starting Material | | |
|---|---|---|
| Reagent ff | Reagent ff' | LCMS Data |
| From Ex 43H | | LCMS (FA): m/z = 413.1 (M + H) |
| From Ex 43Q[1] | | |
| From Ex 43R[2] | | LCMS (FA): m/z = 350.1 (M + H) |
| From Ex 43S[3] | | LCMS (FA): m/z = 338.1 (M + H) |

[1] Conditions for conversion of reagent ff to reagent ff': dimethylamine, MeOH, 95° C.
[2] Conditions for conversion of reagent ff to reagent ff': dimethylamine, THF, 70° C.
[3] Conditions for conversion of reagent ff to reagent ff': methylamine, THF, 70° C.

Synthesis of Reagents (fd) from Example 43x: 5-bromo-2-chloro-4-methylpyridine-3-sulfonyl chloride

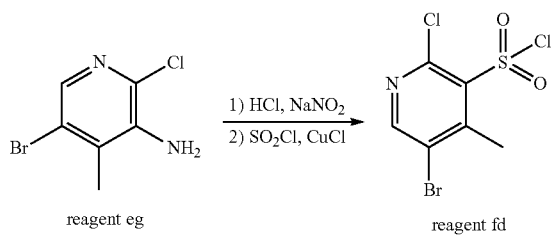

reagent eg → reagent fd

To a flask with 5-bromo-2-chloro-4-methylpyridin-3-amine (1.07 g, 4.82 mmol) cooled in ice bath was added 12.0 M HCl (4.84 mL) portion wise. The mixture was allowed to stir at rt for 15 min. This was cooled in ice/acetone bath at ~8° C. A solution of sodium nitrite (0.399 g, 5.78 mmol) in water (1.56 mL) was added over 45 min. The resulting slurry was then allowed to stir for 30 min. A solution of SO$_2$ was prepared the night before by adding thionyl chloride (0.879 mL, 12.0 mmol) to water (5.20 mL, 289 mmol) at 0° C. over 30 min. The mixture was allowed to stir and then warm to rt overnight. To the SO$_2$ mixture was added cuprous monochloride (9.4 mg, 0.095 mmol). The resulting yellow solution was cooled in ice/acetone at −8° C. To this yellow solution was added the diazotized mixture described earlier maintained at −8° C. (acetone/ice) portion wise with a pipette over 30 min. The mixture was then allowed to stir at 0° C. for 30 min. The resulting yellow solid was filtered off, washed with ice water and dried under vacuum to give 5-bromo-2-chloro-4-methylpyridine-3-sulfonyl chloride (290 mg, 20%) The product was used without further purification.

Reagents (ff''') from Examples 43M and 43N Listed in the Table Below (Table 36b) were Prepared in an Analogous Fashion to that Described in Step 3 of Example 44 from the Appropriate Starting Materials:

TABLE 36b

| Starting Material | | |
|---|---|---|
| Reagent ff | Reagent ff''' | LCMS Data |
| From Ex 43M | | LCMS (FA): m/z = 319.2 (M + H) |
| From Ex 43N | | LCMS (FA): m/z = 263.3 (M + H) |

*Step 2: Cs$_2$CO$_3$ was used instead of K$_2$CO$_3$, and microwave irradiation was used instead of conventional heating
**Step 2: Cs$_2$CO$_3$ was used instead of K$_2$CO$_3$ Example 44: N-[5-(bicyclo[1.1.1]pent-1-ylsulfamoyl)-6-methyl-3,4'-bipyridin-2'-yl]acetamide (I-418) and N-(6-methyl-5-sulfamoyl-3,4'-bipyridin-2'-yl)acetamide (I-395)

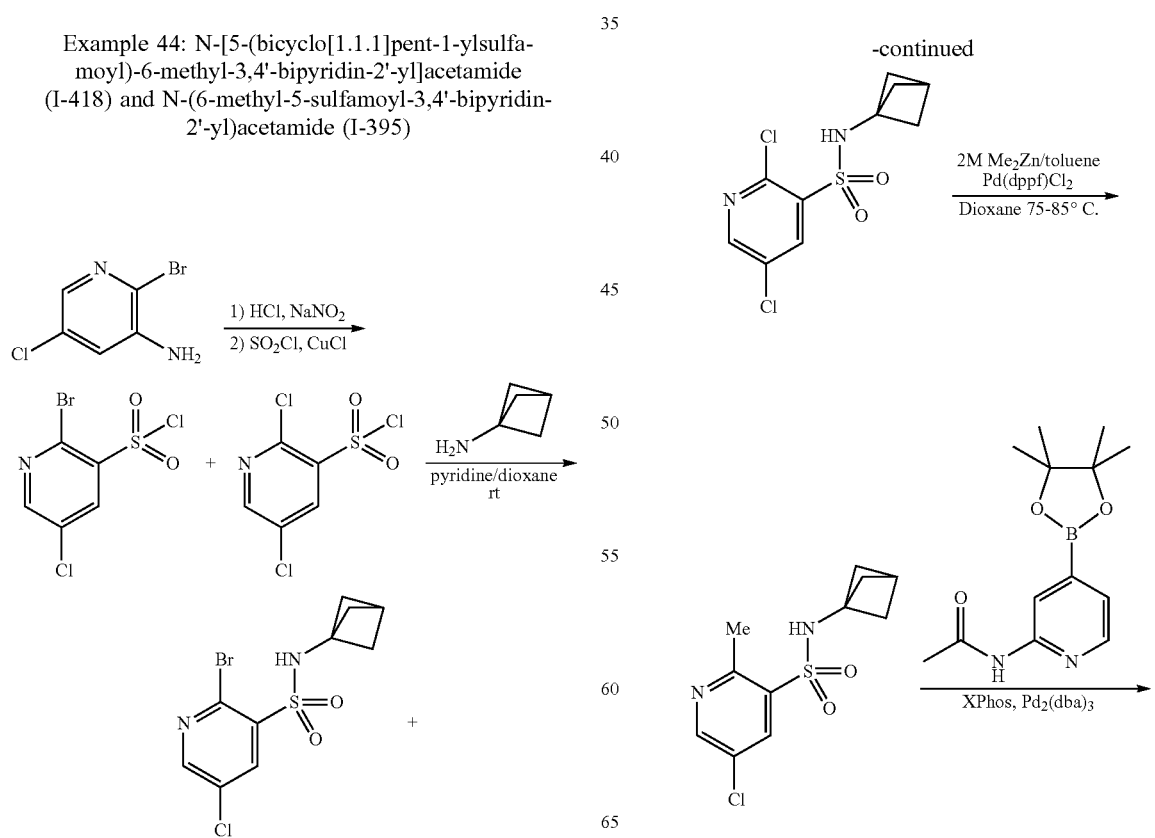

-continued

-continued

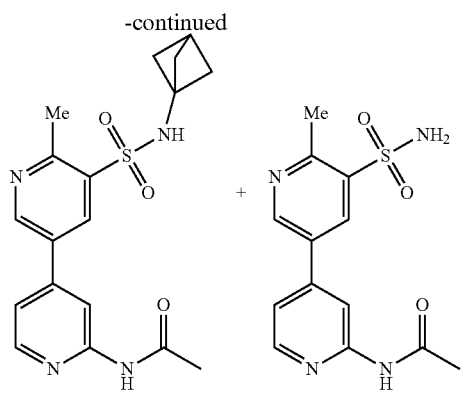

Step 1: 2-bromo-5-chloropyridine-3-sulfonyl chloride and 2,5-dichloropyridine-3-sulfonyl chloride To 2-bromo-3-amino-5-chloropyridine (5.00 g, 24.1 mmol) in a 100 ml flask cooled in ice bath was added portion wise 12.0 M of HCl (24.2 mL). The mixture was allowed to stir at rt for 15 min. This was cooled in ice/acetone bath (~−8° C.). A solution of sodium nitrite (2.00 g, 28.9 mmol) in water (7.82 mL, 434 mmol) was added over 45 min. The resulting slurry was allowed to stir for 30 min. A solution of SO$_2$ in water was prepared the night before by adding thionyl chloride (4.40 mL, 60.2 mmol) over 30 min. to water (26.0 mL, 1440 mmol) cooled in ice/bath. The mixture was then allowed to stir and to warm at rt overnight. To that solution was added cuprous monochloride (47 mg, 0.47 mmol). The resulting yellow solution was cooled in ice/acetone at −8° C. The diazotized mixture described earlier maintained at −8° C. (acetone/ice) was then added portionwise with pipette over 30 min. The mixture was then allowed to stir at 0° C. for 75 min. The mixture was extracted with ether twice. The combined ether extracts were washed with brine, dried over Na$_2$SO$_4$ and concentrated. The oily residue was dried under high vacuum overnight to give a 1:2 mixture (approximate based on 1H NMR (400 MHz, CDCl3)) of 2-bromo-5-chloropyridine-3-sulfonyl chloride and 2,5-dichloropyridine-3-sulfonyl chloride as a red oil (1 g of crude material). The product was used in the next step without further purification.

Step 2: N-(bicyclo[1.1.1]pent-1-yl)-2-bromo-5-chloropyridine-3-sulfonamide and N-(bicyclo[1.1.1]pent-1-yl)-2,5-dichloropyridine-3-sulfonamide To a solution 2-bromo-5-chloropyridine-3-sulfonyl chloride and 2,5-dichloropyridine-3-sulfonyl chloride (1.0 g, 3.8 mmol) in 1,4-dioxane (8.6 mL) and pyridine (1.10 mL) at rt was added bicyclo[1.1.1]pentan-1-amine hydrochloride salt (0.527 g, 4.41 mmol) portion wise. The mixture was allowed to stir at rt for 2 h. Water (2 mL) was added and the mixture was allowed to stir for a few min. The reaction mixture was diluted with water (40 ml) and acidified to pH 4 with 0.5 citric acid and was extracted with EtOAc (2×40 ml). The organic solutions were combined, washed with brine, dried over Na$_2$SO$_4$, filtered and concentrated to dryness. The residue was purified by column chromatography using to give a 1:2 mixture of N-(bicyclo[1.1.1]pent-1-yl)-2-bromo-5-chloropyridine-3-sulfonamide and N-(bicyclo[1.1.1]pent-1-yl)-2,5-dichloropyridine-3-sulfonamide as a light yellow solid (339 mg, 85% yield). LCMS (FA): m/z=337.3 and 293.3 (M+H).

Step 3: N-(bicyclo[1.1.1]pent-1-yl)-5-chloro-2-methylpyridine-3-sulfonamide

To the mixture obtained in Step 2 of N-(bicyclo[1.1.1]pent-1-yl)-2-bromo-5-chloropyridine-3-sulfonamide, N-(bicyclo[1.1.1]pent-1-yl)-2,5-dichloropyridine-3-sulfonamide (327 mg, 1.07 mmol) and [1,1'-bis(diphenylphosphino)ferrocene]dichloropalladium(II), complex with DCM (1:1) (54 mg, 0.066 mmol) in 1,4-dioxane (7.5 mL) was added with caution dimethylzine in toluene (2.0 M, 0.88 mL, 1.8 mmol) under an atmosphere of nitrogen. After a few min the mixture was heated to 75° C. then allowed to stir for 90 min. The reaction mixture was allowed to cool to rt and then added to water. The resulting solution was acidified with 0.5% citric acid and was extracted with EtOAc twice. The organic solutions were combined, washed with brine, dried over Na$_2$SO$_4$, filtered and concentrated. The residue was purified by column chromatography to give N-(bicyclo[1.1.1]pent-1-yl)-5-chloro-2-methylpyridine-3-sulfonamide (85 mg, 28%). LCMS (FA): m/z=273.3 (M+H). $^1$H NMR (400 MHz, DMSO-d$_6$) δ 9.14 (s, 1H), 8.77 (d, J=2.4 Hz, 1H), 8.19 (d, J=2.4 Hz, 1H), 2.74 (s, 3H), 2.31 (s, 1H), 1.74 (s, 6H).

Step 4: N-[5-(bicyclo[1.1.1]pent-1-ylsulfamoyl)-6-methyl-3,4'-bipyridin-2'-yl]acetamide (I-418) and N-(6-methyl-5-sulfamoyl-3,4'-bipyridin-2'-yl)acetamide (I-395)

A microwave tube was charged with N-(bicyclo[1.1.1]pent-1-yl)-5-chloro-2-methylpyridine-3-sulfonamide (83 mg, 0.30 mmol), N-[4-(4,4,5,5-tetramethyl-1,3,2-dioxaborolan-2-yl)pyridin-2-yl]acetamide (98.6 mg, 0.376 mmol), 2-dicyclohexylphosphino-2',4',6'-tri-i-propyl-1,1'-biphenyl (14 mg, 0.029 mmol), tris(dba)dipalladium(0) (8.3 mg, 0.0092 mmol) and potassium acetate (89 mg, 0.91 mmol). The tube was purged with nitrogen and 1,4-dioxane (2.4 mL) was added. The reaction mixture was allowed to stir for 2 min and water (0.51 mL) was added. The tube was purged with nitrogen three times, sealed, and was heated at 110° C. in oil bath for 1.5 h. After the reaction mixture was allowed to cool to rt, the mixture was diluted with EtOAc (25 ml) and water (15 ml). The aqueous solution was separated and further extracted with EtOAc (15 ml). The organic solutions were combined, washed with brine, dried over Na$_2$SO$_4$, filtered and concentrated. The products were purified by column chromatography using 0-3% MeOH/DCM over 25 min. to give N-[5-(bicyclo[1.1.1]pent-1-ylsulfamoyl)-6-methyl-3,4'-bipyridin-2'-yl]acetamide (I-418) (25 mg, 22%) as a white solid. LCMS (FA): m/z=373.4 (M+H). $^1$H NMR (400 MHz, DMSO-d$_6$) δ 10.68 (s, 1H), 9.12 (s, 1H), 9.05 (d, J=2.2 Hz, 1H), 8.44-8.47 (m, 2H), 8.39 (d, J=2.2 Hz, 1H), 7.51-7.55 (m, 1H), 2.83 (s, 3H), 2.31 (s, 1H), 2.14 (s, 3H), 1.77 (s, 6H). Further elution using 6% MeOH/DCM gave by product N-(6-methyl-5-sulfamoyl-3,4'-bipyridin-2'-yl)acetamide (I-395) (24 mg, 26%) as a white solid. LCMS (FA): m/z=307.4 (M+H). $^1$H NMR (400 MHz, DMSO-d$_6$) δ 10.68 (s, 1H), 8.99 (d, J=2.2 Hz, 1H), 8.44-8.47 (m, 1H), 8.43-8.39 (m, 2H), 7.76 (s, 2H), 7.48-7.52 (m, 1H), 2.85 (s, 3H), 2.14 (s, 3H).

575

Example 45: N-[4-(8-{[(2,4-difluorophenyl)sulfonyl]amino}[1,2,4]triazolo[1,5-a]pyridin-6-yl)pyridin-2-yl]acetamide (I-340)

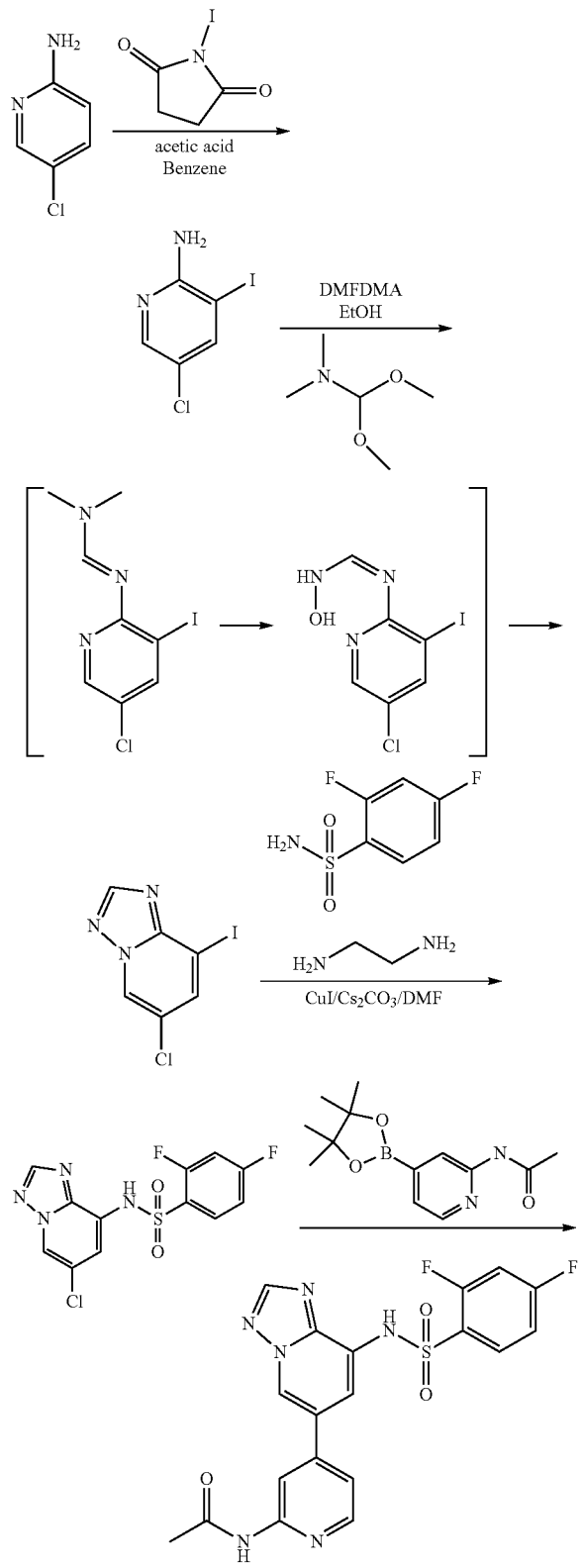

576

Step 1: 5-chloro-3-iodopyridin-2-amine

To a solution of 2-amino-5-chloropyridine (5.11 g, 39.7 mmol) in benzene (110 mL) and AcOH (2.3 mL) was added N-iodosuccinimide (8.94 g, 39.7 mmol). The reaction mixture was allowed to stir at 100° C. overnight. The mixture was diluted with EtOAc and washed with saturated NaHCO$_3$ and brine. The organic solution was dried over sodium sulfate, filtered and evaporated to afford crude product as dark red solid. The crude product was redissolved in EtOAc and washed with sodium bisulfite solution twice followed by brine. The solution was dried over Na$_2$SO$_4$, filtered and concentrated. The crude product was purified by column chromatography to afford 5-chloro-3-iodopyridin-2-amine as a yellow powder (1.75 g, 17.3%). LCMS (FA): m/z=254.0 (M+H).

Step 2: 6-chloro-8-iodo[1,2,4]triazolo[1,5-a]pyridine

To a mixture of 5-chloro-3-iodo-pyridin-2-ylamine (1.54 g, 6.05 mmol) in EtOH (15 mL) was added 1,1-dimethoxy-N,N-dimethylmethanamine (1.1 mL, 8.6 mmol). The reaction mixture was allowed to stir at 80° C. for 1 hr. The reaction mixture was concentrated to dryness and MeOH (7.0 mL) was added. The mixture was cooled in an ice bath. Pyridine (1.2 mL) and hydroxylamine-O-sulfonic acid (1.00 g, 8.84 mmol) were added. The mixture was allowed to stir overnight while warming to rt. The mixture was dry loaded on silica gel and purified by chromatography to afford 6-chloro-8-iodo[1,2,4]triazolo[1,5-a]pyridine as a white powder (1.09 g, 64.4%). LCMS (FA): m/z=279.9 (M+H).

Step 3: N-(6-chloro[1,2,4]triazolo[1,5-a]pyridin-8-yl)-2,4-difluorobenzenesulfonamide A mixture of 6-chloro-8-iodo[1,2,4]triazolo[1,5-a]pyridine (0.315 g, 1.13 mmol), 2,4-difluorobenzenesulfonamide (0.258 g, 1.34 mmol), copper(I) iodide (32 mg, 0.17 mmol) and cesium carbonate (0.776 g, 2.38 mmol) were placed in a microwave vial. The vessel was evacuated and backfilled with argon 3 times. DMF (4.73 mL) and ethylenediamine (82 mg, 1.4 mmol) were added. The mixture was subjected to microwave irradiation at 120° C. for 30 min. The reaction mixture was extracted with EtOAc. The organic solutions were combined, washed with brine, dried over Na$_2$SO$_4$, filtered and concentrated. The crude compound was purified by column chromatography to give N-(6-chloro[1,2,4]triazolo[1,5-a]pyridin-8-yl)-2,4-difluorobenzenesulfonamide (60 mg, 15%) as a gray solid. LCMS (FA): m/z=345.0 (M+H).

Step 4: N-[4-(8-{[(2,4-difluorophenyl)sulfonyl]amino}[1,2,4]triazolo[1,5-a]pyridin-6-yl)pyridin-2-yl]acetamide A mixture of N-(6-chloro[1,2,4]triazolo[1,5-a]pyridin-8-yl)-2,4-difluorobenzenesulfonamide (0.060 g, 0.17 mmol), N-[4-(4,4,5,5-tetramethyl-1,3,2-dioxaborolan-2-yl)pyridin-2-yl]acetamide (0.046 g, 0.17 mmol), (2-dicyclohexylphosphino-2',4',6'-triisopropyl-1,1'-biphenyl)[2-(2'-amino-1,1'-biphenyl)]palladium(II) methanesulfonate (8.19 mg, 0.0087 mmol) and 2-dicyclohexylphosphino-2',4',6'-tri-i-propyl-1,1'-biphenyl (8.30 mg, 0.017 mmol) were placed in a microwave vial. The vessel was evacuated and backfilled with argon 3 times. 1,4-Dioxane (1.36 mL) and potassium phosphate (0.050 M in water, 0.696 mL, 0.348 mmol) was added. The mixture was subjected to microwave irradiation at 130° C. for 30 min. Additional portions of N-[4-(4,4,5,5-tetramethyl-1,3,2-dioxaborolan-2-yl)pyridin-2-yl]acetamide (0.091 g, 0.35 mmol), (2-dicyclohexylphosphino-2',4',6'-triisopropyl-1,1'-biphenyl) [2-(2'-amino-1,1'-biphenyl)]palladium(II) methanesulfonate (8.0 mg, 0.0085 mmol), 2-dicyclohexylphosphino-2',4',6'-tri-i-propyl-1,1'-biphenyl (8.0 mg, 0.017 mmol) and potassium phosphate (0.50 M in water, 1.00 mL) were added and the mixture was allowed to stir at 120° C. for another 20 min. The reaction mixture was extracted with EtOAc. The organic solutions were combined, washed with brine, dried over $Na_2SO_4$, filtered and concentrated. The crude compound was purified by column chromatography to give N-[4-(8-{[(2,4-difluorophenyl)sulfonyl]amino}[1,2,4]triazolo[1,5-a]pyridin-6-yl)pyridin-2-yl]acetamide I-340 (7 mg, 9%) as a white solid. LCMS (FA): t/z=444.8 (M+H). 1H NMR (400 MHz, DMSO-d6) δ 10.70 (s, 1H). 9.25 (s, 1H). 8.55 (m. 1H), 8.40 (d, J=5.6, 1H), 8.38 (m, 1H), 8.03 (dd, J1=6.4, J2=8.4, 2H), 7.70 (m, 1H), 7.50 (d, J=5.6, 1H), 7.23 (t, J1=7.6, J2=10, 1H), 2.15 (s, 3H).

Example 46: N-[5-(1,3-oxazol-2-ylamino)-3,4'-bipyridin-2'-yl]acetamide (I-472)

mmol). $Pd_2(dba)_3$ (24.4 mg, 0.0266 mmol), $Cs_2CO_3$ (217 mg, 0.666 mmol) and Xantphos (30.8 mg, 0.0532 mmol) in 1,4-dioxane (2.3 mL) was allowed to stir for 2 h at 160° C. The reaction mixture was allowed to cool to rt and diluted with DCM, and the organic solution was washed with brine twice. The organic solutions were combined, dried over $Na_2SO_4$, filtered and concentrated. The crude compound was purified by column chromatography to provide N-[5-(1,3-oxazol-2-ylamino)-3,4'-bipyridin-2'-yl]acetamide I-472 (18.5 mg, 23.5%). LCMS (FA): m/z=296.2 (M+H). $^1$H NMR (400 MHz, DMSO-$d_6$) δ 10.66 (s, 1H), 10.60 (s, 1H), 8.83 (d, J=2.4 Hz, 1H), 8.48 (m, 1H), 8.45 (m, 1H), 8.42 (m, 2H), 7.73 (d, J=1.0 Hz, 1H), 7.41 (dd, J=5.2, 1.6 Hz, 1H), 7.07 (d, J=1.0 Hz, 1H), 2.13 (s, 3H).

Example 47: N-[5-(6-methyl-1,1-dioxido-1,2,6-thiadiazinan-2-yl)-3,4'-bipyridin-2'-yl]acetamide (I-452)

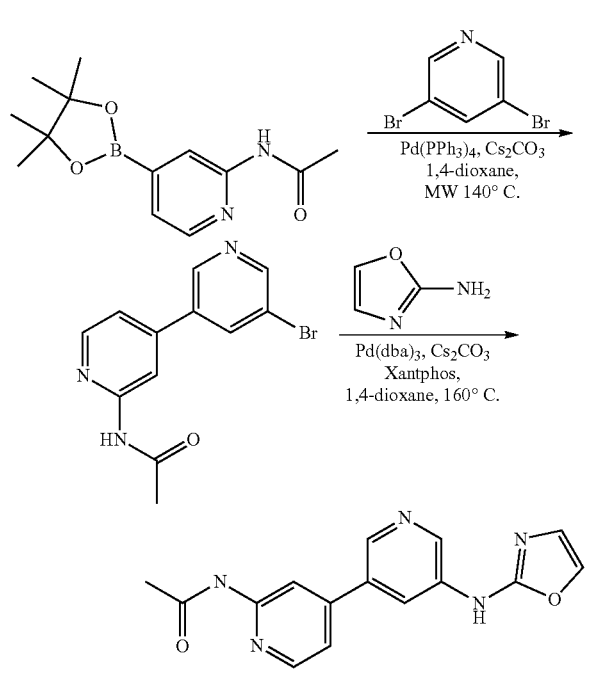

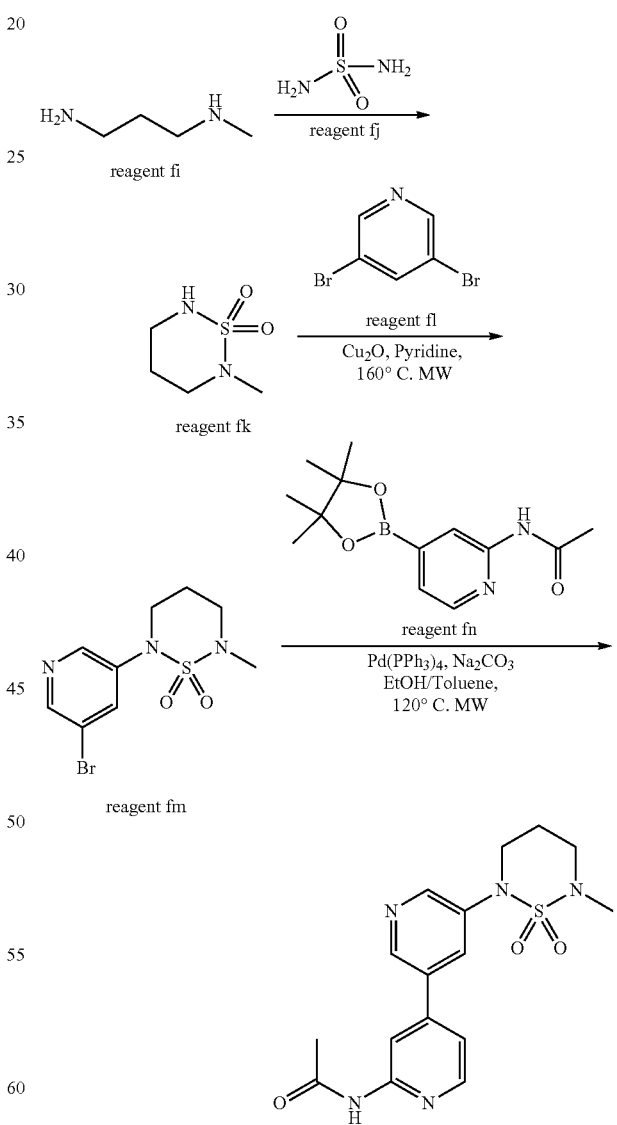

Step 1: N-(5-bromo-3,4'-bipyridin-2'-yl)acetamide

A mixture of 3,5-dibromopyridine (412 mg, 1.74 mmol), N-[4-(4,4,5,5-tetramethyl-1,3,2-dioxaborolan-2-yl)pyridin-2-yl]acetamide (520 mg, 2.00 mmol), $Cs_2CO_3$ (1.30 g, 4.00 mmol) and $Pd(PPh_3)_4$ (100 mg, 0.087 mmol) in 1,4-dioxane (10.0 mL) and water (2.0 mL) was subjected to microwave irradiation for 30 min at 140° C. The reaction mixture was allowed to cool to rt and diluted with DCM. The mixture was extracted with DCM and washed with water, dried over $Na_2SO_4$, filtered and concentrated. The crude compound was purified by column chromatography to provide N-(5-bromo-3,4'-bipyridin-2'-yl)acetamide (210 mg, 41%). LCMS (FA): m/z=292.1 (M+H).

Step 2: N-[5-(1,3-oxazol-2-ylamino)-3,4'-bipyridin-2'-yl]acetamide

A mixture of 1,3-oxazol-2-amine (80.6 mg, 0.959 mmol), N-(5-bromo-3,4'-bipyridin-2'-yl)acetamide (77.8 mg, 0.266

Step 1: 2-methyl-1,2,6-thiadiazinane 1,1-dioxide

A mixture of N-methyl-1,3-propanediamine (2.06 g, 23.4 mmol) and sulfamide (0.748 g, 7.78 mmol) was sealed in a microwave vial and filled with argon. The vial was was allowed to stir at 50° C. overnight and then at 160° C. for 20 min. The reaction mixture was concentrated and the residue was purified by column chromatography to give 2-methyl-1,2,6-thiadiazinane 1,1-dioxide (0.82 g, 70%).

Step 2: 2-(5-bromopyridin-3-yl)-6-methyl-1,2,6-thiadiazinane 1,1-dioxide

A mixture of 3,5-dibromopyridine (0.234 g, 0.988 mmol), 2-methyl-[1,2,6]thiadiazinane 1,1-dioxide (0.148 g, 0.988 mmol) and copper(I) oxide (0.141 g, 0.988 mmol) in pyridine (2.5 mL) was subjected to microwave irradiation at 160° C. for 20 min. The mixture was concentrated and the crude compound was purified by column chromatography 2-(5-bromopyridin-3-yl)-6-methyl-1,2,6-thiadiazinane 1,1-dioxide (0.108 g, 35.7%) as a colorless oil. LCMS (FA) m/z=306.0 (M+H).

Step 3: N-[5-(6-methyl-1,1-dioxido-1,2,6-thiadiazinan-2-yl)-3,4'-bipyridin-2'-yl]acetamide To 2-(5-bromopyridin-3-yl)-6-methyl-1,2,6-thiadiazinane 1,1-dioxide (0.108 g, 0.353 mmol), N-[4-(4,4,5,5-tetramethyl-1,3,2-dioxaborolan-2-yl)pyridin-2-yl]acetamide (0.104 g, 0.395 mmol), and tetrakis(triphenylphosphine)palladium(0) (34.2 mg, 0.0296 mmol) in a mixture of ethanol (1.30 mL) and toluene (1.30 mL) was added sodium carbonate (1.00 M in water, 0.44 mL, 0.44 mmol). The reaction mixture was subjected to microwave irradiation at 120° C. for 20 min. The reaction mixture was extracted with EtOAc. The organic solutions were combined, washed with brine, dried over $Na_2SO_4$, filtered and concentrated. The crude compound was purified by column chromatography to give N-[5-(6-methyl-1,1-dioxido-1,2,6-thiadiazinan-2-yl)-3,4'-bipyridin-2'-yl]acetamide I-452 as a white solid (58 mg, 50%). %). LCMS (FA): m/z=362.2 (M+H). 1H NMR (400 MHz, DMSO-d6) δ 10.68 (s, 1H), 8.82 (s, 1H), 8.67 (s, 1H). 8.43 (d, J=5.2, 1H). 8.39 (s, 1H), 8.01 (s, 1H), 7.49 (d, J=5.2, 1H), 3.84 (dd, J1=5.2, J2=5.2, 2H), 3.63 (dd, J1=5.2, J2=5.2, 2H), 2.92 (s, 3H), 2.13 (s, 3H), 1.96 (m, 2H).

The compounds listed in the table below (Table 37) were prepared in an analogous fashion to that described above from the appropriate starting materials:

TABLE 37

| Example | Starting Material | | Compound No. | LCMS Data |
|---|---|---|---|---|
| 47A | Reagent fk | Reagent fm | I-320 | LCMS (FA): m/z = 347.1 (M + H) |

Example 48: N-[6-methyl-5-(2-oxotetrahydropyrimidin-1(2H)-yl)-3,4'-bipyridin-2'-yl]acetamide (I-460)

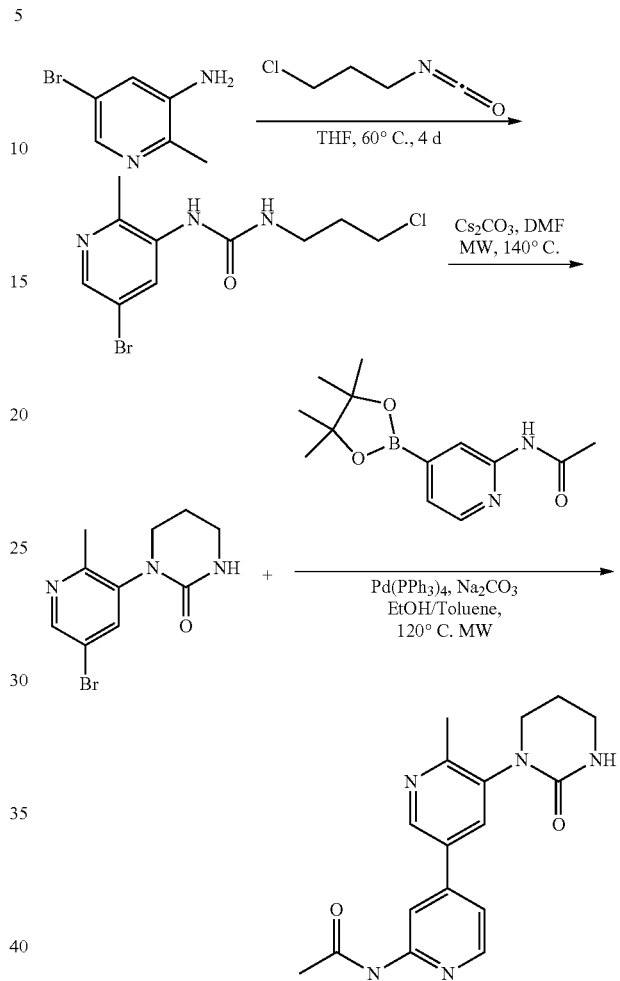

Step 1: 1-(5-bromo-2-methylpyridin-3-yl)-3-(3-chloropropyl)urea

To a suspension of 5-bromo-2-methylpyridin-3-amine (0.400 g, 2.14 mmol) in THF (5.00 mL) was added 3-chloropropyl isocyanate (0.241 mL, 2.35 mmol) under argon at rt. The reaction mixture was allowed to stir at 60° C. for 4 days. The mixture was evaporated to remove all of the solvent. The residue was purified by chromatography to give 1-(5-bromo-2-methylpyridin-3-yl)-3-(3-chloropropyl)urea (469 mg, 71%). LCMS (FA): m/z=308.1 (M+H).

Step 2: 1-(5-bromo-2-methylpyridin-3-yl)tetrahydropyrimidin-2(1H)-one

A mixture of 1-(5-bromo-2-methylpyridin-3-yl)-3-(3-chloropropyl)urea (0.213 g, 0.695 mmol) and cesium carbonate (0.679 g, 2.08 mmol) in DMF (5.00 mL) was subjected to microwave irradiation at 140° C. under argon for 20 min. The reaction mixture was diluted with water and extracted with EtOAc. The organic solutions were combined, washed with brine, dried over sodium sulfate, filtered and concentrated to give a residue, which was purified by column chromatography to give 1-(5-bromo-2-methylpyridin-3-yl)tetrahydropyrimidin-2(1H)-one as a white powder (162 mg, 86%). LCMS (FA): m/z=269.8 (M+H).

Step 3: N-[6-methyl-5-(2-oxotetrahydropyrimidin-1(2H)-yl)-3,4'-bipyridin-2'-yl]acetamide To a mixture of 1-(5-bromo-2-methylpyridin-3-yl)tetrahydropyrimidin-2(1H)-one (0.178 g. 0.658 mmol), N-[4-(4,4,5,5-tetramethyl-1,3,2-dioxaborolan-2-yl)pyridin-2-yl]acetamide (0.207 g, 0.789 mmol) and tetrakis(triphenylphosphine)palladium(0) (22.79 mg, 0.01972 mmol) in EtOH (5.0 mL) and toluene (5.0 mL) under argon was added sodium carbonate (1.0 M in Water, 0.85 mL, 0.85 mmol). The mixture was subjected to microwave irradiation at 120° C. for 20 min. The reaction mixture was extracted with EtOAc. The organic solutions were combined, washed with brine, dried over sodium sulfate, filtered and concentrated. The residue was purified by column chromatography and then by HPLC to give N-[6-methyl-5-(2-oxotetrahydropyrimidin-1(2H)-yl)-3,4'-bipyridin-2'-yl]acetamide I-460 as a white solid (115 mg, 54%). LCMS (FA): m/z=326.4 (M+H). 1H NMR (400 MHz, DMSO-d6) δ 10.63 (s, 1H), 867 (s, 1H), 8.37 (m, 2H), 7.93 (s, 1H), 7.45 (s, 1H), 6.71 (s, 1H), 3.66 (bs, 1H), 3.27 (m, 2H2.46 (m, 4H), 2.05 (m, 2H).

Example 49: N-[6-amino-5-(2-oxopyrrolidin-1-yl)-3,4'-bipyridin-2'-yl]acetamide (I-337)

Steps 1 and 2:
1-(2-amino-5-bromopyridin-3-yl)pyrrolidin-2-one

To a suspension of 2,3-diamino-5-bromopyridine (0.502 g, 2.67 mmol) and pyridine (1.30 mL, 16.0 mmol) in THF (10 mL) at 0° C. was added 4-bromobutyryl chloride (0.495 g, 2.67 mmol) in THF (2 mL) slowly. After addition, the mixture was allowed to stir at the same temperature for 30 min. The mixture was quenched by the addition of saturated sodium bicarbonate solution and extracted with DCM. The organic solution was separated, dried, filtered and evaporated to give crude N-(2-amino-5-bromopyridin-3-yl)-4-bromobutanamide, which was used in the next step directly. LCMS (FA): m/z=338.0 (M+H). N-(2-amino-5-bromopyridin-3-yl)-4-bromobutanamide (430 mg) prepared above was mixed with potassium carbonate (0.74 g, 5.34 mmol) in ACN (4 mL). The mixture was subjected to microwave irradiation at 120° C. for 20 min. The solvent was removed by evaporation and the residue was purified by column chromatography to give 1-(2-amino-5-bromopyridin-3-yl)pyrrolidin-2-one as a white solid (40 mg, 5.9%). LCMS (FA): m/z=256.1 (M+H).

Step 3: N-[6-amino-5-(2-oxopyrrolidin-1-yl)-3,4'-bipyridin-2'-yl]acetamide

A mixture of 1-(2-amino-5-bromopyridin-3-yl)pyrrolidin-2-one (0.0380 g, 0.148 mmol), N-[4-(4,4,5,5-tetramethyl-1,3,2-dioxaborolan-2-yl)pyridin-2-yl]acetamide (0.0506 g, 0.193 mmol) and tetrakis(triphenylphosphine)palladium(0) (5.14 mg, 0.00445 mmol) in toluene (1.3 mL) and EtOH (0.7 mL) was placed in a microwave vial. The vial was sealed, flushed with argon, and sodium carbonate (1.00 M in water, 0.178 mL, 0.178 mmol) was added. The mixture was subjected to microwave irradiation at 120° C. for 15 min. The mixture was concentrated and the crude product was purified by HPLC to give N-[6-amino-5-(2-oxopyrrolidin-1-yl)-3,4'-bipyridin-2'-yl]acetamide I-337 as a white powder (18.2 mg, 39.4%). LCMS (FA): m/z=312.2 (M+H). $^1$H NMR (400 MHz, DMSO-d$_6$) δ 10.58 (s, 1H), 8.60 (br, 1H), 8.42 (m, 2H), 8.37 (d, J=5.2, 1H), 8.15 (d, 1H), 7.49 (d, J=5.2, 1H), 4.66 (br, 1H), 3.30 (m, 2H), 2.90 (m, 2H), 1.95 (m, 2H)

Example 50: 6-chloro-2'-((2-cyclopropylpyrimidin-4-yl)amino)-4-methyl-[3,4'-bipyridine]-5-carboxylic acid (I-369) and azetidin-1-yl(6-chloro-2'-((2-cyclopropylpyrimidin-4-yl)amino)-4-methyl-[3,4'-bipyridin]-5-yl)methanone (I-361)

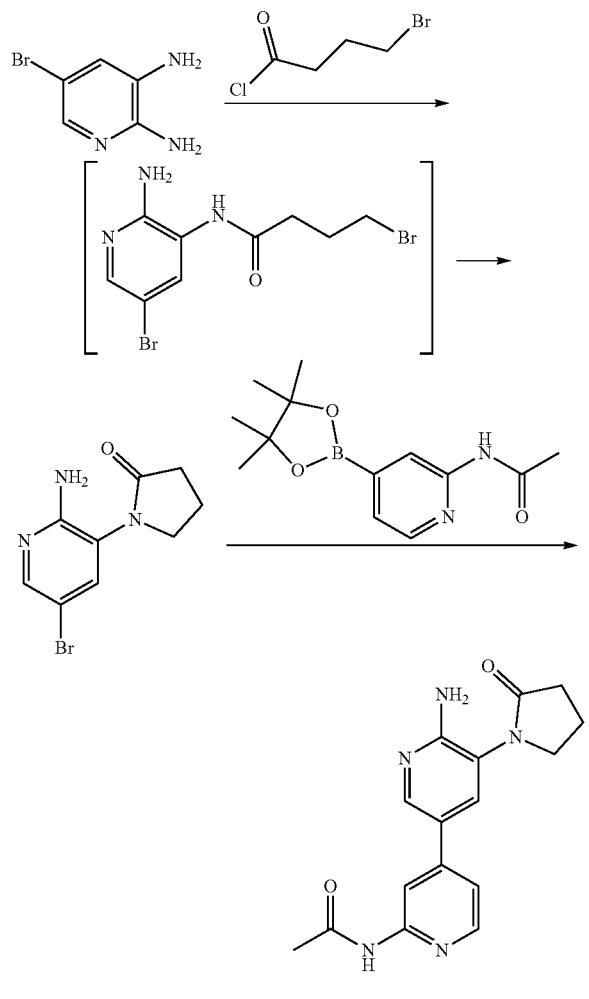

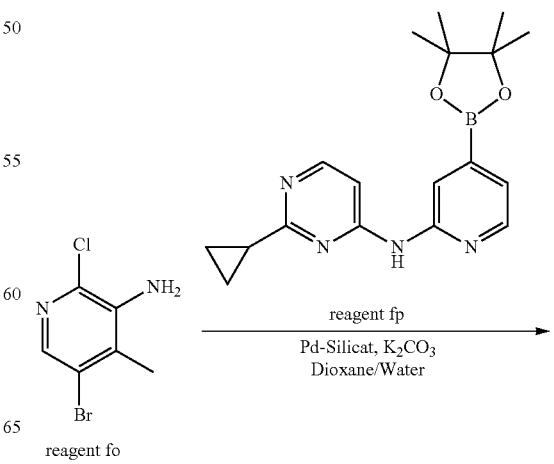

reagent fo reagent fp

Pd-Silicat, K$_2$CO$_3$
Dioxane/Water

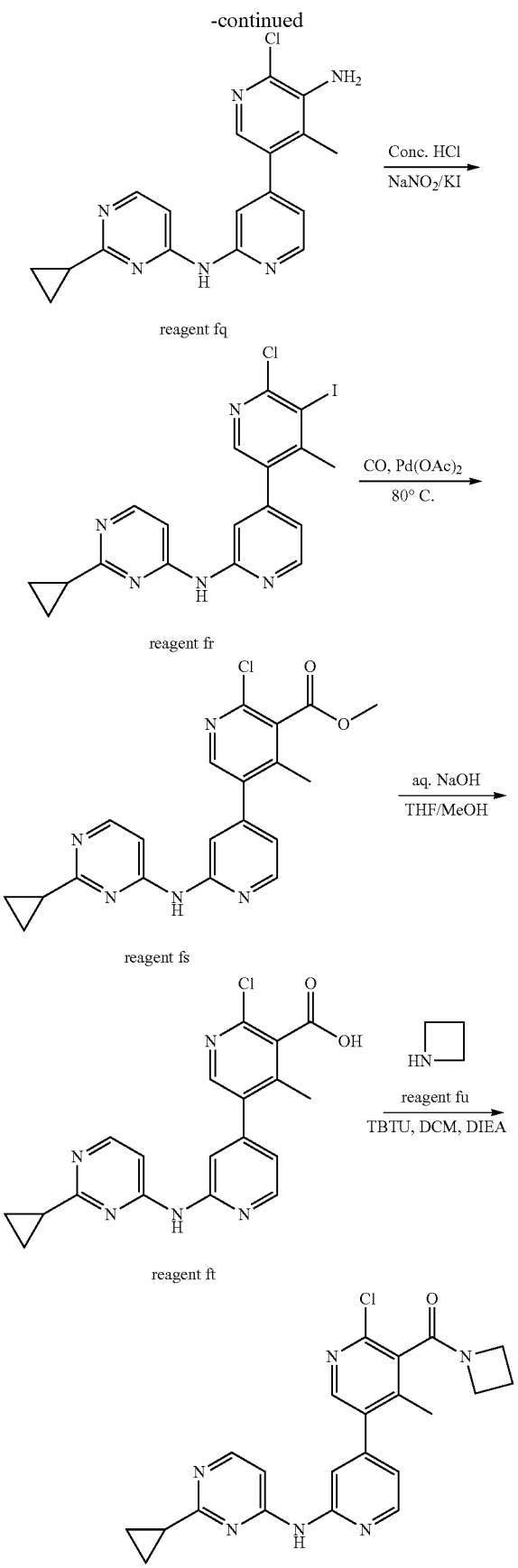

Step 1: 6-chloro-N2'-(2-cyclopropylpyrimidin-4-yl)-4-methyl-[3,4'-bipyridine]-2',5-diamine To a microwave vial were added 2-cyclopropyl-N-[4-(4,4,5,5-tetramethyl-1,3,2-dioxaborolan-2-yl)-2-pyridyl]pyrimidin-4-amine (1374 mg, 4.064 mmol) and 5-bromo-2-chloro-4-methyl-pyridin-3-amine (600 mg, 2.71 mmol) and Pd-Silicat (717 mg, 0.178 mmol,) and potassium carbonate (1030 mg, 0.668 mL, 7.45 mmol) and 1,4-dioxane (43.3 mL,) and Water (5.70 mL). The vial was thoroughly flushed with $N_2$ and the vial was subjected to microwave irradiation at 125° C. for 30 min. The reaction mixture was filtered and the filter bed was washed with fresh MeOH. Excess solvent was removed under reduced pressure. The residue was partitioned into EtOAc and water. The aqueous solution was extracted twice. The org. solutions were combined, washed with brine, dried over $MgSO_4$, filtered and excess solvent was removed under reduced pressure. This was purified by HPLC to give the title compound as a yellow solid (0.72 gm, 76% yield) LCMS (FA): m/z=353.1 (M+H)

Step 2: 6-chloro-N-(2-cyclopropylpyrimidin-4-yl)-5-iodo-4-methyl-[3,4'-bipyridin]-2'-amine To a flask fitted with a $N_2$ gas balloon and an internal temperature probe were added N-[4-(5-amino-6-chloro-4-methyl-3-pyridyl)-2-pyridyl]-2-cyclopropyl-pyrimidin-4-amine (725 mg, 2.05 mmol) and HCl (10 mmol, 1.4 mL). The reaction mixture was cooled to −5° C. and to this a solution of sodium nitrite (223 mg, 3.23 mmol) in water (29 mL) was added slowly over a period of 10 min, maintaining the temperature between −5° C. to −3° C. The reaction mixture was allowed to stir for 1 h. A solution of potassium iodide (570 mg, 3.43 mmol) in water (29 mL) was added dropwise. The reaction mixture was allowed to warm to rt and stir overnight. The reaction mixture was partitioned into water and EtOAc. The aqueous solution was separated and extracted twice. The organic solutions were combined, washed with aqueous $Na_2S_2O_3$ solution and brine, dried over $MgSO_4$, filtered and concentrated. The residue was purified by column chromatography to give 6-chloro-N-(2-cyclopropylpyrimidin-4-yl)-5-iodo-4-methyl-[3,4'-bipyridin]-2'-amine (0.23 g, 23%) as a white solid. LCMS (FA): m/z=464.0 (M+H)

Step 3: methyl 6-chloro-2'-((2-cyclopropylpyrimidin-4-yl)amino)-4-methyl-[3,4'-bipyridine]-5-carboxylate To a flask were added N-[4-(6-chloro-5-iodo-4-methyl-3-pyridyl)-2-pyridyl]-2-cyclopropyl-pyrimidin-4-amine (204 mg, 0.434 mmol), DMSO (2.50 mL), TEA (0.69 mL, 4.95 mmol) and MeOH (1.90 mL). The flask was thoroughly degassed and then palladium (II) acetate (32.6 mg, 0.145 mmol) and 1,3-bis(diphenylphosphino)propane (61.2 mg, 0.148 mmol) were added. The flask was again degassed, flushed with carbon monoxide and then the reaction mixture was allowed to stir at 80° C. under CO overnight. MeOH was removed under reduced pressure and the reaction mixture was diluted with water. The yellowish tan colored solid that precipitated was filtered and dried. The residue was purified by column chromatography to give methyl 6-chloro-2'-((2-cyclopropylpyrimidin-4-yl)amino)-4-methyl-[3,4'-bipyridine]-5-carboxylate. (0.066 mg, 19%). LCMS (FA): m/z=396.1 (M+H).

Step 4: 6-chloro-2'-((2-cyclopropylpyrimidin-4-yl) amino)-4-methyl-[3,4'-bipyridine]-5-carboxylic acid I-369

To a flask were added methyl 2-chloro-5-[2-[(2-cyclopropylpyrimidin-4-yl)amino]-4-pyridyl]-4-methyl-pyridine-3-carboxylate (53 mg, 0.134 mmol), MeOH (0.76 mL), THF (0.76 mL) and sodium hydroxide (1.0 M in water, 0.402 mL, 0.402 mmol). The reaction mixture was allowed to stir at 50° C. overnight. Excess solvent was removed under reduced pressure. The residue was diluted with water and acidified with conc. HCl to pH between 3-4. Excess solvent was removed under reduced pressure and the residue was directly purified by HPLC to give methyl 6-chloro-2'-((2-cyclopropylpyrimidin-4-yl)amino)-4-methyl-[3,4'-bipyridine]-5-carboxylate I-369 (30 mg, 59%). LCMS (FA): m/z=382.1 (M+H).

Step 5: azetidin-1-yl(6-chloro-2'-((2-cyclopropylpyrimidin-4-yl)amino)-4-methyl-[3,4'-bipyridin]-5-yl)methanone I-361

To 2-chloro-5-[2-[(2-cyclopropylpyrimidin-4-yl)amino]-4-pyridyl]-4-methyl-pyridine-3-carboxylic acid (19 mg, 0.0498 mmol) in DCM (0.5 mL) were added DIEA (0.052 mL, 0.296 mmol) and TBTU (44 mg, 0.138 mmol). The reaction mixture was allowed to stir for 30 min and then a solution of azetidine (12.7 mg, 0.222 mmol) in DCM (1 mL) was added. The reaction mixture was allowed to stir at rt for 1 h. Additional portions of TBTU (40 mg) and azetidine (10 mg) in DCM (0.5 mL) were added. The reaction mixture was allowed to stir overnight and then partitioned between EtOAc and aqueous NaHCO$_3$ soln. The aqueous solution was extracted twice. The organic solutions were combined, washed with water, brine, dried over MgSO$_4$, filtered and concentrated. The crude product was purified by HPLC to give azetidin-1-yl(6-chloro-2'-((2-cyclopropylpyrimidin-4-yl)amino)-4-methyl-[3,4'-bipyridin]-5-yl)methanone I-361 (12 mg, 56% yield) as a white solid. LCMS (FA): m/z=421.1 (M+H). $^1$H NMR (MeOH-d$_4$) δ: 8.43 (br d, J=4.9 Hz, 1H), 8.35 (s, 1H), 8.23 (br d, J=6.1 Hz, 1H), 7.89 (s, 1H), 7.40 (br d, J=6.0 Hz, 1H), 7.08 (br d, J=3.9 Hz, 1H, 4.29 (br d, J=5.4 Hz, 2H), 4.14 (q, J=7.8 Hz, 1H), 4.02 (q, J=8.3 Hz, 1H), 2.46 (quin, J=7.6 Hz, 2H), 2.37 (s, 3H), 2.10 (br d, J=6.0 Hz, 1H), 1.00-1.10 (m, 4H)

The compounds listed in the table below (Table 38) were prepared in an analogous fashion to that described above from the appropriate starting materials:

TABLE 38

| Example | Reagent | Starting Material Chemical Structure | Compound No. | LCMS Data |
|---|---|---|---|---|
| 50A | fp | 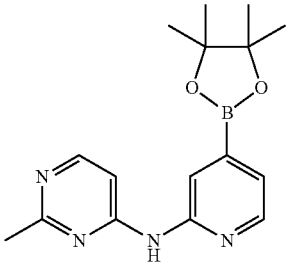 | I-457 | LCMS (FA): m/z = 395.1 (M + H) |
| | ft |  | | |
| | fu | 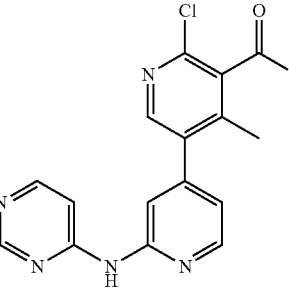 | | |
| 50B | fp |  | I-402 | LCMS (FA): m/z = 356.1 (M + H) |

TABLE 38-continued

| | Starting Material | | Compound | |
|---|---|---|---|---|
| Example | Reagent | Chemical Structure | No. | LCMS Data |
| 50C | fu | ft | I-466 | LCMS (FA): m/z = 449.1 (M + H) |

Example 51: N-[5-(1,3-benzoxazol-2-ylamino)-6-methyl-3,4'-bipyridin-2'-yl]acetamide (I-392)

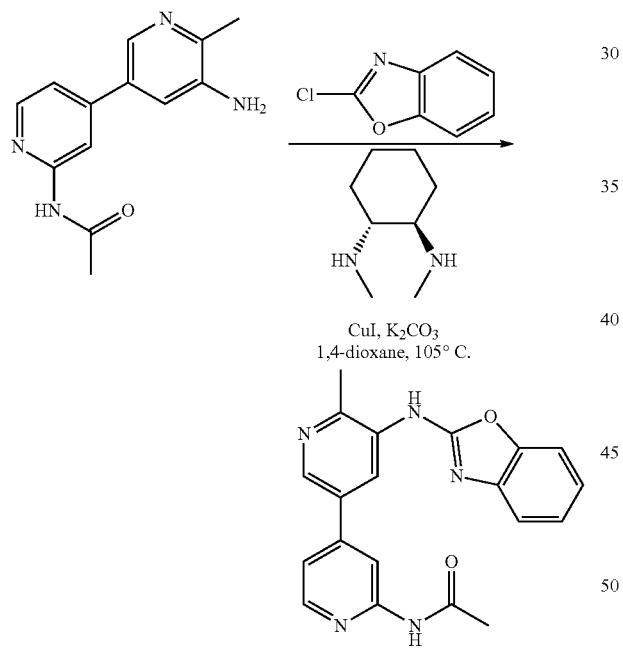

A mixture of 2-chloro-1,3-benzoxazole (40 uL, 0.35 mmol), N-(5-amino-6-methyl-3,4'-bipyridin-2'-yl)acetamide (65 mg, 0.27 mmol), copper iodide (9.8 mg, 0.052 mmol), potassium carbonate (148 mg, 1.07 mmol) and trans-1,2-bis(methylamino)cyclohexane (16.2 uL, 0.103 mmol) in 1,4-dioxane (1.8 mL) was allowed to stir for 48 h at 105° C. The reaction mixture was allowed to cool to rt and diluted with EtOAc, and the solution was washed with 20% ammonia solution once and brine twice. The organic solutions were combined, dried over Na$_2$SO$_4$, filtered and concentrated. The crude compound was purified by column chromatography to provide N-[5-(1,3-benzoxazol-2-ylamino)-6-methyl-3,4'-bipyridin-2'-yl]acetamide I-392 (2.5 mg, 2.6%). LCMS (FA): m/z=360.2 (M+H). $^1$H NMR (400 MHz, DMSO-d$_6$) δ 10.64 (s, 1H), 8.68 (s. 1H), 8.57 (s, 1H), 8.43 (m, 2H), 7.50 (m, 1H), 7.46 (m, 1H), 7.40 (m, 1H), 7.22 (m, 1H), 7.15 (m, 1H), 2.60 (s, 3H), 2.13 (s, 3H).

Example 52: N-(2'-acetamido-3,4'-bipyridin-5-yl)-2,4-difluoro-N-methylbenzamide (I-397)

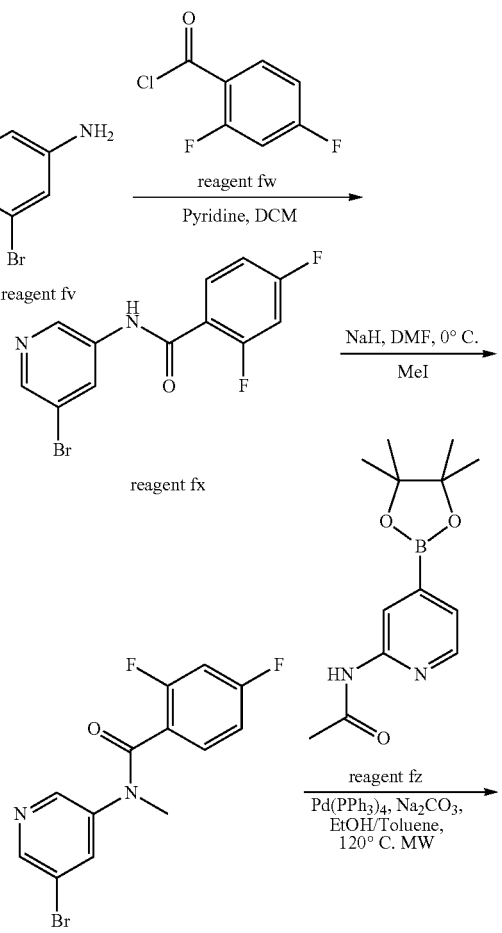

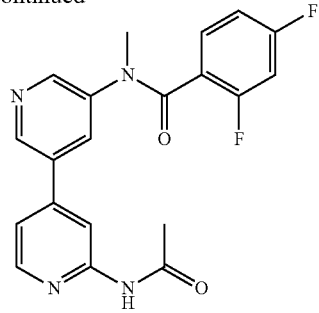

Step 1: N-(5-bromopyridin-3-yl)-2,4-difluorobenzamide

A flask containing 3-amino-5-bromopyridine (0.500 g, 2.89 mmol) was evacuated and backfilled with argon. Pyridine (0.70 mL) and DCM (8 mL) were added and the mixture was allowed to stir at 0° C. 2,4-difluorobenzoyl chloride (0.510 g, 2.89 mmol) was dissolved in DCM (3 mL) and added dropwise to the reaction mixture. The reaction mixture was allowed to stir at the same temperature until the starting material was consumed. The reaction mixture was extracted with EtOAc. The organic solutions were combined, washed with brine, dried over $Na_2SO_4$, filtered and concentrated. The crude compound was purified by column chromatography as a pale yellow powder (0.83 g, 91%). LCMS (FA): m/z=314.0 (M+H).

Step 2: N-(5-bromopyridin-3-yl)-2,4-difluoro-N-methylbenzamide

Sodium hydride (0.125 g, 5.21 mmol) and DMF (5.00 mL) were placed in a vial under argon gas. The reaction mixture was allowed to stir at 0° C. for 10 min. N-(5-bromopyridin-3-yl)-2,4-difluorobenzamide (0.272 g, 0.868 mmol) was added to the mixture, followed by methyl iodide (0.270 mL, 4.34 mmol). The mixture was stirred at the same temperature until starting material was consumed. The reaction mixture was quenched with ammonium chloride solution and extracted with EtOAc. The organic solutions were combined, washed with brine, dried over $Na_2SO_4$, filtered and concentrated. The crude compound was purified by column chromatography as a pale yellow oil (0.212 g, 74%). LCMS (FA): m/z=328.7 (M+H).

Step 3: N-(2'-acetamido-3,4'-bipyridin-5-yl)-2,4-difluoro-N-methylbenzamide

A vial containing N-(5-bromopyridin-3-yl)-2,4-difluoro-N-methylbenzamide (0.200 g, 0.611 mmol), EtOH (4 mL), toluene (4 mL), N-[4-(4,4,5,5-tetramethyl-1,3,2-dioxaborolan-2-yl)pyridin-2-yl]acetamide (0.208 g, 0.795 mmol) and tetrakis(triphenylphosphine)palladium(0) (0.0212 g, 0.0183 mmol) was evacuated and backfilled with argon. Sodium carbonate (1.0 M in Water, 0.734 mL, 0.734 mmol) was added. The mixture was subjected to microwave irradiation at 120° C. for 20 min. The reaction mixture was extracted with EtOAc. The organic solutions were combined, washed with brine, dried over $Na_2SO_4$, filtered and concentrated. The crude compound was purified by column chromatography as a brown oil I-397 (0.238 g, 100%). LCMS (FA): m/z=383.3 (M+H). $^1$H NMR (400 MHz, $CDCl_3$) δ=8.72 (s, 1H), 8.46-8.31 (m, 3H), 7.74 (br s, 1H), 7.50 (q, J=7.7 Hz, 1H), 7.29 (s, 1H), 7.20-7.09 (m, 1H), 6.92 (br t, J=7.5 Hz, 1H), 6.64 (br s, 1H), 3.56 (s, 3H), 3.51 (d, J=4.3 Hz, 1H), 2.27 (s, 3H)

The compounds listed in the table below (Table 39) were prepared in an analogous fashion to that described above from the appropriate starting materials:

TABLE 39

| Example | Reagent | Starting Material Chemical Structure | Compound No. | LCMS Data |
|---|---|---|---|---|
| 52A | fv | Br—pyridine—NH$_2$, OMe | I-331 | LCMS (FA): m/z = 413.1 (M + H) |
| 52B | fv* | Br—pyridine—NH$_2$, Me | I-398 | LCMS (FA): m/z = 397.5 (M + H) |

*Step 2: $Cs_2CO_3$ DMF, 110° C., microwave irradiation

Example 53: N-(2'-((2-cyclopropylpyrimidin-4-yl)amino)-6-methyl-[3,4'-bipyridin]-5-yl)-3,3-difluoroazetidine-1-carboxamide (I-368)

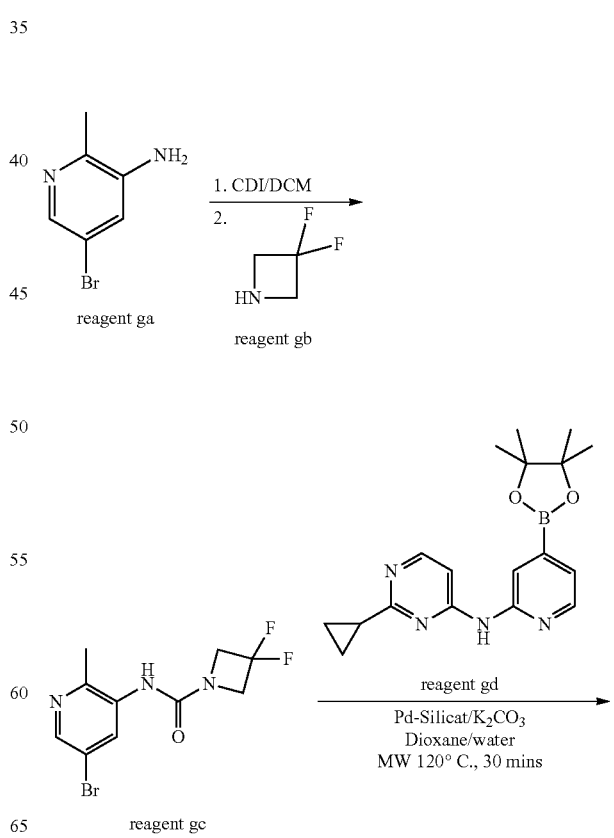

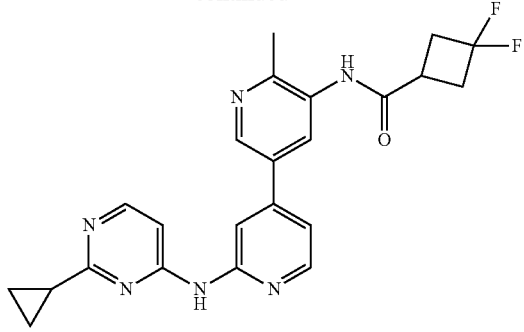

Step 1: N-(5-bromo-2-methyl-3-pyridyl)-3,3-difluoro-azetidine-1-carboxamide

To 5-bromo-2-methyl-pyridin-3-amine (300 mg, 1.60 mmol) were added DCM (9.0 mL) and 1,1'-carbonyldiimidazole (280 mg, 1.73 mmol). The reaction mixture was allowed to stir at rt overnight. To this stirred solution, 3,3-difluoroazetidine hydrochloride salt (300 mg, 2.32 mmol) was added and the reaction mixture was allowed to stir at 50° C. for 6 h. Excess solvent was removed under reduced pressure. The reaction was diluted with DCM and the solution was washed with aqueous saturated NaHCO$_3$ solution. The organic solution was separated, washed with water and brine, dried over MgSO$_4$, filtered and concentrated. The crude product was purified by column chromatography to give N-(5-bromo-2-methyl-3-pyridyl)-3,3-difluoro-azetidine-1-carboxamide (0.093 gm, 19%) as a pale yellow oil. LCMS (FA): m/z=307 (M+H).

Step 2: N-(2'-((2-cyclopropylpyrimidin-4-yl)amino)-6-methyl-[3,4'-bipyridin]-5-yl)-3,3-difluoroazetidine-1-carboxamide To a microwave vial were added 2-cyclopropyl-N-[4-(4,4,5,5-tetramethyl-1,3,2-dioxaborolan-2-yl)-2-pyridyl]pyrimidin-4-amine (129 mg, 0.383 mmol), Pd-silicat (101.9 mg, 0.0254 mmol), K$_2$CO$_3$ (92 mg, 0.66 mmol) and a solution of N-(5-bromo-2-methyl-3-pyridyl)-3,3-difluoroazetidine-1-carboxamide (75 mg, 0.245 mmol) in 1,4-dioxane (3.35 mL) and water (480 μL,). The vial was thoroughly flushed with N$_2$ and then subjected to microwave irradiation at 120° C. for 30 min. The reaction mixture was filtered and washed with MeOH. Excess solvent was removed under reduced pressure. The residue was then diluted with EtOAc and washed with aqueous saturated NaHCO$_3$. The organic solution was separated, washed with water and brine, dried over MgSO$_4$, filtered and concentrated. The residue was purified by column chromatography to give N-(2'-((2-cyclopropylpyrimidin-4-yl)amino)-6-methyl-[3,4'-bipyridin]-5-yl)-3,3-difluoroazetidine-1-carboxamide I-368 (0.054 gm, 51%) as a white solid. LCMS (FA): m/z=438.2 (M+1). $^1$H NMR (MeOH-d$_4$) δ: 8.67 (s, 1H), 8.39 (d, J=5.3 Hz, 1H), 8.31 (s, 1H), 8.22 (s, 1H), 8.23-8.20 (m, 2H), 7.34 (br d, J=5.1 Hz, 1H), 7.27 (d, J=5.9 Hz, 1H), 4.50 (t, J=12.2 Hz, 4H), 2.60 (s, 3H), 2.15 (br d, J=4.4 Hz, 1H), 1.05-1.21 (m, 4H)

The compounds listed in the table below (Table 40) were prepared in an analogous fashion to that described above from the appropriate starting materials:

TABLE 40

| Example | Reagent | Starting Material Chemical Structure | Compound No. | LCMS Data |
|---|---|---|---|---|
| 53A | gd | | I-482 | LCMS (FA): m/z = 412.1 (M + H) |
| 53B | gb* | | I-367 | LCMS (FA): m/z = 364.0 (M + H) |
| | gc | | | |

TABLE 40-continued

| Example | Starting Material Reagent | Chemical Structure | Compound No. | LCMS Data |
|---|---|---|---|---|
| | gd | [pinacol boronate pyridine with 2-methylpyrimidin-4-ylamino substituent] | | |
| 53C | gb | [aniline, PhNH₂] | I-439 | LCMS (FA): m/z = 412.1 (M + H) |
| | gc | [1-(5-bromo-2-methylpyridin-3-yl)-3-phenylurea] | | |
| | gd | [pinacol boronate pyridine with 2-methylpyrimidin-4-ylamino substituent] | | |
| 53E | ga | [6-bromopyrazolo[1,5-a]pyridin-4-amine] | I-407 | LCMS (FA): m/z = 437.1 (M + H) |
| | gc | [N-(6-bromopyrazolo[1,5-a]pyridin-4-yl)-3,3-difluoroazetidine-1-carboxamide] | | |
| | gd | [pinacol boronate pyridine with 2-methylpyrimidin-4-ylamino substituent] | | |

*Step 1 Conditions: THF, 55° C.
**Step 1 Conditions: 1,1'-thiocarbonyl-diimidazole was used instead of CDI Examples 54a and 54b: 6-benzyl-3-[2-[(2-methyl-pyrimidin-4-yl)amino]-4-pyridyl]-7,8-dihydro-1,6-naphthyridin-5-one (I-378) and 3-[2-[(2-methylpyrimidin-4-yl)amino]-4-pyridyl]-7,8-dihydro-6H-1,6-naphthyridin-5-one (I-406)

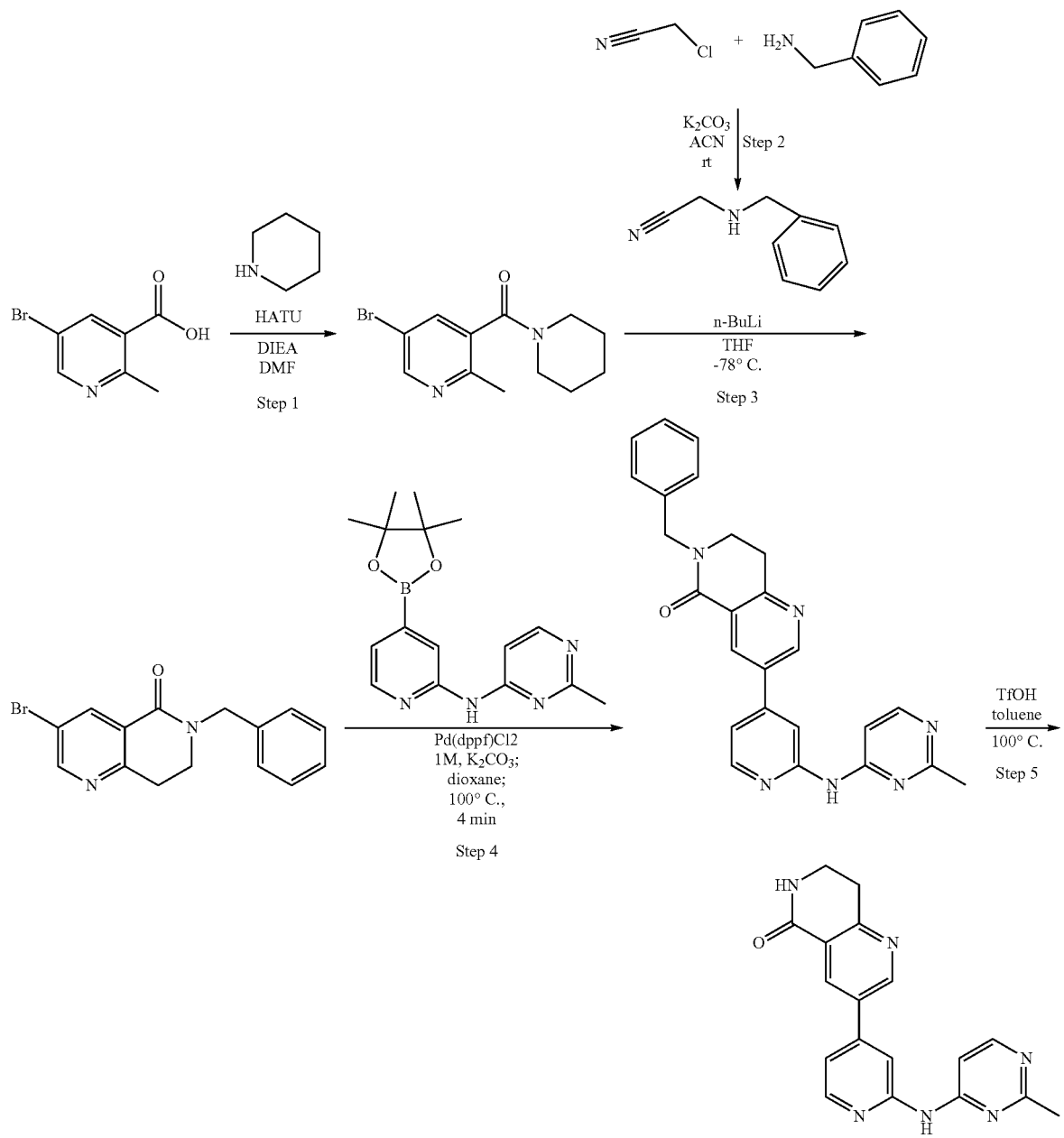

Step 1: (5-bromo-2-methyl-3-pyridyl)-(1-piperidyl)methanone

To (5-bromo-2-methyl-3-pyridyl)-(1-piperidyl)methanone (2.0 g, 7.06 mmol) in DMF (51.6 mL, 666 mmol) were added HATU (6.93 g, 18.2 mmol), piperidine (3.85 mL, 38.9 mmol) and DIEA (6.79 mL, 38.9 mmol). The mixture allowed to stir at rt overnight. Excess solvent was removed under reduced pressure. The reaction mixture was diluted with EtOAc, washed with saturated NaHCO$_3$ solution, washed with brine, dried over MgSO$_4$, filtered and concentrated under reduced pressure. The residue was purified by column chromatography to provide (5-bromo-2-methyl-3-pyridyl)-(1-piperidyl)methanone (2.0 g, 95%). LCMS (FA): m/z=283.1 (M+H)

Step 2: 2-(benzylamino)acetonitrile

To a suspension of benzylamine (1.0 mL, 9.2 mmol) and potassium carbonate (3.0 g, 22.0 mmol) in ACN (25.4 mL)

was added chloroacetonitrile (0.90 mL, 14.0 mmol). The reaction mixture was allowed to stir at 60° C. for 16 h. The reaction was allowed to cool to rt and excess solvent was removed. The reaction mixture was diluted with DCM, washed with saturated NaHCO$_3$ solution and brine, dried over MgSO$_4$, filtered and concentrated under reduced pressure. The residue was purified by column chromatography to give 2-(benzylamino)acetonitrile (1.2 g, 90%). LCMS (FA): m/z=147.2 (M+H).

Step 3: 6-benzyl-3-bromo-7,8-dihydro-1,6-naphthyridin-5-one

To a stirred solution of n-butyllithium (2.5 M in hexane, 3.5 mL, 8.65 mmol) in THF (7.3 mL, 89.0 mmol) was added piperidine, 2,2,6,6-tetramethyl- (1.59 mL, 9.39 mmol) at −10° C. The reaction mixture was allowed to stir at 0° C. for 30 min. Then the reaction mixture was allowed to cool to −78° C. and (5-bromo-2-methyl-3-pyridyl)-(1-piperidyl)methanone (0.70 g, 2.47 mmol) in THF (7.0 mL) was added over 5 min, immediately followed by dropwise addition of 2-(benzylamino)acetonitrile (0.39 g, 2.71 mmol) in THF (6.0 mL). The reaction mixture was allowed to stir to −78° C. for 7 h. The reaction mixture was diluted with saturated aqueous NH$_4$Cl (2 mL) and extracted with EtOAc. The organic solutions were combined, dried over Na$_2$SO$_4$, filtered and concentrated. The crude compound was purified by column chromatography to provide 6-benzyl-3-bromo-7,8-dihydro-1,6-naphthyridin-5-one (0.784 g, 41.6%). LCMS (FA): m/z=318.1 (M+H).

Step 4: 6-benzyl-3-[2-[(2-methylpyrimidin-4-yl)amino]-4-pyridyl]-7,8-dihydro-1,6-naphthyridin-5-one A mixture of [2-methyl-N-[4-(4,4,5,5-tetramethyl-1,3,2-dioxaborolan-2-yl)pyridin-2-yl]pyrimidin-4-amine (0.190 g, 0.609 mmol), 6-benzyl-3-bromo-7,8-dihydro-1,6-naphthyridin-5-one (0.161 g, 0.50 mmol) and Pd(dppf)Cl$_2$, complex with DCM (1:1) (0.060 g, 0.073 mmol) in 1,4-dioxane (3.96 mL) and K$_2$CO$_3$ (1M in water, 1 mL) was allowed to stir at 100° C. overnight. The reaction mixture was diluted with water and extracted with EtOAc. The organic solutions were combined, dried over Na$_2$SO$_4$, filtered and concentrated. The crude product was purified by column chromatography to provide 6-benzyl-3-[2-[(2-methylpyrimidin-4-yl)amino]-4-pyridyl]-7,8-dihydro-1,6-naphthyridin-5-one I-378 (0.212 g, 98%). LCMS (FA): m/z=423.2 (M+H). $^1$H NMR (400 MHz, DMSO-d$_6$) δ 10.28 (s, 1H), 9.03 (d, J=2.4 Hz, 1H), 8.54 (d, J=2.4 Hz, 1H), 8.42 (d, J=5.2 Hz, 1H), 8.36 (d, J=5.9 Hz, 1H), 8.13 (s, 1H), 7.67 (d, J=5.9 Hz, 1H), 7.46 (dd, J=5.3, 1.6 Hz, 1H), 7.37 (d, J=4.4 Hz, 4H), 7.34-7.27 (m, 1H), 4.78 (s, 2H), 3.64 (t, J=6.8 Hz, 2H), 3.19 (t, J=6.7 Hz, 2H), 2.50 (s, 3H).

Step 5: 3-[2-[(2-methylpyrimidin-4-yl)amino]-4-pyridyl]-7,8-dihydro-6H-1,6-naphthyridin-5-one To a solution of 6-benzyl-3-[2-[(2-methylpyrimidin-4-yl)amino]-4-pyridyl]-7,8-dihydro-1,6-naphthyridin-5-one (0.166 g, 0.393 mmol)] in toluene (17 mL) was added trifluoromethansulfonic acid (2 mL, 20.0 mmol). The reaction mixture was allowed to stir at 100° C. for 16 h. Excess solvent was removed under reduced pressure and the crude compound was purified by HPLC to provide 3-[2-[(2-methylpyrimiidin-4-yl)amino]-4-pyridyl]-7,8-dihydro-6H-1,6-naphthyridin-5-one I-406 (0.13 g, 3.8%). LCMS (FA): m/z=333.2 (M+H). $^1$H NMR (400 MHz, DMSO-d$_6$) δ 10.27 (s, 1H), 9.01 (d, J=2.4 Hz, 1H), 8.45 (d, J=2.4 Hz, 1H), 8.41 (d, J=5.3 Hz, 1H), 8.36 (d, J=5.9 Hz, 1H), 8.26 (s, 1H), 8.11 (s, 1H), 7.68 (d, J=5.9 Hz, 1H), 7.44 (dd, J=5.3, 1.6 Hz, 1H), 3.52 (td, J=6.7, 2.7 Hz, 2H), 3.13 (t, J=6.7 Hz, 2H), 2.45 (s, 3H)

Examples 55a and 55b: N-(5-(4-(dimethylamino)-1,1-dioxidoisothiazolidin-2-yl)-6-methyl-[3,4'-bipyridin]-2'-yl)acetamide (I-496 (peak 1)) and (R or S)—N-(5-(4-(dimethylamino)-1,1-dioxidoisothiazolidin-2-yl)-6-methyl-[3,4'-bipyridin]-2'-yl)acetamide (I-497 (peak 2))

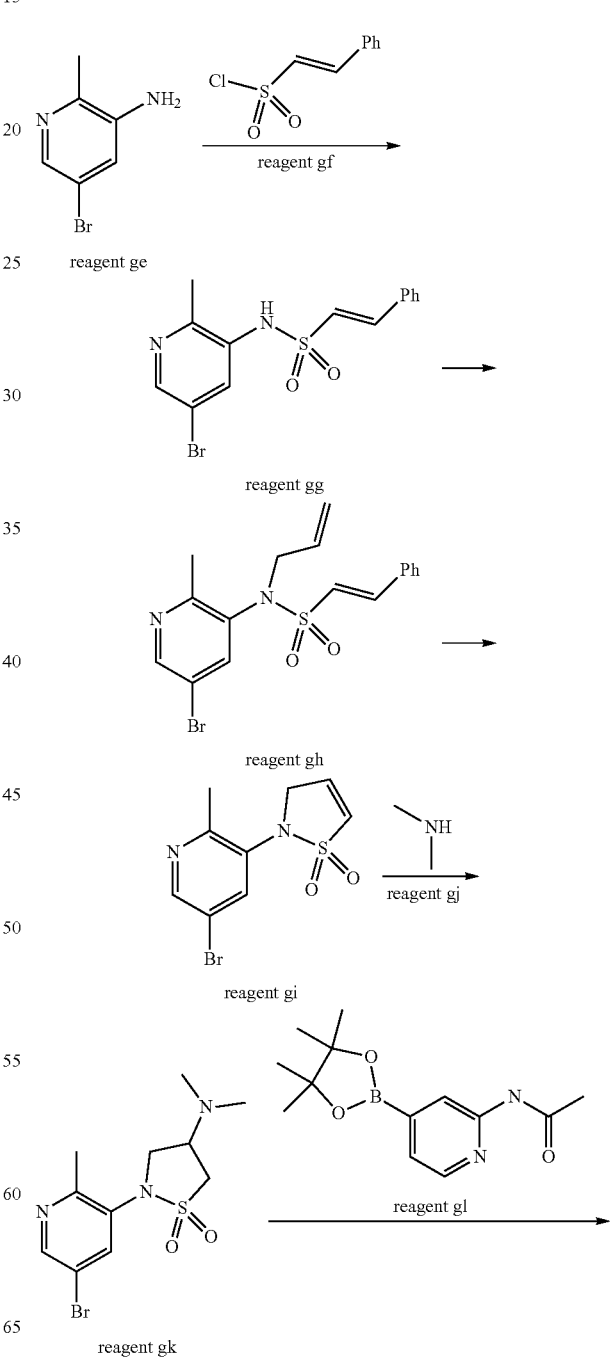

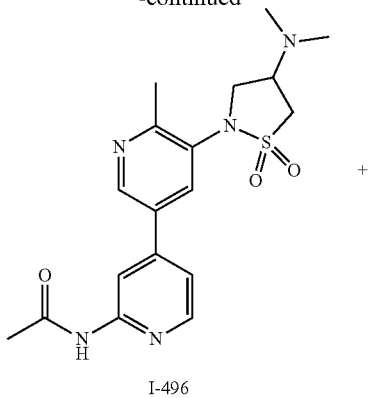

I-496

I-497

Step 1: (E)-N-(5-bromo-2-methylpyridin-3-yl)-2-phenylethenesulfonamide (E)-2-phenylethenesulfonyl chloride (5.4 g, 26.7 mmol) was added in portions over a period of 0.5 h to a stirred solution of 5-bromo-2-methylpyridin-3-amine (5.0 g, 26.7 mmol) in anhydrous pyridine (30 mL). The reaction mixture was allowed to warm to rt and stirred for an additional 0.5 h. The solvent was evaporated under reduced pressure to give crude (E)-N-(5-bromo-2-methylpyridin-3-yl)-2-phenylethenesulfonamide which was used without further purification.

Step 2: (E)-N-allyl-N-(5-bromo-2-methylpyridin-3-yl)-2-phenylethenesulfonamide

A solution of (E)-N-(5-bromo-2-methylpyridin-3-yl)-2-phenylethenesulfonamide (3.4 g, 26.6 mmol) in ACN (90 mL) was treated with potassium carbonate (11.0 g, 80.0 mmol) and sodium iodide (1.3 g, 8.78 mmol) followed by allyl bromide (19.3 g, 160 mmol) and heated under reflux for 3 h. The reaction mixture was partitioned between water (100 mL) and DCM (50 mL) and the organic solution separated, dried over $Na_2SO_4$, filtered and concentrated. The crude product was purified by column chromatography to give (E)-N-allyl-N-(5-bromo-2-methylpyridin-3-yl)-2-phenylethenesulfonamide (6.8 g, 95%) as a yellow solid. LCMS: m/z=396.0.

Step 3: 2-(5-bromo-2-methylpyridin-3-yl)-2,3-dihydroisothiazole 1,1-dioxide

A solution of (E)-N-allyl-N-(5-bromo-2-methylpyridin-3-yl)-2-phenylethenesulfonamide (3.0 g, 7.63 mmol) in degassed DCM (100 mL) was treated with (1,3-Bis(2,4,6-trimethylphenyl)-2-imidazolidinylidene)dichloro(phenylmethylene)(tricyclohexylphosphine)ruthenium, Benzylidene [1,3-bis(2,4,6-trimethylphenyl)-2-imidazolidinylidene] dichloro(tricyclohexylphosphine)ruthenium, [1,3-Bis-(2,4,6-trimethylphenyl)-2-imidazolidinylidene]dichloro (phenylmethylene)(tricyclohexylphosphine) ruthenium Grubbs's second generation catalyst (389 mg, 0.46 mmol) and allowed to stir under under an atmosphere of nitrogen for 3 h at reflux. The crude product was purified by column chromatography to give 2-(5-bromo-2-methylpyridin-3-yl)-2,3-dihydroisothiazole 1,1-dioxide (1.8 g, 82%) LCMS: m/z=289.0.

Step 4: 2-(5-bromo-2-methylpyridin-3-yl)-4-(dimethylamino)isothiazolidine 1,1-dioxide 2-(5-Bromo-2-methylpyridin-3-yl)-2,3-dihydroisothiazole 1,1-dioxide (2.0 g, 6.92 mmol) was suspended in a solution of dimethylamine (6.9 mL, 13.8 mmol) in ethanol (25 mL) and allowed to stir at rt for 16 h. The solvent was removed under reduced pressure and the crude product purified by column chromatography to give 2-(5-bromo-2-methylpyridin-3-yl)-4-(dimethylamino)isothiazolidine 1,1-dioxide (72%). LCMS (FA): m/z=334.0.

Step 5: (N-(5-(4-(dimethylamino)-1,1-dioxidoisothiazolidin-2-yl)-6-methyl-[3,4'-bipyridin]-2'-yl)acetamide (peak 1) and N-(5-(4-(dimethylamino)-1,1-dioxidoisothiazolidin-2-yl)-6-methyl-[3,4'-bipyridin]-2'-yl)acetamide (peak 2)

were prepared according to the procedure in Example 56, Step 4 using 2-(5-bromo-2-methylpyridin-3-yl)-4-(dimethylamino)isothiazolidine 1,1-dioxide and N-[4-(4,4,5,5-tetramethyl-1,3,2-dioxaborolan-2-yl)pyridin-2-yl]acetamide to give N-(5-(4-(dimethylamino)-1,1-dioxidoisothiazolidin-2-yl)-6-methyl-[3,4'-bipyridin]-2'-yl)acetamide. The racemic compound was separated by chiral SFC (Conditions: SFC Column: Chiralpak ID 10×250 mm 5 micron column Solvent: 40% [0.3% DEA in EtOH]/60% [CO2], Flow Rate: 10 mL/min, Back Pressure Regulator: 10 MPa) to provide N-(5-(4-(dimethylamino)-1,1-dioxidoisothiazolidin-2-yl)-6-methyl-[3,4'-bipyridin]-2'-yl)acetamide (peak1) I-496 LCMS (FA): m/z=390.2 (M+H) and N-(5-(4-(dimethylamino)-1,1-dioxidoisothiazolidin-2-yl)-6-methyl-[3,4'-bipyridin]-2'-yl)acetamide (peak2) I-497 LCMS (FA): m/z=390.1 (M+H).

The compounds listed in the table below (Table 41) were prepared in an analogous fashion to that described above from the appropriate starting materials:

TABLE 41

| Example | Starting Material | | Compound | |
|---|---|---|---|---|
| | Reagent | Chemical Structure | No. | LCMS Data |
| 57A | gj | H₂N— | I-325 | LCMS (FA): m/z = 376.3 (M + H) |
| 53B | gj | H₂N-CH₂-C₆H₅ | I-357 | LCMS (FA): m/z = 453.2 (M + H) |

Biological Protocols and Data:

Example 56: VPS34 Enzyme Assays

Cloning, Expression, and Purification of VPS34

VPS34 (accession number GB:BC033004) was cloned into pDEST20-Thrombin as N-terminal GST tagged fusion proteins using the Gateway system (Invitrogen, catalog#11804-013). The sequences were verified before recombinant protein expression using the Baculovirus Expression System with Gateway® Technology.

For expression VPS34 was infected at 1 MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

VPS34 Assay Conditions
Human VPS34 Enzyme Assay Method 100 nL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM $MnCl_2$) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

For the assay methods described above, test compound percent inhibition, at various concentrations, is calculated relative to control (DMSO and EDTA) treated samples. Compound concentration versus percent inhibition curves are fitted to generate $IC_{50}$ values. One skilled in the art will appreciate that the values generated either as percentage inhibition at a single concentration or $IC_{50}$ values are subject to experimental variation.

Inhibition of VPS34

In some embodiments, compounds of the invention were assayed at a concentration of 1.11 μM with the % inhibition values as shown in the table below (Table 37A). Additionally, compounds of the invention inhibit VPS34 with the following $IC_{50}$ ranges: (A)<10 nM; (B) 10 nM-<50 nM; (C) 50 nM-<100 nM; or (D) greater than 100 nM.

TABLE 37

| Compound | Percent Inhibition | $IC_{50}$ |
|---|---|---|
| I-1 | >99 | A |
| I-2 | >99 | B |
| I-3 | 87 | C |
| I-4 | >99 | B |
| I-5 | >99 | A |
| I-6 | >99 | B |
| I-7 | >99 | A |
| I-8 | >99 | D |
| I-9 | >99 | B |
| I-10 | >99 | A |
| I-11 | >99 | A |
| I-12 | >99 | A |
| I-13 | 81 | D |
| I-14 | >99 | B |
| I-15 | >99 | B |

TABLE 37-continued

| Compound | Percent Inhibition | $IC_{50}$ |
|---|---|---|
| I-16 | >99 | A |
| I-17 | >99 | C |
| I-18 | >99 | A |
| I-19 | >99 | C |
| I-20 | >99 | C |
| I-21 | >99 | B |
| I-22 | >99 | B |
| I-23 | >99 | A |
| I-24 | >99 | A |
| I-25 | >99 | B |
| I-26 | >99 | C |
| I-27 | >99 | A |
| I-28 | >99 | A |
| I-29 | >99 | B |
| I-30 | >99 | A |
| I-31 | >99 | B |
| I-32 | >99 | A |
| I-33 | >99 | B |
| I-34 | >99 | A |
| I-35 | >99 | B |
| I-36 | >99 | A |
| I-37 | >99 | A |
| I-38 | >99 | B |
| I-39 | >99 | A |
| I-40 | >99 | A |
| I-41 | >99 | A |
| I-42 | >99 | B |
| I-43 | >99 | A |
| I-44 | >99 | A |
| I-45 | >99 | A |
| I-46 | >99 | B |
| I-47 | >99 | B |
| I-48 | >99 | D |
| I-49 | >99 | C |
| I-50 | >99 | B |
| I-51 | 91 | C |
| I-52 | >99 | A |
| I-53 | 67 | D |
| I-54 | 83 | D |
| I-55 | >99 | A |
| I-56 | >99 | B |
| I-57 | >99 | B |
| I-58 | >99 | A |
| I-59 | >99 | A |
| I-60 | >99 | B |
| I-61 | 95 | B |
| I-62 | >99 | A |
| I-63 | >99 | A |
| I-64 | >99 | A |
| I-65 | 93 | D |
| I-66 | 88 | D |
| I-67 | >99 | C |
| I-68 | 98 | D |
| I-69 | >99 | B |
| I-70 | >99 | A |
| I-71 | >99 | A |
| I-72 | >99 | A |
| I-73 | >99 | A |
| I-74 | >99 | A |
| I-75 | >99 | C |
| I-76 | >99 | A |
| I-77 | >99 | A |
| I-78 | >99 | A |
| I-79 | >99 | B |
| I-80 | >99 | A |
| I-81 | >99 | A |
| I-82 | >99 | B |
| I-83 | 82 | D |
| I-84 | >99 | A |
| I-85 | 90 | D |
| I-86 | >99 | A |
| I-87 | >99 | A |
| I-88 | >99 | B |
| I-89 | >99 | B |
| I-90 | >99 | A |
| I-91 | >99 | A |
| I-92 | >99 | B |
| I-93 | 86 | B |

TABLE 37-continued

| Compound | Percent Inhibition | IC$_{50}$ |
|---|---|---|
| I-94 | 98 | A |
| I-95 | >99 | B |
| I-96 | >99 | B |
| I-97 | >99 | A |
| I-98 | >99 | B |
| I-99 | >99 | B |
| I-100 | >99 | A |
| I-101 | >99 | A |
| I-102 | >99 | B |
| I-103 | >99 | A |
| I-104 | >99 | A |
| I-105 | >99 | D |
| I-106 | 64 | D |
| I-107 | >99 | A |
| I-108 | >99 | B |
| I-109 | >99 | A |
| I-110 | >99 | A |
| I-111 | >99 | A |
| I-112 | >99 | C |
| I-113 | >99 | A |
| I-114 | >99 | B |
| I-115 | 68 | D |
| I-116 | 68 | D |
| I-117 | >99 | B |
| I-118 | >99 | B |
| I-119 | >99 | A |
| I-120 | >99 | A |
| I-121 | >99 | C |
| I-122 | >99 | C |
| I-123 | >99 | A |
| I-124 | 91 | A |
| I-125 | >99 | A |
| I-126 | >99 | C |
| I-127 | >99 | C |
| I-128 | >99 | A |
| I-129 | 100 | D |
| I-130 | >99 | C |
| I-131 | >99 | A |
| I-132 | >99 | A |
| I-133 | >99 | A |
| I-134 | >99 | B |
| I-135 | 99 | D |
| I-136 | >99 | A |
| I-137 | >99 | B |
| I-138 | >99 | B |
| I-139 | 61 | D |
| I-140 | >99 | B |
| I-141 | >99 | A |
| I-142 | >99 | A |
| I-143 | >99 | A |
| I-144 | >99 | A |
| I-145 | >99 | C |
| I-146 | >99 | B |
| I-147 | >99 | A |
| I-148 | >99 | B |
| I-149 | >99 | B |
| I-150 | >99 | A |
| I-151 | >99 | B |
| I-152 | >99 | B |
| I-153 | >99 | A |
| I-154 | >99 | A |
| I-155 | >99 | A |
| I-156 | >99 | A |
| I-157 | >99 | B |
| I-158 | >99 | A |
| I-159 | >99 | A |
| I-160 | >99 | B |
| I-161 | >99 | A |
| I-162 | >99 | B |
| I-163 | >99 | A |
| I-164 | >99 | A |
| I-165 | >99 | A |
| I-166 | >99 | A |
| I-167 | >99 | B |
| I-168 | >99 | A |
| I-169 | >99 | B |
| I-170 | >99 | A |
| I-171 | >99 | A |
| I-172 | >99 | B |
| I-173 | >99 | A |
| I-174 | >99 | A |
| I-175 | >99 | B |
| I-176 | >99 | B |
| I-177 | >99 | B |
| I-178 | >99 | A |
| I-179 | >99 | A |
| I-180 | >99 | C |
| I-181 | >99 | A |
| I-182 | >99 | A |
| I-183 | >99 | A |
| I-184 | 74 | D |
| I-185 | >99 | A |
| I-186 | >99 | B |
| I-187 | >99 | A |
| I-188 | 98 | C |
| I-189 | >99 | C |
| I-190 | 96 | B |
| I-191 | 77 | D |
| I-192 | >99 | C |
| I-193 | >99 | C |
| I-194 | 62 | D |
| I-195 | >99 | A |
| I-196 | >99 | A |
| I-197 | >99 | B |
| I-198 | 68 | D |
| I-199 | >99 | A |
| I-200 | >99 | A |
| I-201 | >99 | A |
| I-202 | >99 | C |
| I-203 | >99 | A |
| I-204 | >99 | A |
| I-205 | >99 | B |
| I-206 | >99 | A |
| I-207 | >99 | A |
| I-208 | >99 | B |
| I-209 | 49 | D |
| I-210 | >99 | C |
| I-211 | >99 | A |
| I-212 | 95 | C |
| I-213 | >99 | C |
| I-214 | >99 | A |
| I-215 | 99 | B |
| I-216 | 97 | C |
| I-217 | >99 | A |
| I-218 | >99 | B |
| I-219 | 92 | C |
| I-220 | 99 | B |
| I-221 | 97 | B |
| I-222 | 93 | B |
| I-223 | 95 | B |
| I-224 | 99 | B |
| I-225 | >99 | A |
| I-226 | 94 | B |
| I-227 | >99 | B |
| I-228 | >99 | A |
| I-229 | >99 | A |
| I-230 | 97 | B |
| I-231 | 26 | D |
| I-232 | 81 | B |
| I-233 | 96 | B |
| I-234 | 90 | B |
| I-235 | 92 | B |
| I-236 | 98 | B |
| I-237 | 91 | B |
| I-238 | 93 | A |
| I-239 | >99 | A |
| I-240 | >99 | B |
| I-241 | 96 | B |
| I-242 | 88 | B |
| I-243 | 85 | B |
| I-244 | 82 | B |
| I-245 | >99 | B |
| I-246 | 91 | B |
| I-247 | >99 | B |
| I-248 | >99 | B |
| I-249 | 85 | C |

TABLE 37-continued

| Compound | Percent Inhibition | IC$_{50}$ |
|---|---|---|
| I-250 | 99 | B |
| I-251 | 97 | B |
| I-252 | >99 | B |
| I-253 | 96 | B |
| I-254 | 77 | B |
| I-255 | 95 | A |
| I-256 | 94 | B |
| I-257 | >99 | B |
| I-258 | 88 | B |
| I-259 | 79 | A |
| I-260 | 91 | B |
| I-262 | 81 | B |
| I-263 | 53 | D |
| I-264 | 100 | A |
| I-265 | >99 | A |
| I-266 | 100 | B |
| I-267a | 97 | B |
| I-267b | 94 | B |
| I-268 | 100 | D |
| I-269 | >99 | B |
| I-271 | 91 | B |
| I-272 | >99 | C |
| I-273 | >99 | A |
| I-274 | >99 | B |
| I-275 | >99 | B |
| I-276 | 96 | A |
| I-277 | 100 | A |
| I-278 | >99 | B |
| I-279 | 93 | B |
| I-280 | 83 | D |
| I-281 | 40 | D |
| I-282 | 94 | A |
| I-283 | >99 | B |
| I-284 | >99 | B |
| I-285 | 85 | B |
| I-286 | >99 | A |
| I-287 | 91 | D |
| I-288 | 91 | B |
| I-289 | >99 | A |
| I-290 | >99 | B |
| I-291 | 95 | A |
| I-292 | 99 | B |
| I-293 | >99 | A |
| I-294 | 94 | A |
| I-295 | 80 | C |
| I-296 | 90 | B |
| I-297 | >99 | B |
| I-298 | 99 | A |
| I-299 | 98 | B |
| I-300 | 96 | B |
| I-301 | 96 | B |
| I-302 | 83 | B |
| I-303 | 95 | B |
| I-304 | 96 | B |
| I-305 | 94 | B |
| I-306 | >99 | B |
| I-307 | >99 | B |
| I-308 | >99 | A |
| I-309 | 99 | A |
| I-310 | >99 | A |
| I-311 | >99 | A |
| I-312 | >99 | B |
| I-313 | 88 | B |
| I-314 | 91 | B |
| I-315 | 92 | B |
| I-318 | 97 | B |
| I-319 | 94 | D |
| I-320 | 95 | B |
| I-321 | >99 | C |
| I-322 | 96 | B |
| I-323 | 73 | B |
| I-324 | >99 | B |
| I-325 | >99 | B |
| I-326 | 96 | A |
| I-329 | >99 | B |
| I-330 | >99 | D |
| I-331 | 93 | D |
| I-332 | >99 | B |
| I-333 | >99 | B |
| I-334 | 82 | D |
| I-335 | 92 | B |
| I-336 | 96 | B |
| I-337 | 52 | D |
| I-338 | >99 | B |
| I-339 | 98 | B |
| I-340 | 91 | B |
| I-341 | >99 | B |
| I-342 | >99 | A |
| I-343 | >99 | B |
| I-344 | >99 | B |
| I-346 | 95 | B |
| I-347 | 22 | D |
| I-348 | >99 | B |
| I-349 | 94 | B |
| I-350 | >99 | A |
| I-352 | 92 | C |
| I-353 | >99 | B |
| I-354 | 98 | B |
| I-355 | 91 | B |
| I-356 | >99 | A |
| I-357 | >99 | B |
| I-358 | >99 | B |
| I-359 | >99 | B |
| I-361 | 90 | B |
| I-362 | 95 | B |
| I-363 | 83 | D |
| I-364 | >99 | B |
| I-365 | >99 | B |
| I-366 | >99 | B |
| I-367 | 76 | C |
| I-368 | 96 | B |
| I-369 | 97 | B |
| I-370 | >99 | B |
| I-371 | >99 | A |
| I-372 | >99 | A |
| I-373 | >99 | B |
| I-374 | >99 | B |
| I-375 | 99 | A |
| I-376 | 94 | B |
| I-377 | 95 | B |
| I-378 | 66 | D |
| I-379 | 47 | D |
| I-380 | 95 | D |
| I-381 | >99 | A |
| I-382 | >99 | A |
| I-383 | 91 | B |
| I-384 | 73 | D |
| I-386 | 96 | B |
| I-387 | >99 | B |
| I-388 | 98 | C |
| I-389 | 95 | A |
| I-390 | 98 | B |
| I-391 | >99 | B |
| I-392 | 82 | D |
| I-394 | >99 | B |
| I-395 | >99 | B |
| I-396 | 94 | B |
| I-397 | 100 | C |
| I-398 | 93 | D |
| I-399 | 100 | B |
| I-401 | >99 | A |
| I-402 | 93 | B |
| I-403 | 92 | D |
| I-404 | 94 | B |
| I-405 | >99 | B |
| I-406 | 80 | D |
| I-407 | 98 | B |
| I-408 | >99 | B |
| I-409 | 82 | D |
| I-410 | 96 | B |
| I-411 | 88 | A |
| I-412 | 97 | B |
| I-413 | >99 | B |
| I-414 | 89 | C |
| I-415 | 82 | B |
| I-416 | >99 | B |

TABLE 37-continued

| Compound | Percent Inhibition | IC$_{50}$ |
|---|---|---|
| I-417 | >99 | A |
| I-418 | >99 | B |
| I-419 | 56 | D |
| I-420 | 59 | D |
| I-421 | 90 | B |
| I-422 | 96 | B |
| I-423 | >99 | B |
| I-424 | >99 | B |
| I-425 | 100 | B |
| I-426 | >99 | B |
| I-427 | >99 | A |
| I-428 | >99 | A |
| I-429 | 96 | B |
| I-430 | 92 | B |
| I-431 | 74 | D |
| I-432 | 98 | B |
| I-433 | 93 | B |
| I-434 | 36 | D |
| I-435 | 96 | A |
| I-436 | 89 | C |
| I-437 | >99 | B |
| I-438 | >99 | B |
| I-439 | 69 | D |
| I-440 | 83 | D |
| I-441 | >99 | A |
| I-442 | >99 | B |
| I-443 | >99 | B |
| I-444 | >99 | B |
| I-445 | >99 | B |
| I-446 | >99 | B |
| I-447 | 98 | A |
| I-448 | 87 | B |
| I-449 | 94 | B |
| I-450 | 87 | B |
| I-452 | >99 | B |
| I-454 | >99 | A |
| I-455 | >99 | B |
| I-456 | >99 | A |
| I-457 | 95 | B |
| I-458 | >99 | B |
| I-459 | 96 | B |
| I-460 | 60 | D |
| I-462 | 98 | D |
| I-463 | >99 | A |
| I-464 | >99 | B |
| I-465 | 97 | B |
| I-466 | 92 | B |
| I-467 | >99 | A |
| I-468 | >99 | B |
| I-469 | >99 | B |
| I-470 | >99 | B |
| I-471 | 98 | B |
| I-472 | 96 | D |
| I-473 | 87 | B |
| I-474 | 89 | B |
| I-475 | >99 | B |
| I-476 | 87 | B |
| I-477 | 93 | B |
| I-478 | 84 | B |
| I-479 | 98 | B |
| I-480 | 99 | C |
| I-481 | >99 | B |
| I-482 | >99 | C |
| I-483 | >99 | B |
| I-484 | 92 | C |
| I-485 | 100 | B |
| I-486 | 84 | A |
| I-487 | 71 | D |
| I-488 | >99 | B |
| I-490 | >99 | A |
| I-491 | 98 | B |
| I-492 | 86 | D |
| I-493 | 99 | B |
| I-494 | 91 | C |
| I-495 | 83 | B |
| I-496 | >99 | B |
| I-497 | >99 | B |
| I-498 | 83 | B |
| I-499 | >99 | B |

Example 57: Cellular Assay for Anti-proliferative Activity of VPS34 Inhibitors in Combination with a Second Therapeutic Agent Cells were plated in 25 µl of media in 384 well plates at 1,000 cells per well (A431, PC9, and NCI-H1650 cell lines), 1,500 cells per well (NCI-H1975) or 2,000 cells per well (NCI-H1650). The plates were incubated for 24 hrs at 37° C., 6% $CO_2$. The test compounds (see Table 38 below) were diluted serially, and 62.5 nL of each compound solution (or DMSO, if it is a single agent experiment) is added so the total added to the cells is 125 nL. Cell plates were incubated for 72 hrs at 37° C., 6% $CO_2$. Cell Titer Glo reagent (Promega) was added. The plates were then incubated for 10 minutes at room temperature before luminescence was read on a plate reader such as the Pherastar Plus, Pherastar FS, or LEADSeeker imaging system.

Synergy was measured by the Bliss synergy (Bliss, C. I. Ann. Appl. Biol. 26: 585-615 (1939). The Bliss independence model assumes that the fraction of cells that survives the treatment with both drugs is equal to the fraction that survives drug A alone times the fraction that survives drug B alone. Thus, the Bliss independence model predicts the cell survival based on ten single drug response curves. Here, Bliss synergy was defined as the percent cell survival predicted by the response surface minus the cell survival predicted by Bliss independence. Each dose combination showed a different Bliss synergy value, so the maximum Bliss synergy over all possible doses was reported. Bliss antagonism was defined similarly.

Bliss dependence was defined as the percent cell survival at a certain dose combination divided by the percent cell survival predicted by Bliss independence. More specifically, the Bliss dependence is vAB/(vA*vB), where vAB is the viability with drug A and drug B added, while vA and vB are the viabilities with each drug alone. The dose for the combination used in this study is the inflection point for each drug alone.

Another way to evaluate additivity is through consideration of Loewe additivity. A difference between Bliss independence and Loewe additivity evaluations of drug combination data is that Bliss independence evaluates whether two drugs interact at all (the null hypothesis is that the mechanisms are entirely independent) and Loewe additivity evaluates whether two drugs interact in an additive fashion (the null hypothesis is that the two drugs work by identical mechanisms). For Bliss independence, the boundary between additivity and synergy must be measured. For Loewe additivity, this boundary is assumed to be at a value of 1. Thus, Bliss independence provides a boundary between antagonism and synergy or additivity. Loewe additivity provides a boundary between synergy and independence or antagonism.

Synergy can also be measured by nonlinear blending synergy. Nonlinear blending synergy [Peterson, J. J. and Novik, S. J. J Recept Signal Transduct Res, 27, 12-146 (2007))] is found by considering the percent cell death values along the nonlinear blending plot. If the maximum cell death occurs between the endpoints, then the blending synergy is the difference between the maximum cell death for the combined drugs and the maximum cell death for the either drug alone.

A derivative of Loewe additivity is the Combination Index, I (see Chou T. C., Talalay P. *Adv. Enzyme Reg.,* 22: 27-55 (1984) and Berenbaum M. C. *J. Theor. Biol.,* 114: 413-431 (1985)). This measure is based on the shape of the the isobologram which represents 50% viability (for a review of the use of isobolograms in analysis of drug combinations, see Tallarida, R. J. *J. Pharm. Exp. Therap.* 319:1-7 (2006)). The Combination Index, I, can be calculated from the equation $I=D_A/EC50_A+D_B/EC50_B$, where $EC50_A$ and $EC50_B$ are the doses of drugs A and B alone, respectively, that result in cell viability of 50% and the dose combination $(D_A,D_B)$ is the point at which the estimated viability is 50%, where $D_A/D_B=EC50A/EC50B$.

The results in Table 38A were summarized by categorizing the Combination Index, 1. A mean Combination Index in the range (0.7-1.3) is classified as Additivity. A mean in the range (0-0.7) is classified as Synergy. A mean in the range (1.3-2) is classified as Subadditivity. A mean greater than 2 is classified as Antagonism. In some cases, the Combination Index does not exist because the 50 percent isobologram does not intersect both axes. In this case, the Nonlinear Blending Synergy is used instead to generate a call (Table 38B). The categorization is similar to the Combination Index. A Nonlinear Blending Synergy within the range (−20, 20) is classified as Additive. A value below −20 is classified as Antagonism, while a value above 20 is classified as Synergy.

TABLE 38A

Anti-proliferative Activity of Compounds of formula I (Compound X) in Combination with a Second Therapeutic Agent (Compound Y)

| Cell Line | Compound X | Compound Y | Combination Index | Meaning |
| --- | --- | --- | --- | --- |
| A431 | I-41 | Afatinib | 0.24 | Synergy |
| A431 | I-41 | Erlotinib | 0.38 | Synergy |
| A431 | I-32 | Afatinib | 0.25 | Synergy |
| A431 | I-32 | Erlotinib | 0.73 | Additivity |
| A431 | I-94 | Erlotinib | 0.38 | Synergy |
| A431 | I-299 | Erlotinib | 1.01 | Additivity |
| A431 | I-299 | Afatinib | 1.01 | Additivity |
| A431 | I-41 | AZD9291 | 0.62 | Synergy |
| A431 | I-299 | AZD9291 | 1.00 | Additivity |
| A431 | I-217 | Erlotinib | 0.46 | Synergy |
| A431 | I-94 | Afatinib | 0.23 | Synergy |
| A431 | I-153 | Afatinib | 0.23 | Synergy |
| A431 | I-217 | Afatinib | 0.36 | Synergy |
| A431 | I-304 | AZD9291 | 0.78 | Additivity |
| A431 | I-299 | CO-1686 | 1.02 | Additivity |
| A431 | I-41 | CO-1686 | 0.74 | Additivity |
| A431 | I-308 | CO-1686 | 0.88 | Additivity |
| A431 | I-304 | CO-1686 | 0.99 | Additivity |
| NCI H-1650 | I-41 | Afatinib | 0.72 | Additivity |
| NCI H-1650 | I-32 | Afatinib | 0.40 | Synergy |
| NCI H-1650 | I-299 | Afatinib | 0.47 | Synergy |
| NCI H-1650 | I-41 | AZD9291 | 0.92 | Additivity |
| NCI H-1650 | I-299 | AZD9291 | 0.87 | Additivity |
| NCI H-1650 | I-94 | Afatinib | 0.65 | Synergy |
| NCI H-1650 | I-153 | Afatinib | 0.64 | Synergy |
| NCI H-1650 | I-217 | Afatinib | 0.31 | Synergy |
| NCI H-1650 | I-308 | Afatinib | 0.55 | Synergy |
| NCI H-1650 | I-308 | AZD9291 | 0.53 | Synergy |
| NCI H-1650 | I-304 | AZD9291 | 0.80 | Additivity |
| NCI H-1650 | I-299 | CO-1686 | 0.43 | Synergy |
| NCI H-1650 | I-41 | CO-1686 | 0.58 | Synergy |
| NCI H-1650 | I-308 | CO-1686 | 0.36 | Synergy |
| NCI H-1650 | I-304 | CO-1686 | 0.47 | Synergy |
| NCI-H1975 | I-41 | Afatinib | 0.58 | Synergy |
| NCI-H1975 | I-32 | Afatinib | 0.66 | Synergy |

TABLE 38A-continued

Anti-proliferative Activity of Compounds of formula I (Compound X) in Combination with a Second Therapeutic Agent (Compound Y)

| Cell Line | Compound X | Compound Y | Combination Index | Meaning |
| --- | --- | --- | --- | --- |
| NCI-H1975 | I-94 | Afatinib | 0.54 | Synergy |
| NCI-H1975 | I-299 | Afatinib | 0.68 | Synergy |
| NCI-H1975 | I-217 | Afatinib | 0.52 | Synergy |
| NCI-H1975 | I-308 | Afatinib | 0.84 | Additivity |
| NCI-H1975 | I-41 | AZD9291 | 0.45 | Synergy |
| NCI-H1975 | I-299 | AZD9291 | 0.54 | Synergy |
| NCI-H1975 | I-308 | AZD9291 | 0.72 | Additivity |
| NCI-H1975 | I-304 | AZD9291 | 1.00 | Additivity |
| NCI-H1975 | I-41 | CO-1686 | 0.51 | Synergy |
| NCI-H1975 | I-299 | CO-1686 | 0.72 | Additivity |
| NCI-H1975 | I-308 | CO-1686 | 0.60 | Synergy |
| NCI-H1975 | I-304 | CO-1686 | 0.77 | Additivity |
| PC9 | I-41 | Afatinib | 1.02 | Additivity |
| PC9 | I-41 | Erlotinib | 1.02 | Additivity |
| PC9 | I-32 | Afatinib | 0.79 | Additivity |
| PC9 | I-32 | Erlotinib | 0.78 | Additivity |
| PC9 | I-94 | Afatinib | 1.04 | Additivity |
| PC9 | I-94 | Erlotinib | 0.91 | Additivity |
| PC9 | I-299 | Erlotinib | 1.18 | Additivity |
| PC9 | I-153 | Erlotinib | 0.97 | Additivity |
| PC9 | I-217 | Erlotinib | 0.87 | Additivity |
| PC9 | I-308 | Erlotinib | 1.36 | Subadditivity |
| PC9 | I-299 | Afatinib | 1.37 | Subadditivity |
| PC9 | I-153 | Afatinib | 1.17 | Additivity |
| PC9 | I-217 | Afatinib | 0.97 | Additivity |
| PC9 | I-308 | Afatinib | 1.49 | Subadditivity |
| PC9 | I-41 | AZD9291 | 0.92 | Additivity |
| PC9 | I-299 | AZD9291 | 1.17 | Additivity |
| PC9 | I-308 | AZD9291 | 1.33 | SubAdditivity |
| PC9 | I-304 | AZD9291 | 0.98 | Additivity |
| PC9 | I-41 | CO-1686 | 0.84 | Additivity |
| PC9 | I-299 | CO-1686 | 1.00 | Additivity |
| PC9 | I-308 | CO-1686 | 1.19 | Additivity |
| PC9 | I-304 | CO-1686 | 0.90 | Additivity |

TABLE 38B

Anti-proliferative Activity of Compounds of formula I (Compound X) in Combination with a Second Therapeutic Agent (Compound Y)

| Cell Line | Compound X | Compound Y | Blending Synergy | Meaning |
| --- | --- | --- | --- | --- |
| A431 | I-153 | Erlotinib | 16.3 | Additivity |
| A431 | I-308 | Erlotinib | 15.2 | Additivity |
| A431 | I-308 | Afatinib | 11.2 | Additivity |
| A431 | I-308 | AZD9291 | 10.2 | Additivity |
| NCI H-1650 | I-299 | Erlotinib | 26.93 | Synergy |
| NCI H-1650 | I-41 | Erlotinib | 20.5 | Synergy |
| NCI H-1650 | I-32 | Erlotinib | 22.29 | Synergy |
| NCI H-1650 | I-94 | Erlotinib | 23.69 | Synergy |
| NCI H-1650 | I-153 | Erlotinib | 23.76 | Synergy |
| NCI H-1650 | I-217 | Erlotinib | 28.65 | Synergy |
| NCI H-1650 | I-308 | Erlotinib | 27.0 | Synergy |
| NCI-H1975 | I-153 | Afatinib | 8.73 | Additive |

Example 58: Tumor Xenograft Model

The in vivo efficacy of the compounds of formula I described herein as, e.g., single agent or combination therapy with a second therapeutic agent, can be studied using tumor xenograft models.

Female nude mice were inoculated subcutaneously in flank with $2.0 \times 10^6$ human colorectal adenocarcinoma cells SW48. Similar experiments were conducted using human non-small cell lung cancer cells PC9, NCI-H1650, and NCI-H1975. In these experiments, female nude mice were inoculated subcutaneously in the flank with $2.0 \times 10^6$ cells+matrigel.

Figure 2:
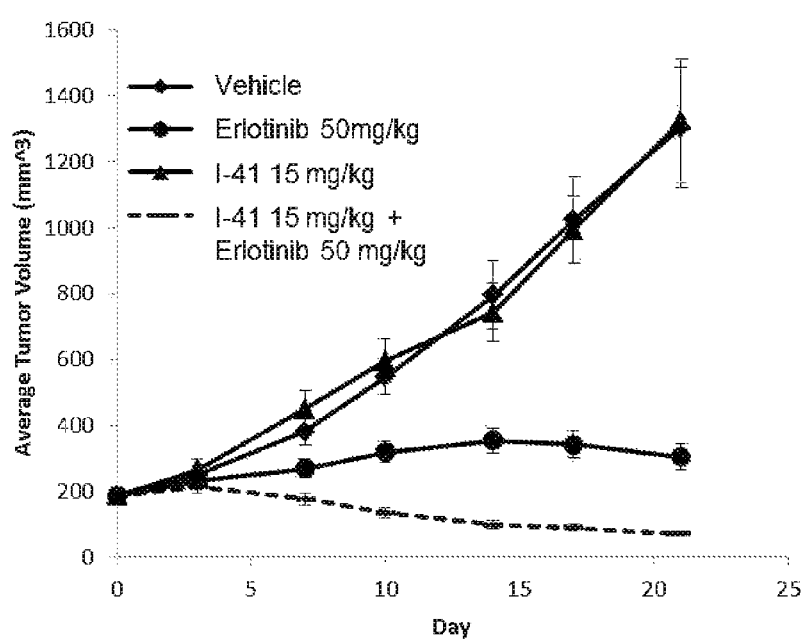
FIG. 2 is a graph showing the effect of treatment with a compound of formula I (I-41) and erlotinib when administered orally (po) daily (qd) as single agents and in combination to nude female mice bearing human non-small cell lung PC9 tumor xenografts.
Figure 3:
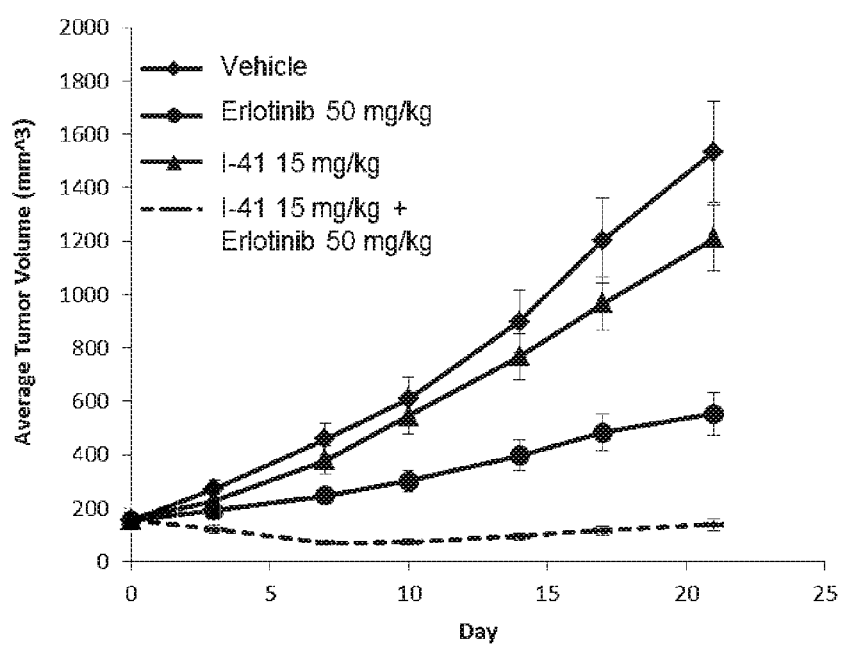
FIG. 3 is a graph showing the effect of treatment with a compound of formula I (I-41) and erlotinib when administered orally (po) daily (qd) as single agents and in combination to nude female mice bearing human non-small cell lung NCI H1650 tumor xenografts.
Figure 4:
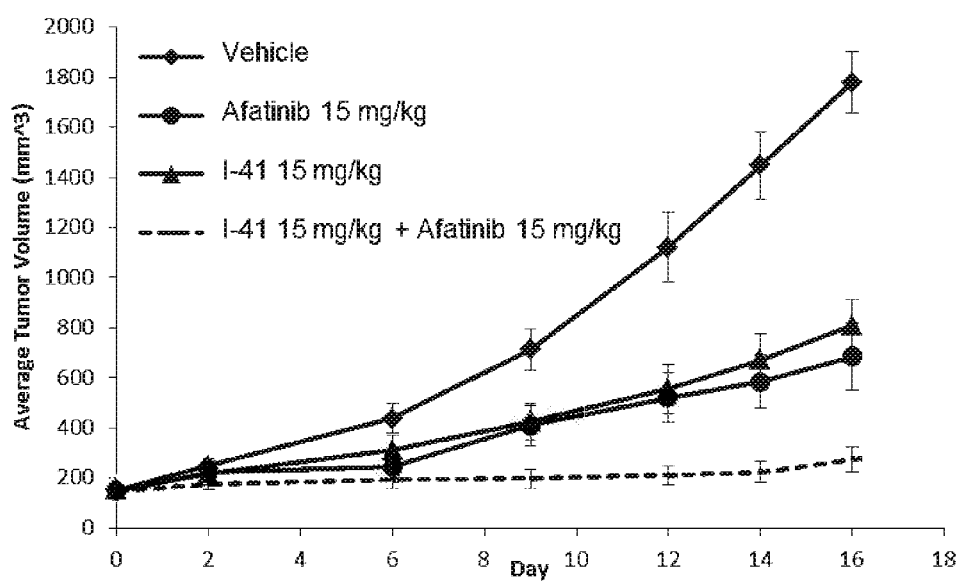
FIG. 4 is a graph showing the effect of treatment with a compound of formula I (I-41) and afatinib when administered orally (po) daily (qd) as single agents and in combination to nude female mice bearing human non-small cell lung NCI-H1975 tumor xenografts.
Figure 5:
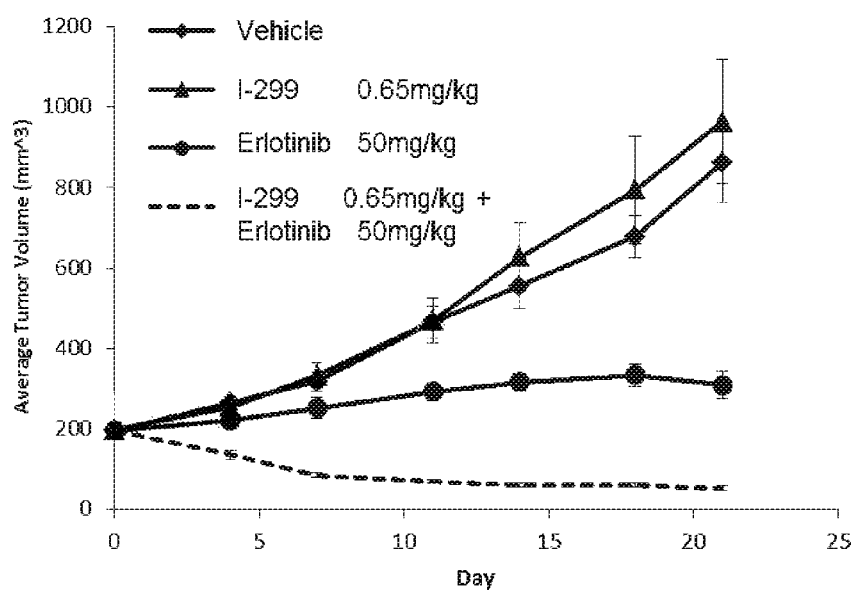
FIG. 5 is a graph showing the effect of treatment with a compound of formula I (I-299) and erlotinib when administered orally (po) daily (qd) as single agents and in combination to nude female mice bearing human non-small cell lung PC9 tumor xenografts.
Figure 6:
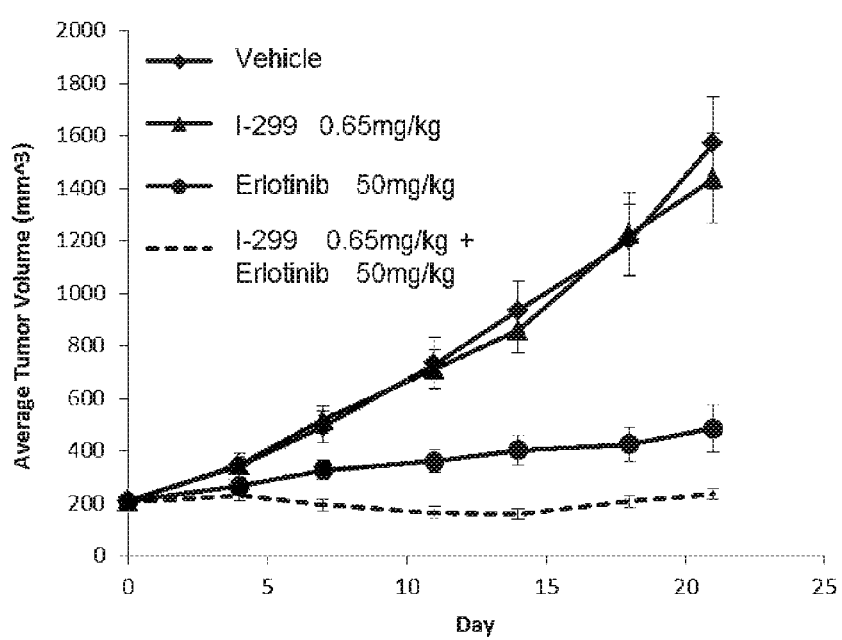
FIG. 6 is a graph showing the effect of treatment with a compound of formula I (I-299) and erlotinib when administered orally (po) daily (qd) as single agents and in combination to nude female mice bearing human non-small cell lung NCI H1650 tumor xenografts.
Figure 7:
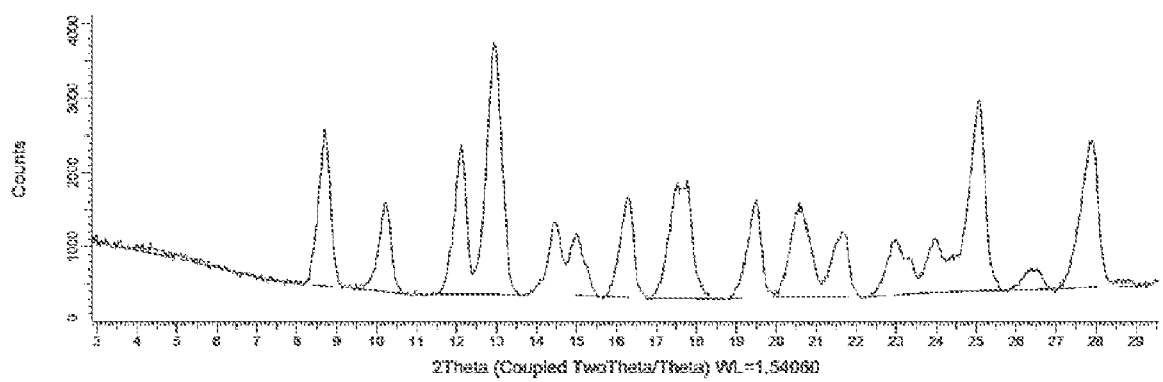
FIG. 7 is a X-ray powder diffraction pattern of compound I-41, which was prepared by slurrying in IPA/Water.
Figure 8:
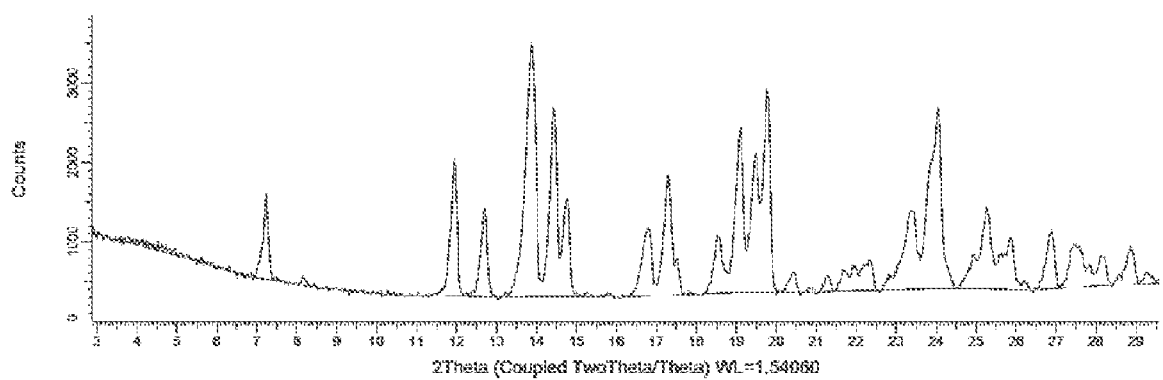
FIG. 8 is a X-ray powder diffraction pattern of compound I-299.

Tumor growth was monitored with vernier calipers. The mean tumor volume was calculated using the formula $V=W^2 \times L/2$. When the mean tumor volume reached approximately 150-200 mm$^3$, the animals were randomized into treatment groups. See Tables 39, 40, and 41 below. Test compounds (either compounds of formula I such as I-41, other therapeutic agents such as erlotinib, or combination thereof), and vehicle control were administered by oral gavage as described in the tables below. The vehicle was 3.5% w/v NaHCO$_3$ in water or 100% PEG400. Tumor growth was measured twice per week. See also FIGS. 1-6.

TABLE 39

Study design for SW48 xenograft model

| Group | Compounds Administered | Dose | Route and Schedule |
| --- | --- | --- | --- |
| 1 | Vehicle (3.5% NaHCO$_3$ + 100% PEG400) | N/A | PO QD × 14 + PO QD × 14 |
| 2 | I-41 | 12.5 mg/kg | PO QD × 14 |
| 3 | erlotinib | 25 mg/kg | PO QD × 14 |
| 4 | I-41 + erlotinib | 12.5 mg/kg + 25 mg/kg | PO QD × 14 + PO QD × 14 |

TABLE 40

Study design for PC9 and H1650 xenograft models

| Group | Compounds Administered | Dose | Route and Schedule |
| --- | --- | --- | --- |
| 1 | Vehicle (3.5% NaHCO$_3$ + 100% PEG400) | N/A | PO QD × 21 + PO QD × 21 |
| 2 | I-41 | 15 mg/kg | PO QD × 21 |
| 3 | erlotinib | 50 mg/kg | PO QD × 21 |
| 4 | I-41 + erlotinib | 15 mg/kg + 50 mg/kg | PO QD × 21 + PO QD × 21 |

TABLE 41

Study design for NCI-1975 xenograft models

| Group | Compounds Administered | Dose | Route and Schedule |
| --- | --- | --- | --- |
| 1 | Vehicle (3.5% NaHCO$_3$ + 0.5% Methylcellulose) | N/A | PO QD × 16 + PO QD × 16 |
| 2 | I-41 | 15 mg/kg | PO QD × 16 |
| 3 | afatinib | 15 mg/kg | PO QD × 16 |
| 4 | I-41 + afatinib | 15 mg/kg + 15 mg/kg | PO QD × 16 + PO QD × 16 |

TABLE 42

Study design for PC9 and H1650 xenograft models

| Group | Compounds Administered | Dose | Route and Schedule |
| --- | --- | --- | --- |
| 1 | Vehicle (10% HPbCD/ 3.5% NaHCO$_3$ + 100% PEG400) | N/A | PO QD × 21 + PO QD × 21 |
| 2 | I-299 | 0.65 mg/kg | PO QD × 21 |
| 3 | Erlotinib | 50 mg/kg | PO QD × 21 |
| 4 | I-299 + Erlotinib | 0.65 mg/kg + 50 mg/kg | PO QD × 21 + PO QD × 21 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A method of treating a proliferative disorder in a patient comprising administering to the patient a therapeutically effective amount of a compound of formula I:

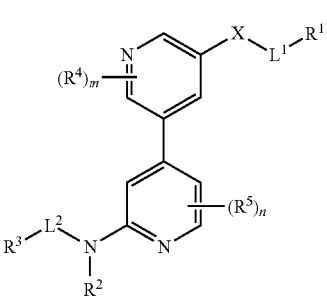

or a pharmaceutically acceptable salt thereof, wherein:
R$^1$ is hydrogen, C$_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which being optionally substituted with 1-5 R$^6$;
R$^3$ is C$_{1-6}$ aliphatic, 3-10-membered cycloaliphatic, phenyl, naphthyl, 3-10-membered heterocyclyl having 1-4 heteroatoms independently selected from nitrogen, oxygen or sulfur, or 5-10-membered heteroaryl having 1-4 heteroatoms independently selected from nitrogen, oxygen or sulfur; each of which being optionally substituted with 1-5 R$^6$;
wherein:
each R$^6$ independently is —CN, halo or -L$^3$-R$^7$ wherein:
L$^3$ is a bond, C$_{1-4}$ alkylene, —O—, —N(R$^x$)—, —S—, —S(O)—, —S(O)$_2$—, —C(O)—, —CO$_2$—, N(R$^x$)C(O)—, —N(R$^x$)CO$_2$—, —S(O)$_2$NR$^x$—, —N(R$^x$)S(O)$_2$—, —OC(O)N(R$^x$)—, —N(R$^x$)C(O)N(R$^x$), —N(R$^x$)S(O)$_2$N(R$^x$)— or —OC(O)—;
each R$^x$, independently, is hydrogen or C$_{1-4}$ alkyl;
R$^7$ is hydrogen, C$_{1-6}$ aliphatic, 3-10-membered cycloaliphatic, phenyl, naphthyl, or 5-10-membered heteroaryl having 1-4 heteroatoms independently selected from nitrogen, oxygen, or sulfur;
X is a bond or C$_{1-4}$ aliphatic;
L$^1$ is —N(R$^8$)C(O)—, —C(O)—N(R$^9$)—, —N(R$^{10}$)S(O)$_2$—, —S(O)$_2$NR$^{11}$—, —C(O)—, —C(S)—, —S(O)$_2$—, —O—C(O)—, —C(O)—O—, —O—S(O)$_2$—, —S(O)₂—O—, —N(R¹³)C(O)N(R¹⁴)—, or —N(R¹⁵)S(O)₂N(R¹⁶)—; and wherein
each of R⁸, R⁹, R¹⁰, R¹¹, R¹³, R¹⁴, R¹⁵, and R¹⁶, independently, is hydrogen or C₁₋₄ alkyl; or X or L¹ optionally joining with R¹ to form an optionally substituted 5-6-membered heterocyclyl;

R² is hydrogen or C₁₋₄ alkyl;

L² is a bond, —C(O)—, —S(O)₂—, —C(O)—O—, —C(O)N(Rʸ)—, or —S(O)₂N(Rʸ)—; wherein each Rʸ, independently, is hydrogen or C₁₋₄ alkyl;

each occurrence of R⁴ and R⁵, independently, is —CN, halo or -L⁴-R¹⁷ wherein
L⁴ is C₁₋₄ alkylene, —O—, —N(Rᶻ)—, —S—, —S(O)—, —S(O)₂—, —C(O)—, —CO₂—, —C(O)N(Rᶻ)—, —N(Rᶻ)C(O)—, —N(Rᶻ)C(O)O—, —S(O)₂N(Rᶻ)—, —N(Rᶻ)S(O)₂—, —OC(O)N(Rᶻ)—, —N(Rᶻ)C(O)N(Rᶻ)—, —N(Rᶻ)S(O)₂N(Rᶻ)— or —OC(O)—;
each Rᶻ, independently, is hydrogen or C₁₋₄ alkyl, and R¹⁷ is hydrogen or C₁₋₆ aliphatic; and each of m and n, independently, is 0-3;
provided that
if one R⁴ is located at the ring carbon between the ring nitrogen and the ring carbon to which —X-L¹-R¹ is located, X or L¹ optionally joining with said R⁴ to form an optionally substituted 5-7-membered heterocyclyl or an optionally substituted 5-6-membered heteroaryl; or
if one R⁴ is located at either ring carbon adjacent to the ring nitrogen, said R⁴ optionally joining with the ring nitrogen to form an optionally substituted 5-7-membered heterocyclyl or an optionally substituted 5-6-membered heteroaryl; or
if L² is a bond and R³ is phenyl, naphthyl, or heteroaryl, R² optionally joining with a substituent of R³ to form an optionally substituted 5-7-membered heterocyclyl or an optionally substituted 5-6-membered heteroaryl.

2. The method of claim 1, wherein L¹ is —N(R⁸)C(O)—, —N(R¹⁰)S(O)₂—, —C(O)—, or —S(O)₂—.

3. The method of claim 2, wherein each of R⁸ and R¹⁰, independently, is hydrogen, methyl or ethyl.

4. The method of claim 1, wherein R¹ is C₁₋₄ aliphatic, 3-6-membered cycloaliphatic, phenyl, naphthyl, 3-6-membered heterocyclyl having 1-3 heteroatoms independently selected from nitrogen, oxygen or sulfur, or 5-6-membered heteroaryl having 1-3 heteroatoms independently selected from nitrogen, oxygen or sulfur.

5. The method of claim 1, wherein R¹ is

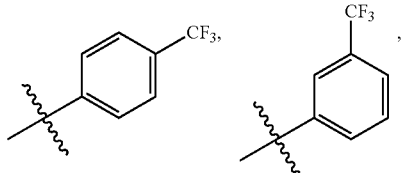

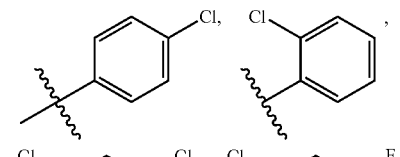

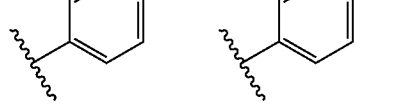

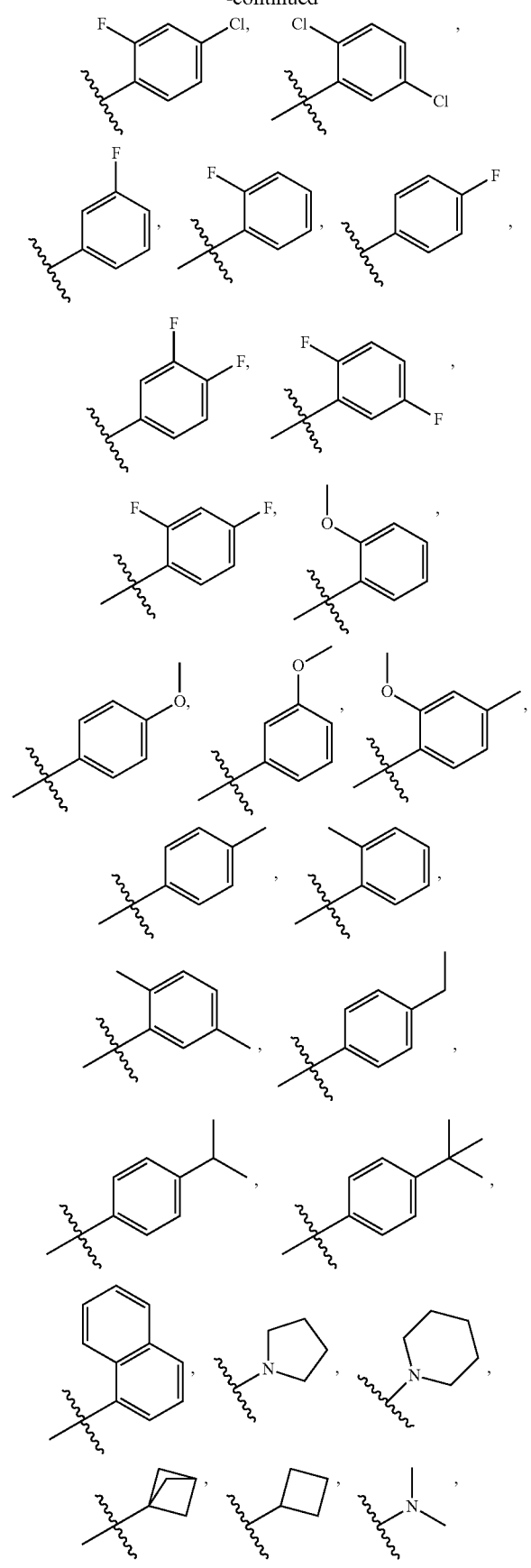

-continued

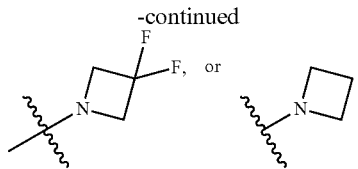

6. The method of claim 1, wherein X is a bond, methylene, or ethylene.

7. The method of claim 1, wherein $R^2$ is hydrogen.

8. The method of claim 1, wherein $L^2$ is a bond, —C(O)— or —C(O)—O—.

9. The method of claim 1, wherein $R^3$ is methyl, cyclopropyl, or 6-membered heteroaryl that is optionally substituted with 1-2 $R^6$.

10. The method of claim 1, wherein $R^4$ is fluoro, chloro, unsubstituted $C_{1-3}$ aliphatic, trifluoromethyl, hydroxyl, methoxy, $NH_2$ or NH—$C_{1-3}$ aliphatic; m is 0-2; and one $R^4$ is substituted at the ring carbon between the ring nitrogen and the ring carbon to which —X-$L^1$-$R^1$ is substituted.

11. The method of claim 1, wherein X is a bond; C is —N($R^8$)C(O)—, —N($R^{10}$)S(O)$_2$—, —C(O)—, or —S(O)$_2$—; $R^2$ is hydrogen, methyl, ethyl, or cyclopropylmethyl; $L^2$ is a bond, —C(O)— or —C(O)—O—; $R^3$ is $C_{1-3}$ alkyl, cyclopropyl, or 6-membered heteroaryl, each of which being optionally substituted with 1-2 $R^6$; $R^4$ is fluoro, chloro, $C_{1-3}$ alkyl, trifluoromethyl, hydroxyl, methoxy, —$NH_2$ or —NH—$C_{1-3}$ aliphatic; m is 0-2; and one $R^4$ is substituted at the ring carbon between the ring nitrogen and the ring carbon to which —X-$L^1$-$R^1$ is substituted: n is 0 or 1; and $R^1$ is

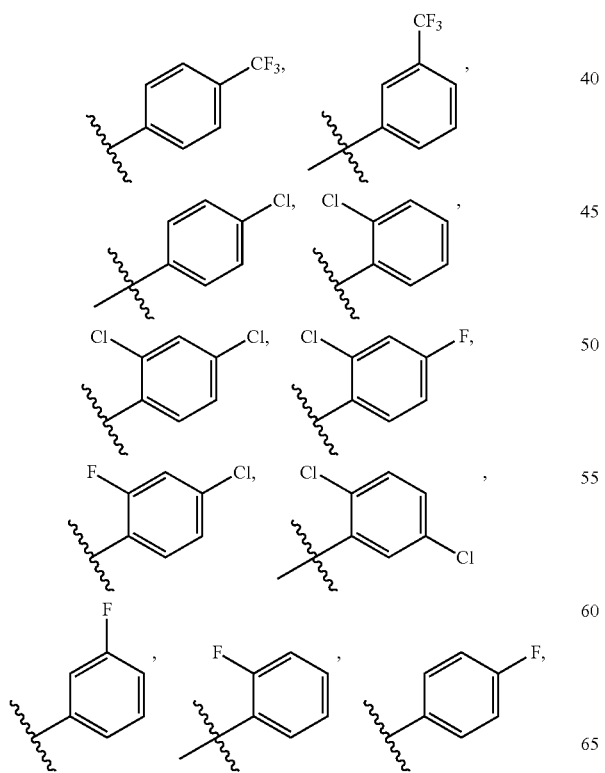

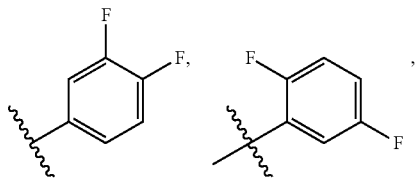

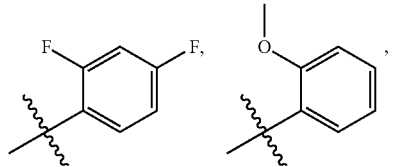

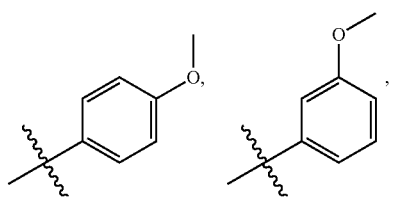

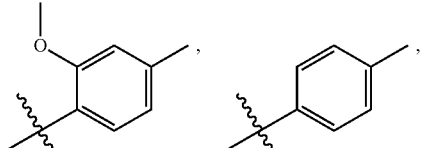

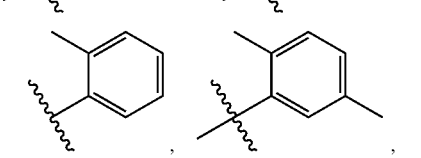

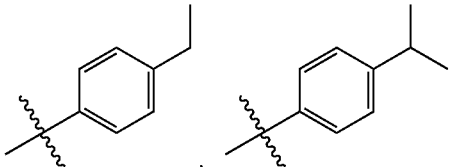

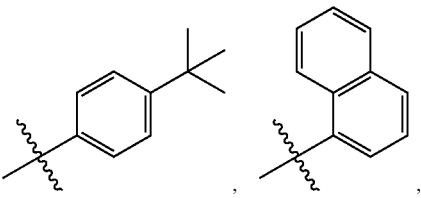

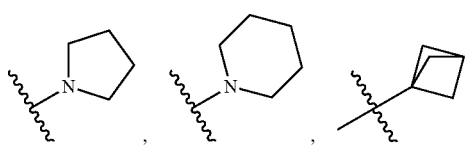

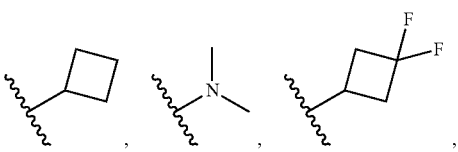

, or

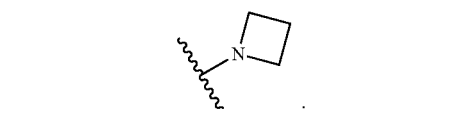

12. The method of claim 1, wherein the compound has formula (II) below:

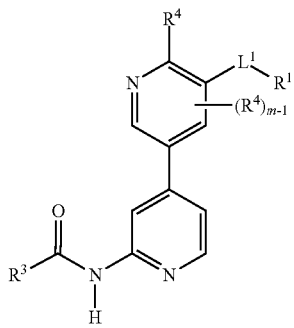

II wherein the value of (m−1) is 0 or 1; and a first $R^4$ is substituted at the ring carbon between the ring nitrogen and the ring carbon to which —X-$L^1$-$R^1$ is substituted, or a pharmaceutically acceptable salt thereof.

13. The method of claim 1, wherein the compound has formula (VIII) below:

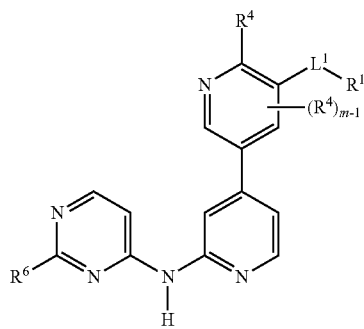

VIII wherein the value of (m−1) is 0 or 1; and a first $R^4$ is substituted at the ring carbon between the ring nitrogen and the ring carbon to which —X-$L^1$-$R^1$ is substituted, or a pharmaceutically acceptable salt thereof.

14. The method of claim 1, wherein the compound is selected from:

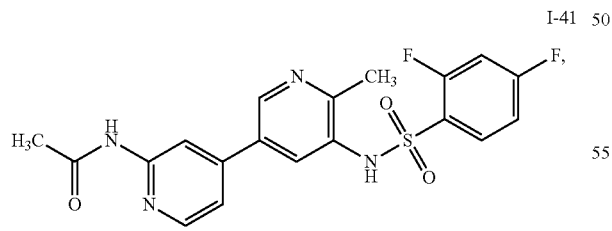

I-41

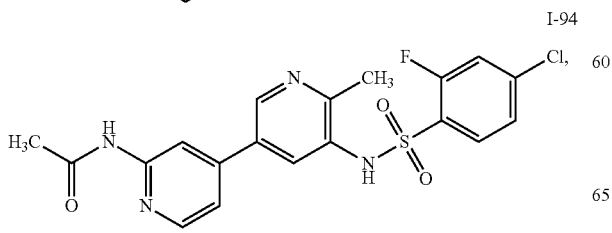

I-94

-continued

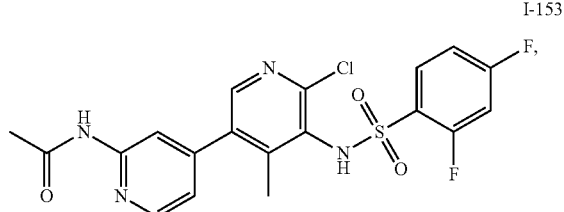

I-153

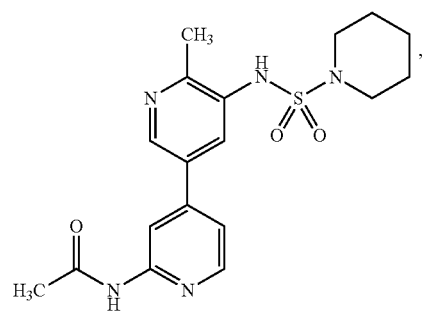

I-214

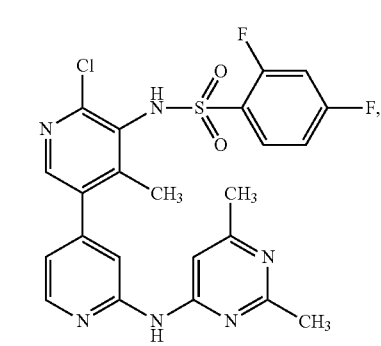

I-218

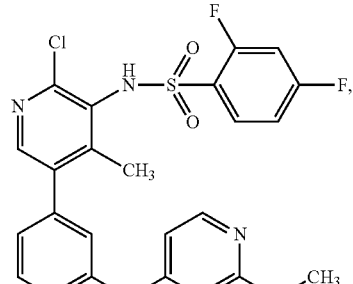

I-225

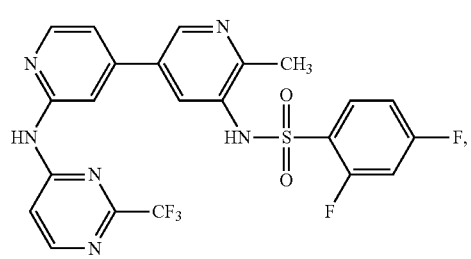

I-237

I-246
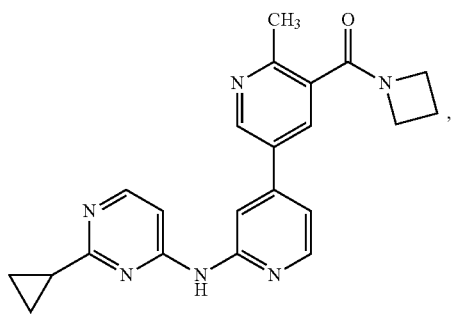
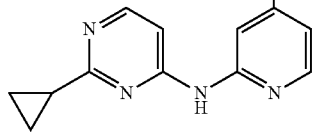
I-294
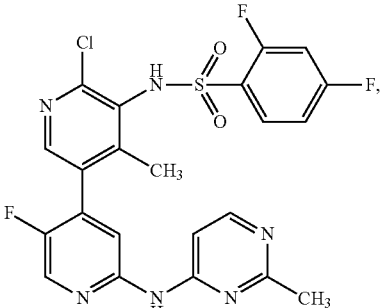
I-291
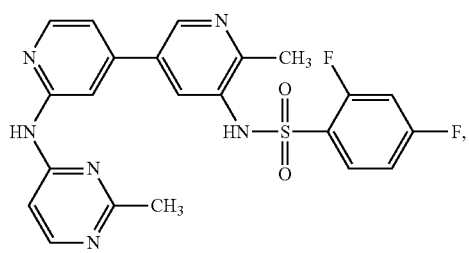
I-296
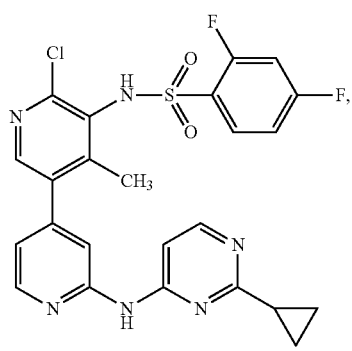
I-292
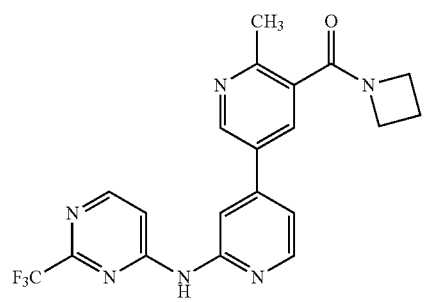
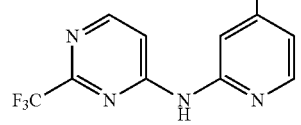
I-299
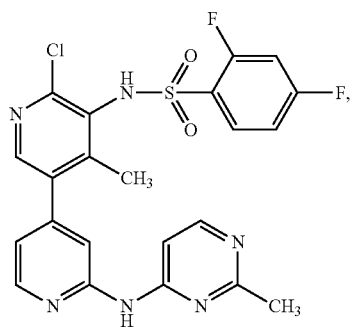
I-293
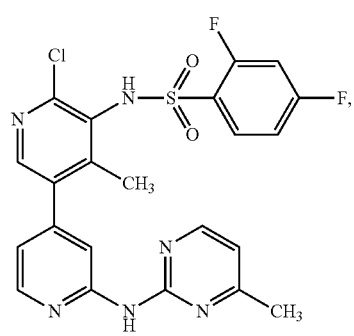
I-304
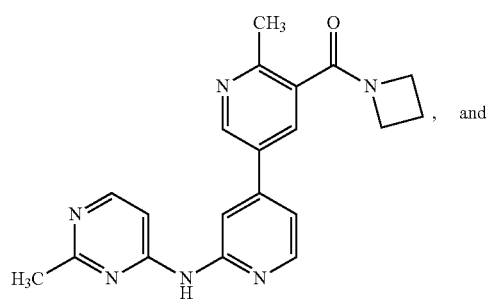
, and -continued

I-308

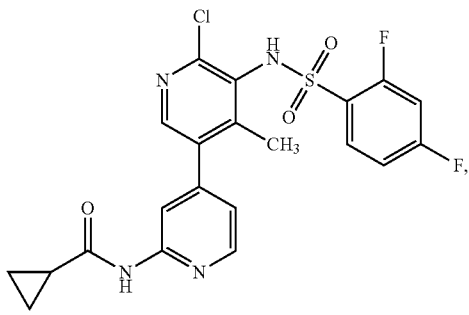

or a pharmaceutically acceptable salt thereof.

15. The method of claim 14, wherein the compound is

I-41

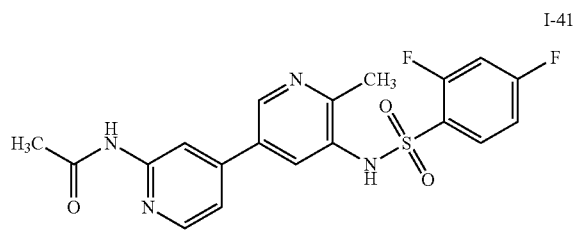 [SMILES: CC(=O)Nc1cc(-c2cnc(C)c(NS(=O)(=O)c3ccc(F)cc3F)c2)ccn1]

or a pharmaceutically acceptable salt thereof.

16. The method of claim 14, wherein the compound is

I-299

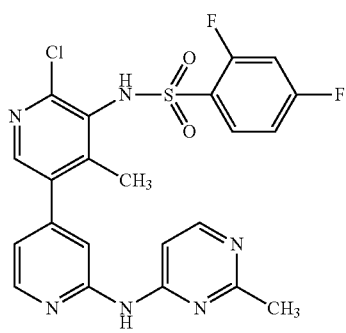

or a pharmaceutically acceptable salt thereof.

17. The method of claim 14, wherein the compound is

I-308

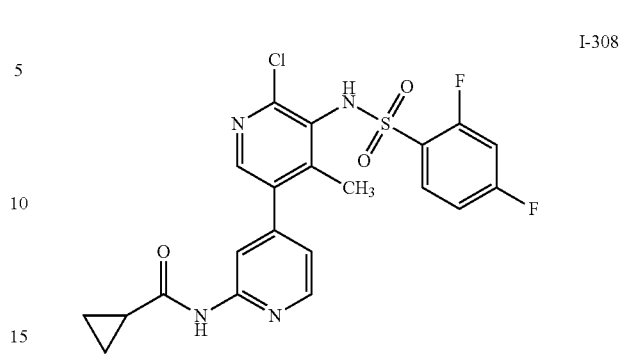

or a pharmaceutically acceptable salt thereof.

18. The method of claim 1, wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, head and neck cancer, squamous cell carcinoma, or ovarian cancer.

19. The method of claim 15, wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, head and neck cancer, squamous cell carcinoma, or ovarian cancer.

20. The method of claim 16 wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, head and neck cancer, squamous cell carcinoma, or ovarian cancer.

21. The method of claim 17, wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, head and neck cancer, squamous cell carcinoma, or ovarian cancer.

22. The method of claim 1, wherein a second therapeutic agent is administered to the patient.

23. The method of claim 22, wherein the second therapeutic agent is an EGFR inhibitor.

* * * * *